US012534463B2

(12) United States Patent
Wu et al.

(10) Patent No.: US 12,534,463 B2
(45) Date of Patent: Jan. 27, 2026

(54) SUBSTITUTED TRICYCLIC COMPOUNDS AS FGFR INHIBITORS

(71) Applicants: Incyte Corporation, Wilmington, DE (US); Incyte Holdings Corporation, Wilmington, DE (US)

(72) Inventors: Liangxing Wu, Wilmington, DE (US); Colin Zhang, Berwyn, PA (US); Chunhong He, Boothwyn, PA (US); Liang Lu, Hockessin, DE (US); Wenqing Yao, Chadds Ford, PA (US)

(73) Assignees: Incyte Corporation, Wilmington, DE (US); Incyte Holdings Corporation, Wilmington, DE (US)

( * ) Notice: Subject to any disclaimer, the term of this patent is extended or adjusted under 35 U.S.C. 154(b) by 280 days.

(21) Appl. No.: 18/382,210

(22) Filed: Oct. 20, 2023

(65) Prior Publication Data

US 2024/0246974 A1 Jul. 25, 2024

Related U.S. Application Data

(62) Division of application No. 17/337,027, filed on Jun. 2, 2021, now Pat. No. 11,840,534, which is a division of application No. 16/842,558, filed on Apr. 7, 2020, now Pat. No. 11,053,246, which is a division of application No. 16/152,827, filed on Oct. 5, 2018, now abandoned, which is a division of application No. 15/408,768, filed on Jan. 18, 2017, now Pat. No. 10,131,667, which is a division of application No. 13/915,775, filed on Jun. 12, 2013, now Pat. No. 9,611,267.

(60) Provisional application No. 61/774,841, filed on Mar. 8, 2013, provisional application No. 61/740,012, filed on Dec. 20, 2012, provisional application No. 61/691,463, filed on Aug. 21, 2012, provisional application No. 61/659,245, filed on Jun. 13, 2012.

(51) Int. Cl.

| | |
|---|---|
| ***C07D 471/14*** | (2006.01) |
| ***A61P 1/16*** | (2006.01) |
| ***A61P 11/00*** | (2006.01) |
| ***A61P 19/02*** | (2006.01) |
| ***C07D 471/20*** | (2006.01) |
| ***C07D 471/22*** | (2006.01) |
| ***C07D 491/22*** | (2006.01) |
| ***C07D 495/14*** | (2006.01) |
| ***C07D 498/14*** | (2006.01) |
| ***C07D 498/22*** | (2006.01) |

(52) U.S. Cl.

CPC .............. *C07D 471/14* (2013.01); *A61P 1/16* (2018.01); *A61P 11/00* (2018.01); *A61P 19/02* (2018.01); *C07D 471/20* (2013.01); *C07D 471/22* (2013.01); *C07D 491/22* (2013.01); *C07D 495/14* (2013.01); *C07D 498/14* (2013.01); *C07D 498/22* (2013.01)

(58) Field of Classification Search

CPC ................ C07D 471/14; C07D 471/20; C07D 471/22; C07D 495/14; C07D 498/14; C07D 498/22; C07D 491/22; A61P 1/16; A61P 11/00; A61P 19/02

See application file for complete search history.

(56) References Cited

U.S. PATENT DOCUMENTS

| | | | |
|---|---|---|---|
| 850,370 | A | 4/1907 | Hynes |
| 3,894,021 | A | 7/1975 | Denzel et al. |
| 4,271,074 | A | 6/1981 | Lohmann et al. |
| 4,339,267 | A | 7/1982 | Levitt |
| 4,347,348 | A | 8/1982 | Chernikhov et al. |
| 4,402,878 | A | 9/1983 | D'Alelio et al. |
| 4,405,519 | A | 9/1983 | D'Alelio et al. |
| 4,405,520 | A | 9/1983 | D'Alelio et al. |
| 4,405,786 | A | 9/1983 | D'Alelio et al. |
| 4,460,773 | A | 7/1984 | Suzuki et al. |
| 4,874,803 | A | 10/1989 | Baron et al. |
| 4,940,705 | A | 7/1990 | Boshagen et al. |
| 5,159,054 | A | 10/1992 | Keller |
| 5,240,941 | A | 8/1993 | Bruneau |
| 5,480,887 | A | 1/1996 | Hornback et al. |
| 5,521,184 | A | 5/1996 | Zimmermann et al. |
| 5,536,725 | A | 7/1996 | Cullen et al. |
| 5,541,324 | A | 7/1996 | TenBrink et al. |
| 5,760,068 | A | 6/1998 | Talley et al. |
| 5,783,577 | A | 7/1998 | Houghten et al. |
| 5,845,025 | A | 12/1998 | Garito et al. |
| 5,994,364 | A | 11/1999 | Njoroge et al. |
| 6,465,484 | B1 | 10/2002 | Bilodeau et al. |

(Continued)

FOREIGN PATENT DOCUMENTS

| | | |
|---|---|---|
| CL | 2014003355 | 6/2015 |
| CL | 2015002628 | 8/2016 |

(Continued)

OTHER PUBLICATIONS

"Sabiosciences.com" [online]. "FGF Pathway," 2000-2012, [retrieved on Jun. 23, 2015]. Retrieved from the Internet: URL <http://www.sabiosciences.com/pathway.php?sn=FGF Signaling>, 3 pages.
"Substance Record for SID 240993001," Feb. 13, 2015, pp. 1-8.
Acevedo et al., "Inducible FGFR-1 Activation Leads to Irreversible Prostate Adenocarcinoma and an Epithelial-to-Mesenchymal Transition," Cancer Cell, Dec. 2007, 12:559-571.
Adib et al., "FGFR2/3 genomic alterations and response to Enfortumab Vedotin in metastatic urothelial carcinoma," BJUI Compass., 2022, 3:169-172.

(Continued)

*Primary Examiner* — Erich A Leeser
(74) *Attorney, Agent, or Firm* — Fish & Richardson P.C.

(57) ABSTRACT

The present invention relates to tricyclic compounds, and pharmaceutical compositions of the same, that are inhibitors of one or more FGFR enzymes and are useful in the treatment of FGFR-associated diseases such as cancer.

2 Claims, No Drawings

Specification includes a Sequence Listing.

(56) References Cited

U.S. PATENT DOCUMENTS 6,998,408 B2 2/2006 Pinto
7,074,801 B1 7/2006 Yoshida et al.
7,125,880 B1 10/2006 Chen
7,488,802 B2 2/2009 Collins et al.
7,589,101 B2 9/2009 Okram et al.
7,618,975 B2 11/2009 Cai et al.
7,642,255 B2 1/2010 Sim
7,648,973 B2 1/2010 DeLuca et al.
7,846,923 B2 12/2010 Ren et al.
7,868,018 B2 1/2011 Xie et al.
7,943,743 B2 5/2011 Korman et al.
8,008,449 B2 8/2011 Korman et al.
8,119,655 B2 2/2012 Dong et al.
8,168,757 B2 5/2012 Finnefrock et al.
8,183,248 B2 5/2012 Nagle et al.
8,217,149 B2 7/2012 Irving et al.
8,426,411 B2 4/2013 Wishart et al.
8,461,328 B2 6/2013 Babu et al.
8,754,114 B2 6/2014 Yao et al.
8,759,398 B2 6/2014 Nelson
8,889,711 B2 11/2014 Bedjeguelal
9,266,892 B2 2/2016 Zhuo et al.
9,388,185 B2 7/2016 Lu et al.
9,440,976 B2 9/2016 Dyke et al.
9,533,954 B2 1/2017 Yao et al.
9,533,984 B2 1/2017 Sun et al.
9,580,423 B2 2/2017 Lu et al.
9,611,267 B2 4/2017 Wu et al.
9,708,318 B2 7/2017 Lu et al.
9,745,311 B2 8/2017 Lu et al.
9,801,889 B2 10/2017 Lu et al.
9,890,156 B2 2/2018 Lu et al.
10,016,348 B2 7/2018 Lu et al.
10,040,790 B2 8/2018 Sun et al.
10,131,667 B2 11/2018 Wu et al.
10,208,024 B2 2/2019 Andrews et al.
10,213,427 B2 2/2019 Yao et al.
10,214,528 B2 2/2019 Lu et al.
10,251,892 B2 4/2019 Sokolsky et al.
10,308,644 B2 6/2019 Wu et al.
10,350,240 B2 7/2019 Gore et al.
10,357,431 B2 7/2019 Staric et al.
10,450,313 B2 10/2019 Lu et al.
10,611,762 B2 4/2020 Jia et al.
10,632,126 B2 4/2020 Lu et al.
10,738,048 B2 8/2020 Lu et al.
10,813,930 B2 10/2020 Yao et al.
10,851,105 B2 12/2020 Wu et al.
10,947,230 B2 3/2021 Sun et al.
11,014,923 B2 5/2021 Lu et al.
11,053,246 B2 7/2021 Wu et al.
11,173,162 B2 11/2021 Sokolsky et al.
11,174,257 B2 11/2021 Jia et al.
11,407,750 B2 8/2022 Tao et al.
11,466,004 B2 10/2022 Burn
11,472,801 B2 10/2022 Pan et al.
11,530,214 B2 12/2022 Lu et al.
11,628,162 B2 4/2023 Ji et al.
11,667,635 B2 6/2023 Lu et al.
11,840,534 B2 12/2023 Wu et al.
2003/0078255 A1 4/2003 Pinto
2003/0078277 A1 4/2003 Hibi et al.
2003/0181622 A1 9/2003 Chiu et al.
2004/0044012 A1 3/2004 Dobrusin et al.
2004/0067948 A1 4/2004 Hallett
2004/0097493 A1 5/2004 Chen et al.
2004/0122029 A1 6/2004 Liu et al.
2004/0127538 A1 7/2004 Oinuma et al.
2004/0204427 A1 10/2004 Chen et al.
2005/0009876 A1 1/2005 Bhagwat et al.
2005/0070542 A1 3/2005 Hodgetts et al.
2005/0148603 A1 7/2005 Jimenez et al.
2005/0197340 A1 9/2005 Arora et al.
2005/0222171 A1 10/2005 Bold et al.
2006/0222637 A1 10/2006 Bamdad
2006/0270849 A1 11/2006 Nishino et al.
2007/0116984 A1 5/2007 Park et al.
2007/0197510 A1 8/2007 Ohmoto et al.
2007/0225286 A1 9/2007 Ren et al.
2007/0280943 A1 12/2007 Friedman et al.
2008/0221098 A1 9/2008 Sim et al.
2008/0249301 A1 10/2008 Hornberger et al.
2009/0098086 A1 4/2009 Zask et al.
2009/0099165 A1 4/2009 Hurley et al.
2009/0099190 A1 4/2009 Flynn et al.
2009/0105233 A1 4/2009 Chua et al.
2009/0131467 A1 5/2009 Kanazawa et al.
2009/0163545 A1 6/2009 Goldfarb
2009/0246198 A1 10/2009 Dong et al.
2010/0032626 A1 2/2010 Akino
2010/0099684 A1 4/2010 Cook, II et al.
2010/0105661 A1 4/2010 Shirakami et al.
2010/0143547 A1 6/2010 Kriegel et al.
2010/0204235 A1 8/2010 Lizos
2010/0210636 A1 8/2010 Ishikawa et al.
2010/0216798 A1 8/2010 Nakai et al.
2010/0239496 A1 9/2010 Gangadharmath et al.
2011/0045511 A1 2/2011 Graus Porta et al.
2011/0118230 A1 5/2011 Chen et al.
2011/0159604 A1 6/2011 Fan et al.
2011/0160203 A1 6/2011 Liu et al.
2011/0178053 A1 7/2011 Arendt et al.
2011/0195968 A1 8/2011 Greul et al.
2011/0212077 A1 9/2011 Noronha et al.
2011/0224155 A1 9/2011 Tachdjian et al.
2011/0262525 A1 10/2011 Wang et al.
2011/0313003 A1 12/2011 Shi et al.
2012/0035153 A1 2/2012 Saxty et al.
2012/0135997 A1 5/2012 Kato et al.
2012/0165305 A1 6/2012 Yao et al.
2012/0295881 A1 11/2012 Lange et al.
2012/0319095 A1 12/2012 Tada et al.
2013/0078731 A1 3/2013 George et al.
2013/0200356 A1 8/2013 Jung et al.
2013/0210825 A1 8/2013 Rehwinkel et al.
2013/0338134 A1 12/2013 Wu et al.
2014/0045814 A1 2/2014 Lu et al.
2014/0054564 A1 2/2014 Kim et al.
2014/0080892 A1 3/2014 Bhanot et al.
2014/0088100 A1 3/2014 Bifulco, Jr. et al.
2014/0103325 A1 4/2014 Shin et al.
2014/0117318 A1 5/2014 Choi et al.
2014/0148548 A1 5/2014 Yamanaka et al.
2014/0171405 A1 6/2014 Zhuo et al.
2014/0187559 A1 7/2014 Miduturu
2014/0194430 A1 7/2014 Eis et al.
2014/0228370 A1 8/2014 Eis et al.
2014/0243308 A1 8/2014 Yao et al.
2014/0288069 A1 9/2014 Eis et al.
2014/0296233 A1 10/2014 D'Agostino et al.
2014/0315902 A1 10/2014 Sun et al.
2014/0374722 A1 12/2014 Kim et al.
2014/0378468 A1 12/2014 Aichholz et al.
2014/0378481 A1 12/2014 Bifulco, Jr. et al.
2014/0378483 A1 12/2014 Benazet et al.
2015/0011548 A1 1/2015 Linnanen et al.
2015/0011560 A1 1/2015 Legeai-Mallet
2015/0011579 A1 1/2015 Clary-Ceccato et al.
2015/0038485 A1 2/2015 Eis et al.
2015/0197519 A1 7/2015 Bifulco
2016/0115164 A1 4/2016 Wu et al.
2016/0244448 A1 8/2016 Lu et al.
2016/0244449 A1 8/2016 Lu et al.
2016/0244450 A1 8/2016 Lu et al.
2016/0280713 A1 9/2016 Lu et al.
2017/0107216 A1 4/2017 Wu et al.
2017/0119782 A1 5/2017 Lu et al.
2017/0137424 A1 5/2017 Wu et al.
2017/0145025 A1 5/2017 Li et al.
2017/0165263 A1 6/2017 Yao et al.
2017/0166564 A1 6/2017 Sun et al.
2017/0174671 A1 6/2017 Wu et al.
2017/0174679 A1 6/2017 Lajkiewicz et al.
2017/0260168 A1 9/2017 Andrews et al.

(56) References Cited

U.S. PATENT DOCUMENTS

| | | | |
|---|---|---|---|
| 2017/0290839 | A1 | 10/2017 | Lu et al. |
| 2017/0320875 | A1 | 11/2017 | Li et al. |
| 2017/0320877 | A1 | 11/2017 | Wu et al. |
| 2017/0342060 | A1 | 11/2017 | Lu et al. |
| 2017/0362253 | A1 | 12/2017 | Xiao et al. |
| 2018/0008610 | A1 | 1/2018 | Lu et al. |
| 2018/0016260 | A1 | 1/2018 | Yu et al. |
| 2018/0022713 | A1 | 1/2018 | D'Agostino et al. |
| 2018/0057486 | A1 | 3/2018 | Wu et al. |
| 2018/0072718 | A1 | 3/2018 | Liu et al. |
| 2018/0177784 | A1 | 6/2018 | Wu et al. |
| 2018/0177870 | A1 | 6/2018 | Liu et al. |
| 2018/0179179 | A1 | 6/2018 | Wu et al. |
| 2018/0179197 | A1 | 6/2018 | Wu et al. |
| 2018/0179201 | A1 | 6/2018 | Wu et al. |
| 2018/0179202 | A1 | 6/2018 | Wu et al. |
| 2018/0244672 | A1 | 8/2018 | Lu et al. |
| 2018/0273519 | A1 | 9/2018 | Wu et al. |
| 2019/0040082 | A1 | 2/2019 | Xiao et al. |
| 2019/0055237 | A1 | 2/2019 | Pan et al. |
| 2019/0062327 | A1 | 2/2019 | Sun et al. |
| 2019/0062345 | A1 | 2/2019 | Xiao et al. |
| 2019/0071439 | A1 | 3/2019 | Li et al. |
| 2019/0092767 | A1 | 3/2019 | Li et al. |
| 2019/0127376 | A1 | 5/2019 | Wu et al. |
| 2019/0127467 | A1 | 5/2019 | Shah et al. |
| 2019/0144439 | A1 | 5/2019 | Wu et al. |
| 2019/0202824 | A1 | 7/2019 | Wu et al. |
| 2019/0225601 | A1 | 7/2019 | Wu et al. |
| 2019/0240220 | A1 | 8/2019 | Yao et al. |
| 2019/0241560 | A1 | 8/2019 | Lu et al. |
| 2019/0269693 | A1 | 9/2019 | Lu et al. |
| 2019/0284187 | A1 | 9/2019 | Wu et al. |
| 2019/0300524 | A1 | 10/2019 | Wu et al. |
| 2019/0337948 | A1 | 11/2019 | Frietze et al. |
| 2019/0345170 | A1 | 11/2019 | Wu et al. |
| 2020/0002338 | A1 | 1/2020 | Jia et al. |
| 2020/0055853 | A1 | 2/2020 | Ellies et al. |
| 2020/0095244 | A1 | 3/2020 | Sun et al. |
| 2020/0255424 | A1 | 8/2020 | Wu et al. |
| 2020/0270245 | A1 | 8/2020 | Pan et al. |
| 2020/0277309 | A1 | 9/2020 | Wu et al. |
| 2020/0281907 | A1 | 9/2020 | Ji et al. |
| 2020/0306256 | A1 | 10/2020 | Lu et al. |
| 2020/0377504 | A1 | 12/2020 | Wu et al. |
| 2020/0399267 | A1 | 12/2020 | Lu et al. |
| 2021/0009582 | A1 | 1/2021 | Vechorkin et al. |
| 2021/0094935 | A1 | 4/2021 | Vechorkin |
| 2021/0106588 | A1 | 4/2021 | Vechorkin et al. |
| 2021/0115053 | A1 | 4/2021 | Shvartsbart et al. |
| 2021/0171522 | A1 | 6/2021 | Tao et al. |
| 2021/0171535 | A1 | 6/2021 | McCammant et al. |
| 2021/0214366 | A1 | 7/2021 | Roach et al. |
| 2021/0380587 | A1 | 12/2021 | Wu et al. |
| 2021/0395246 | A1 | 12/2021 | Sun et al. |
| 2022/0009921 | A1 | 1/2022 | Lu et al. |
| 2022/0153740 | A1 | 5/2022 | Jia et al. |
| 2022/0324986 | A1 | 10/2022 | Koblish et al. |
| 2022/0411423 | A1 | 12/2022 | Tao et al. |
| 2023/0121695 | A1 | 4/2023 | Frietze et al. |
| 2023/0218591 | A1 | 7/2023 | Ji et al. |

FOREIGN PATENT DOCUMENTS

| | | |
|---|---|---|
| CL | 2017000654 | 12/2017 |
| CL | 2017001984 | 3/2018 |
| CL | 2018000089 | 5/2018 |
| CL | 2018000124 | 5/2018 |
| CL | 2017002117 | 6/2018 |
| CL | 2018000036 | 6/2018 |
| CL | 2018000128 | 6/2018 |
| CL | 2018003322 | 1/2019 |
| CN | 1863774 | 11/2006 |
| CN | 101007778 | 8/2007 |
| CN | 101679408 | 3/2010 |
| CN | 101715451 | 5/2010 |
| CN | 102399220 | 4/2012 |
| CN | 102399233 | 4/2012 |
| CN | 102666536 | 9/2012 |
| CN | 103571502 | 2/2014 |
| CN | 103588771 | 2/2014 |
| CN | 104262330 | 1/2015 |
| CN | 107652289 | 2/2018 |
| DE | 2156720 | 5/1973 |
| DE | 2934578 | 3/1981 |
| DE | 3432983 | 4/1985 |
| DE | DD 280853 | 7/1990 |
| DE | 3937633 | 5/1991 |
| DE | 4119767 | 12/1992 |
| DE | 19912638 | 9/2000 |
| EA | 201590005 | 5/2015 |
| EP | 0466452 | 1/1992 |
| EP | 0995751 | 4/2000 |
| EP | 1199070 | 4/2002 |
| EP | 1217000 | 6/2002 |
| EP | 1388541 | 2/2004 |
| EP | 2651404 | 10/2015 |
| EP | 3184521 | 6/2017 |
| FR | 2428654 | 1/1980 |
| FR | 2876582 | 4/2006 |
| FR | 2983196 | 5/2013 |
| FR | 2983199 | 5/2013 |
| FR | 2983200 | 5/2013 |
| JP | 62273979 | 11/1987 |
| JP | 63017882 | 1/1988 |
| JP | S 6310630 | 1/1988 |
| JP | 02009895 | 1/1990 |
| JP | H 0348656 | 3/1991 |
| JP | H 03275669 | 12/1991 |
| JP | 04179576 | 6/1992 |
| JP | H 04158084 | 6/1992 |
| JP | H 04328121 | 11/1992 |
| JP | H 05320173 | 12/1993 |
| JP | H 05320515 | 12/1993 |
| JP | H 09188812 | 7/1997 |
| JP | H 1060426 | 3/1998 |
| JP | H 11171865 | 6/1999 |
| JP | 2000123973 | 4/2000 |
| JP | 2001035664 | 2/2001 |
| JP | 2001265031 | 9/2001 |
| JP | 2002516327 | 6/2002 |
| JP | 2002296731 | 10/2002 |
| JP | 2003335788 | 11/2003 |
| JP | 2004203749 | 7/2004 |
| JP | 2004346145 | 12/2004 |
| JP | 2005015395 | 1/2005 |
| JP | 2005320288 | 11/2005 |
| JP | 2006028027 | 2/2006 |
| JP | 2006514624 | 5/2006 |
| JP | 2006284843 | 10/2006 |
| JP | 2006522756 | 10/2006 |
| JP | 2006316054 | 11/2006 |
| JP | 2007500725 | 1/2007 |
| JP | 2008198769 | 8/2008 |
| JP | 2009536959 | 10/2009 |
| JP | 2009537520 | 10/2009 |
| JP | 2010180147 | 8/2010 |
| JP | 2010248429 | 11/2010 |
| JP | 2010267847 | 11/2010 |
| JP | 2010270245 | 12/2010 |
| JP | 2010272618 | 12/2010 |
| JP | 2010272727 | 12/2010 |
| JP | 2010278114 | 12/2010 |
| JP | 2011009348 | 1/2011 |
| JP | 2011044637 | 3/2011 |
| JP | 2011116840 | 6/2011 |
| JP | 2011222650 | 11/2011 |
| JP | 2012116825 | 6/2012 |
| JP | 2012136476 | 7/2012 |
| JP | 5120580 | 1/2013 |
| JP | 2013049251 | 3/2013 |
| JP | 2013179181 | 9/2013 |
| JP | 2015517376 | 6/2015 |
| JP | 2015521600 | 7/2015 |

(56) References Cited

FOREIGN PATENT DOCUMENTS

| | | |
|---|---|---|
| JP | 2018507214 | 3/2018 |
| JP | 2018511573 | 4/2018 |
| JP | 6336665 | 6/2018 |
| KR | 20010043829 | 5/2001 |
| KR | 20080045536 | 5/2008 |
| KR | 20110023190 | 3/2011 |
| KR | 20110043270 | 4/2011 |
| KR | 20120052034 | 5/2012 |
| KR | 20120078303 | 7/2012 |
| KR | 20130043460 | 4/2013 |
| KR | 20140090411 | 7/2014 |
| KR | 20140099105 | 8/2014 |
| TW | 200602319 | 1/2006 |
| TW | 201402574 | 1/2014 |
| WO | WO 1988/003025 | 5/1988 |
| WO | WO 1991/009835 | 7/1991 |
| WO | WO 1991/010172 | 7/1991 |
| WO | WO 1992/006078 | 4/1992 |
| WO | WO 1992/022552 | 12/1992 |
| WO | WO 1993/024488 | 12/1993 |
| WO | WO 1994/013669 | 6/1994 |
| WO | WO 1994/015995 | 7/1994 |
| WO | WO 1994/025438 | 11/1994 |
| WO | WO 1995/020965 | 8/1995 |
| WO | WO 1996/015128 | 5/1996 |
| WO | WO 1996/040707 | 12/1996 |
| WO | WO 1997/047601 | 12/1997 |
| WO | WO 1998/005661 | 2/1998 |
| WO | WO 1998/006703 | 2/1998 |
| WO | WO 1998/011438 | 3/1998 |
| WO | WO 1998/018781 | 5/1998 |
| WO | WO 1998/028281 | 7/1998 |
| WO | WO 1998/033798 | 8/1998 |
| WO | WO 1998/046609 | 10/1998 |
| WO | WO 1998/054156 | 12/1998 |
| WO | WO 1999/006422 | 2/1999 |
| WO | WO 1999/007732 | 2/1999 |
| WO | WO 1999/009030 | 2/1999 |
| WO | WO 1999/042442 | 8/1999 |
| WO | WO 1999/059975 | 11/1999 |
| WO | WO 1999/061444 | 12/1999 |
| WO | WO 1999/064400 | 12/1999 |
| WO | WO 2000/009495 | 2/2000 |
| WO | WO 2002/000196 | 2/2000 |
| WO | WO 2000/024744 | 5/2000 |
| WO | WO 2000/053595 | 9/2000 |
| WO | WO 2000/068186 | 11/2000 |
| WO | WO 2001/002369 | 1/2001 |
| WO | WO 2001/014402 | 3/2001 |
| WO | WO 2001/022938 | 4/2001 |
| WO | WO 2001/023386 | 4/2001 |
| WO | WO 2001/029041 | 4/2001 |
| WO | WO 2001/029042 | 4/2001 |
| WO | WO 2001/042247 | 6/2001 |
| WO | WO 2001/047892 | 7/2001 |
| WO | WO 2001/053273 | 7/2001 |
| WO | WO 2001/055148 | 8/2001 |
| WO | WO 2001/057037 | 8/2001 |
| WO | WO 2001/057038 | 8/2001 |
| WO | WO 2001/058899 | 8/2001 |
| WO | WO 2001/064655 | 9/2001 |
| WO | WO 2001/066099 | 9/2001 |
| WO | WO 2001/068647 | 9/2001 |
| WO | WO 2001/083472 | 11/2001 |
| WO | WO 2001/085722 | 11/2001 |
| WO | WO 2002/000655 | 1/2002 |
| WO | WO 2002/012442 | 2/2002 |
| WO | WO 2002/014315 | 2/2002 |
| WO | WO 2002/020011 | 3/2002 |
| WO | WO 2002/051831 | 7/2002 |
| WO | WO 2002/055082 | 7/2002 |
| WO | WO 2002/066481 | 8/2002 |
| WO | WO 2002/074754 | 9/2002 |
| WO | WO 2002/076953 | 10/2002 |
| WO | WO 2002/083648 | 10/2002 |
| WO | WO 2002/088095 | 11/2002 |
| WO | WO 2002/094825 | 11/2002 |
| WO | WO 2002/096873 | 12/2002 |
| WO | WO 2002/102793 | 12/2002 |
| WO | WO 2003/000187 | 1/2003 |
| WO | WO 2003/000688 | 1/2003 |
| WO | WO 2003/000690 | 1/2003 |
| WO | WO 2003/009852 | 2/2003 |
| WO | WO 2003/014083 | 2/2003 |
| WO | WO 2003/024967 | 3/2003 |
| WO | WO 2003/037347 | 5/2003 |
| WO | WO 2003/037891 | 5/2003 |
| WO | WO 2003/040131 | 5/2003 |
| WO | WO 2003/042402 | 5/2003 |
| WO | WO 2003/049542 | 6/2003 |
| WO | WO 2003/062236 | 7/2003 |
| WO | WO 2003/075836 | 9/2003 |
| WO | WO 2003/082871 | 10/2003 |
| WO | WO 2003/097609 | 11/2003 |
| WO | WO 2003/099771 | 12/2003 |
| WO | WO 2003/099818 | 12/2003 |
| WO | WO 2003/101985 | 12/2003 |
| WO | WO 2004/002986 | 1/2004 |
| WO | WO 2004/005281 | 1/2004 |
| WO | WO 2004/011465 | 2/2004 |
| WO | WO 2004/014382 | 2/2004 |
| WO | WO 2004/014907 | 2/2004 |
| WO | WO 2004/018472 | 3/2004 |
| WO | WO 2004/020441 | 3/2004 |
| WO | WO 2004/041821 | 5/2004 |
| WO | WO 2004/041822 | 5/2004 |
| WO | WO 2004/041823 | 5/2004 |
| WO | WO 2004/043367 | 5/2004 |
| WO | WO 2004/046120 | 6/2004 |
| WO | WO 2004/046152 | 6/2004 |
| WO | WO 2004/048343 | 6/2004 |
| WO | WO 2004/052291 | 6/2004 |
| WO | WO 2004/052862 | 6/2004 |
| WO | WO 2004/056786 | 7/2004 |
| WO | WO 2004/056822 | 7/2004 |
| WO | WO 2004/056830 | 7/2004 |
| WO | WO 2004/065378 | 8/2004 |
| WO | WO 2004/080980 | 9/2004 |
| WO | WO 2004/083177 | 9/2004 |
| WO | WO 2004/087053 | 10/2004 |
| WO | WO 2004/089955 | 10/2004 |
| WO | WO 2004/094420 | 11/2004 |
| WO | WO 2004/099209 | 11/2004 |
| WO | WO 2004/108139 | 11/2004 |
| WO | WO 2004/110487 | 12/2004 |
| WO | WO 2004/112793 | 12/2004 |
| WO | WO 2004/113307 | 12/2004 |
| WO | WO 2005/007653 | 1/2005 |
| WO | WO 2005/011597 | 2/2005 |
| WO | WO 2005/021533 | 3/2005 |
| WO | WO 2005/028434 | 3/2005 |
| WO | WO 2005/028478 | 3/2005 |
| WO | WO 2005/028480 | 3/2005 |
| WO | WO 2005/028444 | 5/2005 |
| WO | WO 2005/040119 | 5/2005 |
| WO | WO 2005/047289 | 5/2005 |
| WO | WO 2005/056524 | 6/2005 |
| WO | WO 2005/063768 | 6/2005 |
| WO | WO 2005/066162 | 7/2005 |
| WO | WO 2005/070430 | 8/2005 |
| WO | WO 2005/070929 | 8/2005 |
| WO | WO 2005/072412 | 8/2005 |
| WO | WO 2005/073232 | 8/2005 |
| WO | WO 2005/080393 | 9/2005 |
| WO | WO 2005/082903 | 9/2005 |
| WO | WO 2005/085210 | 9/2005 |
| WO | WO 2005/085248 | 9/2005 |
| WO | WO 2005/085249 | 9/2005 |
| WO | WO 2005/087765 | 9/2005 |
| WO | WO 2005/092901 | 10/2005 |
| WO | WO 2005/105097 | 11/2005 |
| WO | WO 2005/113536 | 12/2005 |
| WO | WO 2005/116035 | 12/2005 |
| WO | WO 2005/121130 | 12/2005 |

(56) References Cited

FOREIGN PATENT DOCUMENTS

| | | | |
|---|---|---|---|
| WO | WO 2005/121142 | 12/2005 | |
| WO | WO 2006/000420 | 1/2006 | |
| WO | WO 2006/024486 | 3/2006 | |
| WO | WO 2006/024487 | 3/2006 | |
| WO | WO 2006/024834 | 3/2006 | |
| WO | WO 2006/028289 | 3/2006 | |
| WO | WO 2006/030031 | 3/2006 | |
| WO | WO 2006/038112 | 4/2006 | |
| WO | WO 2006/050076 | 5/2006 | |
| WO | WO 2006/050162 | 5/2006 | |
| WO | WO 2006/052712 | 5/2006 | |
| WO | WO 2006/055752 | 5/2006 | |
| WO | WO 2006/024524 | 6/2006 | |
| WO | WO 2006/056399 | 6/2006 | |
| WO | WO 2006/058120 | 6/2006 | |
| WO | WO 2006/062465 | 6/2006 | |
| WO | WO 2006/065703 | 6/2006 | |
| WO | WO 2006/074293 | 7/2006 | |
| WO | WO 2006/087230 | 8/2006 | |
| WO | WO 2006/092691 | 9/2006 | |
| WO | WO 2006/102588 | 9/2006 | |
| WO | WO 2006/102610 | 9/2006 | |
| WO | WO 2006/105448 | 10/2006 | |
| WO | WO 2006/107644 | 10/2006 | |
| WO | WO 2006/112666 | 10/2006 | |
| WO | WO 2006/119504 | 11/2006 | |
| WO | WO 2006/124462 | 11/2006 | |
| WO | WO 2006/124731 | * 11/2006 | ........... C07D 471/14 |
| WO | WO 2006/135821 | 12/2006 | |
| WO | WO 2006/136442 | 12/2006 | |
| WO | WO 2007/013964 | 2/2007 | |
| WO | WO 2007/017096 | 2/2007 | |
| WO | WO 2007/021795 | 2/2007 | |
| WO | WO 2007/022268 | 2/2007 | |
| WO | WO 2007/023105 | 3/2007 | |
| WO | WO 2007/025949 | 3/2007 | |
| WO | WO 2007/030366 | 3/2007 | |
| WO | WO 2007/032466 | 3/2007 | |
| WO | WO 2007/033780 | 3/2007 | |
| WO | WO 2007/038209 | 4/2007 | |
| WO | WO 2007/044698 | 4/2007 | |
| WO | WO 2007/044729 | 4/2007 | |
| WO | WO 2007/048802 | 5/2007 | |
| WO | WO 2007/053135 | 5/2007 | |
| WO | WO 2007/053452 | 5/2007 | |
| WO | WO 2007/053498 | 5/2007 | |
| WO | WO 2007/055418 | 5/2007 | |
| WO | WO 2007/056023 | 5/2007 | |
| WO | WO 2007/056075 | 5/2007 | |
| WO | WO 2007/056170 | 5/2007 | |
| WO | WO 2007/058392 | 5/2007 | |
| WO | WO 2007/058626 | 5/2007 | |
| WO | WO 2007/059108 | 5/2007 | |
| WO | WO 2007/061554 | 5/2007 | |
| WO | WO 2007/064883 | 6/2007 | |
| WO | WO 2007/064931 | 6/2007 | |
| WO | WO 2007/066189 | 6/2007 | |
| WO | WO 2007/067444 | 6/2007 | |
| WO | WO 2007/071752 | 6/2007 | |
| WO | WO 2007/084314 | 7/2007 | |
| WO | WO 2007/088999 | 8/2007 | |
| WO | WO 2007/092879 | 8/2007 | |
| WO | WO 2007/093901 | 8/2007 | |
| WO | WO 2007/109334 | 9/2007 | |
| WO | WO 2007/110868 | 10/2007 | |
| WO | WO 2007/112347 | 10/2007 | |
| WO | WO 2007/120097 | 10/2007 | |
| WO | WO 2007/120339 | 10/2007 | |
| WO | WO 2007/125351 | 11/2007 | |
| WO | WO 2007/125405 | 11/2007 | |
| WO | WO 2007/126841 | 11/2007 | |
| WO | WO 2007/134259 | 11/2007 | |
| WO | WO 2007/136465 | 11/2007 | |
| WO | WO 2007/140957 | 12/2007 | |
| WO | WO 2007/143600 | 12/2007 | |
| WO | WO 2007/147217 | 12/2007 | |
| WO | WO 2008/001070 | 1/2008 | |
| WO | WO 2008/003766 | 1/2008 | |
| WO | WO 2008/005877 | 1/2008 | |
| WO | WO 2008/008234 | 1/2008 | |
| WO | WO 2008/008747 | 1/2008 | |
| WO | WO 2008/012635 | 1/2008 | |
| WO | WO 2008/021389 | 2/2008 | |
| WO | WO 2008/021851 | 2/2008 | |
| WO | WO 2008/025556 | 3/2008 | |
| WO | WO 2008/033858 | 3/2008 | |
| WO | WO 2008/033999 | 3/2008 | |
| WO | WO 2008/034859 | 3/2008 | |
| WO | WO 2008/034860 | 3/2008 | |
| WO | WO 2008/037459 | 4/2008 | |
| WO | WO 2008/042639 | 4/2008 | |
| WO | WO 2008/052898 | 5/2008 | |
| WO | WO 2008/052934 | 5/2008 | |
| WO | WO 2008/060907 | 5/2008 | |
| WO | WO 2008/063583 | 5/2008 | |
| WO | WO 2008/063609 | 5/2008 | |
| WO | WO 2008/064157 | 5/2008 | |
| WO | WO 2008/071455 | 6/2008 | |
| WO | WO 2008/074068 | 6/2008 | |
| WO | WO 2008/075068 | 6/2008 | |
| WO | WO 2008/076278 | 6/2008 | |
| WO | WO 2008/078091 | 7/2008 | |
| WO | WO 2008/078100 | 7/2008 | |
| WO | WO 2008/079460 | 7/2008 | |
| WO | WO 2008/079933 | 7/2008 | |
| WO | WO 2008/085942 | 7/2008 | |
| WO | WO 2008/089105 | 7/2008 | |
| WO | WO 2008/099075 | 8/2008 | |
| WO | WO 2008/107436 | 9/2008 | |
| WO | WO 2008/107544 | 9/2008 | |
| WO | WO 2008/109181 | 9/2008 | |
| WO | WO 2008/109943 | 9/2008 | |
| WO | WO 2008/115974 | 9/2008 | |
| WO | WO 2008/117269 | 10/2008 | |
| WO | WO 2008/118454 | 10/2008 | |
| WO | WO 2008/123755 | 10/2008 | |
| WO | WO 2008/128141 | 10/2008 | |
| WO | WO 2008/130584 | 10/2008 | |
| WO | WO 2008/131972 | 11/2008 | |
| WO | WO 2008/141065 | 11/2008 | |
| WO | WO 2008/142720 | 11/2008 | |
| WO | WO 2008/144253 | 11/2008 | |
| WO | WO 2008/151184 | 12/2008 | |
| WO | WO 2008/153207 | 12/2008 | |
| WO | WO 2008/153852 | 12/2008 | |
| WO | WO 2008/154221 | 12/2008 | |
| WO | WO 2008/156712 | 12/2008 | |
| WO | WO 2009/013335 | 1/2009 | |
| WO | WO 2009/013354 | 1/2009 | |
| WO | WO 2009/097446 | 1/2009 | |
| WO | WO 2009/016253 | 2/2009 | |
| WO | WO 2009/019518 | 2/2009 | |
| WO | WO 2009/021083 | 2/2009 | |
| WO | WO 2009/029473 | 3/2009 | |
| WO | WO 2009/029625 | 3/2009 | |
| WO | WO 2009/030871 | 3/2009 | |
| WO | WO 2009/032861 | 3/2009 | |
| WO | WO 2009/036012 | 3/2009 | |
| WO | WO 2009/044788 | 4/2009 | |
| WO | WO 2009/046606 | 4/2009 | |
| WO | WO 2009/047255 | 4/2009 | |
| WO | WO 2009/047506 | 4/2009 | |
| WO | WO 2009/047522 | 4/2009 | |
| WO | WO 2009/047993 | 4/2009 | |
| WO | WO 2009/049018 | 4/2009 | |
| WO | WO 2009/050183 | 4/2009 | |
| WO | WO 2009/053737 | 4/2009 | |
| WO | WO 2009/055828 | 4/2009 | |
| WO | WO 2009/056886 | 5/2009 | |
| WO | WO 2009/071535 | 6/2009 | |
| WO | WO 2009/073153 | 6/2009 | |
| WO | WO 2009/085185 | 7/2009 | |
| WO | WO 2009/086130 | 7/2009 | |
| WO | WO 2009/086509 | 7/2009 | |

(56) References Cited

FOREIGN PATENT DOCUMENTS

| | | |
|---|---|---|
| WO | WO 2009/087238 | 7/2009 |
| WO | WO 2009/092764 | 7/2009 |
| WO | WO 2009/093209 | 7/2009 |
| WO | WO 2009/093210 | 7/2009 |
| WO | WO 2009/094528 | 7/2009 |
| WO | WO 2009/099982 | 8/2009 |
| WO | WO 2009/103652 | 8/2009 |
| WO | WO 2009/105717 | 8/2009 |
| WO | WO 2009/108332 | 9/2009 |
| WO | WO 2009/108827 | 9/2009 |
| WO | WO 2009/112826 | 9/2009 |
| WO | WO 2009/114870 | 9/2009 |
| WO | WO 2009/114874 | 9/2009 |
| WO | WO 2009/122180 | 10/2009 |
| WO | WO 2009/123967 | 10/2009 |
| WO | WO 2009/124755 | 10/2009 |
| WO | WO 2009/125808 | 10/2009 |
| WO | WO 2009/125809 | 10/2009 |
| WO | WO 2009/126584 | 10/2009 |
| WO | WO 2009/128520 | 10/2009 |
| WO | WO 2009/131687 | 10/2009 |
| WO | WO 2009/131926 | 10/2009 |
| WO | WO 2009/132980 | 11/2009 |
| WO | WO 2009/133127 | 11/2009 |
| WO | WO 2009/141386 | 11/2009 |
| WO | WO 2009/144205 | 12/2009 |
| WO | WO 2009/144302 | 12/2009 |
| WO | WO 2009/146034 | 12/2009 |
| WO | WO 2009/148887 | 12/2009 |
| WO | WO 2009/148916 | 12/2009 |
| WO | WO 2009/150150 | 12/2009 |
| WO | WO 2009/150240 | 12/2009 |
| WO | WO 2009/151997 | 12/2009 |
| WO | WO 2009/153592 | 12/2009 |
| WO | WO 2009/157423 | 12/2009 |
| WO | WO 2010/006947 | 1/2010 |
| WO | WO 2010/007099 | 1/2010 |
| WO | WO 2010/007116 | 1/2010 |
| WO | WO 2010/009155 | 1/2010 |
| WO | WO 2010/009195 | 1/2010 |
| WO | WO 2010/009207 | 1/2010 |
| WO | WO 2010/009735 | 1/2010 |
| WO | WO 2010/015643 | 2/2010 |
| WO | WO 2010/017047 | 2/2010 |
| WO | WO 2010/019210 | 2/2010 |
| WO | WO 2010/019899 | 2/2010 |
| WO | WO 2010/030027 | 3/2010 |
| WO | WO 2010/036959 | 4/2010 |
| WO | WO 2010/038081 | 4/2010 |
| WO | WO 2010/045371 | 4/2010 |
| WO | WO 2010/049731 | 5/2010 |
| WO | WO 2010/051043 | 5/2010 |
| WO | WO 2010/052448 | 5/2010 |
| WO | WO 2010/059552 | 5/2010 |
| WO | WO 2010/059658 | 5/2010 |
| WO | WO 2010/062571 | 6/2010 |
| WO | WO 2010/064621 | 6/2010 |
| WO | WO 2010/064875 | 6/2010 |
| WO | WO 2010/067886 | 6/2010 |
| WO | WO 2010/067888 | 6/2010 |
| WO | WO 2010/075074 | 7/2010 |
| WO | WO 2010/077647 | 7/2010 |
| WO | WO 2010/077680 | 7/2010 |
| WO | WO 2010/078421 | 7/2010 |
| WO | WO 2010/078427 | 7/2010 |
| WO | WO 2010/080503 | 7/2010 |
| WO | WO 2010/080712 | 7/2010 |
| WO | WO 2010/083145 | 7/2010 |
| WO | WO 2010/083283 | 7/2010 |
| WO | WO 2010/086089 | 8/2010 |
| WO | WO 2010/089411 | 8/2010 |
| WO | WO 2010/092181 | 8/2010 |
| WO | WO 2010/099938 | 9/2010 |
| WO | WO 2010/103306 | 9/2010 |
| WO | WO 2010/104047 | 9/2010 |
| WO | WO 2010/107765 | 9/2010 |
| WO | WO 2010/107768 | 9/2010 |
| WO | WO 2010/111303 | 9/2010 |
| WO | WO 2010/111573 | 9/2010 |
| WO | WO 2010/115279 | 10/2010 |
| WO | WO 2010/117425 | 10/2010 |
| WO | WO 2010/119284 | 10/2010 |
| WO | WO 2010/119285 | 10/2010 |
| WO | WO 2010/117323 | 11/2010 |
| WO | WO 2010/125216 | 11/2010 |
| WO | WO 2010/126960 | 11/2010 |
| WO | WO 2010/127212 | 11/2010 |
| WO | WO 2010/129509 | 11/2010 |
| WO | WO 2010/136031 | 12/2010 |
| WO | WO 2010/142801 | 12/2010 |
| WO | WO 2010/151689 | 12/2010 |
| WO | WO 2011/002038 | 1/2011 |
| WO | WO 2011/007819 | 1/2011 |
| WO | WO 2011/011597 | 1/2011 |
| WO | WO 2011/012816 | 2/2011 |
| WO | WO 2011/014535 | 2/2011 |
| WO | WO 2011/015037 | 2/2011 |
| WO | WO 2011/016472 | 2/2011 |
| WO | WO 2011/016528 | 2/2011 |
| WO | WO 2011/018894 | 2/2011 |
| WO | WO 2011/022439 | 2/2011 |
| WO | WO 2011/026579 | 3/2011 |
| WO | WO 2011/028947 | 3/2011 |
| WO | WO 2011/031740 | 3/2011 |
| WO | WO 2011/032050 | 3/2011 |
| WO | WO 2011/039344 | 4/2011 |
| WO | WO 2011/041143 | 4/2011 |
| WO | WO 2011/042389 | 4/2011 |
| WO | WO 2011/042474 | 4/2011 |
| WO | WO 2011/045344 | 4/2011 |
| WO | WO 2011/049825 | 4/2011 |
| WO | WO 2011/049988 | 4/2011 |
| WO | WO 2011/050245 | 4/2011 |
| WO | WO 2011/051425 | 5/2011 |
| WO | WO 2011/053518 | 5/2011 |
| WO | WO 2011/054843 | 5/2011 |
| WO | WO 2011/055911 | 5/2011 |
| WO | WO 2011/057022 | 5/2011 |
| WO | WO 2011/060295 | 5/2011 |
| WO | WO 2011/062253 | 5/2011 |
| WO | WO 2011/062885 | 5/2011 |
| WO | WO 2011/063159 | 5/2011 |
| WO | WO 2011/066342 | 6/2011 |
| WO | WO 2011/068899 | 6/2011 |
| WO | WO 2011/071821 | 6/2011 |
| WO | WO 2011/075515 | 6/2011 |
| WO | WO 2011/075620 | 6/2011 |
| WO | WO 2011/077043 | 6/2011 |
| WO | WO 2011/077044 | 6/2011 |
| WO | WO 2011/079231 | 6/2011 |
| WO | WO 2011/080755 | 7/2011 |
| WO | WO 2011/082234 | 7/2011 |
| WO | WO 2011/082266 | 7/2011 |
| WO | WO 2011/082267 | 7/2011 |
| WO | WO 2011/082400 | 7/2011 |
| WO | WO 2011/082488 | 7/2011 |
| WO | WO 2011/087776 | 7/2011 |
| WO | WO 2011/090666 | 7/2011 |
| WO | WO 2011/090738 | 7/2011 |
| WO | WO 2011/090760 | 7/2011 |
| WO | WO 2011/093672 | 8/2011 |
| WO | WO 2011/094890 | 8/2011 |
| WO | WO 2011/097717 | 8/2011 |
| WO | WO 2011/101409 | 8/2011 |
| WO | WO 2011/101806 | 8/2011 |
| WO | WO 2011/102441 | 8/2011 |
| WO | WO 2011/103196 | 8/2011 |
| WO | WO 2011/103441 | 8/2011 |
| WO | WO 2011/103460 | 8/2011 |
| WO | WO 2011/103557 | 8/2011 |
| WO | WO 2011/105161 | 9/2011 |
| WO | WO 2011/109237 | 9/2011 |
| WO | WO 2011/111880 | 9/2011 |
| WO | WO 2011/112687 | 9/2011 |

(56) References Cited

FOREIGN PATENT DOCUMENTS

| | | |
|---|---|---|
| WO | WO 2011/112995 | 9/2011 |
| WO | WO 2011/115725 | 9/2011 |
| WO | WO 2011/119894 | 9/2011 |
| WO | WO 2011/120327 | 10/2011 |
| WO | WO 2011/123493 | 10/2011 |
| WO | WO 2011/128403 | 10/2011 |
| WO | WO 2011/130390 | 10/2011 |
| WO | WO 2011/133722 | 10/2011 |
| WO | WO 2011/133750 | 10/2011 |
| WO | WO 2011/133888 | 10/2011 |
| WO | WO 2011/135376 | 11/2011 |
| WO | WO 2011/137313 | 11/2011 |
| WO | WO 2011/140338 | 11/2011 |
| WO | WO 2011/141756 | 11/2011 |
| WO | WO 2011/141848 | 11/2011 |
| WO | WO 2011/143033 | 11/2011 |
| WO | WO 2011/143318 | 11/2011 |
| WO | WO 2011/143430 | 11/2011 |
| WO | WO 2011/147198 | 12/2011 |
| WO | WO 2011/147199 | 12/2011 |
| WO | WO 2011/151360 | 12/2011 |
| WO | WO 2011/153553 | 12/2011 |
| WO | WO 2011/155983 | 12/2011 |
| WO | WO 2011/156610 | 12/2011 |
| WO | WO 2011/159877 | 12/2011 |
| WO | WO 2011/161699 | 12/2011 |
| WO | WO 2011/163330 | 12/2011 |
| WO | WO 2012/000103 | 1/2012 |
| WO | WO 2012/003544 | 1/2012 |
| WO | WO 2012/004217 | 1/2012 |
| WO | WO 2012/004731 | 1/2012 |
| WO | WO 2012/004732 | 1/2012 |
| WO | WO 2012/008563 | 1/2012 |
| WO | WO 2012/008564 | 1/2012 |
| WO | WO 2012/008999 | 1/2012 |
| WO | WO 2012/009258 | 1/2012 |
| WO | WO 2012/009309 | 1/2012 |
| WO | WO 2012/013619 | 2/2012 |
| WO | WO 2012/015274 | 2/2012 |
| WO | WO 2012/019093 | 2/2012 |
| WO | WO 2012/020133 | 2/2012 |
| WO | WO 2012/027236 | 3/2012 |
| WO | WO 2012/027239 | 3/2012 |
| WO | WO 2012/030990 | 3/2012 |
| WO | WO 2012/031004 | 3/2012 |
| WO | WO 2012/032031 | 3/2012 |
| WO | WO 2012/032065 | 3/2012 |
| WO | WO 2012/032067 | 3/2012 |
| WO | WO 2012/032334 | 3/2012 |
| WO | WO 2012/035996 | 3/2012 |
| WO | WO 2012/036233 | 3/2012 |
| WO | WO 2012/038743 | 3/2012 |
| WO | WO 2012/047699 | 4/2012 |
| WO | WO 2012/054364 | 4/2012 |
| WO | WO 2012/057260 | 5/2012 |
| WO | WO 2012/058211 | 5/2012 |
| WO | WO 2012/061156 | 5/2012 |
| WO | WO 2012/061337 | 5/2012 |
| WO | WO 2012/062462 | 5/2012 |
| WO | WO 2012/063207 | 5/2012 |
| WO | WO 2012/064715 | 5/2012 |
| WO | WO 2012/065297 | 5/2012 |
| WO | WO 2012/065546 | 5/2012 |
| WO | WO 2012/066578 | 5/2012 |
| WO | WO 2012/068343 | 5/2012 |
| WO | WO 2012/073017 | 6/2012 |
| WO | WO 2012/078777 | 6/2012 |
| WO | WO 2012/080727 | 6/2012 |
| WO | WO 2012/080729 | 6/2012 |
| WO | WO 2012/083866 | 6/2012 |
| WO | WO 2012/083953 | 6/2012 |
| WO | WO 2012/083954 | 6/2012 |
| WO | WO 2012/084704 | 6/2012 |
| WO | WO 2012/087784 | 6/2012 |
| WO | WO 2012/088266 | 6/2012 |
| WO | WO 2012/091240 | 7/2012 |
| WO | WO 2012/093731 | 7/2012 |
| WO | WO 2012/098068 | 7/2012 |
| WO | WO 2012/101239 | 8/2012 |
| WO | WO 2012/106995 | 8/2012 |
| WO | WO 2012/112961 | 8/2012 |
| WO | WO 2012/112965 | 8/2012 |
| WO | WO 2012/116237 | 8/2012 |
| WO | WO 2012/125812 | 9/2012 |
| WO | WO 2012/127012 | 9/2012 |
| WO | WO 2012/129344 | 9/2012 |
| WO | WO 2012/134943 | 10/2012 |
| WO | WO 2012/138975 | 10/2012 |
| WO | WO 2012/140114 | 10/2012 |
| WO | WO 2012/158704 | 11/2012 |
| WO | WO 2012/158795 | 11/2012 |
| WO | WO 2012/158994 | 11/2012 |
| WO | WO 2012/161812 | 11/2012 |
| WO | WO 2012/167247 | 12/2012 |
| WO | WO 2012/173370 | 12/2012 |
| WO | WO 2013/016197 | 1/2013 |
| WO | WO 2013/024002 | 2/2013 |
| WO | WO 2013/024895 | 2/2013 |
| WO | WO 2013/033981 | 3/2013 |
| WO | WO 2013/039854 | 3/2013 |
| WO | WO 2013/041634 | 3/2013 |
| WO | WO 2013/049352 | 4/2013 |
| WO | WO 2013/053051 | 4/2013 |
| WO | WO 2013/063000 | 5/2013 |
| WO | WO 2013/063003 | 5/2013 |
| WO | WO 2013/108809 | 7/2013 |
| WO | WO 2013/109027 | 7/2013 |
| WO | WO 2013/124316 | 8/2013 |
| WO | WO 2013/136249 | 9/2013 |
| WO | WO 2013/144339 | 10/2013 |
| WO | WO 2014/007951 | 1/2014 |
| WO | WO 2014/011284 | 1/2014 |
| WO | WO 2014/011900 | 1/2014 |
| WO | WO 2014/019186 | 2/2014 |
| WO | WO 2014/022528 | 2/2014 |
| WO | WO 2014/026125 | 2/2014 |
| WO | WO 2014/044846 | 3/2014 |
| WO | WO 2014/048878 | 4/2014 |
| WO | WO 2014/062454 | 4/2014 |
| WO | WO 2014/085216 | 5/2014 |
| WO | WO 2014/089913 | 6/2014 |
| WO | WO 2014/105849 | 7/2014 |
| WO | WO 2014/113191 | 7/2014 |
| WO | WO 2014/136972 | 9/2014 |
| WO | WO 2014/138485 | 9/2014 |
| WO | WO 2014/140184 | 9/2014 |
| WO | WO 2014/144737 | 9/2014 |
| WO | WO 2014/160160 | 10/2014 |
| WO | WO 2014/160478 | 10/2014 |
| WO | WO 2014/160521 | 10/2014 |
| WO | WO 2014/162039 | 10/2014 |
| WO | WO 2014/170063 | 10/2014 |
| WO | WO 2014/171755 | 10/2014 |
| WO | WO 2014/172644 | 10/2014 |
| WO | WO 2014/174307 | 10/2014 |
| WO | WO 2014/182829 | 11/2014 |
| WO | WO 2014/198942 | 12/2014 |
| WO | WO 2014/206343 | 12/2014 |
| WO | WO 2014/206344 | 12/2014 |
| WO | WO 2015/000715 | 1/2015 |
| WO | WO 2015/006492 | 1/2015 |
| WO | WO 2015/006754 | 1/2015 |
| WO | WO 2015/030021 | 3/2015 |
| WO | WO 2015/057938 | 4/2015 |
| WO | WO 2015/057963 | 4/2015 |
| WO | WO 2015/059668 | 4/2015 |
| WO | WO 2015/061572 | 4/2015 |
| WO | WO 2015/066452 | 5/2015 |
| WO | WO 2015/095492 | 6/2015 |
| WO | WO 2015/108992 | 7/2015 |
| WO | WO 2016/064960 | 4/2016 |
| WO | WO 2016/134314 | 8/2016 |
| WO | WO 2016/192680 | 12/2016 |
| WO | WO 2017/023972 | 2/2017 |

(56) References Cited

FOREIGN PATENT DOCUMENTS

| | | |
|---|---|---|
| WO | WO 2017/023988 | 2/2017 |
| WO | WO 2017/023989 | 2/2017 |
| WO | WO 2017/024003 | 2/2017 |
| WO | WO 2017/024004 | 2/2017 |
| WO | WO 2017/024015 | 2/2017 |
| WO | WO 2017/024025 | 2/2017 |
| WO | WO 2017/028314 | 2/2017 |
| WO | WO 2017/223414 | 12/2017 |
| WO | WO 2018/041091 | 3/2018 |
| WO | WO 2018/049214 | 3/2018 |
| WO | WO 2018/067512 | 4/2018 |
| WO | WO 2018/093029 | 5/2018 |
| WO | WO 2018/093215 | 5/2018 |
| WO | WO 2018/105972 | 6/2018 |
| WO | WO 2018/105973 | 6/2018 |
| WO | WO 2018/234354 | 12/2018 |
| WO | WO 2019/037640 | 2/2019 |
| WO | WO 2019/079369 | 4/2019 |
| WO | WO 2019/105886 | 6/2019 |
| WO | WO 2019/213506 | 11/2019 |
| WO | WO 2020/049017 | 3/2020 |
| WO | WO 2020/081898 | 4/2020 |
| WO | WO 2020/131627 | 6/2020 |
| WO | WO 2020/131674 | 6/2020 |
| WO | WO 2021/113462 | 6/2021 |

OTHER PUBLICATIONS

Alexander et al., "Systemtherapie des Harnblasenkarzinoms," Der Urologe, Jan. 4, 2021, 60(2):247-258 (English Abstract).

Ali et al., "Synthesis and structure activity relationship of substituted N,6-diphenyl-5,6-dihydrobenzo[h]quinazolin-2-amine as inhibitors of fibroblast growth factor receptors (FGFR)" Cancer Res, Apr. 15, 2012, 72; 3905.

Angevin et al., "TKI258 (dovitinib lactate) in metastatic renal cell carcinoma (mRCC) patients refractory to approved targeted therapies: A phase I/II dose finding and biomarker study," Journal of Clinical Oncology, May 20, 2009, 27:15S, 1 page.

Anonymous, "American Society for Clinical Pharmacology and Therapeutics," Clin Pharma and Thera., Feb. 13, 2019, 105(S1):S5-S121.

Anonymous, "In Vitro Metabolism- and Transporter-Mediated Drug-Drug Interaction Studies Guidance for Industry", Clinical Pharmacology, Oct. 2017, 47 pages.

Antonios-McCrea et al., "LHMDS mediated tandem acylation-cyclization of 2-aminobenzenecarbonitriles with 2-benzymidazol-2-ylacetates: a short and efficient route to the synthesis of 4-amino-3-benzimidazol-2-ylhydroquinolin-2-ones," Tetrahedron Letters, 2006, 657-660.

Arai et al., "Characterization of the cell or origin and propagation potential of the fibroblast growth factor 9-induced mouse model of lung adenocarcinoma," J. Pathol., Mar. 2015, 235(4): 593-605.

Arai et al., "Fibroblast growth factor receptor 2 tyrosine kinase fusions define a unique molecular subtype of cholangiocarcinoma," Hepatology, 2014, 59(4):1427-1434.

Argentina Office Action in Argentina Application No. 20130102068, dated Jul. 17, 2020, 10 pages.

Argentina Office Action in Argentina Application No. 20180101392, dated Mar. 8, 2022, 6 pages.

Argentina Office Action in Argentina Application No. 20140101651, dated Nov. 21, 2019, 5 pages.

Argentinian Office Action in Argentinian Application No. 20160100443, dated Oct. 11, 2023, 12 pages (with Machine Translation).

Atzrodt et al., "The Renaissance of H/D Exchange," Angew Chem Int Ed., 2007, 7744-7765.

Australian Allowance in Australian Application No. 2020250201, dated Jun. 23, 2022, 4 pages.

Australian Office Action in Australian Application No. 2013287176, dated Sep. 12, 2017, 4 pages.

Australian Office Action in Australian Application No. 2014253798, dated Jul. 31, 2017, 4 pages.

Australian Office Action in Australian Application No. 2016219816, dated Aug. 26, 2019, 3 pages.

Australian Office Action in Australian Application No. 2016219822, dated Jul. 8, 2019, 4 pages.

Australian Office Action in Australian Application No. 2018208772, dated Jul. 1, 2018, 5 pages.

Australian Office Action in Australian Application No. 2018272013, dated Sep. 2, 2021, 4 pages.

Australian Office Action in Australian Application No. 2019200066, dated Aug. 27, 2019, 6 pages.

Australian Office Action in Australian Application No. 2020250211, dated Sep. 13, 2021, 4 pages.

Australian Office Action in Australian Application No. 2020270520, dated Dec. 16, 2021, 4 pages.

Avet-Loiseau et al., "Impact of high-risk cytogenetics and prior therapy on outcomes in patients with advanced relapsed or refractory multiple myeloma treated with lenalidomide plus dexamethasone," Leukemia, 2010, 623-628.

Bai et al., "GP369, an FGFR2-IIIb specific antibody, exhibits potent antitumor activity against human cancers driven by activated FGFR2 signaling," Am. Assoc. for Cancer Research, Aug. 17, 2010, 30 pages.

Balek, L., "ARQ 087 inhibits FGFR signaling and rescues aberrant cell proliferation and differentiation in experimental models of craniosynostoses and chondrodysplasias caused by activating mutations in FGFR1, FGFR2 and FGFR3," Bone, Dec. 2017, 105:57-66.

Bansal et al., "Specific inhibitor of FGF receptor signaling: FGF-2-mediated effects on proliferation, differentiation, and MAPK activation are inhibited by PD173074 in oligodendrocyte-lineage cells," J. Neurosci. Res., 2003, 74: 486.

Bauer, "Pharmaceutical Solids—The Amorphous Phase", Journal of Validation Technology, 2009, 15(3):63-68.

Bavin, "Polymorphism in Process Development," Chemistry & Industry, Society of Chemical Industry, Aug. 1989, 527-529.

Bazyl et al., "The selective ortho-methoxylation of pentafluorobenzoic acid—a new way to tetrafluorosalicylic acid and its derivatives," J Flour Chem., Feb. 11, 1999, 94(1):11-13.

Bazyl' et al., "The selective ortho-methoxylation of pentafluorobenzoic acid—a new way to tetrafluorosalicylic acid and its derivatives." Journal of fluorine chemistry, Feb. 11, 1999, 94(1):11-13.

Beekman et al., "New Molecular Targets and Novel Agents in the Treatment of Advanced Urothelial Cancer," Semin Oncol, 2007, 34: 154-164.

Bello et al., "E-3810 is a potent dual inhibitor of VEGFR and FGFR that exerts antitumor activity in multiple preclinical models," Cancer Res, 2011.

Bello et al., "E-3810 is a potent dual inhibitor of VEGFR and FGFR that exerts antitumor activity in multiple preclinical models," Cancer Res, 2011, Supplemental figures, 4 pages.

Bello et al., "E-3810 is a potent dual inhibitor of VEGFR and FGFR that exerts antitumor activity in multiple preclinical models," Cancer Res, 2011, Supplemental table, 3 pages.

Bello et al., "E-3810 is a potent dual inhibitor of VEGFR and FGFR that exerts antitumor activity in multiple preclinical models," Cancer Res, 2011, Supplementary data, 4 pages.

Benet-Pages et al., "An FGF23 missense mutation causes familial tumoral calcinosis with hyperphosphatemia," Human Molecular Genetics, 2005, 14(3):385-390.

Berge et al., "Pharmaceutical Salts", Journal of Pharmaceutical Science, 1977, 66(2):1-19.

Bergwitz and Juppner, "Regulation of Phosphate Homeostasis by PTH, Vitamin D, and FGF23," Annu. Rev. Med., 2010, 61:91-104.

Bhatia et al., "Polymorphism and its Implications in Pharmaceutical Product Development," Dosage Form Design Parameters, 2018, pp. 31-65.

Bhide et al., "Discovery and Preclinical Studies of (R )-1-(4-(4-Fluoro-2-methyl-1H-indol-5-yloxy)-5-methylpyrrolo[2,1-f][1,2,4]triazin-6-yloxy)propan-2-ol (BMS-540215), an In Vivo Active Potent VEGFR-2 Inhibitor," Journal of Medicinal Chemistry, 2006, 49(7): 2143-2146.

(56) References Cited

OTHER PUBLICATIONS

Billerey et al., "Frequent FGFR3 Mutations in Papillary Non-Invasive Bladder (pTa) Tumors," American Journal of Pathology, Jun. 2001, 158(6): 1955-1959.
Billottet et al., "Targets of Fibroblast Growth Factor 1 (FGF-1) and FGF-2 Signaling Involved in the Invasive and Tumorigenic Behavior of Carchinoma Cells," Molecular Biology of the Cell, Oct. 2004, 15: 4725-4734.
BioCentury, Week of Nov. 10, 2014, 52 pages.
Bisping et al., "Bortezomib, Dexamethasone, and Fibroblast Growth Factor Receptor 3-Specific Tyrosine Kinase Inhibitor in t(4;14) Myeloma," Clin Cancer Res, Jan. 2009, 15(2):520-531.
Black et al., "Targeted therapies in bladder cancer—an update," Urologic Oncology: Seminars and Original Investigations, 2007, 433-438.
Blagden et al., "Crystal engineering of active pharmaceutical ingredients to improve solubility and dissolution rates," Advanced Drug Delivery Reviews, Jul. 2007, 59(7):617-630.
Blom et al., "Optimizing Preparative LC-MS Configurations and Methods for Parallel Synthesis Purification", J Combi Chem., 2003, 5:670.
Blom et al., Preparative LC-MS Purification: Improved Compound Specific Method Optimization, J Combi Chem. 2004, 6(6):874-883.
Blom, K., "Two-Pump At Column Dilution Configuration for Preparative LC-MS", J Combi Chem., 2002, 4:295.
Bonaventure et al., "Common Mutations in the Fibroblast Growth Factor Receptor 3 (FRFR3) Gene Account for Achondroplasia, Hypochondroplasia and Thanatophoric Dwarfism," Clin Pediatr Endocrinol, 1997, 105-113.
Bono et al., "Inhibition of Tumor Angiogenesis and Growth by a Small-Molecule Multi-FGF Receptor Blocker with Allosteric Properties," Cancer Cell, Apr. 2013, 477-488.
Borad et al., "Fibroblast growth factor receptor 2 fusions as a target for treating cholangiocarcinoma," Current opinion in Gastroenterology, May 2015, 31(3):264-268.
Brooks et al., "Fibroblast growth factor signaling: a new therapeutic opportunity in cancer," Clinical Cancer Research, 2012, 1-23.
Byrn et al., "Pharmacautical Solids: A Strategic Approach to Regulatory Considerations," Pharmaceutical Research., Jul. 1995, 12(7):945-954.
Caira, "Crystalline Polymorphism of Organic Compounds," Topics in Current Chemistry, Jan. 1, 1998, 198:163-208.
Canada Office Action in Canada Application No. 2,976,788, dated Apr. 7, 2022, 4 pages.
Canada Office Action in Canada Application No. 2,976,790, dated Apr. 25, 2022, 4 pages.
Cancer [online], [retrieved on Jul. 6, 2007] Retrieved from the Internet, URL: http://www.nlm.nih.gov/medlineplus/cancer.html.
Capelletti et al., "Identification of Recurrent FGFR3-TACC3 Fusion Oncogenes from Lung Adenocarcinoma," AACR Journals, 2014, 6551-6558.
Cappellen et al., "Frequent activating mutations of FGFR3 in human bladder and cervix carcinomas," Nature Genetics, Sep. 1999, 23: 18-20.
Carmichael et al., "Familial Tumoral Calcinosis: A Forty-Year Follow-up on One Family," The Journal of Bone & Joint Surgery, 2009, 664-671.
Casey et al., "Translating in vivo metabolomic analysis of succinate dehydrogenase deficient tumours into clinical utility," JCO Precis Oncol., Mar. 29, 2018, 2:1-12.
Cha et al., "Aberrant Receptor Internalization and Enhanced FRS2-dependent Signaling Contribute to the Transforming Activity of the Fibroblast Growth Factor Receptor 2 IIIb C3 Isoform," The Journal of Biological Chemistry, Mar. 2009, 284(10): 6227-6240.
Chandrani et al., "Drug-sensitive FGFR3 mutations in lung adenocarcinoma," Annals of Oncology, 2017, 28: 597-603.
Chase et al., "Activity of TKI258 against primary cells and cell lines with FGFR1 fusion genes associated with the 8p11 myeloproliferative syndryome," Blood, 2007, 110:3729-3734.
Chefetz and Sprecher, "Familial tumoral calcinosis and the role of O-glycosylation in the maintenance of phosphate homeostasis," Biochimica et Biophysica Acta, 2009, 847-852.
Chefetz et al., "A novel homozygous missense mutation in FGF23 causes Familial Tumoral Calcinosis associated with disseminated visceral calcification," Hum Genet, 2005, 118:261-266.
Chell et al., "Tumour cell responses to new fibroblast growth factor receptor tyrosine kinase inhibitors and identification of a gatekeeper mutation in FGFR3 as a mechanism of acquired resistance," Oncogene, 2012, 1-12.
Chen et al., "Acenaphtho[1,2-b]pyrrole-Based Selective Fibroblast Growth Factor Receptors 1 (FRGR1) Inhibitors: Design, Synthesis, and Biological Activity," Journal of Medicinal Chemistry, 2011, 54: 3732-3745.
Chen et al., "FGFR3 as a therapeutic target of the small molecule inhibitor PKC412 in hematopoietic malignancies," Oncogene, 2005, 24: 8259-8267.
Chen et al., "Genome-Wide Loss of Heterozygosity and DNA Copy Number Aberration in HPV-Negative Oral Squamous Cell Carcinoma and Their Associations with Disease-Specific Survival," PLOS ONE, Aug. 2015, 23 pages.
Cherukupalli et al., "An insight on synthetic and medicinal aspects of pyrazolo[1,5-a]pyrimidine scaffold," European Journal of Medicinal Chemistry, Nov. 10, 2016, 126:298-352.
Chesi et al., "Activated fibroblast growth factor receptor 3 is an oncogene that contributes to tumor progression in multiple myeloma," Blood, 2001, 97:729-736.
Chesi et al., "Frequent translocation t(4;14)(p16.3;q32.3) in multiple myeloma is associated with increased expression and activating mutations of fibroblast growth factor receptor 3," Nature Genetics, 1997, 260-264.
Chilean Office Action in Chilean Application No. 1984-2017, dated Sep. 12, 2019, 9 pages.
Chilean Office Action in Chilean Application No. 2015-003089, dated Apr. 24, 2017, 13 pages (English Summary).
Chilean Office Action in Chilean Application No. 2015-003089, dated Jan. 23, 2018, 8 pages.
Chilean Office Action in Chilean Application No. 2122-2017, dated Apr. 22, 2019, 25 pages.
Chilean Office Action in Chilean Application No. 2122-2017, dated Nov. 15, 2019, 15 pages.
Chilean Office Action in Chilean Application No. 2839-2020, dated Jan. 31, 2022, 42 pages (with English translation).
Chilean Office Action in Chilean Application No. 2848-2020, dated Apr. 3, 2022, 23 pages.
Chilean Office Action in Chilean Application No. 3355-2014, dated Jan. 18, 2017, 17 pages (with English translation).
Chilean Office Action in Chilean Application No. 3439-2019, dated Feb. 10, 2021, 26 pages.
Chilean Office Action in Chilean Application No. 3439-2019, dated Jan. 31, 2022, 15 pages.
Chilean Opposition in Chilean Application No. 3355-2014, received Feb. 3, 2017, 3 pages (English translation only).
Chinese Office Action in Chinese Application No. 10874686.0, dated Oct. 8, 2019, 10 pages.
Chinese Office Action in Chinese Application No. 201380041027.9, dated Feb. 13, 2017, 10 pages (with English translation).
Chinese Office Action in Chinese Application No. 201380041027.9, dated Jul. 12, 2016, 11 pages (with English translation).
Chinese Office Action in Chinese Application No. 201380041027.9, dated Oct. 28, 2015, 17 pages (with English translation).
Chinese Office Action in Chinese Application No. 201480028858.7, dated Apr. 4, 2018, 10 pages (English Translation).
Chinese Office Action in Chinese Application No. 201480028858.7, dated Aug. 19, 2016, 18 pages (English Translation).
Chinese Office Action in Chinese Application No. 201480028858.7, dated Jul. 12, 2017, 10 pages (English Translation).
Chinese Office Action in Chinese Application No. 201680011332.7, dated Aug. 5, 2019, 14 pages.
Chinese Office Action in Chinese Application No. 201680011348.8, dated Aug. 2, 2019, 14 pages.
Chinese Office Action in Chinese Application No. 201710395346.X, dated Jan. 22, 2019, 17 pages.

(56) References Cited

OTHER PUBLICATIONS

Chinese Office Action in Chinese Application No. 201710395346.X, dated Sep. 9, 2019, 10 pages.
Chinese Office Action in Chinese Application No. 201710874686.0, dated Feb. 25, 2019, 17 pages.
Chinese Office Action in Chinese Application No. 201910023729.3, dated Mar. 23, 2022, 11 pages.
Chinese Office Action in Chinese Application No. 201910023729.3, dated Sep. 8, 2021, 11 pages.
Chinese Office Action in Chinese Application No. 201910023729.3, dated Mar. 3, 2021, 15 pages.
Chng et al., "Translocation t(4;14) retains prognostic significance even in the setting of high-risk molecular signature," Leukemia, 2008, 2: 459-461.
Chuaqui et al., "Interaction Profiles of Protein Kinase—Inhibitor Complexes and Their Application to Virtual Screening," J. Med. Chem., 2005, 48: 121-133.
Ciappetti and Geithlen "Molecular Variations Based on Isosteric Replacements," The Practice of Medicinal Chemistry, 2008, Chapter 15, pp. 290-341.
ClinicalTrials.gov, "A Study to Evaluate the Efficacy and Safety of Pemigatinib Versus Cherrotherapy in Unresectable or Metastatic Chol (FIGHT-302)," NCT03656536, Mar. 6, 2019, retrieved from URL <https://www.clinicaltrials.gov/ct2/history/NCT03656536?V_5=View#StudyPageTop,>, 4 pages.
Cole et al., "Inhibition of FGFR2 and FGFR1 increases cisplatin sensitivity in ovarian cancer," Cancer Biol. Therapy, Sep. 1, 2010, 10(5):495-504.
Coleman, "Positive and negative regulation of cellular sensitivity to anti-cancer drugs by FGF-2," Drug Resistance Updates, 2003, 85-94.
Colombian Office Action in Colombian Application No. 14-275934-6, dated May 31, 2016, 3 pages (English translation only).
Colombian Office Action in Colombian Application No. 14-275934-6, dated Nov. 17, 2015, 12 pages (English translation only).
Colombian Office Action in Colombian Application No. 16100866, dated Aug. 10, 2017, 9 pages.
Colombian Office Action in Colombian Application No. NC2017/0008795, dated Aug. 16, 2019, 6 pages.
Colombian Office Action in Colombian Application No. NC2017/0008795, dated Aug. 29, 2017, 2 pages.
Colombian Office Action in Colombian Application No. NC2017/0008795, dated Nov. 29, 2018, 8 pages.
Colombian Office Action in Colombian Application No. NC2017/0008824, dated Aug. 31, 2017, 3 pages.
Colombian Office Action in Colombian Application No. NC2017/0008824, dated Nov. 29, 2018, 8 pages.
Colombian Office Action in Colombian Application No. NC2019/0009690, dated Jan. 22, 2020, 20 pages.
Colombian Office Action in Colombian Application No. NC2019/0014699, dated Jun. 6, 2022, 31 pages.
Colombian Opposition in Colombian Application No. NC 2021/0004568, dated Apr. 15, 2021, 21 pages.
Columbian Office Action in Columbian Application No. 2019/0014699, dated Nov. 1, 2023, 37 pages (with English Translation).
Cordovilla et al., "The Stille Reaction, 38 Years Later," ACS Catal., Apr. 17, 2015, 5(5):3040-3053.
Corre et al., "Synthesis and biological evaluation of a triazole-based library of pyrido[2,3-d]pyrimidines as FGFR3 tyrosine kinase inhibitors," Organic & Biomolecular Chemistry, 2010, 8:2164-2173.
Costa Rican Office Action in Costa Rican Application No. 2014-0577, dated Apr. 15, 2020, 18 pages.
Costa Rican Office Action in Costa Rican Application No. 2014-0577, dated Jun. 13, 2019, 17 pages.
Costa Rican Office Action in Costa Rican Application No. 2015-0578, dated Jun. 11, 2020, 15 pages.
Costa Rican Office Action in Costa Rican Application No. 2019-573, dated Jul. 12, 2022, 12 pages.
Costa Rican Opposition in Costa Rican Application No. PCT/US2013/045309, dated Jun. 29, 2015, 14 pages (English Translation).
Covic et al., "Vascular calcification in chronic kidney disease," Clinical Science, 2010, 119: 111-121.
Crose et al., "FGFR4 Blockade Exerts Distinct Antitumorigenic Effects in Human Embryonal versus Alveolar Rhabdomyosarcoma," Clin Cancer Res., 2012, 18:3780-3790.
Dailey et al., "Mechanisms underlying differential responses to FGF signaling," Cytokine & Growth Factor Reviews, 2005, 233-247.
Dash et al., "A Role for Neoadjuvant Gemcitabine Plus Cisplatin in Muscle-Invasive Urothelial Carcinoma o the Bladder: A Retrospective Experience," Cancer, 2008, 113(9): 2471-2477.
De Luca et al., "FGFR Fusions in Cancer: From Diagnostic Approaches to Therapeutic Intervention," Int J Mol Sci., 2020, 21(8):6856.
Desnoyers et al., "Targeting FGF19 inhibits tumor growth in colon cancer xenograft and FGF19 transgenic hepatocellular carcinoma models," Oncogene, 2008, 27:85-97.
Dey et al., "Targeting Fibroblast Growth Factor Receptors Blocks PI3K/AKT Signaling, Induces Apoptosis, and Impairs Mammary Tumor Outgrowth and Metastasis," Cancer Research, 2010, 4151-4162.
Dieci et al., "Fibroblast Growth Factor Receptor Inhibitors as a Cancer Treatment: From a Biologic Rationale to Medical Perspectives," Cancer Discovery, 2013, 1-16.
Dienstmann et al., "Genomic aberrations in the FGFR pathway: opportunities for targeted therapies in solid tumors," Annals of Oncology, 2013, 1-12.
Diller and Li, "Kinases, Homology Models, and High Throughput Docking," J. Med. Chem., 2003, 46: 4638-4647.
Dimopoulos et al., "Lenalidomide plus Dexamethasone for Relapsed or Refractory Multiple Myeloma," The New England Journal of Medicine, 2007, 357:2123-2132.
Ding et al., "Somatic mutations affect key pathways in lung adenocarcinoma," Nature., Oct. 23, 2008, 455:1069-1075.
Dovedi and Davies, "Emerging targeted therapies for bladder cancer: a disease waiting for a drug," Cancer Metastasis Rev, 2009, 28:355-367.
Dring et al., "A Global Expression-based Analysis of the Consequences of the t(4;14) Translocation in Myeloma," Clinical Cancer Research, Sep. 2004, 10: 5692-5701.
Drueke et al., "Phosphate binders in CKD: bad news or good news?," Journal of the American Society of Nephrology, Aug. 2012, 23(8):1277-1280.
Dutt et al., "Drug-sensitive FGFR2 mutations in endometrial carcinoma," PNAS, Jun. 24, 2008, 105(25):8713-8717.
Dutt et al., "Drug-sensitive FGFR2 mutations in endometrial carcinoma," Supporting Information, Jun. 2008, 8 pages.
Ecuador Office Action in Ecuador Application No. IEPI-2015-1225, dated Dec. 30, 2021, 21 pages.
Ecuador Office Action in Ecuador Application No. IEPI-2015-1225, dated May 11, 2022, 18 pages.
Ecuador Opposition in Ecuador Application No. SENADI-2020-78226, dated Jun. 2022, 19 pages.
Ecuador Opposition in Ecuador Application No. SENADI-2020-78230, dated Jun. 2022, 21 pages.
Edmondson et al., "Aminopiperidine-fused imidazoles as dipeptidyl peptidase-IV inhibitors," Bioorg & Med Chem Lett., 2009, 19(15):4097-4101.
Eissa, "Synthesis and evaluation of some surface active agents from long chain fatty amine," Spanish National Research Council, Jan. 2007, 58(4):379-389.
Elsheikh et al., "FGFR1 amplification in breast carcinomas: a chromogenic in situ hybridisation analysis," Breast Cancer Research, Mar. 2007, 9(2): 1-12.
Erian at al., "2-Aryl-1,1-dicyano-3-phenylsulfonylpropenes in heterocyclic synthesis. A synthetic strategy towards heterocyclic sulfones," Monatshefte fuer Chemie, 1998, 129(10):1049-1056.
Eskens and Verweij, "The clinical toxicity profile of vascular endothelial growth factor (VEGF) and vascular endothelial growth factor receptor (VEGFR) targeting angiogenesis inhibitors; A review," European Journal of Cancer, 2006, 3127-3139.

(56) References Cited

OTHER PUBLICATIONS

Eswarakumar and Schlessinger, "Cellular signaling by fibroblast growth factor receptors," Cytokine & Growth Factor Reviews, 2005, 139-149.
Eurasian Office Action in Eurasian Application No. 201590005, dated Oct. 21, 2015, 6 pages.
Eurasian Office Action in Eurasian Application No. 201590005, Mar. 28, 2018, 6 pages.
Eurasian Office Action in Eurasian Application No. 201791866, dated Feb. 19, 2018, 10 pages (English Translation).
Eurasian Office Action in Eurasian Application No. 201791867, dated Apr. 4, 2018, 4 pages (English Translation).
Eurasian Office Action in Eurasian Application No. 201992794, dated Sep. 17, 2021, 7 pages.
Eurasian Office Action in Eurasian Application No. 202091923, dated Apr. 5, 2022, 4 pages.
Eurasian Office Action in Eurasian Application No. 202091923, dated Jul. 27, 2021, 6 pages (English Translation).
Eurasian Office Action in Eurasian Application No. 202092648, dated Feb. 8, 2022, 7 pages.
Eurasian Office Action in Eurasian Application No. 202092649/26, dated Apr. 22, 2022, 6 pages.
Eurasian Office Action in Eurasian Application No. 202190877, dated Oct. 6, 2021, 4 pages.
European Communication pursuant to Article 94(3) EPC in European Application No. 13783125.1, dated Jan. 26, 2016, 4 pages.
European Office Action in European Application No. 16715139.8, dated Feb. 23, 2024, 5 pages.
European Office Action in European Application No. 16715139.8, dated May 18, 2021, 9 pages.
European Office Action in European Application No. 18733045.1, dated Jan. 11, 2021, 5 pages.
European Office Action in European Application No. 19724670, dated Aug. 31, 2022, 3 pages.
European Office Action in European Application No. 19724670.5, dated Nov. 9, 2021, 4 pages.
European Office Action in European Application No. 19724676.2, dated Aug. 26, 2021, 5 pages.
European Office Action in European Application No. 20192679.7, dated Feb. 11, 2021, 7 pages.
European search report in European Application No. 16203866.5, dated Mar. 1, 2017, 7 pages.
European Search Report in European Application No. 17199421.3, dated Jul. 12, 2018, 15 pages.
European Search Report in European Application No. 17199421.3, dated Mar. 12, 2018, 14 pages.
Extended European Search Report in European Application No. 23197192.0, dated Feb. 22, 2024, 9 pages.
Ezzat et al., "Dual Inhibition of RET and FGFR4 Restrains Medullary Thyroid Cancer Cell Growth," Clinical Cancer Research, 2005, 11:1336-1341.
Faul et al., "FGF23 induces left ventricular hypertrophy," The Journal of Clinical Investigation, 2010, 1-16.
FDA.gov, "FDA grants accelerated approval to pemigatinib for cholangiocarcinoma with an FGFR2 rearrangement or fusion," Apr. 20, 2020, [Retrieved on Apr. 27, 2021], retrieved from URL <https://www.fda.gov/drugs/resources-information-approved-drugs/fda-grants-accelerated-approval-pemigatinib-cholangiocarcinoma-fgfr2-rearrangement-or-fusion>, 2 pages.
Feng et al., "Guidance to rational use of pharmaceuticals in gallbladder sarcomatoid carcinoma using patient-derived cancer cells and whole exome sequencing," Oncotarget, 2017, 8(3): 5349-5360.
Feng et al., "Targeting Fibroblast Growth Factor Receptor Signaling Inhibits Prostate Cancer Progression," Clinical Cancer Research, 2012, 1-9.
Ferrera et al., "Bevacizumab (Avastin), a humanized anti-VEGF monoclonal antibody for cancer therapy," Biochemical and Biophysical Research Communications, 2005, 328-335.
Fillmore et al., "Estrogen expands breast cancer stem-like cells through paracrine FGF/Tbx3 signaling," PNAS, 2010, 1-6.
Fischer et al., "Fibroblast growth factor receptor-mediated signals contribute to the malignant phenotype of non-small cell lung cancer cells: therapeutic implications and synergism with epidermal growth factor receptor inhibition," Mol Cancer Therapy, 2008, 3408-3419.
French et al., Targeting FGFR4 inhibits hepatocellular carcinoma in preclinical mouse models, PLoS One 2012;7:e36713.
Fricker, "Metal based drugs: from serendipity to design," Dalton Transactions, 2007, 43:4903-4917.
Fricker, "The therapeutic application of lanthanides," Chemical Society Reviews, 2006, 35(6):524-533.
Frishberg et al., "Hypertosis-Hyperphosphatemia Syndrome: A Congenital Disorder of O-Glycosylation Associated With Augmented Processing of Fibroblast Growth Factor 23," Journal of Bone and Mineral Research, 2007, 22(20: 235-242.
Frishberg et al., "Identification of a recurrent mutation in GALNT3 demonstrates that hyperostosis-hyperphosphatemia syndrome and familial tumoral calcinosis are allelic disorders," J Mol Med, 2005, 83:33-38.
Fu et al., "Intratumoral inorganic phosphate deprivation: A new anticancer strategy," Medical Hypotheses, Feb. 2020, 135:109497.
Fukumoto and Yamashita, "FGF23 is a hormone-regulating phophate metabolism—Unique biological characteristics of FGF23," Bone, 2007, 1190-1195.
Fun et al., "2-7(7,8-Diphenyl-1H-imidazo[4,5-f]-quinoxalin-2-yl)phenol methanol disolvate," Acta Crystallographica Section E Structure Reports Online, 2008, 64(9):o1741-o1742.
Furniss "Acidic/Basic characteristics for purification," Vogel's Textbook of Practical Organic Chemistry, 5th edition, 1989, 131-133, 135-143.
Galdemard et al., "Regulation of FGF-3 Gene Expression in Tumorigenic and Non-tumorigenic Clones of a Human Colon Carcinoma Cell Line," The Journal of Biological Chemistry, 2000, 275(23): 17364-17373.
Gallo et al., "Functions of Fibroblast Growth Factor Receptors in cancer defined by novel translocations and mutations," Cytokine & Growth Factor Reviews, 2015, 26(4):425-449.
Garringer et al., "Molecular genetic and biochemical analyses of FGF23 mutations in familial tumoral calcinosis," Am J Physiol Endocrinol Metab, 2008, 929-937.
Gattineni et al., "FGF23 decreases renal NaPi-2a and NaPi-2c expression and induces hypophosphatemia in vivo predominantly via FGF receptor 1," Am J Physiol Renal Physiol, 2009, 297: 282-291.
Gavine et al., "AZD4547: An Orally Bioavailable, Potent, and Selective Inhibitor of the Fibroblast Growth Factor Receptor Tyrosine Kinase Family," American Association for Cancer Research, Apr. 2012, 72(8): 2045-2056.
Gennaro et al., "Pharmaceutical Sciences," Remington's Pharmaceutical Sciences 17th Ed., Jan. 1985, 14-18 and 1409-1423.
Gerby et al., "2-Arylidenedihydroindole-3-ones: Design, synthesis, and biological activity on bladder carcinoma cell lines," Bioorganic & Medicinal Chemistry Letters, 2007, 208-213.
Ghorab et al., "Synthesis of some sulfur containing Tetrahydrobenzoabuthieno[b]Thieno(Pyridines, Quinolines, Oxazines and Pyrimidines) as possible radioprotective and Antineoplastic agents," Phosphorus, Sulfur and Silicon, Jan. 1998, 134/135:57-76.
Gibson, "Pharmaceutical Preformulation and Formulation," CRC Press LLC, 2009, 2nd ed, 559 pages.
Goetz et al., "Isolated C-terminal tail of FGF23 alleviates hypophosphatemia by inhibiting FGF23-FGFR-Klotho complex formation," PNAS, Jan. 2010, 107(1): 407-412.
Golub et al., "Molecular Classification of Cancer: Class Discovery and Class Prediction by Gene Expression Monitoring," Science, 1999, 286: 531-537.
Gomez-Rivera et al., "The Tyrosine Kinase Inhibitor, AZD2171, Inhibits Vascular Endothelial Growth Factor Receptor Signaling and Growth of Anaplastic Thyroid Cancer in an Orthotopic Nude Mouse Model," Clin Cancer Res, Aug. 2007, 4519-4527.
Govindan, "Summary of Presentations from the Ninth Annual Targeted Therapies in Lung Cancer Symposium," Journal of Thoracic Oncology, Nov. 2009, 4(11): 1045-1089.

(56) References Cited

OTHER PUBLICATIONS

Goyal et al,. "Polyclonal Secondary FGFR2 Mutations Drive Acquired Resistance to FGFR Inhibition in Patients with FGFR2 Fusion-Positive Cholangiocarcinoma," Cancer Discov., 2016, 7(3):252-263.
Gozgit et al., "Ponatinib (AP24534), a Multitargeted Pan-FGFR Inhibitor with Activity in Multiple FGFR-Amplified or Mutated Cancer Models," Mol Cancer Ther, 2012, 11: 690-699.
Granberg et al., "Strong FGFR3 staining is a marker for FGFR3 fusions in diffuse gliomas," Neuro-Oncology, 2017, 19(9): 1206-1216.
Grand et al., "Targeting FGFR3 in multiple myeloma: inhibition of t(4;14)-positive cells by SU5402 and PD173074," Leukemia, 2004, 18: 962-966.
Greene, T. W. and Wuts, P. G. M., "Protective Groups in Organic Synthesis", 3rd Ed., Wiley & Sons, Inc., New York (1999), 799 pages.
Greulich and Pollock, "Targeting mutant fibroblast growth factor receptors in cancer," Cell Press, May 2011, 17(5): 283-292.
Grose and Dickson, "Fibroblast growth factor signaling in tumorigenesis," Cytokine & Growth Factor Reviews, 2005, 179-186.
Gu et al., "Phosphotyrosine profiling identifies the KG-1 cell line as a model for the study of FGFR1 fusions in acute myeloid leukemia," Blood, Dec. 15, 2006, 108(13):4202-42040.
Guagnano et al., "Discovery of 3-(2,6-Dichloro-3,5-dimethoxy-phenyl)-1-{6-[4-(4-ethyl-piperazin-1-yl)-phenylamino]-pyrimidin-4-yl}-1-methyl-urea (NVP-BGJ398), A Potent and Selective Inhibitor of the Fibroblast Growth Factor Receptor Family of Receptor Tyrosine Kinase," J. Med. Chem., 2011, 54: 7066-7083.
Guan et al., "Design and synthesis of aminopropyl tetrahydroindole-based indolin-2-ones as selective and potent inhibitors of Src and Yes tyrosine kinase," Bioorganic & Medicinal Chemistry Letters, 2004, 187-190.
Gust et al., "Fibroblast Growth Factor Receptor 3 Is a Rational Therapeutic Target in Bladder Cancer," Molecular Cancer Therapeutics, Jul. 2013, 12(7): 1245-1254.
Haas et al., "Recent Developments in Negishi Cross-Coupling Reactions," ACS Catal., 2016, 6(3):1540-1552.
Hackam et al. "Translation of Research Evidence From Animals to Humans," JAMA, 296(14), 2006, 296(14):1731-1732.
Hafner et al., "High Frequency of FGFR3 Mutations in Adenoid Seborrheic Keratoses," Journal of Investigative Dermatology, 2006, 126: 2404-2407.
Hafner, "Seborrheic keratoses and epidermal nevi: new pathogenetic insights and therapeutic implications," Expert Rev Dermatol, 2006, 1(6): 759-761.
Hagel et al., "First Selective Small Molecule Inhibitor of FGFR4 for the Treatment of Hepatocellular Carcinomas with an Activated FGFR4 Signaling Pathway," Cancer Discovery, Apr. 2015, 1-14.
Hara and Saito, "CARD9 versus CARMA1 in innate and adaptive immunity," Cell Press, 2009, 234-242.
Heinrich et al., "Fragment-based discovery of new highly substituted 1 H-pyrrolo [2,3-b]-and 3 H-imidazolo [4, 5-b]-pyridines as focal adhesion kinase inhibitors." Journal of medicinal chemistry, Feb. 14, 2013, 56(3):1160-70.
Heinrich et al., "Fragment-based discovery of new highly substituted 1H-pyrrolo[2,3-b]- and 3H-imidazolo[4,5-b]-pyridines as focal adhesion kinase inhibitors," J of Med Chem., Jan. 8, 2013, 56(3):1160-1170.
Heinzle C, et al., "Differential Effects of Polymorphic Alleles of FGF Receptor 4 on Colon Cancer Growth and Metastasis," Cancer Research, Nov. 2012, 72(22):5767-5777.
Heinzle et al., "Is fibroblast growth factor receptor 4 a suitable target of cancer therapy?," Cur. Pharm. Des., 2014, 20:2881-2898.
Heinzle et al., "Targeting fibroblast-growth-factor-receptor-dependent signaling for cancer therapy," Expert Opinion, 2011, 1-18.
Helsten et al., "The FGFR Landscape in Cancer: Analysis of 4,853 Tumors by Next-Generation Sequencing," Clin. Cancer Res., Jan. 2016, 22:259-267.
Hess et al., "Abstract P245: Synergistic effect of combination of pemigatinib with enfortumab vedotin (EV) in human bladder cancer models," Molecular Cancer Therapeutics, Oct. 1, 2021, 20(12 Supplement):p. 245.
Hess et al., "Synergistic effect of combination of pemigatinib with enfortumab vedotin (EV) in human bladder cancer models," Molecular Cancer Therapeutics, Presented at AACR-NCI-EORT Virtual International Conference on Molecular Targets and Cancer Therapeutics, presented Oct. 7-10, 2021, 9 pages.
Hideshima and Anderson, "Preclinical Studies of Novel Targeted Therapies," Hematol Oncol Clin N Am, 2007, 1071-1091.
Ho et al., "Fibroblast growth factor receptor 4 regulates proliferation, anti apoptosis and alpha-fetoprotein secretion during hepatocellular carcinoma progression and represents a potential target for therapeutic intervention," J Hepatol, 2009, 50:118-127.
Honigberg et al., "The Bruton tyrosine kinase inhibitor PCI-32765 blocks B-cell activation and is efficacious in models of autoimmune disease and B-cell malignancy," Supporting Information, PNAS, Jul. 20, 2010, 107:29.
Hruska et al., "The Pathogenesis of Vascular Calcification in the Chronic Kidney Disease Mineral Bone Disorder (CKD-MBD): The Links Between Bone and Vasculature," Semin Nephrol, Mar. 2009, 29(2): 156-165.
Hu and Cong, "Fibroblast growth factor 19 is correlated with an unfavorable prognosis and promotes progression by activating fibroblast growth factor receptor 4 in advanced-stage serous ovarian cancer," Oncol Rep., Aug. 20, 2015, 34(5):2683-2691.
Huynh, "Tyrosine kinase inhibitors to treat liver cancer," Expert Opinion, 2010, 13-26.
Hynes and Dey, "Potential for Targeting the Fibroblast Growth Factor Receptors in Breast Cancer," Cancer Res, 2010, 70:5199-5202.
ICH Harmonised Tripartite Guideline, "Specifications: Test Procedures and Acceptance Criteria for New Drug Substances and New Drug Products Chemical Substances," ICHTRRPHU, Oct. 6, 1999, 35 pages.
Ichikawa et al., "A homozygous missense mutation in human KLOTHO causes severe tumoral calcinosis," The Journal of Clinical Investigation, Sep. 2007, 117(9): 2684-2691.
Ichikawa et al., "A Novel GALNT3 Mutation in a Pseudoautosomal Dominant Form of Tumoral Calcinosis: Evidence That the Disorder Is Autosomal Recessive," J. Clin. Endocrinol. Metab., 2005, 90:2420-2423.
Ichikawa et al., "Clinical Variability of Familial Tumoral Calcinosis Caused by Novel GALNT3 Mutations," American Journal of Medical Genetics, 2009, 896-903.
Ichikawa et al., "Novel GALNT3 Mutations Causing Hyperostosis-Hyperphosphatemia Syndrome Result in Low Intact Fibroblast Growth Factor 23 Concentrations," J. Clin. Endocrinol. Metab., 2007, 92:1943-1947.
Ichikawa et al., "Tumoral Calcinosis Presenting with Eyelid Calcifications due to Novel Missense Mutations in the Glycosyl Transferase Domain of the GALNT3 Gene," J. Clin. Endocrinol. Metab., 2006, 91: 4472-4475.
Indian Office Action in Indian Application No. 10665/DELNP/2014, dated Jun. 25, 2018, 8 pages.
Indian Office Action in Indian Application No. 201717030265, dated Dec. 12, 2019, 5 pages.
Indian Office Action in Indian Application No. 201717030267, dated Dec. 3, 2019, 7 pages.
Indian Office Action in Indian Application No. 202017052609, dated May 23, 2022, 7 pages.
Indian Office Action in Indian Application No. 202017052853, dated May 13, 2022, 6 pages.
Indian Office Action in Indian Application No. 9781/DELNP/2015, dated Jan. 18, 2019, 6 pages.
Indian Oral Hearing in Indian Application No. 201717030265, dated Jan. 13, 2022, 2 pages.
Indian Oral Hearing Notice in Indian Application No. 201717030267, dated Nov. 29, 2023, 3 pages.

(56) References Cited

OTHER PUBLICATIONS

Indian Oral Hearing Notice in Indian Application No. 201917050123, dated Jan. 29, 2024, 2 pages.
Indian Oral Hearing Notice in Indian Application No. 202017052609, dated Feb. 6, 2024, 3 pages.
Indonesian Office Action in Indonesian Application No. P00201507153, dated Apr. 27, 2018, 5 pages (English Translation).
Indonesian Office Action in Indonesian Application No. PID201705977, Jun. 5, 2020, 5 pages.
Inokuchi et al., "Therapeutic targeting of fibroblast growth factor receptors in gastric cancer," Gastroenterol Res Pract., Apr. 27, 2015, 2015:796380, 8 pages.
International Invitation to Pay Fees in International Appln. No. PCT/US2019/030633, dated Aug. 12, 2019, 5 pages.
International Preliminary Report on Patentability and Written Opinion in International Application No. PCT/US2011/066473, issued Jun. 25, 13, 10 pages.
International Preliminary Report on Patentability in International Application No. PCT/US2013/045309, mailed Dec. 24, 2014, 11 pages.
International Preliminary Report on Patentability in International Application No. PCT/US2013/054361, mailed Feb. 19, 2015, 7 pages.
International Preliminary Report on Patentability in International Application No. PCT/US2014/034662, dated Oct. 29, 2015, 12 pages.
International Preliminary Report on Patentability in International Application No. PCT/US2015/056583, dated Apr. 25, 2017, 7 pages.
International Preliminary Report on Patentability in International Application No. PCT/US2016/018737, dated Aug. 31, 2017, 8 pages.
International Preliminary Report on Patentability in International Application No. PCT/US2016/018770, dated Aug. 22, 2017, 10 pages.
International Preliminary Report on Patentability in International Application No. PCT/US2016/018787, dated Aug. 22, 2017, 7 pages.
International Preliminary Report on Patentability in International Application No. PCT/US2018/034559, dated Nov. 26, 2019, 8 pages.
International Preliminary Report on Patentability in International Application No. PCT/US2019/030578, dated Nov. 10, 2020, 14 pages.
International Preliminary Report on Patentability in International Application No. PCT/US2019/030633, dated Nov. 10, 2020, 10 pages.
International Preliminary Report on Patentability in International Application No. PCT/US2020/021313, dated Aug. 25, 2021, 11 pages.
International Preliminary Report on Patentability in International Application No. PCT/US2020/024210, dated Oct. 12, 2023, 7 pages.
International Preliminary Report on Patentability in International Application No. PCT/US2020/041104, dated Jan. 11, 2022, 7 pages.
International Preliminary Report on Patentability in International Application No. PCT/US2020/053436, dated Apr. 5, 2022, 8 pages.
International Preliminary Report on Patentability in International Application No. PCT/US2020/055547, dated Apr. 19, 2022, 7 pages.
International Preliminary Report on Patentability in International Application No. PCT/US2020/055735, dated Apr. 19, 2022, 8 pages.
International Preliminary Report on Patentability in International Application No. PCT/US2020/063038, dated Jun. 16, 2022, 8 pages.
International Preliminary Report on Patentability in International Application No. PCT/US2020/063064, dated May 17, 2022, 7 pages.
International Preliminary Report on Patentability in International Application No. PCT/US2021/013438, dated Jul. 28, 2022, 7 pages.
International Search Report and Written Opinion for International Application No. PCT/US2015/056583, dated Dec. 15, 2015, 10 pages.
International Search Report and Written Opinion in International Application No. PCT/US2013/045309, mailed on Jan. 22, 2014, 19 pages.
International Search Report and Written Opinion in International Application No. PCT/US2013/054361, dated Oct. 16, 2013, 12 pages.
International Search Report and Written Opinion in International Application No. PCT/US2014/034662, mailed Oct. 24, 2014, 18 pages.
International Search Report and Written Opinion in International Application No. PCT/US2016/018737, dated Jun. 2, 2016, 12 pages.
International Search Report and Written Opinion in International Application No. PCT/US2016/018770, dated Jun. 2, 2016, 14 pages.
International Search Report and Written Opinion in International Application No. PCT/US2016/018787, dated Jun. 2, 2016, 12 pages.
International Search Report and Written Opinion in International Application No. PCT/US2018/034559, dated Mar. 8, 2019, 14 pages.
International Search Report and Written Opinion in International Application No. PCT/US2019/030578, dated Jul. 11, 2019, 26 pages.
International Search Report and Written Opinion in International Application No. PCT/US2019/030633, dated Nov. 28, 2019, 21 pages.
International Search Report and Written Opinion in International Application No. PCT/US2020/021313, dated Jun. 26, 2020, 19 pages.
International Search Report and Written Opinion in International Application No. PCT/US2020/041104, dated Sep. 4, 2020, 14 pages.
International Search Report and Written Opinion in International Application No. PCT/US2020/053436, dated Dec. 4, 2020, 15 pages.
International Search Report and Written Opinion in International Application No. PCT/US2020/055547, dated Jan. 11, 2021, 13 pages.
International Search Report and Written Opinion in International Application No. PCT/US2020/055735, dated Dec. 15, 2020, 16 pages.
International Search Report and Written Opinion in International Application No. PCT/US2021/013438, dated Apr. 20, 2021, 16 pages.
International Search Report and Written Opinion in International Application No. PCT/US2022/024210, dated Jun. 28, 2022, 14 pages.
International Search Report and Written Opinion in International Application. No. PCT/US2011/066473, dated Jun. 19, 2012, 15 pages.
International Search Report and Written Opinion in International Appln. No. PCT/US2020/063038, dated Mar. 15, 2021, 16 pages.
International Search Report and Written Opinion in International Appln. No. PCT/US2020/063064, dated Feb. 12, 2021, 13 pages.
Invitation to Pay Additional Fees and, Where Applicable, Protest Fee in International Application No. PCT/US2013/045309, mailed Nov. 25, 2013, 5 pages.
Isakova et al., "Fibroblast Growth Factor 23 and Risks of Mortality and End-Stage Renal Disease in Patients With Chronic Kidney Disease," JAMA, Jun. 15, 2011, 305:23, 2432-2439.
Ishikawa et al., "Accelerated proliferation of myeloma cells by interleukin-6 cooperating with fibroblast growth factor receptor 3-mediated signals," Oncogene, 2005, 24:6328-6332.
Israeli Office Action in Israeli Application No. 236,078 dated Mar. 21, 2017, 10 pages (English Translation).
Israeli Office Action in Israeli Application No. 289834 dated Jul. 14, 2022, 4 pages.

(56) References Cited

OTHER PUBLICATIONS

Jackson et al., "8p11 Myeloproliferative syndrome: a review," Human Pathology, Apr. 1, 2010, 41:461-476.
Jain et al., "Cholangiocarcinoma With FGFR Genetic Aberrations:A Unique Clinical Phenotype," JCO Precision Oncology, Jan. 17, 2018, 2:1-12.
Jan de Beur, "Tumoral Calcinosis: A Look into the Metabolic Mirror of Phosphate Homeostasis," The Journal of Clinical Endocrinology & Metabolism, 2005, 90: 2469-2471.
Japanese Office Action in Japanese Application No. 2015-517376, dated Feb. 21, 2017, 5 pages (with English translation).
Japanese Office Action in Japanese Application No. 2016-509131, dated Feb. 20, 2018, 5 pages (English Translation).
Japanese Office Action in Japanese Application No. 2017-543981, dated Dec. 3, 2019, 4 pages.
Japanese Office Action in Japanese Application No. 2017-544021, dated Nov. 26, 2019, 6 pages.
Japanese Office Action in Japanese Application No. 2018-228352, dated Aug. 20, 2019, 6 pages.
Japanese Office Action in Japanese Application No. 2019-565177, dated May 13, 2022, 11 pages.
Japanese Office Action in Japanese Application No. 2020-069604, dated Nov. 15, 2021, 7 pages.
Japanese Office Action in Japanese Application No. 2020-093529, dated Mar. 1, 2022, 5 pages.
Javidi-Sharifi et al., "Crosstalk between KIT and FGFR3 Promotes Gastrointestinal Stromal Tumor Cell Growth and Drug Resistance," Cancer Research, Mar. 2015, 75(5): 880-892.
Jebar et al., "FGFR3 and Ras gene mutations are mutually exclusive genetic events in urothelial cell carcinoma," Oncogene, 2005, 24: 5218-5225.
Ji et al., "Embase abstract: Modeling and simulation as gating for clinical pharmacology studies of INCB054828," 119th Annual Meeting of the American Society for Clinical Pharmacology and Therapeutics, Mar. 1, 2018, 2 pages.
Jiang et al., "miR-99a promotes proliferation targeting FGFR3 in human epithelial ovarian cancer cells," Biomedicine & Pharmacotherapy, 2014, 68: 163-169.
Johnson et al., "Pharmacological and Functional Comparison of the Polo-like Kinase Family: Insight into Inhibitor and Substrate Specificity," Biochemistry, 2007, 46: 9551-9563.
Jonker et al., "A phase I study to determine the safety, pharmacokinetics and pharmacodynamics of a dual VEGFR and FGFR inhibitor, brivanib, in patients with advanced or metastatic solid tumors," Annals of Oncology, 2010, 1-7.
Jordan, "Tamoxifen: A Most Unlikely Pioneering Medicine," Nature Reviews: Drug Discovery, Mar. 2003, 2:205-213.
Kang et al., FGFR3 Activates RSK2 to Mediate Hematopoietic Transformation through Tyrosine Phosphorylation of RSK2 and Activation of the MEK/ERK Pathway, Cancer Cell, Sep. 2007, 12:201-214.
Kassack et al., "Structure-activity relationships of analogues of NF449 confirm NF449 as the most potent and selective known $P2X_1$ receptor antagonist," European Journal of Medicinal Chemisty, 2004, 345-357.
Katoh and Katoh, "FGF signaling network in the gastrointestinal tract (Review)," International Journal of Oncology, 2006, 29: 163-168.
Keats et al., "Ten years and counting: so what do we know about t(4;14) (p16;q32) multiple myeloma," Leukemia & Lymphoma, Nov. 2006, 47(11): 2289-2300.
Keer et al., "Enrolling a Rare Patient Population: Establishing Proof of Concept for FP-1039, an FGF "Trap," in Endometrial Cancer Patients with the S252W FGFR2 Mutation," Journal of Clinical Oncology, 2010 ASCO Annual Meeting Abstracts, 28:15, May 20 Supplement, 1 page.
Kerekes et. al., "Aurora kinase inhibitors based on the imidazo[1,2-a]pyrazine core: fluorine and deuterium incorporation improve oral absorption and exposure," J Med Chem., 2011, 54(1):201-210.
Khojasteh et al., "Chemical inhibitors of cytochrome P450 isoforms in human liver microsomes: a re-evaluation of P450 isoform selectivity," Eur J Drug Metab Pharmacokinet., Mar. 2011, 36:1-16.
Kim et al., "Phase I/II and Pharmacodynamic Study of Dovitinib (TKI258), an Inhibitor of Fibroblast Growth Factor Receptors and VEGF Receptors, in Patients with Advanced Melanoma," Clin Cancer Res, 2011, 17: 7451-7461.
Kim et al., "The design, synthesis, and biological evaluation of potent receptor tyrosine kinase inhibitors," Bioorganic & Medicinal Chemistry Letters, 2012, 4979-4985.
Klein et al., "FGFRI Kinase Inhibitors: Close Regioisomers Adopt Divergent Binding Modes and Display Distinct Biophysical Signatures," American Chemical Society, 2014, 166-171.
Knights and Cook, "De-regulated FGF receptors as therapeutic targets in cancer," Pharmacology & Therapeutics, 2010, 125:105-117.
Kompier et al., "Bladder cancer: Novel molecular characteristics, diagnostic, and therapeutic implications," Urologic Oncology: Seminars and Original Investigations, 2010, 91-96.
Kompier et al., "FGFR3, HRAS, KRAS, NRAS and PIK3CA Mutations in Bladder Cancer and Their Potential as Biomarkers for Surveillance and Therapy," PLoS ONE, Nov. 2010, 5(11): 1-13.
Kono et al., "The fibroblast growth factor receptor signaling pathway as a mediator of intrinsic resistance to EGFR-specific tyrosine kinase inhibitors in non-small cell lung cancer," Drug Resistance Updates, 2009, 95-102.
Korean Office Action in Korean Application No. 10-2015-7000701, dated Aug. 26, 2019, 19 pages.
Korean Office Action in Korean Application No. 10-2015-7032502, dated Sep. 9, 2020, 16 pages.
Korean Office Action in Korean Application No. 10-2020-7021884, dated Oct. 25, 2021, 6 pages.
Korean Office Action in Korean Application No. 10-2020-7021884, dated Oct. 28, 2020, 15 pages.
Korean Office Action in Korean Application No. 10-2021-7018897, dated Oct. 1, 2021, 15 pages.
Korean Office Action in Korean Application No. 10-2022-7018808, dated Sep. 16, 2022, 5 pages.
Kotha et al., "Recent applications of the Suzuki-Miyaura cross-coupling reaction in organic synthesis," Tetrahedron, 2002, 58:9633-9695.
Koziczak and Hynes, "Cooperation between Fibroblast Growth Factor Receptor-4 and ErbB2 in Regulation of Cyclin D1 Translation," The Journal of Biological Chemistry, 2004, 279(48): 50004-50011.
Koziczak et al., "Blocking of FGFR signaling inhibits breast cancer cell proliferation through downregulation of D-type cyclins," Oncogene, 2004, 23:3501-3508.
Krejci et al., "Molecular pathology of the fibroblast growth factor family," Hum Mutat, Sep. 2009, 30(9): 1245-1255.
Krejci et al., "NF449 is a novel inhibitor of fibroblast growth factor receptor 3 (FGFR3) signaling active in chondrocytes and multiple myeloma cells," The American Society for Biochemistry and Molecular Biology, 2010, 1-20.
Krejci et al., "NF449 Is a Novel Inhibitor of Fibroblast Growth Factor Receptor 3 (FGFR3) Signaling Active in Chondrocytes and Multiple Myeloma Cells," The Journal of Biological Chemistry, Jul. 2010, 285(27): 20644-20653.
Kunii et al., "FGFR2-Amplified Gastric Cancer Cell Lines Require FGFR2 and Erbb3 Signaling for Growth and Survival," Cancer Res., Apr. 1, 2008, 68(7):2340-2348.
Kunii et al., "FGFR2-Amplified Gastric Cancer Cell Lines Require FGFR2 and Erbb3 Signaling for Growth and Survival," Cancer Res., Apr. 1, 2008, Supplemental figures, 11 pages.
Kuroso et al., "Immunohistochemical Detection of Fibroblast Growth Factor Receptor 3 in Human Breast Cancer: Correlation with Clinicopathological/Molecular Parameteres and Prognosis," Pathobiology, Mar. 2010, 77: 231-240.
Kurosu et al., "Regulation of Fibroblast Growth Factor-23 Signaling by Klotho," The Journal of Biological Chemistry, Mar. 2006, 281(10): 6120-6123.

(56) References Cited

OTHER PUBLICATIONS

Lala et al., "Role of nitric oxide in tumor progression: Lessons from experimental tumors," Cancer and Metastasis Reviews, 1998, 17: 91-106.
Lammoglia and Mericq, "Familial Tumoral Calcinosis Caused by a Novel FGF23 Mutation: Response to Induction of Tubular Renal Acidosis with Acetazolamide and the Non-Calcium Phosphate Binder Sevelamer," Horm Res, 2009, 71:178-184.
Lamont et al., "Small molecule FGF receptor inhibitors block FGFR-dependent urothelial carcinoma growth in vitro and in vivo," Br. J Cancer, 2010, 1-8.
Lamont et al., "Small molecule FGF receptor inhibitors block FGFR-dependent urothelial carcinoma growth in vitro and in vivo," Br. J Cancer, 2011, 104:75-82.
Le Corre et al., "Synthesis and biological evaluation of a triazole-based library of pyrido[2,3-d]pyrimidines as FGFR3 tyrosine kinase inhibitors," Org. Biomol. Chem., 2010, 8, 2164-2173.
Lee et al., "In vivo Target Modulation and Biological Activity of CHIR-258, a Multitargeted Growth Factor Receptor Kinase Inhibitor, in Colon Cancer Models," Clin Cancer Res, May 2005, 3633-3641.
L'Hote and Knowles, "Cell responses to FGFR3 signalling: growth, differentiation and apoptosis," Experimental Cell Research, 2005, 417-431.
Li et al., "Compound deletion of Fgfr3 and Fgfr4 partially rescues the Hyp mouse phenotype," Am. J. Physiology—Endocrinol Metab, Dec. 7, 2010, 300:3, 29 pages.
Liang et al., "Anticancer molecules targeting fibroblast growth factor receptors," Cell Press, 2012, 11 pages.
Liu et al., "Developing Irreversible Inhibitors of the Protein Kinase Cysteinome," Chemistry & Biology, Feb. 2013, 146-159.
Liu et al., "FRFR3 and FRFR4 Do not Mediate Renal Effects of FGF23," J Am Soc Nephrol, 2008, 19:2342-2350.
Liu et al., "Pathogenic role of Fgf23 in Hyp mice," Am J Physiol Endocrinol Metab 291, Jan. 31, 2006, E38-E49.
Lopes de Menezes et al., "CHIR-258: A Potent Inhibitor of FLT3 Kinase in Experimental Tumor Xenograft Models of Human Acute Myelogenous Leukemia," Clin Cancer Res, Jul. 2005, 5281-5291.
Luo et al., "Deficiency of metabolic regulator FGFR4 delays breast cancer progression through systemic and microenvironmental metabolic alterations," Cancer & Metabolism, 2013, 20 pages.
Maeda et al., "Transforming property of TEL-FGFR3 mediated through PI3-K in a T-cell lymphoma that subsequently progressed to AML," Blood, Mar. 2005, 105(5): 2115-2123.
Malaysian Office Action in Malaysian Application No. 2014003396, dated Dec. 15, 2017, 4 pages.
Marek et al., "Fibroblast Growth Factor (FGF) and FGF Receptor-Mediated Autocrine Signaling in Non-Small-Cell Lung Cancer Cells," Molecular Pharmacology, 2009, 75:196-207.
Marfe and Stefano, "in vitro Anti-leukaemia Activity of Pyrrolo[1,2-b][1,2,5]benzothiadiaze-pines (PBTDs)," Recent Patents on Anti-Cancer Drug Discovery, 2010, 58-68.
Marks et al., "Mutational Analysis of EGFR and Related Signaling Pathway Genes in Lung Adenocarcinomas Identifies a Novel Somatic Kinase Domain Mutation in FGFR4," PLoS ONE, May 9, 2007, 2:e426.
Marshall et al., "Fibroblast Growth Factor Receptors are Components of Autocrine Signaling Networks in Head and Neck Squamous Cell Carcinoma Cells," Clin Cancer Res., 2011, 17:5016-5025.
Martinez-Torrecuadrada et al., "Targeting the Extracellular Domain of Fibroblast Growth Factor Receptor 3 with Human Single-Chain Fv Antibodies Inhibits Bladder Carcinoma Cell Line Proliferation," Clin Cancer Res, Sep. 2005, 6280-6290.
Martino et al., "Mutant fibroblast growth factor receptor 3 induces intracellular signaling and cellular transformation in a cell type- and mutation-specific manner," Oncogene, 2009, 28: 4306-4316.
Matsuda et al., "Fibroblast Growth Factor Receptor 2 IIIc as a Therapeutic Target for Colorectal Cancer Cells," Mol Cancer Ther., 2012, 52 pages.
McConkey et al., "Molecular genetics of bladder cancer: Emerging mechanisms of tumor initiation and progression," Urologic Oncology: Seminars and Original Investigations, 2010, 429-440.
McMahon, "VEGF Receptor Signaling in Tumor Angiogenesis," Oncologist, 2000, 5(suppl 1):3-10.
Meijer et al., "Fibroblast growth factor receptor 4 predicts failure on tamoxifen therapy in patients with recurrent breast cancer," Endocrine-Related Cancer, 2008, 15:101-111.
Mellor, "Targeted inhibition of the FGF19-FGFR4 pathway in hepatocellular carcinoma; translational safety considerations," Liver International, 2013, 1-9.
Memon et al., "Does Fgf23-klotho activity influence vascular and soft tissue calcification through regulating phosphate homeostasis," Kidney Int., 2008, 74(5): 566-570.
Metzner, "Fibroblast Growth Factor Receptors as Therapeutic Targets in Human Melanoma: Synergism with BRAF Inhibition," J Investigative Dermatol., 2011, 131:2087-2095.
Mexican Office Action in Mexican Application No. MX/a/2014/015192, dated Jan. 24, 2018, 6 pages.
Mexican Office Action in Mexican Application No. MX/a/2019/014097, dated Aug. 11, 2022, 13 pages.
Mexican Office Action in Mexican Application No. MX/a/2019/014097, dated Mar. 15, 2022, 17 pages (with Machine Translation).
Miyake et al., "1-tert-Butyl-3-[6-(3,5-dimethoxy-phenyl)-2-(4-diethylamino-butylamino)-pyrido[2,3-d]pyrimidin-7-yl]-urea (PD173074), a Selective Tyrosine Kinase Inhibitor of Fibroblast Growth Factor Receptor-3 (FGFR3), Inhibits Cell Proliferation of Bladder Cancer Carrying the FGFR3 Gene Mutation along with Up-Regulation of p27/Kip1 and $G_1/G_0$ Arrest," The Journal of Pharmacology and Experimental Therapeutics, 2010, 332(3):795-802.
Mohammadi et al., "Crystal structure of an angiogenesis inhibitor bound to the FGF receptor tyrosine kinase domain," The EMBO Journal, 1998, 5896-5904.
Mohammadi et al., "Structures of the Tyrosine Kinase Domain of Fibroblast Growth Factor Receptor in Complex with Inhibitors," Science, May 1997, 276:955-960.
Morissette et al., "High-throughput crystallization: polymorphs, salts, co-crystals and solvates of pharmaceutical solids," Advanced drug delivery reviews, Feb. 2004, 56(3):275-300.
Murphy et al., "Evidence for distinct alterations in the FGF axis in prostate cancer progression to an aggressive clinical phenotype," J Pathol., 2010, 220:452-460.
Naito et al., "Progressive tumoral calcinosis as the presenting feature of sarcoidosis in a patient on haemodialysis treatment," Nephrol Dial Transplant, 1999, 14:2716-2719.
Nakatani et al., "In vivo genetic evidence for klotho-dependent, fibroblast growth factor 23 (Fgf23)-mediated regulation of systemic phosphate homeostasis," The FASEB Journal, Feb. 2009, 23:433-441.
Natajaran et al., "p38 MAP kinase inhibitors. Part 3: SAR on 3,4-dihydropyrimido-[4,5-d]pyrimidin-2-ones and 3,4-dihydropyrido[4,3-d]-pyrimidin-2-ones," Bioorgan. Med. Chem. Lett., 2006, 4400-4404.
Neidle et al., "Failure Modes in the Discovery Process," Cancer Drug Design, 2008, pp. 427-431.
New Zealand Examination Report in New Zealand Application No. 743274, dated Jul. 18, 2018, 4 pages.
New Zealand Office Action in New Zealand Application No. 702747, dated Mar. 8, 2019, 2 pages.
New Zealand Office Action in New Zealand Application No. 702747, dated Sep. 16, 2016, 3 pages.
New Zealand Office Action in New Zealand Application No. 713074, dated Feb. 18, 2020, 3 pages.
New Zealand Office Action in New Zealand Application No. 743274, dated Jul. 19, 2018, 5 pages.
New Zealand Office Action in New Zealand Application No. 752422, dated Feb. 18, 2020, 2 pages.
Nitta, "Relationship between Fibroblast Growth Factor-23 and Mineral Metabolism in Chronic Kidney Disease," International Journal of Nephrology, 2010, 1-7.
Nomura et al., "FGF10/FGFR20 signal induces cell migration and invasion in pancreatic cancer," Br. J Cancer, 2008, 99:305-313.

(56) References Cited

OTHER PUBLICATIONS

Norman et al., "Protein-Ligand Crystal Structures Can Guide the Design of Selective Inhibitors of the FGFR Tyrosine Kinase," J. Med. Chem., 2012, 55(11):5003-5012.
Novelli, "Fosrenol (TM) reduces damaging high levels of phosphate in end-stage kidney disease patients," EurekAlert!, Nov. 2, 2002 [retrieved on Dec. 1, 2020], retrieved from URL <https://www.eurekalert.org/pub_releases/2002-11/pn-fr110202.php>, 4 pages.
Office Action from the Intellectual Property Office of the Philippines in Application No. 1-2014-502772, dated Mar. 17, 2016, 3 pages.
Office Action in Argentinian Application No. 20140101651, dated Sep. 22, 2023, 6 pages (with English Translation).
Office Action in Argentinian Application No. 20160100442, dated Feb. 23, 2024, 4 pages (with English Translation).
Office Action in Argentinian Application No. 20210101214, dated Sep. 22, 2023, 8 pages (with English Translation).
Office Action in Brazil Application No. BR122020015574-4, dated Dec. 13, 2022, 12 pages (with Machine Translation).
Office Action in Brazilian Application No. BR112020022392-1, dated Oct. 24, 2023, 7 pages (with English translation).
Office Action in Chilean Application No. 202002848, dated Dec. 12, 2022, 36 pages (with machine translation).
Office Action in Chilean Application No. 202201430, dated Feb. 2, 2024, 26 pages (with machine translation).
Office Action in Chilean Application No. 202202037, dated Jan. 30, 2024, 32 pages (with Machine Translation).
Office Action in Chilean Application No. 202202473, dated Jan. 29, 2024, 38 pages (with Machine Translation).
Office Action in Chinese Application No. 20198004291 5X, dated Feb. 23, 2024, 4 pages (with English Translation).
Office Action in Chinese Application No. 201980042917.9, dated Jan. 18, 2023, 14 pages (with English translation).
Office Action in Chinese Application No. 2019800429179, dated Mar. 2, 2024, 9 pages (with English Translation).
Office Action in Chinese Application No. 202080084260.5, dated Sep. 20, 2023, 30 pages (with English Translation).
Office Action in Chinese Application No. 202211353119.8, dated Dec. 21, 2023, 12 pages (with English Translation).
Office Action in Colombia Application No. NC2020/0015228, dated Jun. 16, 2023, 21 pages (with English Translation).
Office Action in Colombian Application No. NC2019/0014699, dated Apr. 27, 2023, 30 pages (with English translation).
Office Action in Colombian Application No. NC2019/0014699, dated Oct. 31, 2022, 31 pages.
Office Action in Columbian Application No. NC2020/0015226, dated Oct. 6, 2023, 18 pages (with English Translation).
Office Action in Columbian Application No. NC2020/0015228, dated Nov. 22, 2023, 29 pages (with English Translation).
Office Action in Ecuador Application No. IEPI-2015-1225, dated Jan. 9, 2023, 30 pages (with English translation).
Office Action in Eurasian Application No. 202291810, dated Sep. 29, 2023, 8 pages (with English Translation).
Office Action in Indian Application No. 10665/DELNP/2014, dated Nov. 9, 2023, 3 pages.
Office Action in Indian Application No. 201917050123, dated Mar. 29, 2023, 5 pages.
Office Action in Indian Application No. 201918011571, dated Jan. 9, 2024, 8 pages.
Office Action in Indian Application No. 202017052853, dated May 17, 2023, 2 pages.
Office Action in Israeli Application No. 278413, dated Feb. 15, 2024, 4 pages.
Office Action in Japanese Application No. 2020-561731, dated Dec. 5, 2023, 6 pages (with English Translation).
Office Action in Japanese Application No. 2020-561731, dated Mar. 22, 2023, 8 pages (with English translation).
Office Action in Japanese Application No. 2020-561741, dated Dec. 5, 2023, 5 pages (with English Translation).
Office Action in Japanese Application No. 2020-561741, dated Mar. 22, 2023, 11 pages (with English translation).
Office Action in Korean Application No. 10-2019-7038203, dated Jun. 8, 2023, 15 pages (with English translation).
Office Action in Korean Application No. 10-2020-7034837, dated Mar. 18, 2024, 14 pages (with English translation).
Office Action in Korean Application No. 10-2020-7034898, dated Mar. 20, 2024, 17 pages (with English translation).
Office Action in Malaysian Application No. PI2019006934, dated Oct. 16, 2023, 3 pages.
Office Action in Malaysian Application No. PI2020005647, dated Feb. 22, 2024, 4 pages.
Office Action in Mexican Application No. 2020/011639, dated Nov. 1, 2023, 7 pages (with Machine Translation).
Office Action in Mexican Application No. MX/a/2020/011639, dated May 23, 2023, 14 pages (with machine translation).
Office Action in Mexican Application No. MX/a/2020/011639, dated Oct. 25, 2022, 13 pages.
Office Action in Mexican Application No. MX/a/2020/011718, dated Apr. 11, 2023, 12 pages (with machine translation).
Office Action in Mexican Application No. MX/a/2020/011718, dated Sep. 26, 2023, 15 pages (with English Translation).
Office Action in Mexican Application No. MX/a/2022/000517, dated Mar. 5, 2024, 8 pages (with English Translation).
Office Action in Peru Application No. 2468-2019, dated Jan. 26, 2024, 26 pages (with English Translation).
Office Action in Philippines Application No. 1-2017-501483, dated Apr. 16, 2024, 5 pages.
Office Action in Philippines Application No. 1-2019-502675, dated Nov. 28, 2023, 6 pages.
Office Action in Philippines Application No. 1-2019-502809, dated Jun. 1, 2023, 4 pages.
Office Action in Philippines Application No. 1-2020-551843, dated Feb. 8, 2024, 5 pages.
Office Action in Taiwan Application No. 11107608, dated Dec. 26, 2022, 7 pages (with English Translation).
Office Action in Taiwanese Application No. 108115462, dated Jan. 10, 2023, 12 pages (with English translation).
Office Action in Taiwanese Application No. 108115470, dated Mar. 21, 2023, 13 pages (with machine translation).
Office Action in Taiwanese Application No. 110132234, dated Nov. 25, 2022, 8 pages (with english translation).
Office Action in Thai Application No. 2001006317, dated Apr. 1, 2024, 10 pages (with English Translation).
Office Action in Ukraine Application No. a201709220, dated Dec. 9, 2019, 11 pages.
Office Action in Ukraine Application No. a201801562, dated Jul. 28, 2021, 9 pages.
Office Action in Ukraine Application No. a202007685, dated Oct. 31, 2022, 13 pages.
Office Action in Vietnamese Application No. 1-2015-00102, dated Mar. 18, 2015, 4 pages.
Ornitz et al., "Receptor Specificity of the Fibroblast Growth Factor Family," The Journal of Biological Chemistry, 1996, 271(25): 15292-15297.
Pai et al., "Antibody-Mediated Inhibition of Fibroblast Growth Factor 19 Results in Increased Bile Acids Synthesis and lleal Malabsortion of Bile Acides in Cynomolgus Monkeys," Toxicological Sciences, 2012, 126(2): 446-456.
Pan et al., "MK-2461, a Novel Multitargeted Kinase Inhibitor, Preferentially Inhibits the Activated c-Met Receptor," Cancer Res, Feb. 2010, 1524-1533.
Pandith et al., "Oncogenic role of fibroblast growth factor receptor 3 in tumorigenesis of urinary bladder cancer," Urologic Oncology: Seminars and Original Investigations, 2010, 1-9.
Pandith et al., "Oncogenic role of fibroblast growth factor receptor 3 in tumorigenesis of urinary bladder cancer," Urologic Oncology: Seminars and Original Investigations, 2013, 31: 398-406.
Pardo et al., "The Fibroblast Growth Factor Receptor Inhibitor PD173074 Blocks Small Cell Lung Cancer Growth In vitro and In vivo," Cancer Res, Nov. 2009, 8645-8651.
Parmar et al., "Hydrochloride salt co-crystals: preparation, characterization and physicochemical studies," Pharmaceutical Development and Technology, 2013, 18(2):443-453.

(56) References Cited

OTHER PUBLICATIONS

Paterson et al., "Preclinical studies of fibroblast growth factor receptor 3 as a therapeutic target in multiple myeloma," British Journal of Haematology, 2004, 124:595-603.
Peruvian Office Action in Peruvian Application No. 1424, dated Mar. 12, 2021, 13 pages.
Peruvian Office Action in Peruvian Application No. 1429, dated Mar. 19, 2021, 12 pages.
Peruvian Office Action in Peruvian Application No. 2433, dated Nov. 27, 2018, 13 pages.
Peterson et al., "Expanding the Scope of Crystal Form Evaluation in Pharmaceutical Science," J Pharm Pharmaceut Sci., Feb. 2006, 9(3):317-326.
Philippine Allowance in Philippine Application No. 1/2015/502383, dated Jun. 6, 2022, 2 pages.
Philippine Office Action in Philippine Application No. 1/2015/502383, dated Nov. 11, 2021, 4 pages.
Philippine Office Action in Philippine Application No. 1/2017/501483, dated Dec. 12, 2019, 5 pages.
Philippine Office Action in Philippine Application No. 1/2019/502810, dated Dec. 7, 2021, 4 pages.
Philippine Office Action in Philippine Application No. 1-2017-501481, dated Oct. 29, 2019, 4 pages.
Philippine Office Action in Philippine Application No. 1/2015/502383, dated Jul. 8, 2019, 7 pages.
Philippine Office Action in the Philippine Application No. 1/2017/501483, dated Aug. 31, 2020, 4 pages.
Piazza et al., "Towards a new age in the treatment of multiple myeloma," Ann Hematol, 2007, 86:159-172.
Pindelska et al., "Pharmaceutical cocrystals, salts and polymorphs: Advanced characterization techniques," Advanced Drug Delivery Reviews, 2017, 117:111-146.
Pinedo and Slamon, "Translational Research: The Role of VEGF in Tumor Angiogenesis," Oncologist, 2000, 5(suppl 1):1-2.
Piro et al., "An FGFR3 Autocrine Loop Sustains Acquired Resistance to Trastuzumab in Gastric Cancer Patients," Clinical Cancer Research, Dec. 2016, 22(24): 6164-6175.
Platt et al., "Spectrum of Phosphatidylinositol 3-Kinase Pathway Gene Alterations in Bladder Cancer," Clin Cancer Res, Oct. 2009, 6008-6017.
Pliarchopoulou et al., "Current chemotherapeutic options for the treatment of advanced bladder cancer: A review," Urologic Oncology: Seminars and Original Investigations, 2010, 1-9.
Plowright et al., "Ectopic expression of fibroblast growth factor receptor 3 promotes myeloma cell proliferation and prevents apoptosis," Blood, Feb. 2000, 95(3): 992-998.
Podar et al., "Emerging therapies for multiple myeloma," Expert Opin. Emerging Drugs, 2009, 14(1):9-127.
Podar et al., "Targeting signalling pathways for the treatment of multiple myeloma," Expert Opin. Ther. Targets, 2005, 359-381.
Pollett et al., "Overexpression of the myeloma-associated oncogene fibroblast growth factor receptor 3 confers dexamethasone resistance," Blood, Nov. 2002, 100(10): 3819-3821.
Pollock et al., "Frequent activating FGFR2 mutations in endometrial carcinomas parallel germline mutations associated with craniosynostosis and skeletal dysplasia syndromes," Oncogene, 2007, 26:7158-7162.
Polymorphism in Pharmaceutical Solids, 2nd Ed., Brittain (ed), 2009, 288-289.
Porta, "FGFR a promising druggable target in cancer: Molecular biology and new drugs." Critical reviews in oncology hematology, 2017, 113:256-267.
Propper et al., "Phase I and Pharmacokinetic Study of PKC412, an Inhibitor of Protein Kinase C," J Clin Oncol, 2001, 19(5):1485-1492.
Qian et al., "Targeting Tumor Angiogenesis with Histone Deacetylase Inhibitors: the Hydroxamic Acid Derivative LBH589," Clin Cancer Res, Jan. 2006, 634-642.
Qing et al., "Antibody-based targeting of FGFR3 in bladder carcinoma and t(4;14)-positive multiple myeloma in mice," The Journal of Clinical Investigation, May 2009, 119(5): 1216-1229.
Qing et al., "Antibody-based targeting of FGFR3 in bladder carcinoma and t(4;14)-positive multiple myeloma in mice," The Journal of Clinical Investigation, May 2009, Supplemental Table 1: Summary of crystallographic analysis, 21 pages.
Qiu et al., "Over-expression of fibroblast growth factor receptor 3 in human hepatocellular carcinoma," World J Gastroenterol, 2005, 11(34): 5266-5272.
Raab et al., "Multiple myeloma," Lancet, 2009, 374: 324-339.
Ravindranathan et al., "Discovery of Novel Fibroblast Growth Factor Receptor 1 Kinase Inhibitors by Structure-Based Virtual Screening," J. Med. Chem., 2010, 53: 1662-1672.
Razzaque, "FGF23-mediated regulation of systemic phosphate homeostasis: is Klotho an essential player?," Am J Physiol Renal Physiol, 2009, 470-476.
Reimers et al., "NoBP, a Nuclear Fibroblast Growth Factor 3 Binding Protein, Is Cell Cycle Regulated and Promotes Cell Growth," Molecular and Cellular Biology, Aug. 2001, 21(15): 4996-5007.
Reis-Filho et al., "FGFR1 Emerges as a Potential Therapeutic Target for Lobular Breast Carcinomas," Clin Cancer Res, Nov. 2006, 6652-6662.
Reiter et al., "Consistent Fusion of ZNF198 to the Fibroblast Growth Factor Receptor-1 in the t(8;13)(p11;q12) Myeloproliferative Syndrome," Blood, Sep. 1998, 92(5): 1735-1742.
Remington's Pharmaceutical Sciences, 17th ed., Mack Publishing Company, Easton, Pa., 1985, p. 1418*.
Renhowe et al., "Design, Structure—Activity Relationships and in Vivo Characterization of 4-Amino-3-benzimidazol-2-ylhydroquinolin-2-ones: A Novel Class of Receptor Tyrosine Kinase Inhibitors," J. Med. Chem., 2009, 52: 278-292.
Ribatti et al., "The discovery of basic fibroblast growth factor/fibroblast growth factor-2 and its role in haematological malignancies," Cytokine & Growth Factor Reviews, 2007, 18: 327-334.
Ribatti, "Tyrosine Kinase Inhibitors as Antiangiogenic Drugs in Multiple Myeloma," Pharmaceuticals, 2010, 3: 1225-1231.
Roidl et al., "Resistance to Chemotherapy Is Associated with Fibroblast Growth Factor Receptor 4 Up-Regulation," Clin Cancer Res, Mar. 2009, 2058-2066.
Ronchetti et al., "Deregulated FGFR3 mutants in multiple myeloma cell lines with t(4;14): comparative analysis of Y373C, K650E and the novel G384D mutations," Oncogene, 2001, 20: 3553-3562.
Roumiantsev et al., "Distinct stem cell myeloproliferative/T lymphoma syndromes induced by ZNF198-FGFR1 and BCR-FGFR1 fusion genes from 8p11 translocations," Cancer Cell, Mar. 2004, 5: 287-298.
Rowe et al., "Handbook of Pharmaceutical Excipients," The Pharmaceutical Press and the American Pharmaceutical Association, 2009, 6th Edition, 917 pages.
Ryan et al., "Toxicologic Pathology of Unique Biotechnology Agents and Biotherapies," Toxicologic Pathology, 1999, 27(1): 78-86.
Sakurai et al., "A novel angiogenesis inhibitor, Ki23057, is useful for preventing the progression of colon cancer and the spreading of cancer cells to the liver," European Journal of Cancer, 2007, 2612-2620.
Sarker et al., "A Phase I Pharmacokinetic and Pharmacodynamic Study of TKI258, an Oral, Multitargeted Receptor Tyrosine Kinase Inhibitor in Patients with Advanced Solid Tumors," Clin Cancer Res, Apr. 2008, 2075-2081.
Saxty et al., "Fragment-based drug discovery of selective inhibitors of fibroblast growth factor receptor (FGFr)," Cancer Res, Apr. 15, 2010, 70, 5778.
Schenone et al., "Small Molecules ATP-Comptetitive Inhibitors of FLT3: A Chemical Overview," Current Medicinal Chemistry, 2008, 15(29): 3113-3132.
Schlapbach et al., "A novel Pd-catalyzed cyclization rection of ureas for the synthesis of dihydroquinazolinone p38 kinase inhibitors," Bioorg. Med. Chem. Lett., 2004, 357-360.
Science IP Order 3032627, Chemical Structure Search , Science IP, Apr. 2012, 78 pages.

(56) References Cited

OTHER PUBLICATIONS

Science IP Order 3101926, Chemical Structure Search , Science IP, Jan. 2015, 50 pages.
Science IP Order 3101983, Chemical Structure Search , Science IP, Jan. 2015, 70 pages.
Science IP Order 3104564, Patent Chemical Structure Search , Science IP, Mar. 2015, 90 pages.
Science IP Order 3104565, Patent Chemical Structure Search , Science IP, Mar. 2015, 521 pages.
Segev et al., "Restrained chondrocyte proliferation and maturation with abnormal growth plate vascularization and ossification in human FRFR-3$^{G380R}$ transgenic mice," Human Molecular Genetics, 2000, 9(2): 249-258.
Seitzer et al., "A single nucleotide change in the mouse genome accelerates breast cancer progression," Cancer Res., Jan. 2010, 70(2):802-812.
Serajuddin, "Salt formation to improve drug solubility," Adv Drug Deliv Rev, Jul. 2007, 59(7):603-616.
Shariat et al., "Association of Angiogenesis Related Markers With Bladder Cancer Outcomes and Other Molecular Markers," The Journal of Urology, May 2010, 183: 1744-1750.
Sharkey et al., "PKC412 demonstrates JNK-dependent activity against human multiple myeloma cells," Blood, Feb. 2007, 109(4): 1712-1719.
Shi et al., "High Expression of FGFR4 Enhances Tumor Growth and Metastasis in Nasopharyngeal Carcinoma," Journal of Cancer, 2015, 6(12): 1245-1254.
Shinya et al., "Fgf signalling through MAPK cascade is required for development of the subpallial telencephalon in zebrafish embryos," Development, 2001, 4153-4164.
sigmaaldrich.com, "4-Chloro-1H-pyrrolo[2,3-b]pyridine-5-carbaldehyde," CAS # 958230-19-8, [retrieved on Feb. 4, 2021] retrieved from URL <https://www.sigmaaldrich.com/catalog/product/aldrich/ade000976?lang=en&region=US>, 2 pages.
Singh et al., "Transforming Fusions of FGFR and TACC Genes in Human Glioblastoma," Science, Sep. 2012, 337:1231-1235.
Slavin et al., "Familial Tumoral Calcinosis," The American Journal of Surgican Pathology, 1993, 17(8): 188-802.
Smith et al., "Circulating αKlotho influences phosphate handling by controlling FGF23 production," The Journal of Clinical Investigation, Dec. 2012, 122(12): 4710-4715.
Song et al., "Fibroblast growth factors: An epigenetic mechanism of broad spectrum resistance to anticancer drugs," PNAS, Jul. 2000, 97(15): 8658-8663.
Sonvilla et al., "Fibroblast growth factor receptor 3-lllc mediates colorectal cancer growth and migration," British Journal of Cancer, 2010, 1-12.
Soria, "FGFR inhibition overview of clinical development programs," Presentation, presented at TAT in Washington DC on Mar. 5-7, 2014, 54 pages.
Soverini et al., "Novel mutation and RNA splice variant of fibroblast growth factor receptor 3 in multiple myeloma patients at diagnosis," Haematologica, 2002, 87: 1036-1040.
Specktor et al., "Hyperphosphatemic familial tumoral calcinosis caused by a mutation in GALNT3 in a European kindred," J Hum Genet, 2006, 51:487-490.
Squires et al., "Development of inhibitors of the fibroblast growth factor receptor (FGFR) kinase using a fragment based approach," Cancer Res 70, Apr. 15, 2010, 3626.
Squires et al., "Development of inhibitors of the fibroblast growth factor receptor (FGFR) kinase using a fragment based approach," Cancer Res, 2008, 1 page.
Staerk et al., "Pan-Src Family Kinase Inhibitors Replace Sox2 during the Direct Reprogramming of Somatic Cells," Angewandte Chem., Jun. 14, 2011, 50(25):5734-5736.
STN International Search Report for CAS RN 2380276-25-3, dated Nov. 20, 2019, 11 pages.
STN Search Report dated Jan. 6, 2020, 88 pages.
STN Search Report, dated Sep. 11, 2019, 31 pages.
Summons to attend oral proceedings pursuant to Rule 115(1) EPC in European Application No. 19724676.2, dated Feb. 22, 2023, 5 pages.
Sun et al., "Design, Synthesis, and Evaluations of Substituted 3-[(3- or 4-Carboxyethylpyrrol-2-yl)methylidenyl]indolin-2-ones as Inhibitors of VEGF, FGF, and PDGF Receptor Tyrosine Kinases," J. Med. Chem., 1999, 42: 5120-5130.
Sun et al., "Identification of Substituted 3-[(4,5,6,7-Tetrahydro-1H-indol-2-yl)methylene]-1,3-dihydroindol-2-ones as Growth Factor Receptor Inhibitors for VEGF-R2 (Flk-1/KDR), FGF-R1, and PDGF-Rβ Tyrosine Kinases," J. Med. Chem., 2000, 43: 2655-2663.
Sun et al., "Synthesis and Biological Evaluations of 3-Substituated Indolin-2-ones: A Novel Class of Tyrosine Kinase Inhibitors That Exhibit Selectivity toward Particular Receptor Tyrosine Kinases," J. Med. Chem., 1998, 41: 2588-2603.
Surry et al., "Dialkylbiaryl Phosphines in Pd-Catalyzed Amination: A User's Guide," Chem Sci., 2011, 2(1):27-50.
Taiwan Office Action in Taiwan Application No. 103114284, dated Apr. 9, 2018, 4 pages (English Search Report).
Taiwan Office Action in Taiwan Application No. 105104993, dated Feb. 11, 2020, 9 pages.
Taiwan Office Action in Taiwan Application No. 105105018, dated Oct. 22, 2019, 7 pages.
Taiwan Office Action in Taiwan Application No. 107146498, dated Dec. 19, 2019, 7 pages.
Taiwan Office Action in Taiwan Application No. 109132389, dated Aug. 23, 2021, 4 pages.
Taiwanese Office Action in Taiwan Application No. 102120946, dated Nov. 9, 2016, 9 pages (with English translation).
Taiwanese Office Action in Taiwanese Application No. 102120946, dated Jul. 13, 2017, 7 pages (English Translation).
Takeda et al., "AZD2171 Shows Potent Antitumor Activity Against Gastric Cancer Over-Expressing Fibroblast Growth Factor Receptor 2/Keratinocyte Growth Factor Receptor," Clin Cancer Res, May 2007, 3051-3057.
Takii et al., "Serotonin Derivative, N-(p-Coumaroyl)serotonin, Isolated from Safflower (*Carthamus tinctorius* L.) Oil Cake Augments the Proliferation of Normal Human and Mouse Fibroblasts in Synergy with Basic Fibroblast Growth Factor (bFGF) or Epidermal Growth Factor (EGF)", J Biochem., 1995, 125(5):910-915.
Tan et al., "Development of covalent inhibitors that can overcome resistance to first-generation FGFR kinase inhibitors," PNAS, Oct. 2014, E4869-E4877.
Tang et al., "Role of fibroblast growth factor receptor 4 in cancer," Cancer Science, Oct. 2018, 109(10):3024-3031.
Taylor et al., "Identification of FGFR4-activating mutations in human rhabdomyasarcomas that promote metastasis in xenotransplanted models," J Clin Invest., Nov. 2009, 119(11):3395-3407.
Taylor, "Inhibitor PD-173074 Bound to the Tyrosine Kinase Domain of FGFR 1," Molecular & Behavioral Neuroscience Institute , Feb. 2006, 1 page.
Taylor, "Inhibitor SU-5402 Bound to the Tyrosine Kinase Domain of FGFR 1," Molecular & Behavioral Neuroscience Institute , Apr. 2006, 1 page.
Terai et al., "Vascular calcification and secondary hyperparathyroidism of severe chronic kidney disease and its relation to serum phosphate and calcium levels," British Journal of Pharmacology, 2009, 156: 1267-1278.
Thai Office Action in Thai Application No. 1401007417, dated Jun. 5, 2016, 7 pages (with English translation).
Thakuria et al., "Crystal Polymorphism in Pharmaceutical Science," Comprehensive Supramolecular Chemistry II, Jun. 2017, vol. 5, chapter 22, pp. 283-309.
The Cancer Genome Atlas Research Network, "Comprehensive molecular characterization of urothelial bladder carcinoma," Nature, 2014, 507: 315-22.
Thome and Weil, "Post-translational modifications regulate distinct functions of CARMA1 and BCL10," Trends in Immunology, 2007, 28(6): 281-288.
Thompson et al., "3-(3,5-Dimethoxyphenyl)-1,6-naphthyridine-2,7-diamines and Related 2-Urea Derivatives Are Potent and Selective Inhibitors of the FGF Receptor-1 Tyrosine Kinase," J. Med. Chem., 2000, 43: 4200-4211.

(56) References Cited

OTHER PUBLICATIONS

Thompson et al., "Photochemical Preparation of a Pyridone Containing Tetracycle: A Jak Protein Kinase Inhibitor," Bioorganic & Medicinal Chemistry Letters 12:1219-1223, 2002.
Thompson et al., "Synthesis and Structure—Activity Relationships of Soluble 7-Substituted 3-(3,5-Dimethoxyphenyl)-1,6-naphthyridin-2-amines and Related Ureas as Dual Inhibitors of the Fibroblast Growth Factor Receptor-1 and Vascular Endothelial Growth Factor Receptor-2 Tyrosine Kinases," J. Med. Chem., 2005, 48: 4628-2653.
Thussbas et al., "FGFR4 Arg388 Allele Is Associated With Resistance to Adjuvant Therapy in Primary Breast Cancer," J. Clin. Oncol., Aug. 10, 2006, 23:3747-3755.
Tolcher et al., "381 Preliminary results of a dose escalation study of the Fibroblast Growth Factor (FGF) "trap" FP-1039 (FGFR1:Fc) in patients with advanced malignancies," EJC Supplements, Nov. 2010, 8:7, p. 121.
Tomlinson et al., "FGFR3 protein expression and its relationship to mutation status and prognostic variables in bladder cancer," J Pathol, Sep. 2007, 213(1): 91-98.
Tomlinson et al., "Fibroblast Growth Factor Receptor 1 Promotes Proliferation and Survival via Activation of the Mitogen-Activated Protein Kinase Pathway in Bladder Cancer," Cancer Res, 2009, 4613-4620.
Tomlinson et al., "Knockdown by shRNA identifies S249C mutant FGFR3 as a potential therapeutic target in bladder cancer," Oncogene, 2007, 26: 5889-5899.
Topaz et al., "Mutations in GALNT3, encoding a protein involved in O-linked glycosylation, cause familial tumoral calcinosis," Nature Genetics, 2004, 1-3.
Traxler and Furet, "Strategies toward the Design of Novel and Selective Protein Tyrosine Kinase Inhibitors," Pharmacol. Ther., 1999, 82(2-3): 195-206.
Trudel et al., "CHIR-258, a novel, multitargeted tyrosine kinase inhibitor for the potential treatment of t(4;14) multiple myeloma," Blood, Apr. 2005, 105(7): 2941-2948.
Trudel et al., "Inhibition of fibroblast growth factor receptor 3 induces differentiation and apoptosis in t(4;14) myeloma," Blood, May 2004, 103(9):3521-3528.
Trudel et al., "The inhibitory anti-FGFR3 antibody, PRO-001, is cytotoxic to t(4;14) multiple myeloma cells," Blood, May 2006, 107(10): 4039-4046.
Trudel, "CHIR-258, a Novel Multi-targeted Tyrosine KinaseInhibitor, for the Treatment of t(4;14) Multiple Myeloma," Presentation, Presented at International Myeloma Foundation, Apr. 2005, 18 pages.
Turkington et al., "Fibroblast growth factor receptor 4 (FGFR4): a targetable regulator of drug resistance in colorectal cancer," Cell Death Dis., Feb. 6, 2014, 5:e1046.
Turner and Grose, "Fibroblast growth factor signalling: from development to cancer," Nature Reviews Cancer, 2010, 10:116-129.
Turner et al., "FGFR1 Amplification Drives Endocrine Therapy Resistance and Is a Therapeutic Target in Breast Cancer," Cancer Res., Mar. 2010, 2085-2094.
Tvorogov et al., "Effective Suppression of Vascular Network Formation by Combination of Antibodies Blocking VEGFR Ligand Binding and Receptor Dimerization," Cancer Cell, Dec. 2010, 18: 630-640.
Ueno et al., "Enhanced Expression of Fibroblast Growth Factor Receptor 3 IIIc Promotes Human Esophageal Carcinoma Cell Proliferation," Journal of Histochemistry & Cytochemistry, 2016, 64(1): 7-17.
Ukraine Office Action in Ukraine Application No. a 2019 12195, dated Nov. 11, 2021, 7 pages.
Ukraine Office Action in Ukraine Application No. a201500191, dated Dec. 13, 2016, 10 pages (with English translation).
Ukraine Office Action in Ukraine Application No. a201511370, dated Nov. 12, 2018, 6 pages (with English translation).
Ukraine Office Action in Ukraine Application No. a202007700, dated Sep. 13, 2022, 11 pages.
Urakawa et al., "Klotho converts canonical FGF receptor into a specific receptor for FGF23," Nature, Dec. 2006, 444: 770-774.
Uzawa et al., "Targeting fibroblast growth factor receptor 3 enhances radiosensitivity in human squamous cancer cells," Oncogene, 2011, 1-6.
Van Oers et al., "FGFR3 Mutations Indicate Better Survival in Invasive Upper Urinary Tract and Bladder Tumours," European Urology, 2009, 650-658.
Våtsveen et al., "FGFR3 is expressed and is important for survival in INA-6, a human myeloma cell line without a t(4;14)," Eur. J. Haematol., 83:5, Jul. 6, 2009, 471-476.
Verstovsek et al., "Interim Results from Fight-203, a Phase 2, Open-Label, Multicenter Study Evaluating the Efficacy and Safety of Pemigatinib (INCB054828) in Patients with Myeloid/Lymphoid Neoplasms with Rearrangement of Fibroblast Growth Factor Receptor 1 (FGFR1)," Blood, Nov. 29, 2018, retrieved from URL <https://ashpublications.org/blood/article/132/Supplement%201/690/266005/Interim-Results-from-Fight203-a-Phase-2-OpenLabel>, 132(Supplement 1):690.
Vietnamese Office Action in Vietnamese Application No. 1-2022-03016, dated Jul. 8, 2022, 2 pages.
Vogt et al., "FGF23 and phosphate cardiovascular toxins in ckd," Toxins, Nov. 6, 2019, 11(11):647.
Von Massenhausen et al., "Evaluation of FGFR3 as a Therapeutic Target in Head and Neck Squamous Cell Carcinoma," Targ. Oncol., 2016, 11: 631-642.
Walsky and Obach, "Validated assays for human cytochrome P450 activities," Drug Metab Dispos., 2004, 32(6):647-660.
Walsky et al., "Evaluation of 227 drugs for in vitro inhibition of cytochrome P450 2B6," J Clin Pharmacol., Dec. 2006, 46(12):1426-1438.
Wang and Becker, "Antisense targeting of basic fibroblast growth factor and fibroblast growth factor receptor-1 in human melanomas blocks intratumoral angiogenesis and tumor growth," Nature Medicine, Aug. 1997, 887-893.
Wang and Ding, "Fibroblast growth factor receptors in breast cancer," Tumor Biology, May 2017, 1-10.
Wang et al., "The fibroblast growth factor receptor-4 Arg388 allele is associated with prostate cancer initiation and progression," Clin Cancer Res. 2004, 10:6169-6178.
Ware et al., "Rapidly Acquired Resistance to EFGR Tyrosine Kinase Inhibitors in NSCLC Cell Lines through De-Repression of FGFR2 and FGFR3 Expression," PLoS, Nov. 2010, 5(11): 1-9.
Weiss et al., Frequent and Focal FGFR1 Amplification Associates with Therapeutically Tractable FGFR1 Dependency in Squamous Cell Lung Cancer, Sci. Transl. Med., 2010, 2(62):62ra93, pp. 1-7.
Williams et al., "Oncogenic FGFR3 gene fusions in bladder cancer," Hum Mol Genet, 2013, 22:795-803.
Wu, "Urothelial Tumorigenesis: A Tale Of Divergent Pathways," Nature Reviews, Sep. 2005, 5: 713-725.
Wuts et al., "Greene's Protective Groups in Organic Synthesis," 4th Ed., 2006, Chapter 7, 696-926.
Wöhrle et al., "FGF Receptors Control Vitamin D and Phosphate Homeostasis by Mediating Renal FGF-23 Signaling and Regulating FGF-23 Expression in Bone," Journal of Bone and Mineral Research, Oct. 2011, 26(10): 2486-2497.
Wöhrle et al., "Pharmacological inhibition of FGFR signaling ameliorates FGF23-mediated hypophosphatemic rickets," Journal of Bone and Mineral Research, 2012, 1-36.
Xian et al., "Pleiotropic effects of FGFRI on cell proliferation, survival, and migration in a 3D mammary epithelial cell model," JCB, 2005, 171(4): 663-673.
Xin et al., "CHIR-258 Is Efficacious in A Newly Developed Fibroblast Growth Factor Receptor 3-Expressing Orthotopic Multiple Myeloma Model in Mice," Clin Cancer Res, Aug. 2006, 4908-4915.
Xu et al., "Fibroblast growth factor receptor 4 promotes progression and correlates to poor prognosis in cholangiocarcinoma," Biochemical and Biophysical Research Communications, 2014, 446: 54-60.
Xu et al. "Design, synthesis and biological evaluation of deuterated nintedanib for improving pharmacokinetic properties," J Label Compd Radiopharm., 2015, 58(7):308-312.

(56) References Cited

OTHER PUBLICATIONS

Ye et al., "Combination of the FGFR4 inhibitor PD173074 and 5-fluorouracil reduces proliferation and promotes apoptosis in gastric cancer," Oncol Rep., Dec. 2013, 30(6):2777-2784.
Ying et al., "Genome-wide screening for genetic alterations in esophageal cancer by aCGH identifies 11q13 amplification oncogenes associated with nodal metastasis," PLoS One, Jun. 25, 2012, 7:e39797.
Yu et al., "Amorphous pharmaceutical solids: preparation, characterization and stabilization," Advanced Drug Delivery Reviews, May 16, 2001, 48(1):27-42.
Yu et al., "Analysis of the Biochemical Mechanisms for the Endocrine Actions of Fibroblast Growth Factor-23," Endocrinology, Nov. 2005, 146(11): 4647-4656.
Yu et al., "FGFR-4 Arg(3)(8)(8) enhances prostate cancer progression via extracellular signal-related kinase and serum response factor signaling," Clin Cancer Res., Jul. 2011, 17:4355-4366.
Zaid et al., "Identification of FGFR4 as a Potential Therapeutic Target for Advanced-Stage, High-Grade Serous Ovarian Cancer," Clin Cancer Res, 2013, 19(4): 809-820.
Zhang et al., "AZD4547, a potent and selective FGF-receptor inhibitor induces tumor regressions in a human primary model of FGF-receptor 2 amplified gastric cancer and is efficacious in combination with chemotherapy," 2012, AstraZeneca, 1 page.
Zhang et al., "Direct Cell Cycle Regulation by the Fibroblast Growth Factor Receptor (FGFR) Kinase through Phosphorylation-dependent Release of Cks1 from FGFR Substrate 2," The Journal of Biological Chemistry, 2004, 279(53): 55348-55354.
Zhang et al., "Enhanced FGFR signalling predisposes pancreatic cancer to the effect of a potent FGFR inhibitor in preclinical models," British Journal of Cancer, 2014, 110: 320-329.
Zhang et al., "FP-1039 (FGFR1:Fc), A Soluble FGFR1 Receptor Antagonist, Inhibits Tumor Growth and Angiogenesis," Mol Cancer Ther, 6, Nov. 2007, B55.
Zhang et al., "Predicting Drug-Drug Interactions: An FDA Perspective," The AAPS Journal, May 6, 2009, 11(2):300-306.
Zhang et al., "Recent progress in therapeutic and diagnostic applications of lanthanides," Mini-Reviews in Medicinal Chemistry, 2011, 11(8):678-694.
Zhang et al., "Receptor Specificity of the Fibroblast Growth Factor Family," Journal of Biological Chemistry, Jun. 2006, 281(23): 15694-15700.
Zhang et al., "Translating the therapeutic potential of AZD4547 in FGFR1-amplified non-small cell lung cancer through the use of patient derived tumor xenograft (PDTX) models," Clin cancer Res, Oct. 18, 2012, 40 pages.
Zhao et al., "A Novel, Selective Inhibitor of Fibroblast Growth Factor Receptors That Shows a Potent Broad Spectrum of Antitumor Activity in Several Tumor Xenograft Models," Mol Cancer Ther, Nov. 2011, 2200-2210.
Zhao et al., "Homozygous Deletions and Chromosome Amplifications in Human Lung Carcinomas Revealed by Single Nucleotide Polymorphism Array Analysis," Cancer Res, Jul. 2005, 5561-5570.
Zhou et al., "A Structure-Guided Approach to Creating Covalent FGFR Inhibitors," Chemistry and Biology, Mar. 2010, 285-295.
Zhu et al., "Fibroblast growth factor receptor 3 inhibition by short hairpin RNAs leads to apoptosis in multiple myeloma," Mol Cancer Ther, May 2005, 787-798.
Zieger et al., "Role of Activating Fibroblast Growth Factor Receptor 3 Mutations in the Development of Bladder Tumors," Clin Cancer Res, Nov. 2005, 7709-7719.
Zingone et al., "Ectopic expression of wild-type FGFR3 cooperates with MYC to accelerate development of B-cell lineage neoplasms," Leukemia, 2010, 1171-1178.

* cited by examiner

SUBSTITUTED TRICYCLIC COMPOUNDS AS FGFR INHIBITORS

SEQUENCE LISTING

This application contains a Sequence Listing that has been submitted electronically as an XML file named 20443-0257006_SL_ST26.xml. The XML file, created on Oct. 19, 2023, is 1,938 bytes in size. The material in the XML file is hereby incorporated by reference in its entirety.

FIELD OF THE INVENTION

The present invention relates to tricyclic compounds, and pharmaceutical compositions including the same, that are inhibitors of one or more FGFR enzymes and are useful in the treatment of FGFR-associated diseases such as cancer.

BACKGROUND OF THE INVENTION

The Fibroblast Growth Factor Receptors (FGFR) are receptor tyrosine kinases that bind to fibroblast growth factor (FGF) ligands. There are four FGFR proteins (FGFR1-4) that are capable of binding ligands and are involved in the regulation of many physiological processes including tissue development, angiogenesis, wound healing, and metabolic regulation. Upon ligand binding, the receptors undergo dimerization and phosphorylation leading to stimulation of the protein kinase activity and recruitment of many intracellular docking proteins. These interactions facilitate the activation of an array of intracellular signaling pathways including Ras-MAPK, AKT-PI3K, and phospholipase C that are important for cellular growth, proliferation and survival (Reviewed in Eswarakumar et al. Cytokine & Growth Factor Reviews, 2005).

Aberrant activation of this pathway either through overexpression of FGF ligands or FGFR or activating mutations in the FGFRs can lead to tumor development, progression, and resistance to conventional cancer therapies. In human cancer, genetic alterations including gene amplification, chromosomal translocations and somatic mutations that lead to ligand-independent receptor activation have been described. Large scale DNA sequencing of thousands of tumor samples has revealed that components of the FGFR pathway are among the most frequently mutated in human cancer. Many of these activating mutations are identical to germline mutations that lead to skeletal dysplasia syndromes. Mechanisms that lead to aberrant ligand-dependent signaling in human disease include overexpression of FGFs and changes in FGFR splicing that lead to receptors with more promiscuous ligand binding abilities (Reviewed in Knights and Cook Pharmacology & Therapeutics, 2010; Turner and Grose, Nature Reviews Cancer, 2010). Therefore, development of inhibitors targeting FGFR may be useful in the clinical treatment of diseases that have elevated FGF or FGFR activity.

The cancer types in which FGF/FGFRs are implicated include, but are not limited to: carcinomas (e.g., bladder, breast, cervical, colorectal, endometrial, gastric, head and neck, kidney, liver, lung, ovarian, prostate); hematopoietic malignancies (e.g., multiple myeloma, chronic lymphocytic lymphoma, adult T cell leukemia, acute myelogenous leukemia, non-Hodgkin lymphoma, myeloproliferative neoplasms, and Waldenstrom's Macroglubulinemia); and other neoplasms (e.g., glioblastoma, melanoma, and rhabdosarcoma). In addition to a role in oncogenic neoplasms, FGFR activation has also been implicated in skeletal and chondrocyte disorders including, but not limited to, achrondroplasia and craniosynostosis syndromes.

There is a continuing need for the development of new drugs for the treatment of cancer and other diseases, and the FGFR inhibitors described herein help address this need.

SUMMARY OF THE INVENTION

The present invention is directed to a compound of Formula I:

I

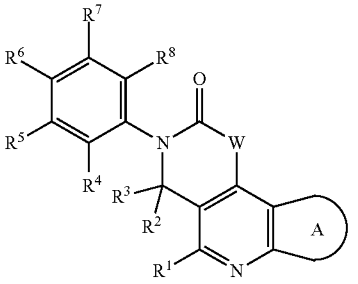

or a pharmaceutically acceptable salt thereof, wherein constituent variables are defined hereinbelow.

The present invention is further directed to a compound of Formula II, III, or IV:

II

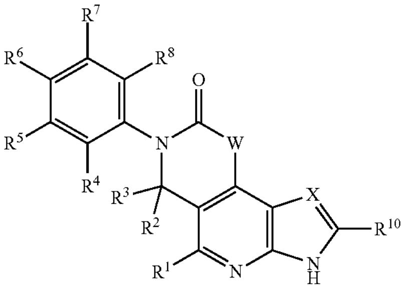

III

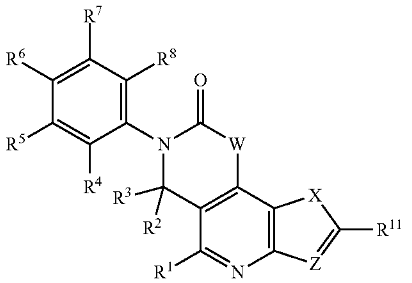

IV

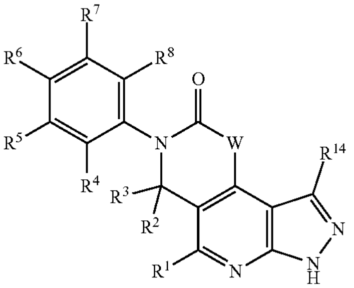

or a pharmaceutically acceptable salt thereof, wherein constituent variables are defined hereinbelow.

The present invention is further directed to a compound of Formula V:

V

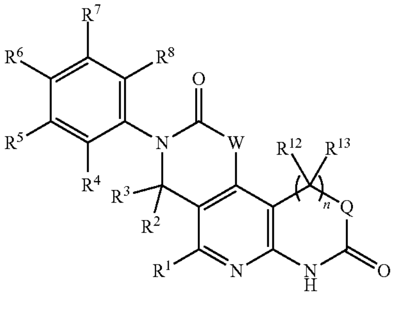

or a pharmaceutically acceptable salt thereof, wherein constituent variables are defined hereinbelow.

The present invention is further directed to a pharmaceutical composition comprising a compound of any one of Formulas I, II, III, IV, and V, or a pharmaceutically acceptable salt thereof, and at least one pharmaceutically acceptable carrier.

The present invention is further directed to a method of treating cancer in a patient comprising administering to the patient a therapeutically effective amount of a compound of any one of Formulas I, II, III, IV, and V, or a pharmaceutically acceptable salt thereof.

The present invention is further directed to a method of treating a myeoloproliferative disease in a patient comprising administering to the patient a therapeutically effective amount of a compound of any one of Formulas I, II, III, IV, and V, or a pharmaceutically acceptable salt thereof.

The present invention is further directed to a method of treating a skeletal or chondrocyte disorder in a patient comprising administering to the patient a therapeutically effective amount of a compound of any one of Formulas I, II, III, IV, and V, or a pharmaceutically acceptable salt thereof.

DETAILED DESCRIPTION

The present invention is related to an FGFR inhibitor which is a compound of Formula I:

I

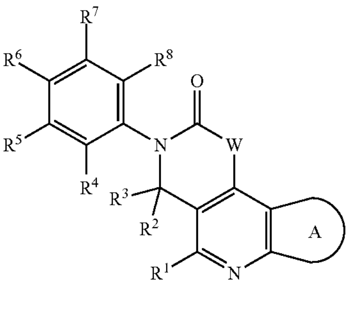

or a pharmaceutically acceptable salt thereof, wherein:

W is $NR^9$, O, or $CR^{17}R^{18}$;

ring A is:

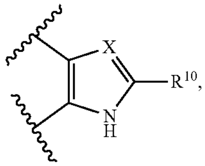
,
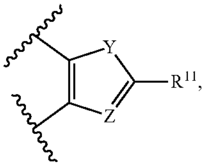
,
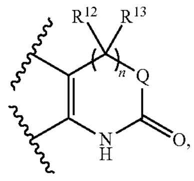
, or
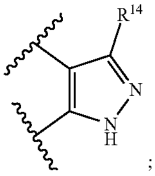
;

X is $CR^{15}$ or N;

Y is $NR^{16}$, O, or S;

Z is N or CH;

Q is absent, O, $NR^{16}$a or $CR^{12a}R^{13a}$;

n is 0 or 1, wherein when n is 0 then Q is not absent;

$R^1$ is H, $NR^AR^B$, halo, and $C_{1-3}$ alkyl;

$R^2$ and $R^3$ are each independently selected from H, CN, $C(O)NR^cR^d$, and $C_{1-7}$ alkyl, wherein said $C_{1-7}$ alkyl is optionally substituted by 1, 2, or 3 substituents independently selected from halo, $OR^a$, CN, $NR^cR^d$, and $C(O)NR^cR^d$;

or $R^2$ and $R^3$ together with the carbon atom to which they are attached form a 3-7 membered cycloalkyl ring or a 4-7 membered heterocycloalkyl ring, each optionally substituted by 1, 2, or 3 substituents independently selected from halo, $C_{1-6}$ alkyl, $C_{1-6}$ haloalkyl, CN, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, and $NR^cC(O)OR^a$;

$R^4$, $R^5$, $R^6$, $R^7$, and $R^8$ are each independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C({=}NR^{e1})R^{b1}$, $C({=}NR^{e1})NR^{c1}R^{d1}$, $NR^{c1}C({=}NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C({=}NR^{e1})NR^{c1}R^{d1}$, $NR^{c1}C({=}R^{c1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

$R^9$ is H, $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl are each optionally substituted with 1, 2, 3, 4, or 5 substituents independently selected from $R^{9a}$;

each $R^{9a}$ is independently selected from $Cy^1$, halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$, wherein said $C_{1-6}$ alkyl, $C_{2-6}$ alkenyl, and $C_{2-6}$ alkynyl are each optionally substituted with 1, 2, or 3 substituents independently selected from $Cy^1$, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$ $S(O)_2R^{b2}$, and $S(O)_2NR^{c2}R^{d2}$;

$R^{10}$, $R^{11}$, $R^{12}$, $R^{13}$, $R^{12a}$, $R^{13a}$, $R^{14}$, $R^1$, $R^{17}$, and $R^{18}$ are each independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from $R^{10a}$;

each $R^{10a}$ is independently selected from $Cy^2$, halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$, wherein said $C_{1-6}$ alkyl, $C_{2-6}$ alkenyl, and $C_{2-6}$ alkynyl are each optionally substituted with 1, 2, or 3 substituents independently selected from $Cy^2$, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

or $R^{12}$ and $R^{13}$ together with the carbon atom to which they are attached form a 3-, 4-, 5-, 6-, or 7-membered cycloalkyl group or a 4-, 5-, 6-, or 7-membered heterocycloalkyl group, each optionally substituted with 1, 2, or 3 substituents independently selected from $Cy^2$, $C_{1-6}$ alkyl, $C_{1-6}$ haloalkyl, halo, CN, $OR^{a3}$, $SR^{a3}$, $C(O)R^{b3}$, $C(O)NR^{c3}R^{d3}$, $C(O)OR^3$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$, wherein said $C_{1-6}$ alkyl is optionally substituted by 1, 2, or 3 substituents independently selected from $Cy^2$, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

or $R^{12a}$ and $R^{13a}$ together with the carbon atom to which they are attached form a 3-, 4-, 5-, 6-, or 7-membered cycloalkyl group or a 4-, 5-, 6-, or 7-membered heterocycloalkyl group, each optionally substituted with 1, 2, or 3 substituents independently selected from $Cy^2$, $C_{1-6}$ alkyl, $C_{1-6}$ haloalkyl, halo, CN, $OR^{a3}$, $SR^{a3}$, $C(O)R^{b3}$, $C(O)NR^{c3}R^{d3}$, $C(O)OR^3$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$, wherein said $C_{1-6}$ alkyl is optionally substituted by 1, 2, or 3 substituents independently selected from $Cy^2$, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

or $R^{17}$ and $R^{18}$ together with the carbon atom to which they are attached form a 3-, 4-, 5-, 6-, or 7-membered cycloalkyl group or a 4-, 5-, 6-, or 7-membered heterocycloalkyl group, each optionally substituted with 1, 2, or 3 substituents independently selected from $Cy^2$, $C_{1-6}$ alkyl, $C_{1-6}$ haloalkyl, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$ and $S(O)_2NR^{c3}R^{d3}$, wherein said $C_{1-6}$ alkyl is optionally substituted by 1, 2, or 3 substituents independently selected from $Cy^2$, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$ and $S(O)_2NR^{c3}R^{d3}$.

$R^{16}$ and $R^{16a}$ are each independently selected from H, $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, aryl-$C_{1-4}$ alkyl, cycloalkyl-$C_{1-4}$ alkyl, (5-10 membered heteroaryl)-$C_{1-4}$ alkyl, and (4-10 membered heterocycloalkyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, aryl-$C_{1-4}$ alkyl, cycloalkyl-$C_{1-4}$ alkyl, (5-10 membered heteroaryl)-$C_{1-4}$ alkyl, and (4-10 membered heterocycloalkyl)-$C_{1-4}$ alkyl are each optionally substituted with 1, 2, 3, 4, or 5 substituents independently selected from $Cy^3$, halo, $C_{1-6}$ alkyl, $C_{2-6}$ alkenyl, $C_{2-6}$ alkynyl, $C_{1-6}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$ $S(O)_2R^{b4}$, and $S(O)_2NR^{c4}R^{d4}$, wherein said $C_{1-6}$ alkyl, $C_{2-6}$ alkenyl, and $C_{2-6}$ alkynyl are each optionally substituted with 1, 2, or 3 substituents independently selected from $Cy^3$, halo, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$ $S(O)_2R^{b4}$, and $S(O)_2NR^{c4}R^{d4}$;

$R^A$ and $R^B$ are each independently selected from H, $C_{1-4}$ alkyl, $C_{1-4}$ haloalkyl, $C_{2-4}$ alkenyl, $C_{2-4}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl, wherein said $C_{1-4}$ alkyl, $C_{2-4}$ alkenyl, $C_{2-4}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

$Cy^1$, $Cy^2$, and $Cy^3$ are each independently selected from $C_{6-10}$ aryl, $C_{3-10}$ cycloalkyl, 5-10 membered heteroaryl, 4-10 membered heterocycloalkyl, each of which is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 3-10 membered heterocycloalkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $C(=NR^{e5})NR^{c5}R^{d5}$, $NR^{c5}C(=NR^{e5})NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$;

each $R^a$, $R^b$, $R^c$, $R^d$, $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, and $R^{d4}$, $R^{a5}$, $R^{b5}$, $R^{c5}$, and $R^{d5}$ is independently selected from H, $C_{1-6}$ alkyl, $C_{1-4}$haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl is optionally substituted with 1, 2, 3, 4, or 5 substituents independently selected from $C_{1-4}$ alkyl, $C_{1-4}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$ and $S(O)_2NR^{c6}R^{d6}$;

or any $R^c$ and $R^d$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, OR a, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(R^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, OR a, SR a, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$ and $S(O)_2NR^{c6}R^{d6}$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, OR a, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, OR a, SR a, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, and 5-6 membered heteroaryl, $C_{1-6}$ haloalkyl, halo, CN, OR a, SR a, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})R^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, OR a, SR a, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, S(O)

$R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$ and $S(O)_2NR^{c6}R^{d6}$;

or any $R^{c3}$ and $R^{d3}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, OR a, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(R^{e6})NR^{c6}R^{d6}$, $S(O)R^{6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, OR a, SR a, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$ and $S(O)_2NR^{c6}R^{d6}$;

or any $R^{c4}$ and $R^{d4}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, OR a, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, OR a, SR a, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c5}$ and $R^{d5}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, OR a, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, OR a, SR a, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$ and $S(O)_2NR^{c6}R^{d6}$;

each $R^{e1}$, $R^{e2}$, $R^{e3}$, $R^{e4}$, and $R^{e5}$ is independently selected from H, $C_{1-4}$ alkyl, CN, $OR^{a6}$ $SR^{b6}$, $S(O)_2R^{b6}$, $C(O)R^{b6}$, $S(O)_2NR^{c6}R^{d6}$, and $C(O)NR^{c6}R^{d6}$;

each $R^{a6}$, $R^{b6}$, $R^{c6}$, and $R^{d6}$ is independently selected from H, $C_{1-4}$ alkyl, $C_{1-4}$ haloalkyl, $C_{2-4}$ alkenyl, and $C_{2-4}$ alkynyl, wherein said $C_{1-4}$ alkyl, $C_{2-4}$ alkenyl, and $C_{2-4}$ alkynyl, is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

or any $R^{c6}$ and $R^{d6}$ together with the N atom to which they are attached form a 4-, 5-, 6-, or 7-membered heterocycloalkyl group optionally substituted with 1, 2, or 3 substituents independently selected from OH, CN, amino, halo, $C_{1-6}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy; and each $R^{e6}$ is independently selected from H, $C_{1-4}$ alkyl, and CN;

provided that when ring A is

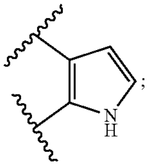 [SMILES: *c1cc[nH]c1*]

W is $NR^9$;

$R^1$, $R^2$, $R^3$ are each H; and $R^9$ is $C_{1-6}$ alkyl;

then at least four of $R^4$, $R^5$, $R^6$, $R^7$, and $R^8$ are other than H.

In some embodiments, the present invention is related to an FGFR inhibitor which is a compound of Formula I:

I

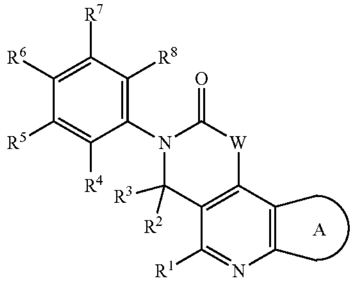

or a pharmaceutically acceptable salt thereof, wherein:

W is $NR^9$ or O;

ring A is:

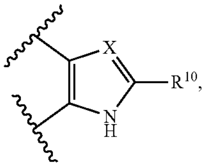

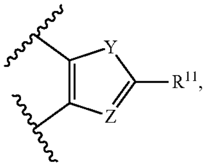

-continued

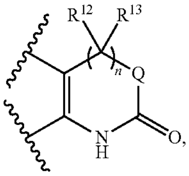 , or 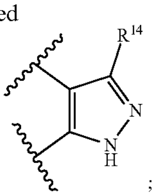 ;

X is $CR^{15}$ or N;

Y is $NR^{16}$, O, or S;

Z is N or CH;

Q is absent, O, $NR^{16}$a or $CR^{12a}R^{13a}$;

n is 0 or 1, wherein when n is 0 then Q is not absent;

$R^1$ is H, $NR^AR^B$, halo, and $C_{1-3}$ alkyl;

$R^2$ and $R^3$ are each independently selected from H, CN, $C(O)NR^cR^d$, and $C_{1-7}$ alkyl, wherein said $C_{1-7}$ alkyl is optionally substituted by 1, 2, or 3 substituents independently selected from halo, $OR^a$, CN, $NR^cR^d$, and $C(O)NR^cR^d$;

or $R^2$ and $R^3$ together with the carbon atom to which they are attached form a 3-7 membered cycloalkyl ring or a 4-7 membered heterocycloalkyl ring, each optionally substituted by 1, 2, or 3 substituents independently selected from halo, $C_{1-6}$ alkyl, $C_{1-6}$ haloalkyl, CN, $OR^{a1}$, $SR^{a1}$, $C(O)R^b$, $C(O)NR^cR^d$, $C(O)OR^a$, $OC(O)R^b$, $OC(O)NR^cR^d$, $NR^cR^d$, $NR^cC(O)R^b$, and $NR^cC(O)OR^a$;

$R^4$, $R^5$, $R^6$, $R^7$, and $R^8$ are each independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 3-10 membered heterocycloalkyl, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{c1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 3-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

$R^9$ is H, $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 3-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (3-10 membered heterocycloalkyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 3-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (3-10 membered heterocycloalkyl)-$C_{1-4}$ alkyl are each optionally substituted with 1, 2, 3, 4, or 5 substituents independently selected from $R^{9a}$;

each $R^{9a}$ is independently selected from $Cy^1$, halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^2S(O)_2NR^{c2}R^{d2}$, $S(O)R^{b2}$ $S(O)NR^{c2}R^{d2}$, $S(O)_2R^{b2}$, and $S(O)_2NR^{c2}R^{d2}$, wherein said $C_{1-6}$ alkyl, $C_{2-6}$ alkenyl, and $C_{2-6}$ alkynyl are each optionally substituted with 1, 2, or 3 substituents independently selected from $Cy^1$, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$ $S(O)_2R^{b2}$, and $S(O)_2NR^{c2}R^{d2}$;

$R^{10}$, $R^{11}$, $R^{12}$, $R^{13}$, $R^{12a}$, $R^{13a}$, $R^{14}$ and $R^{15}$ are each independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 3-10 membered heterocycloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 3-10 membered heterocycloalkyl are each optionally substituted with 1, 2, 3, 4, or 5 substituents independently selected from $R^{10a}$;

each $R^{10a}$ is independently selected from $Cy^2$, halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$, wherein said $C_{1-6}$ alkyl, $C_{2-6}$ alkenyl, and $C_{2-6}$ alkynyl are each optionally substituted with 1, 2, or 3 substituents independently selected from $Cy^2$, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$ $S(O)_2R^{b3}$, and $S(O)_2NR^{c3}R^{d3}$;

or $R^{12}$ and $R^{13}$ together with the carbon atom to which they are attached form a 3-, 4-, 5-, 6-, or 7-membered cycloalkyl group or a 4-, 5-, 6-, or 7-membered heterocycloalkyl group, each optionally substituted with 1, 2, or 3 substituents independently selected from $Cy^2$, $C_{1-6}$ alkyl, $C_{1-6}$ haloalkyl, halo, CN, $OR^{a3}$, $SR^{a3}$, $C(O)R^{b3}$, $C(O)NR^{c3}R^{d3}$, $C(O)OR^3$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$ and $S(O)_2NR^{c3}R^{d3}$, wherein said $C_{1-6}$ alkyl is optionally substituted by 1, 2, or 3 substituents independently selected from $Cy^2$, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$ and $S(O)_2NR^{c3}R^{d3}$;

or $R^{12a}$ and $R^{13a}$ together with the carbon atom to which they are attached form a 3-, 4-, 5-6-, or 7-membered cycloalkyl group or a 4-, 5-, 6-, or 7-membered heterocycloalkyl group, each optionally substituted with 1, 2, or 3 substituents independently selected from $Cy^2$, $C_{1-6}$ alkyl, $C_{1-6}$ haloalkyl, halo, CN, $OR^{a3}$, $SR^{a3}$, $C(O)R^{b3}$, $C(O)NR^{c3}R^{d3}$, $C(O)OR^3$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$ and $S(O)_2NR^{c3}R^{d3}$, wherein said $C_{1-6}$ alkyl is optionally substituted by 1, 2, or 3 substituents independently selected from $Cy^2$, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

$R^{16}$ and $R^{16a}$ are each independently selected from H, $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 3-10 membered heterocycloalkyl, aryl-$C_{1-4}$ alkyl, cycloalkyl-$C_{1-4}$ alkyl, heteroaryl-$C_{1-4}$ alkyl, and heterocycloalkyl-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 3-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (3-10 membered heterocycloalkyl)-$C_{1-4}$ alkyl are each optionally substituted with 1, 2, 3, 4, or 5 substituents independently selected from $Cy^3$, halo, $C_{1-6}$ alkyl, $C_{2-6}$ alkenyl, $C_{2-6}$ alkynyl, $C_{1-6}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$, wherein said $C_{1-6}$ alkyl, $C_{2-6}$ alkenyl, and $C_{2-6}$ alkynyl are each optionally substituted with 1, 2, or 3 substituents independently selected from $Cy^3$, halo, CN, $NO_2$, $OR^{a4}$, $SR^{a4}$, $C(O)R^{b4}$, $C(O)NR^{c4}R^{d4}$, $C(O)OR^{a4}OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$;

$R^A$ and $R^B$ are each independently selected from H, $C_{1-4}$ alkyl, $C_{1-4}$ haloalkyl, $C_{2-4}$ alkenyl, $C_{2-4}$ alkynyl, $C_{6-10}$ aryl, $C_{3-10}$ cycloalkyl, 5-10 membered heteroaryl, 3-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (3-10 membered heterocycloalkyl)-$C_{1-4}$ alkyl, wherein said $C_{1-4}$ alkyl, $C_{2-4}$ alkenyl, $C_{2-4}$ alkynyl, $C_{6-10}$ aryl, $C_{3-10}$ cycloalkyl, 5-10 membered heteroaryl, 3-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (3-10 membered heterocycloalkyl)-$C_{1-4}$ alkyl is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

$Cy^1$, $Cy^2$, and $Cy^3$ are each independently selected from $C_{6-10}$ aryl, $C_{3-10}$ cycloalkyl, 5-10 membered heteroaryl, 3-10 membered heterocycloalkyl, each of which is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 3-10 membered heterocycloalkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 3-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $C(=NR^{e5})NR^{c5}R^{d5}$, $NR^{c5}C(=NR^{e5})NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$;

each $R^a$, $R^b$, $R^c$, $R^d$, $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, and $R^{d4}$, $R^{a5}$, $R^{b5}$, $R^{c5}$, and $R^{d5}$ is independently selected from H, $C_{1-6}$ alkyl, $C_{1-4}$haloalkyl, $C_{2-6}$ alkenyl, $C_{2-6}$ alkynyl, $C_{6-10}$ aryl, $C_{3-10}$ cycloalkyl, 5-10 membered heteroaryl, 3-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (3-10 membered heterocycloalkyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 3-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (3-10 membered heterocycloalkyl)-$C_{1-4}$ alkyl is optionally substituted with 1, 2, 3, 4, or 5 substituents independently selected from $C_{1-4}$ alkyl, $C_{1-4}$ haloalkyl, halo, CN, OR a, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$ and $S(O)_2NR^{c6}R^{d6}$;

or any $R^c$ and $R^d$ together with the N atom to which they are attached form a 3-, 4-, 5-, 6-, or 7-membered heterocycloalkyl group optionally substituted with 1, 2, or 3 substituents independently selected from $C_{1-6}$ alkyl, $C_{3-7}$ cycloalkyl, 3-7 membered heterocycloalkyl, $C_{6-10}$ aryl, 5-6 membered heteroaryl, $C_{1-6}$ haloalkyl, halo, CN, OR a, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(R^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 3-7 membered heterocycloalkyl, $C_{6-10}$ aryl, and 5-6 membered heteroaryl are optionally substituted by 1, 2, or 3 substituents independently selected from halo, CN, OR a, SR a, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$ and $S(O)_2NR^{c6}R^{d6}$;

or any $R^{c1}$ and $R^{d1}$ together with the N atom to which they are attached form a 3-, 4-, 5-, 6-, or 7-membered heterocycloalkyl group optionally substituted with 1, 2, or 3 substituents independently selected from $C_{1-6}$ alkyl, $C_{3-7}$ cycloalkyl, 3-7 membered heterocycloalkyl, $C_{6-10}$ aryl, 5-6 membered heteroaryl, $C_{1-6}$ haloalkyl, halo, CN, OR a, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 3-7 membered heterocycloalkyl, $C_{6-10}$ aryl, and 5-6 membered heteroaryl are optionally substituted by 1, 2, or 3 substituents independently selected from halo, CN, OR a, SR a, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c2}$ and $R^{d2}$ together with the N atom to which they are attached form a 3-, 4-, 5-, 6-, or 7-membered heterocycloalkyl group optionally substituted with 1, 2, or 3 substituents independently selected from $C_{1-6}$ alkyl, $C_{3-7}$ cycloalkyl, 3-7 membered heterocycloalkyl, $C_{6-10}$ aryl, and 5-6 membered heteroaryl, $C_{1-6}$ haloalkyl, halo, CN, $OR^{a6}$, $SR^{a6}$, $C(O)R^{b6}$, $C(O)NR^{c6}R^{d6}$ $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 3-7 membered heterocycloalkyl, $C_{6-10}$ aryl, and 5-6 membered heteroaryl are optionally substituted by 1, 2, or 3 substituents independently selected from halo, CN, OR a, SR a, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c3}$ and $R^{d3}$ together with the N atom to which they are attached form a 3-, 4-, 5-, 6-, or 7-membered heterocycloalkyl group optionally substituted with 1, 2, or 3 substituents independently selected from $C_{1-6}$ alkyl, $C_{3-7}$ cycloalkyl, 3-7 membered heterocycloalkyl, $C_{6-10}$ aryl, 5-6 membered heteroaryl, $C_{1-6}$ haloalkyl, halo, CN, OR a, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 3-7 membered heterocycloalkyl, $C_{6-10}$ aryl, and 5-6 membered heteroaryl are optionally substituted by 1, 2, or 3 substituents independently selected from halo, CN, OR a, SR a, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c4}$ and $R^{d4}$ together with the N atom to which they are attached form a 3-, 4-, 5-, 6-, or 7-membered heterocycloalkyl group optionally substituted with 1, 2, or 3 substituents independently selected from $C_{1-6}$ alkyl, $C_{3-7}$ cycloalkyl, 3-7 membered heterocycloalkyl, $C_{6-10}$ aryl, 5-6 membered heteroaryl, $C_{1-6}$ haloalkyl, halo, CN, OR a, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 3-7 membered heterocycloalkyl, $C_{6-10}$ aryl, and 5-6 membered heteroaryl are optionally substituted by 1, 2, or 3 substituents independently selected from halo, CN, OR a, SR a, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$ and $S(O)_2NR^{c6}R^{d6}$;

or any $R^{c5}$ and $R^{d5}$ together with the N atom to which they are attached form a 3-, 4-, 5-, 6-, or 7-membered heterocycloalkyl group optionally substituted with 1, 2, or 3 substituents independently selected from $C_{1-6}$ alkyl, $C_{3-7}$ cycloalkyl, 3-7 membered heterocycloalkyl, $C_{6-10}$ aryl, 5-6 membered heteroaryl, $C_{1-6}$ haloalkyl, halo, CN, OR a, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 3-7 membered heterocycloalkyl, $C_{6-10}$ aryl, and 5-6 membered heteroaryl are optionally substituted by 1, 2, or 3 substituents independently selected from halo, CN, OR a, SR a, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$ and $S(O)_2NR^{c6}R^{d6}$; each $R^{e1}$, $R^{e2}$, $R^{e3}$, $R^{e4}$, and $R^{e5}$ is independently selected from H, $C_{1-4}$ alkyl, CN, $OR^{a6}$, $SR^{b6}$, $S(O)_2R^6$, $C(O)R^{b6}$, $S(O)_2NR^{c6}R^{d6}$, and $C(O)NR^{c6}R^{d6}$;

each $R^{a6}$, $R^{b6}$, $R^{c6}$, and $R^{d6}$ is independently selected from H, $C_{1-4}$ alkyl, $C_{1-4}$ haloalkyl, $C_{2-4}$ alkenyl, and $C_{2-4}$ alkynyl, wherein said $C_{1-4}$ alkyl, $C_{2-4}$ alkenyl, and $C_{2-4}$ alkynyl, is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

or any $R^{c6}$ and $R^{d6}$ together with the N atom to which they are attached form a 3-, 4-, 5-, 6-, or 7-membered heterocycloalkyl group optionally substituted with 1, 2, or 3 substituents independently selected from OH, CN, amino, halo, $C_{1-6}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy; and each $R^{e6}$ is independently selected from H, $C_{1-4}$ alkyl, and CN;

provided that when ring A is

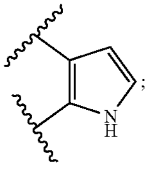 [SMILES: *c1cc[nH]c1*];

W is $NR^9$;

$R^1$, $R^2$, $R^3$ are each H; and $R^9$ is $C_{1-6}$ alkyl;

then at least four of $R^4$, $R^5$, $R^6$, $R^7$, and $R^8$ are other than H.

In some embodiments:

$R^4$, $R^5$, $R^6$, $R^7$, and $R^8$ are each independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$ $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=R^{c1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

$R^9$ is H, $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl are each optionally substituted with 1, 2, 3, 4, or 5 substituents independently selected from $R^{9a}$;

each $R^{9a}$ is independently selected from $Cy^1$, halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{e2}R^{d2}$, $S(O)R^{b2}$ $S(O)NR^{c2}R^{d2}$, $S(O)_2R^{b2}$, and $S(O)_2NR^{e2}R^{d2}$, wherein said $C_{1-6}$ alkyl, $C_{2-6}$ alkenyl, and $C_{2-6}$ alkynyl are each optionally substituted with 1, 2, or 3 substituents independently selected from $Cy^1$, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$ $S(O)_2R^{12}$, and $S(O)_2NR^{c2}R^{d2}$;

$R^{10}$, $R^{11}$, $R^{12}$, $R^{13}$, $R^{12a}$, $R^{13a}$, $R^{14}$ and $R^{15}$ are each independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from $R^{10a}$;

each $R^{10a}$ is independently selected from $Cy^2$, halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{d3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$, wherein said $C_{1-6}$ alkyl, $C_{2-6}$ alkenyl, and $C_{2-6}$ alkynyl are each optionally substituted with 1, 2, or 3 substituents independently selected from $Cy^2$, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$ $S(O)_2R^{b3}$, and $S(O)_2NR^{c3}R^{d3}$;

or $R^{12}$ and $R^{13}$ together with the carbon atom to which they are attached form a 3-, 4-, 5-, 6-, or 7-membered cycloalkyl group or a 4-, 5-, 6-, or 7-membered heterocycloalkyl group, each optionally substituted with 1, 2, or 3 substituents independently selected from $Cy^2$, $C_{1-6}$ alkyl, $C_{1-6}$ haloalkyl, halo, CN, $OR^{a3}$, $SR^{a3}$, $C(O)R^{b3}$, $C(O)NR^{c3}R^{d3}$, $C(O)OR^3$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$ and $S(O)_2NR^{c3}R^{d3}$, wherein said $C_{1-6}$ alkyl is optionally substituted by 1, 2, or 3 substituents independently selected from $Cy^2$, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$ and $S(O)_2NR^{c3}R^{d3}$;

or $R^{12a}$ and $R^{13a}$ together with the carbon atom to which they are attached form a 3-, 4-, 5-, 6-, or 7-membered cycloalkyl group or a 4-, 5-, 6-, or 7-membered heterocycloalkyl group, each optionally substituted with 1, 2, or 3 substituents independently selected from $Cy^2$, $C_{1-6}$ alkyl, $C_{1-6}$ haloalkyl, halo, CN, $OR^{a3}$, $SR^{a3}$, $C(O)R^{b3}$, $C(O)NR^{c3}R^{d3}$, $C(O)OR^3$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$ and $S(O)_2NR^{C3}R^{d3}$, wherein said $C_{1-6}$ alkyl is optionally substituted by 1, 2, or 3 substituents independently selected from $Cy^2$, halo, CN, $OR^{a3}$, $SR^{a3}$, $C(O)R^{b3}$, $C(O)NR^{C3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

$R^{16}$ and $R^{16a}$ are each independently selected from H, $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl are each optionally substituted with 1, 2, 3, 4, or 5 substituents independently selected from $Cy^3$, halo, $C_{1-6}$ alkyl, $C_{2-6}$ alkenyl, $C_{2-6}$ alkynyl, $C_{1-6}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$ $S(O)_2R^{b4}$, and $S(O)_2NR^{c4}R^{d4}$, wherein said $C_{1-6}$ alkyl, $C_{2-6}$ alkenyl, and $C_{2-6}$ alkynyl are each optionally substituted with 1, 2, or 3 substituents independently selected from $Cy^3$, halo, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$ $S(O)_2R^{b4}$, and $S(O)_2NR^{c4}R^{d4}$;

$R^A$ and $R^B$ are each independently selected from H, $C_{1-4}$ alkyl, $C_{1-4}$ haloalkyl, $C_{2-4}$ alkenyl, $C_{2-4}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl, wherein said $C_{1-4}$ alkyl, $C_{2-4}$ alkenyl, $C_{2-4}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

$Cy^1$, $Cy^2$, and $Cy^3$ are each independently selected from $C_{6-10}$ aryl, $C_{3-10}$ cycloalkyl, 5-10 membered heteroaryl, 4-10 membered heterocycloalkyl, each of which is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{c5})NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $C(=NR^{e5})NR^{c5}R^{d5}$, $NR^{c5}C(=NR^{e5})NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$;

each $R^a$, $R^b$, $R^c$, $R^d$, $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, and $R^{d4}$, $R^{a5}$, $R^{b5}$, $R^{c5}$, and $R^{d5}$ is independently selected from H, $C_{1-6}$ alkyl, $C_{1-4}$haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl is optionally substituted with 1, 2, 3, 4, or 5 substituents independently selected from $C_{1-4}$ alkyl, $C_{1-4}$ haloalkyl, halo, CN, OR a, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$ and $S(O)_2NR^{c6}R^{d6}$;

or any $R^c$ and $R^d$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, OR a, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(R^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, OR a, SR a, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$ and $S(O)_2NR^{c6}R^{d6}$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, OR a, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})R^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, OR a, SR a, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, and 5-6 membered heteroaryl, $C_{1-6}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(R^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, OR a, SR a, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$ and $S(O)_2NR^{c6}R^{d6}$;

or any $R^{c3}$ and $R^{d3}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, OR a, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, OR a, SR a, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c4}$ and $R^{d4}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, OR a, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})R^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, OR a, SR a, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$ and $S(O)_2NR^{c6}R^{d6}$;

or any $R^{c5}$ and $R^{d5}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, OR a, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, OR a, SR a, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$ and $S(O)_2NR^{c6}R^{d6}$; each $R^{e1}$, $R^{e2}$, $R^{e3}$, $R^{e4}$, and $R^{e5}$ is independently selected from H, $C_{1-4}$ alkyl, CN, $OR^{a6}$, $SR^{b6}$, $S(O)_2R^{b6}$, $C(O)R^{b6}$, $S(O)_2NR^{c6}R^{d6}$, and $C(O)NR^{c6}R^{d6}$;

each $R^{a6}$, $R^{b6}$, $R^{c6}$, and $R^{d6}$ is independently selected from H, $C_{1-4}$ alkyl, $C_{1-4}$ haloalkyl, $C_{2-4}$ alkenyl, and $C_{2-4}$ alkynyl, wherein said $C_{1-4}$ alkyl, $C_{2-4}$ alkenyl, and $C_{2-4}$ alkynyl, is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

or any $R^{c6}$ and $R^{d6}$ together with the N atom to which they are attached form a 4-, 5-, 6-, or 7-membered heterocycloalkyl group optionally substituted with 1, 2, or 3 substituents independently selected from OH, CN, amino, halo, $C_{1-6}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy; and each $R^6$ is independently selected from H, $C_{1-4}$ alkyl, and CN.

In some embodiments, W is $NR^9$ or O.

In some embodiments, W is O.

In some embodiments, W is $NR^9$ or $CR^{17}CR^{18}$.

In some embodiments, W is $CR^{17}CR^{18}$.

In some embodiments, W is $NR^9$.

In some embodiments, $R^9$ is H, $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl are each optionally substituted with 1, 2, 3, 4, or 5 substituents independently selected from $R^{9a}$.

In some embodiments, $R^9$ is H, $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl, wherein said $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_1$-4 alkyl, and (4-10 membered heterocycloalkyl)-$C_{1-4}$alkyl are each optionally substituted with 1, 2, or 3 $R^{9a}$.

In some embodiments, $R^9$ is H, $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl, wherein said $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_1$-4 alkyl, and (4-10 membered heterocycloalkyl)-$C_{1-4}$ alkyl are each optionally substituted with $R^{9a}$.

In some embodiments, $R^9$ is H, $C_{1-6}$ alkyl, $C_{3-10}$ cycloalkyl, 5-10 membered heteroaryl, 4-10 membered heterocycloalkyl, $C_{6-10}$ aryl, $C_{6-10}$ aryl-$C_{1-4}$ alkyl, $C_{3-10}$ cycloalkyl-$C_{1-4}$ alkyl, or (5-10 membered heteroaryl)-$C_{1-4}$ alkyl, each optionally substituted with with 1, 2, or 3 substituents independently selected from $R^{9a}$.

In some embodiments, $R^9$ is H, $C_{1-6}$ alkyl, $C_{3-10}$ cycloalkyl, 5-10 membered heteroaryl, 4-10 membered heterocycloalkyl, $C_{6-10}$ aryl, $C_{6-10}$ aryl-$C_{1-4}$ alkyl, or $C_{3-10}$ cycloalkyl-$C_{1-4}$ alkyl, each optionally substituted with with 1, 2, or 3 substituents independently selected from $R^{9a}$.

In some embodiments, $R^9$ is H, $C_{1-6}$ alkyl, $C_{3-10}$ cycloalkyl, 3-10 membered heterocycloalkyl, $C_{6-10}$ aryl, $C_{6-10}$ aryl-$C_{1-4}$ alkyl, or $C_{3-10}$ cycloalkyl-$C_{1-4}$ alkyl, each optionally substituted with with 1, 2, or 3 substituents independently selected from $R^{9a}$.

In some embodiments, $R^9$ is H, $C_{1-6}$ alkyl optionally substituted by OH, $C_{3-10}$ cycloalkyl, 3-10 membered heterocycloalkyl, $C_{6-10}$ aryl-$C_{1-4}$ alkyl, or $C_{3-10}$ cycloalkyl-$C_{1-4}$ alkyl.

In some embodiments, $R^9$ is H, $C_{1-6}$ alkyl optionally substituted by OH, $C_{3-10}$ cycloalkyl, 4-10 membered heterocycloalkyl, $C_{6-10}$ aryl-$C_{1-4}$ alkyl, or $C_{3-10}$ cycloalkyl-$C_{1-4}$ alkyl.

In some embodiments, $R^9$ is H, $C_{1-6}$ alkyl, $C_{3-10}$ cycloalkyl, 3-10 membered heterocycloalkyl, $C_{6-10}$ aryl-$C_{1-4}$ alkyl, or $C_{3-10}$ cycloalkyl-$C_{1-4}$ alkyl.

In some embodiments, $R^9$ is H, $C_{1-6}$ alkyl, $C_{3-10}$ cycloalkyl, 4-10 membered heterocycloalkyl, $C_{6-10}$ aryl-$C_{1-4}$ alkyl, or $C_{3-10}$ cycloalkyl-$C_{1-4}$ alkyl.

In some embodiments, $R^9$ is $C_{1-6}$ alkyl.

In some embodiments, $R^9$ is methyl.

In some embodiments, $R^9$ is phenyl optionally substituted with with 1, 2, or 3 substituents independently selected from $R^{9a}$.

In some embodiments, $R^9$ is 5-10 membered heteroaryl optionally substituted with with 1, 2, or 3 substituents independently selected from $R^{9a}$.

In some embodiments, $R^9$ is pyridyl optionally substituted with with 1, 2, or 3 substituents independently selected from $R^{9a}$.

In some embodiments, $R^9$ is pyridyl.

In some embodiments, $R^{17}$ and $R^{18}$ are each independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{c3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from $R^{10a}$.

In some embodiments, $R^{17}$ and $R^{18}$ are each independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, and CN, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from $R^{10a}$.

In some embodiments, $R^{17}$ and $R^{18}$ are each independently selected from H, halo, $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, $C_{2-6}$ alkynyl, are each optionally substituted with 1, 2, 3, 4, or 5 substituents independently selected from $R^{10a}$.

In some embodiments, $R^{17}$ and $R^{18}$ are each independently selected from H and $C_{1-6}$ alkyl.

In some embodiments, $R^{17}$ is H.

In some embodiments, $R^{18}$ is H.

In some embodiments, $R^{17}$ and $R^{18}$ are both H.

In some embodiments, $R^{17}$ and $R^{18}$ are both $C_{1-6}$ alkyl.

In some embodiments, $R^{17}$ and $R^{18}$ together with the carbon atom to which they are attached form $C_{3-7}$ cycloalkyl.

In some embodiments, $R^2$ and $R^3$ are each independently selected from H, CN, $C(O)NR^cR^d$, and $C_{1-7}$ alkyl, wherein said $C_{1-7}$ alkyl is optionally substituted by 1, 2, or 3 substituents independently selected from halo, $OR^{a1}$, CN, $NR^cR^d$, and $C(O)NR^cR^d$.

In some embodiments, $R^2$ and $R^3$ are each H.

In some embodiments, each of $R^1$, $R^2$, and $R^3$ is H.

In some embodiments, each of $R^1$, $R^2$, $R^3$, $R^{12}$, and $R^{13}$ is H.

In some embodiments, $R^4$, $R^5$, $R^6$, $R^7$, and $R^8$ are each independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$ $S(O)_2R^{b1}$, and $S(O)_2NR^{c1}R^{d1}$.

In some embodiments, at least one of $R^4$, $R^5$, $R^6$, $R^7$, and $R^8$ is other than H.

In some embodiments, at least two of $R^4$, $R^5$, $R^6$, $R^7$, and $R^8$ is other than H.

In some embodiments, $R^4$, $R^5$, $R^6$, $R^7$, and $R^8$ are each independently selected from H, halo, $C_{1-6}$ alkyl, $C_{1-6}$ haloalkyl, CN, and $OR^{a1}$.

In some embodiments, $R^4$, $R^5$, $R^6$, $R^7$, and $R^8$ are each independently selected from H, halo, and methoxy.

In some embodiments, $R^5$ and $R^7$ are both methoxy and $R^4$, $R^6$, and $R^8$ are each independently selected from H and halo.

In some embodiments, $R^4$ is halo, $R^5$ is methoxy, $R^6$ is H, $R^7$ is methoxy, and $R^8$ is halo.

In some embodiments, $R^{10}$, $R^{11}$, $R^{12}$, $R^{13}$, $R^{12a}$, $R^{13a}$, $R^{14}$ and $R^{15}$ are each independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C({=}NR^{c3})R^{b3}$, $C({=}NR^{e3})NR^{c3}R^{d3}$, $NR^{c3}C({=}NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from $R^{10a}$.

In some embodiments, $R^{12}$ and $R^{13}$ are each independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 3-10 membered heterocycloalkyl, CN, $NO_2$, $OR^{a3}$, $SR^3$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C({=}NR^{e3})R^{b3}$, $C({=}NR^{e3})NR^{c3}R^{d3}$, $NR^{c3}C({=}NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 3-10 membered heterocycloalkyl are each optionally substituted with 1, 2, 3, 4, or 5 substituents independently selected from $R^{10a}$.

In some embodiments, $R^{12}$ and $R^{13}$ are each independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C({=}NR^{e3})R^{b3}$, $C({=}NR^{e3})NR^{c3}R^{d3}$, $NR^{c3}C({=}NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from $R^{10a}$.

In some embodiments, $R^{12}$ and $R^{13}$ together with the carbon atom to which they are attached form a 3-, 4-, 5-, 6-, or 7-membered cycloalkyl group optionally substituted with 1, 2, or 3 substituents independently selected from $Cy^2$, $C_{1-6}$ alkyl, $C_{1-6}$ haloalkyl, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C({=}NR^{e3})NR^{c3}R^{d3}$, $NR^{c3}C({=}NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$, wherein said $C_{1-6}$ alkyl is optionally substituted by 1, 2, or 3 substituents independently selected from $Cy^2$, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C({=}NR^{e3})NR^{c3}R^{d3}$, $NR^{c3}C({=}NR^{e3})NR^{c3}R^{d3}$ $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$. In some embodiments, $R^{12}$ and $R^{13}$ together with the carbon atom to which they are attached form a 3-, 4-, 5-, 6-, or 7-membered cycloalkyl group.

In some embodiments, the compound has Formula II, III, or IV:

II

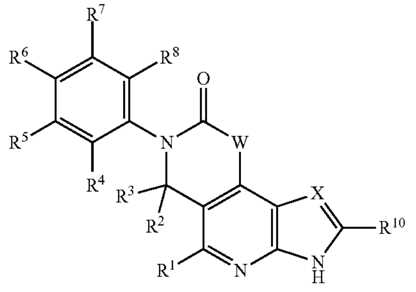

III

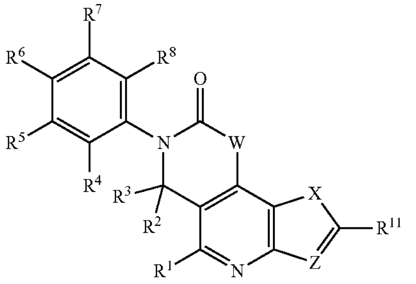

IV

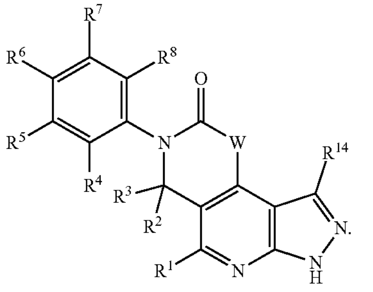

In some embodiments, the compound has Formula II.

In some embodiments where the compound has Formula II, W is $NR^9$ or $CR^{17}R^{18}$.

In some embodiments where the compound has Formula II, W is $NR^9$.

In some embodiments where the compound has Formula II, W is $CR^{17}R^{18}$.

In some embodiments where the compound has Formula II, X is $CR^5$.

In some embodiments where the compound has Formula II, X is CH.

In some embodiments, $R^{15}$ is H or 5-10 membered heteroaryl optionally substituted by $C_{1-6}$ alkyl.

In some embodiments, $R^{10}$ is H, $C_{1-6}$ alkyl, $C_{6-10}$ aryl, $C_{3-10}$ cycloalkyl, 5-10 membered heteroaryl, 4-10 membered heterocycloalkyl, CN, or $C(O)NR^{c3}R^{d3}$, wherein said $C_{1-6}$ alkyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from $Cy^2$, halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C({=}NR^{e3})NR^{c3}R^{d3}$, $NR^3C({=}NR^3)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$, wherein said $C_{1-6}$ alkyl, $C_{2-6}$ alkenyl, and $C_{2-6}$ alkynyl are each optionally substituted with 1, 2, or 3 substituents independently selected from $Cy^2$, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$.

In some embodiments, $R^{10}$ is H, $C_{6-10}$ aryl, $C_{3-10}$ cycloalkyl, 5-10 membered heteroaryl, 4-10 membered heterocycloalkyl, CN, or $C(O)NR^{c3}R^{d3}$, wherein said $C_{10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from $Cy^2$, halo, $C_{1-6}$ alkyl, $C_{2-6}$ alkenyl, $C_{2-6}$ alkynyl, $C_{1-6}$ haloalkyl, CN, $NO_2$, $OR^3$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$, wherein said $C_{1-6}$ alkyl, $C_{2-6}$ alkenyl, and $C_{2-6}$ alkynyl are each optionally substituted with 1, 2, or 3 substituents independently selected from $Cy^2$, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$ $S(O)_2R^{b3}$, and $S(O)_2NR^{c3}R^{d3}$.

In some embodiments where the compound has Formula II, $R^{10}$ is H, $C_{6-10}$ aryl, $C_{3-10}$ cycloalkyl, 5-10 membered heteroaryl, 3-10 membered heterocycloalkyl, CN, or $C(O)NR^{c3}R^{d3}$ wherein said $C_{6-10}$ aryl, $C_{3-10}$ cycloalkyl, 5-10 membered heteroaryl, and 3-10 membered heterocycloalkyl are each optionally substituted with 1, 2, 3, 4, or 5 substituents independently selected from $R^{10a}$.

In some embodiments where the compound has Formula II, $R^{10}$ is H, $C_{6-10}$ aryl, $C_{3-10}$ cycloalkyl, 5-10 membered heteroaryl, 4-10 membered heterocycloalkyl, CN, or $C(O)NR^{c3}R^{d3}$ wherein said $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from $R^{10a}$.

In some embodiments where the compound has Formula II, $R^{10}$ is H, methyl, ethyl, phenyl, pyrazolyl, piperidinyl, tetrahydropyridinyl, CN, or $C(O)NR^{c3}R^{d3}$, wherein said methyl, ethyl, phenyl, pyrazolyl, piperidinyl, and tetrahydropyridinyl are each optionally substituted with 1, 2, or 3 substituents independently selected from $Cy^2$, $NR^{c3}R^{d3}$, and $C_{1-6}$ alkyl optionally substituted with $OR^{a3}$.

In some embodiments where the compound has Formula II, $R^{10}$ is H, phenyl, pyrazolyl, piperidinyl, tetrahydropyridinyl, CN, or $C(O)NR^{c3}R^{d3}$, wherein said phenyl, pyrazolyl, piperidinyl, and tetrahydropyridinyl are each optionally substituted with 1, 2, or 3 substituents independently selected from $Cy^2$ and $C_{1-6}$ alkyl optionally substituted with $OR^{a3}$.

In some embodiments where the compound has Formula II, $R^{10}$ is H, (4-methylpiperazin-1-yl)phenyl, 1-methyl-1H-pyrazolyl, 1-(2-hydroxyethyl)-1H-pyrazolyl, methylaminocarbonyl, cyano, 1-methyl-1,2,3,6-tetrahydropyridinyl, 1-methylpiperidin-4-yl, dimethylaminocarbonyl, (3-hydroxyazetidin-1-yl)carbonyl, (3-hydroxypyrrolidin-1-yl)carbonyl, (4-methylpiperazin-1-yl)carbonyl, cyclopropylaminocarbonyl, (3-cyanopyrrolidin-1-yl)carbonyl, (3-hydroxypiperidin-1-yl)carbonyl, tetrahydro-2H-pyran-4-yl, (4-methylpiperazin-1-yl)carbonyl, morpholin-4-ylcarbonyl, or (4,4-difluoropiperidin-1-yl)carbonyl.

In some embodiments where the compound has Formula II, $R^{10}$ is H, (4-methylpiperazin-1-yl)phenyl, 1-methyl-1H-pyrazolyl, 1-(2-hydroxyethyl)-1H-pyrazolyl, methylaminocarbonyl, cyano, 1-methyl-1,2,3,6-tetrahydropyridinyl, 1-methylpiperidin-4-yl, dimethylaminocarbonyl, (3-hydroxyazetidin-1-yl)carbonyl, (3-hydroxypyrrolidin-1-yl)carbonyl, (4-methylpiperazin-1-yl)carbonyl, cyclopropylaminocarbonyl, (3-cyanopyrrolidin-1-yl)carbonyl, or (3-hydroxypiperidin-1-yl)carbonyl.

In some embodiments where the compound has Formula II, $R^{10}$ is H, (4-methylpiperazin-1-yl)phenyl, 1-methyl-1H-pyrazolyl, 1-(2-hydroxyethyl)-1H-pyrazolyl, methylaminocarbonyl, cyano, 1-methyl-1,2,3,6-tetrahydropyridinyl, 1-methylpiperidin-4-yl, dimethylaminocarbonyl, (3-hydroxyazetidin-1-yl)carbonyl, (3-hydroxypyrrolidin-1-yl)carbonyl, (4-methylpiperazin-1-yl)carbonyl, cyclopropylaminocarbonyl, (3-cyanopyrrolidin-1-yl)carbonyl, (3-hydroxypiperidin-1-yl)carbonyl, morpholin-4-ylmethyl, (4-methylpiperazin-1-yl)methyl, 4-ethylpiperazin-1-yl)methyl, 4-(2-hydroxyethyl)piperazin-1-yl]methyl, cyanoethylpiperazinylmethyl, cyanopiperidinylmethyl, cyanopyrolidinylmethyl, (1-methylpiperidin-4-yl)aminomethyl, (tetrahydrofuran-3-ylamino)methyl, 1H-imidazol-1-ylmethyl, 1H-pyrazol-1-ylmethyl, (1-methyl-1H-pyrazol-4-yl)methyl, 2-pyridin-2-ylethyl, 2-morpholin-4-ylethyl, 2-(diethylamino)ethyl, 2-(3-fluoroazetidin-1-yl)ethyl, 2-(3-methoxyazetidin-1-yl)ethyl, (4-ethylpiperazin-1-yl)methyl, 3-(dimethylamino)pyrrolidin-1-yl]methyl, 2-(4-ethylpiperazin-1-yl)ethyl, 2-(4-methylpiperazin-1-yl)ethyl, (pyridin-3-yloxy)methyl, (2-oxopyridin-1(2H)-yl)methyl, (3-cyanoazetidin-1-yl)methyl, (3-fluoroazetidin-1-yl)methyl, or (3-hydroxyazetidin-1-yl)methyl.

In some embodiments where the compound has Formula II, $R^{10}$ is morpholin-4-ylmethyl, (4-methylpiperazin-1-yl)methyl, 4-ethylpiperazin-1-yl)methyl, (4-methylpiperazin-1-yl)methyl, 4-(2-hydroxyethyl)piperazin-1-yl]methyl, cyanoethylpiperazinylmethyl, cyanopiperidinylmethyl, cyanopyrolidinylmethyl, (1-methylpiperidin-4-yl)aminomethyl, (tetrahydrofuran-3-ylamino)methyl, 1H-imidazol-1-ylmethyl, 1H-pyrazol-1-ylmethyl, (1-methyl-1H-pyrazol-4-yl)methyl, 2-pyridin-2-ylethyl, 2-morpholin-4-ylethyl, 2-(diethylamino)ethyl, 2-(3-fluoroazetidin-1-yl)ethyl, 2-(3-methoxyazetidin-1-yl)ethyl, (4-ethylpiperazin-1-yl)methyl, 3-(dimethylamino)pyrrolidin-1-yl]methyl, or 2-(4-ethylpiperazin-1-yl)ethyl, 2-(4-methylpiperazin-1-yl)ethyl.

In some embodiments where the compound has Formula II, $R^{10}$ is morpholin-4-ylmethyl, (4-methylpiperazin-1-yl)methyl, 4-ethylpiperazin-1-yl)methyl, (4-methylpiperazin-1-yl)methyl, 4-(2-hydroxyethyl)piperazin-1-yl]methyl, cyanoethylpiperazinylmethyl, cyanopiperidinylmethyl, cyanopyrolidinylmethyl, 1H-imidazol-1-ylmethyl, 1H-pyrazol-1-ylmethyl, (1-methyl-1H-pyrazol-4-yl)methyl, (4-ethylpiperazin-1-yl)methyl, or 3-(dimethylamino)pyrrolidin-1-yl]methyl.

In some embodiments where the compound has Formula II, $R^{10}$ is 2-pyridin-2-ylethyl, 2-morpholin-4-ylethyl, 2-(diethylamino)ethyl, 2-(3-fluoroazetidin-1-yl)ethyl, 2-(3-methoxyazetidin-1-yl)ethyl, 2-(4-ethylpiperazin-1-yl)ethyl, or 2-(4-methylpiperazin-1-yl)ethyl.

In some embodiments $R^{10}$ is $C_{1-6}$ alkyl optionally substituted with 1, 2, or 3 substituents independently selected from $Cy^2$, $NR^{c3}R^{d3}$, and $C_{1-6}$ alkyl optionally substituted with $OR^{a3}$.

In some embodiments $R^{10}$ is $C_{1-6}$ alkyl optionally substituted with 4-7 membered heterocycloalkyl wherein said 4-7 membered heterocycloalkyl is optionally substituted by 1, 2, or 3 substituents independently selected from halo, $C_{1-6}$ alkyl, $C_{1-6}$ haloalkyl, CN, $OR^{a5}$, $C(O)R^{b5}$, $C(O)NR^{c5}R^{d5}$, $C(O)OR^{a5}$, $OC(O)R^{b5}$, $NR^{c5}R^{d5}$ and $NR^{c5}C(O)R^{b5}$.

In some embodiments where the compound has Formula II, $R^{10}$ is $C_{1-6}$ alkyl optionally substituted with 4-7 membered heterocycloalkyl wherein said 4-7 membered heterocycloalkyl is selected from morpholinyl, piperazinyl, piperidinyl, pyrrolidinyl, tetrahydrofuranyl, and azetidinyl, and wherein said 4-7 membered heterocycloalkyl is optionally substituted by 1, 2, or 3 substituents independently selected from halo, $C_{1-6}$ alkyl, $C_{1-6}$ haloalkyl, CN, $OR^{a5}$, $C(O)R^{b}s$, $C(O)NR^{c5}R^{d5}$, $C(O)OR^{a5}$, $OC(O)R^{b5}$, $NR^{c5}R^{d5}$ and $NR^{c5}C(O)R^{b5}$.

In some embodiments $R^{c3}$ and $R^{d3}$ together with the N atom to which they are attached form a 4-, 5-, 6-, or 7-membered heterocycloalkyl group optionally substituted with 1, 2, or 3 substituents independently selected from $C_{1-6}$ alkyl, $C_{1-6}$ haloalkyl, halo, CN, $OR^{a6}$, and $NR^{c6}R^{d6}$.

In some embodiments $Cy^2$ is selected from 4-7 membered heterocycloalkyl optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a5}$, $SR^{a5}$, $C(O)R^{b5}$, $C(O)NR^{c5}R^{d5}$, $C(O)OR^{a5}OC(O)R^{b5}$, $OC(O)NR^{c5}R^{d5}$, $NR^{c5}R^{d5}$, $NR^{c5}C(O)R^{d5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$.

In some embodiments where the compound has Formula II, $R^{10}$ is H.

In some embodiments where the compound has Formula II, $R^{10}$ is other than H.

In some embodiments where the compound has Formula II, $R^{17}$ and $R^{18}$ are each independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{c3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{13}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from $R^{10a}$.

In some embodiments where the compound has Formula II, $R^{17}$ and $R^{18}$ are each independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, and CN, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from $R^{10a}$.

In some embodiments where the compound has Formula II, $R^{17}$ and $R^{18}$ are each independently selected from H, halo, $C_{1-6}$ alkyl, $C_{2-6}$ alkenyl, $C_{2-6}$ alkynyl, and $C_{1-6}$ haloalkyl, wherein said $C_{1-6}$ alkyl, $C_{2-6}$ alkenyl, $C_{2-6}$ alkynyl, are each optionally substituted with 1, 2, 3, 4, or 5 substituents independently selected from $R^{10a}$.

In some embodiments where the compound has Formula II, $R^{17}$ and $R^{18}$ are both $C_{1-6}$ alkyl.

In some embodiments where the compound has Formula II, $R^{17}$ and $R^{18}$ are both methyl.

In some embodiments where the compound has Formula II, $R^{17}$ and $R^{18}$ are each independently selected from H and halo.

In some embodiments where the compound has Formula II, $R^{17}$ is H.

In some embodiments where the compound has Formula II, $R^{18}$ is H.

In some embodiments where the compound has Formula II, both $R^{17}$ and $R^{18}$ are H.

In some embodiments, $R^{17}$ and $R^{18}$ together with the carbon atom to which they are attached form a 3-, 4-, 5-, 6-, or 7-membered cycloalkyl group or a 4-, 5-, 6-, or 7-membered heterocycloalkyl group, each optionally substituted with 1, 2, or 3 substituents independently selected from $Cy^2$, $C_{1-6}$ alkyl, $C_{1-6}$ haloalkyl, halo, CN, $OR^{a3}$, $SR^3$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$, wherein said $C_{1-6}$ alkyl is optionally substituted by 1, 2, or 3 substituents independently selected from $Cy^2$, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$ and $S(O)_2NR^{c3}R^{d3}$.

In some embodiments, $R^{17}$ and $R^{18}$ together with the carbon atom to which they are attached form a 3-, 4-, 5-, 6-, or 7-membered cycloalkyl group.

In some embodiments, $R^{17}$ and $R^{18}$ together with the carbon atom to which they are attached form a cyclobutyl or cyclopentyl group.

In some embodiments, $R^{17}$ and $R^{18}$ together with the carbon atom to which they are attached form a 4-, 5-, 6-, or 7-membered heterocycloalkyl group optionally substituted with 1, 2, or 3 substituents independently selected from $Cy^2$, $C_{1-6}$ alkyl, $C_{1-6}$ haloalkyl, halo, CN, $OR^{a3}$ $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$, wherein said $C_{1-6}$ alkyl is optionally substituted by 1, 2, or 3 substituents independently selected from $Cy^2$, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^3)NR^{c3}R^{d3}$ $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$ and $S(O)_2NR^{c3}R^{d3}$.

In some embodiments, $R^{17}$ and $R^{18}$ together with the carbon atom to which they are attached form a 4-, 5-, 6-, or 7-membered heterocycloalkyl group optionally substituted with $C_{1-6}$ alkyl.

In some embodiments, $R^{17}$ and $R^{18}$ together with the carbon atom to which they are attached form a 4-, 5-, 6-, or 7-membered heterocycloalkyl group.

In some embodiments, $R^{17}$ and $R^{18}$ together with the carbon atom to which they are attached form a tetrahydropyran ring or N-methylpiperidine ring.

In some embodiments, the compound has Formula IIa:

IIa

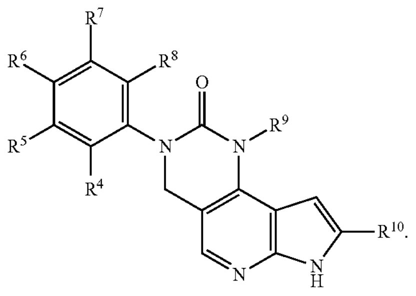

In some embodiments, the compound has Formula IIb:

IIb

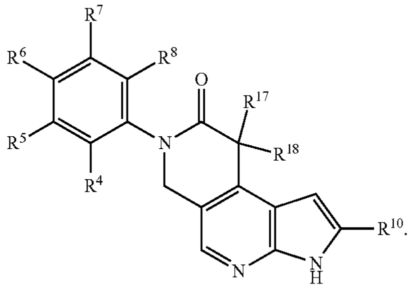

In some embodiments, the compound has Formula III.

In some embodiments where the compound has Formula III, Z is CH.

In some embodiments where the compound has Formula III, Y is S.

In some embodiments where the compound has Formula III, $R^{11}$ is H.

In some embodiments, the compound has Formula IIIa:

IIIa

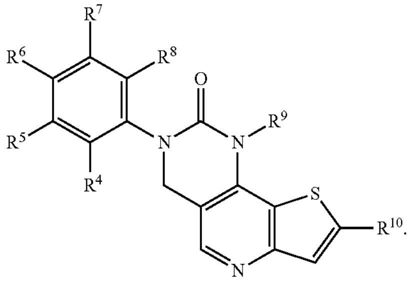

In some embodiments, the compound has Formula IIIb:

IIIb

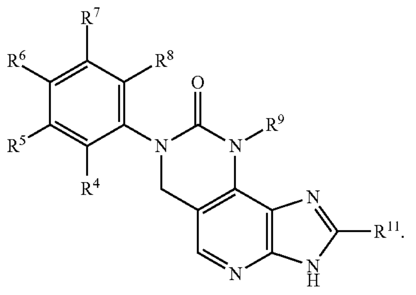

In some embodiments, the compound has Formula IV.

In some embodiments, $R^{14}$ selected from H, $C_{1-6}$ alkyl, $C_{6-10}$ aryl, $C_{3-10}$ cycloalkyl, 5-10 membered heteroaryl, 4-10 membered heterocycloalkyl, and CN; wherein said $C_{1-6}$ alkyl, $C_{6-10}$ aryl, $C_{3-10}$ cycloalkyl, 5-10 membered heteroaryl, and 4-10 membered heterocycloalkyl are each optionally substituted with 1, 2, or 3 substituents independently selected from $R^{10a}$.

In some embodiments where the compound has Formula IV, $R^{14}$ is H, $C_{1-6}$ alkyl, 3-10 membered heterocycloalkyl, or CN; wherein said $C_{1-6}$ alkyl and 3-10 membered heterocycloalkyl are each optionally substituted with 1, 2, 3, 4, or 5 substituents independently selected from $R^{10a}$.

In some embodiments where the compound has Formula IV, $R^{14}$ is H, $C_{1-6}$ alkyl, 4-10 membered heterocycloalkyl, or CN; wherein said $C_{1-6}$ alkyl and 4-10 membered heterocycloalkyl are each optionally substituted with 1, 2, 3, 4, or 5 substituents independently selected from $R^{10a}$.

In some embodiments where the compound has Formula IV, $R^{14}$ is H, methyl, 1-methylpiperidinyl, CN, cyanomethyl, or 2-hydroxyethyl.

In some embodiments where the compound has Formula IV, $R^{14}$ is H.

In some embodiments where the compound has Formula IV, $R^{14}$ is phenyl optionally substituted with 1, 2, or 3 substituents independently selected from $R^{10a}$.

In some embodiments, $R^{14}$ is phenyl optionally substituted with $R^{10a}$.

In some embodiments, $R^{14}$ is (4-ethylpiperazin-1-yl)phenyl.

In some embodiments, the compound has Formula IVa:

IVa

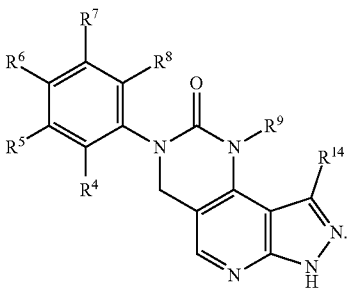

In some embodiments, the compound has Formula IVb:

IVb

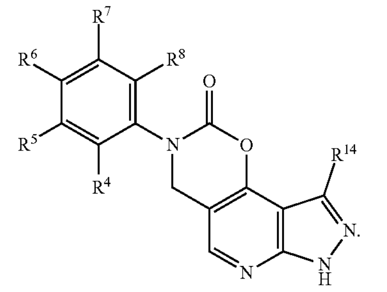

In some embodiments, the compound has Formula V:

V

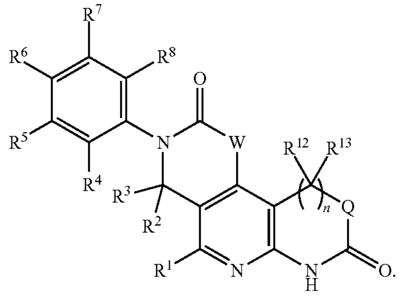

In some embodiments where the compound has Formula V, W is $NR^9$.

In some embodiments where the compound has Formula V, $R^9$ is H, $C_{1-6}$ alkyl, $C_{3-10}$ cycloalkyl, 3-10 membered heterocycloalkyl, $C_{6-10}$ aryl, $C_{6-10}$ aryl-$C_{1-4}$ alkyl, or $C_{3-10}$ cycloalkyl-$C_{1-4}$ alkyl, each optionally substituted with 1, 2, or 3 substituents independently selected from $R^{9a}$.

In some embodiments where the compound has Formula V, $R^9$ is H, $C_{1-6}$ alkyl, $C_{3-10}$ cycloalkyl, 3-10 membered heterocycloalkyl, $C_{6-10}$ aryl-$C_{1-4}$ alkyl, or $C_{3-10}$ cycloalkyl-$C_{1-4}$ alkyl.

In some embodiments where the compound has Formula V, $R^9$ is $C_{6-10}$ aryl-$C_{1-4}$ alkyl optionally substituted with 1, 2, 3, 4, or 5 substituents independently selected from $R^{9a}$.

In some embodiments where the compound has Formula V, $R^9$ is benzyl optionally substituted with 1, 2, or 3 substituents independently selected from $R^{9a}$.

In some embodiments where the compound has Formula V, $R^9$ is phenyl optionally substituted with 1, 2, or 3 substituents independently selected from $R^{9a}$.

In some embodiments where the compound has Formula V, $R^9$ is H, $C_{1-6}$ alkyl, $C_{3-10}$ cycloalkyl, 4-10 membered heterocycloalkyl, $C_{6-10}$ aryl-$C_{1-4}$ alkyl, or $C_{3-10}$ cycloalkyl-$C_{1-4}$ alkyl.

In some embodiments where the compound has Formula V, $R^9$ is $C_{3-10}$ cycloalkyl.

In some embodiments where the compound has Formula V, $R^9$ is cyclobutyl.

In some embodiments where the compound has Formula V, $R^9$ is $C_{1-6}$ alkyl.

In some embodiments, $R^9$ is methyl, ethyl, cyclopropyl, cyclopropylmethyl, cyclobutyl, 3-fluorophenylmethyl, or 4-chloro-2-fluorophenyl.

In some embodiments where the compound has Formula V, $R^9$ is methyl, ethyl, cyclopropyl, or cyclopropylmethyl.

In some embodiments where the compound has Formula V, $R^9$ is methyl.

In some embodiments where the compound has Formula V, $R^2$ and $R^3$ are each independently selected from H, CN, $C(O)NR^cR^d$, and $C_{1-7}$ alkyl, wherein said $C_{1-7}$ alkyl is optionally substituted by 1, 2, or 3 substituents independently selected from halo, $OR^{a1}$, CN, $NR^cR^d$, and $C(O)NR^cR^d$.

In some embodiments where the compound has Formula V, $R^2$ and $R^3$ are each H.

In some embodiments where the compound has Formula V, $R^2$, and $R^3$ are each H.

In some embodiments where the compound has Formula V, $R^1$, $R^2$, and $R^3$ are each H.

In some embodiments where the compound has Formula V, $R^4$, $R^5$, $R^6$, $R^7$, and $R^8$ are each independently selected from H, halo, $C_{1-6}$ alkyl, $C_{1-6}$ haloalkyl, CN, and $OR^{a1}$.

In some embodiments where the compound has Formula V, $R^4$, $R^5$, $R^6$, $R^7$, and $R^8$ are each independently selected from H, halo, and methoxy.

In some embodiments where the compound has Formula V, $R^5$ and $R^7$ are both methoxy and $R^4$, $R^6$, and $R^8$ are each independently selected from H and halo.

In some embodiments where the compound has Formula V, $R^4$ is halo, $R^5$ is methoxy, $R^6$ is H, $R^7$ is methoxy, and $R^8$ is halo.

In some embodiments where the compound has Formula V, Q is absent.

In some embodiments where the compound has Formula V, Q is O, $NR^{16a}$ or $CR^{12a}R^{13a}$.

In some embodiments where the compound has Formula V, $R^{12}$ and $R^{13}$ are each independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 3-10 membered heterocycloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 3-10 membered heterocycloalkyl are each optionally substituted with 1, 2, 3, 4, or 5 substituents independently selected from $R^{10a}$.

In some embodiments where the compound has Formula V, $R^{12}$ and $R^{13}$ are each independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{13}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from $R^{10a}$.

In some embodiments where the compound has Formula V, $R^{12}$ and $R^{13}$ together with the carbon atom to which they are attached form a 3-, 4-, 5-, 6-, or 7-membered cycloalkyl group or a 4-, 5-, 6-, or 7-membered heterocycloalkyl group, each optionally substituted with 1, 2, or 3 substituents independently selected from $Cy^2$, $C_{1-6}$ alkyl, $C_{1-6}$ haloalkyl, halo, CN, $OR^{a3}$, $SR^{a3}$, $C(O)R^{b3}$, $C(O)NR^{c3}R^{d3}$, $C(O)OR^{a3}$, OC(O)$R^{b3}$, OC(O)N$R^{c3}R^{d3}$, N$R^{c3}R^{d3}$, N$R^{c3}$C(O)$R^{b3}$, N$R^{c3}$C(O)N$R^{c3}R^{d3}$, N$R^{c3}$C(O)O$R^{a3}$, C(=N$R^{e3}$)N$R^{c3}R^{d3}$, N$R^{c3}$C(=N$R^{e3}$)N$R^{c3}R^{d3}$, S(O)$R^{b3}$, S(O)N$R^{c3}R^{d3}$, $S(O)_2R^{b3}$, N$R^{c3}S(O)_2R^{b3}$, N$R^{c3}S(O)_2$N$R^{c3}R^{d3}$, and $S(O)_2$N$R^{c3}R^{d3}$, wherein said $C_{1-6}$ alkyl is optionally substituted by 1, 2, or 3 substituents independently selected from $Cy^2$, halo, CN, O$R^{a3}$, S$R^{a3}$, C(O)$R^{b3}$, C(O)N$R^{c3}R^{d3}$, C(O)O$R^{a3}$, OC(O)$R^{b3}$, OC(O)N$R^{c3}R^{d3}$, N$R^{c3}R^{d3}$, N$R^{c3}$C(O)$R^{b3}$, N$R^{c3}$C(O)N$R^{c3}R^{d3}$, N$R^{c3}$C(O)O$R^{a3}$, C(=N$R^{e3}$)N$R^{c3}R^{d3}$, N$R^{c3}$C(=N$R^{e3}$)N$R^{c3}R^{d3}$ S(O)$R^{b3}$, S(O)N$R^{c3}R^{d3}$, $S(O)_2R^{b3}$, N$R^{c3}S(O)_2R^{b3}$, N$R^{c3}S(O)_2$N$R^{c3}R^{d3}$, and $S(O)_2$N$R^{c3}R^{d3}$.

In some embodiments where the compound has Formula V, $R^{12}$ and $R^{13}$ together with the carbon atom to which they are attached form a 3-, 4-, 5-, 6-, or 7-membered cycloalkyl group.

In some embodiments where the compound has Formula V, $R^{12}$ and $R^{13}$ are each H.

In some embodiments where the compound has Formula V, $R^2$, $R^3$, $R^{12}$ and $R^{13}$ are each H.

In some embodiments where the compound has Formula V, n is 1.

In some embodiments where the compound has Formula V, n is 1 and Q is absent.

In some embodiments where the compound has Formula V, n is 0.

In some embodiments, the compound has Formula Va:

Va

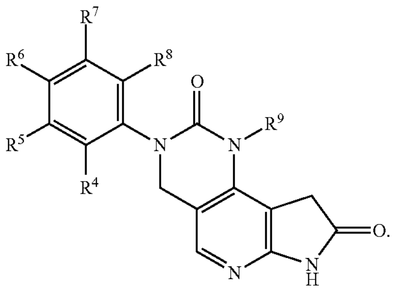

In some embodiments, the compound has Formula Vb.

Vb

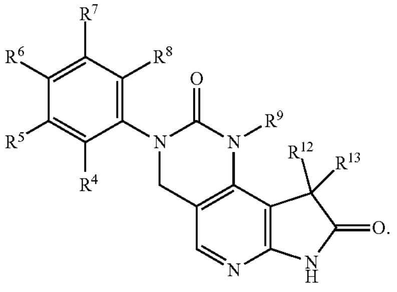

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification various aryl, heteroaryl, cycloalkyl, and heterocycloalkyl rings are described. Unless otherwise specified, these rings can be attached to the rest of the molecule at any ring member as permitted by valency. For example, the term "a pyridine ring" may refer to a pyridin-2-yl, pyridin-3-yl, or pyridin-4-yl ring.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-10 membered heteroaryl ring, pyridyl is an example of a 6-membered heteroaryl ring, and 1,2,3,4-tetrahydro-naphthalene is an example of a 10-membered cycloalkyl group.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R.

As used herein, the phrase "optionally substituted" means unsubstituted or substituted.

As used herein, the term "substituted" means that a hydrogen atom is replaced by a non-hydrogen group. It is to be understood that substitution at a given atom is limited by valency.

As used herein, the term "$C_{i-j}$", where i and j are integers, employed in combination with a chemical group, designates a range of the number of carbon atoms in the chemical group with i-j defining the range. For example, $C_{1-6}$ alkyl refers to an alkyl group having 1, 2, 3, 4, 5, or 6 carbon atoms.

As used herein, the term "alkyl", employed alone or in combination with other terms, refers to a saturated hydrocarbon group that may be straight-chain or branched. In some embodiments, the alkyl group contains 1 to 7, 1 to 6, 1 to 4, or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, n-heptyl, and the like. In some embodiments, the alkyl group is methyl, ethyl, or propyl.

As used herein, "alkenyl", employed alone or in combination with other terms, refers to an alkyl group having one or more carbon-carbon double bonds. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, "alkynyl", employed alone or in combination with other terms, refers to an alkyl group having one or more carbon-carbon triple bonds. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, "halo" or "halogen", employed alone or in combination with other terms, includes fluoro, chloro, bromo, and iodo. In some embodiments, halo is F or Cl.

As used herein, the term "haloalkyl", employed alone or in combination with other terms, refers to an alkyl group having up to the full valency of halogen atom substituents, which may either be the same or different. In some embodiments, the halogen atoms are fluoro atoms. In some embodiments, the alkyl group has 1 to 6 or 1 to 4 carbon atoms. Example haloalkyl groups include $CF_3$, $C_2F_5$, $CHF_2$, $CCl_3$, $CHCl_2$, $C_2Cl_5$, and the like.

As used herein, the term "alkoxy", employed alone or in combination with other terms, refers to a group of formula —O-alkyl. Example alkoxy groups include methoxy, ethoxy, propoxy (e.g., n-propoxy and isopropoxy), t-butoxy, and the like. In some embodiments, the alkyl group has 1 to 6 or 1 to 4 carbon atoms.

As used herein, "haloalkoxy", employed alone or in combination with other terms, refers to a group of formula —O-(haloalkyl). In some embodiments, the alkyl group has 1 to 6 or 1 to 4 carbon atoms. An example haloalkoxy group is —$OCF_3$.

As used herein, "amino", employed alone or in combination with other terms, refers to $NH_2$.

As used herein, the term "alkylamino", employed alone or in combination with other terms, refers to a group of formula —NH(alkyl). In some embodiments, the alkylamino group has 1 to 6 or 1 to 4 carbon atoms. Example alkylamino groups include methylamino, ethylamino, propylamino (e.g., n-propylamino and isopropylamino), and the like.

As used herein, the term "dialkylamino", employed alone or in combination with other terms, refers to a group of formula —$N(alkyl)_2$. Example dialkylamino groups include dimethylamino, diethylamino, dipropylamino (e.g., di(n-propyl)amino and di(isopropyl)amino), and the like. In some embodiments, each alkyl group independently has 1 to 6 or 1 to 4 carbon atoms.

As used herein, the term "alkylthio", employed alone or in combination with other terms, refers to a group of formula —S-alkyl. In some embodiments, the alkyl group has 1 to 6 or 1 to 4 carbon atoms.

As used herein, the term "cycloalkyl", employed alone or in combination with other terms, refers to a non-aromatic cyclic hydrocarbon including cyclized alkyl and alkenyl groups. Cycloalkyl groups can include mono- or polycyclic (e.g., having 2, 3, or 4 fused, bridged, or spiro rings) ring systems. Also included in the definition of cycloalkyl are moieties that have one or more aromatic rings (e.g., aryl or heteroaryl rings) fused (i.e., having a bond in common with) to the cycloalkyl ring, for example, benzo derivatives of cyclopentane, cyclohexene, cyclohexane, and the like, or pyrido derivatives of cyclopentane or cyclohexane. Ring-forming carbon atoms of a cycloalkyl group can be optionally substituted by oxo. Cycloalkyl groups also include cycloalkylidenes. The term "cycloalkyl" also includes bridgehead cycloalkyl groups (e.g., non-aromatic cyclic hydrocarbon moieties containing at least one bridgehead carbon, such as admantan-1-yl) and spirocycloalkyl groups (e.g., non-aromatic hydrocarbon moieties containing at least two rings fused at a single carbon atom, such as spiro[2.5]octane and the like). In some embodiments, the cycloalkyl group has 3 to 10 ring members, or 3 to 7 ring members. In some embodiments, the cycloalkyl group is monocyclic or bicyclic. In some embodiments, the cycloalkyl group is monocyclic. In some embodiments, the cycloalkyl group is a $C_{3-7}$ monocyclic cycloalkyl group. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, tetrahydronaphthalenyl, octahydronaphthalenyl, indanyl, and the like. In some embodiments, the cycloalkyl group is cyclopropyl, cyclobutyl, cyclopentyl, or cyclohexyl.

As used herein, the term "cycloalkylalkyl", employed alone or in combination with other terms, refers to a group of formula cycloalkyl-alkyl-. In some embodiments, the alkyl portion has 1 to 4, 1 to 3, 1 to 2, or 1 carbon atom(s). In some embodiments, the alkyl portion is methylene. In some embodiments, the cycloalkyl portion has 3 to 10 ring members or 3 to 7 ring members. In some embodiments, the cycloalkyl group is monocyclic or bicyclic. In some embodiments, the cycloalkyl portion is monocyclic. In some embodiments, the cycloalkyl portion is a $C_{3-7}$ monocyclic cycloalkyl group.

As used herein, the term "heterocycloalkyl", employed alone or in combination with other terms, refers to a non-aromatic ring or ring system, which may optionally contain one or more alkenylene or alkynylene groups as part of the ring structure, which has at least one heteroatom ring member independently selected from nitrogen, sulfur, oxygen, and phosphorus. Heterocycloalkyl groups can include mono- or polycyclic (e.g., having 2, 3 or 4 fused, bridged, or spiro rings) ring systems. In some embodiments, the heterocycloalkyl group is a monocyclic or bicyclic group having 1, 2, 3, or 4 heteroatoms independently selected from nitrogen, sulfur and oxygen. Also included in the definition of heterocycloalkyl are moieties that have one or more aromatic rings (e.g., aryl or heteroaryl rings) fused (i.e., having a bond in common with) to the non-aromatic heterocycloalkyl ring, for example, 1,2,3,4-tetrahydro-quinoline and the like. Heterocycloalkyl groups can also include bridgehead heterocycloalkyl groups (e.g., a heterocycloalkyl moiety containing at least one bridgehead atom, such as azaadmantan-1-yl and the like) and spiroheterocycloalkyl groups (e.g., a heterocycloalkyl moiety containing at least two rings fused at a single atom, such as [1,4-dioxa-8-aza-spiro[4.5]decan-N-yl] and the like). In some embodiments, the heterocycloalkyl group has 3 to 10 ring-forming atoms, 4 to 10 ring-forming atoms, or about 3 to 8 ring forming atoms. In some embodiments, the heterocycloalkyl group has 2 to 20 carbon atoms, 2 to 15 carbon atoms, 2 to 10 carbon atoms, or about 2 to 8 carbon atoms. In some embodiments, the heterocycloalkyl group has 1 to 5 heteroatoms, 1 to 4 heteroatoms, 1 to 3 heteroatoms, or 1 to 2 heteroatoms. The carbon atoms or heteroatoms in the ring(s) of the heterocycloalkyl group can be oxidized to form a carbonyl, an N-oxide, or a sulfonyl group (or other oxidized linkage) or a nitrogen atom can be quaternized. In some embodiments, the heterocycloalkyl portion is a $C_{2-7}$ monocyclic heterocycloalkyl group. In some embodiments, the heterocycloalkyl group is a morpholine ring, pyrrolidine ring, piperazine ring, piperidine ring, tetrahydropyran ring, tetrahyropyridine, azetidine ring, or tetrahydrofuran ring.

As used herein, the term "heterocycloalkylalkyl", employed alone or in combination with other terms, refers to a group of formula heterocycloalkyl-alkyl-. In some embodiments, the alkyl portion has 1 to 4, 1 to 3, 1 to 2, or 1 carbon atom(s). In some embodiments, the alkyl portion is methylene. In some embodiments, the heterocycloalkyl portion has 3 to 10 ring members, 4 to 10 ring members, or 3 to 7 ring members. In some embodiments, the heterocycloalkyl group is monocyclic or bicyclic. In some embodiments, the heterocycloalkyl portion is monocyclic. In some embodiments, the heterocycloalkyl portion is a $C_{2-7}$ monocyclic heterocycloalkyl group.

As used herein, the term "aryl", employed alone or in combination with other terms, refers to a monocyclic or polycyclic (e.g., having 2 fused rings) aromatic hydrocarbon moiety, such as, but not limited to, phenyl, 1-naphthyl, 2-naphthyl, and the like. In some embodiments, aryl groups have from 6 to 10 carbon atoms or 6 carbon atoms. In some embodiments, the aryl group is a monocyclic or bicyclic group. In some embodiments, the aryl group is phenyl or naphthyl.

As used herein, the term "arylalkyl", employed alone or in combination with other terms, refers to a group of formula aryl-alkyl-. In some embodiments, the alkyl portion has 1 to 4, 1 to 3, 1 to 2, or 1 carbon atom(s). In some embodiments, the alkyl portion is methylene. In some embodiments, the aryl portion is phenyl. In some embodiments, the aryl group is a monocyclic or bicyclic group. In some embodiments, the arylalkyl group is benzyl.

As used herein, the term "heteroaryl", employed alone or in combination with other terms, refers to a monocyclic or polycyclic (e.g., having 2 or 3 fused rings) aromatic hydrocarbon moiety, having one or more heteroatom ring members independently selected from nitrogen, sulfur and oxygen. In some embodiments, the heteroaryl group is a monocyclic or bicyclic group having 1, 2, 3, or 4 heteroatoms independently selected from nitrogen, sulfur and oxygen. Example heteroaryl groups include, but are not limited to, pyridyl, pyrimidinyl, pyrazinyl, pyridazinyl, triazinyl, furyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, pyrrolyl, azolyl, quinolinyl, isoquinolinyl, benzisoxazolyl, imidazo[1,2-b]thiazolyl or the like. The carbon atoms or heteroatoms in the ring(s) of the heteroaryl group can be oxidized to form a carbonyl, an N-oxide, or a sulfonyl group (or other oxidized linkage) or a nitrogen atom can be quaternized, provided the aromatic nature of the ring is preserved. In some embodiments, the heteroaryl group has from 3 to 10 carbon atoms, from 3 to 8 carbon atoms, from 3 to 5 carbon atoms, from 1 to 5 carbon atoms, or from 5 to 10 carbon atoms. In some embodiments, the heteroaryl group contains 3 to 14, 4 to 12, 4 to 8, 9 to 10, or 5 to 6 ring-forming atoms. In some embodiments, the heteroaryl group has 1 to 4, 1 to 3, or 1 to 2 heteroatoms.

As used herein, the term "heteroarylalkyl", employed alone or in combination with other terms, refers to a group of formula heteroaryl-alkyl-. In some embodiments, the alkyl portion has 1 to 4, 1 to 3, 1 to 2, or 1 carbon atom(s). In some embodiments, the alkyl portion is methylene. In some embodiments, the heteroaryl portion is a monocyclic or bicyclic group having 1, 2, 3, or 4 heteroatoms independently selected from nitrogen, sulfur and oxygen. In some embodiments, the heteroaryl portion has 5 to 10 carbon atoms.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C═N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Other resolving agents suitable for fractional crystallization methods include stereoisomerically pure forms of methylbenzyl-amine (e.g., S and R forms, or diastereomerically pure forms), 2-phenylglycinol, norephedrine, ephedrine, N-methylephedrine, cyclohexylethylamine, 1,2-diaminocyclohexane, and the like. Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric iosomers, tautomers, and isotopes of the structures depicted.

All compounds, and pharmaceutically acceptable salts thereof, can be found together with other substances such as water and solvents (e.g., in the form of hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis,* 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), or mass spectrometry, or by chromatography such as high performance liquid chromatography (HPLC) or thin layer chromatography.

The expressions, "ambient temperature," "room temperature," and "r.t.", as used herein, are understood in the art, and refer generally to a temperature, e.g. a reaction temperature, that is about the temperature of the room in which the reaction is carried out, for example, a temperature from about 20° C. to about 30° C.

Compounds of the invention can be prepared according to numerous preparatory routes known in the literature. Example synthetic methods for preparing compounds of the invention are provided in the Schemes below.

A series of urea derivatives of formula 5 can be prepared by the methods outlined in Scheme 1. Compound 2 can be prepared by treating suitable amines $R^9NH_2$ with aldehyde 1; followed by reductive amination with aniline 3 to provide diamino compound 4. Cyclization of diamino compound 4 with triphosgene or equivalent including, but not limited to, carbonyldiimidazole (CDI), phosgene, diphosgene, etc. can afford the urea derivatives of formula 5.

Scheme 1

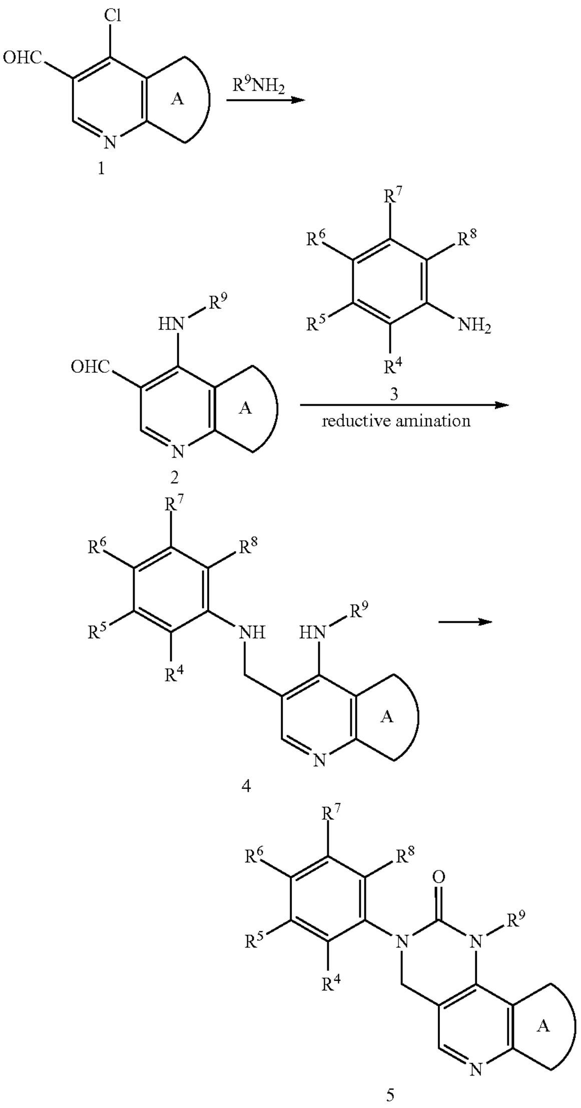

Similarly, a series of urea derivatives of formula 9 can be prepared by the methods outlined in Scheme 2. The ketone 6 can be obtained by reaction of the aldehyde 1 with appropriate Grignard reagent $R^2MgX$ or alkyllithium $R^2Li$ followed by oxidation. Conversion of the ketone 6 to the corresponding amino ketone 7 can be achieved by displacement of the chlorine with an appropriate amine $R^9NH_2$. The diamino derivative 8 can be obtained by reductive amination of the ketone 7 with aniline 3 using a suitable reducing agent such as, but not limited to, sodium cyanoborohydride, or sodium borohydride. Cyclization of diamino compound 8 with triphosgene or carbonyldiimidazole (CDI), phosgene, diphosgene, etc. can afford the urea derivatives of formula 9.

Scheme 2

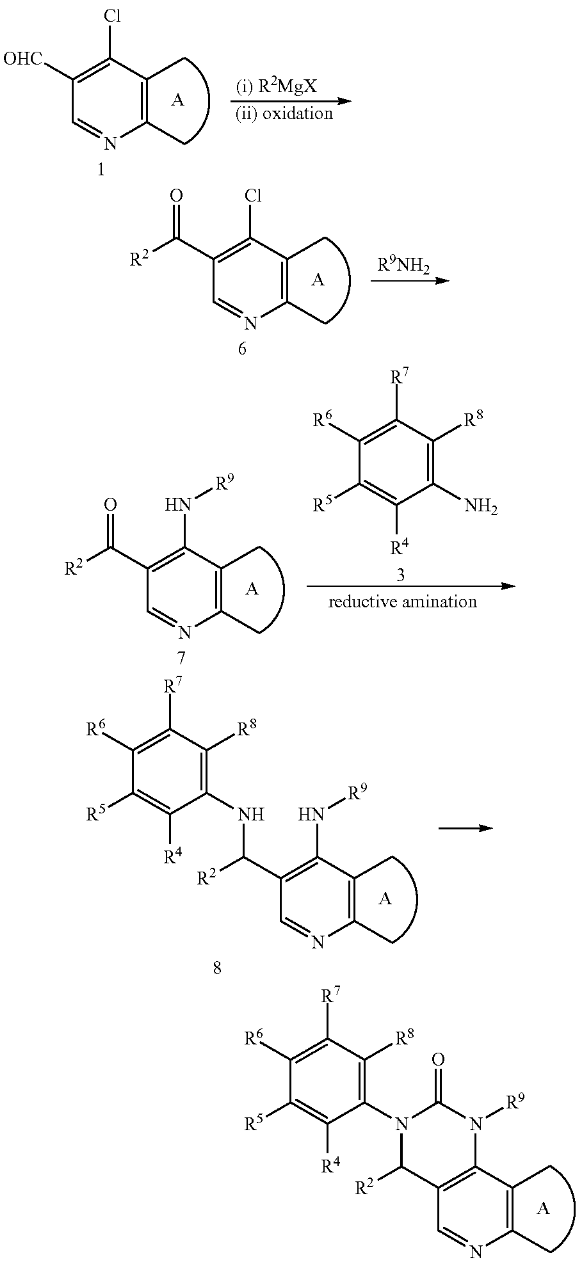

1 6 3 7 8 9

A series of aniline derivatives 14 can be prepared according to the procedures outlined in Scheme 3. Displacement of fluorine in compound 10 with benzylamine ($BnNH_2$) provides the aniline 11 which can be converted to bis-ether by reacting with a suitable sodium alkoxide (NaOR where R is, e.g., methyl, alkyl, or $R^{a1}$) followed by saponification to provide acid 12. Compound 13 can be obtained by decarboxylation of benzoic acid 12, followed by hydrogenation to remove the protecting group to afford aniline 14.

Scheme 3

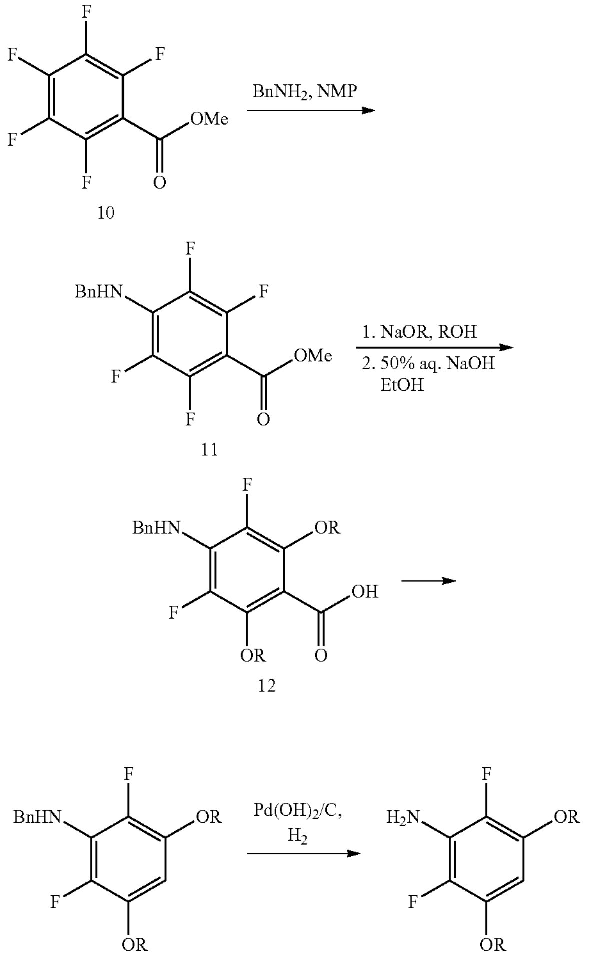

10 11 12 13 14

A series of aniline derivatives 18 can be prepared according to the procedures outlined in Scheme 4. Compound 16 can be obtained by treatment of the aniline 15 (where R=methyl or alkyl) with acetic anhydride or acetyl chloride at low temperature. Treatment of compound 16 with sulfuryl chloride can afford compound 17 which can be then converted to the aniline derivatives 18 by removal of the acetyl group under basic conditions.

Scheme 4

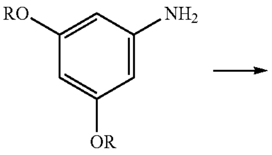

15

-continued

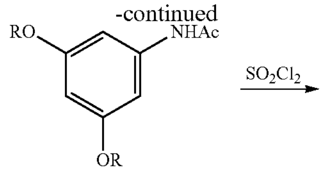

16

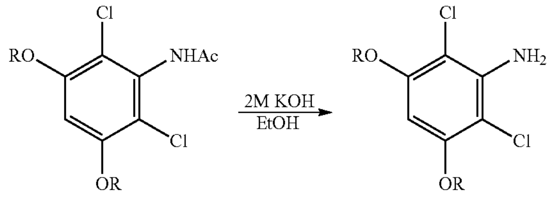

17 18

A series of aniline derivatives 21 can be prepared according to the procedures outlined in Scheme 5. Treatment of compound 16 with Selectfluor® can provide the desired mono-fluoride 19 which can then be converted to compound 20 by treating with sulfuryl chloride. The acetyl group of 20 can be removed under basic conditions to give the aniline derivatives 21.

Scheme 5

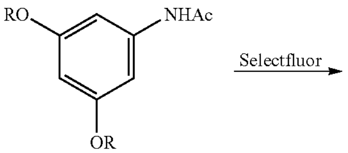

16

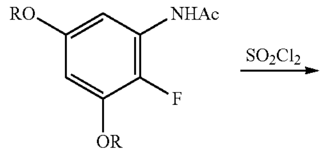

19

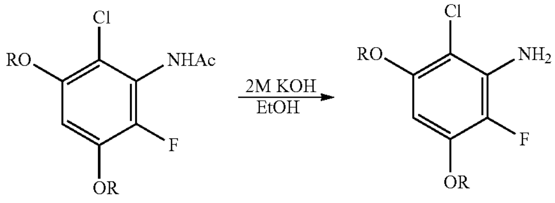

20 21

A series of 1H-pyrrolo[2,3-b]pyridine urea derivatives 26 can be prepared according to the procedures outlined in Scheme 6. Protection of the 1H-pyrrolo[2,3-b]pyridine urea 22, which can be prepared according to the procedures described in Scheme 1, with suitable protection reagents such as $PhSO_2Cl$ under basic conditions can afford the corresponding protected urea 23. The urea halide 24 (L=halo) can be prepared by treatment of the urea 23 with a strong base such as, but not limited to, LDA, LiHMDS, NaHMDS or butyllithium in an inert solvent such as THF, ether, or HMPA at low temperature to provide the metallated intermediate, and followed by treatment with a halogen reagent such as iodine, bromine, 1,2-dibromo-1,1,2,2-tetrachloroethane, NBS or NIS. Deprotection of the urea halide 24 can give the corresponding deprotected product 25, which can be further converted to the desired urea derivatives 26 by Suzuki coupling with an appropriate boronic acid or ester $R^{10B}(OR'')_2$ (R''=H or alkyl).

Scheme 6

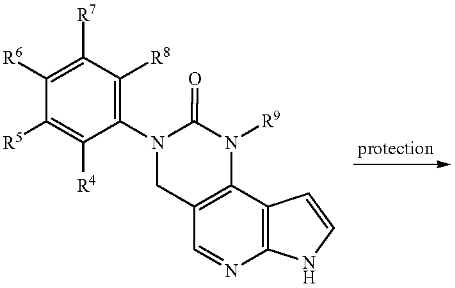

22

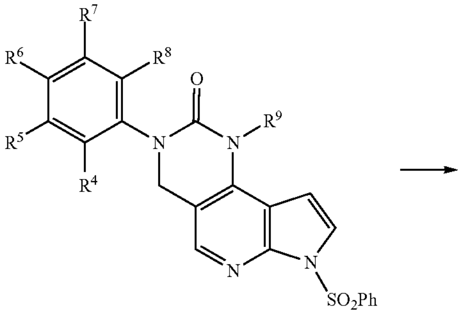

23

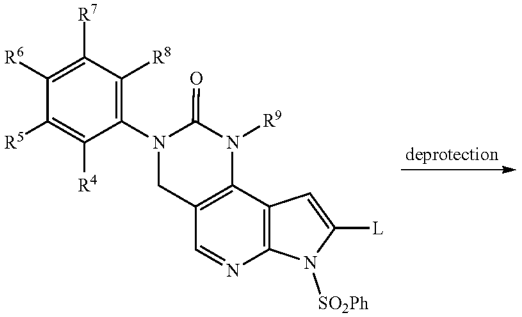

24

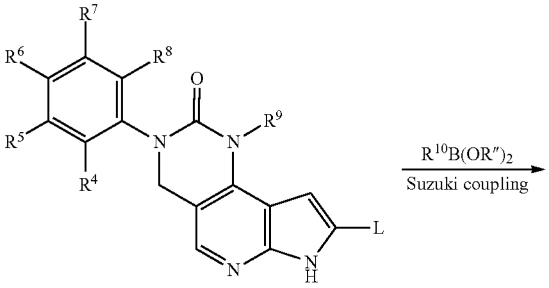

25

-continued

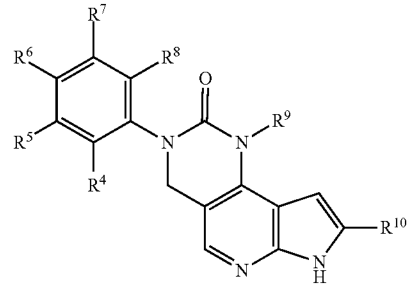

26

Alternatively, a series of 1H-pyrrolo[2,3-b]pyridine urea derivatives 30 can be prepared according to the procedures outlined in Scheme 7. Compound 27 can be prepared using procedures as described in the Scheme 6. Chlorination of compound 27 with sulfuryl chloride can give dichloride 28 ($X^1$=$X^2$=Cl). Treating compound 27 with Selectfluor® can yield fluoro-substituted compound 28 ($X^1$=$X^2$=F). The protecting group of compound 28 can be removed then followed by Suzuki coupling of compound 29 with an appropriate boronic acid or ester $R^{10}B(OR'')_2$ (R''=H or alkyl) as described above to provide 1H-pyrrolo[2,3-b]pyridine urea derivatives 30.

Scheme 7

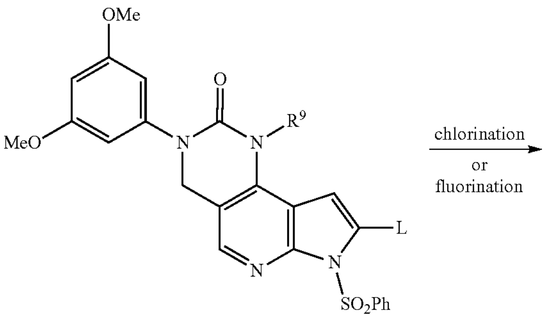

27

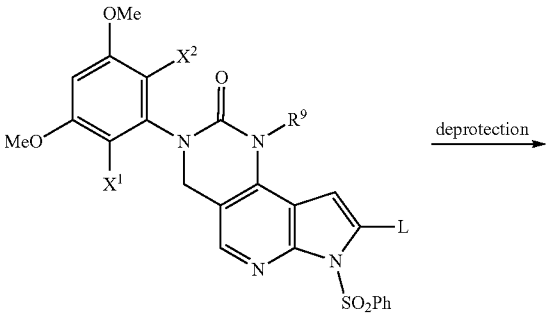

28

-continued

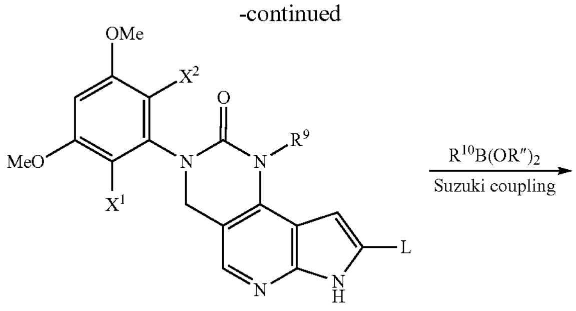

29

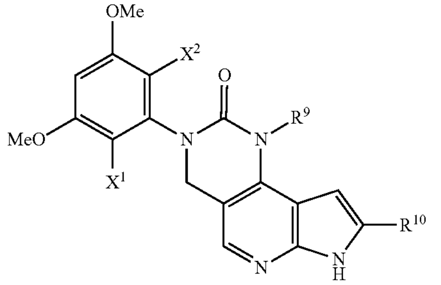

30

A series of amide derivatives 33 can be prepared according to the methods outlined in Scheme 8. The carboxylic acid 31 can be obtained by treating the protected urea 23 with a strong base such as, but not limited to, LDA, LiHMDS, NaHMDS, or butyllithium in an inert solvent such as THF, ether, or HMPA at low temperature, and followed by addition of dry-ice to the reaction mixture. Deprotection of the carboxylic acid 31 yields the corresponding acid 32, which can be converted to the amide 33 by coupling with an appropriate amine (e.g., $NHR^{c3}R^{d3}$) in the presence of a suitable amide coupling reagent such as, but not limited to, HATU, HBTU, BOP, EDCI/HOBT, EDCI/HOAT, or CDI. Alternatively, the amide 33 can be obtained by conversion of the acid 32 to the corresponding chloride by treating with oxalyl chloride or thionyl chloride followed by reacting with the appropriate amine.

Scheme 8

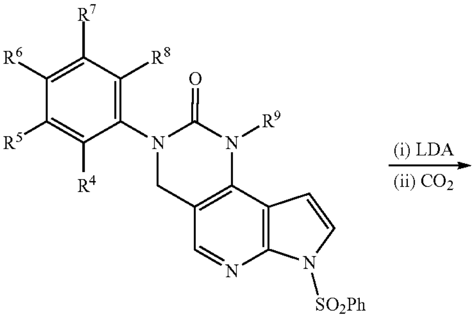

23

-continued

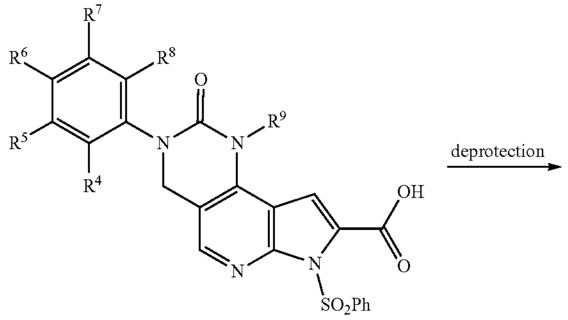

31

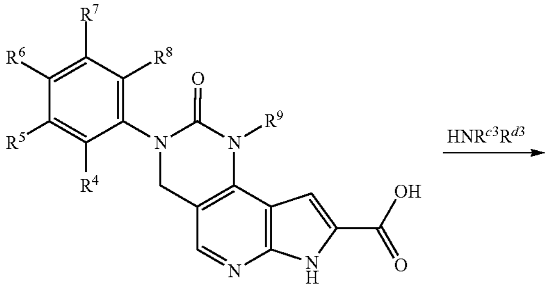

32

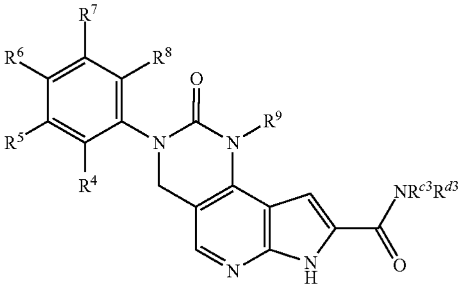

33

A series of urea derivatives 37 can be prepared according to the procedures outlined in Scheme 9. Protection of the 1H-pyrrolo[2,3-b]pyridine urea 34 can be achieved by reacting with suitable protection reagent (PG) under basic conditions to afford the urea 35. Alkylation of the urea 35 with an alkyl halide (e.g., $R^9$-halide) under basic conditions can yield the corresponding substituted urea 36, followed by removal of the protection group PG under conditions standard in the art to provide the final compound 37.

Scheme 9

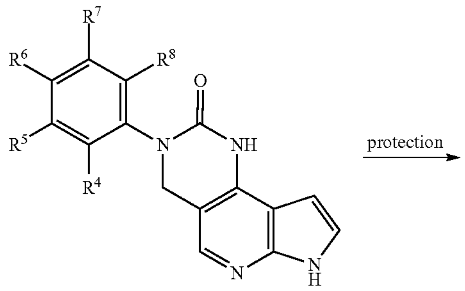

34

-continued

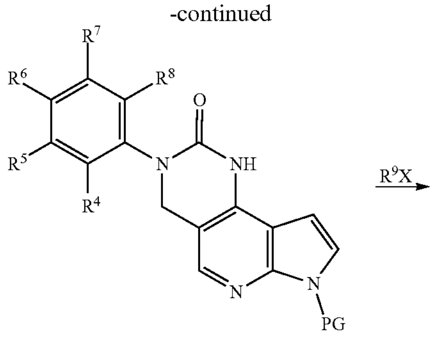

35

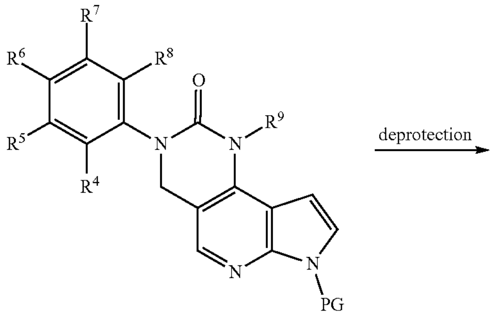

36

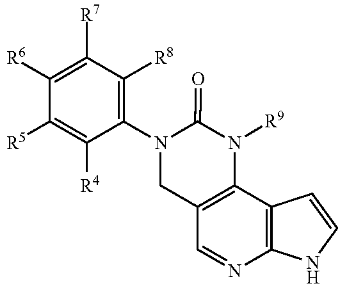

37

A series of urea derivatives 41 can be prepared according to the procedures outlined in Scheme 10. Urea 38 can be treated with pyridinium tribromide or bromine to give the dibromo and/or monobromo intermediates 39 and 40, respectively, which can be then subjected to a Zn/acetic acid-mediated reduction to afford the urea derivatives 41.

Scheme 10

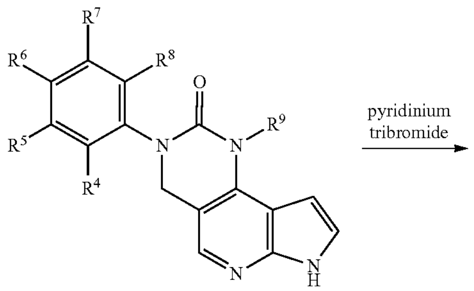

38

-continued

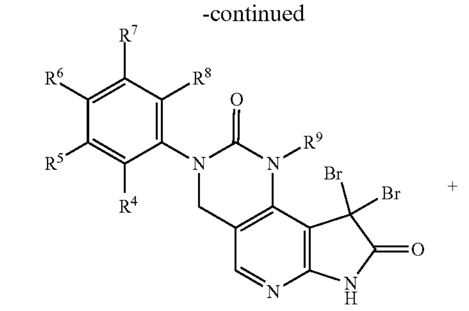

39

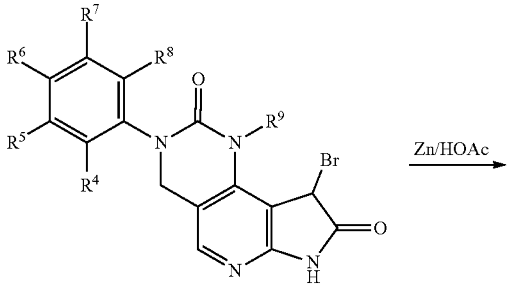

40

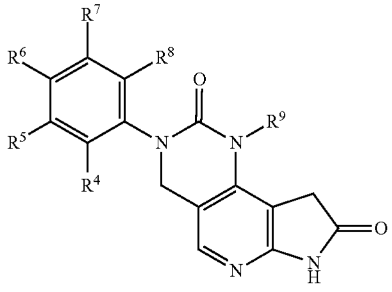

41

A series of 3H-imidazo[4,5-b]pyridine urea derivatives 50 can be prepared according to the procedures outlined in Scheme 11. Condensation of the pyridinyl diamine 42 (CAS #1131604-99-3) with an appropriate acid $R^{10}COOH$ under acidic condition such as $H_3PO_4$ or polyphosphoric acid (PPA) at elevated temperature can yield 3H-imidazo[4,5-b] pyridine 43. The free NH functional group of compound 43 can be protected by treating it with PG-Cl such as (but not limited to) $MeOCH_2Cl$ or SEMCl, under basic conditions. Palladium catalyzed coupling of compound 44 with tributyl (vinyl)stannane can afford compound 45 which can be then subjected to ozonolysis to give the corresponding aldehyde 46. The chlorine in compound 46 can be displaced with an appropriate amine $R^9NH_2$ to yield the corresponding amino aldehyde 47. The diamino derivative 48 can be obtained by reductive amination of the amino aldehyde 47 with aniline 3 using a suitable reducing agent such as, but not limited to, sodium cyanoborohydride, or sodium borohydride. Cyclization of diamino compound 48 with triphosgene can afford the urea derivatives 49. Removal of the protecting group PG in 49 can give the urea derivatives 50.

Scheme 11

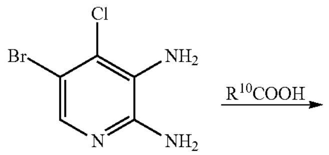

42

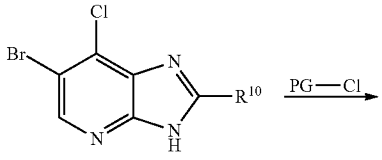

43

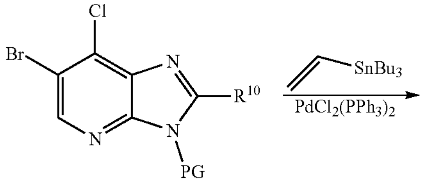

44

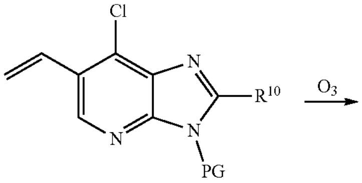

45

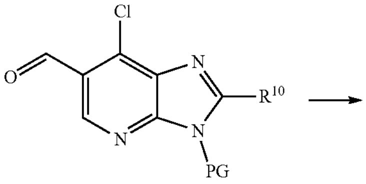

46

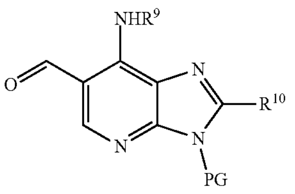

47

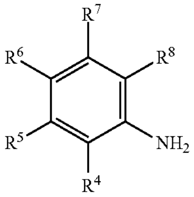

3

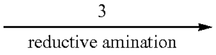

-continued

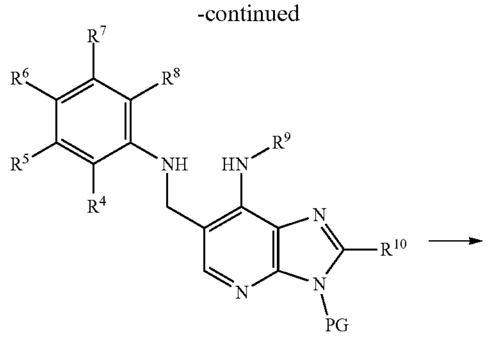

48

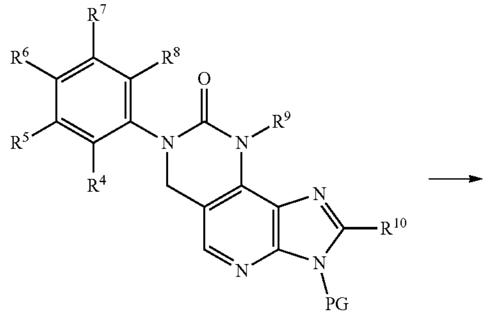

49

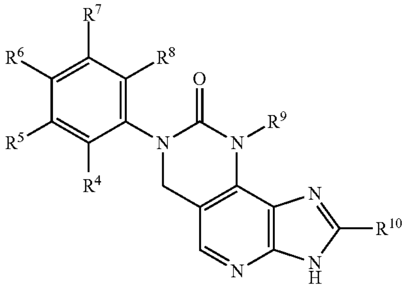

50

A series of urea derivatives 51 can be prepared according to the procedures outlined in Scheme 12. The free NH functional group of compound 52 ($R^{14}$=H, CAS #1034769-88-4) can be protected by a suitable protecting group to afford the protected product 53. Palladium catalyzed coupling of compound 53 with tributyl(vinyl)stannane can afford compound 54 which can then be subjected to ozonolysis to give the corresponding aldehyde 55. The chlorine group of 55 can be displaced with an appropriate amine $R^9NH_2$ to yield the corresponding amino aldehyde 56. The diamino derivative 57 can be obtained by reductive amination of the amino aldehyde 56 with aniline 3 using a suitable reducing agent such as, but not limited to, sodium cyanoborohydride, or sodium borohydride. Cyclization of the diamino compound 57 with triphosgene or equivalent can afford the urea derivatives 58. Removal of the protecting group of 58 can provide the urea derivatives 51.

Compounds of the invention having thieno[3,2-b]pyridine cores can also be made according to Scheme 12 starting with 6-bromo-7-chlorothieno[3,2-b]pyridine (CAS #875340-63-9) in place of 52.

Scheme 12

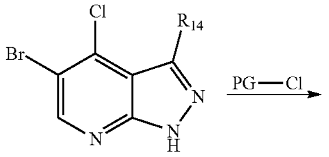

52

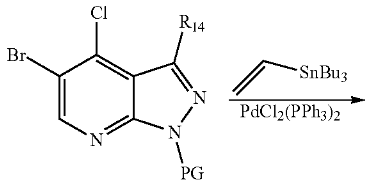

53

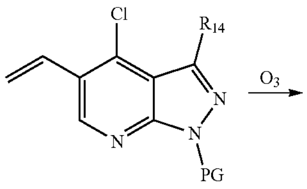

54

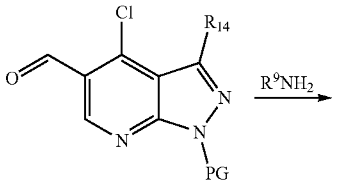

55

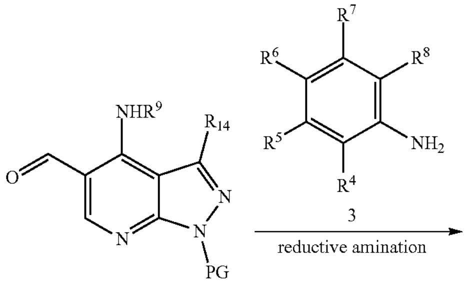

56

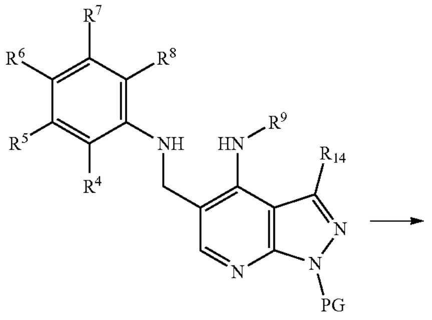

57

-continued

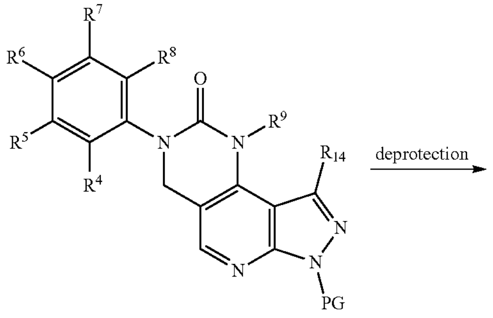

58

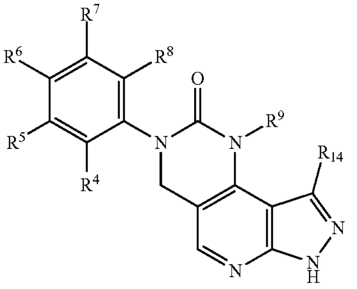

51

A series of urea derivatives of Formula 5 can be alternatively prepared by the procedures outlined in Scheme 13. Reductive amination of aldehyde derivatives 1 with aniline 3 can generate the chloro-compound 59. Palladium-catalyzed amination of compound 59 can afford the diamino-compound 4. The urea derivative 5 can be obtained by intramolecular cyclization of compound 4 with triphosgene or equivalent.

Scheme 13

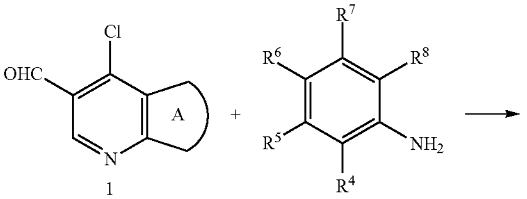

1 3

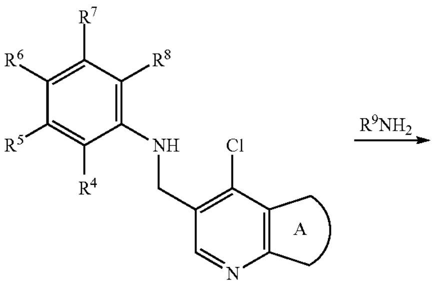

59

-continued

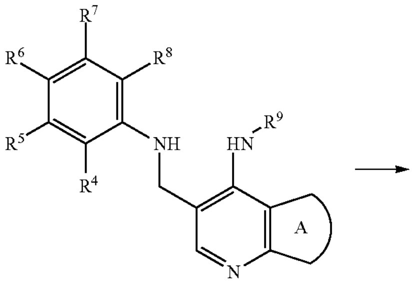

4

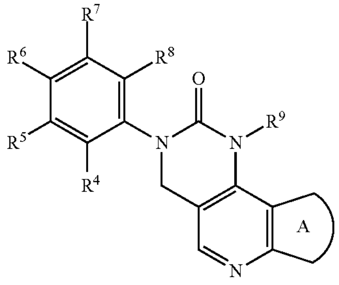

5

A series of aza-oxindole derivatives 62 can be prepared according to the procedures outlined in Scheme 14. Alkylation of compound 60, which can be prepared from compound 36 using similar conditions as described in Scheme 10, under basic conditions such as but not limited to $Cs_2CO_3$, NaH and etc. can generate compound 61. Removal of the protecting group can afford the aza-oxindole derivatives 62.

Scheme 14

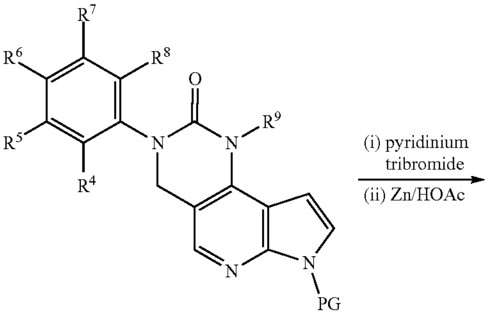

36

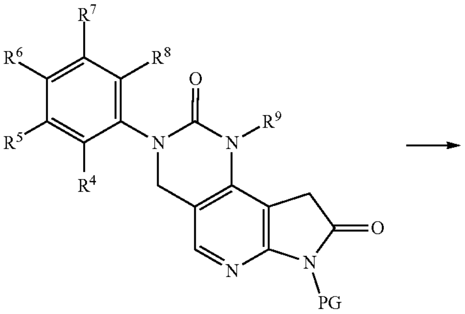

60

-continued

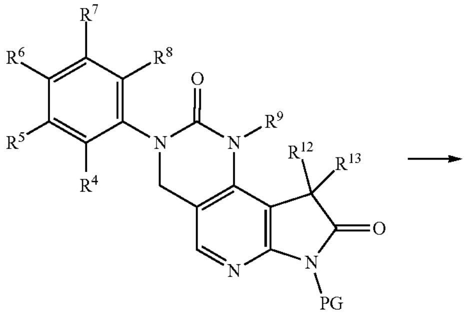

61

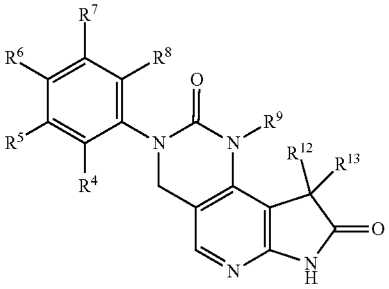

62

A series of lactam derivatives 64 can be prepared according to the procedures outlined in Scheme 15. Palladium catalyzed coupling of chloro-compound 59 with potassium ethyl malonate or equivalent, followed by in situ intramolecular cyclization can generate the lactam 63, which can be then alkylated to afford the lactam derivative 64.

Scheme 15

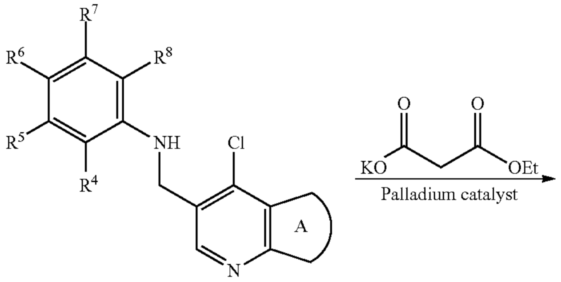

59

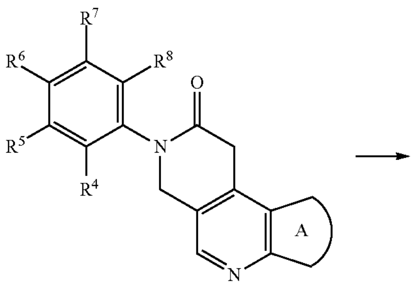

63

-continued

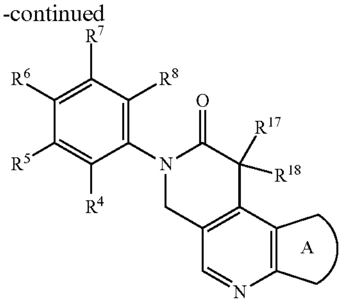

64

A series of cyclic carbamate derivatives 67 can be prepared according to the procedures outlined in Scheme 16. Displacement of the chloride in compound 59 by alkoxide under basic conditions can form compound 65, which can react with chloroformate or equivalent to give the carbamate compound 66. Removal of the protecting group followed by in situ cyclization of compound 66 can afford the cyclic carbamate derivative 67.

Scheme 16

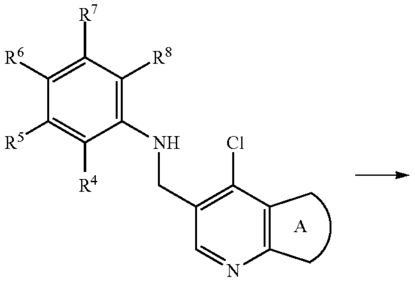

59

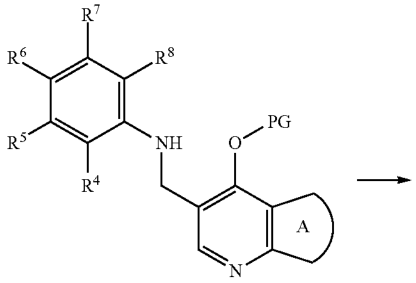

65

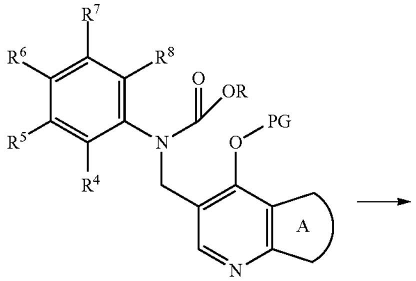

66

-continued

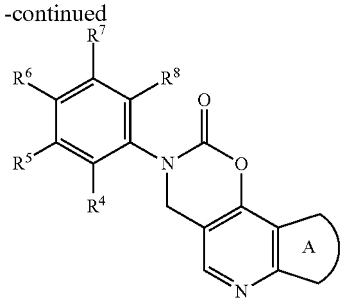

67

A series of pyrazolo[3,4-b]pyridine urea derivatives 51 can be prepared alternatively according to the procedures outlined in Scheme 17. Halogenation of compound 68, which can be generated by using procedures as described in Scheme 12 or Scheme 13, with a suitable reagent such as, but not limited to NCS, NBS or NIS can give the corresponding halide 69 (L=Cl, Br or I). Coupling of the halide 69 with $R^{14}$-M, where M is a boronic acid, boronic ester or an appropriately substituted metal reagent (e.g., M is $B(OR)_2$, $SnBu_3$ or ZnBr), under standard Suzuki, Stille or Negishi coupling conditions can give compound 51.

Scheme 17

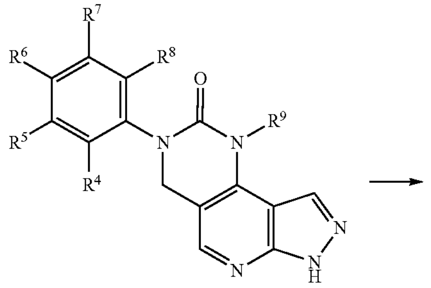

68

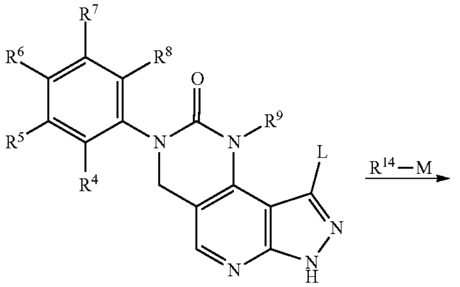

69

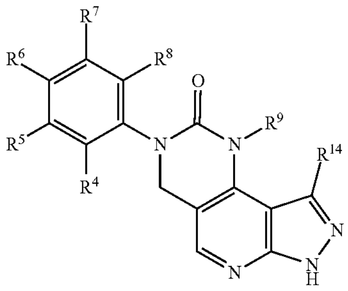

51

A series of tricyclic amino-derivatives 74 can be prepared according to the procedures outlined in Scheme 18. Protection of the 1H-pyrrolo[2,3-b]pyridine derivative 70 with suitable protecting reagents such as, for example, $PhSO_2Cl$ under basic conditions can afford the corresponding protected compound 71. Treatment of compound 71 with a strong base such as, for example, lithium diisopropylamide (LDA), butyllithium, or lithium bis(trimethylsilyl)amide (LiHMDS) in an inert solvent such as THF at low temperature can afford the metallated intermediate, which can be quenched with a suitable formyl-reagent such as, for example, dimethylformamide (DMF) to provide the aldehyde derivative 72. The amino-derivative 74 can be prepared by reductive amination of aldehyde 72 with an appropriate amine (e.g. $NHR^{c3}R^{d3}$) to give compound 73, followed by removal of the $PhSO_2$-protecting group in the presence of a suitable base such as, for example, $K_2CO_3$, KOH, $KO^tBu$, or tetra-n-butylammonium fluoride (TBAF).

Scheme 18

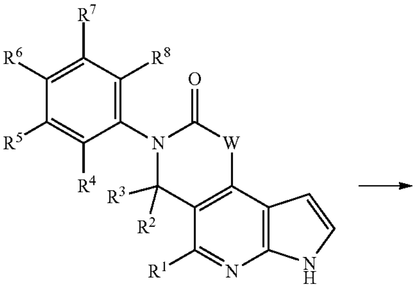

70

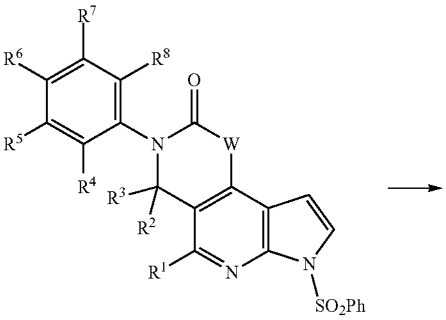

71

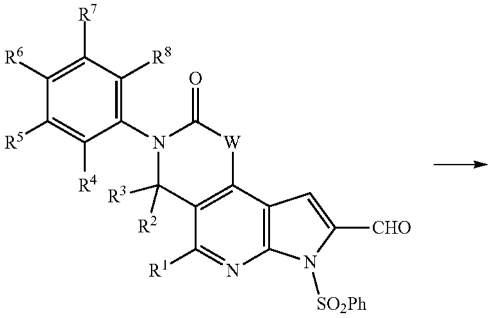

72

-continued

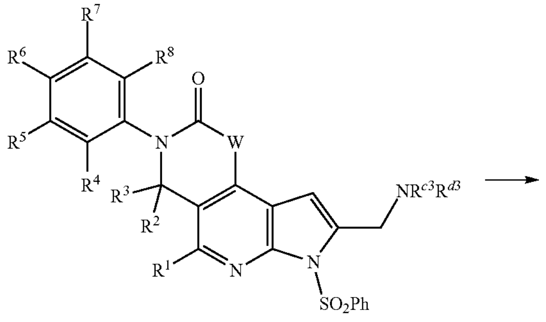

73

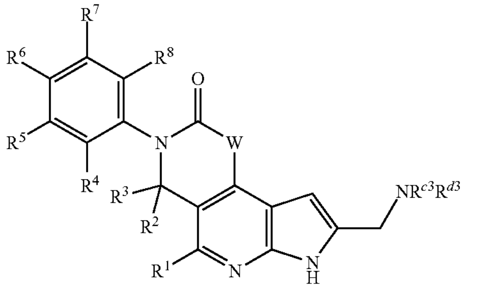

74

Alternatively, compound 74 can be prepared according to the procedures outlined in Scheme 19. Removal of the $PhSO_2$-protecting group in compound 72 in the presence of a suitable base such as, for example, $K_2CO_3$, KOH, $KO^tBu$ or tetra-n-butylammonium fluoride (TBAF), can generate compound 75. Reductive amination of aldehyde 75 with an appropriate amine (e.g. $NHR^{c3}R^{d3}$) can give compound 74.

Scheme 19

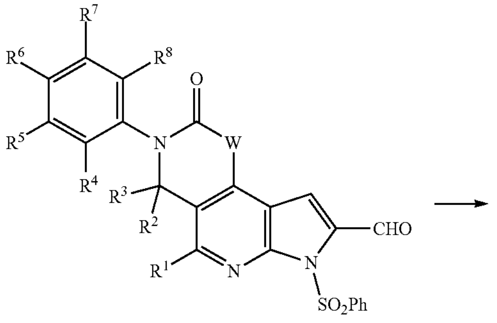

72

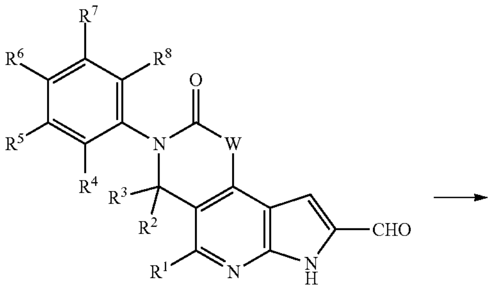

75

-continued

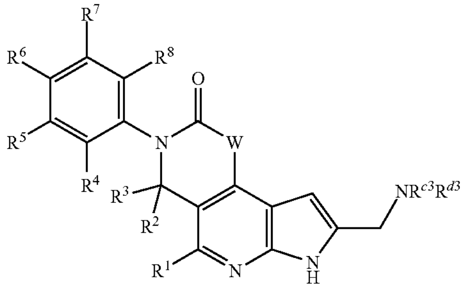

74

A series of tricyclic amino-derivatives 80 can be prepared according to the procedures outlined in Scheme 20. Suzuki coupling of compound 76 (L=halogen), which can be prepared using similar procedures as described in Scheme 6, with an appropriate boronic acid or ester can provide the vinylether derivative 77, which then can be hydrolyzed in aqueous acidic conditions to give the aldehyde derivative 78. Reductive amination of aldehyde 78 with an appropriate amine (e.g. $NHR^{c3}R^{d3}$) can give compound 79, followed by removal of the $PhSO_2$-protecting group in the presence of a suitable base such as, for example, $K_2CO_3$, KOH, $KO^tBu$ or tetra-n-butylammonium fluoride (TBAF), to provide the amino-derivatives 80.

Scheme 20

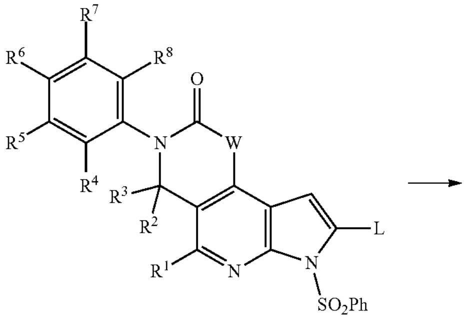

76

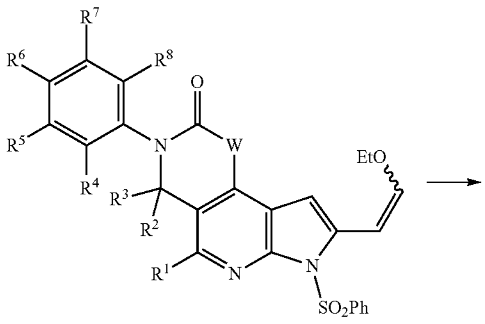

77

-continued

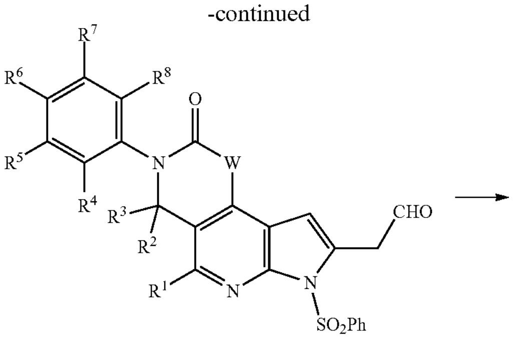

78

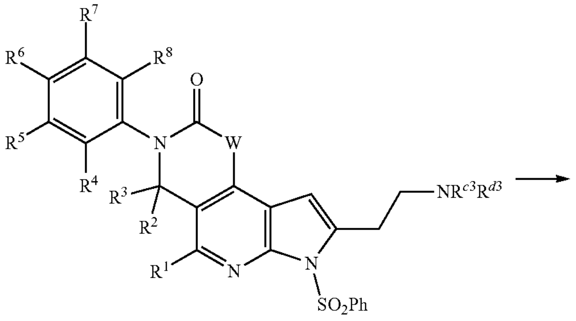

79

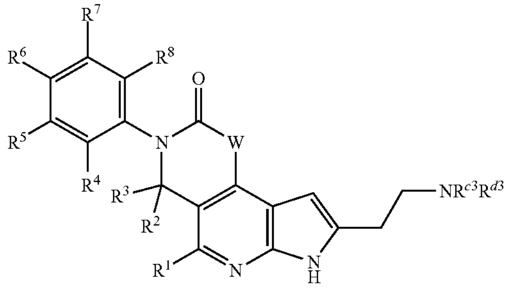

80

Methods of Use

Compounds of the invention can inhibit activity of one or more FGFR enzymes. For example, the compounds of the invention can be used to inhibit activity of an FGFR enzyme in a cell or in an individual or patient in need of inhibition of the enzyme by administering an inhibiting amount of a compound of the invention to the cell, individual, or patient.

In some embodiments, the compounds of the invention are inhibitors of one or more of FGFR1, FGFR2, FGFR3, and FGFR4. In some embodiments, the compounds of the invention inhibit each of FGFR1, FGFR2, and FGFR3. In some embodiments, the compounds of the invention are selective for one or more FGFR enzymes. In some embodiments, the compounds of the invention are selective for one or more FGFR enzymes over VEGFR2. In some embodiments, the selectivity is 2-fold or more, 3-fold or more, 5-fold or more, 10-fold or more, 50-fold or more, or 100-fold or more.

As FGFR inhibitors, the compounds of the invention are useful in the treatment of various diseases associated with abnormal expression or activity of FGFR enzymes or FGFR ligands.

For example, the compounds of the invention are useful in the treatment of cancer. Example cancers include bladder cancer, breast cancer, cervical cancer, colorectal cancer, endometrial cancer, gastric cancer, head and neck cancer, kidney cancer, liver cancer, lung cancer (e.g., adenocarcinoma, small cell lung cancer and non-small cell lung carcinomas), ovarian cancer, prostate cancer, esophageal cancer, gall bladder cancer, pancreatic cancer (e.g. exocrine pancreatic carcinoma), stomach cancer, thyroid cancer, skin cancer (e.g., squamous cell carcinoma).

Further example cancers include hematopoietic malignancies such as leukemia, multiple myeloma, chronic lymphocytic lymphoma, adult T cell leukemia, B-cell lymphoma, acute myelogenous leukemia, Hodgkin's or non-Hodgkin's lymphoma, myeloproliferative neoplasms (e.g., polycythemia vera, essential thrombocythemia, and primary myelofibrosis), Waldenstrom's Macroglubulinemia, hairy cell lymphoma, and Burkett's lymphoma.

Other cancers treatable with the compounds of the invention include glioblastoma, melanoma, and rhabdosarcoma.

Other cancers treatable with the compounds of the invention include gastrointestinal stromal tumors.

In addition to oncogenic neoplasms, the compounds of the invention can be useful in the treatment of skeletal and chondrocyte disorders including, but not limited to, achrondroplasia, hypochondroplasia, dwarfism, thanatophoric dysplasia (TD) (clinical forms TD I and TD II), Apert syndrome, Crouzon syndrome, Jackson-Weiss syndrome, Beare-Stevenson cutis gyrate syndrome, Pfeiffer syndrome, and craniosynostosis syndromes.

The compounds of the invention may further be useful in the treatment of fibrotic diseases, such as where a disease symptom or disorder is characterized by fibrosis. Example fibrotic diseases include liver cirrhosis, glomerulonephritis, pulmonary fibrosis, systemic fibrosis, rheumatoid arthritis, and wound healing.

In some embodiments, the compounds of the invention can be used in the treatment of a hypophosphatemia disorder such as, for example, X-linked hypophosphatemic rickets, autosomal recessive hypophosphatemic rickets, and autosomal dominant hypophosphatemic rickets, or tumor-induced osteromalacia.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the FGFR enzyme with a compound of the invention includes the administration of a compound of the present invention to an individual or patient, such as a human, having FGFR, as well as, for example, introducing a compound of the invention into a sample containing a cellular or purified preparation containing the FGFR enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) preventing the disease; for example, preventing a disease, condition or disorder in an individual who may be predisposed to the disease, condition or disorder but does not yet experience or display the pathology or symptomatology of the disease; 2) inhibiting the disease; for example, inhibiting a disease, condition or disorder in an individual who is experiencing or displaying the pathology or symptomatology of the disease, condition or disorder (i.e., arresting further development of the pathology and/or symptomatology), or 3) ameliorating the disease; for example, ameliorating a disease, condition or disorder in an individual who is experiencing or displaying the pathology or symptomatology of the disease, condition or disorder (i.e., reversing the pathology and/or symptomatology).

Combination Therapy

One or more additional pharmaceutical agents or treatment methods such as, for example, chemotherapeutics or other anti-cancer agents, immune enhancers, immunosuppressants, immunotherapies, radiation, anti-tumor and anti-viral vaccines, cytokine therapy (e.g., IL2, GM-CSF, etc.), and/or kinase (tyrosine or serine/threonine), epigenetic or signal transduction inhibitors can be used in combination with the compounds of the present invention for treatment of diseases, disorders or conditions associated with FGF ligand, receptor or pathway activation. The agents can be combined with the present compounds in a single dosage form, or the agents can be administered simultaneously or sequentially as separate dosage forms.

Suitable agents for use in combination with the compounds of the present invention for the treatment of cancer include chemotherapeutic agents, targeted cancer therapies, immunotherapies or radiation therapy. Compounds of this invention may be effective in combination with anti-hormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with compounds of the present invention. These include anti-androgens including but not limited to flutamide, bicalutamide, and nilutamide, luteinizing hormone-releasing hormone (LHRH) analogs including leuprolide, goserelin, triptorelin, and histrelin, LHRH antagonists (e.g. degarelix), androgen receptor blockers (e.g. enzalutamide) and agents that inhibit androgen production (e.g. abiraterone).

Compounds of the present invention may be combined with or in sequence with other agents against membrane receptor kinases especially for patients who have developed primary or acquired resistance to the targeted therapy. These therapeutic agents include inhibitors or antibodies against EGFR, Her2, VEGFR, c-Met, Ret, IGFR1, or Flt-3 and against cancer-associated fusion protein kinases such as Bcr-Abl and EML4-Alk. Inhibitors against EGFR include gefitinib and erlotinib, and inhibitors against EGFR/Her2 include but are not limited to dacomitinib, afatinib, lapitinib and neratinib. Antibodies against the EGFR include but are not limited to cetuximab, panitumumab and necitumumab. Inhibitors of c-Met may be used in combination with FGFR inhibitors. These include (onartumzumab, tivantnib, INC-280). Agents against Abl (or Bcr-Abl) include imatinib, dasatinib, nilotinib, and ponatinib and those against Alk (or EML4-ALK) include crizotinib.

Angiogenesis inhibitors may be efficacious in some tumors in combination with FGFR inhibitors. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Activation of intracellular signaling pathways is frequent in cancer, and agents targeting components of these pathways have been combined with receptor targeting agents to enhance efficacy and reduce resistance. Examples of agents that may be combined with compounds of the present invention include inhibitors of the PI3K-AKT-mTOR pathway, inhibitors of the Raf-MAPK pathway, inhibitors of JAK-STAT pathway, and inhibitors of protein chaperones and cell cycle progression.

Agents against the PI3 kinase include but are not limited topilaralisib, idelalisib, buparlisib. Inhibitors of mTOR such as rapamycin, sirolimus, temsirolimus, and everolimus may be combined with FGFR inhibitors. Other suitable examples include but are not limited to vemurafenib and dabrafenib (Raf inhibitors) and trametinib, selumetinib and GDC-0973 (MEK inhibitors). Inhibitors of JAK (ruxolitinib), Hsp90 (tanespimycin), cyclin dependent kinases (palbociclib), HDACs (panobinostat), PARP (olaparib), and proteasomes (bortezomib, carfilzomib) can also be combined with compounds of the present invention.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Other suitable agents for use in combination with the compounds of the present invention include chemotherapy combinations such as platinum-based doublets used in lung cancer (cisplatin or carboplatin plus gemcitabine; cisplatin or carboplatin plus docetaxel; cisplatin or carboplatin plus paclitaxel; cisplatin or carboplatin plus pemetrexed) or gemcitabine plus paclitaxel bound particles (Abraxane).

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (TAXOL™), mithramycin, deoxycoformycin, mitomycin-C, L-asparaginase, interferons (especially IFN-α), etoposide, and teniposide.

Other cytotoxic agents include navelbene, CPT-11, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; leucovorin; tegafur; and haematopoietic growth factors.

Compounds according to the invention may also be combined with immunotherapy drugs, including cytokines such as interferon alpha, interleukin 2, and tumor necrosis factor (TNF).

Other anti-cancer agent(s) include antibody therapeutics to costimulatory molecules such as CTLA-4, 4-1BB and PD-1, or antibodies to cytokines (IL-10, TGF-β, etc.).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, NJ), the disclosure of which is incorporated herein by reference as if set forth in its entirety.

Pharmaceutical Formulations and Dosage Forms

When employed as pharmaceuticals, the compounds of the invention can be administered in the form of pharmaceutical compositions which refers to a combination of a compound of the invention, or its pharmaceutically acceptable salt, and at least one pharmaceutically acceptable carrier. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal, or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as antiviral agents, vaccines, antibodies, immune enhancers, immune suppressants, anti-inflammatory agents and the like.

Labeled Compounds and Assay Methods

Another aspect of the present invention relates to fluorescent dye, spin label, heavy metal or radio-labeled compounds of the invention that would be useful not only in imaging but also in assays, both in vitro and in vivo, for localizing and quantitating the FGFR enzyme in tissue samples, including human, and for identifying FGFR enzyme ligands by inhibition binding of a labeled compound. Accordingly, the present invention includes FGFR enzyme assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro FGFR enzyme labeling and competition assays, compounds that incorporate $^{3}H$, $^{14}C$, $^{82}Br$, $^{125}I$, $^{131}I$, or $^{35}S$ will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a compound that has incorporated at least one radionuclide. In some embodiments the radionuclide is selected from the group consisting of $^{3}H$, $^{14}C$, $^{125}I$, $^{35}S$ and $^{82}Br$.

Synthetic methods for incorporating radio-isotopes into organic compounds are applicable to compounds of the invention and are well known in the art.

A radio-labeled compound of the invention can be used in a screening assay to identify/evaluate compounds. In general terms, a newly synthesized or identified compound (i.e., test compound) can be evaluated for its ability to reduce binding of the radio-labeled compound of the invention to the FGFR enzyme. Accordingly, the ability of a test compound to compete with the radio-labeled compound for binding to the FGFR enzyme directly correlates to its binding affinity.

Kits

The present invention also includes pharmaceutical kits useful, for example, in the treatment or prevention of FGFR-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of one or more FGFR's as described below.

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, *J. Combi. Chem.,* 4, 295 (2002); "Optimizing Preparative LC-MS Configurations and Methods for Parallel Synthesis Purification", K. Blom, R. Sparks, J. Doughty, G. Everlof, T. Haque, A. Combs, *J. Combi. Chem.,* 5, 670 (2003); and "Preparative LC-MS Purification: Improved Compound Specific Method Optimization", K. Blom, B. Glass, R. Sparks, A. Combs, *J. Combi. Chem.,* 6, 874-883 (2004). The compounds separated were typically subjected to analytical liquid chromatography mass spectrometry (LCMS) for purity check under the following conditions: Instrument; Agilent 1100 series, LC/MSD, Column: Waters Sunfire™ $C_{18}$ 5 μm, 2.1×5.0 mm, Buffers: mobile phase A: 0.025% TFA in water and mobile phase B: 0.025% TFA in acetonitrile; gradient 2% to 80% of B in 3 minutes with flow rate 1.5 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm, 19×100 mm column, eluting with mobile phase A: 0.1% TFA (trifluoroacetic acid) in water and mobile phase B: 0.1% TFA in acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, *J. Comb. Chem.,* 6, 874-883 (2004)]. Typically, the flow rate used with the 30×100 mm column was 60 mL/minute.

pH=10 purifications: Waters XBridge $C_{18}$ 5 μm, 19×100 mm column, eluting with mobile phase A: 0.15% $NH_4OH$ in water and mobile phase B: 0.15% $NH_4OH$ in acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, *J. Comb. Chem.,* 6, 874-883 (2004)]. Typically, the flow rate used with 30×100 mm column was 60 mL/minute.

Example 1

3-(3,5-Dimethoxyphenyl)-1-methyl-1,3,4,7-tetrahydro-2H-pyrrolo[3',2':5,6]pyrido[4,3-d]pyrimidin-2-one

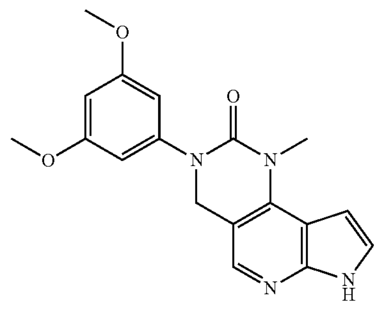 [SMILES: COc1cc(OC)cc(N2Cc3cnc4[nH]ccc4c3N(C)C2=O)c1]

Step 1: 4-(methylamino)-1H-pyrrolo[2,3-b]pyridine-5-carbaldehyde

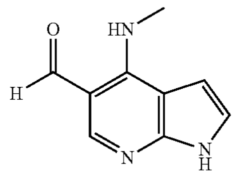

A mixture of 4-chloro-1H-pyrrolo[2,3-b]pyridine-5-carbaldehyde (CAS #958230-19-8) from Adesis, cat #4-263; Synnovator, cat #PBN2011188: 2.71 g, 15 mmol) and methylamine (33 wt. % in ethanol, 24 mL, 200 mmol) in 2-methoxyethanol (6 mL) was heated to 110° C. and stirred overnight in a sealed pressure flask. Then the reaction mixture was cooled to room temperature and concentrated. The residue was dissolved in HCl solution (1 N, 25 mL) and heated to 50° C. After stirring for 2 h, the reaction mixture was cooled to room temperature and neutralized with saturated $NaHCO_3$ solution. The light yellow precipitate was collected via filtration, washed with water and hexanes then dried in vacuo to afford the desired product (2.54 g, 97%) as a light yellow solid. LC-MS calculated for $C_9H_{10}N_3O$ $[M+H]^+$ m/z: 176.1; found 176.1.

Step 2: 5-{[(3,5-dimethoxyphenyl)amino]methyl}-N-methyl-1H-pyrrolo[2,3-b]pyridin-4-amine

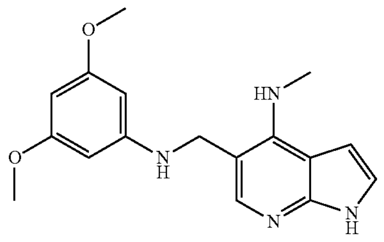 [SMILES: CNc1c(CNc2cc(OC)cc(OC)c2)cnc2[nH]ccc12]

To a mixture of 4-(methylamino)-1H-pyrrolo[2,3-b]pyridine-5-carbaldehyde (1.75 g, 10 mmol) and 3,5-dimethoxybenzenamine (2.30 g, 15.0 mmol) in ethanol (50 mL) was added acetic acid (8.5 mL, 150 mmol). The resulting light yellow suspension was heated to reflux. After stirring for 3 h, the resulting red solution was cooled to room temperature and sodium cyanoborohydride (1.9 g, 30 mmol) was added. The reaction mixture was stirred at room temperature overnight then neutralized with saturated $Na_2CO_3$ solution. The mixture was extracted with ethyl acetate (EtOAc). The organic layer was washed with water and brine then dried over $Na_2SO_4$. The solvent was removed under reduced pressure. The residue was purified by column (Biotage®): 40 g silica gel column, eluted with 0 to 10% MeOH/DCM to afford the desired product (2.33 g, 75%) as a light yellow solid. LC-MS calculated for $C_{17}H_{21}N_4O_2$ $[M+H]^+$ m/z: 313.2; found 313.1.

Step 3: 3-(3,5-dimethoxyphenyl)-1-methyl-1,3,4,7-tetrahydro-2H-pyrrolo[3',2':5,6]pyrido[4,3-d]pyrimidin-2-one To a stirred solution of 5-{[(3,5-dimethoxyphenyl)amino]methyl}-N-methyl-1H-pyrrolo[2,3-b]pyridin-4-amine (16 mg, 0.05 mmol) and triethylamine (21 μL, 0.15 mmol) in tetrahydrofuran (1.5 mL) was added triphosgene (18 mg, 0.06 mmol) in tetrahydrofuran (0.5 mL) at 0° C. The resulting yellow suspension was stirred at 0° C. for 30 min then NaOH solution (1 N, 1 mL) was added. All the precipitate dissolved to afford two layers of solutions and the reaction mixture was stirred at 0° C. for another 30 min. The organic layer containing the desired product was purified by RP-HPLC (pH=2) to afford the desired product as a white solid. LC-MS calculated for $C_{18}H_{19}N_4O_3$ $[M+H]^+$ m/z: 339.1; found: 339.1.

Example 2

3-(3,5-Dimethoxyphenyl)-1,3,4,7-tetrahydro-2H-pyrrolo[3',2':5,6]pyrido[4,3-d]pyrimidin-2-one

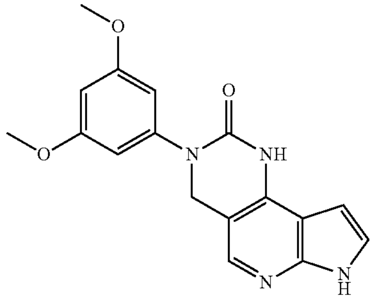 [SMILES: COc1cc(OC)cc(N2Cc3cnc4[nH]ccc4c3NC2=O)c1]

This compound was prepared using procedures analogous to those described for Example 1 with ammonium hydroxide solution replacing methylamine and the reaction temperature raised to 130° C. in Step 1. LC-MS calculated for $C_{17}H_{17}N_4O_3$ $[M+H]^+$ m/z: 325.1; found: 325.1.

Example 3

3-(3,5-Dimethoxyphenyl)-1-ethyl-1,3,4,7-tetrahydro-2H-pyrrolo[3',2':5,6]pyrido[4,3-d]pyrimidin-2-one

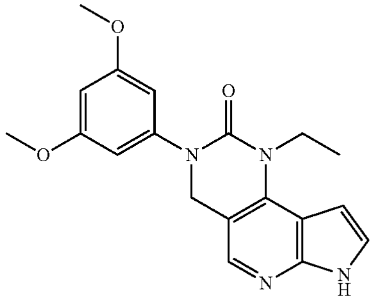 [SMILES: CCN1C(=O)N(c2cc(OC)cc(OC)c2)Cc2cnc3[nH]ccc3c21]

This compound was prepared using procedures analogous to those described for Example 1 with ethylamine (2 M in THF) replacing methylamine and the reaction temperature raised to 130° C. in Step 1. LC-MS calculated for $C_{19}H_{21}N_4O_3$ $[M+H]^+$ m/z: 353.2; found: 353.1. $^1H$ NMR (500 MHz, DMSO) δ 12.18 (s, 1H), 8.12 (s, 1H), 7.58-7.53 (m, 1H), 6.75 (d, J=2.9 Hz, 1H), 6.56 (d, J=2.2 Hz, 2H), 6.42 (t, J=2.2 Hz, 1H), 4.86 (s, 2H), 4.21 (q, J=6.9 Hz, 2H), 3.75 (s, 6H), 1.38 (t, J=6.9 Hz, 3H).

Example 4

1-Cyclopropyl-3-(3,5-dimethoxyphenyl)-1,3,4,7-tetrahydro-2H-pyrrolo [3',2':5,6]pyrido[4,3-d]pyrimidin-2-one

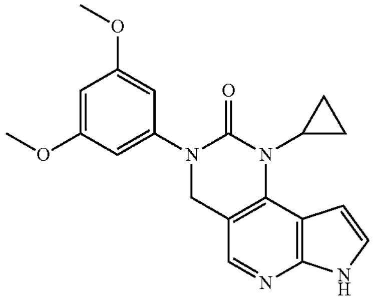 [SMILES: COc1cc(OC)cc(N2Cc3cnc4[nH]ccc4c3N(C3CC3)C2=O)c1]

This compound was prepared using procedures analogous to those described for Example 1 with cyclopropylamine replacing methylamine and the reaction temperature raised to 130° C. in Step 1. LC-MS calculated for $C_{20}H_{21}N_4O_3$ $[M+H]^+$ m/z: 365.2; found: 365.2. $^1H$ NMR (500 MHz, DMSO) δ 12.20 (s, 1H), 8.16 (s, 1H), 7.55-7.51 (m, 1H), 7.03 (d, J=2.5 Hz, 1H), 6.54 (d, J=2.2 Hz, 2H), 6.39 (t, J=2.2 Hz, 1H), 4.77 (s, 2H), 3.74 (s, 6H), 3.39-3.33 (m, 1H), 1.14-1.08 (m, 2H), 0.76-0.66 (m, 2H).

Example 5

1-(Cyclopropylmethyl)-3-(3,5-dimethoxyphenyl)-1,3,4,7-tetrahydro-2H-pyrrolo[3',2':5,6]pyrido[4,3-d]pyrimidin-2-one

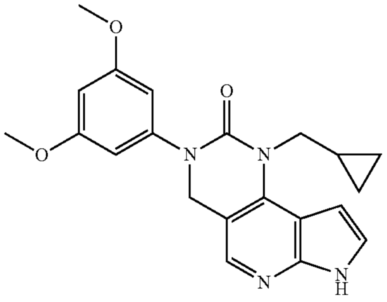 [SMILES: COc1cc(OC)cc(N2Cc3cnc4[nH]ccc4c3N(CC3CC3)C2=O)c1]

This compound was prepared using procedures analogous to those described for Example 1 with cyclopropylmethylamine replacing methylamine and the reaction temperature raised to 130° C. in Step 1. LC-MS calculated for $C_{21}H_{23}N_4O_3$ $[M+H]^+$ m/z: 379.2; found: 379.1.

Example 6

1-Benzyl-3-(3,5-dimethoxyphenyl)-1,3,4,7-tetrahydro-2H-pyrrolo [3',2':5,6]pyrido[4,3-d]pyrimidin-2-one

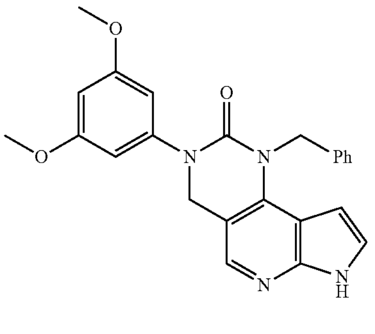 [SMILES: COc1cc(OC)cc(N2Cc3cnc4[nH]ccc4c3N(Cc3ccccc3)C2=O)c1]

This compound was prepared using procedures analogous to those described for Example 1 with benzylamine replacing methylamine and the reaction temperature raised to 130° C. in Step 1. LC-MS calculated for $C_{24}H_{23}N_4O_3$ $[M+H]^+$ m/z: 415.2; found: 415.2.

Example 7

3-(2-Chloro-3,5-dimethoxyphenyl)-1-methyl-1,3,4,7-tetrahydro-2H-pyrrolo[3',2':5,6]pyrido[4,3-d]pyrimidin-2-one

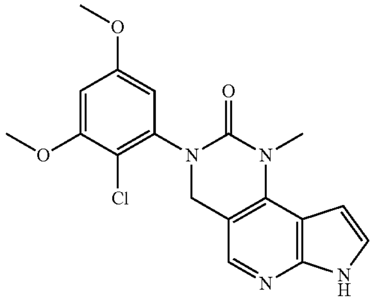

Step 1: 3-(3,5-dimethoxyphenyl)-1-methyl-7-(phenylsulfonyl)-1,3,4,7-tetrahydro-2H-pyrrolo[3',2':5,6]pyrido[4,3-d]pyrimidin-2-one

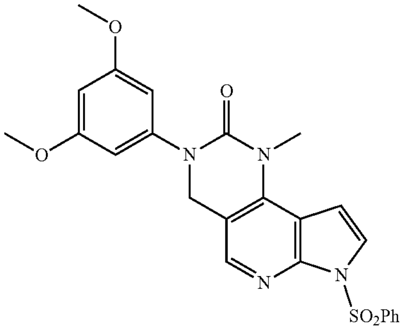

To a stirred solution of 5-{[(3,5-dimethoxyphenyl)amino]methyl}-N-methyl-1H-pyrrolo[2,3-b]pyridin-4-amine (Example 1, step 2: 2.33 g, 7.46 mmol) and triethylamine (3.1 mL, 22 mmol) in tetrahydrofuran (50 mL) was added triphosgene (2.66 g, 8.95 mmol) in tetrahydrofuran (20 mL) at 0° C. The resulting yellow suspension was stirred at 0° C. for 30 min then NaOH solution (1 N, 20 mL) was added. All the precipitate dissolved to give two layers of solutions and the reaction mixture was stirred at 0° C. for another 30 min. The mixture was extracted with ethyl acetate (EtOAc). The organic layers were combined and washed with water, brine then dried over $Na_2SO_4$. The solvents were removed under reduced pressure. The residue was dissolved in tetrahydrofuran (50 mL) and cooled to 0° C. then sodium hydride (60 wt. % dispersion in mineral oil, 600 mg, 15 mmol) was added in three portions. The resulting brown solution was stirred at 0° C. for 30 min then benzensulfonyl chloride (1.4 mL, 11 mmol) was added dropwise. After stirring at 0° C. for 30 min, the reaction was quenched with water and the mixture was extracted with EtOAc. The organic layers were combined and washed with water, brine then dried over $Na_2SO_4$. The solvents were removed under reduced pressure and the residue was purified by column (Biotage®): 40 g silica gel column, eluted with 20 to 50% EtOAc/Hexanes to give a light yellow solid which was triturated with diethyl ether to give the pure product (2.75 g, 77%) as a white solid. LC-MS calculated for $C_{24}H_{23}N_4O_5S$ $[M+1]^+$ m/z: 479.1; found: 479.1.

Step 2: 3-(2-chloro-3,5-dimethoxyphenyl)-1-methyl-1,3,4,7-tetrahydro-2H-pyrrolo[3',2':5,6]pyrido[4,3-d]pyrimidin-2-one To a stirred solution of 3-(3,5-dimethoxyphenyl)-1-methyl-7-(phenylsulfonyl)-1,3,4,7-tetrahydro-2H-pyrrolo[3',2':5,6]pyrido[4,3-d]pyrimidin-2-one (29 mg, 0.06 mmol) in acetonitrile (3 mL, 60 mmol) at 0° C. was added sulfuryl chloride (7.36 μL, 0.09 mmol) in dichloromethane (0.2 mL) dropwise over 5 min. The resulting light yellow solution was stirred at 0° C. for 10 min, at which time LC-MS indicated complete consumption of the starting material. The reaction was quenched with saturated $NaHCO_3$ solution at 0° C. then extracted with EtOAc. The organic layer was washed with water, brine and dried over $Na_2SO_4$. The solvent was removed under reduced pressure. The residue and potassium carbonated (50 mg, 0.36 mmol) were dissolved in methanol (9.5 mL) and water (0.5 mL). The resulting solution was heated to 65° C. and stirred for 2 h. The mixture was purified by RP-HPLC (pH=2) to afford the desired product as a white solid. LC-MS calculated for $C_{18}H_{18}ClN_4O_3[M+H]^+$ m/z: 373.1; found: 373.2. $^1$H NMR (500 MHz, DMSO) δ 12.05 (s, 1H), 8.07 (s, 1H), 7.53-7.48 (m, 1H), 6.85 (d, J=2.1 Hz, 1H), 6.79 (d, J=2.7 Hz, 1H), 6.73 (d, J=2.7 Hz, 1H), 4.89 (d, J=13.4 Hz, 1H), 4.66 (d, J=13.4 Hz, 1H), 3.87 (s, 3H), 3.80 (s, 3H), 3.66 (s, 3H).

Example 8

3-(2,6-Dichloro-3,5-dimethoxyphenyl)-1-methyl-1,3,4,7-tetrahydro-2H-pyrrolo[3',2':5,6]pyrido[4,3-d]pyrimidin-2-one

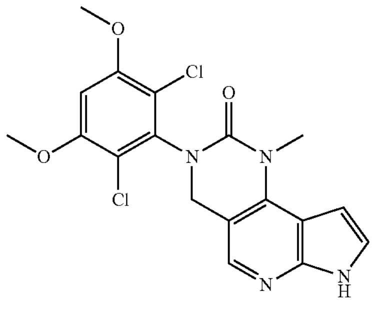

This compound was formed in the same reaction as described for Example 7, Step 2. Purified by RP-HPLC (pH=2) to afford the pure product as a white solid. LC-MS calculated for $C_{18}H_{17}Cl_2N_4O_3$ $[M+H]^+$ m/z: 407.1; found: 407.1. $^1$H NMR (500 MHz, DMSO) δ 12.07 (s, 1H), 8.06 (s, 1H), 7.53-7.48 (m, 1H), 7.00 (s, 1H), 6.86 (d, J=2.6 Hz, 2H), 4.73 (s, 2H), 3.96 (s, 6H), 3.66 (s, 3H).

Example 9

3-(2,4-Dichloro-3,5-dimethoxyphenyl)-1-methyl-1,3,4,7-tetrahydro-2H-pyrrolo[3',2':5,6]pyrido[4,3-d]pyrimidin-2-one

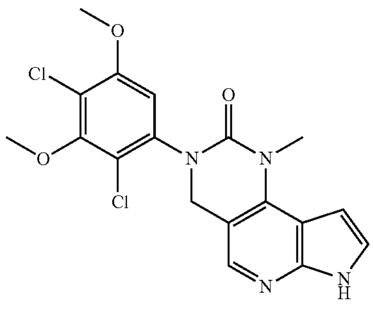 [SMILES: COc1cc(N2Cc3cnc4[nH]ccc4c3N(C)C2=O)c(Cl)c(OC)c1Cl]

This compound was formed as a minor-product in the same reaction as described for Example 7, Step 2. Purified by RP-HPLC (pH=2) to afford the pure compound as a white solid. LC-MS calculated for $C_{18}H_{17}Cl_2N_4O_3$ $[M+H]^+$ m/z: 407.1; found: 407.0. $^1$H NMR (500 MHz, DMSO) δ 11.96 (s, 1H), 8.05 (s, 1H), 7.51-7.46 (m, 1H), 7.28 (s, 1H), 6.83 (br, 1H), 4.95 (d, J=12.9 Hz, 1H), 4.69 (d, J=12.9 Hz, 1H), 3.89 (s, 3H), 3.83 (s, 3H), 3.66 (s, 3H).

Example 10

3-(3,5-Dimethoxyphenyl)-1-methyl-8-[4-(4-methylpiperazin-1-yl)phenyl]-1,3,4,7-tetrahydro-2H-pyrrolo[3',2':5,6]pyrido[4,3-d]pyrimidin-2-one

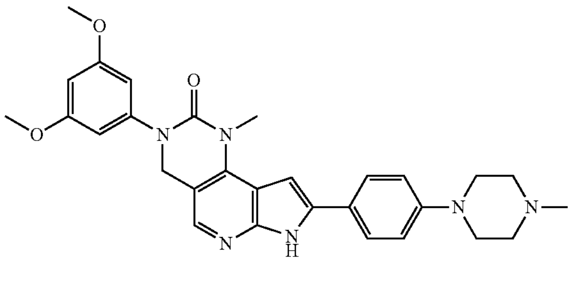

Step 1: Preparation of Lithium Diisopropylamide (LDA) Solution (1M in THF)

To a cooled (−78° C.) solution of N,N-diisopropylamine (0.14 mL, 1.0 mmol) in tetrahydrofuran (0.46 mL) was added n-butyllithium (2.5 M in hexanes, 0.40 mL, 1.0 mmol) dropwise. The mixture was stirred at −78° C. for 5 min then warmed to 0° C. and stirred for 20 min to afford 1 mL of 1 M LDA solution in THF.

Step 2: 8-bromo-3-(3,5-dimethoxyphenyl)-1-methyl-7-(phenylsulfonyl)-1,3,4,7-tetrahydro-2H-pyrrolo[3',2':5,6]pyrido[4,3-d]pyrimidin-2-one

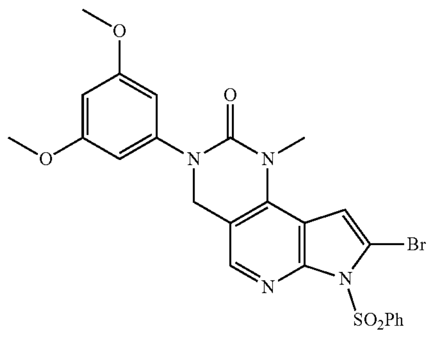

To a cooled (−78° C.) solution of 3-(3,5-dimethoxyphenyl)-1-methyl-7-(phenylsulfonyl)-1,3,4,7-tetrahydro-2H-pyrrolo[3',2':5,6]pyrido[4,3-d]pyrimidin-2-one (Example 7, Step 1; 49 mg, 0.10 mmol) in tetrahydrofuran (3 mL) was added freshly prepared lithium diisopropylamide (LDA) solution (1 M in THF, 0.30 mL) dropwise. The resulting solution was stirred at −78° C. for 30 min then a solution of 1,2-dibromo-1,1,2,2-tetrachloroethane (37 mg, 0.11 mmol) in tetrahydrofuran (0.2 mL) was added. After stirring at −78° C. for 1 h, the reaction was quenched with saturated $NH_4Cl$ solution at −78° C. then warmed to room temperature. The mixture was extracted with EtOAc. The organic layers were combined then washed with water, brine and dried over $Na_2SO_4$. The solvents were removed under reduced pressure. The residue was used in the next step without further purification. LC-MS calculated for $C_{24}H_{22}BrN_4O_5S$ $[M+H]^+$ m/z: 557.0; found: 557.1.

Step 3: 3-(3,5-dimethoxyphenyl)-1-methyl-8-[4-(4-methylpiperazin-1-yl)phenyl]-7-(phenylsulfonyl)-1,3,4,7-tetrahydro-2H-pyrrolo[3',2':5,6]pyrido[4,3-d]pyrimidin-2-one

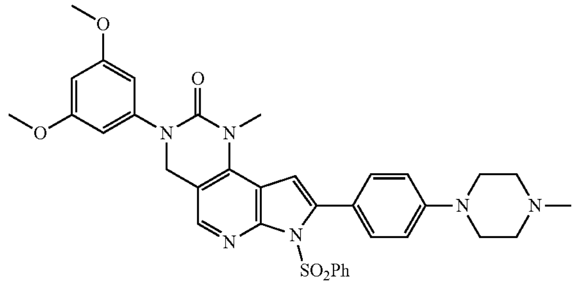

A mixture of 8-bromo-3-(3,5-dimethoxyphenyl)-1-methyl-7-(phenylsulfonyl)-1,3,4,7-tetrahydro-2H-pyrrolo[3',2':5,6]pyrido[4,3-d]pyrimidin-2-one (12 mg, 0.022 mmol), 1-methyl-4-[4-(4,4,5,5-tetramethyl-1,3,2-dioxaborolan-2-yl)phenyl]piperazine (from Alfa Aesar, cat #H51659, 13 mg, 0.043 mmol), [1,1'-bis(diphenylphosphino)ferrocene]dichloro-palladium (II) complexed with dichloromethane (1:1) (4 mg, 0.004 mmol), and potassium carbonate (6.0 mg, 0.043 mmol) was dissolved in 1,4-dioxane (3 mL) then water (0.3 mL) was added. The mixture was degassed then back-filled with nitrogen. This process was repeated for three times. The reaction mixture was heated to 90° C. and stirred for 1 h, at which time LC-MS indicated the reaction was complete. The mixture was cooled to room temperature and concentrated. The residue was purified by column (Biotage®): 12 g silica gel column, eluted with 0 to 10% MeOH/DCM to afford the desired product (12 mg, 86%) as a yellow solid. LC-MS calculated for $C_{35}H_{37}N_6O_5S$ $[M+H]^+$ m/z: 653.3; found: 653.3.

Step 4: 3-(3,5-dimethoxyphenyl)-1-methyl-8-[4-(4-methylpiperazin-1-yl)phenyl]-1,3,4,7-tetrahydro-2H-pyrrolo[3',2':5,6]pyrido[4,3-d]pyrimidin-2-one To a stirred solution of 3-(3,5-dimethoxyphenyl)-1-methyl-8-[4-(4-methylpiperazin-1-yl)phenyl]-7-(phenylsulfonyl)-1,3,4,7-tetrahydro-2H-pyrrolo[3',2':5,6]pyrido[4,3-d]-pyrimidin-2-one (12 mg, 0.02 mmol) in tetrahydrofuran (2 mL) was added potassium t-butoxide (1 M in THF, 0.2 mL). The resulting yellow solution was stirred at room temperature for 15 min then diluted with methanol and purified by RP-HPLC (pH=2) to afford the desired product as a yellow solid. LC-MS calculated for $C_{29}H_{33}N_6O_3$ $[M+H]^+$ m/z: 513.3; found: 513.3. $^1H$ NMR (500 MHz, DMSO) δ 12.27 (s, 1H), 8.00 (s, 1H), 7.89 (d, J=8.8 Hz, 2H), 7.15 (s, 1H), 7.11 (d, J=8.9 Hz, 2H), 6.55 (d, J=2.1 Hz, 2H), 6.40 (t, J=2.1 Hz, 1H), 4.83 (s, 2H), 3.98 (br, 2H), 3.75 (s, 6H), 3.70 (s, 3H), 3.54 (br, 2H), 3.18 (br, 2H), 3.05 (br, 2H), 2.88 (s, 3H).

Example 11

3-(3,5-Dimethoxyphenyl)-1-methyl-8-(1-methyl-1H-pyrazol-4-yl)-1,3,4,7-tetrahydro-2H-pyrrolo[3',2':5,6]pyrido[4,3-d]pyrimidin-2-one

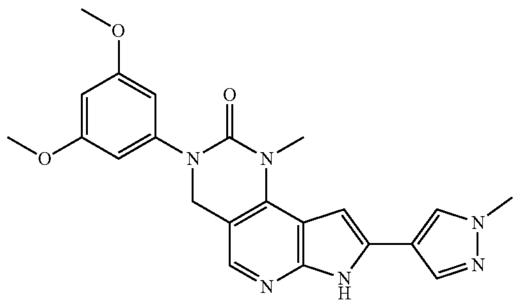

This compound was prepared using procedures analogous to those described for Example with 1-methyl-4-(4,4,5,5-tetramethyl-1,3,2-dioxaborolan-2-yl)-1H-pyrazole replacing 1-methyl-4-[4-(4,4,5,5-tetramethyl-1,3,2-dioxaborolan-2-yl)phenyl]piperazine. LC-MS calculated for $C_{22}H_{23}N_6O_3$ $[M+H]^+$ m/z: 419.2; found: 419.2. $^1H$ NMR (500 MHz, DMSO) δ 12.34 (s, 1H), 8.22 (s, 1H), 8.01 (d, J=1.6 Hz, 2H), 7.02 (d, J=1.5 Hz, 1H), 6.55 (d, J=2.2 Hz, 2H), 6.40 (t, J=2.2 Hz, 1H), 4.84 (s, 2H), 3.90 (s, 3H), 3.75 (s, 6H), 3.67 (s, 3H).

Example 12

3-(3,5-Dimethoxyphenyl)-N,1-dimethyl-2-oxo-2,3,4,7-tetrahydro-1H-pyrrolo[3',2':5,6]pyrido[4,3-d]pyrimidine-8-carboxamide

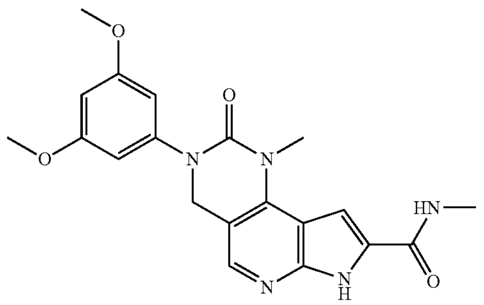

Step 1: 3-(3,5-dimethoxyphenyl)-1-methyl-2-oxo-7-(phenylsulfonyl)-2,3,4,7-tetrahydro-1H-pyrrolo[3',2':5,6]pyrido[4,3-d]pyrimidine-8-carboxylic acid

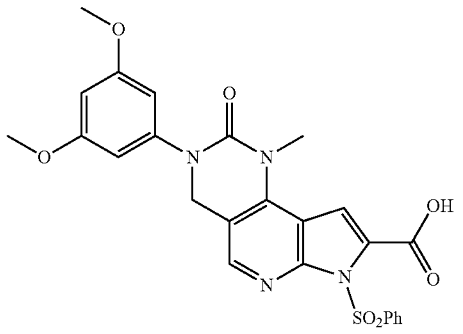

To a cooled (−78° C.) solution of 3-(3,5-dimethoxyphenyl)-1-methyl-7-(phenylsulfonyl)-1,3,4,7-tetrahydro-2H-pyrrolo[3',2':5,6]pyrido[4,3-d]pyrimidin-2-one (44 mg, 0.092 mmol) in tetrahydrofuran (3 mL) was added LDA solution (freshly prepared, 1M in THF, 0.30 mL, 0.3 mmol) dropwise. The resulting solution was stirred at −78° C. for 30 min then dry $CO_2$ gas (prepared from dry ice by passing through a drying tube) was bubbled into the reaction mixture for 30 min. The mixture was warmed to room temperature slowly and acidified with 1 N HCl then extracted with EtOAc. The organic layer was washed with water, brine then dried over $Na_2SO_4$. The solvent was removed under reduced pressure. The residue was used in the next step without further purification. LC-MS calculated for $C_{25}H_{23}N_4O_7S$ $[M+H]^+$ m/z: 523.1; found: 523.2.

Step 2: 3-(3,5-dimethoxyphenyl)-N,1-dimethyl-2-oxo-7-(phenylsulfonyl)-2,3,4,7-tetrahydro-1H-pyrrolo[3',2':5,6]pyrido[4,3-d]pyrimidine-8-carboxamide

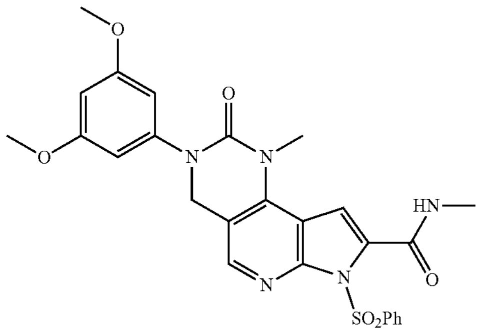

The crude product from Step 1 and benzotriazol-1-yloxy-tris(dimethylamino)-phosphoniumhexafluorophosphate (41 mg, 0.092 mmol) were dissolved in tetrahydrofuran (5 mL) then triethylamine (38 μL, 0.28 mmol) was added. The mixture was stirred at room temperature for 5 min then methylamine (2 M in THF, 140 μL, 0.28 mmol) was added. After stirring at room temperature for 30 min, the reaction mixture was diluted with EtOAc then washed with water, brine and dried over $Na_2SO_4$. The solvents were removed under reduced pressure and the residue was purified by column (Biotage®): 12 g silica gel column, eluted with to 100% EtOAc/Hexanes to afford the desired product (21 mg, 43%). LC-MS calculated for $C_{26}H_{26}N_5O_6S$ $[M+H]^+$ m/z: 536.2; found: 536.1.

Step 3: 3-(3,5-dimethoxyphenyl)-N,1-dimethyl-2-oxo-2,3,4,7-tetrahydro-1H-pyrrolo[3',2':5,6]pyrido[4,3-d]pyrimidine-8-carboxamide To a stirred solution of 3-(3,5-dimethoxyphenyl)-N,1-dimethyl-2-oxo-7-(phenylsulfonyl)-2,3,4,7-tetrahydro-1H-pyrrolo[3',2':5,6]pyrido[4,3-d]pyrimidine-8-carboxamide (21 mg, 0.039 mmol) in tetrahydrofuran (3 mL) was added potassium tert-butoxide (1 M in THF, 0.4 mL, 0.4 mmol). The resulting yellow solution was stirred at room temperature for 15 min then diluted with MeOH and purified by RP-HPLC (pH=2) to afford the desired product as a white solid. LC-MS calculated for $C_{20}H_{22}N_5O_4$ $[M+H]^+$ m/z: 396.2; found: 396.2.

Example 13

3-(2-Chloro-3,5-dimethoxyphenyl)-1-methyl-8-(1-methyl-1H-pyrazol-4-yl)-1,3,4,7-tetrahydro-2H-pyrrolo[3',2':5,6]pyrido[4,3-d]pyrimidin-2-one

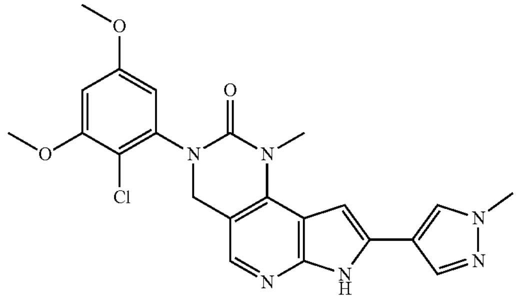

Step 1: 8-bromo-3-(2-chloro-3,5-dimethoxyphenyl)-1-methyl-7-(phenylsulfonyl)-1,3,4,7-tetrahydro-2H-pyrrolo[3',2':5,6]pyrido[4,3-d]pyrimidin-2-one

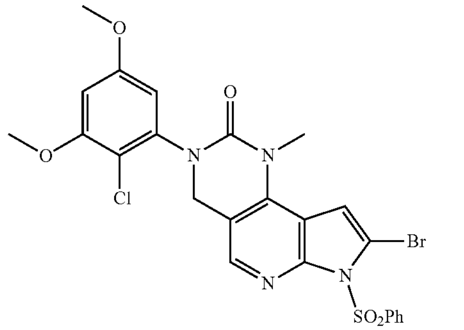

To a cooled (0° C.) solution of 3-(3,5-dimethoxyphenyl)-1-methyl-7-(phenylsulfonyl)-1,3,4,7-tetrahydro-2H-pyrrolo[3',2':5,6]pyrido[4,3-d]pyrimidin-2-one (96 mg, 0.20 mmol) in acetonitrile (3 mL) was added a solution of sulfuryl chloride (16 μL, 0.20 mmol) in methylene chloride (1 mL) dropwise. After stirring at 0° C. for 5 min, the reaction was quenched with water then extracted with EtOAc. The organic layer was then washed with water, brine and dried over $Na_2SO_4$. The solvent was removed under reduced pressure. The residue was dissolved in tetrahydrofuran (3 mL, 40 mmol) and cooled to −78° C. then LDA solution (freshly prepared, 1M in THF, 0.70 mL, 0.70 mmol) was added. The resulting yellow solution was stirred at −78° C. for 30 min then a solution of 1,2-dibromo-1,1,2,2-tetrachloroethane (72 mg, 0.22 mmol) in 0.5 mL of THF was added. The resulting brown solution was stirred at −78° C. for 1 h, at which time LC-MS indicated the reaction was complete. The reaction was quenched with saturated $NH_4Cl$ solution at −78° C. then warmed to room temperature. The mixture was extracted with EtOAc and the organic layer was washed with water, brine then dried over $Na_2SO_4$. The solvent was removed under reduced pressure and the residue was purified by Biotage®: 12 g silica gel column, eluted with 0 to 5% EtOAc/DCM to afford the desired product (45 mg, 38%) as a yellow solid.

Step 2: 3-(2-chloro-3,5-dimethoxyphenyl)-1-methyl-8-(1-methyl-1H-pyrazol-4-yl)-1,3,4,7-tetrahydro-2H-pyrrolo[3',2':5,6]pyrido[4,3-d]pyrimidin-2-one A mixture of 8-bromo-3-(2-chloro-3,5-dimethoxyphenyl)-1-methyl-7-(phenylsulfonyl)-1,3,4,7-tetrahydro-2H-pyrrolo[3',2':5,6]pyrido[4,3-d]pyrimidin-2-one (15 mg, 0.025 mmol), 1-methyl-4-(4,4,5,5-tetramethyl-1,3,2-dioxaborolan-2-yl)-1H-pyrazole (10 mg, 0.051 mmol), [1,1'-bis(diphenylphosphino)ferrocene]dichloropalladium(II), complex with dichloromethane (1:1) (2 mg, 0.002 mmol) and potassium carbonate (10. mg, 0.076 mmol) was dissolved in 1,4-dioxane (3 mL, 40 mmol) then water (0.3 mL, 20 mmol) was added. The mixture was degassed then back-filled with nitrogen three times. The resulting red solution was heated to 90° C. and stirred for 30 min, at which time LC-MS indicated the reaction was complete. The reaction mixture was cooled to room temperature and diluted with EtOAc then washed with water and brine. The organic layer was dried over $Na_2SO_4$ and the solvent was removed under reduced pressure. The residue was dissolved in tetrahydrofuran (3 mL) then potassium tert-butoxide (1M in THF, 0.2 mL, 0.2 mmol) was added. The resulting yellow solution was stirred at room temperature for 30 min then diluted with MeOH and purified by RP-HPLC (pH=2) to afford the desired product as a white solid. LC-MS calculated for $C_{22}H_{22}ClN_6O_3[M+H]^+$ m/z: 453.1; found: 453.1. $^1H$ NMR (500 MHz, DMSO) δ 12.25 (s, 1H), 8.20 (s, 1H), 8.00 (s, 1H), 7.96 (s, 1H), 7.00 (d, J=1.8 Hz, 1H), 6.78 (d, J=2.7 Hz, 1H), 6.73 (d, J=2.7 Hz, 1H), 4.87 (d, J=13.4 Hz, 1H), 4.64 (d, J=13.4 Hz, 1H), 3.90 (s, 3H), 3.87 (s, 3H), 3.80 (s, 3H), 3.67 (s, 3H).

Example 14

3-(2-Chloro-3,5-dimethoxyphenyl)-8-[1-(2-hydroxyethyl)-1H-pyrazol-4-yl]-1-methyl-1,3,4,7-tetrahydro-2H-pyrrolo[3',2':5,6]pyrido[4,3-d]pyrimidin-2-one

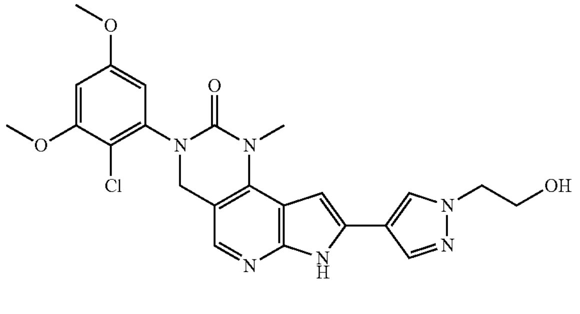 [SMILES: COc1cc(OC)c(Cl)c(N2Cc3cnc4[nH]c(-c5cnn(CCO)c5)cc4c3N(C)C2=O)c1]

Step 1: 8-bromo-3-(2-chloro-3,5-dimethoxyphenyl)-1-methyl-1,3,4,7-tetrahydro-2H-pyrrolo[3',2':5,6]pyrido[4,3-d]pyrimidin-2-one

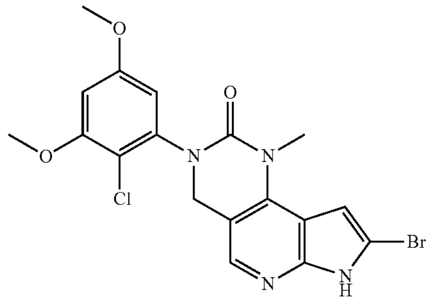 [SMILES: COc1cc(OC)c(Cl)c(N2Cc3cnc4[nH]c(Br)cc4c3N(C)C2=O)c1]

To a solution of 8-bromo-3-(2-chloro-3,5-dimethoxyphenyl)-1-methyl-7-(phenylsulfonyl)-1,3,4,7-tetrahydro-2H-pyrrolo[3',2':5,6]pyrido[4,3-d]pyrimidin-2-one (15 mg, 0.025 mmol) in tetrahydrofuran (3 mL) was added potassium tert-butoxide (1 M in THF, 0.1 mL, 0.1 mmol). After stirring at room temperature for 20 min, the reaction was quenched with water then extracted with EtOAc. The organic layer was washed with brine and dried over $Na_2SO_4$. The solvent was removed under reduced pressure and the residue was used in the next step without further purification. LC-MS calculated for $C_{18}H_{17}BrClN_4O_3[M+H]^+$ m/z: 451.0; found: 451.0.

Step 2: 3-(2-chloro-3,5-dimethoxyphenyl)-8-[1-(2-hydroxyethyl)-1H-pyrazol-4-yl]-1-methyl-1,3,4,7-tetrahydro-2H-pyrrolo[3',2':5,6]pyrido[4,3-d]pyrimidin-2-one A mixture of the crude product from Step 1, 2-[4-(4,4,5,5-tetramethyl-1,3,2-dioxaborolan-2-yl)-1H-pyrazol-1-yl]ethanol (12 mg, 0.051 mmol), [1,1'-bis(diphenylphosphino)ferrocene]dichloropalladium(II) complexed with dichloromethane (1:1) (2 mg, 0.002 mmol), and potassium carbonate (10 mg, 0.076 mmol) was dissolved in 1,4-dioxane (3 mL) and water (0.3 mL). The reaction mixture was degassed then back-filled with nitrogen three times. The resulting solution was heated to 90° C. After stirring for 7 h, the reaction mixture was cooled to room temperature and diluted with MeOH, then filtered and purified by RP-HPLC (pH=10) to afford the product as a yellow solid. LC-MS calculated for $C_{23}H_{24}ClN_6O_4[M+H]^+$ m/z: 483.2; found: 483.2.

Example 15

3-(2-Chloro-3,5-dimethoxyphenyl)-1-methyl-8-(1-methyl-1H-pyrazol-5-yl)-1,3,4,7-tetrahydro-2H-pyrrolo[3',2':5,6]pyrido[4,3-d]pyrimidin-2-one

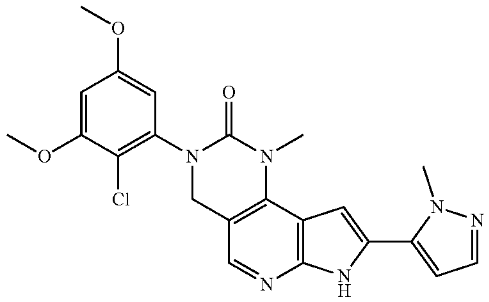 [SMILES: COc1cc(OC)c(Cl)c(N2Cc3cnc4[nH]c(-c5ccnn5C)cc4c3N(C)C2=O)c1]

This compound was prepared using procedures analogous to those described for Example 14, Step 2 with 1-methyl-5-(4,4,5,5-tetramethyl-1,3,2-dioxaborolan-2-yl)-1H-pyrazole replacing 2-[4-(4,4,5,5-tetramethyl-1,3,2-dioxaborolan-2-yl)-1H-pyrazol-1-yl]ethanol and a reaction time of 2 h. LC-MS calculated for $C_{22}H_{22}ClN_6O_3[M+H]^+$ m/z: 453.1; found: 453.1. $^1$H NMR (500 MHz, DMSO) δ 12.31 (s, 1H), 8.06 (s, 1H), 7.52 (d, J=1.9 Hz, 1H), 7.07 (s, 1H), 6.79 (d, J=2.7 Hz, 1H), 6.76 (d, J=1.9 Hz, 1H), 6.73 (d, J=2.7 Hz, 1H), 4.90 (d, J=13.4 Hz, 1H), 4.65 (d, J=13.4 Hz, 1H), 4.07 (s, 3H), 3.87 (s, 3H), 3.81 (s, 3H), 3.70 (s, 3H).

Example 16

3-(2-Chloro-3,5-dimethoxyphenyl)-1-methyl-2-oxo-2,3,4,7-tetrahydro-1H-pyrrolo[3',2':5,6]pyrido[4,3-d]pyrimidine-8-carbonitrile

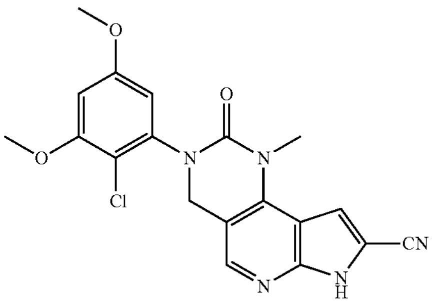 [SMILES: COc1cc(OC)c(Cl)c(N2Cc3cnc4[nH]c(C#N)cc4c3N(C)C2=O)c1]

Step 1: 3-(2-chloro-3,5-dimethoxyphenyl)-1-methyl-2-oxo-7-(phenylsulfonyl)-2,3,4,7-tetrahydro-1H-pyrrolo[3',2':5,6]pyrido[4,3-d]pyrimidine-8-carbonitrile

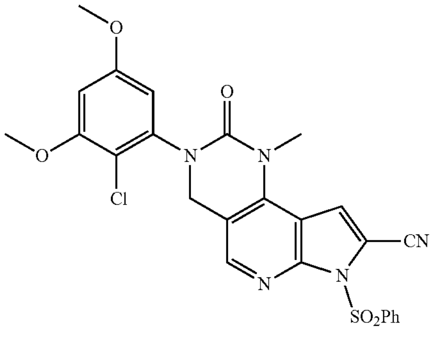

This compound was prepared using procedures analogous to those described for Example 13, Step 1 with 4-methylbenzenesulfonylcyanide replacing 1,2-dibromo-1,1,2,2-tetrachloroethane. The reaction mixture was purified by RP-HPLC (pH=10) to afford the desired product as a white solid.

Step 2: 3-(2-chloro-3,5-dimethoxyphenyl)-1-methyl-2-oxo-2,3,4,7-tetrahydro-1H-pyrrolo[3',2':5,6]pyrido[4,3-d]pyrimidine-8-carbonitrile The phenylsulfonyl-protecting group was removed using similar conditions as described in Example 10, Step 4. The product was purified by RP-HPLC (pH=10) to afford a white solid. LC-MS calculated for $C_{19}H_{17}ClN_5O_3[M+H]^+$ m/z: 398.1; found: 398.0.

Example 17

3-(3,5-Dimethoxyphenyl)-1-methyl-8-(1-methyl-1,2,3,6-tetrahydropyridin-4-yl)-1,3,4,7-tetrahydro-2H-pyrrolo[3',2':5,6]pyrido[4,3-d]pyrimidin-2-one

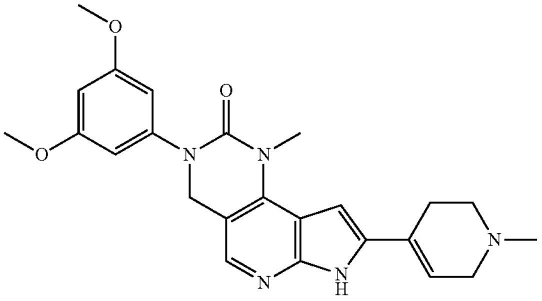

This compound was prepared using procedures analogous to those described for Example with 1-methyl-4-(4,4,5,5-tetramethyl-1,3,2-dioxaborolan-2-yl)-1,2,3,6-tetrahydropyridine replacing 1-methyl-4-[4-(4,4,5,5-tetramethyl-1,3,2-dioxaborolan-2-yl)phenyl]-piperazine. Purified by RP-HPLC (pH=2) to afford the pure product as a white solid. LC-MS calculated for $C_{24}H_{28}N_5O_3$ $[M+H]^+$ m/z: 434.2; found: 434.2.

Example 18

3-(3,5-Dimethoxyphenyl)-1-methyl-8-(1-methylpiperidin-4-yl)-1,3,4,7-tetrahydro-2H-pyrrolo[3',2':5,6]pyrido[4,3-d]pyrimidin-2-one

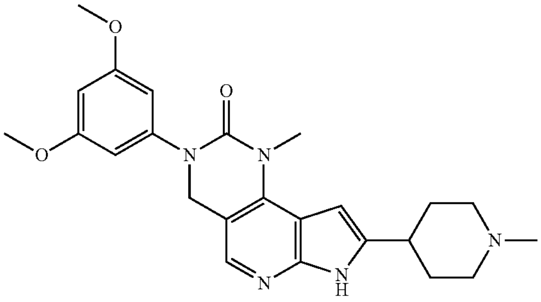

A mixture of 3-(3,5-dimethoxyphenyl)-1-methyl-8-(1-methyl-1,2,3,6-tetrahydropyridin-4-yl)-1,3,4,7-tetrahydro-2H-pyrrolo[3',2':5,6]pyrido[4,3-d]pyrimidin-2-one (8 mg, 0.02 mmol) and palladium (10 wt. % on carbon, 10 mg, 0.009 mmol) was dissolved in methanol (5 mL). The reaction mixture was stirred under a balloon of hydrogen at room temperature for 2 h, at which time LC-MS indicated the reaction was complete. The mixture was filtered and purified by RP-HPLC (pH=2) to afford the product as a white solid. LC-MS calculated for $C_{24}H_{30}N_5O_3$ $[M+H]^+$ m/z: 436.2; found: 436.2.

Example 19

3-(3,5-Dimethoxyphenyl)-N,N,1-trimethyl-2-oxo-2,3,4,7-tetrahydro-1H-pyrrolo[3',2':5,6]pyrido[4,3-d]pyrimidine-8-carboxamide

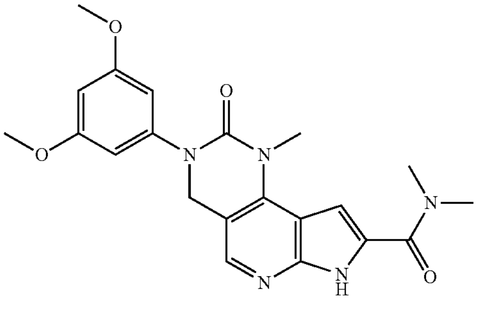

Step 1: 3-(3,5-dimethoxyphenyl)-1-methyl-2-oxo-2,3,4,7-tetrahydro-1H-pyrrolo[3',2':5,6]pyrido[4,3-d]pyrimidine-8-carboxylic acid

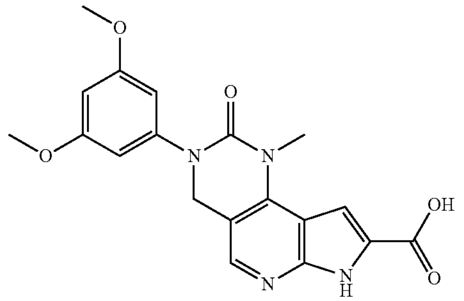 [SMILES: COc1cc(OC)cc(N2Cc3cnc4[nH]c(C(=O)O)cc4c3N(C)C2=O)c1]

To a stirred solution of 3-(3,5-dimethoxyphenyl)-1-methyl-2-oxo-7-(phenylsulfonyl)-2,3,4,7-tetrahydro-1H-pyrrolo[3',2':5,6]pyrido[4,3-d]pyrimidine-8-carboxylic acid (prepared as described in Example 12, Step 1; 1 eq.) in THF was added potassium tert-butoxide (1M in THF, eq.). The resulting mixture was stirred at room temperature for 20 min then acidified with 1N HCl. The mixture was diluted with water then extracted with dichloromethane/isopropyl alcohol (2:1). The organic layers were combined and dried over $Na_2SO_4$. The solvents were removed under reduced pressure and the residue was used in the next step without further purification. LC-MS calculated for $C_{19}H_{19}N_4O_5$ $[M+H]^+$ m/z: 383.1; found: 383.1.

Step 2: 3-(3,5-dimethoxyphenyl)-N,N,1-trimethyl-2-oxo-2,3,4,7-tetrahydro-1H-pyrrolo [3',2':5,6]pyrido[4,3-d]pyrimidine-8-carboxamide To a solution of 3-(3,5-dimethoxyphenyl)-1-methyl-2-oxo-2,3,4,7-tetrahydro-1H-pyrrolo[3',2':5,6]pyrido[4,3-d]pyrimidine-8-carboxylic acid (13 mg, 0.034 mmol) and benzotriazol-1-yloxytris(dimethylamino)phosphonium hexafluorophosphate (16 mg, 0.037 mmol) in N,N-dimethylformamide (4 mL) was added triethylamine (50 μL, 0.3 mmol) and dimethylamine (2M in THF, 80 μL, 0.2 mmol). The mixture was stirred at room temperature for 30 min, at which time LC-MS indicated the reaction was complete. The mixture was diluted with MeOH then purified by RP-HPLC (pH=2) to afford the desired product as a white solid. LC-MS calculated for $C_{21}H_{24}N_5O_4$ $[M+H]^+$ m/z: 410.2; found: 410.2.

Example 20

3-(3,5-Dimethoxyphenyl)-8-[(3-hydroxyazetidin-1-yl)carbonyl]-1-methyl-1,3,4,7-tetrahydro-2H-pyrrolo[3',2':5,6]pyrido[4,3-d]pyrimidin-2-one

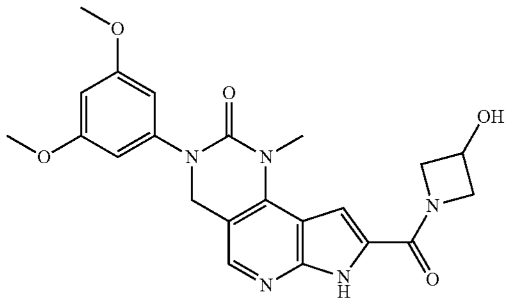 [SMILES: COc1cc(OC)cc(N2Cc3cnc4[nH]c(C(=O)N5CC(O)C5)cc4c3N(C)C2=O)c1]

This compound was prepared using procedure analogous to those for Example 19, Step 2 with azetidin-3-ol hydrochloride replacing dimethylamine. Purified by RP-HPLC (pH=2) to afford the desired product as a white solid. LC-MS calculated for $C_{22}H_{24}N_5O_5$ $[M+H]^+$ m/z: 438.2; found: 438.2.

Example 21

3-(3,5-Dimethoxyphenyl)-8-[(3-hydroxypyrrolidin-1-yl)carbonyl]-1-methyl-1,3,4,7-tetrahydro-2H-pyrrolo[3',2':5,6]pyrido[4,3-d]pyrimidin-2-one

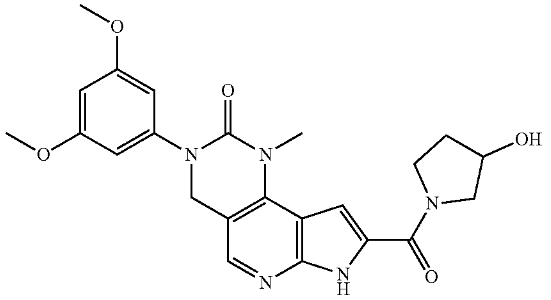 [SMILES: COc1cc(OC)cc(N2Cc3cnc4[nH]c(C(=O)N5CCC(O)C5)cc4c3N(C)C2=O)c1]

This compound was prepared using procedure analogous to those for Example 19, Step 2 with 3-pyrrolidinol replacing dimethylamine. Purified by RP-HPLC (pH=2) to afford the desired product as a white solid. LC-MS calculated for $C_{23}H_{26}N_5O_5$ $[M+H]^+$ m/z: 452.2; found: 452.2.

Example 22

3-(3,5-Dimethoxyphenyl)-1-methyl-8-[(4-methylpiperazin-1-yl)carbonyl]-1,3,4,7-tetrahydro-2H-pyrrolo[3',2':5,6]pyrido[4,3-d]pyrimidin-2-one

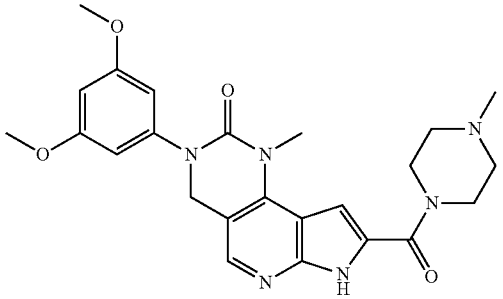

This compound was prepared using procedure analogous to those for Example 19, Step 2 with 1-methyl-piperazine replacing dimethylamine. Purified by RP-HPLC (pH=2) to afford the desired product as a white solid. LC-MS calculated for $C_{24}H_{29}N_6O_4$ $[M+H]^+$ m/z: 465.2; found: 465.2.

Example 23

3-(2-Chloro-3,5-dimethoxyphenyl)-N,1-dimethyl-2-oxo-2,3,4,7-tetrahydro-1H-pyrrolo[3',2':5,6]pyrido[4,3-d]pyrimidine-8-carboxamide

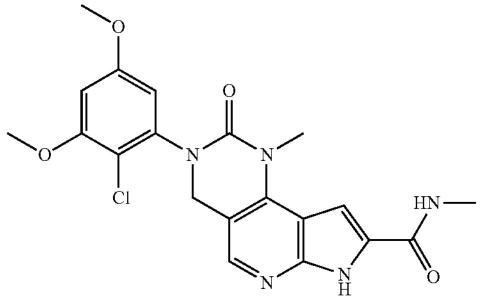

Step 1: 3-(2-chloro-3,5-dimethoxyphenyl)-1-methyl-2-oxo-7-(phenylsulfonyl)-2,3,4,7-tetrahydro-1H-pyrrolo[3',2':5,6]pyrido[4,3-d]pyrimidine-8-carboxylic acid

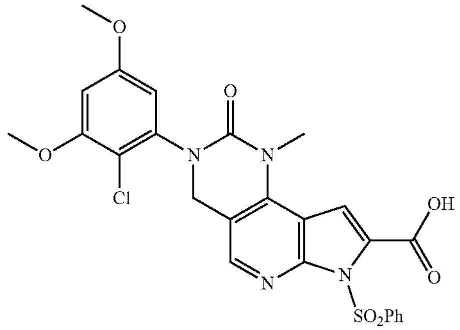

To a cooled (0° C.) solution of 3-(3,5-dimethoxyphenyl)-1-methyl-7-(phenylsulfonyl)-1,3,4,7-tetrahydro-2H-pyrrolo[3',2':5,6]pyrido[4,3-d]pyrimidin-2-one (107 mg, 0.224 mmol) in acetonitrile (3 mL) was added a solution of sulfuryl chloride (18 μL, 0.224 mmol) in methylene chloride (1 mL) dropwise. After stirring at 0° C. for 5 min, the reaction was quenched with water then extracted with EtOAc. The organic layer was then washed with water, brine and dried over $Na_2SO_4$. The solvent was removed under reduced pressure and the residue was dissolved in tetrahydrofuran (3 mL) and cooled to −78° C. then LDA solution (freshly prepared, 1 M in THF, 0.78 mL, 0.78 mmol) was added. The resulting yellow solution was stirred at −78° C. for 30 min then dry $CO_2$ gas (prepared from dry ice by passing through a drying tube) was bubbled into the reaction mixture for 30 min. The mixture was warmed to room temperature slowly and acidified with 1 N HCl then extracted with EtOAc. The organic layer was washed with water, brine then dried over $Na_2SO_4$. The solvent was removed under reduced pressure. The residue was used in the next step without further purification. LC-MS calculated for $C_{25}H_{22}ClN_4O_7S$ $[M+H]^+$ m/z: 557.1; found: 557.1.

Step 2: 3-(2-chloro-3,5-dimethoxyphenyl)-1-methyl-2-oxo-2,3,4,7-tetrahydro-1H-pyrrolo[3',2':5,6]pyrido[4,3-d]pyrimidine-8-carboxylic acid

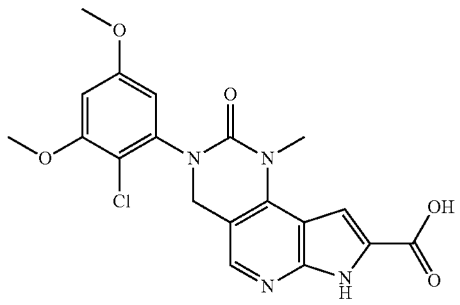 [SMILES: COc1cc(OC)c(Cl)c(N2Cc3cnc4[nH]c(C(=O)O)cc4c3N(C)C2=O)c1]

To a solution of 3-(2-chloro-3,5-dimethoxyphenyl)-1-methyl-2-oxo-7-(phenylsulfonyl)-2,3,4,7-tetrahydro-1H-pyrrolo[3',2':5,6]pyrido[4,3-d]pyrimidine-8-carboxylic acid (20 mg, 0.04 mmol) in tetrahydrofuran (3 mL, 40 mmol) was added potassium tert-butoxide (1 M in THF, 0.2 mL, 0.2 mmol). The resulting yellow solution was stirred at room temperature for 30 min then quenched with water and acidified with 1 N HCl. The mixture was extracted with EtOAc. The organic layers were combined then washed with brine and dried over $Na_2SO_4$. The solvent was removed under reduced pressure to afford the crude product which was used in the next step without further purification. LC-MS calculated for $C_{19}H_{18}ClN_4O_5[M+H]^+$ m/z: 417.1; found: 417.1.

Step 3: 3-(2-chloro-3,5-dimethoxyphenyl)-N,1-dimethyl-2-oxo-2,3,4,7-tetrahydro-1H-pyrrolo[3',2':5,6]pyrido[4,3-d]pyrimidine-8-carboxamide To a solution of the crude product from Step 2 and benzotriazol-1-yloxytris(dimethylamino)phosphonium hexafluorophosphate (17 mg, 0.039 mmol) in N,N-dimethylformamide (4 mL) was added triethylamine (25 μL, 0.18 mmol) and methylamine (2M in THF, 54 μL, 0.11 mmol). The mixture was stirred at room temperature for 30 min, at which time LC-MS indicated the reaction was complete. The mixture was diluted with MeOH then purified by RP-HPLC (pH=10) to afford the desired product as a white solid. LC-MS calculated for $C_{20}H_{21}ClN_5O_4[M+H]^+$ m/z: 430.1; found: 430.1. $^1H$ NMR (500 MHz, DMSO) δ 12.11 (s, 1H), 8.46 (d, J=4.6 Hz, 1H), 8.06 (s, 1H), 7.46 (s, 1H), 6.78 (d, J=2.7 Hz, 1H), 6.72 (d, J=2.7 Hz, 1H), 4.86 (d, J=13.4 Hz, 1H), 4.64 (d, J=13.4 Hz, 1H), 3.87 (s, 3H), 3.80 (s, 3H), 3.66 (s, 3H), 2.83 (d, J=4.6 Hz, 3H).

Example 24

3-(2-Chloro-3,5-dimethoxyphenyl)-N,N,1-trimethyl-2-oxo-2,3,4,7-tetrahydro-1H-pyrrolo[3',2':5,6]pyrido[4,3-d]pyrimidine-8-carboxamide

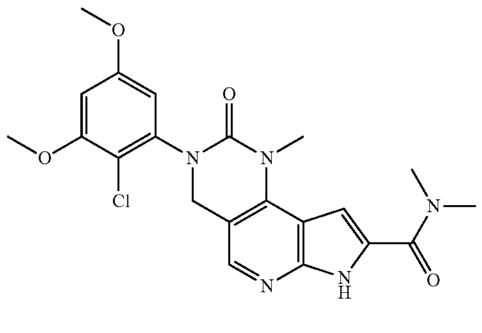

This compound was prepared using procedures analogous to those for Example 23, Step 3 with dimethylamine (2 M in THF) replacing methylamine. Purified by RP-HPLC (pH=2) to afford the desired product as a white solid. LC-MS calculated for $C_{21}H_{23}ClN_5O_4[M+H]^+$ m/z: 444.1; found: 444.1.

Example 25

3-(2-Chloro-3,5-dimethoxyphenyl)-8-[(3-hydroxyazetidin-1-yl)carbonyl]-1-methyl-1,3,4,7-tetrahydro-2H-pyrrolo[3',2':5,6]pyrido[4,3-d]pyrimidin-2-one

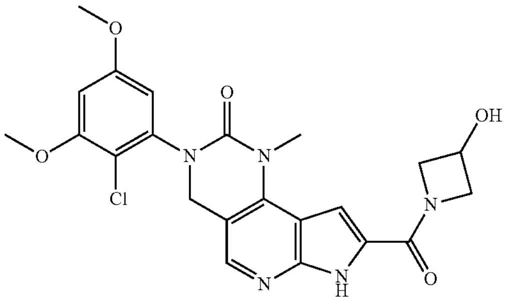 [SMILES: COc1cc(OC)c(Cl)c(N2Cc3cnc4[nH]c(C(=O)N5CC(O)C5)cc4c3N(C)C2=O)c1]

This compound was prepared using procedure analogous to those for Example 23, Step 3 with azetidin-3-ol hydrochloride replacing methylamine. Purified by RP-HPLC (pH=2) to afford the desired product as a white solid. LC-MS calculated for $C_{22}H_{23}ClN_5O_5[M+H]^+$ m/z: 472.1; found: 472.2.

Example 26

3-(2-Chloro-3,5-dimethoxyphenyl)-1-methyl-8-[(4-methylpiperazin-1-yl)carbonyl]-1,3,4,7-tetrahydro-2H-pyrrolo[3',2':5,6]pyrido[4,3-d]pyrimidin-2-one

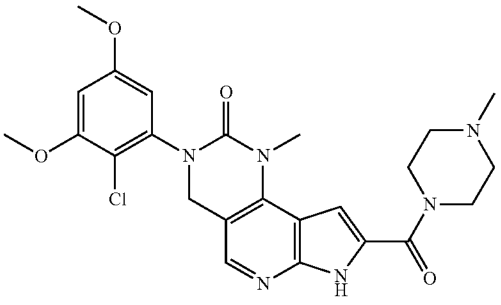

This compound was prepared using procedures analogous to those for Example 23, Step 3 with 1-methyl-piperazine replacing methylamine. Purified by RP-HPLC (pH=2) to afford the desired product as a white solid. LC-MS calculated for $C_{24}H_{28}ClN_6O_4[M+H]^+$ m/z: 499.2; found: 499.2. $^1H$ NMR (500 MHz, DMSO) δ 11.50 (br, 1H), 8.31 (s, 1H), 7.32 (s, 1H), 6.80 (d, J=2.7 Hz, 1H), 6.74 (d, J=2.7 Hz, 1H), 4.95 (d, J=13.9 Hz, 1H), 4.73 (d, J=13.9 Hz, 1H), 4.50 (br, 2H), 3.86 (s, 3H), 3.79 (s, 3H), 3.72 (s, 3H), 3.52 (br, 2H), 3.42 (br, 2H), 3.13 (br, 2H), 2.87 (s, 3H).

Example 27

N-Cyclopropyl-3-(2-fluoro-3,5-dimethoxyphenyl)-1-methyl-2-oxo-2,3,4,7-tetrahydro-1H-pyrrolo[3',2':5,6]pyrido[4,3-d]pyrimidine-8-carboxamide

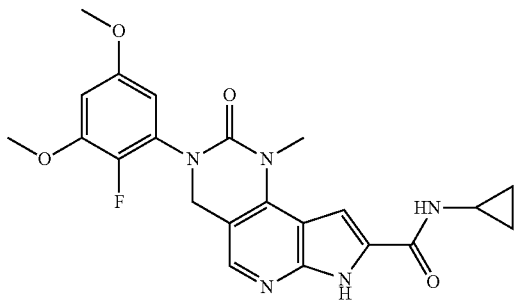 [SMILES: COc1cc(OC)c(F)c(N2Cc3cnc4[nH]c(C(=O)NC5CC5)cc4c3N(C)C2=O)c1]

Step 1: 3-(2-fluoro-3,5-dimethoxyphenyl)-1-methyl-2-oxo-2,3,4,7-tetrahydro-1H-pyrrolo[3',2':5,6]pyrido[4,3-d]pyrimidine-8-carboxylic acid

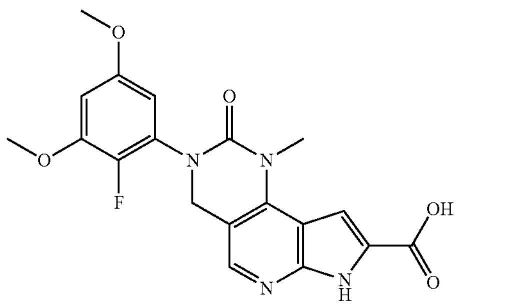 [SMILES: COc1cc(OC)c(F)c(N2Cc3cnc4[nH]c(C(=O)O)cc4c3N(C)C2=O)c1]

To a stirred solution of 3-(3,5-dimethoxyphenyl)-1-methyl-2-oxo-7-(phenylsulfonyl)-2,3,4,7-tetrahydro-1H-pyrrolo[3',2':5,6]pyrido[4,3-d]pyrimidine-8-carboxylic acid (125 mg, 0.239 mmol) in acetonitrile (5 mL) was added 1-(chloromethyl)-4-fluoro-1,4-diazoniabicyclo[2.2.2]octane ditetrafluoroborate (from Aldrich, cat #439479, 102 mg, 0.287 mmol). The resulting yellow solution was stirred at room temperature for 2 h, at which time LCMS indicated completion of the reaction to the desired product. The reaction mixture was diluted with EtOAc then washed with water and brine. The organic layer was dried over $Na_2SO_4$ then concentrated. The residue was dissolved in tetrahydrofuran (5 mL) then potassium tert-butoxide (1M in THF, 1.2 mL, 1.2 mmol) was added. The mixture was stirred at room temperature for 20 min then acidified with 1 N HCl. The mixture was extracted with DCM/IPA (2:1) and the organic layer was dried over $Na_2SO_4$ and concentrated. The residue was used in the next step without further purification. LC-MS calculated for $C_{19}H_{18}FN_4O_5[M+H]^+$ m/z: 401.1; found: 401.1.

Step 2: N-cyclopropyl-3-(2-fluoro-3,5-dimethoxyphenyl)-1-methyl-2-oxo-2,3,4,7-tetrahydro-1H-pyrrolo[3',2':5,6]pyrido[4,3-d]pyrimidine-8-carboxamide To a solution of 3-(2-fluoro-3,5-dimethoxyphenyl)-1-methyl-2-oxo-2,3,4,7-tetrahydro-1H-pyrrolo[3',2':5,6]pyrido[4,3-d]pyrimidine-8-carboxylic acid (6 mg, 0.015 mmol) and benzotriazol-1-yloxytris(dimethylamino)phosphonium hexafluorophosphate (8 mg, 0.018 mmol) in N,N-dimethylformamide (2.5 mL) was added triethylamine (20 μL, 0.1 mmol) and cyclopropylamine (5.2 μL, 0.075 mmol). The resulting yellow solution was stirred at room temperature for 30 min, at which time LC-MS indicated the reaction was complete. The mixture was diluted with MeOH then purified by RP-HPLC (pH=2) to afford the desired product as a white solid. LC-MS calculated for $C_{22}H_{23}FN_5O_4[M+H]^+$ m/z: 440.2; found: 440.1.

Example 28

3-(2-Fluoro-3,5-dimethoxyphenyl)-8-[(3-hydroxyazetidin-1-yl)carbonyl]-1-methyl-1,3,4,7-tetrahydro-2H-pyrrolo[3',2':5,6]pyrido[4,3-d]pyrimidin-2-one

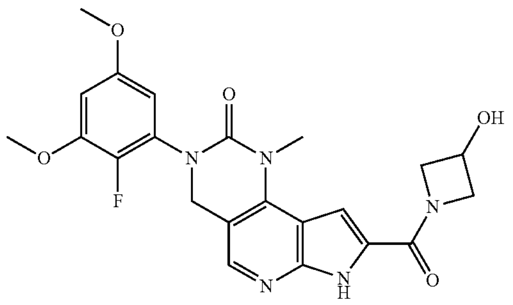 [SMILES: COc1cc(OC)c(F)c(N2Cc3cnc4[nH]c(C(=O)N5CC(O)C5)cc4c3N(C)C2=O)c1]

This compound was prepared using procedures analogous to those for Example 27, Step 2 with azetidin-3-ol hydrochloride replacing cyclopropylamine. Purified by RP-HPLC (pH=2) to afford the desired product as a white solid. LC-MS calculated for $C_{22}H_{23}FN_5O_5[M+H]^+$ m/z: 456.2; found: 456.2.

Example 29

1-{[3-(2-Fluoro-3,5-dimethoxyphenyl)-1-methyl-2-oxo-2,3,4,7-tetrahydro-1H-pyrrolo[3',2':5,6]pyrido[4,3-d]pyrimidin-8-yl]carbonyl}pyrrolidine-3-carbonitrile

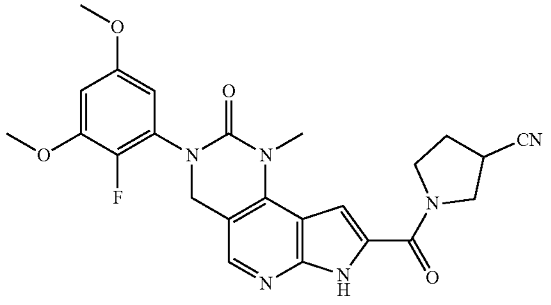 [SMILES: COc1cc(OC)c(F)c(N2Cc3cnc4[nH]c(C(=O)N5CCC(C#N)C5)cc4c3N(C)C2=O)c1]

This compound was prepared using procedures analogous to those for Example 27, Step 2 with pyrrolidine-3-carbonitrile hydrochloride replacing cyclopropylamine. Purified by RP-HPLC (pH=2) to afford the desired product as a white solid. LC-MS calculated for $C_{24}H_{24}FN_6O_4$ [M+H]$^+$ m/z: 479.2; found: 479.2.

Example 30

3-(2-Fluoro-3,5-dimethoxyphenyl)-1-methyl-8-[(4-methylpiperazin-1-yl)carbonyl]-1,3,4,7-tetrahydro-2H-pyrrolo[3',2':5,6]pyrido[4,3-d]pyrimidin-2-one

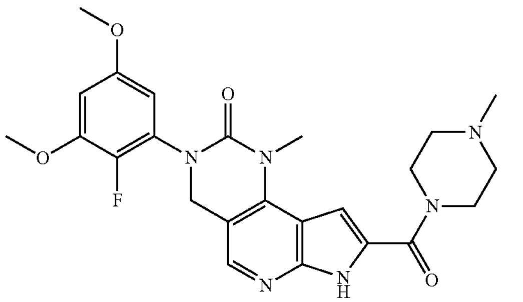

This compound was prepared using procedures analogous to those for Example 27, Step 2 with 1-methyl-piperazine replacing cyclopropylamine. Purified by RP-HPLC (pH=2) to afford the desired product as a white solid. LC-MS calculated for $C_{24}H_{28}FN_6O_4$[M+H]$^+$ m/z: 483.2; found: 483.2. $^1$H NMR (500 MHz, DMSO) δ 12.32 (s, 1H), 8.11 (s, 1H), 7.07 (s, 1H), 6.69 (dd, J=6.7, 2.9 Hz, 1H), 6.62 (dd, J=6.7, 2.9 Hz, 1H), 4.81 (s, 2H), 4.50 (br, 2H), 3.84 (s, 3H), 3.76 (s, 3H), 3.65 (s, 3H), 3.49 (br, 2H), 3.39 (br, 2H), 3.14 (br, 2H), 2.86 (s, 3H).

Example 31

3-(2-Fluoro-3,5-dimethoxyphenyl)-8-[(3-hydroxypiperidin-1-yl)carbonyl]-1-methyl-1,3,4,7-tetrahydro-2H-pyrrolo[3',2':5,6]pyrido[4,3-d]pyrimidin-2-one

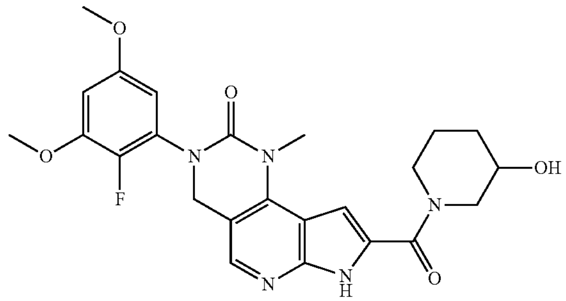 [SMILES: COc1cc(OC)c(F)c(N2Cc3cnc4[nH]c(C(=O)N5CCCC(O)C5)cc4c3N(C)C2=O)c1]

This compound was prepared using procedures analogous to those for Example 27, Step 2 with piperidin-3-ol replacing cyclopropylamine. Purified by RP-HPLC (pH=2) to afford the desired product as a white solid. LC-MS calculated for $C_{24}H_{27}FN_5O_5$[M+H]$^+$ m/z: 484.2; found: 484.2.

Example 32

3-(2-Fluoro-3,5-dimethoxyphenyl)-1-methyl-1,3,4,7-tetrahydro-2H-pyrrolo[3',2':5,6]pyrido[4,3-d]pyrimidin-2-one

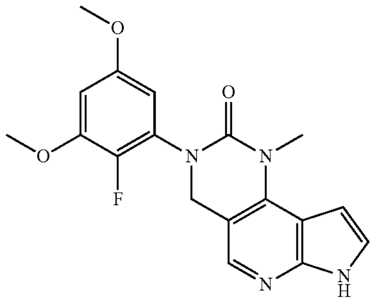 [SMILES: COc1cc(OC)c(F)c(N2Cc3cnc4[nH]ccc4c3N(C)C2=O)c1]

Step 1: 3-(2-fluoro-3,5-dimethoxyphenyl)-1-methyl-7-(phenylsulfonyl)-1,3,4,7-tetrahydro-2H-pyrrolo[3',2':5,6]pyrido[4,3-d]pyrimidin-2-one

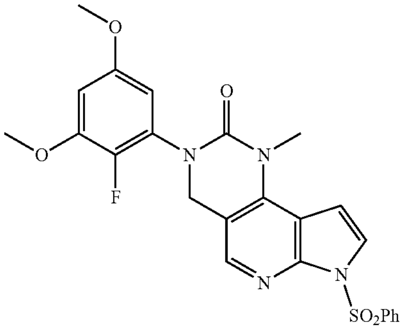

To a solution of 3-(3,5-dimethoxyphenyl)-1-methyl-7-(phenylsulfonyl)-1,3,4,7-tetrahydro-2H-pyrrolo[3',2':5,6]pyrido[4,3-d]pyrimidin-2-one (Example 7, Step 1: 63.0 mg, 0.132 mmol) in acetonitrile (9 mL) was added 1-(chloromethyl)-4-fluoro-1,4-diazoniabicyclo[2.2.2]octane ditetrafluoroborate (95.6 mg, 0.270 mmol). The suspension was stirred at room temperature overnight. Then the resulting solution was concentrated to remove solvents. The residue was dissolved in AcOEt, and washed with $NaHCO_3$ aqueous solution, brine then dried over $MgSO_4$. The solvents were removed under reduced pressure to afford the desired compound which was used in the next step without further purification. LC-MS calculated for $C_{24}H_{22}FN_4O_5S$ [M+H]$^+$ m/z: 497.1; found: 497.1.

Step 2: 3-(2-fluoro-3,5-dimethoxyphenyl)-1-methyl-1,3,4,7-tetrahydro-2H-pyrrolo[3',2':5, 6]pyrido[4,3-d]pyrimidin-2-one

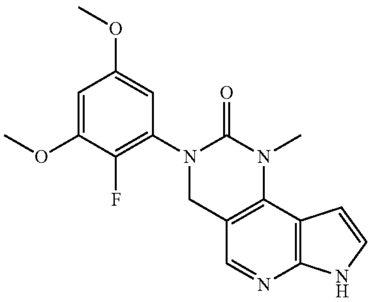 [SMILES: COc1cc(OC)c(F)c(N2Cc3cnc4[nH]ccc4c3N(C)C2=O)c1]

To a solution of the above residue in Step 1 in THF (2 mL) was added 1.0 M potassium tert-butoxide in THF (390 μL, 0.39 mmol). The solution was stirred at r.t. 30 min, then concentrated to remove solvent. The residue was dissolved in MeOH and purified by RP-HPLC (pH=2) to afford the desired product. LC-MS calculated for $C_{18}H_{18}FN_4O_3$[M+H]$^+$ m/z: 357.1; found: 357.1. $^1$H NMR (500 MHz, DMSO) δ 12.10 (s, 1H), 8.08 (s, 1H), 7.53-7.49 (m, 1H), 6.85 (d, J=2.3 Hz, 1H), 6.70 (dd, J=6.7, 2.9 Hz, 1H), 6.63 (dd, J=5.2, 2.9 Hz, 1H), 4.82 (s, 2H), 3.84 (s, 3H), 3.76 (s, 3H), 3.65 (s, 3H).

Example 33

3-(2,6-Difluoro-3,5-dimethoxyphenyl)-1-methyl-1,3,4,7-tetrahydro-2H-pyrrolo[3',2':5,6]pyrido[4,3-d]pyrimidin-2-one

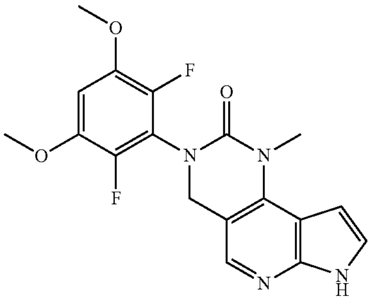 [SMILES: COc1cc(OC)c(F)c(N2Cc3cnc4[nH]ccc4c3N(C)C2=O)c1F]

This compound was formed in the same reaction as described for Example 32. LC-MS calculated for $C_{18}H_{17}F_2N_4O_3$[M+H]$^+$ m/z: 375.1; found: 375.2. $^1$H NMR (500 MHz, DMSO) δ 11.98 (s, 1H), 8.03 (s, 1H), 7.52-7.46 (m, 1H), 7.04 (t, J=8.1 Hz, 1H), 6.82 (d, J=2.0 Hz, 1H), 4.78 (s, 2H), 3.89 (s, 6H), 3.65 (s, 3H).

Example 34

3-(2-Fluoro-3,5-dimethoxyphenyl)-N,N,1-trimethyl-2-oxo-2,3,4,7-tetrahydro-1H-pyrrolo[3',2':5,6]pyrido[4,3-d]pyrimidine-8-carboxamide

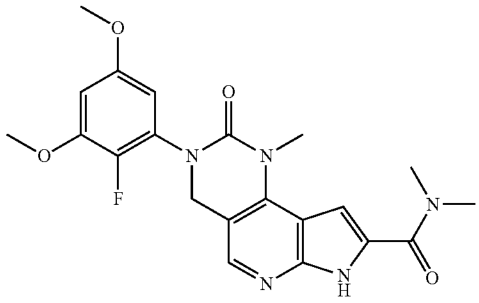

Step 1: 3-(2-fluoro-3,5-dimethoxyphenyl)-N,N,1-trimethyl-2-oxo-7-(phenylsulfonyl)-2,3,4,7-tetrahydro-1H-pyrrolo[3',2':5,6]pyrido[4,3-d]pyrimidine-8-carboxamide

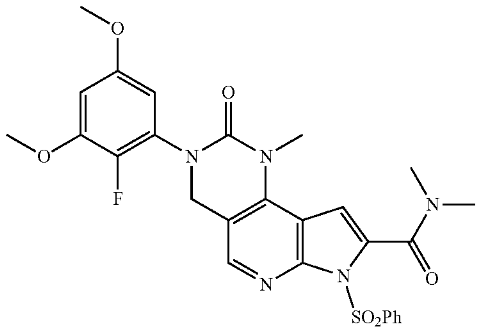

To a solution of N,N-diisopropylamine (1.0E2 μL, 0.76 mmol) in THF (0.5 mL) was added 2.5 M n-butyllithium in hexanes (0.30 mL, 0.76 mmol) dropwise at −78° C. The mixture was stirred at −78° C. for 5 min, then warmed up to 0° C. and stirred for 20 min. then cooled to −78° C. again. To a solution of 3-(2-fluoro-3,5-dimethoxyphenyl)-1-methyl-7-(phenylsulfonyl)-1,3,4,7-tetrahydro-2H-pyrrolo[3',2':5,6]pyrido[4,3-d]pyrimidin-2-one (75.0 mg, 0.151 mmol) (mixed with 3-(2,6-difluoro-3,5-dimethoxyphenyl)-1-methyl-7-(phenylsulfonyl)-1,3,4,7-tetrahydro-2H-pyrrolo[3',2':5,6]pyrido[4,3-d]pyrimidin-2-one, Example 32, Step 1) in tetrahydrofuran (1.0 mL) was added prepared LDA solution dropwise at −78° C. The resulting yellow suspension was stirred at −78° C. for 50 min, then a solution of N,N-dimethylcarbamoyl chloride (70 μL, 0.76 mmol) in tetrahydrofuran (1.0 mL) was added dropwise. The reaction mixture was stirred at −20° C. for 1 hour then quenched with saturated $NH_4Cl$ solution, and then extracted with AcOEt twice. The combined organic phase was washed with brine and dried over $MgSO_4$, The solvents were removed under reduced pressure to afford the desired compound which was used in the next step without further purification. LC-MS calculated for $C_{27}H_{27}FN_5O_6S$ [M+H]$^+$ m/z: 568.2; found: 568.2.

Step 2: 3-(2-fluoro-3,5-dimethoxyphenyl)-N,N,1-trimethyl-2-oxo-2,3,4,7-tetrahydro-1H-pyrrolo[3',2':5,6]pyrido[4,3-d]pyrimidine-8-carboxamide To as solution of the above residue made in Step 1 in THF (2 mL) was added 1.0 M potassium tert-butoxide in THF (450 μL, 0.45 mmol). The solution was stirred at r.t. 30 min, then concentrated to remove solvent. The residue was dissolved in MeOH and purified by RP-HPLC (pH=2) to afford the desired product. LC-MS calculated for $C_{21}H_{23}FN_5O_4$ $[M+H]^+$ m/z: 428.2; found: 428.2. $^1H$ NMR (500 MHz, DMSO) δ 12.27 (s, 1H), 8.10 (s, 1H), 7.07 (s, 1H), 6.72-6.66 (m, 1H), 6.64-6.60 (m, 1H), 4.81 (s, 2H), 3.84 (s, 3H), 3.76 (s, 3H), 3.64 (s, 3H), 3.35-2.95 (m, 6H).

Example 35

3-(2,6-Difluoro-3,5-dimethoxyphenyl)-N,N,1-trimethyl-2-oxo-2,3,4,7-tetrahydro-1H-pyrrolo[3',2':5,6]pyrido[4,3-d]pyrimidine-8-carboxamide

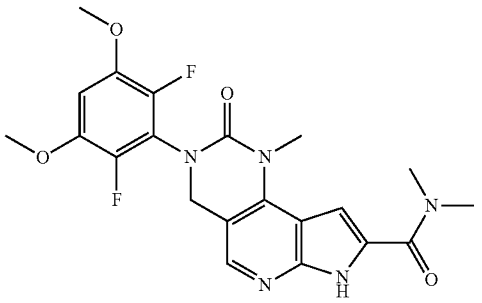

This compound was formed in the same reaction as described for Example 34, LC-MS calculated for $C_{21}H_{22}F_2N_5O_4[M+H]^+$ m/z: 446.2; found: 446.2. $^1H$ NMR (500 MHz, DMSO) δ 12.23 (s, 1H), 8.07 (s, 1H), 7.08-7.00 (m, 2H), 4.78 (s, 2H), 3.89 (s, 6H), 3.65 (s, 3H), 3.36-2.92 (m, 6H).

Example 36

3-(2-Chloro-6-fluoro-3,5-dimethoxyphenyl)-1-methyl-1,3,4,7-tetrahydro-2H-pyrrolo[3',2':5,6]pyrido[4,3-d]pyrimidin-2-one

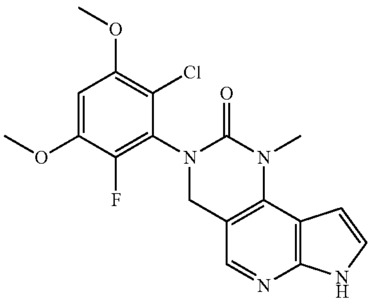 [SMILES: COc1cc(OC)c(Cl)c(N2Cc3cnc4[nH]ccc4c3N(C)C2=O)c1F]

Step 1: 3-(2-chloro-6-fluoro-3,5-dimethoxyphenyl)-1-methyl-7-(phenylsulfonyl)-1,3,4,7-tetrahydro-2H-pyrrolo[3',2':5,6]pyrido[4,3-d]pyrimidin-2-one

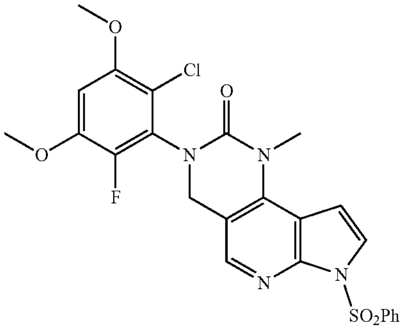

To a solution of 3-(2-fluoro-3,5-dimethoxyphenyl\)-1-methyl-7-(phenylsulfonyl)-1,3,4,7-tetrahydro-2H-pyrrolo[3',2':5,6]pyrido[4,3-d]pyrimidin-2-one (290.0 mg, 0.5841 mmol) in acetonitrile (8 mL) was added a solution of sulfuryl chloride (49.6 μL, 0.613 mmol) in methylene chloride (2 mL) dropwise at 0° C. The resulting solution was stirred at 0° C. for 10 min. The reaction was quenched with water then extracted with EtOAc. The organic layer was then washed with water, brine and dried over $Na_2SO_4$. The solvents were removed under reduced pressure to afford the desired compound which was used in the next step without further purification. LC-MS calculated for $C_{24}H_{21}ClFN_4O_5S$ $[M+H]^+$ m/z: 531.1; found: 531.1.

Step 2: 3-(2-chloro-6-fluoro-3,5-dimethoxyphenyl)-1-methyl-1,3,4,7-tetrahydro-2H-pyrrolo[3',2':5,6]pyrido[4,3-d]pyrimidin-2-one To a solution of the above residue formed in Step 2 in THF (3 mL) was added 1.0 M potassium tert-butoxide in THF (1.8 mL, 1.8 mmol). The solution was stirred at r.t. 30 min, then concentrated to remove solvent. The residue was dissolved in MeOH and purified by RP-HPLC (pH=2) to afford the desired product. LC-MS calculated for $C_{18}H_{17}ClFN_4O_3[M+H]^+$ m/z: 391.1; found: 391.1. $^1H$ NMR (500 MHz, DMSO) δ 12.10 (s, 1H), 8.07 (s, 1H), 7.52 (s, 1H), 7.03 (d, J=7.7 Hz, 1H), 6.86 (d, J=3.2 Hz, 1H), 4.79-4.71 (m, 2H), 3.94 (s, 3H), 3.91 (s, 3H), 3.66 (s, 3H).

Example 37

3-(2,6-Difluoro-3,5-dimethoxyphenyl)-1-methyl-3,4,7,9-tetrahydro-1H-pyrrolo[3',2':5,6]pyrido[4,3-d]pyrimidine-2,8-dione

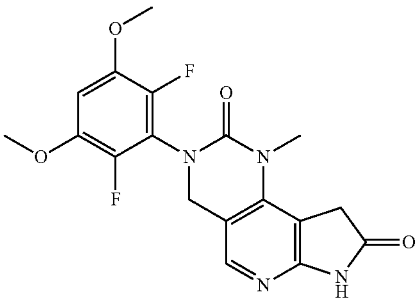 [SMILES: COc1cc(OC)c(F)c(N2Cc3cnc4c(c3N(C)C2=O)CC(=O)N4)c1F]

Step 1: 9,9-Dibromo-3-(2,6-difluoro-3,5-dimethoxyphenyl)-1-methyl-3,4,7,9-tetrahydro-1H-pyrrolo[3',2':5,6]pyrido[4,3-d]pyrimidine-2,8-dione and 9-bromo-3-(2,6-difluoro-3,5-dimethoxyphenyl)-1-methyl-3,4,7,9-tetrahydro-1H-pyrrolo[3',2':5,6]pyrido[4,3-d]pyrimidine-2,8-dione

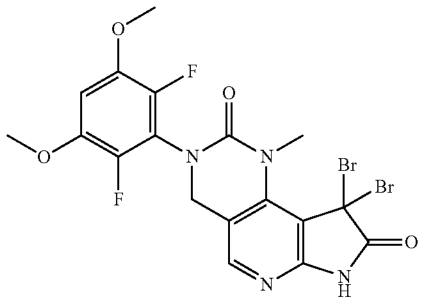

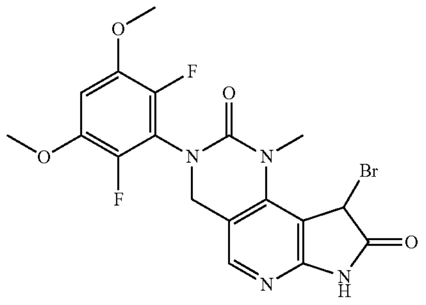

Pyridinium tribromide (120 mg, 0.37 mmol) was added to a mixture of 3-(2,6-difluoro-3,5-dimethoxyphenyl)-1-methyl-1,3,4,7-tetrahydro-2H-pyrrolo[3',2':5,6]pyrido[4,3-d]pyrimidin-2-one (40.0 mg, 0.107 mmol) in tert-butyl alcohol (1.2 mL) and then the reaction was stirred at 30° C. overnight. The mixture was diluted with ethyl acetate, washed with saturated $NaHCO_3$, water, brine, dried over $Na_2SO_4$, filtered, and then concentrated to provide the crude product as a mixture of the above two products which were used in the next step directly. LCMS $(M+H)^+$: m/z=549.0, 471.0.

Step 2: 3-(2,6-difluoro-3,5-dimethoxyphenyl)-1-methyl-3,4,7,9-tetrahydro-1H-pyrrolo[3',2':5,6]pyrido[4,3-d]pyrimidine-2,8-dione Zinc (10 mg, 0.2 mmol) was added to a mixture of 9-bromo-3-(2,6-difluoro-3,5-dimethoxyphenyl)-1-methyl-3,4,7,9-tetrahydro-1H-pyrrolo[3',2':5,6]pyrido[4,3-d]pyrimidine-2,8-dione (10.0 mg, 0.0213 mmol) and 9,9-dibromo-3-(2,6-difluoro-3,5-dimethoxyphenyl)-1-methyl-3,4,7,9-tetrahydro-1H-pyrrolo[3',2':5,6]pyrido[4,3-d]pyrimidine-2,8-dione (10.0 mg, 0.0182 mmol) in methanol (0.3 mL)/acetic acid (0.3 mL), then the mixture was stirred at room temperature for 3 h. The reaction mixture was filtered and then the product was purified by RP-HPLC (pH=2). LC-MS calculated for $C_{18}H_{17}F_2N_4O_4[M+H]^+$ m/z: 391.1; found: 391.1. $^1H$ NMR (500 MHz, DMSO) δ 10.99 (s, 1H), 7.82 (s, 1H), 7.03 (t, J=8.1 Hz, 1H), 4.60 (s, 2H), 4.00 (s, 2H), 3.88 (s, 6H), 3.39 (s, 3H).

Example 38

3-(2,6-Difluoro-3,5-dimethoxyphenyl)-1-methyl-3,4-dihydrothieno[2',3':5,6]pyrido[4,3-d]pyrimidin-2(1H)-one

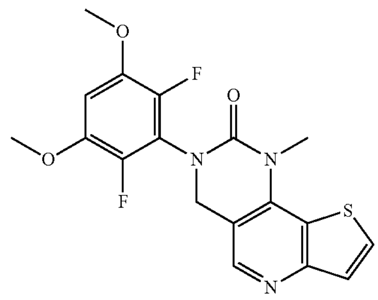 [SMILES: COc1cc(OC)c(F)c(N2Cc3cnc4ccsc4c3N(C)C2=O)c1F]

Step 1: 7-chlorothieno[3,2-b]pyridine-6-carbaldehyde

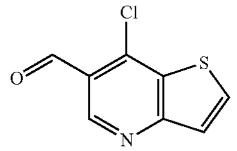 [SMILES: O=Cc1cnc2ccsc2c1Cl]

To a solution of ethyl 7-chlorothieno[3,2-b]pyridine-6-carboxylate (CAS #90690-94-1) purchased from Synthonix, Inc, cat #E4282, 409 mg, 1.69 mmol) in tetrahydrofuran (5.0 mL) at 0° C. was added diisobutylaluminum hydride (1.0 M in hexane, 5.1 mL, 5.1 mmol). The resulting mixture was stirred at this temperature for 2 h before it was quenched with MeOH (5 mL) and $NaHCO_3$ solution (10 mL). The aqueous phase was extracted with EtOAc (3×10 mL), and it was dried over $Na_2SO_4$ and concentrated in vacuo. The crude alcohol was used without further purification. LC-MS calculated for $C_8H_7ONSCl$ $[M+H]^+$ m/z: 200.1; found 200.1.

To a solution of the alcohol obtained above in methylene chloride (5.0 mL) was added sodium bicarbonate (710 mg, 8.5 mmol) and Dess-Martin periodinane (860 mg, 2.0 mmol). The resulting mixture was stirred for 1 h before it was quenched with $Na_2S_2O_3$ solution (5 mL) and $NaHCO_3$ solution (5 mL). The aqueous phase was extracted with methylene chloride (3×10 mL), dried over $Na_2SO_4$, and concentrated in vacuo. The crude mixture was purified by flash column (MeOH/DCM, 3%~20%) to afford the aldehyde (237 mg, 72% for two steps) as a white solid. LC-MS calculated for $C_8H_5ONSCl$ $[M+H]^+$ m/z: 198.1; found 198.1.

Step 2: 7-(methylamino)thieno[3,2-b]pyridine-6-carbaldehyde

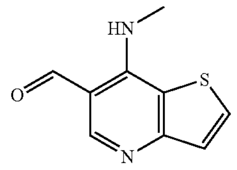

A solution of 7-chlorothieno[3,2-b]pyridine-6-carbaldehyde (237 mg, 1.20 mmol) in methylamine (33% in ethanol, 2.0 mL, 16.0 mmol) was heated to 110° C. for 3 h. After cooling to room temperature, the solution was concentrated in vacuo. The crude imine was dissolved in hydrogen chloride (1.0 M in water, 3.6 mL, 3.6 mmol), and the resulting mixture was stirred at 60° C. for 3 h. The solution was neutralized with NaOH (2.0 M, 1.7 mL, 3.4 mmol) and $NaHCO_3$ sat. solution. After it was filtered and dried over high vacuum, the pure 7-(methylamino)thieno[3,2-b]pyridine-6-carbaldehyde (150 mg, 65%) was obtained as a yellow solid. LC-MS calculated for $C_9H_9ON_2S$ $[M+H]^+$ m/z: 193.2; found 193.2.

Step 3: 6-{[(3,5-dimethoxyphenyl)amino]methyl}-N-methylthieno[3,2-b]pyridin-7-amine

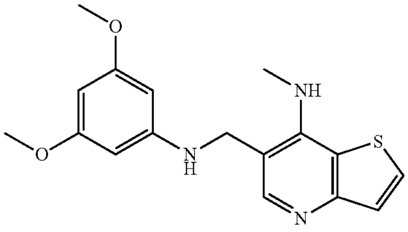 [SMILES: CNc1c(CNc2cc(OC)cc(OC)c2)cnc2ccsc12]

To a solution of 7-(methylamino)thieno[3,2-b]pyridine-6-carbaldehyde (75 mg, 0.39 mmol) in ethanol (3.0 mL) was added 3,5-dimethoxyaniline (120 mg, 0.78 mmol) and acetic acid (0.223 mL, 3.92 mmol). The resulting mixture was stirred at 90° C. for 2 h before it was cooled to room temperature. Sodium cyanoborohydride (120 mg, 2.0 mmol) was added to the solution and the mixture was stirred for another 2 h. The reaction mixture was diluted with MeOH and purified by RF-HPLC (pH 10) to afford 6-{[(3,5-dimethoxyphenyl)amino]methyl}-N-methylthieno[3,2-b]pyridin-7-amine (96 mg, 74%) as a white solid. LC-MS calculated for $C_{17}H_{20}O_2N_3S$ $[M+H]^+$ m/z: 330.1; found 330.1.

Step 4: 3-(3,5-dimethoxyphenyl)-1-methyl-3,4-dihydrothieno[2',3':5,6]pyrido[4,3-d]pyrimidin-2(1H)-one

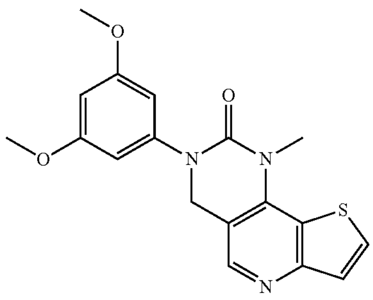 [SMILES: COc1cc(OC)cc(N2Cc3cnc4ccsc4c3N(C)C2=O)c1]

To a solution of 6-{[(3,5-dimethoxyphenyl)amino]methyl}-N-methylthieno[3,2-b]pyridin-7-amine (96 mg, 0.13 mmol) in $CH_3CN$ (3.0 mL) was added 1,1'-thiocarbonyldiimidazole (210 mg, 1.2 mmol). The resulting mixture was stirred at 110° C. for 12 h before it was concentrated in vacuo. The crude mixture was purified by flash column (MeOH/DCM 5%~20%) to afford 3-(3,5-dimethoxyphenyl)-1-methyl-3,4-dihydrothieno[2',3':5,6]pyrido[4,3-d]pyrimidin-2(1H)-one (120 mg, 86%) as a yellow solid. LC-MS calculated for $C_{18}H_{18}O_3N_3S$ $[M+H]^+$ m/z: 356.1; found 356.1.

Step 5: 3-(2,6-difluoro-3,5-dimethoxyphenyl)-1-methyl-3,4-dihydrothieno[2',3':5,6]pyrido[4,3-d]pyrimidin-2(1H)-one To a solution of 3-(3,5-dimethoxyphenyl)-1-methyl-3,4-dihydrothieno[2',3':5,6]pyrido [4,3-d]pyrimidin-2(1H)-one (10.0 mg, 0.0281 mmol) in $CH_3CN$ (1.0 mL) was added 1-(chloromethyl)-4-fluoro-1,4-diazoniabicyclo[2.2.2]octane ditetrafluoroborate (Selectfluor®) (24.9 mg, 0.0703 mmol) at room temperature. The resulting mixture was stirred at room temperature for 2 h before it was diluted with MeOH (9 mL). The compound was purified by RF-HPLC (pH=10) to afford 3-(2,6-difluoro-3,5-dimethoxyphenyl)-1-methyl-3,4-dihydrothieno[2',3':5,6]pyrido[4,3-d]pyrimidin-2(1H) (3.0 mg, 27%) as a white solid. LC-MS calculated for $C_{18}H_{16}F_2N_3O_3S$ $[M+H]^+$ m/z: 392.1; found 392.1. $^1H$ NMR (500 MHz, DMSO) δ 8.40 (s, 1H), 8.15 (d, J=5.6 Hz, 1H), 7.55 (d, J=5.6 Hz, 1H), 7.05 (t, J=8.2 Hz, 1H), 4.85 (s, 2H), 3.89 (s, 6H), 3.71 (s, 3H).

Example 39

3-(2,6-Difluoro-3,5-dimethoxyphenyl)-1-methyl-8-(tetrahydro-2H-pyran-4-yl)-1,3,4,7-tetrahydro-2H-pyrrolo[3',2':5,6]pyrido[4,3-d]pyrimidin-2-one

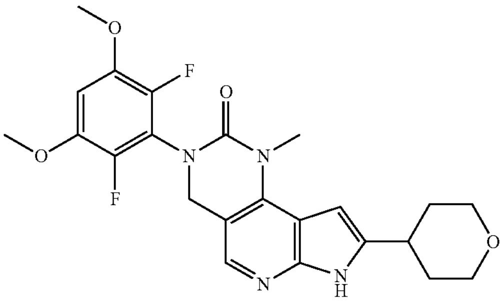 [SMILES: COc1cc(OC)c(F)c(N2Cc3cnc4[nH]c(C5CCOCC5)cc4c3N(C)C2=O)c1F]

Step 1: 5-{(E)-[(2,6-difluoro-3,5-dimethoxyphenyl)imino]methyl}-N-methyl-1H-pyrrolo[2,3-b]pyridin-4-amine

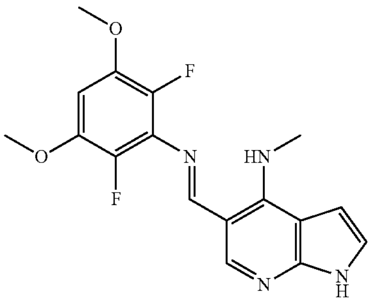 [SMILES: CNc1c(/C=N/c2c(F)c(OC)cc(OC)c2F)cnc2[nH]ccc12]

A mixture of 4-(methylamino)-1H-pyrrolo[2,3-b]pyridine-5-carbaldehyde (1.98 g, 11.3 mmol, prepared as described in Example 1, Step 1), 2,6-difluoro-3,5-dimethoxyaniline (2.6 g, 14 mmol) and D-(+)-10-camphorsulfonic acid (Aldrich, cat #21360: 0.72 g, 3.1 mmol) in toluene (200 mL) was heated to reflux with azeotropic removal of water via a Dean-stark trap for 48 h. The reaction mixture was concentrated and the residue was used in the next step without further purification. LC-MS calculated for $C_{17}H_{17}F_2N_4O_2[M+H]^+$ m/z: 347.1; found 347.1.

Step 2: 5-{[(2,6-difluoro-3,5-dimethoxyphenyl)amino]methyl}-N-methyl-1H-pyrrolo[2,3-b]pyridine-4-amine

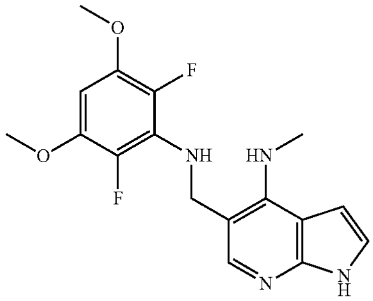 [SMILES: CNc1c(CNc2c(F)c(OC)cc(OC)c2F)cnc2[nH]ccc12]

The crude product from Step 1 was dissolved in tetrahydrofuran (200 mL) and cooled to 0° C. then $LiAlH_4$ (0.86 g, 23 mmol) was added. The reaction mixture was warmed to 50° C. and stirred overnight. The reaction was quenched by addition of a minimum amount of water at 0° C. then filtered through Celite and washed with THF. The filtrate was concentrated under reduced pressure. The residue was purified by flash chromatography on a silica gel column eluted with 0-5% methanol in dichloromethane to afford the desired product (2.00, 51%) as a yellow solid. LC-MS calculated for $C_{17}H_{19}F_2N_4O_2[M+H]^+$ m/z: 349.1; found 349.1.

Step 3: 3-(2,6-difluoro-3,5-dimethoxyphenyl)-1-methyl-1,3,4,7-tetrahydro-2H-pyrrolo[3',2':5,6]pyrido[4,3-d]pyrimidin-2-one

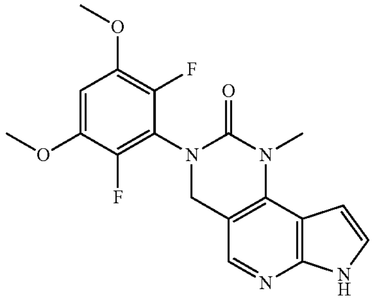

Triphosgene (2.0 g, 6.8 mmol) was added to a solution of the product from Step 2 and triethylamine (7.9 mL, 56 mmol) in tetrahydrofuran (160 mL) at 0° C. The reaction mixture was stirred at room temperature for 1 h, then 1M NaOH (50 mL) was added. After stirring for 30 min at room temperature, saturated aqueous solution of $NH_4Cl$ (10 mL) was added. The mixture was extracted with ethyl acetate (2×100 mL). The combined organic layers were washed with brine, dried over $MgSO_4$, filtered and concentrated under reduced pressure. The mixture was used for next step without further purification. LC-MS calculated for $C_{18}H_{17}F_2N_4O_3[M+H]^+$ m/z: 375.1; found 375.0.

Step 4: 3-(2,6-difluoro-3,5-dimethoxyphenyl)-1-methyl-7-(phenylsulfonyl)-1,3,4,7-tetrahydro-2H-pyrrolo[3',2':5,6]pyrido[4,3-d]pyrimidin-2-one

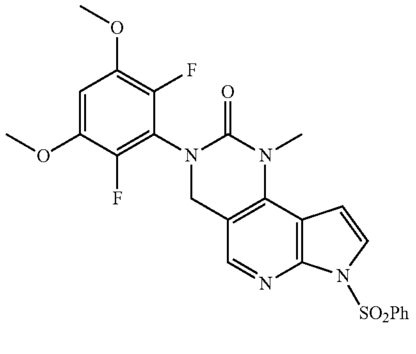

To a stirred solution of 3-(2,6-difluoro-3,5-dimethoxyphenyl)-1-methyl-1,3,4,7-tetrahydro-2H-pyrrolo[3',2':5,6]pyrido[4,3-d]pyrimidin-2-one (2.30 g, 6.14 mmol) in tetrahydrofuran (30 mL) was added NaH (60% in mineral oil, 0.344 g, 8.60 mmol) at 0° C. The reaction mixture was stirred at 0° C. for 30 min then benzenesulfonyl chloride (0.94 mL, 7.4 mmol) was added. After stirring at 0° C. for 1 h, the reaction was quenched with saturated aqueous solution of $NH_4Cl$ then extracted with ethyl acetate (3×40 mL). The combined organic layers were washed with brine, dried over $MgSO_4$, then filtered and concentrated under reduced pressure. The residue was purified by flash chromatography on a silica gel column eluted with ethyl acetate in DCM (0-30%) to afford the desired product (1.89 g, 68.8%). LC-MS calculated for $C_{24}H_{21}F_2N_4O_5S$ $[M+H]^+$ m/z: 515.1; found 515.0.

Step 5: 8-bromo-3-(2,6-difluoro-3,5-dimethoxyphenyl)-1-methyl-7-(phenylsulfonyl)-1,3,4,7-tetrahydro-2H-pyrrolo[3',2':5,6]pyrido[4,3-d]pyrimidin-2-one

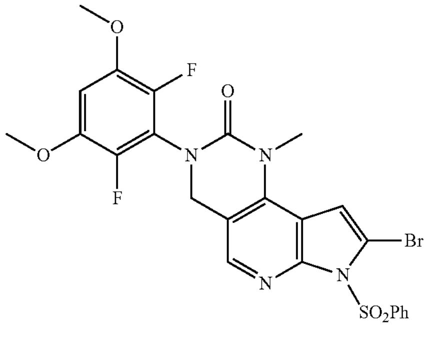

(1) Preparation of LDA solution: To a stirred solution of N,N-diisopropylamine (0.632 mL, 4.51 mmol) in tetrahydrofuran (10 mL) at −78° C. was added 2.5 M n-butyllithium in hexanes (1.6 mL, 4.0 mmol) dropwise. After a white precipitate formed, the mixture was warmed up to 0° C. and stirred for 10 min.

(2) To a stirred solution of 3-(2,6-difluoro-3,5-dimethoxyphenyl)-1-methyl-7-(phenylsulfonyl)-1,3,4,7-tetrahydro-2H-pyrrolo[3',2':5,6]pyrido[4,3-d]pyrimidin-2-one (1.60 g, 3.11 mmol) in tetrahydrofuran (100 mL) at −78° C. was added the freshly prepared LDA solution dropwise. After 30 min, a solution of 1,2-dibromo-1,1,2,2-tetrachloroethane (1.06 g, 3.26 mmol) in tetrahydrofuran (6 mL) was added dropwise. The resulting clear yellow solution was stirred at −78° C. for 1 h. The reaction mixture was quenched with saturated aqueous solution of $NH_4Cl$ then extracted with ethyl acetate (3×40 mL). The combined organic layers were washed with brine, dried over $MgSO_4$, filtered and concentrated under reduced pressure. The residue was purified by flash chromatography on a silica gel column with EtOAc in DCM (0-10%) to afford the desired product (1.50 g, 81.3%). LC-MS calculated for $C_{24}H_{20}BrF_2N_4O_5S$ $[M+H]^+$ m/z: 593.0; found 592.9.

Step 6: 8-bromo-3-(2,6-difluoro-3,5-dimethoxyphenyl)-1-methyl-1,3,4,7-tetrahydro-2H-pyrrolo[3',2':5,6]pyrido[4,3-d]pyrimidin-2-one

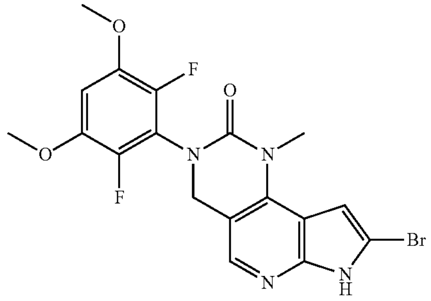 [SMILES: COc1cc(OC)c(F)c(N2Cc3cnc4[nH]c(Br)cc4c3N(C)C2=O)c1F]

To a stirred solution of 8-bromo-3-(2,6-difluoro-3,5-dimethoxyphenyl)-1-methyl-7-(phenylsulfonyl)-1,3,4,7-tetrahydro-2H-pyrrolo[3',2':5,6]pyrido[4,3-d]pyrimidin-2-one (1.50 g) in tetrahydrofuran (10 mL) was added 5.0 M sodium methoxide in methanol (1.9 mL, 9.3 mmol). After stirring at room temperature for 1 h, the mixture was diluted with water and adjusted to pH=8 with 1 N HCl, then concentrated to remove THF. The solid was filtered, washed with water and dried in vacuum to afford the desired product (0.83 g). LC-MS calculated for $C_{18}H_{16}BrF_2N_4O_3$ $[M+H]^+$ m/z: 453.0; found 453.0.

Step 7: 3-(2,6-difluoro-3,5-dimethoxyphenyl)-8-(3,6-dihydro-2H-pyran-4-yl)-1-methyl-1,3,4,7-tetrahydro-2H-pyrrolo[3',2':5,6]pyrido[4,3-d]pyrimidin-2-one

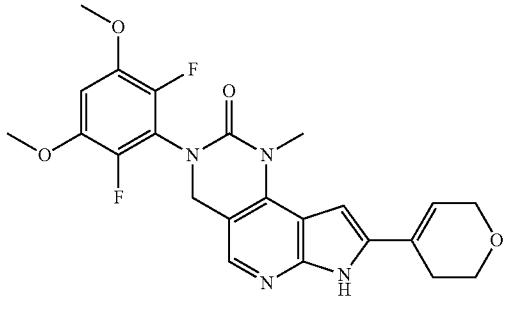 [SMILES: COc1cc(OC)c(F)c(N2Cc3cnc4[nH]c(C5=CCOCC5)cc4c3N(C)C2=O)c1F]

A mixture of 8-bromo-3-(2,6-difluoro-3,5-dimethoxyphenyl)-1-methyl-1,3,4,7-tetrahydro-2H-pyrrolo[3',2':5,6]pyrido[4,3-d]pyrimidin-2-one (10.0 mg, 0.0221 mmol), 4-(4,4,5,5-tetramethyl-1,3,2-dioxaborolan-2-yl)-3,6-dihydro-2H-pyran (6.0 mg, 0.029 mmol), [1,1'-bis(diphenylphosphino)ferrocene]dichloropalladium(II) dichloromethane complex (1:1) (2 mg, 0.003 mmol) and potassium carbonate (9.1 mg, 0.066 mmol) in 1,4-dioxane (0.80 mL) and water (0.20 mL) was degassed and filled with nitrogen. After stirring at 95° C. for 3 h, the reaction mixture was diluted with MeOH, and filtered. The solution was used in the next step. LC-MS calculated for $C_{23}H_{23}F_2N_4O_4[M+H]^+$ m/z: 457.2; found 457.1.

Step 8: 3-(2,6-difluoro-3,5-dimethoxyphenyl)-1-methyl-8-(tetrahydro-2H-pyran-4-yl)-1,3,4,7-tetrahydro-2H-pyrrolo[3',2':5,6]pyrido[4,3-d]pyrimidin-2-one Palladium on activated carbon (10 wt %, 10 mg) was added to the solution of product from Step 7 in methanol (5 mL) and the reaction mixture was stirred at room temperature under a balloon of $H_2$ for 2 h. The mixture was filtered and purified by RP-HPLC (pH=2) to afford the desired product. LC-MS calculated for $C_{23}H_{25}F_2N_4O_4[M+H]^+$ m/z: 459.2; found 459.1.

Example 40

3-(2,6-Difluoro-3,5-dimethoxyphenyl)-1-methyl-8-[(4-methylpiperazin-1-yl)carbonyl]-1,3,4, 7-tetrahydro-2H-pyrrolo[3',2':5,6]pyrido[4,3-d]pyrimidin-2-one

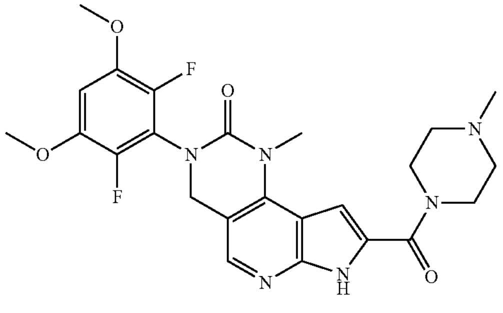

Step 1: 3-(2,6-difluoro-3,5-dimethoxyphenyl)-1-methyl-2-oxo-7-(phenylsulfonyl)-2,3,4,7-tetrahydro-1H-pyrrolo[3',2':5,6]pyrido[4,3-d]pyrimidine-8-carboxylic acid

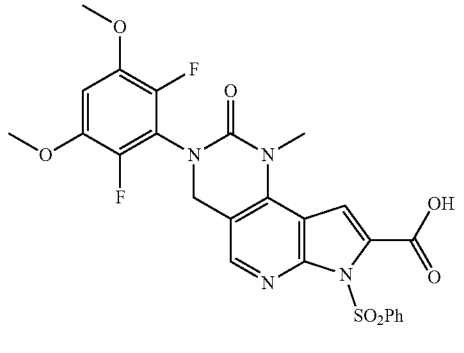

To a stirred solution of 3-(2,6-difluoro-3,5-dimethoxyphenyl)-1-methyl-7-(phenylsulfonyl)-1,3,4,7-tetrahydro-2H-pyrrolo[3',2':5,6]pyrido[4,3-d]pyrimidin-2-one (700 mg, 1.36 mmol) in tetrahydrofuran (20 mL) was added freshly prepared LDA solution (1M in THF, 1.95 mL, 1.4 eq) at −78° C. The mixture was stirred at −78° C. for 30 min then dry $CO_2$ gas (prepared from dry ice by passing through a drying tube) was bubbled into the reaction mixture for 30 min. The reaction was then quenched with 1N HCl at −78° C. After warming to room temperature, the reaction mixture was extracted with EtOAc. The combined organic layers were washed with brine, dried over $Na_2SO_4$, filtered and concentrated under reduced pressure. The residue was purified by column: 0 to 5% MeOH/DCM, to give the desired product (519 mg, 68%). LC-MS calculated for $C_{25}H_{21}F_2N_4O_7S$ $[M+H]^+$ m/z: 559.1; found 559.1.

Step 2: 3-(2,6-difluoro-3,5-dimethoxyphenyl)-1-methyl-2-oxo-2,3,4,7-tetrahydro-1H-pyrrolo [3',2':5, 6]pyrido[4,3-d]pyrimidine-8-carboxylic acid

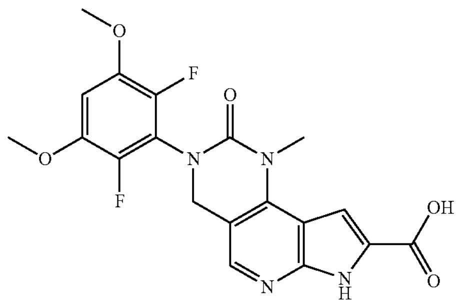

To a solution of 3-(2,6-difluoro-3,5-dimethoxyphenyl)-1-methyl-2-oxo-7-(phenylsulfonyl)-2,3,4,7-tetrahydro-1H-pyrrolo[3',2':5,6]pyrido[4,3-d]pyrimidine-8-carboxylic acid (762 mg, 1.36 mmol) in tetrahydrofuran (23 mL) was added 1.0 M potassium tert-butoxide in THF (6.0 mL, 6.0 mmol). The resulting light yellow suspension was stirred at room temperature for 30 min at which time LC-MS indicated the reaction was complete to the desired product. The reaction was quenched with water then extracted with EtOAc. The aqueous layer was acidified with 1N HCl and the white precipitate was collected via filtration and dried to afford the pure product (528 mg, 93%) as a white solid. LC-MS calculated for $C_{19}H_{17}F_2N_4O_5$ $[M+H]^+$ m/z: 419.1; found 419.1.

Step 3: 3-(2,6-difluoro-3,5-dimethoxyphenyl)-1-methyl-8-[(4-methylpiperazin-1-yl) carbonyl]-1, 3,4,7-tetrahydro-2H-pyrrolo[3',2':5,6]pyrido[4,3-d] pyrimidin-2-one To a stirred solution of 3-(2,6-difluoro-3,5-dimethoxyphenyl)-1-methyl-2-oxo-2,3,4,7-tetrahydro-1H-pyrrolo[3',2':5,6]pyrido[4,3-d]pyrimidine-8-carboxylic acid (207 mg, 0.495 mmol) in N,N-dimethylformamide (15 mL) was added triethylamine (210 μL, 1.5 mmol), followed by benzotriazol-1-yloxytris(dimethylamino)phosphonium hexafluorophosphate (230 mg, 0.52 mmol). The mixture was stirred for 5 min at room temperature then 1-methylpiperazine (160 μL, 1.5 mmol) was added. After stirred at room temperature for 30 min, the reaction mixture was diluted with MeOH then purified by RP-HPLC (pH=2) to give the desired product (200 mg, 81%) as a white solid. LC-MS calculated for $C_{24}H_{27}F_2N_6O_4[M+H]^+$ m/z: 501.2; found 501.1.

Example 41

3-(2,6-Difluoro-3,5-dimethoxyphenyl)-1-methyl-8-(morpholin-4-ylcarbonyl)-1,3,4,7-tetrahydro-2H-pyrrolo[3',2':5,6]pyrido[4,3-d]pyrimidin-2-one

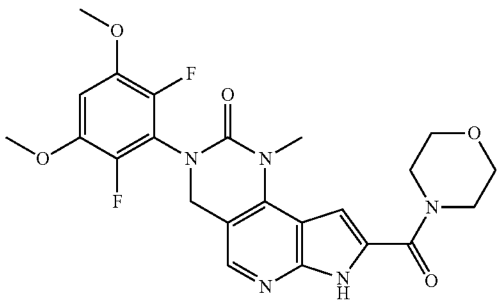 [SMILES: COc1cc(OC)c(F)c(N2Cc3cnc4[nH]c(C(=O)N5CCOCC5)cc4c3N(C)C2=O)c1F]

This compound was prepared using procedures analogous to those for Example 40, Step 3 with morpholine replacing 1-methylpiperazine. Purified by RP-HPLC (pH=2) to afford the desired product as a white solid. LC-MS calculated for $C_{23}H_{24}F_2N_5O_5[M+H]^+$ m/z: 488.2; found: 488.2.

Example 42

3-(2,6-Difluoro-3,5-dimethoxyphenyl)-8-[(4,4-difluoropiperidin-1-yl)carbonyl]-1-methyl-1,3,4,7-tetrahydro-2H-pyrrolo[3',2':5,6]pyrido[4,3-d]pyrimidin-2-one

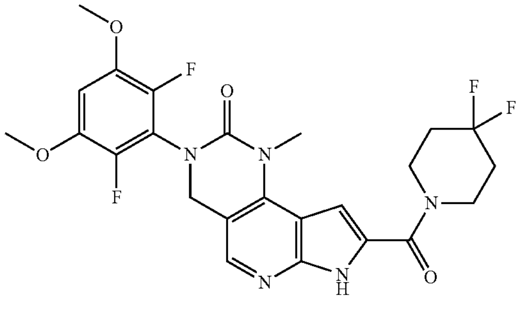 [SMILES: COc1cc(OC)c(F)c(N2Cc3cnc4[nH]c(C(=O)N5CCC(F)(F)CC5)cc4c3N(C)C2=O)c1F]

This compound was prepared using procedure analogous to those for Example 40, Step 3 with 4,4-difluoropiperidine hydrochloride replacing 1-methylpiperazine. Purified by RP-HPLC (pH=2) to afford the desired product as a white solid. LC-MS calculated for $C_{24}H_{24}F_4N_5O_4$ $[M+H]^+$ m/z: 522.2; found: 522.1.

Example 43

3-(2,6-Difluoro-3,5-dimethoxyphenyl)-1-methyl-9-(1-methyl-1H-pyrazol-4-yl)-1,3,4,7-tetrahydro-2H-pyrrolo[3',2':5,6]pyrido[4,3-d]pyrimidin-2-one

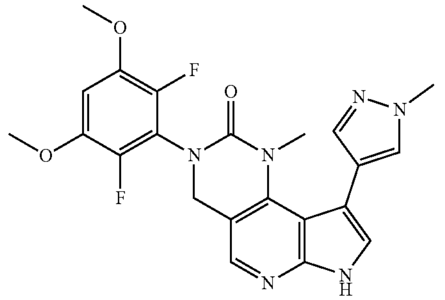

Step 1: 9-bromo-3-(2,6-difluoro-3,5-dimethoxyphenyl)-1-methyl-1,3,4,7-tetrahydro-2H-pyrrolo[3',2':5,6]pyrido[4,3-d]pyrimidin-2-one

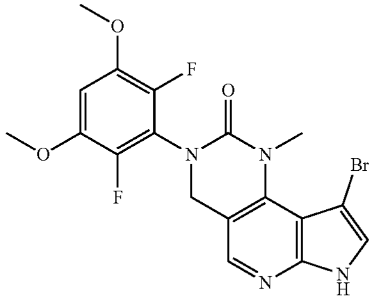 [SMILES: COc1cc(OC)c(F)c(N2Cc3cnc4[nH]cc(Br)c4c3N(C)C2=O)c1F]

To a solution of 3-(2,6-difluoro-3,5-dimethoxyphenyl)-1-methyl-1,3,4,7-tetrahydro-2H-pyrrolo[3',2':5,6]pyrido[4,3-d]pyrimidin-2-one (168.0 mg, 0.4488 mmol) in N,N-dimethylformamide (4 mL) was added a solution of N-bromosuccinimide (88 mg, 0.49 mmol) in N,N-dimethylformamide (0.56 mL) dropwise at 0° C. The resulting solution was stirred at room temperature for 2 h. The reaction was quenched with water and extracted with $CH_2Cl_2$. The combined organic phase was washed with brine, dried over $Na_2SO_4$. The solvents were removed under reduced pressure to afford the desired compound which was used in the next step without further purification. LC-MS calculated for $C_{18}H_{16}BrF_2N_4O_3$ $[M+H]^+$ m/z: 453.0; found: 453.1.

Step 2: tert-butyl 9-bromo-3-(2,6-difluoro-3,5-dimethoxyphenyl)-1-methyl-2-oxo-1,2,3,4-tetrahydro-7H-pyrrolo[3',2':5,6]pyrido[4,3-d]pyrimidine-7-carboxylate

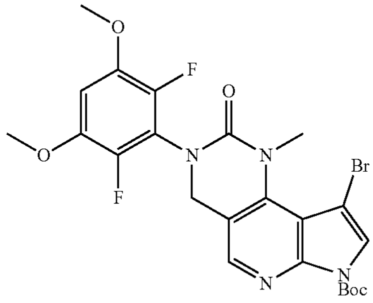 [SMILES: COc1cc(OC)c(F)c(N2Cc3cnc4c(c(Br)cn4C(=O)OC(C)(C)C)c3N(C)C2=O)c1F]

To a stirred solution of 9-bromo-3-(2,6-difluoro-3,5-dimethoxyphenyl)-1-methyl-1,3,4,7-tetrahydro-2H-pyrrolo[3',2':5,6]pyrido[4,3-d]pyrimidin-2-one (200 mg, 0.4 mmol) in methylene chloride (3 mL) was added di-tert-butyl carbonate (180 mg, 1.0 mmol) and 4-dimethylaminopyridine (10.8 mg, 0.088 mmol). The resulting solution was stirred at room temperature for 2 h at which time LC-MS analysis showed that the reaction was complete. The reaction mixture was concentrated and the residue was purified by flash chromatography on a silica gel column eluting with 10% AcOEt in $CH_2Cl_2$ to afford the desired compound (170 mg, 70%). LC-MS calculated for $C_{23}H_{24}BrF_2N_4O_5$ $[M+H]^+$ m/z: 553.1; found: 553.0.

Step 3: 3-(2,6-difluoro-3,5-dimethoxyphenyl)-1-methyl-9-(1-methyl-1H-pyrazol-4-yl)-1,3,4,7-tetrahydro-2H-pyrrolo[3',2':5,6]pyrido[4,3-d]pyrimidin-2-one A mixture of tert-butyl 9-bromo-3-(2,6-difluoro-3,5-dimethoxyphenyl)-1-methyl-2-oxo-1,2,3,4-tetrahydro-7H-pyrrolo[3',2':5,6]pyrido[4,3-d]pyrimidine-7-carboxylate (35.0 mg, 0.063 mmol), 1-methyl-4-(4,4,5,5-tetramethyl-1,3,2-dioxaborolan-2-yl)-1H-pyrazole (26 mg, 0.13 mmol), bis(tri-t-butylphosphine)palladium (6 mg, 0.01 mmol), and N,N-diisopropylethylamine (33 μL, 0.19 mmol) in 1,4-dioxane (1.7 mL) and water (0.2 mL) was degassed then filled with nitrogen. After stirring at 120° C. for 2 h, the reaction mixture was filtered and concentrated to dryness. The residue was dissolved in TFA/$CH_2Cl_2$ (1:1, 1 mL) and stirred at room temperature for 1 h. The reaction mixture was concentrated and the residue was dissolved in MeOH and purified by RP-HPLC (pH=2) to afford the desired product. LC-MS calculated for $C_{22}H_{21}F_2N_6O_3$$[M+H]^+$ m/z: 455.2; found: 455.1.

Example 44

3-(2,6-Difluoro-3,5-dimethoxyphenyl)-1-(2-hydroxyethyl)-1,3,4,7-tetrahydro-2H-pyrrolo[3', 2':5,6]pyrido[4,3-d]pyrimidin-2-one

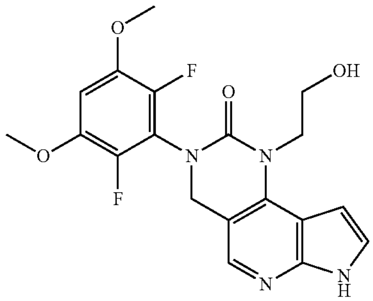 [SMILES: COc1cc(OC)c(F)c(N2Cc3cnc4[nH]ccc4c3N(CCO)C2=O)c1F]

Step 1: 1-allyl-3-(2,6-difluoro-3,5-dimethoxyphenyl)-1,3,4,7-tetrahydro-2H-pyrrolo[3',2':5, 6]pyrido[4,3-d]pyrimidin-2-one

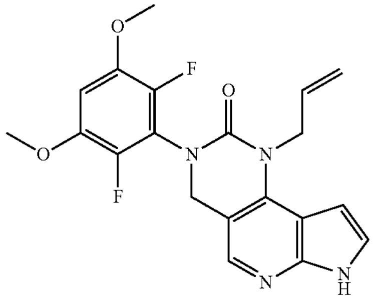 [SMILES: C=CCN1C(=O)N(c2c(F)c(OC)cc(OC)c2F)Cc2cnc3[nH]ccc3c21]

This compound was prepared by using procedures analogous to those described for the synthesis of Example 39, Steps 1-3, with 4-(allylamino)-1H-pyrrolo[2,3-b]pyridine-5-carbaldehyde (prepared according to Example 1, Step 1) replacing 4-(methylamino)-1H-pyrrolo[2,3-b]pyridine-5-carbaldehyde. LC-MS calculated for $C_{20}H_{19}F_2N_4O_3$$[M+H]^+$ m/z: 401.1; found: 401.1.

Step 2: 1-allyl-3-(2,6-difluoro-3,5-dimethoxyphenyl)-7-(phenylsulfonyl)-1,3,4,7-tetrahydro-2H-pyrrolo[3',2':5,6]pyrido[4,3-d]pyrimidin-2-one

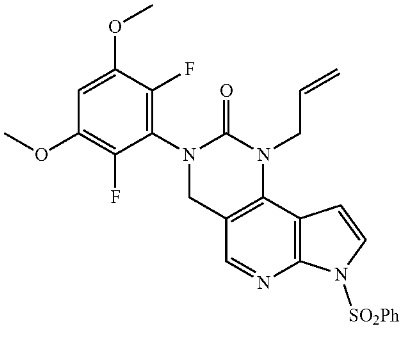

To a solution of 1-allyl-3-(2,6-difluoro-3,5-dimethoxy-phenyl)-1,3,4,7-tetrahydro-2H-pyrrolo[3',2':5,6]pyrido[4,3-d]pyrimidin-2-one (0.35 g, 0.89 mmol) in DMF (4 mL) was added sodium hydride ((60% dispersion in mineral oil, 0.053 g, 1.3 mmol) at 0° C. The mixture was stirred for 20 minutes then benzenesulfonyl chloride (0.14 mL, 1.1 mmol) was added and the reaction was stirred for another 1 h at 0° C. The mixture was diluted with water and the formed precipitate was collected via filtration then washed with water and dried to provide the desired product. LC-MS calculated for $C_{26}H_{23}F_2N_4O_5S$ $[M+H]^+$ m/z: 541.1; found: 541.1.

Step 3. [3-(2,6-difluoro-3,5-dimethoxyphenyl)-2-oxo-7-(phenylsulfonyl)-2,3,4,7-tetrahydro-1H-pyrrolo[3',2':5,6]pyrido[4,3-d]pyrimidin-1-yl]acetaldehyde

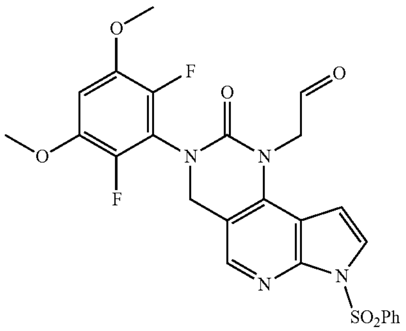

To a solution of 1-allyl-3-(2,6-difluoro-3,5-dimethoxy-phenyl)-7-(phenylsulfonyl)-1,3,4,7-tetrahydro-2H-pyrrolo [3',2':5,6]pyrido[4,3-d]pyrimidin-2-one (120 mg, 0.22 mmol) in tert-butyl alcohol (2 mL) was added N-methylmorpholine N-oxide (28.6 mg, 0.244 mmol) and water (0.70 mL, 39 mmol). To this solution was then added aqueous osmium tetraoxide (0.070 mL, 0.011 mmol, 4%). Another portion of N-methylmorpholine N-oxide (28.6 mg, 0.244 mmol) was added after 3 h. The reaction mixture was stirred at room temperature for 3 days. The solution was diluted with water, extracted with methylene chloride. The combined organic layers were dried over $MgSO_4$, filtered then concentrated. The residue was dissolved in THF (1.7 mL)/water (0.83 mL) and then sodium periodate (0.14 g, 0.66 mmol) was added, followed by acetic acid (0.0032 mL, 0.055 mmol) at 0° C. After stirring for 2 h, the reaction mixture was diluted with water, extracted with methylene chloride. The organic layer was washed with brine, dried over $MgSO_4$, filtered and concentrated. The residue was purified by flash chromatography on a silica gel column eluting with $EtOAc/CH_2Cl_2$ (0 to 20%). LC-MS calculated for $C_{25}H_{21}F_2N_4O_6S$ $[M+H]^+$ m/z: 543.1; found: 543.1.

Step 4. 3-(2,6-difluoro-3,5-dimethoxyphenyl)-1-(2-hydroxyethyl)-7-(phenylsulfonyl)-1,3,4,7-tetrahydro-2H-pyrrolo[3',2':5,6]pyrido[4,3-d]pyrimidin-2-one

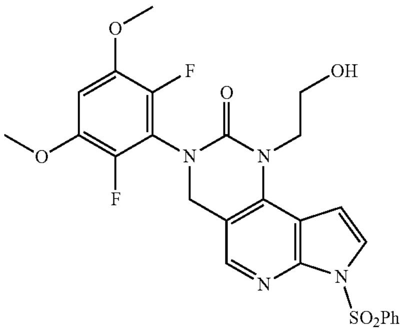

To a solution of [3-(2,6-difluoro-3,5-dimethoxyphenyl)-2-oxo-7-(phenylsulfonyl)-2,3,4,7-tetrahydro-1H-pyrrolo[3',2':5,6]pyrido[4,3-d]pyrimidin-1-yl]acetaldehyde (50.0 mg, 0.0922 mmol) in methanol (1.5 mL) was added sodium tetrahydroborate (7.0 mg, 0.18 mmol). After stirring at room temperature for 30 min, the mixture was diluted with methylene chloride then washed with saturated aqueous solution of $NaHCO_3$, water, and brine, and then the mixture was dried over $Na_2SO_4$, filtered and concentrated to provide the product which was used in the next step directly. LC-MS calculated for $C_{25}H_{23}F_2N_4O_6S$ $[M+H]^+$ m/z: 545.1; found: 545.1.

Step 5. 3-(2,6-difluoro-3,5-dimethoxyphenyl)-1-(2-hydroxyethyl)-1,3,4,7-tetrahydro-2H-pyrrolo[3',2':5,6]pyrido[4,3-d]pyrimidin-2-one 6.0 M Potassium hydroxide in water (0.1 mL, 0.6 mmol) was added to a solution of 3-(2,6-difluoro-3,5-dimethoxy-phenyl)-1-(2-hydroxyethyl)-7-(phenylsulfonyl)-1,3,4,7-tetrahydro-2H-pyrrolo[3',2':5,6]pyrido[4,3-d]pyrimidin-2-one (30.0 mg, 0.0551 mmol) in THF (0.6 mL) and then the mixture was stirred at 70° C. overnight. The product was purified by RP-HPLC (pH=2) to afford the desired product as a white solid. LC-MS calculated for $C_{19}H_{19}F_2N_4O_4$$[M+H]^+$ m/z: 405.1; found: 405.2. $^1H$ NMR (400 MHz, DMSO) δ 12.03 (s, 1H), 8.03 (s, 1H), 7.54 (s, 1H), 7.04 (t, J=8.0 Hz, 3H), 6.73 (s, 1H), 4.78 (s, 2H), 4.23 (t, J=6.8 Hz, 2H), 3.89 (s, 6H), 3.70 (t, J=6.8 Hz, 2H).

Example 45

1-Cyclopropyl-3-(2,6-difluoro-3,5-dimethoxyphenyl)-1,3,4,7-tetrahydro-2H-pyrrolo[3',2':5,6]pyrido[4,3-d]pyrimidin-2-one

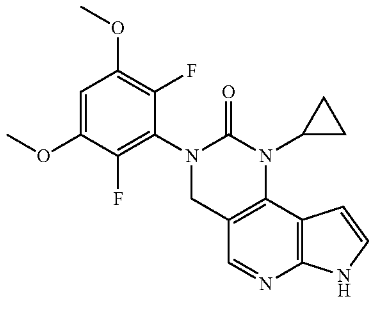 [SMILES: COc1cc(OC)c(F)c(N2Cc3cnc4[nH]ccc4c3N(C3CC3)C2=O)c1F]

Step 1: N-[(1E)-(4-chloro-1H-pyrrolo[2,3-b]pyridin-5-yl)methylene]-2,6-difluoro-3,5-dimethoxyaniline

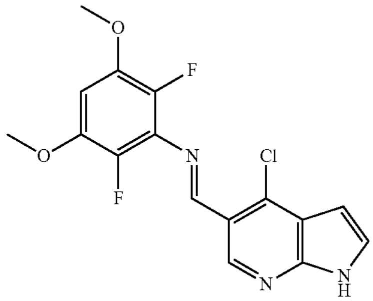 [SMILES: COc1cc(OC)c(F)c(/N=C/c2cnc3[nH]ccc3c2Cl)c1F]

A mixture of 4-chloro-1H-pyrrolo[2,3-b]pyridine-5-carbaldehyde (5.00 g, 27.7 mmol), 2,6-difluoro-3,5-dimethoxyaniline (6.3 g, 33 mmol) and p-toluenesulfonic acid monohydrate (1.1 g, 5.8 mmol) in toluene (300 mL) was heated to reflux with azeotropic removal of water via a Dean-Stark trap. After stirred for overnight, the reaction mixture was concentrated and the residue was used in the next step without further purification.

Step 2: N-[(4-chloro-1H-pyrrolo[2,3-b]pyridin-5-yl)methyl]-2,6-difluoro-3,5-dimethoxyaniline

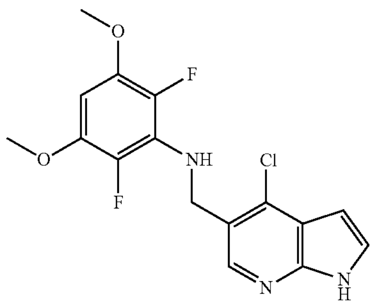 [SMILES: COc1cc(OC)c(F)c(NCc2cnc3[nH]ccc3c2Cl)c1F]

The crude product from Step 1 was dissolved in tetrahydrofuran (300 mL) and cooled to 0° C. then LiAlH4 (3.6 g, 96 mmol) was added. The reaction mixture was warmed to 50° C. and stirred overnight. The reaction was then quenched with a minimum amount of water and diluted with ethyl acetate. The mixture was filtered through Celite and the filtrate was concentrated under reduced pressure. The residue was purified by flash chromatography on a silica gel column eluting with methanol in dichloromethane (0-5%) to afford the desired product (7.00 g, 71.5%). LC-MS calculated for $C_{16}H_{15}ClF_2N_3O_2$ $[M+H]^+$ m/z: 354.1; found 354.0.

Step 3: N-cyclopropyl-5-{[(2,6-difluoro-3,5-dimethoxyphenyl)amino]methyl}-1H-pyrrolo[2,3-b]pyridin-4-amine

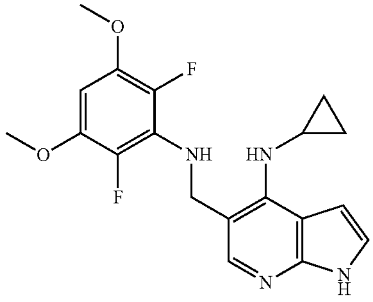 [SMILES: COc1cc(OC)c(F)c(NCc2cnc3[nH]ccc3c2NC2CC2)c1F]

A mixture of of N-[(4-chloro-1H-pyrrolo[2,3-b]pyridin-5-yl)methyl]-2,6-difluoro-3,5-dimethoxyaniline (0.25 g, 0.71 mmol), cyclopropylamine (0.088 mL, 1.3 mmol), palladium acetate (16 mg, 0.071 mmol), (R)-(+)-2,2'-bis(diphenylphosphino)-1,1'-binaphthyl (44 mg, 0.071 mmol), and cesium carbonate (0.70 g, 2.1 mmol) in 1,4-dioxane (10 mL) was degassed then filled with nitrogen. After stirring at 160° C. overnight, the reaction mixture was diluted with ethyl acetate, filtered and concentrated under reduced pressure. The residue was purified by flash chromatography on a silica gel column eluting with MeOH in DCM (0-5%) to afford the desired product (0.17 g, 64%). LC-MS calculated for $C_{19}H_{21}F_2N_4O_2[M+H]^+$ m/z: 375.2; found 375.1.

Step 4: 1-cyclopropyl-3-(2,6-difluoro-3,5-dimethoxyphenyl)-1,3,4,7-tetrahydro-2H-pyrrolo[3',2':5,6]pyrido[4,3-d]pyrimidin-2-one Triphosgene (0.20 g, 0.6 mmol) was added to a solution of N-cyclopropyl-5-{[(2,6-difluoro-3,5-dimethoxyphenyl)amino]methyl}-1H-pyrrolo[2,3-b]pyridin-4-amine (0.17 g, 0.44 mmol) and triethylamine (590 μL, 4.2 mmol) in tetrahydrofuran (5 mL) at 0° C. The reaction mixture was stirred at room temperature for 30 min, then 2 N NaOH (2.0 mL) was added. After stirring at room temperature for 1 h, the reaction mixture was extracted with ethyl acetate (3×10 mL). The combined organic layers were washed with brine, dried over $MgSO_4$, filtered and concentrated under reduced pressure. The residue was purified by flash chromatography on a silica gel column eluting with MeOH in DCM (0-5%) to afford the desired product. LC-MS calculated for $C_{20}H_{19}F_2N_4O_3[M+H]^+$ m/z: 401.1; found 401.1. $^1H$ NMR (400 MHz, DMSO) δ 11.97 (s, 1H), 8.04 (s, 1H), 7.52-7.46 (m, 1H), 7.03 (t, J=8.2 Hz, 1H), 6.97-6.93 (m, 1H), 4.66 (s, 2H), 3.88 (s, 6H), 3.38-3.28 (m, 1H), 1.13-1.03 (m, 2H), 0.70-0.62 (m, 2H).

Example 46

3-(2,6-Difluoro-3,5-dimethoxyphenyl)-1-(tetrahydro-2H-pyran-4-yl)-1,3,4,7-tetrahydro-2H-pyrrolo[3',2':5,6]pyrido[4,3-d]pyrimidin-2-one

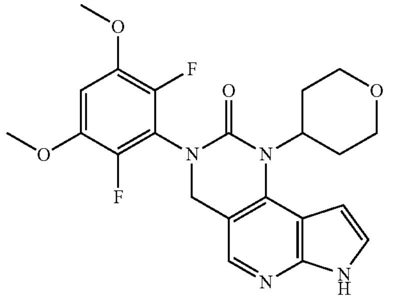 [SMILES: COc1cc(OC)c(F)c(N2Cc3cnc4[nH]ccc4c3N(C3CCOCC3)C2=O)c1F]

This compound was prepared using procedures analogous to those for Example 45 with tetrahydro-2H-pyran-4-amine replacing cyclopropylamine. Purified by RP-HPLC (pH=2) to afford the desired product as a white solid. LC-MS calculated for $C_{22}H_{23}F_2N_4O_4[M+H]^+$ m/z: 445.2; found 445.0. $^1H$ NMR (300 MHz, DMSO) δ 11.95 (s, 1H), 8.03 (s, 1H), 7.56-7.49 (m, 1H), 7.03 (t, J=8.2 Hz, 1H), 6.45-6.36 (m, 1H), 4.69 (s, 2H), 4.48-4.32 (m, 1H), 4.03-3.92 (m, 2H), 3.88 (s, 6H), 3.52-3.37 (m, 2H), 2.82-2.62 (m, 2H), 1.94-1.83 (m, 2H).

Example 47

3-(2,6-difluoro-3,5-dimethoxyphenyl)-1-phenyl-1,3,4,7-tetrahydro-2H-pyrrolo[3',2':5,6]pyrido[4,3-d]pyrimidin-2-one

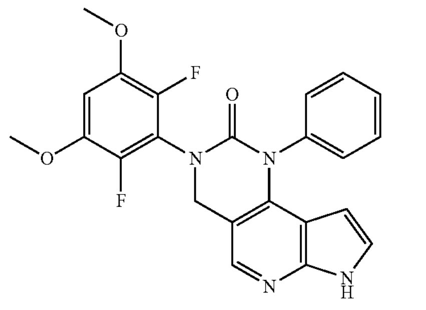 [SMILES: COc1cc(OC)c(F)c(N2Cc3cnc4[nH]ccc4c3N(c3ccccc3)C2=O)c1F]

This compound was prepared using procedures analogous to those for Example 45 with aniline replacing cyclopropylamine. Purified by RP-HPLC (pH=2) to afford the desired product as a white solid. LC-MS calculated for C23H19F2N4O3 $[M+H]^+$ m/z: 437.1; found 437.1. $^1H$ NMR (500 MHz, DMSO) δ 11.81 (s, 1H), 8.11 (s, 1H), 7.57-7.51 (m, 3H), 7.50-7.44 (m, 2H), 7.13-7.09 (m, 1H), 7.06 (t, J=8.2 Hz, 1H), 4.99 (s, 2H), 4.31-4.27 (m, 1H), 3.89 (s, 6H).

Example 48

1-Cyclopropyl-3-(2,6-difluoro-3,5-dimethoxyphenyl)-3,4,7,9-tetrahydro-1H-pyrrolo[3',2':5,6]pyrido[4,3-d]pyrimidine-2,8-dione

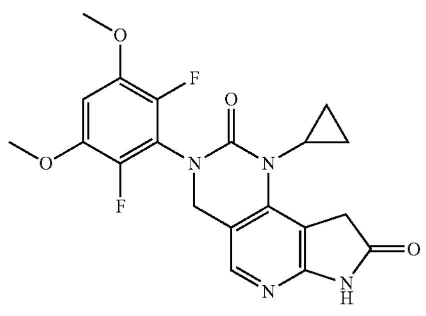 [SMILES: COc1cc(OC)c(F)c(N2Cc3cnc4c(c3N(C3CC3)C2=O)CC(=O)N4)c1F]

This compound was prepared using procedures analogous to those for Example 37 with 1-cyclopropyl-3-(2,6-difluoro-3,5-dimethoxyphenyl)-1,3,4,7-tetrahydro-2H-pyrrolo[3',2':5,6]pyrido[4,3-d]pyrimidin-2-one (Example 45) replacing 3-(2,6-difluoro-3,5-dimethoxyphenyl)-1-methyl-1,3,4,7-tetrahydro-2H-pyrrolo[3',2':5,6]pyrido[4,3-d]pyrimidin-2-one. Purified by RP-HPLC (pH=10) to afford the desired product as a white solid. LC-MS calculated for $C_{20}H_{19}F_2N_4O_4[M+H]^+$ m/z: 417.1; found 417.0. $^1H$ NMR (300 MHz, DMSO) δ 11.03 (s, 1H), 7.82 (s, 1H), 7.02 (t, J=8.2 Hz, 1H), 4.48 (s, 2H), 3.99 (s, 2H), 3.87 (s, 6H), 3.14-3.00 (m, 1H), 1.08-0.94 (m, 2H), 0.69-0.58 (m, 2H).

Example 49

3-(2,6-Difluoro-3,5-dimethoxyphenyl)-1-ethyl-3,4,7,9-tetrahydro-1H-pyrrolo[3',2':5,6]pyrido[4,3-d]pyrimidine-2,8-dione

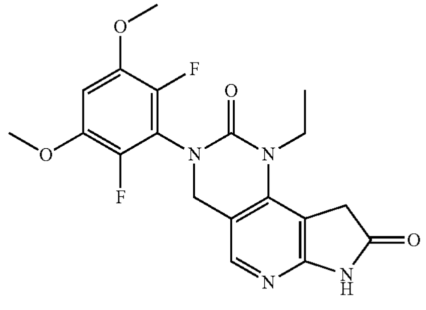 [SMILES: CCN1C(=O)N(c2c(F)c(OC)cc(OC)c2F)Cc2cnc3c(c21)CC(=O)N3]

Step 1: 4-(ethylamino)-1H-pyrrolo[2,3-b]pyridine-5-carbaldehyde

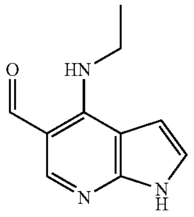

A mixture of 4-chloro-1H-pyrrolo[2,3-b]pyridine-5-carbaldehyde (CAS #958230-19-8, Lakestar Tech, Lot: 124-132-29: 3.0 g, 17 mmol) and ethylamine (10M in water, 8.3 mL, 83 mmol) in 2-methoxyethanol (20 mL, 200 mmol) was heated to 130° C. and stirred overnight. The mixture was cooled to room temperature then concentrated under reduced pressure. The residue was treated with 1N HCl (30 mL) and stirred at room temperature for 1 h then neutralized with saturated $NaHCO_3$ aqueous solution. The precipitate was collected via filtration then washed with water and dried to provide the desired product (2.9 g, 92%). LC-MS calculated for $C_{10}H_{12}N_3O$ $[M+H]^+$ m/z: 190.1; found: 190.1.

Step 2: 5-{[(2,6-difluoro-3,5-dimethoxyphenyl)amino]methyl}-N-ethyl-1H-pyrrolo[2,3-b]pyridin-4-amine

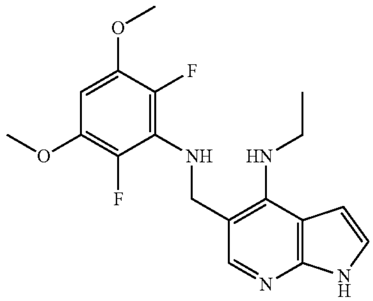 [SMILES: CCNc1c(CNc2c(F)c(OC)cc(OC)c2F)cnc2[nH]ccc12]

A mixture of 4-(ethylamino)-1H-pyrrolo[2,3-b]pyridine-5-carbaldehyde (7.0 g, 37 mmol), 2,6-difluoro-3,5-dimethoxyaniline (9.1 g, 48 mmol) and [(1S)-7,7-dimethyl-2-oxobicyclo[2.2.1]hept-1-yl]methanesulfonic acid (Aldrich, cat #21360: 2 g, 7 mmol) in xylenes (250 mL) was heated to reflux with azeotropic removal of water using Dean-Stark for 2 days at which time LC-MS showed the reaction was complete. The mixture was cooled to room temperature and the solvent was removed under reduced pressure. The residue was dissolved in tetrahydrofuran (500 mL) and then 2.0 M lithium tetrahydroaluminate in THF (37 mL, 74 mmol) was added slowly and the resulting mixture was stirred at 50° C. for 3 h then cooled to room temperature. The reaction was quenched by addition of water, 15% aqueous NaOH and water. The mixture was filtered and washed with THF. The filtrate was concentrated and the residue was washed with $CH_2Cl_2$ and then filtered to get the pure product (11 g, 82%). LC-MS calculated for $C_{18}H_{21}F_2N_4O_2$$[M+H]^+$ m/z: 363.2; found: 363.1.

Step 3: 3-(2,6-Difluoro-3,5-dimethoxyphenyl)-1-ethyl-1,3,4,7-tetrahydro-2H-pyrrolo[3',2':5,6]pyrido[4,3-d]pyrimidin-2-one

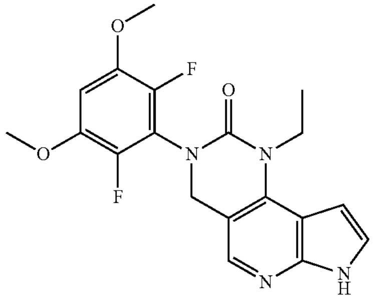 [SMILES: CCN1C(=O)N(c2c(F)c(OC)cc(OC)c2F)Cc2cnc3[nH]ccc3c21]

A solution of triphosgene (5.5 g, 18 mmol) in tetrahydrofuran (30 mL) was added slowly to a mixture of 5-{[(2,6-difluoro-3,5-dimethoxyphenyl)amino]methyl}-N-ethyl-1H-pyrrolo[2,3-b]pyridin-4-amine (5.6 g, 15 mmol) in tetrahydrofuran (100 mL) at 0° C. and then the mixture was stirred at room temperature for 6 h. The mixture was cooled to 0° C. and then 1.0 M sodium hydroxide in water (100 mL, 100 mmol) was added slowly. The reaction mixture was stirred at room temperature overnight and the formed precipitate was collected via filtration, washed with water, and then dried to provide the first batch of the purified desired product. The organic layer in the filtrate was separated and the aqueous layer was extracted with methylene chloride. The combined organic layer was concentrated and the residue was triturated with methylene chloride then filtered and dried to provide another batch of the product (total 5.5 g, 92%). LC-MS calculated for $C_{19}H_{19}F_2N_4O_3$$[M+H]^+$ m/z: 389.1; found: 389.1.

Step 4: 3-(2,6-Difluoro-3,5-dimethoxyphenyl)-1-ethyl-3,4,7,9-tetrahydro-1H-pyrrolo [3',2':5,6]pyrido[4,3-d]pyrimidine-2,8-dione To a mixture of 3-(2,6-difluoro-3,5-dimethoxyphenyl)-1-ethyl-1,3,4,7-tetrahydro-2H-pyrrolo[3',2':5,6]pyrido[4,3-d]pyrimidin-2-one (3.0 g, 7.7 mmol) in isopropyl alcohol (70 mL, 900 mmol)/water (7 mL, 400 mmol) was added pyridinium tribromide (11 g, 31 mmol). Then the reaction mixture was stirred at 40° C. for 3 h. The mixture was cooled to room temperature and then acetic acid (10 mL, 200 mmol) and zinc (5.05 g, 77.2 mmol) were added. The resulting mixture was stirred at room temperature overnight then filtered. The filtrate was concentrated and the residue was triturated with water (100 mL)/AcCN (10 mL) and stirred for 30 min. The solid was collected via filtration then dried. The solid was then stirred with $CH_2Cl_2$/MeOH (100 mL/10 mL) for 30 min then filtered and dried to provide the pure desired product. The filtrate was concentrated and the residue was stirred with AcCN/Water (40 mL/5 mL) at 40° C. for 10 min then filtered and dried to provide another batch of pure product. LC-MS calculated for $C_{19}H_{19}F_2N_4O_4$$[M+H]^+$ m/z: 405.1; found: 405.2. $^1H$ NMR (500 MHz, DMSO-$d_6$): δ 1.19 (t, 3H), 3.86 (m, 2H), 3.88 (s, 6H), 3.90 (m, 2H), 4.61 (s, 2H), 7.03 (m, 1H), 7.83 (s, 1H), 11.01 (s, 1H) ppm.

Example 50

1-(Cyclopropylmethyl)-3-(2,6-difluoro-3,5-dimethoxyphenyl)-3,4,7,9-tetrahydro-1H-pyrrolo[3',2':5,6]pyrido[4,3-d]pyrimidine-2,8-dione

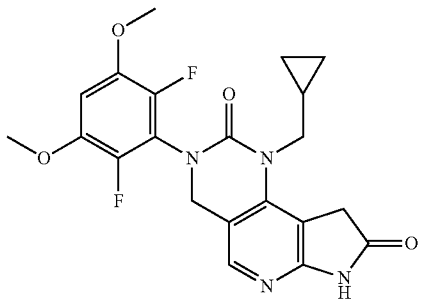 [SMILES: COc1cc(OC)c(F)c(N2Cc3cnc4c(c3N(CC3CC3)C2=O)CC(=O)N4)c1F]

This compound was prepared by using procedure analogous to those described for the synthesis of Example 49 with 4-(cyclopropylmethylamino)-1H-pyrrolo[2,3-b]pyridine-5-carbaldehyde (prepared according to Example 1, Step 1) replacing 4-(ethylamino)-1H-pyrrolo[2, 3-b]pyridine-5-carbaldehyde. LC-MS calculated for $C_{21}H_{21}F_2N_4O_4[M+H]^+$ m/z: 431.2; found: 431.1. $^1H$ NMR (500 MHz, DMSO) δ 11.03 (s, 1H), 7.85 (s, 1H), 7.04 (t, J=8.1 Hz, 1H), 4.62 (s, 2H), 3.19-3.87 (m, 8H), 3.83 (d, J=6.6 Hz, 2H), 1.16-1.07 (m, 1H), 0.50-0.43 (m, 2H), 0.31-0.24 (m, 2H).

Example 51

3-(2,6-Difluoro-3,5-dimethoxyphenyl)-1-methyl-1,3,4,7-tetrahydro-2H-pyrazolo[4',3':5,6]pyrido[4,3-d]pyrimidin-2-one

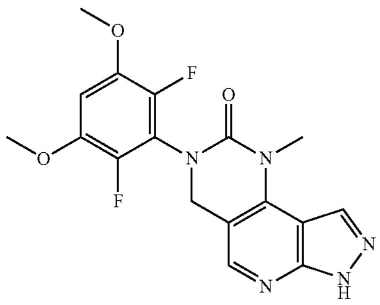 [SMILES: COc1cc(OC)c(F)c(N2Cc3cnc4[nH]ncc4c3N(C)C2=O)c1F]

Step 1: 5-{[(2,6-difluoro-3,5-dimethoxyphenyl)amino]methyl}-1-(4-methoxybenzyl)-N-methyl-1H-pyrazolo[3,4-b]pyridin-4-amine

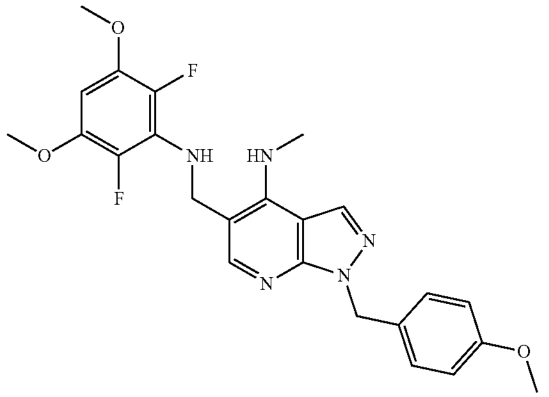

This compound was prepared using procedures analogous to those for Example 39, Steps 1-2, from 1-(4-methoxybenzyl)-4-(methylamino)-1H-pyrazolo[3,4-b]pyridine-5-carbaldehyde (Prepared by the same method as described in WO 2007/134259). The crude mixture was purified by flash column (MeOH/DCM, 3%~20%) to afford the aniline as a white solid. LC-MS calculated for $C_{24}H_{26}F_2N_5O_3[M+H]^+$ m/z: 470.2; found 470.2.

Step 2: 3-(2,6-difluoro-3,5-dimethoxyphenyl)-7-(4-methoxybenzyl)-1-methyl-1,3,4,7-tetrahydro-2H-pyrazolo[4',3':5,6]pyrido[4,3-d]pyrimidin-2-one

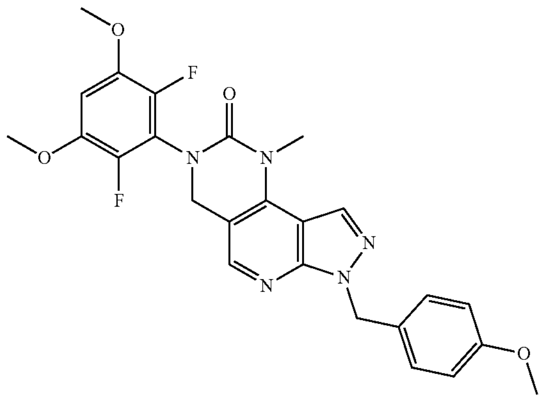

This compound was prepared using procedures analogous to those for Example 39, Step 3. The product was purified by flash column (EtOAc/hexanes, 30%~80%) to afford the urea as a white solid. LC-MS calculated for $C_{25}H_{24}F_2N_5O_4[M+H]^+$ m/z: 496.2; found 496.1.

Step 3: 3-(2,6-difluoro-3,5-dimethoxyphenyl)-1-methyl-1,3,4,7-tetrahydro-2H-pyrazolo [4',3':5,6]pyrido[4,3-d]pyrimidin-2-one A solution of 3-(2,6-difluoro-3,5-dimethoxyphenyl)-7-(4-methoxybenzyl)-1-methyl-1,3,4,7-tetrahydro-2H-pyrazolo[4',3':5,6]pyrido[4,3-d]pyrimidin-2-one (300 mg, 0.6 mmol)

in TFA (4.0 mL) was heated to 70° C. for 2 h. The solution was cooled to room temperature and concentrated under reduced pressure. The residue was purified by RP-HPLC (pH 2) to afford the desired product as a white solid. LC-MS calculated for $C_{17}H_{16}O_3N_5F_2[M+H]^+$ m/z: 376.1; found 376.1. $^1H$ NMR (300 MHz, DMSO) δ 13.67 (s, 1H), 8.41 (s, 1H), 8.24 (s, 1H), 7.06 (t, J=8.2 Hz, 1H), 4.83 (s, 2H), 3.89 (s, 6H), 3.66 (s, 3H).

Example 52

3-(2,6-Difluoro-3,5-dimethoxyphenyl)-1,9-dimethyl-1,3,4,7-tetrahydro-2H-pyrazolo[4',3':5,6]pyrido[4,3-d]pyrimidin-2-one

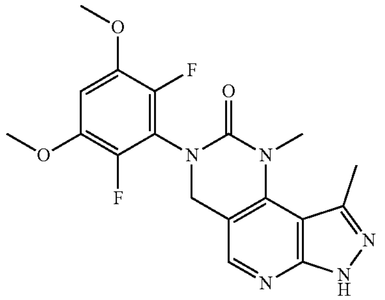 [SMILES: COc1cc(OC)c(F)c(N2Cc3cnc4[nH]nc(C)c4c3N(C)C2=O)c1F]

Step 1: 9-bromo-3-(2,6-difluoro-3,5-dimethoxyphenyl)-1-methyl-1,3,4,7-tetrahydro-2H-pyrazolo[4',3':5,6]pyrido[4,3-d]pyrimidin-2-one

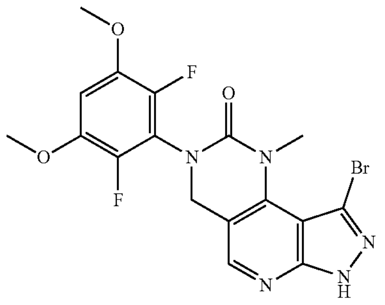 [SMILES: COc1cc(OC)c(F)c(N2Cc3cnc4[nH]nc(Br)c4c3N(C)C2=O)c1F]

To a solution of 3-(2,6-difluoro-3,5-dimethoxyphenyl)-1-methyl-1,3,4,7-tetrahydro-2H-pyrazolo[4',3':5,6]pyrido[4,3-d]pyrimidin-2-one (250.0 mg, 0.6661 mmol) in $CH_3CN$ (6.0 mL) at 0° C. was added N-bromosuccinimide (150 mg, 0.86 mmol). The mixture was stirred for 2 h before concentrated under reduced pressure. The residue was purified by column (MeOH/DCM, 3%~30%) to afford the product (300.0 mg, 99%) as a white solid. LC-MS calculated for $C_{17}H_{15}BrO_3N_5F_2$ $[M+H]^+$ m/z: 454.0; found 454.1.

Step 2: 3-(2,6-difluoro-3,5-dimethoxyphenyl)-1,9-dimethyl-1,3,4,7-tetrahydro-2H-pyrazolo[4',3':5,6]pyrido[4,3-d]pyrimidin-2-one To a solution of 9-bromo-3-(2,6-difluoro-3,5-dimethoxyphenyl)-1-methyl-1,3,4,7-tetrahydro-2H-pyrazolo[4',3':5,6]pyrido[4,3-d]pyrimidin-2-one (80.0 mg, 0.176 mmol) in 1,4-dioxane (2.0 mL) was added [1,1'-bis(diphenylphosphino)ferrocene]dichloropalladium(II) complex with dichloromethane (20.0 mg, 0.0245 mmol). To this solution was added $ZnMe_2$ (0.50 mL, 2.0 M solution in toluene, 1.0 mmol). The resulting mixture was heated to 100° C. for 1 h before it was diluted with MeOH and purified by RP-HPLC (pH 2). LC-MS calculated for $C_{18}H_{18}O_3N_5F_2[M+H]^+$ m/z: 390.1; found 390.1. $^1H$ NMR (300 MHz, DMSO) δ 8.22 (s, 1H), 7.03 (t, J=9.0 Hz, 1H), 4.78 (s, 2H), 3.88 (s, 6H), 3.55 (s, 3H), 2.67 ppm (s, 3H).

Example 53

3-(2,6-Difluoro-3,5-dimethoxyphenyl)-1-methyl-2-oxo-2,3,4,7-tetrahydro-1H-pyrazolo[4',3':5,6]pyrido[4,3-d]pyrimidine-9-carbonitrile

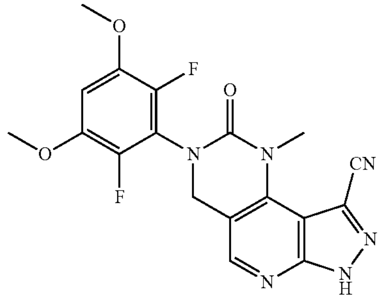

To a solution of 9-bromo-3-(2,6-difluoro-3,5-dimethoxyphenyl)-1-methyl-1,3,4,7-tetrahydro-2H-pyrazolo[4',3':5,6]pyrido[4,3-d]pyrimidin-2-one (15.0 mg, 0.033 mmol) in DMF (1.0 mL) was added zinc cyanide (12.0 mg, 0.099 mmol) and [1,1'-bis(diphenylphosphino)ferrocene]dichloropalladium(II) complexed with dichloromethane (5.0 mg, 0.007 mmol). The resulting mixture was heated to 180° C. for 1 h before it was diluted with MeOH and purified by RP-HPLC (pH 2). LC-MS calculated for $C_{18}H_{15}O_3N_6F_2$ $[M+H]^+$ m/z: 401.1; found 401.1.

Example 54

[3-(2,6-Difluoro-3,5-dimethoxyphenyl)-1-methyl-2-oxo-2,3,4,7-tetrahydro-1H-pyrazolo[4',3':5,6]pyrido[4,3-d]pyrimidin-9-yl]acetonitrile

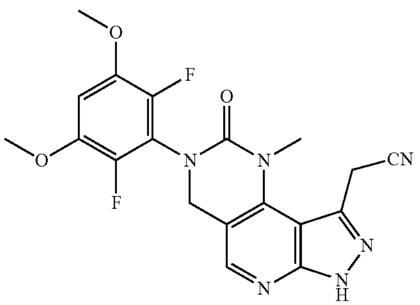 [SMILES: COc1cc(OC)c(F)c(N2Cc3cnc4[nH]nc(CC#N)c4c3N(C)C2=O)c1F]

To a mixture of (9,9-dimethyl-9H-xanthene-4,5-diyl)bis(diphenylphosphine) (3.3 mg, 0.0057 mmol), tris(dibenzylideneacetone)dipalladium(O) (2.6 mg, 0.0029 mmol), 9-bromo-3-(2,6-difluoro-3,5-dimethoxyphenyl)-1-methyl-1,3,4,7-tetrahydro-2H-pyrazolo[4',3':5,6]pyrido[4,3-d]pyrimidin-2-one (13.0 mg, 0.0286 mmol) in N,N-dimethylformamide (1.0 mL, 13 mmol) under an atmosphere of nitrogen was added (trimethylsilyl)acetonitrile (12 µL, 0.086 mmol), followed by zinc difluoride (5.9 mg, 0.057 mmol). The reaction mixture was stirred at 140° C. for 4.5 h under microwave conditions. The mixture was diluted with MeOH and purified by RP-HPLC (pH 2) to afford the product. LC-MS calculated for $C_{19}H_{17}O_3N_6F_2[M+H]^+$ m/z: 415.1; found 415.1. $^1$H NMR (400 MHz, DMSO) δ 13.82 (s, 1H), 8.26 (s, 1H), 7.04 (t, J=8.1 Hz, 1H), 4.80 (s, 2H), 4.59 (s, 2H), 3.88 (s, 6H), 3.52 (s, 3H).

Example 55

3-(2,6-Difluoro-3,5-dimethoxyphenyl)-1-methyl-9-(1-methylpiperidin-4-yl)-1,3,4,7-tetrahydro-2H-pyrazolo[4',3':5,6]pyrido[4,3-d]pyrimidin-2-one

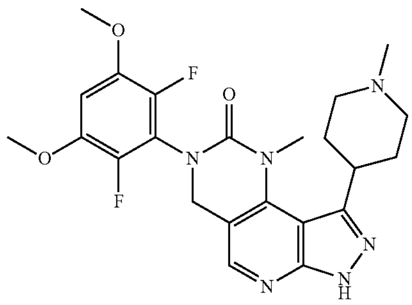 [SMILES: COc1cc(OC)c(F)c(N2Cc3cnc4[nH]nc(C5CCN(C)CC5)c4c3N(C)C2=O)c1F]

This compound was prepared from 9-bromo-3-(2,6-difluoro-3,5-dimethoxyphenyl)-1-methyl-1,3,4,7-tetrahydro-2H-pyrazolo[4',3':5,6]pyrido[4,3-d]pyrimidin-2-one and 1-methyl-4-(4,4,5,5-tetramethyl-1,3,2-dioxaborolan-2-yl)-1,2,3,6-tetrahydro-pyridine using procedures analogous to those for Examples 39, step 7-8. The residue was purified by RP-HPLC (pH 2) to afford the product as a white solid. LC-MS calculated for $C_{23}H_{27}F_2N_6O_3[M+H]^+$ m/z: 473.2; found 473.2.

Example 56

3-(2,6-Difluoro-3,5-dimethoxyphenyl)-9-(2-hydroxyethyl)-1-methyl-1,3,4,7-tetrahydro-2H-pyrazolo[4',3':5,6]pyrido[4,3-d]pyrimidin-2-one

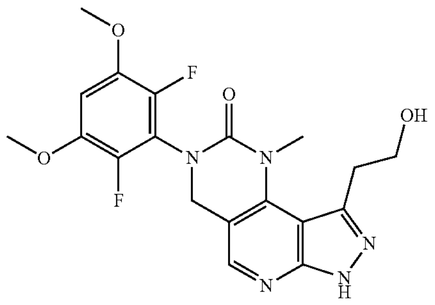 [SMILES: COc1cc(OC)c(F)c(N2Cc3cnc4[nH]nc(CCO)c4c3N(C)C2=O)c1F]

A mixture of 4,4,5,5-tetramethyl-2-vinyl-1,3,2-dioxaborolane (13.6 mg, 0.0881 mmol) 9-bromo-3-(2,6-difluoro-3,5-dimethoxyphenyl)-1-methyl-1,3,4,7-tetrahydro-2H-pyrazolo[4',3':5,6]pyrido[4,3-d]pyrimidin-2-one (20.0 mg, 0.0440 mmol), [1,1'-bis(diphenylphosphino)ferrocene]dichloropalladium(II) complexed with dichloromethane (1:1) (5.4 mg, 0.0066 mmol) and potassium carbonate (18.0 mg, 0.13 mmol) in 1,4-dioxane (0.80 mL, 10. mmol)/water (0.20 mL, 11 mmol) was heated at 88° C. After 1.5 h, the reaction was quenched with water, extracted with DCM, dried over $Na_2SO_4$ and concentrated under reduced pressure. The crude mixture was purified via flash column chromatography (MeOH/DCM, 3%-30%) to afford 3-(2,6-difluoro-3,5-dimethoxyphenyl)-1-methyl-9-vinyl-1,3,4,7-tetrahydro-2H-pyrazolo[4',3':5,6]pyrido[4,3-d]pyrimidin-2-one.

To a solution of 3-(2,6-difluoro-3,5-dimethoxyphenyl)-1-methyl-9-vinyl-1,3,4,7-tetrahydro-2H-pyrazolo[4',3':5,6]pyrido[4,3-d]pyrimidin-2-one (17.0 mg, 0.036 mmol) in THF (1.0 mL) was added $BH_3$-THF (0.40 mmol). The resulting mixture was stirred at room temperature for 12 h before it was quenched with NaOH (2 N, 0.2 mL) and $H_2O_2$ (0.2 mL). The mixture was diluted with MeOH and purified by RP-HPLC (pH 2) to afford the product as a white solid. LC-MS calculated for $C_{19}H_{20}F_2N_5O_4[M+H]^+$ m/z: 420.1; found 420.1.

Example 57

3-(2,6-Difluoro-3,5-dimethoxyphenyl)-1-ethyl-1,3,4,7-tetrahydro-2H-pyrazolo[4',3':5,6]pyrido[4,3-d]pyrimidin-2-one

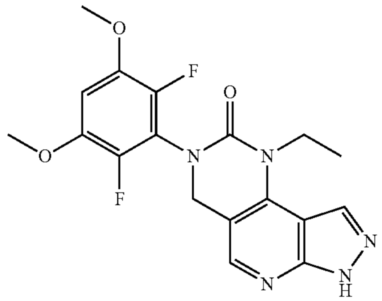 [SMILES: CCN1C(=O)N(c2c(F)c(OC)cc(OC)c2F)Cc2cnc3[nH]ncc3c21]

This compound was prepared using procedures analogous to those for Example 51. The residue was purified by RP-HPLC (pH 2) to afford the product as a white solid. LC-MS calculated for $C_{18}H_{18}O_3N_5F_2[M+H]^+$ m/z: 390.1; found 390.1. $^1$H NMR (300 MHz, DMSO) δ 13.71 (s, 1H), 8.29 (s, 1H), 8.23 (s, 1H), 7.06 (t, J=8.2 Hz, 1H), 4.83 (s, 2H), 4.19 (q, J=6.8 Hz, 2H), 3.89 (s, 6H), 1.32 (t, J=6.8 Hz, 3H).

Example 58

3-(2,6-Difluoro-3,5-dimethoxyphenyl)-1-(2-hydroxyethyl)-1,3,4,7-tetrahydro-2H-pyrazolo[4',3':5,6]pyrido[4,3-d]pyrimidin-2-one

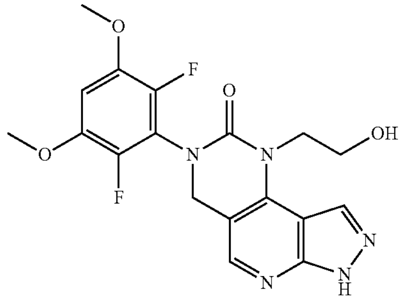 [SMILES: COc1cc(OC)c(F)c(N2Cc3cnc4[nH]ncc4c3N(CCO)C2=O)c1F]

This compound was prepared using procedures analogous to those for Example 44. The residue was purified by RP-HPLC (pH 2) to afford the product as a white solid. LC-MS calculated for $C_{18}H_{18}O_4N_5F_2[M+H]^+$ m/z: 406.1; found 406.1.

Example 59

3'-(2,6-Difluoro-3,5-dimethoxyphenyl)-1'-methyl-4',7'-dihydrospiro [cyclopropane-1,9'-pyrrolo[3',2':5,6] pyrido[4,3-d]pyrimidine]-2',8'(1'H,3'H)-dione

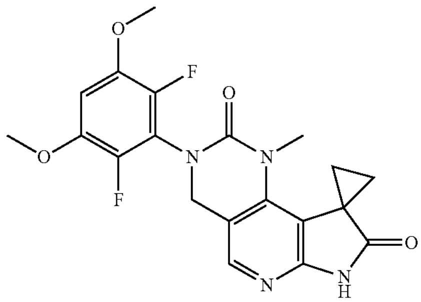 [SMILES: COc1cc(OC)c(F)c(N2Cc3cnc4c(c3N(C)C2=O)C2(CC2)C(=O)N4)c1F]

Step 1. 3-(2,6-Difluoro-3,5-dimethoxyphenyl)-1-methyl-7-{[2-(trimethylsilyl)ethoxy]methyl}-1,3,4,7-tetrahydro-2H-pyrrolo[3',2':5,6]pyrido[4,3-d]pyrimidin-2-one

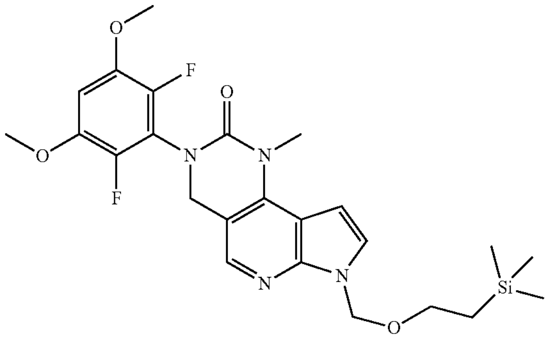

To a solution of 3-(2,6-difluoro-3,5-dimethoxyphenyl)-1-methyl-1,3,4,7-tetrahydro-2H-pyrrolo[3',2':5,6]pyrido[4,3-d]pyrimidin-2-one (0.10 g, 0.27 mmol) in DMF (0.8 mL) was added sodium hydride (60 wt % dispersion in mineral oil, 0.013 g, 0.32 mmol) at 0° C. and stirred for 20 minutes. Then (trimethylsilyl)ethoxymethyl chloride (0.057 mL, 0.32 mmol) was added and the reaction mixture was stirred for 1 h at 0° C. The mixture was diluted with ethyl acetate and then washed with water, brine, dried over $Na_2SO_4$ and concentrated. The product was isolated by chromatography eluted with 0 to 40% $EtOAc/CH_2Cl_2$. LC-MS calculated for $C_{24}H_{31}F_2N_4O_4Si$ $(M+H)^+$ m/z: 505.2; found 505.2.

Step 2. 3-(2,6-Difluoro-3,5-dimethoxyphenyl)-1-methyl-7-{[2-(trimethylsilyl)ethoxy]methyl}-3,4,7,9-tetrahydro-1H-pyrrolo[3',2':5,6]pyrido[4,3-d]pyrimidine-2,8-dione

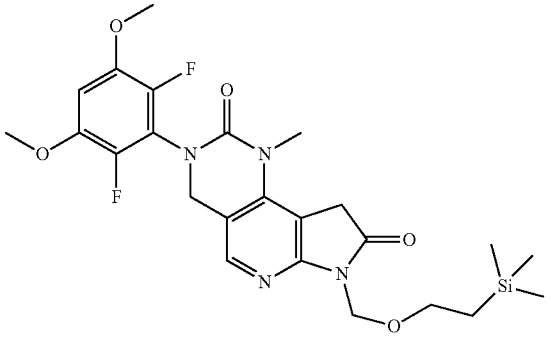

Pyridinium tribromide (0.299 g, 0.841 mmol) was added to a mixture of 3-(2,6-difluoro-3,5-dimethoxyphenyl)-1-methyl-7-{[2-(trimethylsilyl)ethoxy]methyl}-1,3,4,7-tetrahydro-2H-pyrrolo[3',2':5,6]pyrido[4,3-d]pyrimidin-2-one (0.12 g, 0.24 mmol) in isopropyl alcohol (2 mL)/water (0.12 mL), and then the reaction mixture was stirred at 50° C. for 2 h. The mixture was cooled to room temperature and then acetic acid (0.9 mL) and zinc (0.157 g, 2.40 mmol) were added. The mixture was stirred for 6 h then filtered and the solvent was removed. The residue was diluted with methylene chloride, and then washed with saturated $NaHCO_3$, water, and brine. The organic layer was dried over $Na_2SO_4$ then filtered and concentrated. The residue was purified by chromatography eluted with 0 to 50% EtOAc/$CH_2Cl_2$. LC-MS calculated for $C_{24}H_{31}F_2N_4O_5Si$ $(M+H)^+$ m/z: 521.2; found: 521.1.

Step 3. 3'-(2,6-Difluoro-3,5-dimethoxyphenyl)-1'-methyl-4',7'-dihydrospiro[cyclopropane-1,9'-pyrrolo[3',2':5,6]pyrido[4,3-d]pyrimidine]-2',8'(1'H,3'H)-dione Nitrogen was bubbled through a solution of 3-(2,6-difluoro-3,5-dimethoxyphenyl)-1-methyl-7-{[2-(trimethylsilyl)ethoxy]methyl}-3,4,7,9-tetrahydro-1H-pyrrolo[3',2':5,6]pyrido[4,3-d]pyrimidine-2,8-dione (100.0 mg, 0.192 mmol) in DMF (2.0 mL) for 20 minutes then cesium carbonate (190 mg, 0.58 mmol) and 1-bromo-2-chloroethane (48 μL, 0.58 mmol) were added under nitrogen. After stirred at room temperature overnight, the mixture was filtered and then the solvent was removed under reduced pressure. The residue was dissolved in $CH_2Cl_2$ (0.5 mL) and then TFA (0.8 mL) was added and the reaction mixture was stirred for 1 h. The solvent was removed and the residue was dissolved in methanol (2 mL) and then ethylenediamine (0.15 mL) was added and the mixture was stirred at room temperature for 2 h. The product was purified by prep-HPLC (pH 2). LC-MS calculated for $C_{20}H_{19}F_2N_4O_4(M+H)^+$ m/z: 417.1; found: 417.1. $^1H$ NMR (500 MHz, DMSO) δ 11.31 (s, 1H), 7.90 (s, 1H), 7.01 (t, J=8.1 Hz, 1H), 4.59 (s, 2H), 3.87 (s, 6H), 3.14 (s, 3H), 1.92-1.87 (m, 2H), 1.49-1.43 (m, 2H).

Example 60

7-(2,6-difluoro-3,5-dimethoxyphenyl)-3,6,7,9-tetrahydro-8H-pyrrolo[2,3-c]-2,7-naphthyridin-8-one

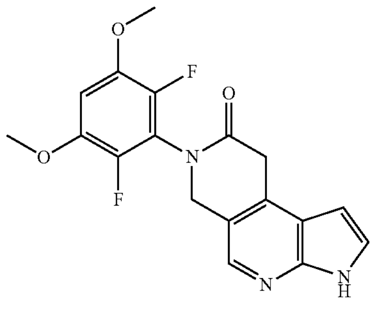 [SMILES: COc1cc(OC)c(F)c(N2Cc3cnc4[nH]ccc4c3CC2=O)c1F]

Step 1. N-[(4-Chloro-1-{[2-(trimethylsilyl)ethoxy]methyl}-1H-pyrrolo[2,3-b]pyridin-5-yl)methyl]-2,6-difluoro-3,5-dimethoxyaniline

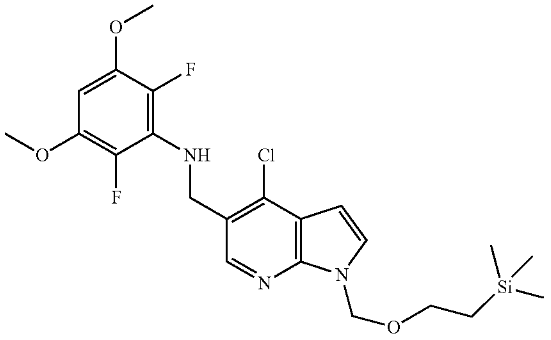

To a solution of N-[(4-chloro-1H-pyrrolo[2,3-b]pyridin-5-yl)methyl]-2,6-difluoro-3,5-dimethoxyaniline (0.35 g, 0.99 mmol) in DMF (3.0 mL) was added sodium hydride (60 wt % dispersion in mineral oil, 48 mg, 1.19 mmol) at 0° C. The mixture was stirred for 20 minutes then trimethylsilylethoxymethyl chloride (0.210 mL, 1.19 mmol) was added and the reaction mixture was stirred for 1 h at 0° C. The mixture was diluted with ethyl acetate and then washed with water and brine. The organic layer was dried over $Na_2SO_4$ and concentrated. The residue was isolated by chromatography eluted with 0 to 10% EtOAc/$CH_2Cl_2$. LC-MS calculated for $C_{22}H_{29}ClF_2N_3O_3Si$ $(M+H)^+$ m/z: 484.2; found: 484.2.

Step 2. 7-(2,6-Difluoro-3,5-dimethoxyphenyl)-3-{[2-(trimethylsilyl)ethoxy]methyl}-3,6,7,9-tetrahydro-8H-pyrrolo[2,3-c]-2,7-naphthyridin-8-one

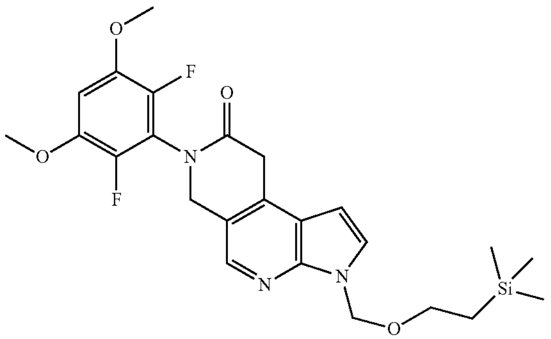

Preparation of potassium ethyl malonate: A 100 mL two-necked round-bottom flask was charged with diethyl malonate (22.0 mmol), water (20.5 mmol) and ethanol (20 mL), and then the reaction mixture was stirred at 40° C. A solution of potassium tert-butoxide (2.24 g, 20.0 mmol) in ethanol (20 mL) was added dropwise over 30 minutes. After completion of addition, the reaction mixture was stirred at 40° C. until consumption of the starting material. The reaction mixture was concentrated then diethyl ether (20 mL) was added. The resulting solid was collected by filtration, washed sequentially with 1:1 mixture of diethyl ether and ethanol, then diethyl ether. The solid was dried to give the potassium salt.

A mixture of N-[(4-chloro-1-{[2-(trimethylsilyl)ethoxy]methyl}-1H-pyrrolo[2,3-b]pyridin-5-yl)methyl]-2,6-difluoro-3,5-dimethoxyaniline (200.0 mg, 0.4132 mmol), potassium ethyl malonate (140 mg, 0.83 mmol), dicyclohexyl(2',6'-diisopropoxybiphenyl-2-yl)phosphine (5.8 mg, 0.012 mmol) and 7r-allylpalladium chloride dimer (14 mg, 0.037 mmol) in mesitylene (2.0 mL) was evacuated and refilled with nitrogen for 3 times. The reaction mixture was stirred at 160° C. overnight. The mixture was cooled to room temperature and filtered then washed with ethyl acetate. The filtrate was concentrated. The residue was purified by chromatography eluted with 0 to 40% $EtOAc/CH_2Cl_2$. LC-MS calculated for $C_{24}H_{30}F_2N_3O_4Si$ $(M+H)^+$ m/z: 490.2; found: 490.2.

Step 3. 7-(2,6-Difluoro-3,5-dimethoxyphenyl)-3,6,7,9-tetrahydro-8H-pyrrolo[2,3-c]-2,7-naphthyridin-8-one Trifluoroacetic acid (1.0 mL) was added to a solution of 7-(2,6-difluoro-3,5-dimethoxyphenyl)-3-{[2-(trimethylsilyl)ethoxy]methyl}-3,6,7,9-tetrahydro-8H-pyrrolo[2,3-c]-2,7-naphthyridin-8-one (60.0 mg, 0.122 mmol) in methylene chloride (1.0 mL). The mixture was stirred at room temperature for 2 h then concentrated. The residue was dissolved in methanol (1.0 mL) then ethylenediamine (0.2 mL) was added. The mixture was stirred at room temperature for overnight. The product was purified by prep-HPLC (pH 2). LC-MS calculated for $C_{18}H_{16}F_2N_3O_3(M+H)^+$ m/z: 360.1; found: 360.2. $^1H$ NMR (500 MHz, DMSO) δ 11.77 (s, 1H), 8.17 (s, 1H), 7.53-7.48 (m, 1H), 7.05 (t, J=8.2 Hz, 1H), 6.64-6.60 (m, 1H), 4.90 (s, 2H), 4.06 (s, 2H), 3.89 (s, 6H).

Example 61

7-(2,6-difluoro-3,5-dimethoxyphenyl)-9-methyl-3,6,7,9-tetrahydro-8H-imidazo [4',5':5,6]pyrido[4,3-d]pyrimidin-8-one

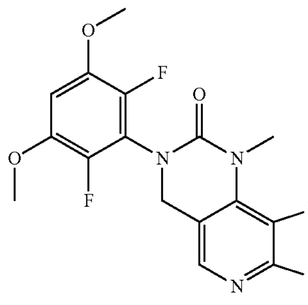

Step 1: 6-bromo-7-chloro-3-{[2-(trimethylsilyl)ethoxy]methyl}-3Himidazo[4,5-b]pyridine

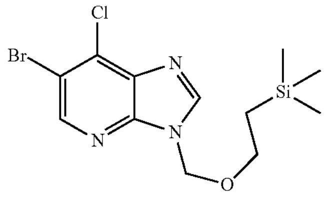 [SMILES: C[Si](C)(C)CCOCn1cnc2c(Cl)c(Br)cnc21]

To a solution of 6-bromo-7-chloro-3H-imidazo[4,5-b]pyridine (560 mg, 2.4 mmol, PharmaBlock Inc., Cat #PB02862) in N,N-dimethylformamide (10 mL) was added sodium hydride (60% NaH dispersion in mineral oil, 125 mg, 3.13 mmol) portion-wise at 0° C. The resulting mixture was stirred at 0° C. for 30 minutes. Then [β-(Trimethylsilyl)ethoxy]methylchloride (0.51 mL, 2.89 mmol) was added and the reaction mixture was stirred for 2 h at 0° C. The reaction was quenched with saturated $NH_4Cl$ aqueous solution then extracted with ethyl acetate. The organic layer was washed with water, brine then dried over $Na_2SO_4$ and concentrated. The residue was purified by chromatography on a silica gel column eluted with 0 to 10% EtOAc/DCM to afford the desired product (615 mg, 70%) as a yellow oil. LC-MS calculated for $Cl_2H_{18}BrClN_3OSi$ $[M+H]^+$ m/z: 362.0; found: 362.0.

Step 2: 7-chloro-3-{[2-(trimethylsilyl)ethoxy]methyl}-6-vinyl-3H-imidazo[4,5-b]pyridine

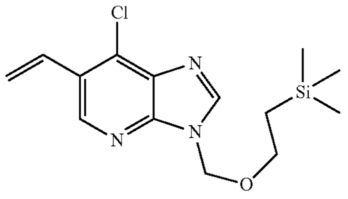 [SMILES: C=Cc1cnc2c(ncn2COCC[Si](C)(C)C)c1Cl]

A solution of 6-bromo-7-chloro-3-{[2-(trimethylsilyl)ethoxy]methyl}-3H-imidazo[4,5-b]pyridine (615 mg, 1.70 mmol), 4-methyl-2,6-dioxo-8-vinyltetrahydro[1,3,2]oxazaborolo[2,3-b][1,3,2]oxazaborol-4-ium-8-uide (326 mg, 1.78 mmol), potassium carbonate (470 mg, 3.4 mmol) and bis(di-tert-butyl(4-dimethylaminophenyl)phosphine)dichloropalladium (II) (Aldrich, Cat #678740; 36 mg, 0.05 mmol) in 1,4-dioxane (9 mL, 100 mmol) and water (1 mL, 60 mmol) was evacuated then filled with nitrogen for three times. The resulting mixture was heated to 95° C. and stirred for 5 h, at which time LC-MS indicated the reaction was complete. The mixture was cooled to room temperature, diluted with EtOAc then washed with water and brine. The organic layer was dried over $Na_2SO_4$ and concentrated. The residue was purified by chromatography on a silica gel column eluted with 0 to 10% EtOAc/DCM to afford the desired product (454 mg, 86%) as a yellow oil. LC-MS calculated for $C_{14}H_{21}ClN_3OSi$ $[M+H]^+$ m/z: 310.1; found: 310.0.

Step 3: 7-chloro-3-{[2-(trimethylsilyl)ethoxy]methyl}-3H-imidazo[4,5-b]pyridine-6-carbaldehyde

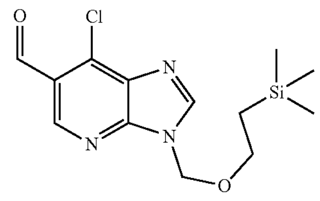 [SMILES: C[Si](C)(C)CCOCn1cnc2c(Cl)c(C=O)cnc21]

To a solution of 7-chloro-3-{[2-(trimethylsilyl)ethoxy]methyl}-6-vinyl-3H-imidazo[4,5-b]pyridine (454 mg, 1.46 mmol) in tert-butyl alcohol (10 mL, 100 mmol) and water (2 mL, 100 mmol) was added N-methylmorpholine N-oxide (257 mg, 2.20 mmol), followed by Osmium tetraoxide (4 wt % in water, 0.46 mL, 0.073 mmol). The reaction mixture was stirred at room temperature for overnight. The mixture was then diluted with water and extracted with EtOAc. The organic layer was washed with brine then dried over $Na_2SO_4$ and concentrated. The residue was dissolved in tetrahydrofuran (11 mL, 140 mmol) and water (5.5 mL, 3.0E2 mmol) then cooled to 0° C. To the solution was added sodium periodate (940 mg, 4.4 mmol) and acetic acid (21 μL, 0.37 mmol). After stirred at 0° C. for 2 h, the reaction mixture was diluted with water then extracted with EtOAc. The organic layer was washed with brine then dried over $Na_2SO_4$ and concentrated. The residue was purified by chromatography on a silica gel column eluted with 0 to 20% EtOAc/DCM to afford the desired product (290 mg, 63%) as a white solid. LC-MS calculated for $C_{13}H_{19}ClN_3O_2Si$ $[M+H]^+$ m/z: 312.1; found: 312.0.

Step 4: 7-(methylamino)-3H-imidazo[4,5-b]pyridine-6-carbaldehyde

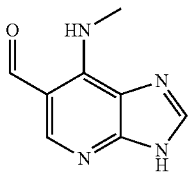

To a solution of 7-chloro-3-{[2-(trimethylsilyl)ethoxy]methyl}-3H-imidazo[4,5-b]pyridine-6-carbaldehyde (225 mg, 0.722 mmol) in 2-methoxyethanol (2 mL) was added methylamine (33 wt % in EtOH, 2 mL, 16 mmol). The mixture was stirred at 110° C. in a sealed tube overnight. The mixture was concentrated and the residue was dissolved in 10 mL 0.5 N HCl and stirred at room temperature for 1 h. The mixture was neutralized with saturated $NaHCO_3$ aqueous solution. The resulting white precipitate was collected via filtration then dried. The above solid was dissolved in 3 mL DCM and 3 mL TFA was added. The resulting clear solution was stirred at room temperature for 1 h. The reaction mixture was concentrated then dried in vacuo. The crude product was used in the next step without further purification. LC-MS calculated for $C_8H_9N_4O$ $[M+H]^+$ m/z: 177.1; found: 177.1.

Step 5: 6-{[(2,6-difluoro-3,5-dimethoxyphenyl)amino]methyl}-N-methyl-3H-imidazo[4,5-b]pyridin-7-amine

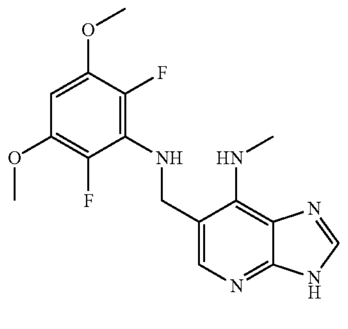 [SMILES: CNc1c(CNc2c(F)c(OC)cc(OC)c2F)cnc2[nH]cnc12]

A mixture of 7-(methylamino)-3H-imidazo[4,5-b]pyridine-6-carbaldehyde (100 mg, 0.6 mmol), 2,6-difluoro-3,5-dimethoxyaniline (160 mg, 0.85 mmol) and D-(+)-10-camphorsulfonic acid (40 mg, 0.2 mmol) in toluene (20 mL, 200 mmol) was heated to reflux with azotropic removal of water with a Dean-Stark trap. The mixture was refluxed for 24 h then cooled to room temperature and concentrated. The residue was dissolved in tetrahydrofuran (15 mL, 180 mmol) and cooled to 0° C. then lithium tetrahydroaluminate (75 mg, 2.0 mmol) was added portion-wise. The reaction mixture was warmed to 45° C. and stirred for 1 h. The reaction was quenched by addition of 0.1 mL of water then 0.1 mL of 15% NaOH solution followed by 0.3 mL of water. The mixture was stirred for 10 min then filtered. The filtrate was concentrated and the residue was purified by column eluted with 0 to 10% MeOH/DCM to afford the desired product (155 mg, 80%) as a yellow solid. LC-MS calculated for $C_{16}H_{18}F_2N_5O_2[M+H]^+$ m/z: 350.1; found: 350.0.

Step 6: 7-(2,6-difluoro-3,5-dimethoxyphenyl)-9-methyl-3,6,7,9-tetrahydro-8H-imidazo[4',5':5,6]pyrido[4,3-d]pyrimidin-8-one To the solution of 6-{[(2,6-difluoro-3,5-dimethoxyphenyl)amino]methyl}-Nmethyl-3H-imidazo[4,5-b]pyridin-7-amine (155 mg, 0.44 mmol) in tetrahydrofuran (5 mL, 60 mmol) was added triethylamine (0.31 mL, 2.2 mmol), followed by triphosgene (140 mg, 0.49 mmol). The resulting yellow suspension was stirred at room temperature for 1 h then 5 mL of 1N NaOH aqueous solution was added. After stirred at room temperature for 30 min, the mixture was diluted with EtOAc. The organic layer was washed with water, brine then dried over $Na_2SO_4$ and concentrated. The residue was dissolved in MeOH and purified by prep HPLC (pH 2, ACN/water) to give the desired product as a white solid. LC-MS calculated for $C_{17}H_{16}F_2N_5O_3$ $[M+H]^+$ m/z: 376.1; found: 376.1. $^1H$ NMR (500 MHz, DMSO) δ 8.41 (s, 1H), 8.10 (s, 1H), 7.05 (t, J=8.2 Hz, 1H), 4.83 (s, 2H), 3.89 (s, 6H), 3.85 (s, 3H).

Example 62

3-(2,6-difluoro-3,5-dimethoxyphenyl)-4,7-dihydropyrazolo[4',3':5,6]pyrido [3,4-e][1,3]oxazin-2(3H)-one

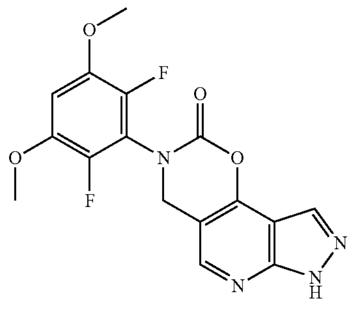 [SMILES: COc1cc(OC)c(F)c(N2Cc3cnc4[nH]ncc4c3OC2=O)c1F]

Step 1: 4-chloro-5-(chloromethyl)-1-(4-methoxybenzyl)-1H-pyrazolo[3,4-b]pyridine

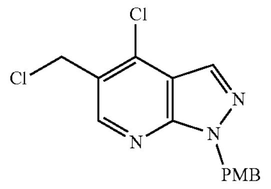

To a stirred solution of [4-chloro-1-(4-methoxybenzyl)-1H-pyrazolo[3,4-b]pyridin-5-yl]methanol (2.70 g, 8.9 mmol) (Lakestar Tech: Lot #123-017-22) in methylene chloride (30 mL, 500 mmol) were added N,N-diisopropylethylamine (3.10 mL, 17.8 mmol) and methanesulfonyl chloride (820 μL, 11 mmol) sequentially at 0° C. After 15 minutes, the reaction mixture was warmed up to room temperature. After another 2 hours, the reaction was quenched with saturated aq. $NaHCO_3$, then extracted with methylene chloride. The combined organic layers were dried over $MgSO_4$, and then concentrated. The residue (2.50 g) was used directly in the next step without further purification. LC-MS calculated for $C_{15}H_{14}Cl_2N_3O$ $(M+H)^+$: m/z=322.1; Found: 322.1.

Step 2: N-{[4-chloro-1-(4-methoxybenzyl)-1H-pyrazolo[3,4-b]pyridin-5-yl]methyl}-2,6-difluoro-3,5-dimethoxyaniline

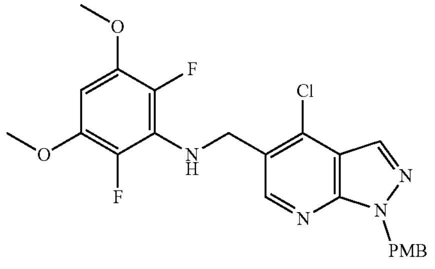

A stirred slurry of 2,6-difluoro-3,5-dimethoxyaniline (0.88 g, 4.6 mmol) and 4-chloro-5-(chloromethyl)-1-(4-methoxybenzyl)-1H-pyrazolo[3,4-b]pyridine (1.00 g, 3.10 mmol) in N,N-diisopropylethylamine (15 mL) was heated to 90° C. After 8 hours, the volatiles were removed under reduced pressure and the residue was purified on flash column (eluting with 0-45% EtOAc in hexanes) to afford the desired product as a white solid (1.02 g, 71%). LC-MS calculated for $C_{23}H_{22}ClF_2N_4O_3$ $(M+H)^+$: m/z=475.1; Found: 475.1.

Step 3: N-{[4-(allyloxy)-1-(4-methoxybenzyl)-1H-pyrazolo[3,4-b]pyridin-5-yl]methyl}-2,6-difluoro-3,5-dimethoxyaniline

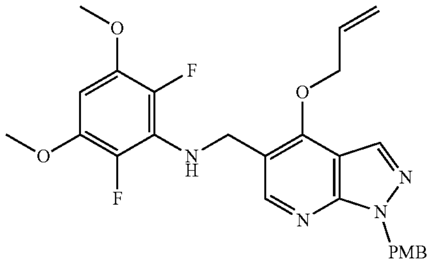

To a stirred solution of 2-propen-1-ol (43 μL, 0.63 mmol) in N,N-dimethylformamide (9 mL, 100 mmol) was added sodium hydride (60 wt % in mineral oil, 34 mg, 0.84 mmol) at 0° C. After 15 minutes, N-{[4-chloro-1-(4-methoxybenzyl)-1H-pyrazolo[3,4-b]pyridin-5-yl]methyl}-2,6-difluoro-3,5-dimethoxyaniline (200 mg, 0.4 mmol) was added and the resulted mixture was heated to 100° C. After stirred at 100° C. for 30 minutes, the reaction mixture was cooled to room temperature and quenched with saturated aq. $NH_4Cl$, then extracted with methylene chloride. The combined organic layers were dried over $MgSO_4$, and then concentrated. The residue (0.2 g, 96%) was used directly in the next step without further purification. LC-MS calculated for $C_{26}H_{27}F_2N_4O_4(M+H)^+$: m/z=497.2; Found: 497.1.

Step 4: {[4-(allyloxy)-1-(4-methoxybenzyl)-1H-pyrazolo[3,4-b]pyridin-5-yl]methyl}(2,6-difluoro-3,5-dimethoxyphenyl)carbamic chloride

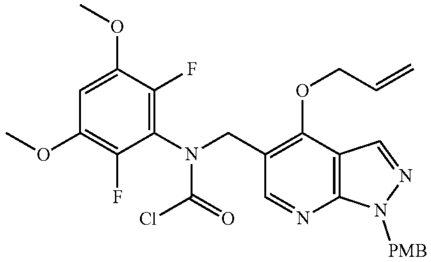

To a stirred solution of N-{[4-(allyloxy)-1-(4-methoxybenzyl)-1H-pyrazolo[3,4-b]pyridin-5-yl]methyl}-2,6-difluoro-3,5-dimethoxyaniline (150 mg, 0.30 mmol) in THF (6 mL) were added triethylamine (84.2 μL, 0.604 mmol) and triphosgene (134 mg, 0.453 mmol) sequentially at room temperature. After 3 hours, the reaction mixture was quenched with saturated aq. $NH_4Cl$, then extracted with methylene chloride. The combined organic layers were dried over $MgSO_4$, and then concentrated. The residue (0.16 g, 95%) was used directly in the next step without further purification. LC-MS calculated for $C_{27}H_{25}ClF_2N_4O_5$ $(M+H)^+$: m/z=559.2; Found: 559.2.

Step 5: 3-(2,6-difluoro-3,5-dimethoxyphenyl)-4,7-dihydropyrazolo[4',3':5,6]pyrido[3,4-e][1,3]oxazin-2(3H)-one To a stirred solution of crude {[4-(allyloxy)-1-(4-methoxybenzyl)-1H-pyrazolo[3,4-b]pyridin-5-yl]methyl}

(2,6-difluoro-3,5-dimethoxyphenyl)carbamic chloride (0.16 g, 0.287 mmol) in THF (0.5 mL)/1-propanol (3 mL, 40 mmol) was added rhodium chloride trihydrate (7.95 mg, 0.0302 mmol). The mixture was then warmed up to 90° C. After 2 hours, the reaction was quenched with saturated aq. $NH_4Cl$, then extracted with methylene chloride. The combined organic layers were dried over $MgSO_4$, and then concentrated. The residue was dissolved in trifluoroacetic acid (2 mL, 20 mmol) and was heated to 75° C. for 1 hour. The volatiles were then removed under reduced pressure and the residue was purified on RP-HPLC (XBridge C18 column, eluting with a gradient of acetonitrile/water containing 0.05% TFA, at flow rate of 60 mL/min) to give the desired product (50 mg, 46%) as its TFA salt. LC-MS calculated for $C_{16}H_{13}F_2N_4O_4(M+H)^+$: m/z=363.1; Found: 363.1; $^1H$ NMR (500 MHz, DMSO-$d_6$): δ 8.41 (s, 1H), 8.26 (s, 1H), 7.14 (t, J=10.0 Hz, 1H), 4.99 (s, 2H), 3.92 (s, 6H) ppm.

Example 63

3-(2-chloro-6-fluoro-3,5-dimethoxyphenyl)-1-ethyl-3,4,7,9-tetrahydro-1H-pyrrolo[3',2':5,6]pyrido[4,3-d]pyrimidine-2,8-dione

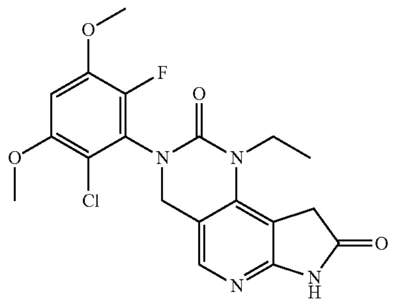 [SMILES: CCN1C(=O)N(c2c(F)c(OC)cc(OC)c2Cl)Cc2cnc3c(c21)CC(=O)N3]

Step 1: N-(2-fluoro-3,5-dimethoxyphenyl)acetamide

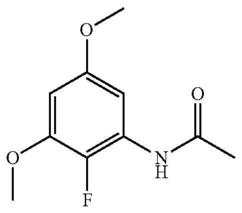

To a solution of N-(3,5-dimethoxyphenyl)acetamide (14.8 g, 75.8 mmol) in acetonitrile (200 mL) was added 1-(chloromethyl)-4-fluoro-1,4-diazoniabicyclo[2.2.2]octane ditetrafluoroborate (Alfa Aesar, cat #L17003: 29 g, 81 mmol). The resulting suspension was stirred at room temperature overnight then concentrated under reduced pressure. The residue was dissolved in ethyl acetate (AcOEt) then washed with saturated $NaHCO_3$ aqueous solution and brine. The organic layer was dried over $Na_2SO_4$ then filtered and concentrated. The residue was purified by chromatography eluted with 0 to 50% AcOEt in hexanes to give the desired product (7.8 g, 48%). LC-MS calculated for $C_{10}H_{13}FNO_3$ $(M+H)^+$ m/z: 214.1; found 214.0.

Step 2: N-(2-chloro-6-fluoro-3,5-dimethoxyphenyl)acetamide

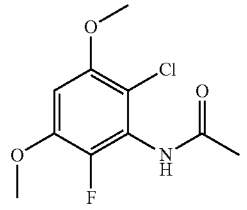 [SMILES: COc1cc(OC)c(Cl)c(NC(C)=O)c1F]

To a solution of N-(2-fluoro-3,5-dimethoxyphenyl)acetamide (3.50 g, 16.4 mmol) in acetonitrile (40 mL) was added sulfuryl chloride (1.3 mL, 16 mmol) dropwise at 0° C. The resulting yellow solution was warmed to room temperature and stirred for 30 min. Then the reaction was quenched by dropwise addition of saturated $NaHCO_3$ solution (25 mL). The precipitate was collected via filtration then washed with water, and dried to afford the desired product (3.0 g, 77%). LC-MS calculated for $C_{10}H_{12}ClFNO_3$ $(M+H)^+$ m/z: 248.0; found 248.0.

Step 3: 2-chloro-6-fluoro-3,5-dimethoxyaniline

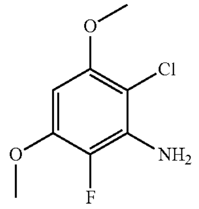

To a solution of N-(2-chloro-6-fluoro-3,5-dimethoxyphenyl)acetamide (3.0 g, 12 mmol) in ethanol (120 mL) was added 2.0 M potassium hydroxide in water (60 mL). The resulting solution was refluxed overnight then cooled to room temperature and concentrated to remove ethanol. The precipitate was collected via filtration then washed with water and hexanes, then dried to give the product (1.44 g, 58%). LC-MS calculated for $C_8H_{10}ClFNO_2$ $(M+H)^+$ m/z: 206.0; found 206.1.

Step 4: 5-{[(2-chloro-6-fluoro-3,5-dimethoxyphenyl)amino]methyl}-N-ethyl-1H-pyrrolo[2,3-b]pyridin-4-amine

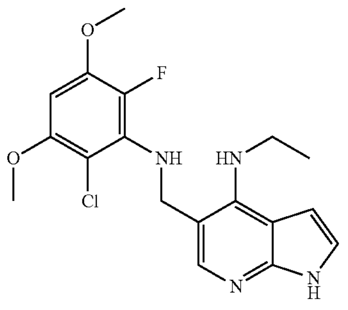 [SMILES: CCNc1c(CNc2c(F)c(OC)cc(OC)c2Cl)cnc2[nH]ccc12]

A mixture of 4-(ethylamino)-1H-pyrrolo[2,3-b]pyridine-5-carbaldehyde (Example 49, Step 1: 1.6 g, 8.3 mmol), 2-chloro-6-fluoro-3,5-dimethoxyaniline (1.7 g, 8.3 mmol) and [(1S)-7,7-dimethyl-2-oxobicyclo[2.2.1]hept-1-yl]methanesulfonic acid (Aldrich, cat #21360: 0.6 g, 2 mmol) in toluene (200 mL, 2000 mmol) was heated to reflux with azotropic removal of water using a Dean-Stark trap for 4 days. The reaction mixture was cooled to room temperature and concentrated. The residue was dissolved in tetrahydrofuran (40 mL) and then lithium tetrahydroaluminate (0.78 g, 21 mmol) was added dropwise. The mixture was stirred at 50° C. for 3 h then cooled to room temperature. The reaction was quenched by addition of water (0.8 mL), 15% aqueous NaOH (0.8 mL) then water (2.4 mL). The mixture was filtered and washed with THF. The filtrate was concentrated and the residue was purified by chromatography eluted with 0 to 5% MeOH in $CH_2Cl_2$ to give the desired product (1.1 g, 35%). LC-MS calculated for $C_{18}H_{21}$ $ClFN_4O_2(M+H)^+$ m/z: 379.1; found 379.1.

Step 5: 3-(2-chloro-6-fluoro-3,5-dimethoxyphenyl)-1-ethyl-1,3,4,7-tetrahydro-2H-pyrrolo [3',2':5,6] pyrido[4,3-d]pyrimidin-2-one

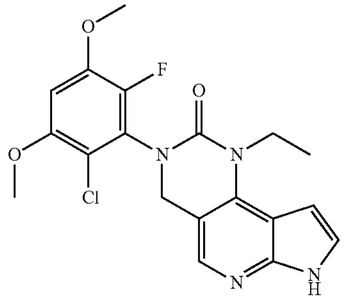 [SMILES: CCN1C(=O)N(c2c(F)c(OC)cc(OC)c2Cl)Cc2cnc3[nH]ccc3c21]

To a mixture of 5-{[(2-chloro-6-fluoro-3,5-dimethoxyphenyl)amino]methyl}-N-ethyl-1H-pyrrolo[2,3-b]pyridin-4-amine (1.55 g, 4.09 mmol) in tetrahydrofuran (30 mL) at 0° C. was added triethylamine (2.8 mL, 20 mmol), followed by a solution of triphosgene (1.8 g, 6.1 mmol) in tetrahydrofuran (8 mL). The resulting mixture was stirred at room temperature for 3 h then cooled to 0° C. and then 1.0 M sodium hydroxide in water (30 mL) was added slowly. After stirring at room temperature overnight, the reaction mixture was then extracted with $CH_2Cl_2$. The organic layer was washed with brine then dried over $Na_2SO_4$ and concentrated. The residue was purified by chromatography eluted with 0 to 5% MeOH in $CH_2Cl_2$ to give the desired product (1.1 g, 66%). LC-MS calculated for $C_{19}H_{19}ClFN_4O_3(M+H)^+$ m/z: 405.1; found: 405.1.

Step 6: 3-(2-chloro-6-fluoro-3,5-dimethoxyphenyl)-1-ethyl-3,4,7,9-tetrahydro-1H-pyrrolo[3',2':5,6] pyrido[4,3-d]pyrimidine-2,8-dione To a mixture of 3-(2-chloro-6-fluoro-3,5-dimethoxyphenyl)-1-ethyl-1,3,4,7-tetrahydro-2H-pyrrolo[3',2':5,6]pyrido [4,3-d]pyrimidin-2-one (1.14 g, 2.82 mmol) in isopropyl alcohol (10 mL, 100 mmol) and water (0.8 mL, 40 mmol) was added pyridinium tribromide (3.5 g, 9.8 mmol). The resulting mixture was stirred at 30° C. overnight then cooled to room temperature and acetic acid (10 mL, 200 mmol) and zinc (1.84 g, 28.2 mmol) were added. After stirring at room temperature for 2 h, the mixture was filtered and the filtrate was concentrated. The residue was triturated with water and the precipitate was collected via filtration then washed with water. The solid was purified by chromatography eluted with 0 to 5% MeOH in $CH_2Cl_2$ to give the desired product. LC-MS calculated for $C_{19}H_{19}ClFN_4O_4(M+H)^+$ m/z: 421.1; found: 421.0. $^1$H NMR (500 MHz, DMSO) δ 11.02 (s, 1H), 7.83 (s, 1H), 7.01 (d, J=7.7 Hz, 1H), 4.56 (s, 2H), 3.94-3.85 (m, 10H), 1.19 (t, J=7.0 Hz, 3H).

Example 64

1-cyclobutyl-3-(2,6-difluoro-3,5-dimethoxyphenyl)-3,4,7,9-tetrahydro-1H-pyrrolo[3',2':5,6]pyrido[4,3-d] pyrimidine-2,8-dione

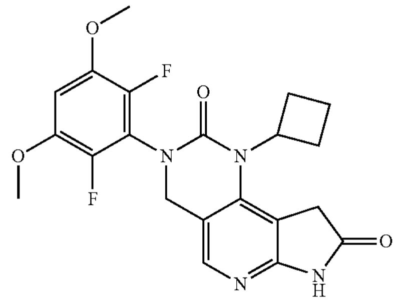 [SMILES: COc1cc(OC)c(F)c(N2Cc3cnc4c(c3N(C3CCC3)C2=O)CC(=O)N4)c1F]

Step 1: 1-cyclobutyl-3-(2,6-difluoro-3,5-dimethoxyphenyl)-1,3,4,7-tetrahydro-2H-pyrrolo[3',2':5,6] pyrido[4,3-d]pyrimidin-2-one

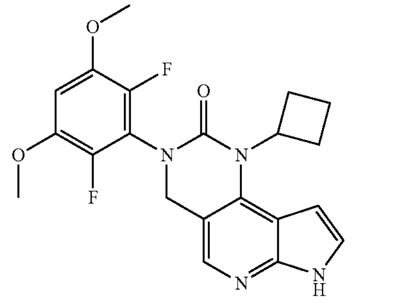 [SMILES: COc1cc(OC)c(F)c(N2Cc3cnc4[nH]ccc4c3N(C3CCC3)C2=O)c1F]

This compound was prepared using procedures analogous to those for Example 45 with cyclobutylamine replacing cyclopropylamine. LC-MS calculated for $C_{21}H_{21}F_2N_4O_3$ $(M+H)^+$ m/z: 415.2; found: 415.1.

Step 2: 1-cyclobutyl-3-(2,6-difluoro-3,5-dimethoxyphenyl)-3,4,7,9-tetrahydro-1H-pyrrolo[3',2':5,6] pyrido[4,3-d]pyrimidine-2,8-dione This compound was prepared using procedures analogous to those for Example 63, Step 6 with 1-cyclobutyl-3-(2,6-difluoro-3,5-dimethoxyphenyl)-1,3,4,7-tetrahydro-2H-pyrrolo[3',2':5,6]pyrido[4,3-d]pyrimidin-2-one replacing 3-(2-chloro-6-fluoro-3,5-dimethoxyphenyl)-1-ethyl-1,3,4,7-tetrahydro-2H-pyrrolo [3',2':5,6]pyrido[4,3-d]pyrimidin-2-one. LC-MS calculated for $C_{21}H_{21}F_2N_4O_4(M+H)^+$ m/z: 431.2; found: 431.1. $^1$H NMR (500 MHz, DMSO) δ 11.00

(s, 1H), 7.86 (s, 1H), 7.02 (t, J=8.2 Hz, 1H), 4.53 (s, 2H), 4.51-4.42 (m, 1H), 3.88 (s, 6H), 3.80 (s, 2H), 2.64-2.53 (m, 2H), 2.32-2.22 (m, 2H), 1.77-1.64 (m, 2H).

Example 65

3-(2,6-difluoro-3,5-dimethoxyphenyl)-1-(3-fluorobenzyl)-3,4,7,9-tetrahydro-1H-pyrrolo[3',2':5,6]pyrido[4,3-d]pyrimidine-2,8-dione

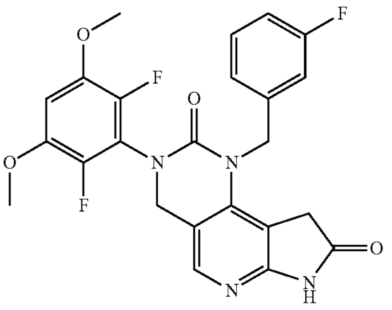 [SMILES: COc1cc(OC)c(F)c(N2Cc3cnc4c(c3N(Cc3cccc(F)c3)C2=O)CC(=O)N4)c1F]

Step 1: 3-(2,6-difluoro-3,5-dimethoxyphenyl)-1-(3-fluorobenzyl)-1,3,4,7-tetrahydro-2H-pyrrolo[3',2':5,6]pyrido[4,3-d]pyrimidin-2-one

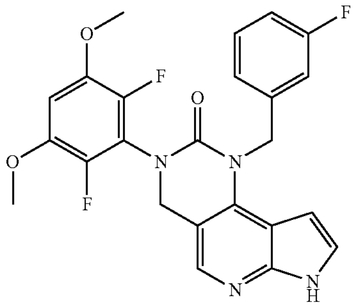 [SMILES: COc1cc(OC)c(F)c(N2Cc3cnc4[nH]ccc4c3N(Cc3cccc(F)c3)C2=O)c1F]

This compound was prepared using procedures analogous to those for Example 45 with 1-(3-fluorophenyl)methanamine replacing cyclopropylamine. LC-MS calculated for $C_{24}H_{20}F_3N_4O_3(M+H)^+$ m/z: 469.1; found: 469.1.

Step 2: 3-(2,6-difluoro-3,5-dimethoxyphenyl)-1-(3-fluorobenzyl)-3,4,7,9-tetrahydro-1H-pyrrolo[3',2':5,6]pyrido[4,3-d]pyrimidine-2,8-dione This compound was prepared using procedures analogous to those for Example 63, Step 6 with 3-(2,6-difluoro-3,5-dimethoxyphenyl)-1-(3-fluorobenzyl)-1,3,4,7-tetrahydro-2H-pyrrolo[3',2':5,6]pyrido[4,3-d]pyrimidin-2-one replacing 3-(2-chloro-6-fluoro-3,5-dimethoxyphenyl)-1-ethyl-1,3,4,7-tetrahydro-2H-pyrrolo [3',2':5,6]pyrido[4,3-d]pyrimidin-2-one. LC-MS calculated for $C_{24}H_{20}F_3N_4O_4(M+H)^+$ m/z: 485.1; found: 485.0. $^1H$ NMR (500 MHz, DMSO) δ 10.99 (s, 1H), 7.89 (s, 1H), 7.44-7.37 (m, 1H), 7.12-6.96 (m, 4H), 5.18 (s, 2H), 4.77 (s, 2H), 3.88 (s, 6H), 3.41 (s, 2H).

Example 66

7'-(2,6-difluoro-3,5-dimethoxyphenyl)-6',7'-dihydrospiro[cyclopropane-1,9'-pyrrolo[2,3-c][2,7]naphthyridin]-8'(3'H)-one

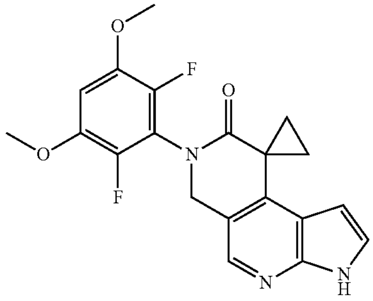 [SMILES: COc1cc(OC)c(F)c(N2Cc3cnc4[nH]ccc4c3C3(CC3)C2=O)c1F]

Nitrogen was bubbled through a solution of 7-(2,6-difluoro-3,5-dimethoxyphenyl)-3-{[2-(trimethylsilyl)ethoxy]methyl}-3,6,7,9-tetrahydro-8H-pyrrolo[2,3-c]-2,7-naphthyridin-8-one (40 mg, 0.082 mmol) in N,N-dimethylformamide (0.85 mL, 11 mmol) for 20 min and then cesium carbonate (80 mg, 0.24 mmol) and 1-bromo-2-chloro-ethane (20.3 μL, 0.245 mmol) were added under nitrogen. After stirred at room temperature overnight, the reaction mixture was filtered and then concentrated. The residue was dissolved in $CH_2Cl_2$ (1 mL) and then TFA (1 mL) was added. After stirred at room temperature for 1 h, the mixture was concentrated and the residue was dissolved in methanol (2 mL) and then ethylene diamine (0.15 mL) was added. The mixture was stirred at room temperature for 2 h. The product was purified by prep-HPLC (pH=2, acetonitrile/water) to give the desired product. LC-MS calculated for $C_{20}H_{18}F_2N_3O_3(M+H)^+$ m/z: 386.1; found: 386.1.

Example 67

7-(2,6-difluoro-3,5-dimethoxyphenyl)-9,9-dimethyl-3,6,7,9-tetrahydro-8H-pyrrolo[2,3-c]-2,7-naphthyridin-8-one

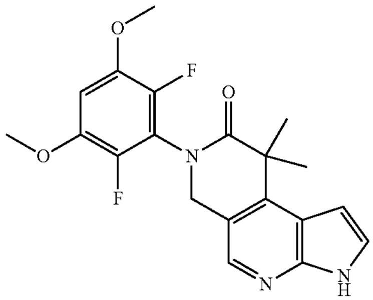 [SMILES: COc1cc(OC)c(F)c(N2Cc3cnc4[nH]ccc4c3C(C)(C)C2=O)c1F]

This compound prepared using procedures analogous to those for Example 66 with methyl iodide replacing 1-bromo-2-chloroethane. The product was purified by prep-HPLC (pH=2, acetonitrile/water) to give the desired product. LC-MS calculated for $C_{20}H_{20}F_2N_3O_3(M+H)^+$ m/z: 388.1; found: 388.0. $^1H$ NMR (500 MHz, DMSO) δ 11.82 (s, 1H), 8.12 (s, 1H), 7.56-7.46 (m, 1H), 7.07 (t, J=8.2 Hz, 1H), 6.73-6.70 (m, 1H), 4.90 (s, 2H), 3.90 (s, 6H), 1.72 (s, 6H).

Example 68

1-(4-chloro-2-fluorophenyl)-3-(2,6-difluoro-3,5-dimethoxyphenyl)-3,4,7,9-tetrahydro-1H-pyrrolo[3',2':5,6]pyrido[4,3-d]pyrimidine-2,8-dione

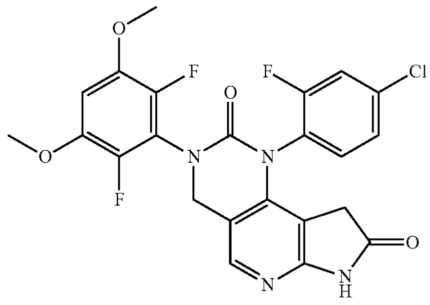 [SMILES: COc1cc(OC)c(F)c(N2Cc3cnc4c(c3N(c3ccc(Cl)cc3F)C2=O)CC(=O)N4)c1F]

Step 1: 1-(4-chloro-2-fluorophenyl)-3-(2,6-difluoro-3,5-dimethoxyphenyl)-1,3,4,7-tetrahydro-2H-pyrrolo[3',2':5,6]pyrido[4,3-d]pyrimidin-2-one

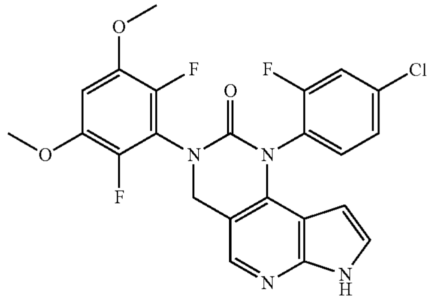 [SMILES: COc1cc(OC)c(F)c(N2Cc3cnc4[nH]ccc4c3N(c3ccc(Cl)cc3F)C2=O)c1F]

This compound was prepared using procedures analogous to those for Example 45 with 4-chloro-2-fluoroaniline replacing cyclopropylamine. LC-MS calculated for $C_{23}H_{17}ClF_3N_4O_3$ $[M+H]^+$ m/z: 489.1; found 489.0.

Step 2: 1-(4-chloro-2-fluorophenyl)-3-(2,6-difluoro-3,5-dimethoxyphenyl)-3,4,7,9-tetrahydro-1H-pyrrolo[3',2':5,6]pyrido[4,3-d]pyrimidine-2,8-dione This compound was prepared using procedures analogous to those for Example 63, Step 6 with 1-(4-chloro-2-fluorophenyl)-3-(2,6-difluoro-3,5-dimethoxyphenyl)-1,3,4,7-tetrahydro-2H-pyrrolo[3',2':5,6]pyrido[4,3-d]pyrimidin-2-one replacing 3-(2-chloro-6-fluoro-3,5-dimethoxyphenyl)-1-ethyl-1,3,4,7-tetrahydro-2H-pyrrolo [3',2':5,6]pyrido[4,3-d]pyrimidin-2-one. LC-MS calculated for $C_{23}H_{17}ClF_3N_4O_4$ $(M+H)^+$ m/z: 505.1; found: 505.0. $^1H$ NMR (300 MHz, DMSO) δ 11.03 (s, 1H), 7.95 (s, 1H), 7.73-7.62 (m, 2H), 7.50-7.41 (m, 1H), 7.06 (t, J=8.2 Hz, 1H), 4.93 (d, J=14.0 Hz, 1H), 4.76 (d, J=14.0 Hz, 1H), 3.88 (s, 6H), 2.58-2.34 (m, 2H).

Example 69

3-(2,6-difluoro-3,5-dimethoxyphenyl)-9-[4-(4-ethylpiperazin-1-yl)phenyl]-1-methyl-1,3,4,7-tetrahydro-2H-pyrazolo[4',3':5,6]pyrido[4,3-d]pyrimidin-2-one

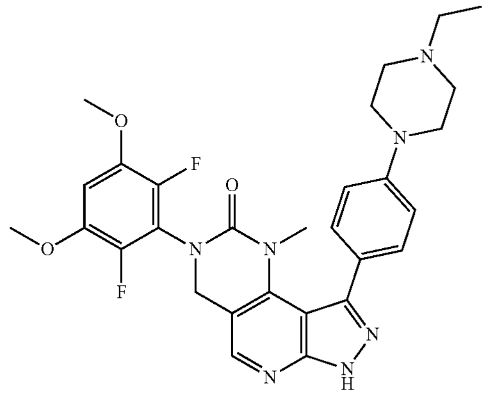 [SMILES: CCN1CCN(c2ccc(-c3n[nH]c4ncc5c(c34)N(C)C(=O)N(c3c(F)c(OC)cc(OC)c3F)C5)cc2)CC1]

To a solution of 9-bromo-3-(2,6-difluoro-3,5-dimethoxyphenyl)-1-methyl-1,3,4,7-tetrahydro-2H-pyrazolo[4',3':5,6]pyrido[4,3-d]pyrimidin-2-one (30.0 mg, 0.066 mmol) and 1-ethyl-4-[4-(4,4,5,5-tetramethyl-1,3,2-dioxaborolan-2-yl)phenyl]piperazine (31.0 mg, 0.099 mmol) in 1,4-dioxane (0.75 mL) and water (0.25 mL) were added potassium carbonate (36.0 mg, 0.26 mmol) and tetrakis(triphenylphosphine)palladium(O) (7.6 mg, 0.0066 mmol). The resulting mixture was heated to 100° C. for 12 h before it was diluted with MeOH and purified by RP-HPLC (pH 2). LC-MS calculated for $C_{29}H_{32}F_2N_7O_3[M+H]^+$ m/z: 564.3; found 564.3. $^1H$ NMR (300 MHz, DMSO) δ 13.8 (s, 1H), 8.27 (s, 1H), 7.42 (d, J=9.0 Hz, 2H), 7.13 (d, J=9.0 Hz, 2H), 7.03 (t, J=6.0 Hz, 1H), 4.82 (s, 2H), 3.98 (d, J=9.0 Hz, 2H), 3.88 (s, 6H), 3.59 (d, J=9.0 Hz, 2H), 3.22-2.98 (m, 6H), 2.78 (s, 3H), 1.24 (t, J=6.0 Hz, 3H).

Example 70

3-(2,6-difluoro-3,5-dimethoxyphenyl)-8-[(4-ethylpiperazin-1-yl)methyl]-1-methyl-1,3,4,7-tetrahydro-2H-pyrrolo[3',2':5,6]pyrido[4,3-d]pyrimidin-2-one

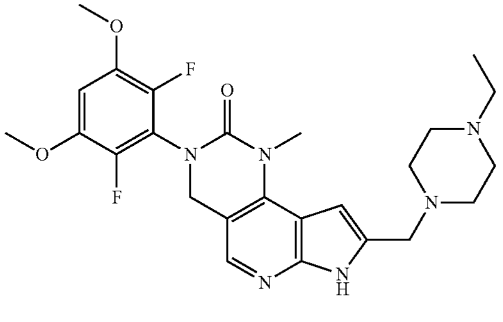 [SMILES: CCN1CCN(Cc2cc3c4c(cnc3[nH]2)CN(c2c(F)c(OC)cc(OC)c2F)C(=O)N4C)CC1]

Step 1: 3-(2,6-difluoro-3,5-dimethoxyphenyl)-1-methyl-2-oxo-7-(phenylsulfonyl)-2,3,4,7-tetrahydro-1H-pyrrolo[3',2':5,6]pyrido[4,3-d]pyrimidine-8-carbaldehyde

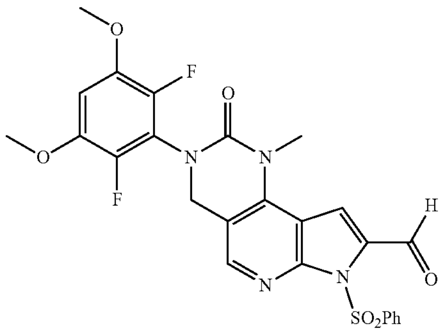

To a solution of 3-(2,6-difluoro-3,5-dimethoxyphenyl)-1-methyl-7-(phenylsulfonyl)-1,3,4,7-tetrahydro-2H-pyrrolo[3',2':5,6]pyrido[4,3-d]pyrimidin-2-one (Example 39, Step 4: 885 mg, 1.72 mmol) in tetrahydrofuran (20 mL) cooled to −78° C. was added a freshly prepared lithium diisopropylamide (LDA) solution (1 M in THF, 2.6 mL). The resulting yellow suspension was stirred at −78° C. for 30 min then N,N-dimethylformamide (2 mL) was added. The mixture was stirred at −78° C. for 1 h then quenched with 1N HCl. The reaction mixture was then warmed to room temperature and extracted with EtOAc. The organic layer was washed with water, brine then dried over $Na_2SO_4$ and concentrated. The residue was purified by flash chromatography on a silica gel column eluted with 0 to 10% EtOAc in DCM to afford the desired product (730 mg, 78%) as a white solid. LC-MS calculated for $C_{25}H_{21}F_2N_4O_6S$ $[M+H]^+$ m/z: 543.1; found 543.1.

Step 2: 3-(2,6-difluoro-3,5-dimethoxyphenyl)-8-[(4-ethylpiperazin-1-yl)methyl]-1-methyl-7-(phenylsulfonyl)-1,3,4,7-tetrahydro-2H-pyrrolo[3',2':5,6]pyrido[4,3-d]pyrimidin-2-one

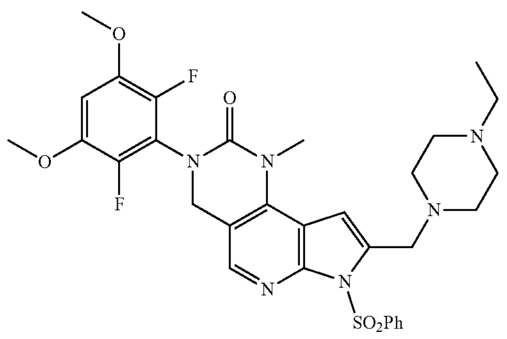

To a solution of sodium triacetoxyborohydride (680 mg, 3.2 mmol) in trifluoroacetic acid (2.1 mL, 28 mmol) cooled to 0° C. was added 3 mL of dichloromethane (DCM) then 1-ethylpiperazine (580 μL, 4.6 mmol) was added to give a yellow solution. Then a solution of 3-(2,6-difluoro-3,5-dimethoxyphenyl)-1-methyl-2-oxo-7-(phenylsulfonyl)-2,3,4,7-tetrahydro-1H-pyrrolo[3',2':5,6]pyrido[4,3-d]pyrimidine-8-carbaldehyde (500 mg, 0.92 mmol) in DCM (10 mL) was dropwise over 5 min. The mixture was stirred at 0° C. for 2 h then warmed to room temperature and stirred for overnight. The mixture was poured into saturated $NaHCO_3$ then extracted with DCM. The organic layer was then washed with water, brine and dried over $Na_2SO_4$ and concentrated. The residue was purified by flash chromatography on a silica gel column eluted with 0 to 10% MeOH in DCM to afford the desired product (590 mg, 100%) as a white solid. LC-MS calculated for $C_{31}H_{35}F_2N_6O_5S$ $[M+H]^+$ m/z: 641.2; found 641.2.

Step 3: 3-(2,6-difluoro-3,5-dimethoxyphenyl)-8-[(4-ethylpiperazin-1-yl)methyl]-1-methyl-1,3,4,7-tetrahydro-2H-pyrrolo[3',2':5,6]pyrido[4,3-d]pyrimidin-2-one To a solution of 3-(2,6-difluoro-3,5-dimethoxyphenyl)-8-[(4-ethylpiperazin-1-yl)methyl]-1-methyl-7-(phenylsulfonyl)-1,3,4,7-tetrahydro-2H-pyrrolo[3',2':5,6]pyrido[4,3-d]pyrimidin-2-one (590 mg, 0.92 mmol) in 25 mL of THF was added potassium tert-butoxide (1 M in THF, 4.6 mL). The mixture was stirred at room temperature for 1 h then the reaction was quenched with saturated $NH_4Cl$ solution and extracted with EtOAc. The organic layer was washed with water, brine then dried over $Na_2SO_4$ and concentrated. The residue was purified by prep HPLC (pH=2, ACN/$H_2O$) to give the desired product as a white solid. LC-MS calculated for $C_{25}H_{31}F_2N_6O_3$ $[M+H]^+$ m/z: 501.2; found 501.2. $^1H$ NMR (500 MHz, DMSO) δ 12.01 (s, 1H), 8.00 (s, 1H), 7.04 (t, J=8.1 Hz, 1H), 6.77 (s, 1H), 4.77 (s, 2H), 3.89 (s, 8H), 3.63 (s, 3H), 3.49 (br, 2H), 3.21-2.91 (m, 6H), 2.57 (br, 2H), 1.19 (t, J=7.3 Hz, 3H).

Example 71

3-(2,6-difluoro-3,5-dimethoxyphenyl)-8-[2-(4-ethylpiperazin-1-yl)ethyl]-1-methyl-1,3,4,7-tetrahydro-2H-pyrrolo[3',2':5,6]pyrido[4,3-d]pyrimidin-2-one

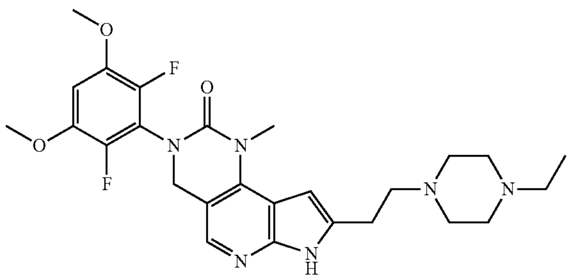 [SMILES: CCN1CCN(CCc2cc3c4c(cnc3[nH]2)CN(c2c(F)c(OC)cc(OC)c2F)C(=O)N4C)CC1]

Step 1: 3-(2,6-difluoro-3,5-dimethoxyphenyl)-8-[(Z)-2-ethoxyvinyl]-1-methyl-7-(phenylsulfonyl)-1,3,4,7-tetrahydro-2H-pyrrolo[3',2':5,6]pyrido[4,3-d]pyrimidin-2-one

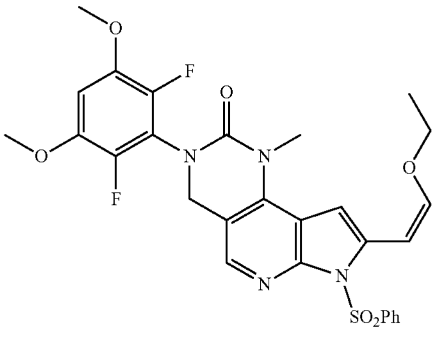

A flask containing a mixture of 8-bromo-3-(2,6-difluoro-3,5-dimethoxyphenyl)-1-methyl-7-(phenylsulfonyl)-1,3,4,7-tetrahydro-2H-pyrrolo[3',2':5,6]pyrido[4,3-d]pyrimidin-2-one (Example 39, Step 5: 120 mg, 0.20 mmol), 2-[(Z)-2-ethoxyvinyl]-4,4,5,5-tetramethyl-1,3,2-dioxaborolane (Synthonix, Cat #E2791: 79 mg, 0.40 mmol), [1,1'-bis(diphenylphosphino)ferrocene]-dichloropalladium(II) complexed with dichloromethane (1:1) (Aldrich, cat #379670: 20 mg, 0.02 mmol) and potassium carbonate (83 mg, 0.60 mmol) in 1,4-dioxane (5 mL, 60 mmol) and water (0.5 mL, 30 mmol) was evacuated then filled with nitrogen three times. The reaction mixture was stirred at 95° C. for 1 h then cooled to room temperature and concentrated. The residue was purified by flash chromatography on a silica gel column eluted with 0 to 20% EtOAc in hexanes to afford the desired product (106 mg, 91%). LC-MS calculated for $C_{28}H_{27}F_2N_4O_6S$ $[M+H]^+$ m/z: 585.2; found 585.1.

Step 2: [3-(2,6-difluoro-3,5-dimethoxyphenyl)-1-methyl-2-oxo-7-(phenylsulfonyl)-2,3,4,7-tetrahydro-1H-pyrrolo[3',2':5,6]pyrido[4,3-d]pyrimidin-8-yl]acetaldehyde

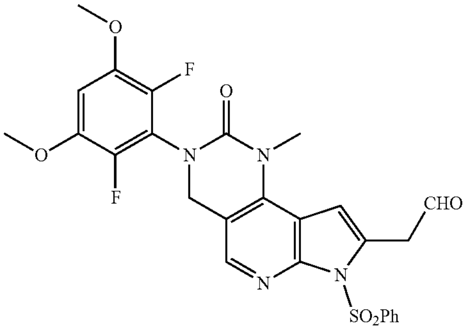

To a solution of 3-(2,6-difluoro-3,5-dimethoxyphenyl)-8-[(Z)-2-ethoxyvinyl]-1-methyl-7-(phenylsulfonyl)-1,3,4,7-tetrahydro-2H-pyrrolo[3',2':5,6]pyrido[4,3-d]pyrimidin-2-one (97 mg, 0.16 mmol) in tetrahydrofuran (10 mL, 100 mmol) was added 1.0 M hydrogen chloride in water (1.6 mL, 1.6 mmol). The mixture was stirred at 60° C. for 2 h then cooled to room temperature and neutralized with saturated $NaHCO_3$ solution. The mixture was extracted with EtOAc. The organic layer was washed with water, brine then dried over $Na_2SO_4$ and concentrated. The residue was used in the next step without further purification. LC-MS calculated for $C_{26}H_{23}F_2N_4O_6S$ $[M+H]^+$ m/z: 557.1; found 557.1.

Step 3: 3-(2,6-difluoro-3,5-dimethoxyphenyl)-8-[2-(4-ethylpiperazin-1-yl)ethyl]-1-methyl-7-(phenylsulfonyl)-1,3,4,7-tetrahydro-2H-pyrrolo[3',2':5,6]pyrido[4,3-d]pyrimidin-2-one

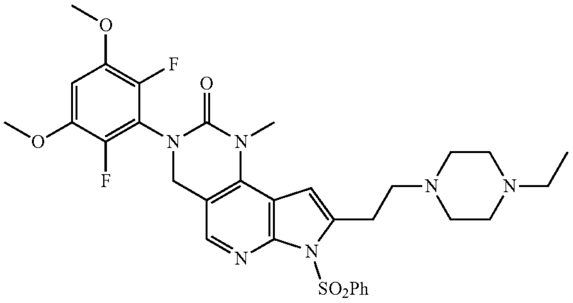

To a solution of [3-(2,6-difluoro-3,5-dimethoxyphenyl)-1-methyl-2-oxo-7-(phenylsulfonyl)-2,3,4,7-tetrahydro-1H-pyrrolo[3',2':5,6]pyrido[4,3-d]pyrimidin-8-yl]acetaldehyde (30 mg, 0.054 mmol) in methylene chloride (2 mL) were added 1-ethylpiperazine (21 μL, 0.16 mmol) and acetic acid (100 μL). The resulting yellow solution was stirred at room temperature for 2 h then sodium triacetoxyborohydride (35 mg, 0.16 mmol) was added and the reaction mixture was stirred at room temperature overnight. The mixture was neutralized with saturated $Na_2CO_3$ then extracted with EtOAc. The organic layer was washed with brine, dried over $Na_2SO_4$, then concentrated. The residue was used in the next step without further purification. LC-MS calculated for $C_{32}H_{37}F_2N_6O_5S$ $[M+H]^+$ m/z: 655.3; found 655.2.

Step 4: 3-(2,6-difluoro-3,5-dimethoxyphenyl)-8-[2-(4-ethylpiperazin-1-yl)ethyl]-1-methyl-1,3,4,7-tetrahydro-2H-pyrrolo[3',2':5,6]pyrido[4,3-d]pyrimidin-2-one The crude product from step 3 was dissolved in tetrahydrofuran (3 mL) then 1.0 M potassium tert-butoxide in THF (0.20 mL, 0.20 mmol) was added. The resulting yellow suspension was stirred at room temperature for 30 min then diluted with MeOH and purified by prep HPLC (pH 2, ACN/$H_2O$) to give the desired product as a white solid. LC-MS calculated for $C_{26}H_{33}F_2N_6O_3$$[M+H]^+$ m/z: 515.3; found 515.2. $^1$H NMR (500 MHz, DMSO) δ 11.43 (s, 1H), 7.91 (s, 1H), 7.00 (t, J=8.2 Hz, 1H), 6.57 (s, 1H), 4.74 (s, 2H), 3.89 (s, 6H), 3.65 (s, 3H), 3.18 (br, 4H), 3.07 (q, J=7.3 Hz, 2H), 3.02-2.93 (m, 4H), 2.88 (br, 4H), 1.22 (t, J=7.3 Hz, 3H).

Example 72

3-(2,6-difluoro-3,5-dimethoxyphenyl)-8-[3-(4-ethylpiperazin-1-yl)propyl]-1-methyl-1,3,4,7-tetrahydro-2H-pyrrolo[3',2':5,6]pyrido[4,3-d]pyrimidin-2-one

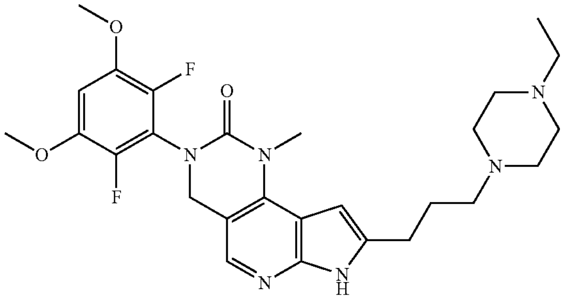 [SMILES: CCN1CCN(CCCc2cc3c4c(cnc3[nH]2)CN(c2c(F)c(OC)cc(OC)c2F)C(=O)N4C)CC1]

Step 1: 3-(2,6-difluoro-3,5-dimethoxyphenyl)-8-(3-hydroxyprop-1-yn-1-yl)-1-methyl-1,3,4,7-tetrahydro-2H-pyrrolo[3',2':5,6]pyrido[4,3-d]pyrimidin-2-one

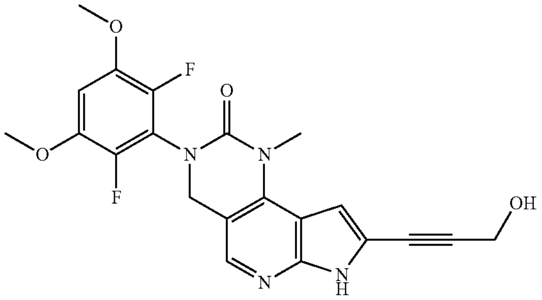 [SMILES: COc1cc(OC)c(F)c(N2Cc3cnc4[nH]c(C#CCO)cc4c3N(C)C2=O)c1F]

A flask containing a mixture of 8-bromo-3-(2,6-difluoro-3,5-dimethoxyphenyl)-1-methyl-1,3,4,7-tetrahydro-2H-pyrrolo[3',2':5,6]pyrido[4,3-d]pyrimidin-2-one (40 mg, 0.088 mmol), tetrakis(triphenylphosphine)palladium(O) (10 mg, 0.009 mmol) and copper(I) iodide (3 mg, 0.02 mmol) in N,N-dimethylformamide (2 mL, 20 mmol) was evacuated then filled with nitrogen. Then 2-propyn-1-ol (26 μL, 0.44 mmol) and N,N-diisopropylethylamine (77 μL, 0.44 mmol) were added. The resulting solution was heated to 80° C. and stirred for 1 h. The mixture was cooled to room temperature and filtered then purified by prep HPLC (pH 2, ACN/$H_2O$) to give the desired product as a yellow solid. LC-MS calculated for $C_{21}H_{19}F_2N_4O_4[M+H]^+$ m/z: 429.1; found 429.1.

Step 2: 3-(2,6-difluoro-3,5-dimethoxyphenyl)-8-(3-hydroxypropyl)-1-methyl-1,3,4,7-tetrahydro-2H-pyrrolo[3',2':5,6]pyrido[4,3-d]pyrimidin-2-one

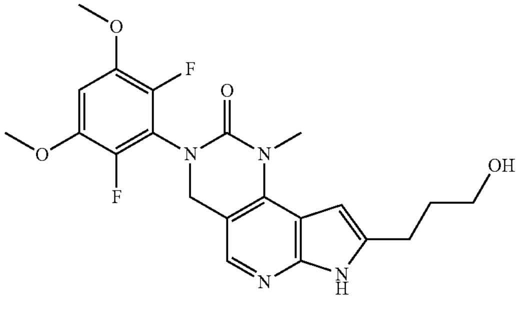 [SMILES: COc1cc(OC)c(F)c(N2Cc3cnc4[nH]c(CCCO)cc4c3N(C)C2=O)c1F]

The product from step 1 was dissolved in tetrahydrofuran (3 mL, 60 mmol) and methanol (3 mL, 100 mmol) then palladium (10 wt % on carbon, 20 mg) was added. The mixture was stirred under a balloon of hydrogen for 2 h at room temperature then filtered through celite and concentrated to give the crude product, which was used in the next step without further purification. LC-MS calculated for $C_{21}H_{23}F_2N_4O_4[M+H]^+$ m/z: 433.2; found 433.2.

Step 3: 3-[3-(2,6-difluoro-3,5-dimethoxyphenyl)-1-methyl-2-oxo-2,3,4,7-tetrahydro-1H-pyrrolo[3',2':5,6]pyrido[4,3-d]pyrimidin-8-yl]propanal

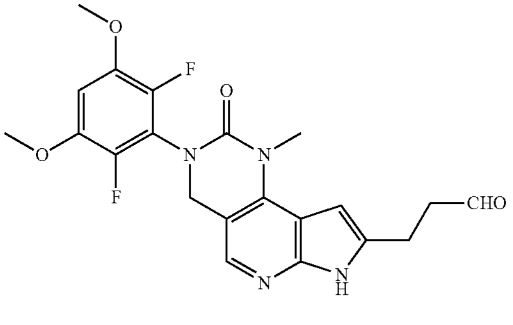 [SMILES: COc1cc(OC)c(F)c(N2Cc3cnc4[nH]c(CCC=O)cc4c3N(C)C2=O)c1F]

To a solution of 3-(2,6-difluoro-3,5-dimethoxyphenyl)-8-(3-hydroxypropyl)-1-methyl-1,3,4,7-tetrahydro-2H-pyrrolo[3',2':5,6]pyrido[4,3-d]pyrimidin-2-one (40. mg, 0.092 mmol) in methylene chloride (5 mL, 80 mmol) was added Dess-Martin periodinane (59 mg, 0.14 mmol). The mixture was stirred at room temperature for 2 h then the reaction was quenched with saturated $NaHCO_3$ solution and extracted with EtOAc. The organic layer was washed with water, brine then dried over $Na_2SO_4$ and concentrated. The residue was used in the next step without further purification. LC-MS calculated for $C_{21}H_{21}F_2N_4O_4[M+H]^+$ m/z: 431.2; found 431.1.

Step 4: 3-(2,6-difluoro-3,5-dimethoxyphenyl)-8-[3-(4-ethylpiperazin-1-yl)propyl]-1-methyl-1,3,4,7-tetrahydro-2H-pyrrolo[3',2':5,6]pyrido[4,3-d]pyrimidin-2-one The crude product from step 3 was dissolved in methanol (10 mL) then 1-ethylpiperazine (59 μL, 0.46 mmol) and acetic acid (100 μL, 2 mmol) were added. The mixture was stirred at room temperature for 1 h then sodium cyanoborohydride (29 mg, 0.46 mmol) was added. The reaction mixture was stirred at room temperature overnight then the reaction was quenched with saturated $Na_2CO_3$ solution and extracted with EtOAc. The organic layer was washed with water, brine, then dried over $Na_2SO_4$ and concentrated. The residue was dissolved in MeOH then purified by prep HPLC (pH 2, ACN/$H_2O$) to give the desired product as a white solid. LC-MS calculated for $C_{27}H_{35}F_2N_6O_3[M+H]^+$ m/z: 529.3; found 529.3. $^1H$ NMR (500 MHz, DMSO) δ 11.37 (s, 1H), 7.89 (s, 1H), 7.00 (t, J=8.2 Hz, 1H), 6.49 (s, 1H), 4.73 (s, 2H), 3.89 (s, 6H), 3.64 (s, 3H), 3.09 (br, 4H), 3.03-2.94 (m, 2H), 2.87 (br, 4H), 2.80 (t, J=7.4 Hz, 2H), 2.73-2.64 (m, 2H), 2.02-1.92 (m, 2H), 1.19 (t, J=7.3 Hz, 3H).

Example 73

3-(2,6-difluoro-3,5-dimethoxyphenyl)-8-[(1-ethylpiperidin-4-yl)methyl]-1-methyl-1,3,4,7-tetrahydro-2H-pyrrolo[3',2':5,6]pyrido[4,3-d]pyrimidin-2-one

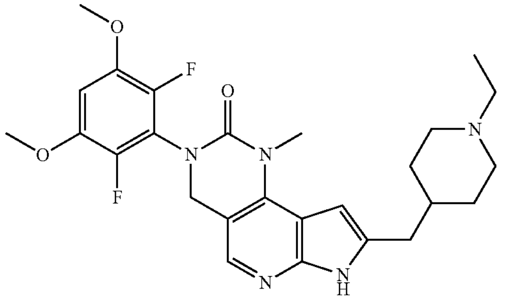 [SMILES: CCN1CCC(Cc2cc3c4c(cnc3[nH]2)CN(c2c(F)c(OC)cc(OC)c2F)C(=O)N4C)CC1]

Step 1: {[1-(tert-butoxycarbonyl)piperidin-4-yl]methyl}(iodo)zinc

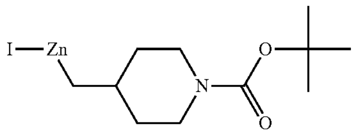

To a slurry of zinc (255 mg, 3.90 mmol) and celite P65 (50 mg) in N,N-dimethylformamide (0.6 mL, 8 mmol) was added dropwise a 7:5 V/V mixture (81 μL) of chlorotrimethylsilane:1,2-dibromoethane over five minutes. The slurry was stirred at 15 min at room temperature then a solution of tert-butyl 4-(iodomethyl)piperidine-1-carboxylate (prepared using reported procedures as described in WO 2007/030366: 976 mg, 3.00 mmol) in N,N-dimethylformamide (1.5 mL, 19 mmol) was added dropwise. After completion of addition, the reaction mixture was heated at 65° C. for 5 min then cooled to room temperature and stirred for 30 min. The mixture was filtered and the filtrate was used directly in the next step.

Step 2: tert-butyl 4-{[3-(2,6-difluoro-3,5-dimethoxyphenyl)-1-methyl-2-oxo-7-(phenylsulfonyl)-2,3,4,7-tetrahydro-1H-pyrrolo[3',2':5,6]pyrido[4,3-d]pyrimidin-8-yl]methyl}piperidine-1-carboxylate

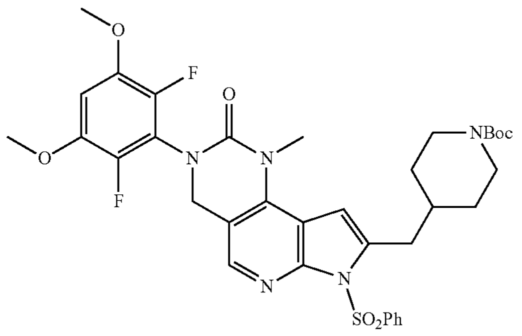

A flask containing a mixture of 8-bromo-3-(2,6-difluoro-3,5-dimethoxyphenyl)-1-methyl-7-(phenylsulfonyl)-1,3,4,7-tetrahydro-2H-pyrrolo[3',2':5,6]pyrido[4,3-d]pyrimidin-2-one (163 mg, 0.275 mmol), [1,1'-bis(diphenylphosphino)ferrocene]dichloropalladium(II) complexed with dichloromethane (1:1) (22 mg, 0.027 mmol) and copper(I) iodide (16 mg, 0.082 mmol) in N,N-dimethylformamide (5 mL) was evacuated then filled with nitrogen. The solution from step 1 (0.82 mL) was added then the reaction mixture was evacuated again and filled with nitrogen. The resulting mixture was heated to 85° C., and stirred for overnight. The mixture was cooled to room temperature then filtered through celite and washed with EtOAc. The filtrate was then washed with water and brine. The organic layer was dried over $Na_2SO_4$ and concentrated. The residue was purified by flash chromatography on a silica gel column eluted with 0 to 30% EtOAc in DCM to afford the desired product (148 mg, 76%) as a light yellow solid. LC-MS calculated for $C_{35}H_{40}F_2N_5O_7S$ [M+H]$^+$ m/z: 712.3; found 712.1.

Step 3: 3-(2,6-difluoro-3,5-dimethoxyphenyl)-1-methyl-8-(piperidin-4-ylmethyl)-1,3,4,7-tetrahydro-2H-pyrrolo[3',2':5,6]pyrido[4,3-d]pyrimidin-2-one

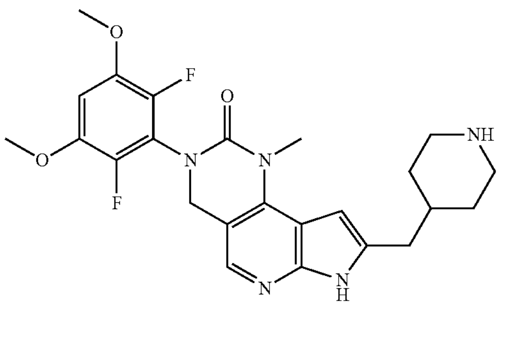 [SMILES: COc1cc(OC)c(F)c(N2Cc3cnc4[nH]c(CC5CCNCC5)cc4c3N(C)C2=O)c1F]

To a solution of tert-butyl 4-{[3-(2,6-difluoro-3,5-dimethoxyphenyl)-1-methyl-2-oxo-7-(phenylsulfonyl)-2,3,4,7-tetrahydro-1H-pyrrolo[3',2':5,6]pyrido[4,3-d]pyrimidin-8-yl]methyl}piperidine-1-carboxylate (140 mg, 0.20 mmol) in tetrahydrofuran (5 mL, 60 mmol) was added 1.0 M potassium tert-butoxide in THF (1.0 mL). The mixture was stirred at room temperature for 1 h. The reaction was quenched with saturated $NH_4Cl$ solution then extracted with EtOAc. The organic layer was washed with water, brine and dried over $Na_2SO_4$ then concentrated. The residue was dissolved in 2 mL of DCM then 2 mL of TFA was added. The resulting mixture was stirred at room temperature for 1 h and concentrated. The residue was dissolved in EtOAc then washed with saturated $NaHCO_3$ solution. The organic layer was washed with water, brine and dried over $Na_2SO_4$ then concentrated to give the desired product as a yellow solid, which was used in the next step without further purification. LC-MS calculated for $C_{24}H_{28}F_2N_5O_3[M+H]^+$ m/z: 472.2; found 472.1.

Step 4: 3-(2,6-difluoro-3,5-dimethoxyphenyl)-8-[(1-ethylpiperidin-4-yl)methyl]-1-methyl-1,3,4,7-tetrahydro-2H-pyrrolo[3',2':5,6]pyrido[4,3-d]pyrimidin-2-one To a stirred solution of 3-(2,6-difluoro-3,5-dimethoxyphenyl)-1-methyl-8-(piperidin-4-ylmethyl)-1,3,4,7-tetrahydro-2H-pyrrolo[3',2':5,6]pyrido[4,3-d]pyrimidin-2-one (17 mg, 0.035 mmol) in MeOH (2 mL) and THF (2 mL) was added 5.0 M acetaldehyde in THF (35 μL). The mixture was stirred at room temperature for 30 min then sodium cyanoborohydride (11 mg, 0.18 mmol) was added. The resulting mixture was stirred at room temperature for 1 h then purified by prep HPLC (pH 2, ACN/$H_2O$) to give the desired product as a white solid. LC-MS calculated for $C_{26}H_{32}F_2N_5O_3[M+H]^+$ m/z: 500.2; found 500.2.

Example 74

3-(2,6-difluoro-3,5-dimethoxyphenyl)-1-[(1R,2R)-2-hydroxycyclopentyl]-1,3,4,7-tetrahydro-2H-pyrrolo[3',2':5,6]pyrido[4,3-d]pyrimidin-2-one

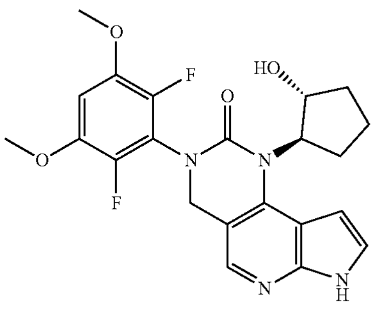 [SMILES: COc1cc(OC)c(F)c(N2Cc3cnc4[nH]ccc4c3N([C@@H]3CCC[C@H]3O)C2=O)c1F]

Step 1: N-[(1R,2R)-2-(benzyloxy)cyclopentyl]-5-{[(2,6-difluoro-3,5-dimethoxyphenyl)amino]methyl}-1H-pyrrolo[2,3-b]pyridin-4-amine

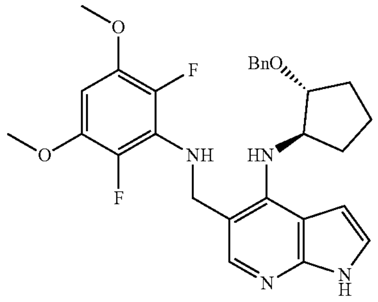 [SMILES: COc1cc(OC)c(F)c(NCc2cnc3[nH]ccc3c2N[C@@H]2CCC[C@H]2OCc2ccccc2)c1F]

A mixture of N-[(4-chloro-1H-pyrrolo[2,3-b]pyridin-5-yl)methyl]-2,6-difluoro-3,5-dimethoxyaniline (prepared as described in Example 45, Step 1-2: 100. mg, 0.283 mmol), (1R,2R)-2-(benzyloxy)cyclopentanamine (Aldrich, Cat #671533: 81.1 mg, 0.424 mmol), palladium acetate (6 mg, 0.03 mmol), (R)-(+)-2,2'-bis(diphenylphosphino)-1,1'-binaphthyl (20 mg, 0.03 mmol), and cesium carbonate (280 mg, 0.85 mmol) in 1,4-dioxane (3 mL, 40 mmol) was evacuated then filled with nitrogen. The mixture was heated to 160° C. and stirred for overnight. After cooled to room temperature, the mixture was diluted with EtOAc and filtered then concentrated under reduced pressure. The residue was purified by flash chromatography eluted with 0 to 5% MeOH in DCM to give the desired product (63 mg, 44%) as a yellow solid. LC-MS calculated for $C_{28}H_{31}F_2N_4O_3[M+H]^+$ m/z: 509.2; found 509.3.

Step 2: 1-[(]R,2R)-2-(benzyloxy)cyclopentyl]-3-(2,6-difluoro-3,5-dimethoxyphenyl)-1,3,4,7-tetrahydro-2H-pyrrolo[3',2':5,6]pyrido[4,3-d]pyrimidin-2-one

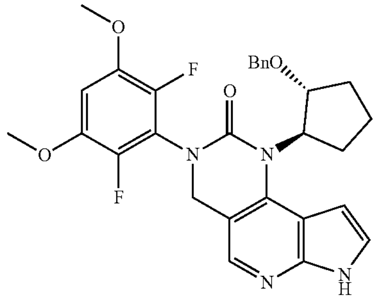 [SMILES: COc1cc(OC)c(F)c(N2Cc3cnc4[nH]ccc4c3N([C@@H]3CCC[C@H]3OCc3ccccc3)C2=O)c1F]

To a solution of the product from Step 1 in tetrahydrofuran (3 mL, 40 mmol) was added triethylamine (90 μL, 0.65 mmol) and triphosgene (56 mg, 0.19 mmol). The resulting yellow suspension was stirred at room temperature for 1 h then 3 mL of 1 N NaOH was added. The mixture was stirred at room temperature for another 1 h then diluted with EtOAc. The organic layer was washed with water, brine, then dried over $Na_2SO_4$ and concentrated under reduced pressure. The residue was purified by flash chromatography eluted with 0 to 5% MeOH in DCM to give the desired product as a yellow solid. LC-MS calculated for $C_{29}H_{29}F_2N_4O_4[M+H]^+$ m/z: 535.2; found 535.1.

Step 3: 3-(2,6-difluoro-3,5-dimethoxyphenyl)-1-[(1R,2R)-2-hydroxycyclopentyl]-1,3,4,7-tetrahydro-2H-pyrrolo[3',2':5,6]pyrido[4,3-d]pyrimidin-2-one To a solution of the product from Step 2 in methanol (5 mL) and tetrahydrofuran (5 mL) was added palladium (10 wt % on activated carbon, 20 mg) and a few drops of concentrated HCl. The mixture was stirred under a balloon of hydrogen at room temperature for 6 h then filtered through celite and concentrated. The residue was purified by prep HPLC (pH 2, ACN/$H_2O$) to give the desired product as a white solid. LC-MS calculated for $C_{22}H_{23}F_2N_4O_4$ $[M+H]^+$ m/z: 445.2; found 445.2. $^1H$ NMR (500 MHz, DMSO) δ 11.93 (s, 1H), 8.04 (s, 1H), 7.54-7.47 (m, 1H), 7.03 (t, J=8.1 Hz, 1H), 6.86-6.81 (m, 1H), 4.83 (d, J=13.2 Hz, 1H), 4.63 (d, J=13.2 Hz, 1H), 4.61-4.55 (m, 1H), 4.54-4.47 (m, 1H), 3.90 (s, 3H), 3.87 (s, 3H), 2.29-2.12 (m, 2H), 2.06-1.96 (m, 1H), 1.86-1.66 (m, 2H), 1.56-1.44 (m, 1H).

Example 75

3-(2,6-difluoro-3,5-dimethoxyphenyl)-1-[(1R,2R)-2-hydroxycyclopentyl]-3,4,7,9-tetrahydro-1H-pyrrolo[3',2':5,6]pyrido[4,3-d]pyrimidine-2,8-dione

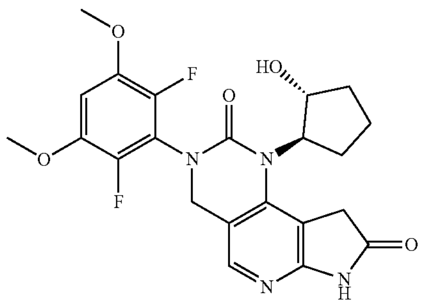 [SMILES: COc1cc(OC)c(F)c(N2Cc3cnc4c(c3N([C@@H]3CCC[C@H]3O)C2=O)CC(=O)N4)c1F]

To a solution of 3-(2,6-difluoro-3,5-dimethoxyphenyl)-1-[(1R,2R)-2-hydroxycyclopentyl]-1,3,4,7-tetrahydro-2H-pyrrolo[3',2':5,6]pyrido[4,3-d]pyrimidin-2-one (Example 74: 8 mg, 0.02 mmol) in isopropyl alcohol (5 mL) and water (0.25 mL) was added pyridinium tribromide (29 mg, 0.09 mmol). The resulting yellow solution was warmed up to 30° C. and stirred for overnight. The reaction mixture was cooled to room temperature then zinc (24 mg, 0.37 mmol) and acetic acid (0.2 mL, 4 mmol) were added. The mixture was stirred at room temperature for 2 h then filtered and concentrated. The residue was dissolved in MeOH then purified by prep HPLC (pH 2, ACN/$H_2O$) to give the desired product as a white solid. LC-MS calculated for $C_{22}H_{23}F_2N_4O_5$$[M+H]^+$ m/z: 461.2; found 461.2.

Example 76

3-(2,6-difluoro-3,5-dimethoxyphenyl)-1-(2,3-difluorophenyl)-1,3,4,7-tetrahydro-2H-pyrrolo[3',2':5,6]pyrido[4,3-d]pyrimidin-2-one

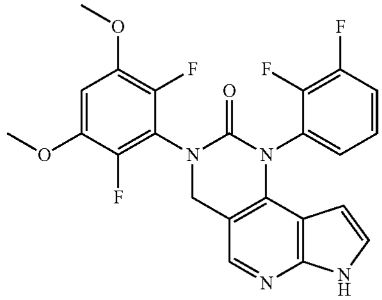 [SMILES: COc1cc(OC)c(F)c(N2Cc3cnc4[nH]ccc4c3N(c3cccc(F)c3F)C2=O)c1F]

This compound was prepared using procedures analogous to those for Example 45 with 2,3-difluoroaniline replacing cyclopropylamine. LC-MS calculated for $C_{23}H_{17}F_4N_4O_3$ $(M+H)^+$ m/z: 473.1; found: 473.0. $^1H$ NMR (300 MHz, DMSO) δ 11.84 (s, 1H), 8.09 (s, 1H), 7.77-7.65 (m, 1H), 7.57-7.48 (m, 1H), 7.45-7.35 (m, 1H), 7.23-7.17 (m, 1H), 7.07 (t, J=8.2 Hz, 1H), 5.15-4.85 (m, 2H), 4.48-4.42 (m, 1H), 3.90 (s, 6H).

Example 77

3-(2,6-difluoro-3,5-dimethoxyphenyl)-1-(2,3-difluorophenyl)-3,4,7,9-tetrahydro-1H-pyrrolo[3',2':5,6]pyrido[4,3-d]pyrimidine-2,8-dione

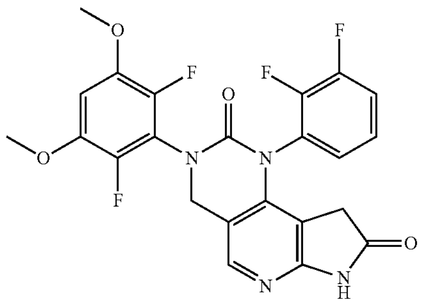 [SMILES: COc1cc(OC)c(F)c(N2Cc3cnc4c(c3N(c3cccc(F)c3F)C2=O)CC(=O)N4)c1F]

This compound was prepared using procedures analogous to those for Example 75 with 3-(2,6-difluoro-3,5-dimethoxyphenyl)-1-(2,3-difluorophenyl)-1,3,4,7-tetrahydro-2H-pyrrolo[3',2':5,6]pyrido[4,3-d]pyrimidin-2-one (Example 76) replacing 3-(2,6-difluoro-3,5-dimethoxyphenyl)-1-[(1R,2R)-2-hydroxycyclopentyl]-1,3,4,7-tetrahydro-2H-pyrrolo[3',2':5,6]pyrido[4,3-d]pyrimidin-2-one. LC-MS calculated for $C_{23}H_{17}F_4N_4O_4(M+H)^+$ m/z: 489.1; found: 489.0. $^1H$ NMR (500 MHz, DMSO) δ 11.01 (s, 1H), 7.96 (s, 1H), 7.66 (q, J=8.4 Hz, 1H), 7.48 (t, J=7.2 Hz, 1H), 7.36 (q, J=7.2 Hz, 1H), 7.06 (t, J=8.1 Hz, 1H), 4.95 (d, J=14.0 Hz, 1H), 4.77 (d, J=14.0 Hz, 1H), 3.89 (s, 6H), 2.55 (d, J=21.7 Hz, 1H), 2.35 (d, J=21.7 Hz, 1H).

Example 78

3-(2,6-difluoro-3,5-dimethoxyphenyl)-1-(pyridin-2-ylmethyl)-1,3,4,7-tetrahydro-2H-pyrrolo[3',2':5,6]pyrido[4,3-d]pyrimidin-2-one

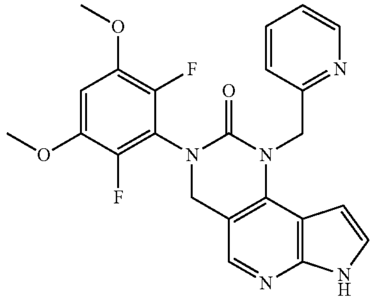 [SMILES: COc1cc(OC)c(F)c(N2Cc3cnc4[nH]ccc4c3N(Cc3ccccn3)C2=O)c1F]

This compound was prepare using procedures analogous to those or Example 45 with 2-pyridinemethanamine replacing cyclopropylamine. LC-MS calculated for $C_{23}H_{20}F_2N_5O_3$ $(M+H)^+$ m/z: 452.2; found: 452.1. $^1$H NMR (500 MHz, DMSO) δ 11.65 (s, 1H), 8.54 (d, J=4.2 Hz, 1H), 8.01 (s, 1H), 7.71 (td, J=7.7, 1.7 Hz, 1H), 7.27-7.20 (m, 2H), 7.17 (d, J=7.9 Hz, 1H), 7.04 (t, J=8.1 Hz, 1H), 6.11-6.06 (m, 1H), 5.44 (s, 2H), 4.91 (s, 2H), 3.89 (s, 6H).

Example 79

3-(2,6-difluoro-3,5-dimethoxyphenyl)-1-(pyridin-2-ylmethyl)-3,4,7,9-tetrahydro-1H-pyrrolo[3',2':5,6]pyrido[4,3-d]pyrimidine-2,8-dione

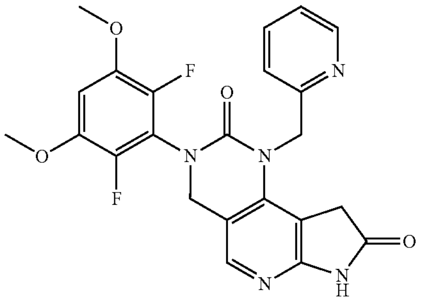 [SMILES: COc1cc(OC)c(F)c(N2Cc3cnc4c(c3N(Cc3ccccn3)C2=O)CC(=O)N4)c1F]

This compound was prepared using procedures analogous to those for Example 75 with 3-(2,6-difluoro-3,5-dimethoxyphenyl)-1-(pyridin-2-ylmethyl)-1,3,4,7-tetrahydro-2H-pyrrolo[3',2':5,6]pyrido[4,3-d]pyrimidin-2-one (Example 78) replacing 3-(2,6-difluoro-3,5-dimethoxyphenyl)-1-[(1R,2R)-2-hydroxycyclopentyl]-1,3,4,7-tetrahydro-2H-pyrrolo[3',2':5,6]pyrido[4,3-d]pyrimidin-2-one. LC-MS calculated for $C_{23}H_{20}F_2N_5O_4(M+H)^+$ m/z: 468.1; found: 468.1.

Example 80

1-(4-chlorophenyl)-3-(2,6-difluoro-3,5-dimethoxyphenyl)-3,4,7,9-tetrahydro-1H-pyrrolo[3',2':5,6]pyrido[4,3-d]pyrimidine-2,8-dione

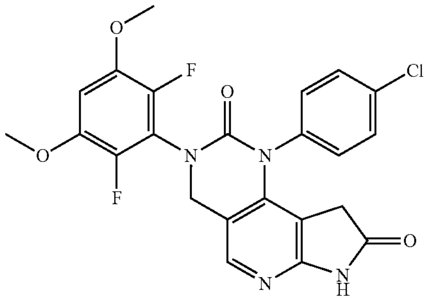 [SMILES: COc1cc(OC)c(F)c(N2Cc3cnc4c(c3N(c3ccc(Cl)cc3)C2=O)CC(=O)N4)c1F]

Step 1: 1-(4-chlorophenyl)-3-(2,6-difluoro-3,5-dimethoxyphenyl)-1,3,4,7-tetrahydro-2H-pyrrolo[3',2':5,6]pyrido[4,3-d]pyrimidin-2-one

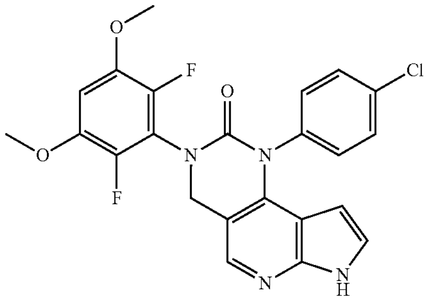 [SMILES: COc1cc(OC)c(F)c(N2Cc3cnc4[nH]ccc4c3N(c3ccc(Cl)cc3)C2=O)c1F]

This compound was prepared using procedures analogous to those for Example 45 with p-chloroaniline replacing cyclopropylamine. LC-MS calculated for $C_{23}H_{18}ClF_2N_4O_3$ $(M+H)^+$ m/z: 471.1; found: 471.0.

Step 2: 1-(4-chlorophenyl)-3-(2,6-difluoro-3,5-dimethoxyphenyl)-3,4,7,9-tetrahydro-1H-pyrrolo[3',2':5,6]pyrido[4,3-d]pyrimidine-2,8-dione This compound was prepared using procedures analogous to those for Example 75 with 1-(4-chlorophenyl)-3-(2,6-difluoro-3,5-dimethoxyphenyl)-1,3,4,7-tetrahydro-2H-pyrrolo[3',2':5,6]pyrido[4,3-d]pyrimidin-2-one replacing 3-(2,6-difluoro-3,5-dimethoxyphenyl)-1-[(1R,2R)-2-hydroxycyclopentyl]-1,3,4,7-tetrahydro-2H-pyrrolo[3',2':5,6]pyrido[4,3-d]pyrimidin-2-one. LC-MS calculated for $C_{23}H_{18}ClF_2N_4O_4$ $(M+H)^+$ m/z: 487.1; found: 487.1. $^1$H NMR (400 MHz, DMSO) δ 10.97 (s, 1H), 7.93 (s, 1H), 7.60-7.54 (m, 2H), 7.52-7.46 (m, 2H), 7.05 (t, J=8.2 Hz, 1H), 4.83 (s, 2H), 3.88 (s, 6H), 2.36 (s, 2H).

Example 81

1-(5-chloropyridin-2-yl)-3-(2,6-difluoro-3,5-dimethoxyphenyl)-3,4,7,9-tetrahydro-1H-pyrrolo[3',2':5,6]pyrido[4,3-d]pyrimidine-2,8-dione

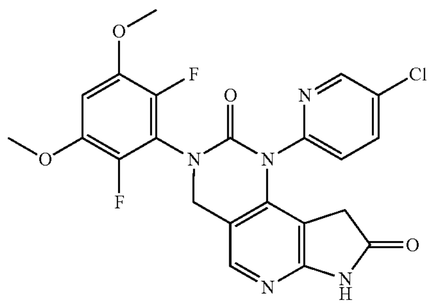 [SMILES: COc1cc(OC)c(F)c(N2Cc3cnc4c(c3N(c3ccc(Cl)cn3)C2=O)CC(=O)N4)c1F]

Step 1: 1-(5-chloropyridin-2-yl)-3-(2,6-difluoro-3,5-dimethoxyphenyl)-1,3,4,7-tetrahydro-2H-pyrrolo[3',2':5,6]pyrido[4,3-d]pyrimidin-2-one

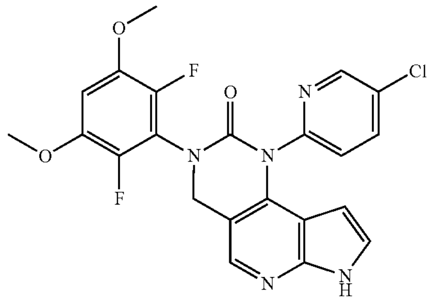 [SMILES: COc1cc(OC)c(F)c(N2Cc3cnc4[nH]ccc4c3N(c3ccc(Cl)cn3)C2=O)c1F]

This compound was prepared using procedures analogous to those for Example 45 with 2-amino-5-chloropyridine replacing cyclopropylamine. LC-MS calculated for $C_{22}H_{17}ClF_2N_5O_3$ $(M+H)^+$ m/z: 472.1; found: 472.0.

Step 2: 1-(5-chloropyridin-2-yl)-3-(2,6-difluoro-3,5-dimethoxyphenyl)-3,4,7,9-tetrahydro-1H-pyrrolo[3',2':5,6]pyrido[4,3-d]pyrimidine-2,8-dione This compound was prepared using procedures analogous to those for Example 75 with 1-(5-chloropyridin-2-yl)-3-(2,6-difluoro-3,5-dimethoxyphenyl)-1,3,4,7-tetrahydro-2H-pyrrolo[3',2':5,6]pyrido[4,3-d]pyrimidin-2-one replacing 3-(2,6-difluoro-3,5-dimethoxyphenyl)-1-[(1R,2R)-2-hydroxycyclopentyl]-1,3,4,7-tetrahydro-2H-pyrrolo[3',2':5,6]pyrido[4,3-d]pyrimidin-2-one. LC-MS calculated for $C_{22}H_{17}ClF_2N_5O_4$ $(M+H)^+$ m/z: 488.1; found: 488.1.

Example 82

3-[3-(2,6-difluoro-3,5-dimethoxyphenyl)-2-oxo-2,3,4,7-tetrahydro-1H-pyrrolo[3',2':5,6]pyrido[4,3-d]pyrimidin-1-yl]benzonitrile

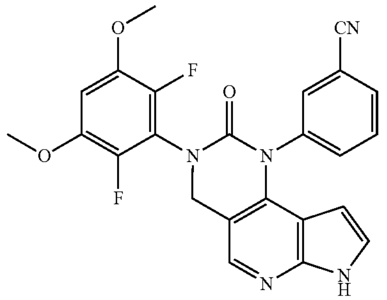 [SMILES: COc1cc(OC)c(F)c(N2Cc3cnc4[nH]ccc4c3N(c3cccc(C#N)c3)C2=O)c1F]

This compound was prepared using procedures analogous to those for Example 45 with 3-amino-benzonitrile replacing cyclopropylamine. LC-MS calculated for $C_{24}H_{18}F_2N_5O_3$ $(M+H)^+$ m/z: 462.1; found: 462.1.

Example 83

3-(2,6-difluoro-3,5-dimethoxyphenyl)-1-pyridin-3-yl-1,3,4,7-tetrahydro-2H-pyrrolo[3',2':5,6]pyrido[4,3-d]pyrimidin-2-one

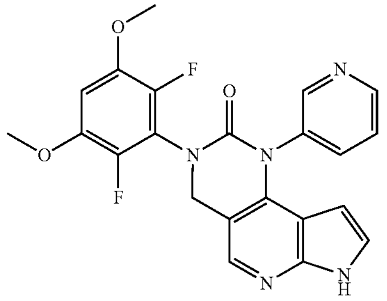 [SMILES: COc1cc(OC)c(F)c(N2Cc3cnc4[nH]ccc4c3N(c3cccnc3)C2=O)c1F]

This compound was prepared using procedures analogous to those for Example 45 with 3-pyridinamine replacing cyclopropylamine. LC-MS calculated for $C_{22}H_{18}F_2N_5O_3$ $(M+H)^+$ m/z: 438.1; found: 438.1. $^1H$ NMR (400 MHz, DMSO) δ 11.84 (s, 1H), 8.75-8.68 (m, 2H), 8.11 (s, 1H), 8.03-7.97 (m, 1H), 7.67-7.60 (m, 1H), 7.19-7.13 (m, 1H), 7.07 (t, J=8.2 Hz, 1H), 5.01 (s, 2H), 4.31-4.26 (m, 1H), 3.90 (s, 6H).

Example 84

1-(3-chloro-2-fluorophenyl)-3-(2,6-difluoro-3,5-dimethoxyphenyl)-1,3,4,7-tetrahydro-2H-pyrrolo[3',2':5,6]pyrido[4,3-d]pyrimidin-2-one

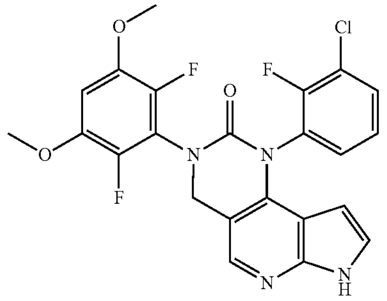 [SMILES: COc1cc(OC)c(F)c(N2Cc3cnc4[nH]ccc4c3N(c3cccc(Cl)c3F)C2=O)c1F]

This compound was prepared using procedures analogous to those for Example 45 with 3-chloro-2-fluoroaniline replacing cyclopropylamine. LC-MS calculated for $C_{23}H_{17}ClF_3N_4O_3$ $(M+H)^+$ m/z: 489.1; found: 489.0.

Example 85

3-(2,6-difluoro-3,5-dimethoxyphenyl)-1-(1-methyl-1H-pyrazol-4-yl)-1,3,4,7-tetrahydro-2H-pyrazolo[4',3':5,6]pyrido[4,3-d]pyrimidin-2-one

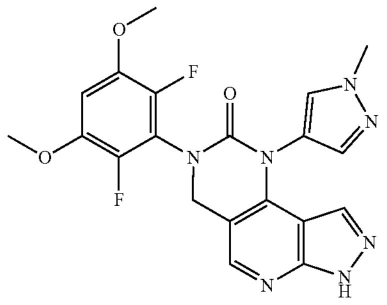 [SMILES: COc1cc(OC)c(F)c(N2Cc3cnc4[nH]ncc4c3N(c3cnn(C)c3)C2=O)c1F]

Step 1: 5-{[(2,6-difluoro-3,5-dimethoxyphenyl)amino]methyl}-1-(4-methoxybenzyl)-N-(1-methyl-1H-pyrazol-4-yl)-1H-pyrazolo[3,4-b]pyridin-4-amine

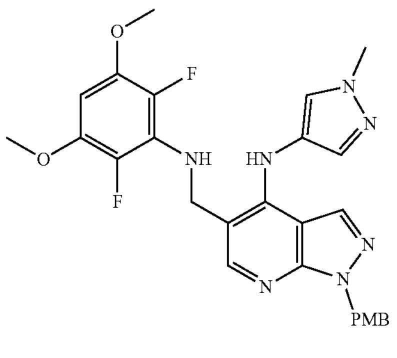

A container having a mixture of N-{[4-chloro-1-(4-methoxybenzyl)-1H-pyrazolo[3,4-b]pyridin-5-yl]methyl}-2,6-difluoro-3,5-dimethoxyaniline (prepared as described in Example 62, step 2; 100 mg, 0.2 mmol), 1-methyl-1H-pyrazol-4-amine (Astatech, Cat #CL4553: 31 mg, 0.32 mmol), cesium carbonate (380 mg, 1.2 mmol), (9,9-dimethyl-9H-xanthene-4,5-diyl)bis(diphenylphosphine) (24 mg, 0.042 mmol) and palladium acetate (9.4 mg, 0.042 mmol) in toluene (3 mL) was evacuated then filled with nitrogen. The mixture was stirred at 150° C. for 1 hour then cooled to room temperature and diluted with ethyl acetate, washed with water. The organic layer was dried over $Na_2SO_4$ and concentrated. The residue was used in the next step without further purification. LC-MS calculated for $C_{27}H_{28}F_2N_7O_3(M+H)^+$ m/z: 536.2; found: 536.2.

Step 2: 3-(2,6-difluoro-3,5-dimethoxyphenyl)-7-(4-methoxybenzyl)-1-(1-methyl-1H-pyrazol-4-yl)-1,3,4,7-tetrahydro-2H-pyrazolo[4',3':5,6]pyrido[4,3-d]pyrimidin-2-one

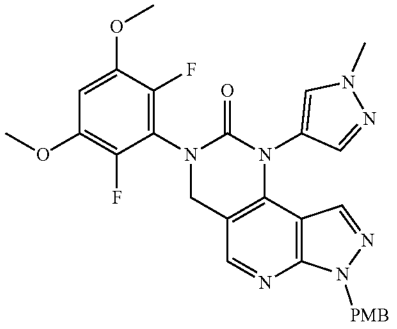

The crude product from step 1 was dissolved in tetrahydrofuran (3 mL, 40 mmol) and cooled to 0° C. then triphosgene (75 mg, 0.25 mmol) and triethylamine (150 μL, 1.0 mmol) were added. The mixture was stirred at room temperature for 1 hour then concentrated. The residue was purified by flash chromatography to give the desired product. LC-MS calculated for $C_{28}H_{26}F_2N_7O_4(M+H)^+$ m/z: 562.2; found: 562.2.

Step 3: 3-(2,6-difluoro-3,5-dimethoxyphenyl)-1-(1-methyl-1H-pyrazol-4-yl)-1,3,4,7-tetrahydro-2H-pyrazolo[4',3':5,6]pyrido[4,3-d]pyrimidin-2-one The product from Step 2 was dissolved in trifluoroacetic acid (2 mL, 20 mmol) and the resulting solution stirred at 70° C. for 1 hour. Then it was concentrated and the residue was purified by prep HPLC (pH 2, ACN/$H_2O$) to give the desired product as a white solid. LC-MS calculated for $C_{20}H_{18}F_2N_7O_3(M+H)^+$ m/z: 442.1; found: 442.1. $^1H$ NMR (500 MHz, DMSO) δ 8.30 (s, 1H), 8.06 (s, 1H), 7.62 (s, 1H), 7.07 (t, J=8.1 Hz, 1H), 6.26 (s, 1H), 4.97 (s, 2H), 3.96 (s, 3H), 3.90 (s, 6H).

Example 86

3-(2,6-difluoro-3,5-dimethoxyphenyl)-1-(pyridin-2-ylmethyl)-1,3,4,7-tetrahydro-2H-pyrazolo[4',3':5,6]pyrido[4,3-d]pyrimidin-2-one

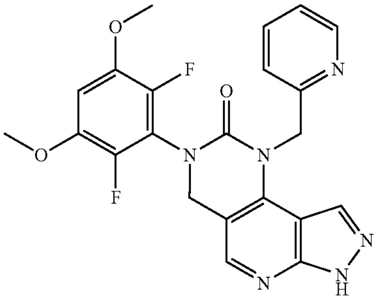 [SMILES: COc1cc(OC)c(F)c(N2Cc3cnc4[nH]ncc4c3N(Cc3ccccn3)C2=O)c1F]

This compound was prepared using procedures analogous to those for Example 85 with 2-pyridinemethanamine replacing 1-methyl-1H-pyrazol-4-amine in Step 1. LC-MS calculated for $C_{22}H_{19}F_2N_6O_3(M+H)^+$ m/z: 453.1; found: 453.1. $^1H$ NMR (500 MHz, DMSO) δ 8.61-8.55 (m, 1H), 8.29 (s, 1H), 7.85 (td, J=7.8, 1.7 Hz, 1H), 7.78 (s, 1H), 7.39-7.31 (m, 2H), 7.06 (t, J=8.1 Hz, 1H), 5.54 (s, 2H), 4.98 (s, 2H), 3.89 (s, 6H).

Example 87

1-cyclopropyl-3-(2,6-difluoro-3,5-dimethoxyphenyl)-1,3,4,7-tetrahydro-2H-pyrazolo[4',3':5,6]pyrido[4,3-d]pyrimidin-2-one

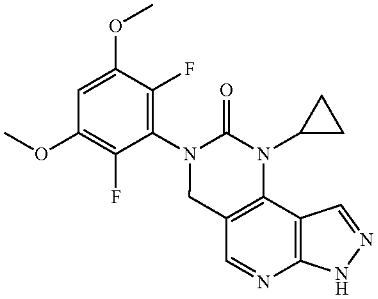 [SMILES: COc1cc(OC)c(F)c(N2Cc3cnc4[nH]ncc4c3N(C3CC3)C2=O)c1F]

This compound was prepared using procedures analogous to those for Example 85 with cyclopropylamine replacing 1-methyl-1H-pyrazol-4-amine in Step 1. LC-MS calculated for $C_{19}H_{18}F_2N_5O_3(M+H)^+$ m/z: 402.1; found: 402.1. $^1H$ NMR (500 MHz, DMSO) δ 13.58 (br, 1H), 8.47 (s, 1H), 8.24 (s, 1H), 7.04 (t, J=8.2 Hz, 1H), 4.70 (s, 2H), 3.88 (s, 6H), 3.38-3.29 (m, 1H), 1.19-1.12 (m, 2H), 0.73-0.66 (m, 2H).

Example 88

3-(2,6-difluoro-3,5-dimethoxyphenyl)-1-[(3S)-tetrahydro-2H-pyran-3-yl]-1,3,4,7-tetrahydro-2H-pyrazolo[4',3':5,6]pyrido[4,3-d]pyrimidin-2-one

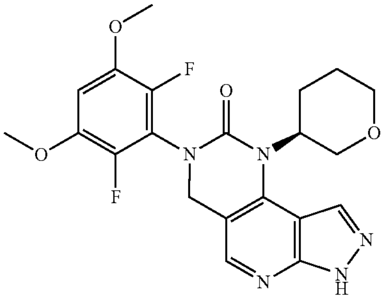 [SMILES: COc1cc(OC)c(F)c(N2Cc3cnc4[nH]ncc4c3N([C@H]3CCCOC3)C2=O)c1F]

This compound was prepared using procedures analogous to those for Example 85 with (3S)-tetrahydro-2H-pyran-3-amine hydrochloride (J & W PharmLab, Cat #20-1041S) replacing 1-methyl-1H-pyrazol-4-amine in Step 1. LC-MS calculated for $C_{21}H_{22}F_2N_5O_4(M+H)^+$ m/z: 446.2; found: 446.1.

Example 89

3-(2,6-difluoro-3,5-dimethoxyphenyl)-1-[(3S)-tetrahydrofuran-3-yl]-1,3,4,7-tetrahydro-2H-pyrazolo[4',3':5,6]pyrido[4,3-d]pyrimidin-2-one

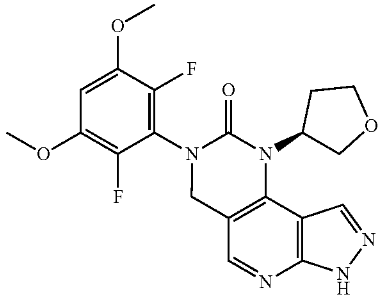 [SMILES: COc1cc(OC)c(F)c(N2Cc3cnc4[nH]ncc4c3N([C@H]3CCOC3)C2=O)c1F]

This compound was prepared using procedures analogous to those for Example 85 with (3S)-tetrahydrofuran-3-amine hydrochloride (Advanced ChemBlocks, Cat #F4071) replacing 1-methyl-1H-pyrazol-4-amine in Step 1. LC-MS calculated for $C_{20}H_{20}F_2N_5O_4(M+H)^+$ m/z: 432.1; found: 432.2.

Example 90

3-(2,6-difluoro-3,5-dimethoxyphenyl)-1-[(3R)-tetrahydrofuran-3-yl]-1,3,4,7-tetrahydro-2H-pyrazolo[4',3':5,6]pyrido[4,3-d]pyrimidin-2-one

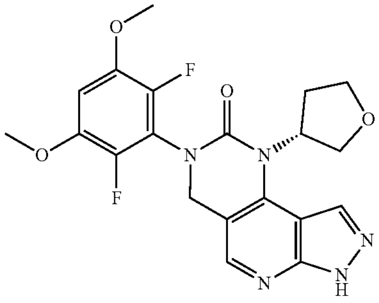 [SMILES: COc1cc(OC)c(F)c(N2Cc3cnc4[nH]ncc4c3N([C@@H]3CCOC3)C2=O)c1F]

This compound was prepared using procedures analogous to those for Example 85 with (3R)-tetrahydrofuran-3-amine hydrochloride (Advanced ChemBlocks, Cat #F4072) replacing 1-methyl-1H-pyrazol-4-amine in Step 1. LC-MS calculated for $C_{20}H_{20}F_2N_5O_4(M+H)^+$ m/z: 432.1; found: 432.1.

Example 91

3-(2,6-difluoro-3,5-dimethoxyphenyl)-1-isopropyl-1,3,4,7-tetrahydro-2H-pyrazolo[4',3':5,6]pyrido[4,3-d]pyrimidin-2-one

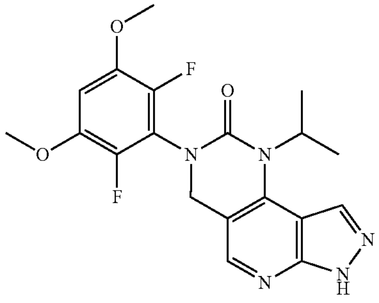 [SMILES: COc1cc(OC)c(F)c(N2Cc3cnc4[nH]ncc4c3N(C(C)C)C2=O)c1F]

This compound was prepared using procedures analogous to those for Example 85 with 2-propanamine replacing 1-methyl-1H-pyrazol-4-amine in Step 1. LC-MS calculated for $C_{19}H_{20}F_2N_5O_3(M+H)^+$ m/z: 404.2; found: 404.1.

Example 92

3-(2,6-difluoro-3,5-dimethoxyphenyl)-1-[2-(trifluoromethoxy)phenyl]-1,3,4,7-tetrahydro-2H-pyrazolo[4',3':5,6]pyrido[4,3-d]pyrimidin-2-one

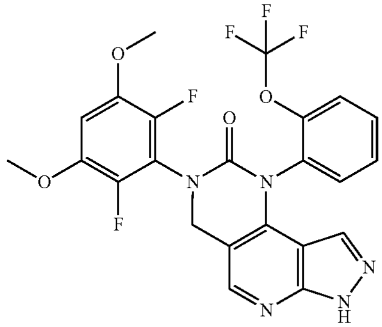 [SMILES: COc1cc(OC)c(F)c(N2Cc3cnc4[nH]ncc4c3N(c3ccccc3OC(F)(F)F)C2=O)c1F]

This compound was prepared using procedures analogous to those for Example 85 with 2-(trifluoromethoxy)aniline replacing 1-methyl-1H-pyrazol-4-amine in Step 1. LC-MS calculated for $C_{23}H_{17}F_5N_5O_4(M+H)^+$ m/z: 522.1; found: 522.1.

Example 93

3-[3-(2,6-difluoro-3,5-dimethoxyphenyl)-2-oxo-2,3,4,7-tetrahydro-1H-pyrazolo[4',3':5,6]pyrido[4,3-d]pyrimidin-1-yl]benzonitrile

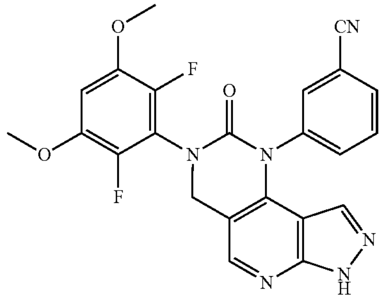 [SMILES: COc1cc(OC)c(F)c(N2Cc3cnc4[nH]ncc4c3N(c3cccc(C#N)c3)C2=O)c1F]

This compound was prepared using procedures analogous to those for Example 85 with 3-aminobenzonitrile replacing 1-methyl-1H-pyrazol-4-amine in Step 1. LC-MS calculated for $C_{23}H_{17}F_2N_6O_3(M+H)^+$ m/z: 463.1; found: 463.0.

Example 94

3-(2,6-difluoro-3,5-dimethoxyphenyl)-1-pyridin-3-yl-1,3,4,7-tetrahydro-2H-pyrazolo[4',3':5,6]pyrido[4,3-d]pyrimidin-2-one

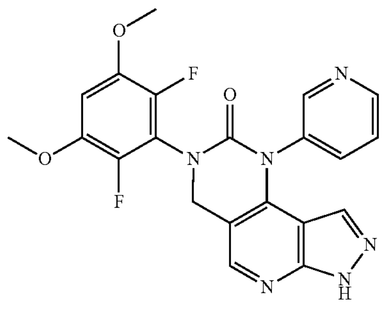 [SMILES: COc1cc(OC)c(F)c(N2Cc3cnc4[nH]ncc4c3N(c3cccnc3)C2=O)c1F]

This compound was prepared using procedures analogous to those for Example 85 with 3-pyridinamine replacing 1-methyl-1H-pyrazol-4-amine in Step 1. LC-MS calculated for $C_{21}H_{17}F_2N_6O_3(M+H)^+$ m/z: 439.1; found: 439.2. $^1$H NMR (500 MHz, DMSO) δ 13.68 (s, 1H), 8.80 (dd, J=4.8, 1.4 Hz, 1H), 8.76 (d, J=2.3 Hz, 1H), 8.35 (s, 1H), 8.08-8.03 (m, 1H), 7.71-7.66 (m, 1H), 7.11-7.05 (m, 1H), 5.72 (s, 1H), 5.06 (s, 2H), 3.90 (s, 6H).

Example 95

3-(2,6-difluoro-3,5-dimethoxyphenyl)-1-(2-methyl-2H-tetrazol-5-yl)-1,3,4,7-tetrahydro-2H-pyrazolo[4',3':5,6]pyrido[4,3-d]pyrimidin-2-one

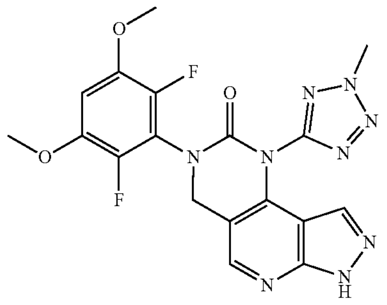 [SMILES: COc1cc(OC)c(F)c(N2Cc3cnc4[nH]ncc4c3N(c3nnn(C)n3)C2=O)c1F]

This compound was prepared using procedures analogous to those for Example 85 with 2-methyl-2H-tetrazol-5-amine (Ark Pharm, Cat #AK-25219) replacing 1-methyl-1H-pyrazol-4-amine in Step 1. LC-MS calculated for $C_{18}H_{16}F_2N_9O_3$ $(M+H)^+$ m/z: 444.1; found: 444.1. $^1$H NMR (300 MHz, DMSO) δ 13.84 (s, 1H), 8.39 (s, 1H), 7.11 (t, J=8.2 Hz, 1H), 6.07 (s, 1H), 5.12 (s, 2H), 4.59 (s, 3H), 3.91 (s, 6H).

Example 96

3-(2,6-difluoro-3,5-dimethoxyphenyl)-1-quinolin-8-yl-1,3,4,7-tetrahydro-2H-pyrazolo[4',3':5,6]pyrido[4,3-d]pyrimidin-2-one

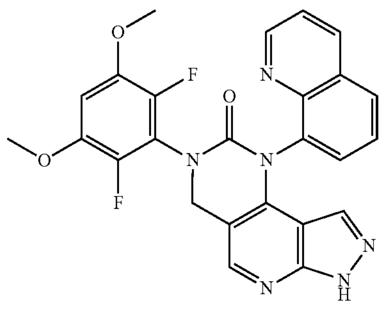 [SMILES: COc1cc(OC)c(F)c(N2Cc3cnc4[nH]ncc4c3N(c3cccc4cccnc34)C2=O)c1F]

This compound was prepared using procedures analogous to those for Example 85 with 8-quinolinamine replacing 1-methyl-1H-pyrazol-4-amine in Step 1. LC-MS calculated for $C_{25}H_{19}F_2N_6O_3(M+H)^+$ m/z: 489.1; found: 489.2.

Example 97

1-cyclopropyl-3-(2,6-difluoro-3,5-dimethoxyphenyl)-9-methyl-1,3,4,7-tetrahydro-2H-pyrazolo[4',3':5,6]pyrido[4,3-d]pyrimidin-2-one

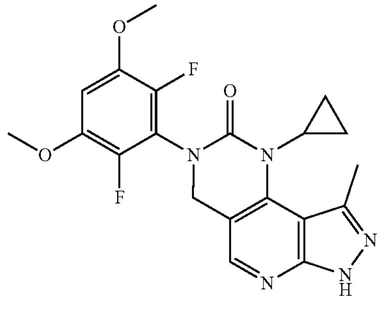 [SMILES: COc1cc(OC)c(F)c(N2Cc3cnc4[nH]nc(C)c4c3N(C3CC3)C2=O)c1F]

This compound was prepared using procedures analogous to those for Example 52 with 1-cyclopropyl-3-(2,6-difluoro-3,5-dimethoxyphenyl)-1,3,4,7-tetrahydro-2H-pyrazolo[4',3':5,6]pyrido[4,3-d]pyrimidin-2-one (Example 87) replacing 3-(2,6-difluoro-3,5-dimethoxyphenyl)-1-methyl-1,3,4,7-tetrahydro-2H-pyrazolo[4',3':5,6]pyrido[4,3-d]pyrimidin-2-one in Step 1. LC-MS calculated for $C_{20}H_{20}F_2N_5O_3(M+H)^+$ m/z: 416.2; found: 416.1.

Example 98

3-(2,6-difluoro-3,5-dimethoxyphenyl)-1-ethyl-9-methyl-1,3,4,7-tetrahydro-2H-pyrazolo[4',3':5,6] pyrido[4,3-d]pyrimidin-2-one

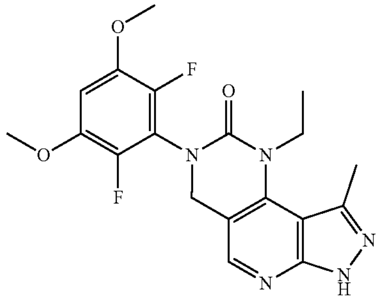 [SMILES: CCN1C(=O)N(c2c(F)c(OC)cc(OC)c2F)Cc2cnc3[nH]nc(C)c3c21]

This compound was prepared using procedures analogous to those for Example 52 with 3-(2,6-difluoro-3,5-dimethoxyphenyl)-1-ethyl-1,3,4,7-tetrahydro-2H-pyrazolo[4',3':5,6]pyrido[4,3-d]pyrimidin-2-one (Example 57) replacing 3-(2,6-difluoro-3,5-dimethoxyphenyl)-1-methyl-1,3,4,7-tetrahydro-2H-pyrazolo[4',3':5,6]pyrido[4,3-d]pyrimidin-2-one in Step 1. LC-MS calculated for $C_{19}H_{20}F_2N_5O_3(M+H)^+$ m/z: 404.2; found: 404.2. $^1H$ NMR (500 MHz, DMSO) δ 13.35 (s, 1H), 8.24 (s, 1H), 7.04 (t, J=8.1 Hz, 1H), 4.74 (s, 2H), 4.13 (q, J=6.9 Hz, 2H), 3.88 (s, 6H), 2.65 (s, 3H), 1.21 (t, J=6.9 Hz, 3H).

Example 99

3-(2,6-difluoro-3,5-dimethoxyphenyl)-1,3,4,7-tetrahydro-2H-pyrazolo[4',3':5,6]pyrido[4,3-d]pyrimidin-2-one

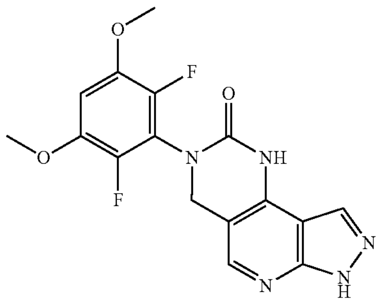 [SMILES: COc1cc(OC)c(F)c(N2Cc3cnc4[nH]ncc4c3NC2=O)c1F]

Step 1: 1-allyl-3-(2,6-difluoro-3,5-dimethoxyphenyl)-7-(4-methoxybenzyl)-1,3,4,7-tetrahydro-2H-pyrazolo[4',3':5,6]pyrido[4,3-d]pyrimidin-2-one

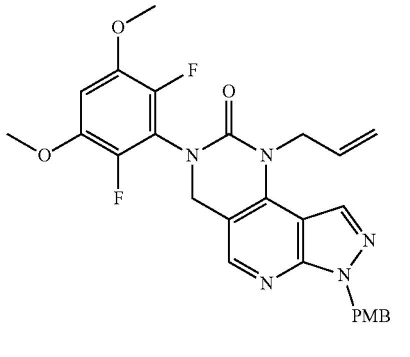

This compound was prepared using procedures analogous to those for Example 51, Step 1-2. LC-MS calculated for $C_{27}H_{26}F_2N_5O_4(M+H)^+$ m/z: 522.2; found: 522.2.

Step 2: 3-(2,6-difluoro-3,5-dimethoxyphenyl)-7-(4-methoxybenzyl)-1,3,4,7-tetrahydro-2H-pyrazolo[4',3':5,6]pyrido[4,3-d]pyrimidin-2-one

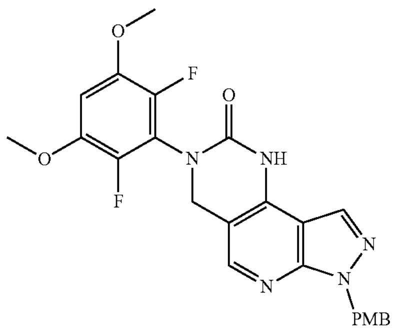

To a solution of 1-allyl-3-(2,6-difluoro-3,5-dimethoxyphenyl)-7-(4-methoxybenzyl)-1,3,4,7-tetrahydro-2H-pyrazolo[4',3':5,6]pyrido[4,3-d]pyrimidin-2-one (30.0 mg, 0.0575 mmol) in ethanol (1.0 mL, 17 mmol) and N-ethylethanamine (1.0 mL, 9.7 mmol) under nitrogen were added 1,4-bis(diphenylphosphino)butane (7.6 mg, 0.017 mmol) and tris(dibenzylideneacetone)dipalladium(O) (16 mg, 0.017 mmol). The resulting mixture was heated to 90° C. and stirred for 6 h then concentrated. The residue was purified by column eluted with 1 to 10% MeOH in DCM to afford the desired product. LC-MS calculated for $C_{24}H_{22}F_2N_5O_4(M+H)^+$ m/z: 482.2; found: 482.2.

Step 3: 3-(2,6-difluoro-3,5-dimethoxyphenyl)-1,3,4,7-tetrahydro-2H-pyrazolo[4',3':5,6]pyrido [4,3-d] pyrimidin-2-one The product from step 2 was dissolved in TFA (1 mL) then heated to 75° C. and stirred for 1 h. The mixture was cooled to room temperature and concentrated. The residue was purified by prep HPLC (pH 2, acetonitrile/water) to give the desired product. LC-MS calculated for $C_{16}H_{14}F_2N_5O_3(M+H)^+$ m/z: 362.1; found: 362.2.

Example 100

3-(2,6-difluoro-3,5-dimethoxyphenyl)-1-methyl-9-(2-morpholin-4-ylethyl)-1,3,4,7-tetrahydro-2H-pyrazolo[4',3':5,6]pyrido[4,3-d]pyrimidin-2-one

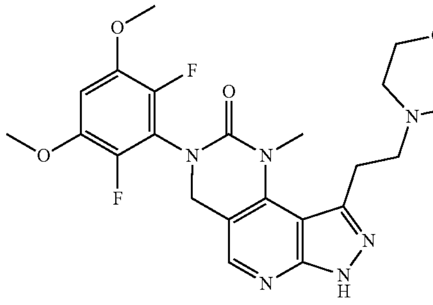

Step 1: 3-(2,6-difluoro-3,5-dimethoxyphenyl)-9-[(Z)-2-ethoxyvinyl]-1-methyl-1,3,4,7-tetrahydro-2H-pyrazolo[4',3':5,6]pyrido[4,3-d]pyrimidin-2-one

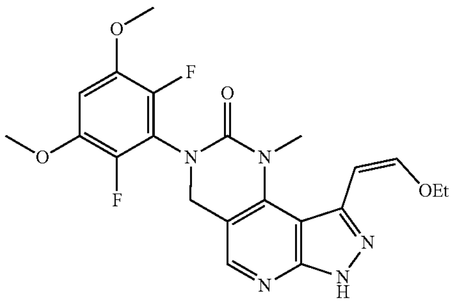 [SMILES: CCO/C=C\c1n[nH]c2ncc3c(c12)N(C)C(=O)N(c1c(F)c(OC)cc(OC)c1F)C3]

A mixture of 2-[(Z)-2-ethoxyvinyl]-4,4,5,5-tetramethyl-1,3,2-dioxaborolane (157 mg, 0.792 mmol), 9-bromo-3-(2,6-difluoro-3,5-dimethoxyphenyl)-1-methyl-1,3,4,7-tetrahydro-2H-pyrazolo[4',3':5,6]pyrido[4,3-d]pyrimidin-2-one (180.0 mg, 0.3963 mmol), [1,1'-bis(diphenylphosphino)ferrocene]dichloropalladium(II) complexed with dichloromethane (1:1) (48 mg, 0.059 mmol) and potassium carbonate (160 mg, 1.2 mmol) in 1,4-dioxane (3.0 mL)/water (1.0 mL) was heated at 88° C. for 1.5 h. The mixture was cooled to room temperature then diluted with water, extracted with DCM. The organic layer was washed with brine then dried over $Na_2SO_4$ and concentrated. The residue was purified via flash column to afford the desired product. LC-MS calculated for $C_{21}H_{22}F_2N_5O_4(M+H)^+$ m/z: 446.2; found: 446.1.

Step 2: [3-(2,6-difluoro-3,5-dimethoxyphenyl)-1-methyl-2-oxo-2,3,4,7-tetrahydro-1H-pyrazolo[4',3':5,6]pyrido[4,3-d]pyrimidin-9-yl]acetaldehyde

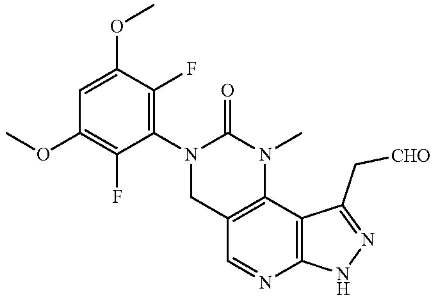 [SMILES: COc1cc(OC)c(F)c(N2Cc3cnc4[nH]nc(CC=O)c4c3N(C)C2=O)c1F]

The product from Step 2 was dissolved in acetone (2 mL) and ten drops of concentrated HCl was added. The resulting mixture was stirred at room temperature for 5 h then diluted with EtOAc and washed with saturated $NaHCO_3$ and brine. The organic layer was dried over $Na_2SO_4$ and concentrated. The residue was used in the next step without further purification.

Step 3: 3-(2,6-difluoro-3,5-dimethoxyphenyl)-1-methyl-9-(2-morpholin-4-ylethyl)-1,3,4,7-tetrahydro-2H-pyrazolo[4',3':5,6]pyrido[4,3-d]pyrimidin-2-one To a solution of the product from step 1 in MeOH was added morpholine (3 eq.) and sodium cyanoborohydride (3 eq.). The resulting mixture was stirred at room temperature for 1 h then purified by prep HPLC (pH 2, acetonitrile/water) to give the desired product. LC-MS calculated for $C_{23}H_{27}F_2N_6O_4(M+H)^+$ m/z: 489.2; found: 489.2. $^1H$ NMR (300 MHz, DMSO) δ 13.67 (s, 1H), 8.25 (s, 1H), 7.04 (t, J=8.2 Hz, 1H), 4.81 (s, 2H), 4.07-3.97 (m, 2H), 3.88 (s, 6H), 3.77-3.46 (m, 11H), 3.30-3.13 (m, 2H).

Example 101

3-(2-chloro-6-fluoro-3,5-dimethoxyphenyl)-1-cyclopropyl-1,3,4,7-tetrahydro-2H-pyrazolo[4',3':5,6]pyrido[4,3-d]pyrimidin-2-one

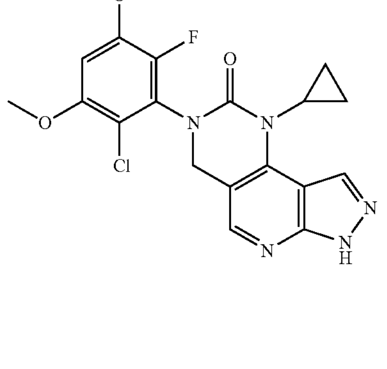

Step 1: 2-chloro-N-{[4-chloro-1-(4-methoxybenzyl)-1H-pyrazolo[3,4-b]pyridin-5-yl]methyl}-6-fluoro-3,5-dimethoxyaniline

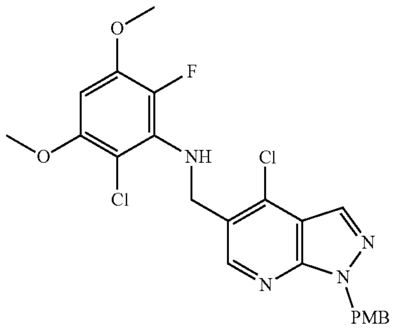

This compound was prepared using procedures analogous to those for Example 62, Step 2 with 2-chloro-6-fluoro-3,5-dimethoxyaniline replacing 2,6-difluoro-3,5-dimethoxyaniline. LC-MS calculated for $C_{23}H_{22}Cl_2FN_4O_3(M+H)^+$ m/z: 491.1; found: 491.1.

Step 2: 3-(2-chloro-6-fluoro-3,5-dimethoxyphenyl)-1-cyclopropyl-1,3,4,7-tetrahydro-2H-pyrazolo[4',3':5,6]pyrido[4,3-d]pyrimidin-2-one This compound was prepared using procedures analogous to those for Example 85 with 2-chloro-N-{[4-chloro-1-(4-methoxybenzyl)-1H-pyrazolo[3,4-b]pyridin-5-yl]methyl}-6-fluoro-3,5-dimethoxyaniline replacing N-{[4-chloro-1-(4-methoxybenzyl)-1H-pyrazolo[3,4-b]pyridin-5-yl]methyl}-2,6-difluoro-3,5-dimethoxyaniline and cyclopropylamine replacing 1-methyl-1H-pyrazol-4-amine dihydrochloride. LC-MS calculated for $C_{19}H_{18}ClFN_5O_3(M+H)^+$ m/z: 418.1; found: 418.0.

Example 102

3-(2-chloro-6-fluoro-3,5-dimethoxyphenyl)-1-cyclobutyl-1,3,4,7-tetrahydro-2H-pyrazolo[4',3':5,6]pyrido[4,3-d]pyrimidin-2-one

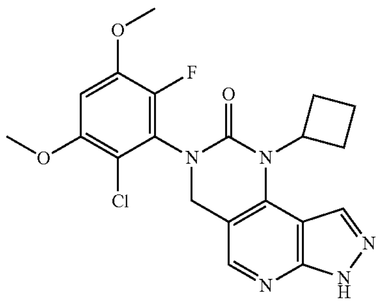 [SMILES: COc1cc(OC)c(Cl)c(N2Cc3cnc4[nH]ncc4c3N(C3CCC3)C2=O)c1F]

This compound was prepared using procedures analogous to those for Example 101 with cyclobutylamine replacing cyclopropylamine. LC-MS calculated for $C_{20}H_{20}ClFN_5O_3$ $(M+H)^+$ m/z: 432.1; found: 432.1. $^1H$ NMR (500 MHz, DMSO) δ 13.63 (s, 1H), 8.29 (s, 2H), 7.01 (d, J=7.7 Hz, 1H), 4.90-4.80 (m, 1H), 4.69 (s, 2H), 3.93 (s, 3H), 3.90 (s, 3H), 2.55-2.45 (m, 2H), 2.40-2.30 (m, 2H), 1.88-1.71 (m, 2H).

Example 103

3-(2,6-difluoro-3,5-dimethoxyphenyl)-1,3,4,7-tetrahydro-2H-pyrrolo[3',2':5,6]pyrido[4,3-d]pyrimidin-2-one

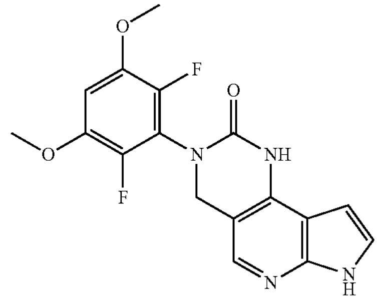 [SMILES: COc1cc(OC)c(F)c(N2Cc3cnc4[nH]ccc4c3NC2=O)c1F]

A mixture of 3-(2,6-difluoro-3,5-dimethoxyphenyl)-1-(2-hydroxyethyl)-7-(phenylsulfonyl)-1,3,4,7-tetrahydro-2H-pyrrolo[3',2':5,6]pyrido[4,3-d]pyrimidin-2-one (Example 44, Step 4: 52 mg, 0.095 mmol) and 1.0 M potassium tert-butoxide in THF (1.0 mL, 1.0 mmol) was stirred at room temperature for 1 h. The mixture was diluted with methylene chloride, washed with saturated $NaHCO_3$, water and brine. The organic layer was dried over $Na_2SO_4$ and concentrated. The residue was dissolved in methanol and Pd/C (10%, 10 mg) was added and the reaction mixture was stirred under hydrogen balloon for 3 h. The mixture was filtered and the filtrate was purified by prep-HPLC (pH 2, acetonitrile/water) to give the desired product. LC-MS calculated for $C_{17}H_{15}F_2N_4O_3(M+H)^+$ m/z: 361.1; found: 361.1.

Example 104

3-(2,6-difluoro-3,5-dimethoxyphenyl)-1,9-dimethyl-1,3,4,7-tetrahydro-2H-pyrrolo[3',2':5,6]pyrido[4,3-d]pyrimidin-2-one

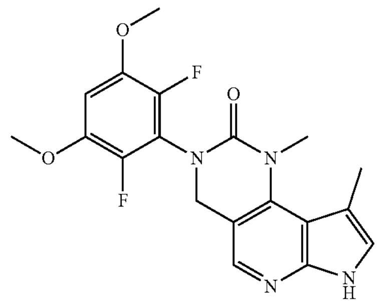 [SMILES: COc1cc(OC)c(F)c(N2Cc3cnc4[nH]cc(C)c4c3N(C)C2=O)c1F]

Step 1: tert-butyl 3-(2,6-difluoro-3,5-dimethoxyphenyl)-9-iodo-1-methyl-2-oxo-1,2,3,4-tetrahydro-7H-pyrrolo[3',2':5,6]pyrido[4,3-d]pyrimidine-7-carboxylate

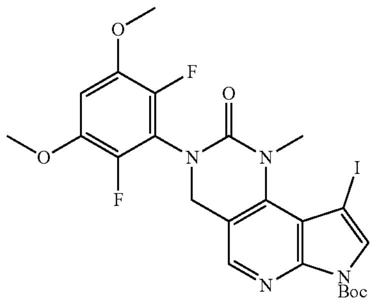 [SMILES: COc1cc(OC)c(F)c(N2Cc3cnc4c(c(I)cn4C(=O)OC(C)(C)C)c3N(C)C2=O)c1F]

To a solution of 3-(2,6-difluoro-3,5-dimethoxyphenyl)-1-methyl-1,3,4,7-tetrahydro-2H-pyrrolo[3',2':5,6]pyrido[4,3-d]pyrimidin-2-one (Example 33: 0.99 g, 2.6 mmol) in N,N-dimethylformamide (20 mL, 200 mmol) was added potassium hydroxide (160 mg, 2.9 mmol). The mixture was stirred at room temperature for 15 min then iodine (1.0 g, 4.0 mmol) was added. The resulting solution was stirred at room temperature for 1 h then di-tert-butyldicarbonate (860 mg, 4.0 mmol) and 4-dimethylaminopyridine (60 mg, 0.5 mmol) were added. The reaction mixture was stirred at room temperature for 1 h. The mixture was diluted with EtOAc then washed with water and brine. The organic layer was dried over $Na_2SO_4$ and concentrated. The residue was purified by column eluted with 0 to 10% AcOEt in $CH_2Cl_2$. LC-MS calculated for $C_{23}H_{24}F_{21}N_4O_5(M+H)^+$ m/z: 601.1; found: 601.0.

Step 2: 3-(2,6-difluoro-3,5-dimethoxyphenyl)-1,9-dimethyl-1,3,4,7-tetrahydro-2H-pyrrolo[3',2':5,6]pyrido[4,3-d]pyrimidin-2-one A mixture of tert-butyl 3-(2,6-difluoro-3,5-dimethoxyphenyl)-9-iodo-1-methyl-2-oxo-1,2,3,4-tetrahydro-7H-pyrrolo[3',2':5,6]pyrido[4,3-d]pyrimidine-7-carboxylate (100.0 mg, 0.1666 mmol), 2.0 M dimethylzinc in toluene (0.17 mL, 0.33 mmol), bis(tri-t-butylphosphine)palladium (5 mg, 0.01 mmol) in tetrahydrofuran (5 mL, 60 mmol) was evacuated and filled with nitrogen. The reaction mixture was stirred at 65° C. for 2.5 h then cooled to room temperature and filtered. The filtrate was diluted with methanol and purified with prep-HPLC (pH 2, acetonitrile/water) to give the desired product. LC-MS calculated for $C_{19}H_{19}F_2N_4O_3$ $(M+H)^+$ m/z: 389.1; found: 389.0. $^1H$ NMR (500 MHz, DMSO) δ 11.78 (s, 1H), 8.02 (s, 1H), 7.35 (s, 1H), 7.02 (t, J=8.1 Hz, 1H), 4.76 (s, 2H), 3.88 (s, 6H), 3.51 (s, 3H), 2.42 (s, 3H).

Example 105

[3-(2,6-difluoro-3,5-dimethoxyphenyl)-1-methyl-2-oxo-2,3,4,7-tetrahydro-1H-pyrrolo[3',2':5,6]pyrido[4,3-d]pyrimidin-9-yl]acetonitrile

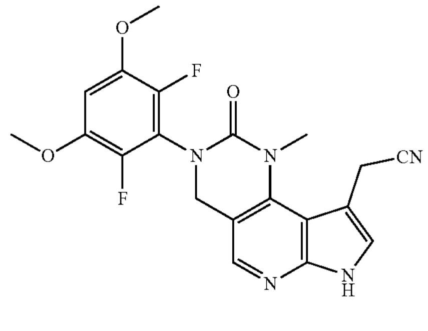 [SMILES: COc1cc(OC)c(F)c(N2Cc3cnc4[nH]cc(CC#N)c4c3N(C)C2=O)c1F]

Step 1: 9-bromo-3-(2,6-difluoro-3,5-dimethoxyphenyl)-1-methyl-7-{[2-(trimethylsilyl)ethoxy]methyl}-1,3,4,7-tetrahydro-2H-pyrrolo[3',2':5,6]pyrido[4,3-d]pyrimidin-2-one

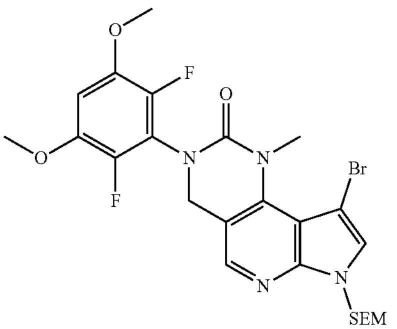 [SMILES: COc1cc(OC)c(F)c(N2Cc3cnc4c(c(Br)cn4COCC[Si](C)(C)C)c3N(C)C2=O)c1F]

To a solution of 3-(2,6-difluoro-3,5-dimethoxyphenyl)-1-methyl-1,3,4,7-tetrahydro-2H-pyrrolo[3',2':5,6]pyrido[4,3-d]pyrimidin-2-one (Example 33: 400 mg, 1.07 mmol) in N,N-dimethylformamide (10 mL) was added N-bromosuccinimide (210 mg, 1.2 mmol). The resulting red solution was stirred at room temperature for 2 h. The reaction was quenched with water and extracted with DCM. The organic layer was washed with brine then dried over $Na_2SO_4$ and concentrated. The residue was dissolved in DMF (5 mL) and cooled to 0° C., then NaH in mineral oil (60 wt %, 0.13 g, 3.2 mmol) was added. The mixture was stirred at 0° C. for 30 min then [(3-(trimethylsilyl)ethoxy]methyl chloride (0.36 g, 2.1 mmol) was added. The reaction mixture was stirred at room temperature for 2 h then diluted with water and extracted with DCM. The organic layer was washed with water, brine, then dried over $Na_2SO_4$ and concentrated. The residue was purified by column eluted with 0 to 10% AcOEt in DCM to give the desired product. LC-MS calculated for $C_{24}H_{30}BrF_2N_4O_4Si$ $(M+H)^+$ m/z: 583.1; found: 583.0.

Step 2: [3-(2,6-difluoro-3,5-dimethoxyphenyl)-1-methyl-2-oxo-2,3,4,7-tetrahydro-1H-pyrrolo[3',2':5,6]pyrido[4,3-d]pyrimidin-9-yl]acetonitrile To a mixture of 9-bromo-3-(2,6-difluoro-3,5-dimethoxyphenyl)-1-methyl-7-{[2-(trimethylsilyl)ethoxy]methyl}-1, 3,4,7-tetrahydro-2H-pyrrolo[3',2':5,6]pyrido[4,3-d]pyrimidin-2-one (60 mg, 0.10 mmol), (9,9-dimethyl-9H-xanthene-4,5-diyl)bis(diphenylphosphine) (1.2 mg, 0.002 mmol), tris (dibenzylideneacetone)dipalladium(O) (1.9 mg, 0.002 mmol), in N,N-dimethylformamide (2 mL) was added (trimethylsilyl)acetonitrile (17.6 μL, 0.128 mmol), followed by zinc difluoride (8.50 mg, 0.0823 mmol). The mixture was evacuated then filled with nitrogen. The reaction mixture was stirred at 110° C. for overnight then cooled to room temperature and diluted with water. The mixture was extracted with EtOAc. The organic layer was washed with water, brine then dried over $Na_2SO_4$ and concentrated. The residue was dissolved in DCM (2 mL) and TFA (2 mL) was added. The resulting solution was stirred at room temperature for 1 h then concentrated. The residue was dissolved in MeOH then ethylenediamine was added. The mixture was stirred at room temperature for 1 h then purified by prep HPLC (pH 2, acetonitrile/water) to give the desired product. LC-MS calculated for $C_{20}H_{18}F_2N_5O_3(M+H)^+$ m/z: 414.1; found: 414.1.

Example 106

3-(2-chloro-6-fluoro-3,5-dimethoxyphenyl)-1-cyclobutyl-3,4,7,9-tetrahydro-1H-pyrrolo[3', 2':5,6] pyrido[4,3-d]pyrimidine-2,8-dione

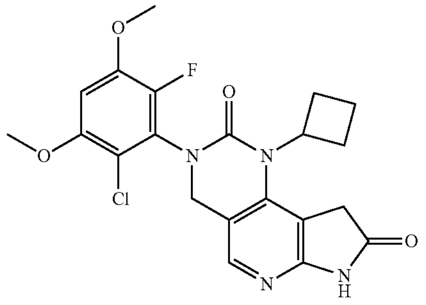 [SMILES: COc1cc(OC)c(Cl)c(N2Cc3cnc4c(c3N(C3CCC3)C2=O)CC(=O)N4)c1F]

Step 1: 4-chloro-1-{[2-(trimethylsilyl)ethoxy] methyl}-1H-pyrrolo[2,3-b]pyridine-5-carbaldehyde

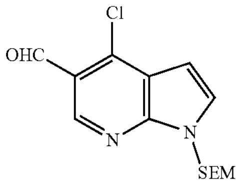 [SMILES: C[Si](C)(C)CCOCn1ccc2c(Cl)c(C=O)cnc21]

To a solution of 4-chloro-1H-pyrrolo[2,3-b]pyridine-5-carbaldehyde (2.0 g, 11 mmol) in N,N-dimethylformamide (20 mL) was added sodium hydride (60 wt % in mineral oil, 580 mg, 14 mmol) portion-wise at 0° C. The mixture was stirred at 0° C. for 30 min then [β-(Trimethylsilyl)ethoxy] methyl chloride (2.4 mL, 13 mmol) was added dropwise. The reaction mixture was stirred at 0° C. for 1.5 h then quenched with saturated $NH_4Cl$ solution. The mixture was then extracted with EtOAc. The combined organic layer was washed with water, brine then dried over $Na_2SO_4$ and concentrated. The residue was purified by column eluted with 0 to 20% EtOAc in Hexanes to give the desired product (2.3 g, 67%) as a white solid. LC-MS calculated for $C_{14}H_{20}ClN_2O_2Si$ $(M+H)^+$ m/z: 311.1; found: 311.0.

Step 2: 2-chloro-N-[(4-chloro-1-{[2-(trimethylsilyl) ethoxy]methyl}-1H-pyrrolo[2,3-b]pyridin-5-yl) methyl]-6-fluoro-3,5-dimethoxyaniline

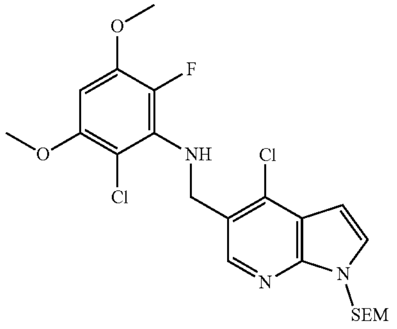

To a solution of sodium triacetoxyborohydride (1.8 g, 8.8 mmol) in trifluoroacetic acid (4 mL) at 0° C. was added dropwise a solution of 4-chloro-1-{[2-(trimethylsilyl) ethoxy]methyl}-1H-pyrrolo[2,3-b]pyridine-5-carbaldehyde (600 mg, 1.9 mmol) and 2-chloro-6-fluoro-3,5-dimethoxyaniline (400.0 mg, 1.945 mmol) in methylene chloride (10 mL). The reaction mixture was stirred at 0° C. for 1 h then poured into ice-water and neutralized with $NaHCO_3$. The mixture was extracted with $CH_2Cl_2$. The organic layer was washed with brine, dried over $Na_2SO_4$ and concentrated. The residue was purified by column eluted with 0 to 5% AcOEt in $CH_2Cl_2$ to give the desired product (0.6 g, 60%). LC-MS calculated for $C_{22}H_{29}Cl_2FN_3O_3Si$ $(M+H)^+$ m/z: 500.1; found: 500.0.

Step 3: 5-{[(2-chloro-6-fluoro-3,5-dimethoxyphenyl)amino]methyl}-N-cyclobutyl-1-{[2-(trimethylsilyl)ethoxy]methyl}-1H-pyrrolo[2,3-b]pyridin-4-amine

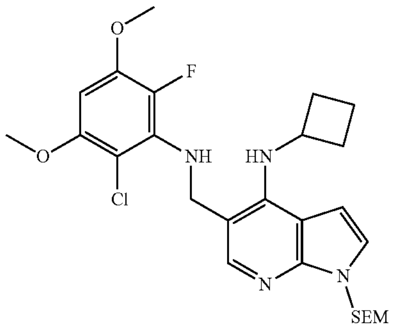 [SMILES: COc1cc(OC)c(Cl)c(NCc2cnc3c(ccn3COCC[Si](C)(C)C)c2NC2CCC2)c1F]

A mixture of 2-chloro-N-[(4-chloro-1-{[2-(trimethylsilyl) ethoxy]methyl}-1H-pyrrolo[2,3-b]pyridin-5-yl)methyl]-6-fluoro-3,5-dimethoxyaniline (0.10 g, 0.20 mmol), cyclobutylamine (34 μL, 0.40 mmol), palladium acetate (4.5 mg, 0.020 mmol), (9,9-dimethyl-9H-xanthene-4,5-diyl)bis (diphenylphosphine) (10 mg, 0.02 mmol), and cesium carbonate ($2.0\times10^2$ mg, 0.60 mmol) in 1,4-dioxane (2 mL, 20 mmol) was evacuated then filled with nitrogen. The mixture was stirred at 160° C. for overnight. The reaction mixture was cooled to room temperature then diluted with ethyl acetate (20 mL), filtered and concentrated under reduced pressure. The residue was purified by flash chromatography on a silica gel column eluted with MeOH in DCM (0-5%) to afford the desired product. LC-MS calculated for $C_{26}H_{37}ClFN_4O_3Si$ $(M+H)^+$ m/z: 535.2; found: 535.1.

Step 4: 3-(2-chloro-6-fluoro-3,5-dimethoxyphenyl)-1-cyclobutyl-7-{[2-(trimethylsilyl)ethoxy]methyl}-1,3,4,7-tetrahydro-2H-pyrrolo[3',2':5,6]pyrido[4,3-d]pyrimidin-2-one

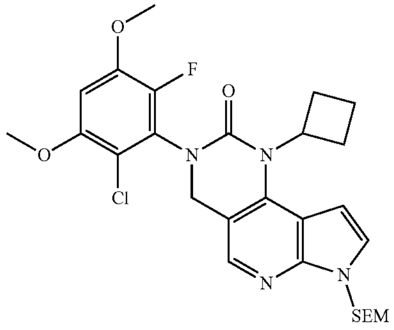 [SMILES: COc1cc(OC)c(Cl)c(N2Cc3cnc4c(ccn4COCC[Si](C)(C)C)c3N(C3CCC3)C2=O)c1F]

To a solution of 5-{[(2-chloro-6-fluoro-3,5-dimethoxyphenyl)amino]methyl}-N-cyclobutyl-1-{[2-(trimethylsilyl)ethoxy]methyl}-1H-pyrrolo[2,3-b]pyridin-4-amine (82 mg, 0.15 mmol) in THF (5 mL) at 0° C. was added triethylamine (110 μL, 0.76 mmol), followed by triphosgene (68 mg, 0.23 mmol). The resulting mixture was stirred at 0° C. for 30 min then 1 N NaOH (2 mL) was added. The mixture was stirred at 0° C. for 10 min then diluted with water and extracted with EtOAc. The organic layer was washed with brine then dried over $Na_2SO_4$ and concentrated. The residue was used in the next step without further purification. LC-MS calculated for $C_{27}H_{35}ClFN_4O_4Si$ $(M+H)^+$ m/z: 561.2; found: 561.1.

Step 5: 3-(2-chloro-6-fluoro-3,5-dimethoxyphenyl)-1-cyclobutyl-3,4,7,9-tetrahydro-1H-pyrrolo[3',2':5,6]pyrido[4,3-d]pyrimidine-2,8-dione To a mixture of 3-(2-chloro-6-fluoro-3,5-dimethoxyphenyl)-1-cyclobutyl-7-{[2-(trimethylsilyl)ethoxy]methyl}-1,3,4,7-tetrahydro-2H-pyrrolo[3',2':5,6]pyrido[4,3-d]pyrimidin-2-one (82 mg, 0.15 mmol) in isopropyl alcohol (0.6 mL) and water (0.04 mL) was added pyridinium tribromide (180 mg, 0.51 mmol). The resulting solution was stirred at 30° C. for 2 h then cooled to room temperature and acetic acid (0.5 mL, 9 mmol) and zinc (95 mg, 1.5 mmol) were added. The mixture was stirred at room temperature for 2 h then filtered and the filtrate was concentrated. The residue was dissolved in DCM (1 mL) and TFA (1 mL) was added. The resulting solution was stirred at room temperature for 1 h then concentrated. The residue was dissolved in MeOH (2 mL) then ethylenediamine (0.2 mL) was added. The mixture was stirred at room temperature for 1 h then purified by prep HPLC (pH 2, acetonitrile/water) to give the desired product. LC-MS calculated for $C_{21}H_{21}ClFN_4O_4(M+H)^+$ m/z: 447.1; found: 447.0.

Example 107

3-(2-chloro-6-fluoro-3,5-dimethoxyphenyl)-1-(1-methyl-1H-pyrazol-4-yl)-1,3,4,7-tetrahydro-2H-pyrrolo[3',2':5,6]pyrido[4,3-d]pyrimidin-2-one

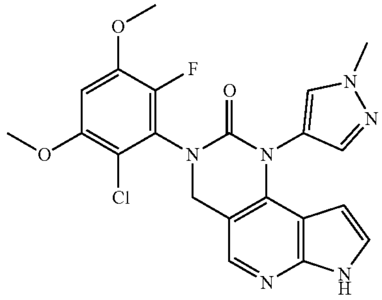 [SMILES: COc1cc(OC)c(Cl)c(N2Cc3cnc4[nH]ccc4c3N(c3cnn(C)c3)C2=O)c1F]

This compound was prepared using procedures analogous to those for Example 45 with 2-chloro-6-fluoro-3,5-dimethoxyaniline replacing 2,6-difluoro-3,5-dimethoxyaniline in Step 1 and 1-methyl-1H-pyrazol-4-amine dihydrochloride replacing cyclopropylamine in Step 3. LC-MS calculated for $C_{21}H_{19}ClFN_6O_3(M+H)^+$ m/z: 457.1; found: 457.0.

Example 108

3-(2-chloro-6-fluoro-3,5-dimethoxyphenyl)-1-pyridin-3-yl-1,3,4,7-tetrahydro-2H-pyrrolo[3',2':5,6]pyrido[4,3-d]pyrimidin-2-one

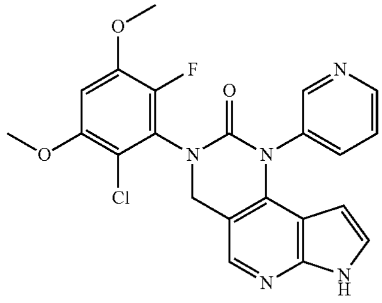

This compound was prepared using procedures analogous to those for Example 107 with 3-pyridinamine replacing 1-methyl-1H-pyrazol-4-amine dihydrochloride. LC-MS calculated for $C_{22}H_{18}ClFN_5O_3(M+H)^+$ m/z: 454.1; found: 454.1.

Example 109

3-(2,6-difluoro-3,5-dimethoxyphenyl)-1-pyridazin-3-yl-1,3,4,7-tetrahydro-2H-pyrrolo[3',2':5,6]pyrido[4,3-d]pyrimidin-2-one

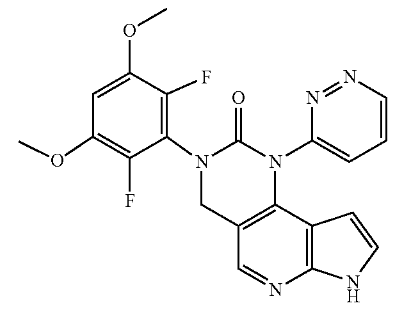 [SMILES: COc1cc(OC)c(F)c(N2Cc3cnc4[nH]ccc4c3N(c3cccnn3)C2=O)c1F]

This compound was prepared using procedures analogous to those for Example 45 with pyridazin-3-amine replacing cyclopropylamine in Step 3. LC-MS calculated for $C_{21}H_{17}F_2N_6O_3$ $(M+H)^+$ m/z: 439.1; found: 439.2.

Example 110

3-(2,6-difluoro-3,5-dimethoxyphenyl)-1-methyl-8-(morpholin-4-ylmethyl)-1,3,4,7-tetrahydro-2H-pyrrolo[3',2':5,6]pyrido[4,3-d]pyrimidin-2-one

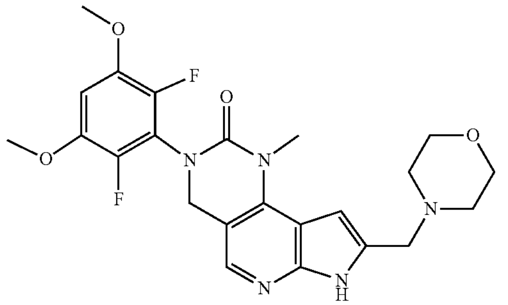 [SMILES: COc1cc(OC)c(F)c(N2Cc3cnc4[nH]c(CN5CCOCC5)cc4c3N(C)C2=O)c1F]

Step 1: 3-(2,6-difluoro-3,5-dimethoxyphenyl)-1-methyl-8-(morpholin-4-ylmethyl)-7-(phenylsulfonyl)-1,3,4,7-tetrahydro-2H-pyrrolo[3',2':5,6]pyrido[4,3-d]pyrimidin-2-one

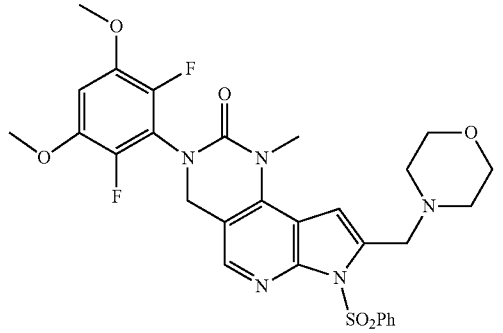

To a solution of 3-(2,6-difluoro-3,5-dimethoxyphenyl)-1-methyl-2-oxo-7-(phenylsulfonyl)-2,3,4,7-tetrahydro-1H-pyrrolo[3',2':5,6]pyrido[4,3-d]pyrimidine-8-carbaldehyde (Example 70, Step 1: 1.09 g, 2.01 mmol) in methylene chloride (30 mL) was added morpholine (880 μL, 10. mmol), followed by acetic acid (1.0 mL, 18 mmol). The resulting yellow solution was stirred at room temperature overnight, then sodium triacetoxyborohydride (1.3 g, 6.0 mmol) was added. The mixture was stirred at room temperature for 4 h at which time LC-MS indicated the reaction completed to the desired product. The reaction was quenched with saturated $NaHCO_3$ solution then extracted with DCM. The organic extracts were combined then washed with water and brine. The organic layer was dried over $Na_2SO_4$ then concentrated. The residue was purified by column eluted with 0 to 40% EtOAc/DCM to give the desired product as white solid (930 mg, 75%). LC-MS calculated for $C_{29}H_{30}F_2N_5O_6S$ $(M+H)^+$ m/z: 614.2; found: 614.0.

Step 2: 3-(2,6-difluoro-3,5-dimethoxyphenyl)-1-methyl-8-(morpholin-4-ylmethyl)-1,3,4,7-tetrahydro-2H-pyrrolo[3',2':5,6]pyrido[4,3-d]pyrimidin-2-one The product from Step 1 was dissolved in tetrahydrofuran (65 mL) then 1.0 M tetra-n-butylammonium fluoride in THF (4.5 mL, 4.5 mmol) was added. The mixture was heated to 60° C. and stirred for 1.5 h at which time LC-MS indicated the reaction completed to the desired product. The mixture was cooled to room temperature then quenched with water and extracted with DCM. The combined extracts were combined then washed with water and brine. The organic layer was dried over $Na_2SO_4$ and concentrated. The residue was purified by column eluted with 0 to 10% MeOH/DCM to give the desired product (649 mg, 68%) which was further purified by prep HPLC (pH=2, acetonitrile/water). LC-MS calculated for $C_{23}H_{26}F_2N_5O_4$ $(M+H)^+$ m/z: 474.2; found: 474.2. $^1H$ NMR (500 MHz, DMSO) δ 11.75 (s, 1H), 8.04 (s, 1H), 7.03 (t, J=8.2 Hz, 1H), 6.95 (s, 1H), 4.77 (s, 2H), 4.39 (s, 2H), 3.89 (s, 6H), 3.81 (br, 4H), 3.67 (s, 3H), 3.18 (br, 4H).

Example 111

3-(2,6-difluoro-3,5-dimethoxyphenyl)-8-[(4-hydroxypiperidin-1-yl)methyl]-1-methyl-1,3,4,7-tetrahydro-2H-pyrrolo[3',2':5,6]pyrido[4,3-d]pyrimidin-2-one

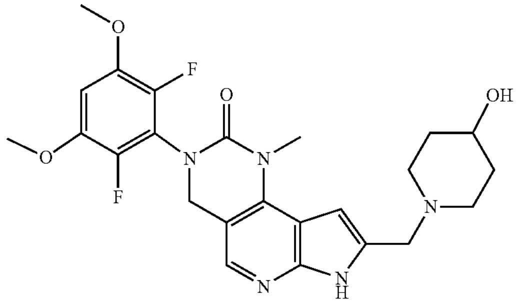 [SMILES: COc1cc(OC)c(F)c(N2Cc3cnc4[nH]c(CN5CCC(O)CC5)cc4c3N(C)C2=O)c1F]

This compound was prepared using procedures analogous to those for Example 70 with 4-hydroxypiperidine replacing 1-ethylpiperazine in Step 2. LC-MS calculated for $C_{24}H_{28}F_2N_5O_4$ (M+H)$^+$ m/z: 488.2; found: 488.1.

Example 112

3-(2,6-difluoro-3,5-dimethoxyphenyl)-8-[(4,4-difluoropiperidin-1-yl)methyl]-1-methyl-1,3,4,7-tetrahydro-2H-pyrrolo[3',2':5,6]pyrido[4,3-d]pyrimidin-2-one

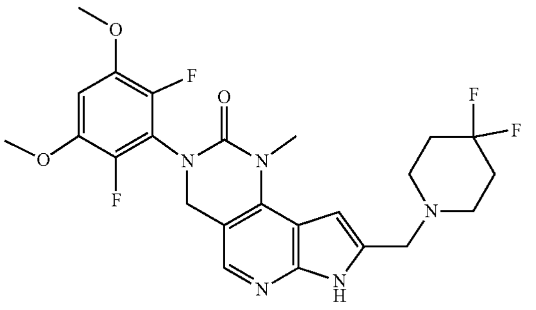 [SMILES: COc1cc(OC)c(F)c(N2Cc3cnc4[nH]c(CN5CCC(F)(F)CC5)cc4c3N(C)C2=O)c1F]

This compound was prepared using procedures analogous to those for Example 70 with 4,4-difluoropiperidine hydrochloride replacing 1-ethylpiperazine in Step 2. LC-MS calculated for $C_{24}H_{26}F_4N_5O_3$(M+H)$^+$ m/z: 508.2; found: 508.2.

Example 113

3-(2,6-difluoro-3,5-dimethoxyphenyl)-8-[(3,3-difluoropiperidin-1-yl)methyl]-1-methyl-1,3,4,7-tetrahydro-2H-pyrrolo[3',2':5,6]pyrido[4,3-d]pyrimidin-2-one

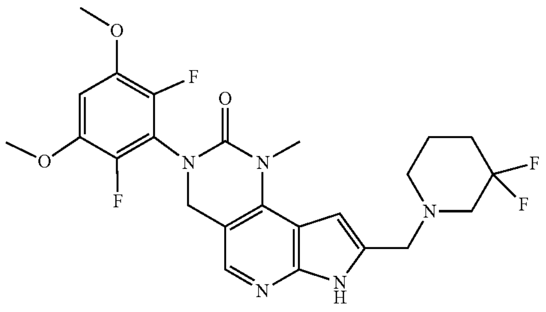 [SMILES: COc1cc(OC)c(F)c(N2Cc3cnc4[nH]c(CN5CCCC(F)(F)C5)cc4c3N(C)C2=O)c1F]

This compound was prepared using procedures analogous to those for Example 70 with 3,3-difluoropiperidine hydrochloride replacing 1-ethylpiperazine in Step 2. LC-MS calculated for $C_{24}H_{26}F_4N_5O_3$(M+H)$^+$ m/z: 508.2; found: 508.2.

Example 114

3-(2,6-difluoro-3,5-dimethoxyphenyl)-1-methyl-8-(2-morpholin-4-ylethyl)-1,3,4,7-tetrahydro-2H-pyrrolo[3',2':5,6]pyrido[4,3-d]pyrimidin-2-one

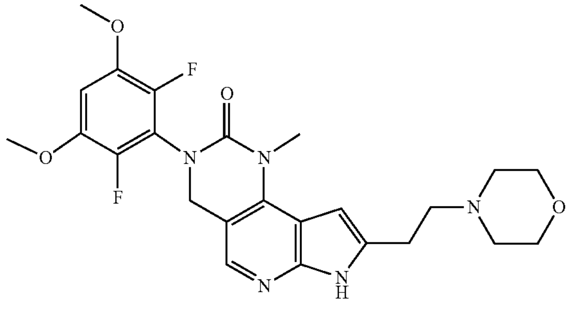 [SMILES: COc1cc(OC)c(F)c(N2Cc3cnc4[nH]c(CCN5CCOCC5)cc4c3N(C)C2=O)c1F]

Step 1: 3-(2,6-difluoro-3,5-dimethoxyphenyl)-1-methyl-8-(2-morpholin-4-ylethyl)-7-(phenylsulfonyl)-1,3,4,7-tetrahydro-2H-pyrrolo[3',2':5,6]pyrido[4,3-d]pyrimidin-2-one

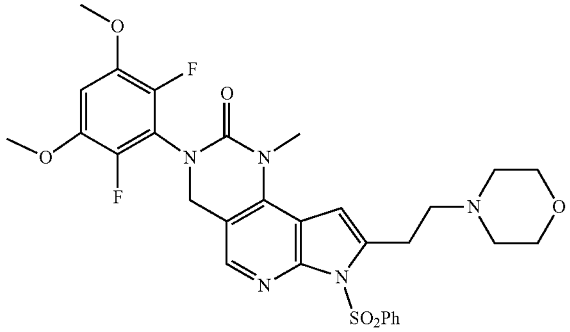

To a solution of [3-(2,6-difluoro-3,5-dimethoxyphenyl)-1-methyl-2-oxo-7-(phenylsulfonyl)-2,3,4,7-tetrahydro-1H-pyrrolo[3',2':5,6]pyrido[4,3-d]pyrimidin-8-yl]acetaldehyde (Example 71, Step 2: 522 mg, 0.938 mmol) in methylene chloride (25 mL, 390 mmol) was added morpholine (0.41 mL, 4.7 mmol), followed by acetic acid (0.32 mL, 5.6 mmol). The mixture was stirred at room temperature for 1 h then sodium triacetoxyborohydride (696 mg, 3.28 mmol) was added. The resulting mixture was stirred at room temperature for 1 h at which time LC-MS indicated the reaction completed to the desired product. The mixture was neutralized with saturated $NaHCO_3$ then extracted with DCM. The combined extracts were washed with brine then dried over $Na_2SO_4$ and concentrated. The residue was purified by column eluted with 0 to 50% EtOAc/DCM then 0 to 10% MeOH/DCM to give the desired product (483 mg, 82%) as a yellow solid. LC-MS calculated for $C_{30}H_{32}F_2N_5O_6S$ (M+H)$^+$ m/z: 628.2; found: 628.0.

Step 2: 3-(2,6-difluoro-3,5-dimethoxyphenyl)-1-methyl-8-(2-morpholin-4-ylethyl)-1,3,4,7-tetrahydro-2H-pyrrolo[3',2':5,6]pyrido[4,3-d]pyrimidin-2-one The product from Step 1 was dissolved in tetrahydrofuran (25 mL) then 1.0 M potassium tert-butoxide in THF (2.3 mL, 2.3 mmol) was added. The resulting mixture was stirred at room temperature for 30 min at which time LC-MS indicated the reaction completed to the desired product. The reaction was quenched with saturated $NH_4Cl$ solution then extracted with EtOAc. The combined extracts were washed with water and brine then dried over $Na_2SO_4$ and concentrated. The residue was purified by column eluted with 0 to 10% MeOH/DCM, to give the desired product (258 mg, 56%) as a white solid which was further purified by prep HPLC (pH=2, acetonitrile/water). LC-MS calculated for $C_{24}H_{28}F_2N_5O_4(M+H)^+$ m/z: 488.2; found: 488.2. $^1H$ NMR (500 MHz, DMSO) δ 11.88 (s, 1H), 7.95 (s, 1H), 7.04 (t, J=8.2 Hz, 1H), 6.67 (s, 1H), 4.75 (s, 2H), 4.06-3.95 (m, 2H), 3.88 (s, 6H), 3.73-3.64 (m, 2H), 3.62 (s, 3H), 3.57-3.46 (m, 4H), 3.22-3.09 (m, 4H).

Example 115

8-(2-azetidin-1-ylethyl)-3-(2,6-difluoro-3,5-dimethoxyphenyl)-1-methyl-1,3,4,7-tetrahydro-2H-pyrrolo[3',2':5,6]pyrido[4,3-d]pyrimidin-2-one

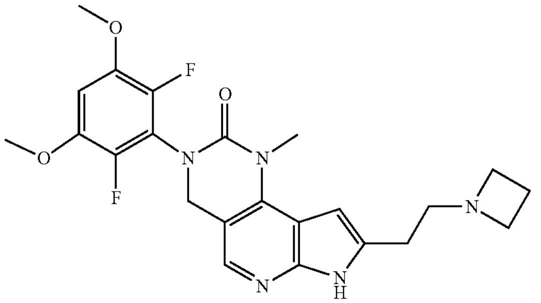 [SMILES: COc1cc(OC)c(F)c(N2Cc3cnc4[nH]c(CCN5CCC5)cc4c3N(C)C2=O)c1F]

This compound was prepared using procedures analogous to those for Example 71 with azetidine hydrochloride replacing 1-ethylpiperazine in Step 3. LC-MS calculated for $C_{23}H_{26}F_2N_5O_3(M+H)^+$ m/z: 458.2; found: 458.3.

Example 116

3-(2,6-difluoro-3,5-dimethoxyphenyl)-1-methyl-8-(2-pyrrolidin-1-ylethyl)-1,3,4,7-tetrahydro-2H-pyrrolo[3',2':5,6]pyrido[4,3-d]pyrimidin-2-one

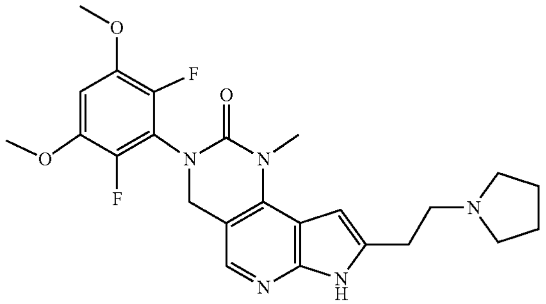 [SMILES: COc1cc(OC)c(F)c(N2Cc3cnc4[nH]c(CCN5CCCC5)cc4c3N(C)C2=O)c1F]

This compound was prepared using procedures analogous to those for Example 71 with pyrrolidine replacing 1-ethylpiperazine in Step 3. LC-MS calculated for $C_{24}H_{28}F_2N_5O_3(M+H)^+$ m/z: 472.2; found: 472.3.

Example 117

3-(2,6-difluoro-3,5-dimethoxyphenyl)-1-methyl-8-(3-morpholin-4-ylpropyl)-1,3,4,7-tetrahydro-2H-pyrrolo[3',2':5,6]pyrido[4,3-d]pyrimidin-2-one

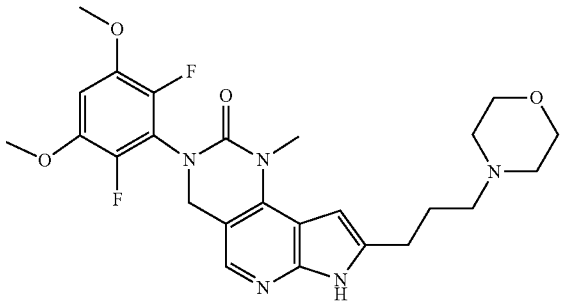 [SMILES: COc1cc(OC)c(F)c(N2Cc3cnc4[nH]c(CCCN5CCOCC5)cc4c3N(C)C2=O)c1F]

This compound was prepared using procedures analogous to those for Example 72 with morpholine replacing 1-ethylpiperazine in Step 4. LC-MS calculated for $C_{25}H_{30}F_2N_5O_4(M+H)^+$ m/z: 502.2; found: 502.2.

Example 118

8-[3-(4-cyclopropylpiperazin-1-yl)propyl]-3-(2,6-difluoro-3,5-dimethoxyphenyl)-1-methyl-1,3,4,7-tetrahydro-2H-pyrrolo[3',2':5,6]pyrido[4,3-d]pyrimidin-2-one

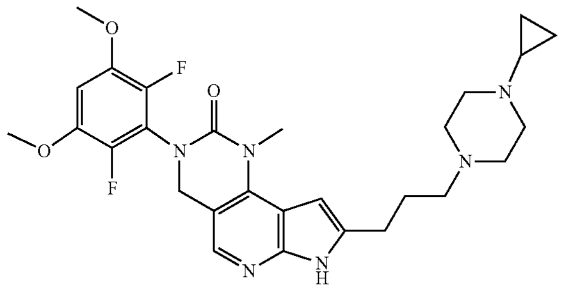 [SMILES: COc1cc(OC)c(F)c(N2Cc3cnc4[nH]c(CCCN5CCN(C6CC6)CC5)cc4c3N(C)C2=O)c1F]

This compound was prepared using procedures analogous to those for Example 72 with 1-cyclopropylpiperazine dihydrochloride (Oakwood, Cat #029229) replacing 1-ethylpiperazine in Step 4. LC-MS calculated for $C_{28}H_{35}F_2N_6O_3(M+H)^+$ m/z: 541.3; found: 541.2.

Example 119

3-(2,6-difluoro-3,5-dimethoxyphenyl)-8-[(4-ethylpiperazin-1-yl)carbonyl]-1-methyl-1,3,4,7-tetrahydro-2H-pyrrolo[3',2':5,6]pyrido[4,3-d]pyrimidin-2-one

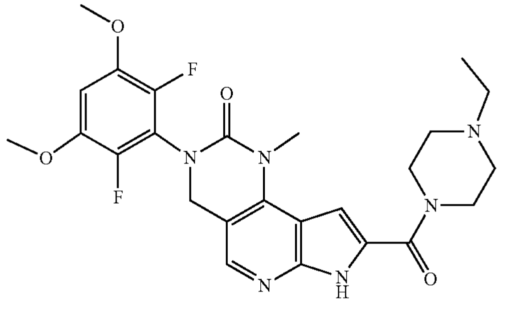 [SMILES: CCN1CCN(C(=O)c2cc3c4c(cnc3[nH]2)CN(c2c(F)c(OC)cc(OC)c2F)C(=O)N4C)CC1]

This compound was prepared using procedures analogous to those for Example 40, Step 3 with 1-ethylpiperazine replacing 1-methylpiperazine. Purified by RP-HPLC (pH=2) to afford the desired product as a white solid. LC-MS calculated for $C_{25}H_{29}F_2N_6O_4[M+H]^+$ m/z: 515.2; found: 515.2.

Example 120

3-(2,6-difluoro-3,5-dimethoxyphenyl)-8-{[(3R,5S)-3,5-dimethylpiperazin-1-yl]carbonyl}-1-methyl-1,3,4,7-tetrahydro-2H-pyrrolo[3',2':5,6]pyrido[4,3-d]pyrimidin-2-one

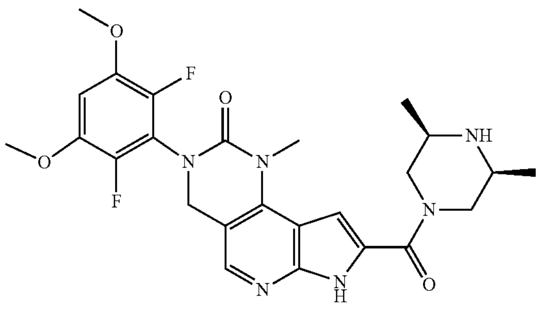

This compound was prepared using procedures analogous to those for Example 40, Step 3 with cis-2,6-dimethylpiperazine (Aldrich, Cat #D179809) replacing 1-methylpiperazine. Purified by RP-HPLC (pH=2) to afford the desired product as a white solid. LC-MS calculated for $C_{25}H_{29}F_2N_6O_4[M+H]^+$ m/z: 515.2; found: 515.1.

Example 121

3-(2,6-Difluoro-3,5-dimethoxyphenyl)-1-ethyl-1,3,4,7-tetrahydro-2H-pyrrolo[3',2':5,6]pyrido[4,3-d]pyrimidin-2-one

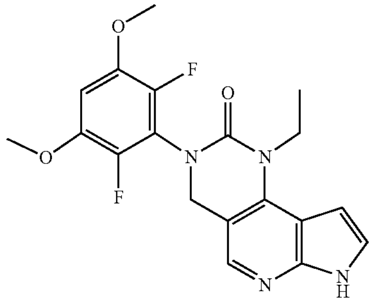 [SMILES: CCN1C(=O)N(c2c(F)c(OC)cc(OC)c2F)Cc2cnc3[nH]ccc3c21]

This compound was prepared as described in Example 49, Steps 1-3. LC-MS calculated for $C_{19}H_{19}F_2N_4O_3[M+H]^+$ m/z: 389.1; found: 389.1. $^1H$ NMR (500 MHz, DMSO) δ 11.86 (s, 1H), 7.99 (s, 1H), 7.52-7.46 (m, 1H), 7.04 (t, J=8.2 Hz, 1H), 6.67-6.62 (m, 1H), 4.76 (s, 2H), 4.18 (q, J=6.9 Hz, 2H), 3.89 (s, 6H), 1.34 (t, J=6.9 Hz, 3H).

Example 122

4-[3-(2,6-difluoro-3,5-dimethoxyphenyl)-2,8-dioxo-2,3,4,7,8,9-hexahydro-1H-pyrrolo[3',2':5,6]pyrido[4,3-d]pyrimidin-1-yl]benzonitrile

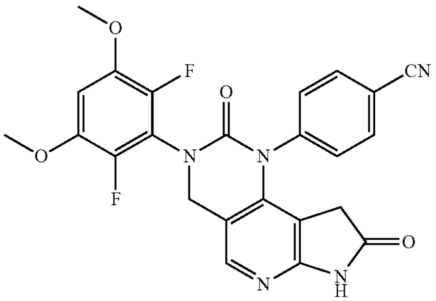 [SMILES: COc1cc(OC)c(F)c(N2Cc3cnc4c(c3N(c3ccc(C#N)cc3)C2=O)CC(=O)N4)c1F]

Step 1: 4-[3-(2,6-difluoro-3,5-dimethoxyphenyl)-2-oxo-2,3,4,7-tetrahydro-1H-pyrrolo[3',2':5,6]pyrido[4,3-d]pyrimidin-1-yl]benzonitrile

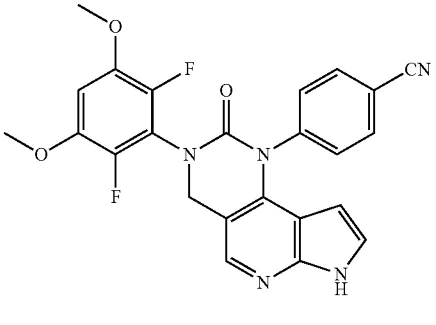 [SMILES: COc1cc(OC)c(F)c(N2Cc3cnc4[nH]ccc4c3N(c3ccc(C#N)cc3)C2=O)c1F]

This compound was prepared using procedures analogous to those for Example 45 with 4-aminobenzonitrile replacing cyclopropylamine. LC-MS calculated for $C_{24}H_{18}F_2N_5O_3$ $(M+H)^+$ m/z: 462.1; found: 462.0.

Step 2: 4-[3-(2,6-difluoro-3,5-dimethoxyphenyl)-2,8-dioxo-2,3,4,7,8,9-hexahydro-1H-pyrrolo[3',2':5,6]pyrido[4,3-d]pyrimidin-1-yl]benzonitrile This compound was prepared using procedures analogous to those for Example 75 with 4-[3-(2,6-difluoro-3,5-dimethoxyphenyl)-2-oxo-2,3,4,7-tetrahydro-1H-pyrrolo[3',2':5,6]pyrido[4,3-d]pyrimidin-1-yl]benzonitrile (prepared in Step 1) replacing 3-(2,6-difluoro-3,5-dimethoxyphenyl)-1-[(1R,2R)-2-hydroxycyclopentyl]-1,3,4,7-tetrahydro-2H-pyrrolo[3',2':5,6]pyrido[4,3-d]pyrimidin-2-one. LC-MS calculated for $C_{24}H_{18}F_2N_5O_4(M+H)^+$ m/z: 478.1; found: 478.0.

Example 123

3-{[3-(2,6-difluoro-3,5-dimethoxyphenyl)-2,8-dioxo-2,3,4,7,8,9-hexahydro-1H-pyrrolo[3',2':5,6]pyrido[4,3-d]pyrimidin-1-yl]methyl}benzonitrile

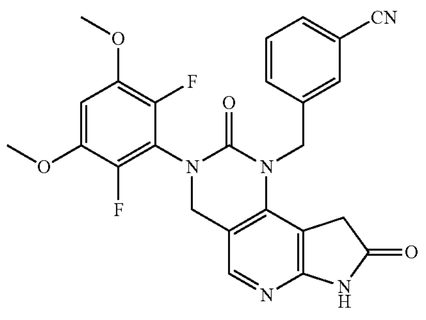 [SMILES: COc1cc(OC)c(F)c(N2Cc3cnc4c(c3N(Cc3cccc(C#N)c3)C2=O)CC(=O)N4)c1F]

Step 1: N-[(4-chloro-1-{[2-(trimethylsilyl)ethoxy]methyl}-1H-pyrrolo[2,3-b]pyridin-5-yl)methyl]-2,6-difluoro-3,5-dimethoxyaniline

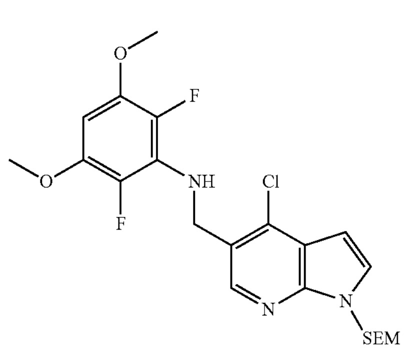 [SMILES: COc1cc(OC)c(F)c(NCc2cnc3c(ccn3COCC[Si](C)(C)C)c2Cl)c1F]

To a solution of sodium triacetoxyborohydride (6.2 g, 29 mmol) in trifluoroacetic acid (10.0 mL, 1.30E2 mmol) at 0° C. was added a solution of 2,6-difluoro-3,5-dimethoxyaniline (1.52 g, 8.03 mmol) in methylene chloride (10 mL), followed by a solution of 4-chloro-1-{[2-(trimethylsilyl)ethoxy]methyl}-1H-pyrrolo[2,3-b]pyridine-5-carbaldehyde (Example 106, Step 1: 2.27 g, 7.30 mmol) in methylene chloride (40 mL, 700 mmol). The reaction mixture was stirred at 0° C. for 1 h then poured into a cold aqueous solution of $NaHCO_3$ and then extracted with methylene chloride. The organic phase was washed with brine then dried over $Na_2SO_4$ and concentrated. The residue was purified by flash chromatography eluted with 0 to 40% EtOAc in DCM to give the desired product as a yellow oil which solidified on standing (3.32 g, 94%). LC-MS calculated for $C_{22}H_{29}ClF_2N_3O_3Si$ $(M+H)^+$ m/z: 484.2; found: 484.1.

Step 2: 3-{[(5-{[(2,6-difluoro-3,5-dimethoxyphenyl)amino]methyl}-1-{[2-(trimethylsilyl)ethoxy]methyl}-1H-pyrrolo[2,3-b]pyridin-4-yl)amino]methyl}benzonitrile

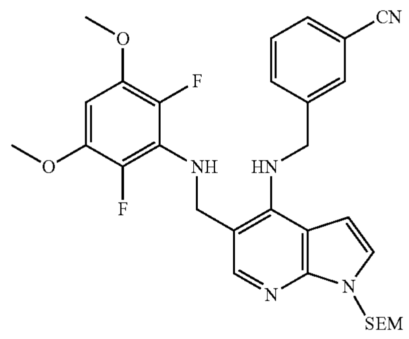 [SMILES: COc1cc(OC)c(F)c(NCc2cnc3c(ccn3COCC[Si](C)(C)C)c2NCc2cccc(C#N)c2)c1F]

A mixture of N-[(4-chloro-1-{[2-(trimethylsilyl)ethoxy]methyl}-1H-pyrrolo[2,3-b]pyridin-5-yl)methyl]-2,6-difluoro-3,5-dimethoxyaniline (110 mg, 0.23 mmol), 3-(aminomethyl)benzonitrile (45.0 mg, 0.341 mmol), palladium acetate (5.1 mg, 0.023 mmol), (R)-(+)-2,2'-bis(diphenylphosphino)-1,1'-binaphthyl (14 mg, 0.023 mmol), and cesium carbonate (220 mg, 0.68 mmol) in 1,4-dioxane (3 mL, 40 mmol) was evacuated then filled with nitrogen. The resulting mixture was stirred at 150° C. for 2 h then cooled to room temperature and diluted with water and extracted with EtOAc. The organic layer was washed with water, brine then dried over $Na_2SO_4$ and concentrated. The residue was used in the next step without further purification. LC-MS calculated for $C_{30}H_{36}F_2N_5O_3Si$ $(M+H)^+$ m/z: 580.3; found: 580.2.

Step 3: 3-[(3-(2,6-difluoro-3,5-dimethoxyphenyl)-2-oxo-7-{[2-(trimethylsilyl)ethoxy]methyl}-2,3,4,7-tetrahydro-1H-pyrrolo[3',2':5,6]pyrido[4,3-d]pyrimidin-1-yl)methyl]benzonitrile

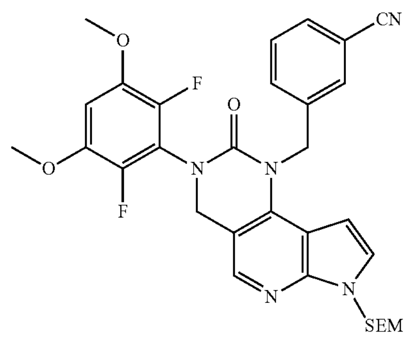 [SMILES: COc1cc(OC)c(F)c(N2Cc3cnc4c(ccn4COCC[Si](C)(C)C)c3N(Cc3cccc(C#N)c3)C2=O)c1F]

The crude product from step 2 was dissolved in tetrahydrofuran (5 mL, 60 mmol) then triethylamine (0.16 mL, 1.1 mmol) was added, followed by triphosgene (74 mg, 0.25 mmol). The resulting brown suspension was stirred at room temperature for 30 min and then the reaction was quenched with 3 mL of 1N NaOH solution. The mixture was stirred at room temperature for 20 min then extracted with EtOAc. The organic layer was then washed with water, brine and dried over $Na_2SO_4$ and concentrated. The residue was purified by column eluted with 0 to 50% EtOAc in hexanes to give the desired product. LC-MS calculated for $C_{31}H_{34}F_2N_5O_4Si$ $(M+H)^+$ m/z: 606.2; found: 606.3.

Step 4: 3-{[3-(2,6-difluoro-3,5-dimethoxyphenyl)-2,8-dioxo-2,3,4,7,8,9-hexahydro-1H-pyrrolo[3',2':5,6]pyrido[4,3-d]pyrimidin-1-yl]methyl}benzonitrile To a solution of 3-[(3-(2,6-difluoro-3,5-dimethoxyphenyl)-2-oxo-7-{[2-(trimethylsilyl)ethoxy]methyl}-2,3,4,7-tetrahydro-1H-pyrrolo[3',2':5,6]pyrido[4,3-d]pyrimidin-1-yl)methyl]benzonitrile (60. mg, 0.099 mmol) in isopropyl alcohol (5 mL, 60 mmol) and water (0.5 mL, 30 mmol) was added pyridinium tribromide (160 mg, 0.50 mmol). The resulting yellow solution was stirred at 35° C. for 1 h then cooled to room temperature and zinc (130 mg, 2.0 mmol) and acetic acid (0.11 mL, 2.0 mmol) were added. The reaction mixture was stirred at room temperature for 2 h then filtered and washed with MeOH/DCM. The filtrate was concentrated and the residue was triturated with water and the white solid was collected via filtration then washed with water and dried.

The above solid was dissolved in 2 mL of DCM then 2 mL of TFA was added. The resulting yellow solution was stirred at room temperature 2 h then concentrated. The residue was dissolved in 5 mL of MeOH then ethylenediamine (0.33 mL, 5.0 mmol) was added. The resulting yellow solution was stirred at room temperature for 2 h then purified by prep HPLC (pH 2, acetonitrile/water) to give the desired product as a white solid. LC-MS calculated for $C_{25}H_{20}F_2N_5O_4(M+H)^+$ m/z: 492.1; found: 492.1.

Example 124

3-(2-chloro-6-fluoro-3,5-dimethoxyphenyl)-1-(2,3-difluorophenyl)-3,4,7,9-tetrahydro-1H-pyrrolo[3',2':5,6]pyrido[4,3-d]pyrimidine-2,8-dione

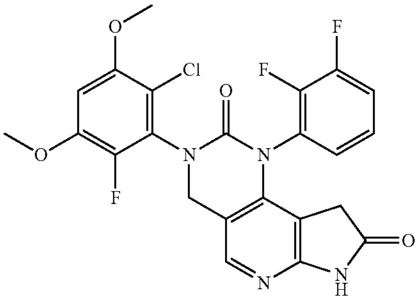 [SMILES: COc1cc(OC)c(Cl)c(N2Cc3cnc4c(c3N(c3cccc(F)c3F)C2=O)CC(=O)N4)c1F]

This compound was prepared using procedures analogous to those for Example 106 with 2,3-difluoroaniline replacing cyclobutylamine in Step 3. LC-MS calculated for $C_{23}H_{17}ClF_3N_4O_4$ $(M+H)^+$ m/z: 505.1; found: 505.0.

Example 125

4-[3-(2,6-difluoro-3,5-dimethoxyphenyl)-2,8-dioxo-2,3,4,7,8,9-hexahydro-1H-pyrrolo[3', 2':5,6]pyrido[4,3-d]pyrimidin-1-yl]-3-fluorobenzonitrile

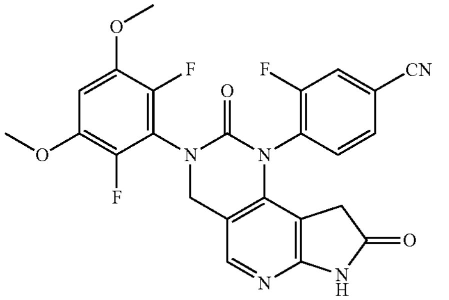 [SMILES: COc1cc(OC)c(F)c(N2Cc3cnc4c(c3N(c3ccc(C#N)cc3F)C2=O)CC(=O)N4)c1F]

This compound was prepared using procedures analogous to those for Example 123 with 4-amino-3-fluorobenzonitrile replacing 3-(aminomethyl)benzonitrile in Step 2. LC-MS calculated for $C_{24}H_{17}F_3N_5O_4(M+H)^+$ m/z: 496.1; found: 496.0.

Example 126

3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one

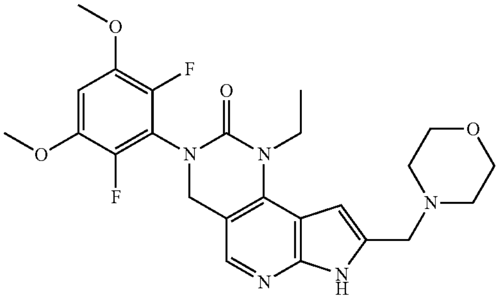 [SMILES: CCN1C(=O)N(c2c(F)c(OC)cc(OC)c2F)Cc2cnc3[nH]c(CN4CCOCC4)cc3c21]

Step 1: 3-(2,6-difluoro-3,5-dimethoxyphenyl)-1-ethyl-7-(phenylsulfonyl)-1,3,4,7-tetrahydro-2H-pyrrolo[3',2':5,6]pyrido[4,3-d]pyrimidin-2-one

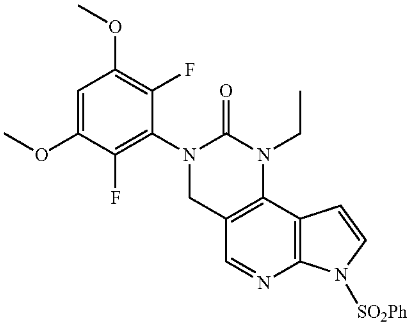

To a solution of 3-(2,6-difluoro-3,5-dimethoxyphenyl)-1-ethyl-1,3,4,7-tetrahydro-2H-pyrrolo[3',2':5,6]pyrido[4,3-d]pyrimidin-2-one (Example 49, Step 3: 900 mg, 2.32 mmol) in N,N-dimethylformamide (20 mL) cooled to 0° C. was added sodium hydride (185 mg, 4.63 mmol, 60 wt % in mineral oil). The resulting mixture was stirred at 0° C. for 30 min then benzenesulfonyl chloride (0.444 mL, 3.48 mmol) was added. The reaction mixture was stirred at 0° C. for 1.5 h at which time LC-MS showed the reaction completed to the desired product. The reaction was quenched with saturated $NH_4Cl$ solution and diluted with water. The white precipitate was collected via filtration then washed with water and hexanes, dried to afford the desired product (1.2 g, 98%) as a white solid which was used in the next step without further purification. LC-MS calculated for $C_{25}H_{23}F_2N_4O_5S$ $[M+H]^+$ m/z: 529.1; found: 529.1.

Step 2: 3-(2,6-difluoro-3,5-dimethoxyphenyl)-1-ethyl-2-oxo-7-(phenylsulfonyl)-2,3,4,7-tetrahydro-1H-pyrrolo[3',2':5,6]pyrido[4,3-d]pyrimidine-8-carbaldehyde

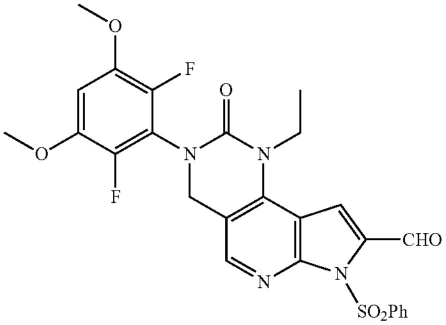

To a solution of 3-(2,6-difluoro-3,5-dimethoxyphenyl)-1-ethyl-7-(phenylsulfonyl)-1,3,4,7-tetrahydro2H-pyrrolo[3',2':5,6]pyrido[4,3-d]pyrimidin-2-one (1.75 g, 3.31 mmol) in tetrahydrofuran (80 mL) at −78° C. was added freshly prepared lithium diisopropylamide (1M in tetrahydrofuran (THF), 3.48 mL, 3.48 mmol). The resulting mixture was stirred at −78° C. for 30 min then N,N-dimethylformamide (1.4 mL, 18 mmol) was added slowly. The reaction mixture was stirred at −78° C. for 30 min then quenched with water and extracted with EtOAc. The organic extracts were combined then washed with water and brine. The organic layer was dried over $Na_2SO_4$ and concentrated. The residue was purified by flash chromatography eluted with 0 to 20% EtOAc in DCM to give the desired product as a white solid (1.68 g, 91%). LC-MS calculated for $C_{26}H_{23}F_2N_4O_6S$ $(M+H)^+$ m/z: 557.1; found: 556.9.

Step 3: 3-(2,6-difluoro-3,5-dimethoxyphenyl)-1-ethyl-8-(morpholin-4-ylmethyl)-7-(phenylsulfonyl)-1,3,4,7-tetrahydro-2H-pyrrolo[3',2':5,6]pyrido[4,3-d]pyrimidin-2-one

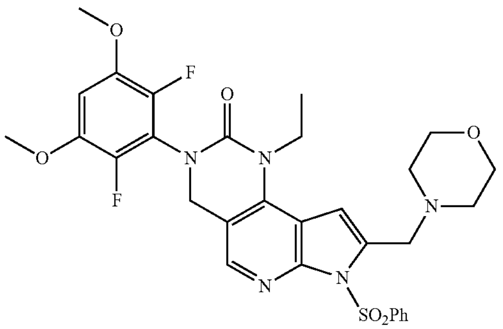

To a solution 3-(2,6-difluoro-3,5-dimethoxyphenyl)-1-ethyl-2-oxo-7-(phenylsulfonyl)-2,3,4,7-tetrahydro-1H-pyrrolo[3',2':5,6]pyrido[4,3-d]pyrimidine-8-carbaldehyde (1.73 g, 3.11 mmol) in dichloromethane (50 mL) was added morpholine (0.95 mL, 11 mmol), followed by acetic acid (2 mL, 30 mmol). The resulting yellow solution was stirred at room temperature overnight then sodium triacetoxyborohydride (2.3 g, 11 mmol) was added. The mixture was stirred at room temperature for 3 h at which time LC-MS showed the reaction went to completion to the desired product. The reaction was quenched with saturated $NaHCO_3$ then extracted with ethyl acetate (EtOAc). The organic extracts were combined then washed with water and brine. The organic layer was dried over $Na_2SO_4$ and concentrated. The residue was purified by flash chromatography eluted with 0 to 40% EtOAc in DCM to give the desired product as a yellow solid (1.85 g, 95%). LC-MS calculated for $C_{30}H_{32}F_2N_5O_6S$ $(M+H)^+$ m/z: 628.2; found: 628.0.

Step 4: 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one To a solution of 3-(2,6-difluoro-3,5-dimethoxyphenyl)-1-ethyl-8-(morpholin-4-ylmethyl)-7-(phenylsulfonyl)-1,3,4,7-tetrahydro-2H-pyrrolo[3',2':5,6]pyrido[4,3-d]pyrimidin-2-one (1.5 g, 2.4 mmol) in tetrahydrofuran (40 mL) was added tetra-n-butylammonium fluoride (1M in THF, 7.2 mL, 7.2 mmol). The resulting solution was stirred at 50° C. for 1.5 h then cooled to room temperature and quenched with water. The mixture was extracted with dichloromethane (DCM) and the organic extracts were combined then washed with water and brine. The organic layer was dried over $Na_2SO_4$ and concentrated. The residue was purified by flash chromatography eluted with 0 to 10% MeOH in DCM to give the desired product as a white solid, which was further purified by prep HPLC (pH=2, acetonitrile/$H_2O$). LC-MS calculated for $C_{24}H_{28}F_2N_5O_4(M+H)^+$ m/z: 488.2; found: 488.0. $^1H$ NMR (500 MHz, DMSO) δ 12.09 (s, 1H), 8.06 (s, 1H), 7.05 (t, J=8.1 Hz, 1H), 6.87 (s, 1H), 4.78 (s, 2H), 4.50 (s, 2H), 4.17 (q, J=6.8 Hz, 2H), 3.97 (br, 2H), 3.89 (s, 6H), 3.65 (br, 2H), 3.37 (br, 2H), 3.15 (br, 2H), 1.37 (t, J=6.8 Hz, 3H).

Example 127

3-(2,6-difluoro-3,5-dimethoxyphenyl)-1-ethyl-8-[(4-methylpiperazin-1-yl)methyl]-1,3,4,7-tetrahydro-2H-pyrrolo[3',2':5,6]pyrido[4,3-d]pyrimidin-2-one

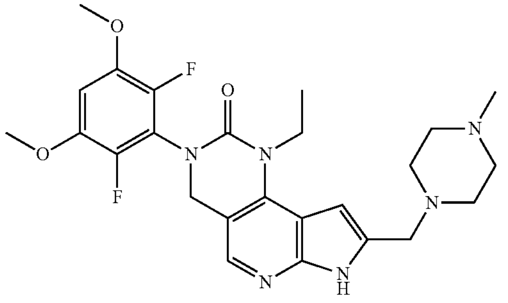

This compound was prepared using procedures analogous to those for Example 126 with 1-methylpiperazine replacing morpholine in Step 3. The product was purified by prep HPLC (pH=2, acetonitrile/$H_2O$). LC-MS calculated for $C_{25}H_{31}F_2N_6O_3(M+H)^+$ m/z: 501.2; found: 501.1.

Example 128

3-(2,6-difluoro-3,5-dimethoxyphenyl)-1-ethyl-8-[(4-ethylpiperazin-1-yl)methyl]-1,3,4,7-tetrahydro-2H-pyrrolo[3',2':5,6]pyrido[4,3-d]pyrimidin-2-one

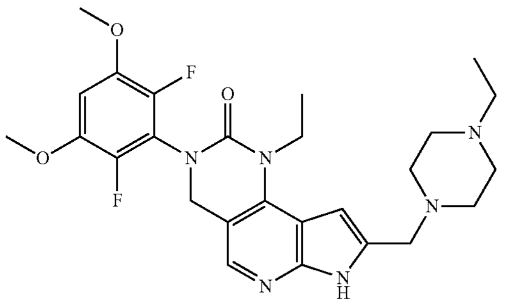 [SMILES: CCN1CCN(Cc2cc3c4c(cnc3[nH]2)CN(c2c(F)c(OC)cc(OC)c2F)C(=O)N4CC)CC1]

This compound was prepared using procedures analogous to those for Example 126 with 1-ethylpiperazine replacing morpholine in Step 3. The product was purified by prep HPLC (pH=2, acetonitrile/$H_2O$). LC-MS calculated for $C_{26}H_{33}F_2N_6O_3(M+H)^+$ m/z: 515.3; found: 515.1.

Example 129

3-(2,6-difluoro-3,5-dimethoxyphenyl)-1-methyl-8-[(4-methylpiperazin-1-yl)methyl]-1,3,4,7-tetrahydro-2H-pyrrolo[3',2':5,6]pyrido[4,3-d]pyrimidin-2-one

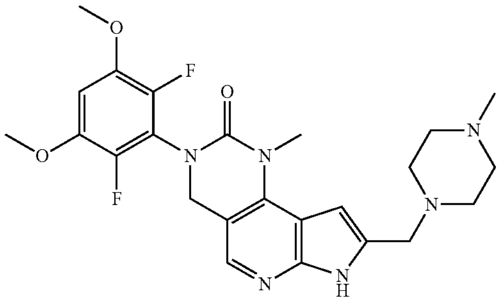

This compound was prepared using procedures analogous to those for Example 126 starting with 3-(2,6-difluoro-3,5-dimethoxyphenyl)-1-methyl-2-oxo-7-(phenylsulfonyl)-2,3,4,7-tetrahydro-1H-pyrrolo[3',2':5,6]pyrido[4,3-d]pyrimidine-8-carbaldehyde (Example 70, Step 1) and 1-methylpiperazine. The product was purified by prep HPLC (pH=2, acetonitrile/$H_2O$). LC-MS calculated for $C_{24}H_{29}F_2N_6O_3(M+H)^+$ m/z: 487.2; found: 487.1.

Example 130

3-(2,6-difluoro-3,5-dimethoxyphenyl)-8-{[4-(2-hydroxyethyl)piperazin-1-yl]methyl}-1-methyl-1,3,4,7-tetrahydro-2H-pyrrolo[3',2':5,6]pyrido[4,3-d]pyrimidin-2-one

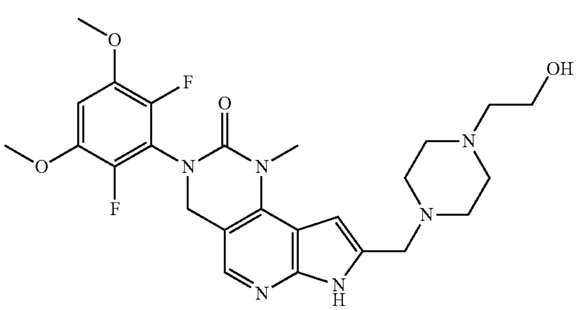 [SMILES: COc1cc(OC)c(F)c(N2Cc3cnc4[nH]c(CN5CCN(CCO)CC5)cc4c3N(C)C2=O)c1F]

Step 1: 3-(2,6-difluoro-3,5-dimethoxyphenyl)-1-methyl-2-oxo-2,3,4,7-tetrahydro-1H-pyrrolo[3',2':5,6]pyrido[4,3-d]pyrimidine-8-carbaldehyde

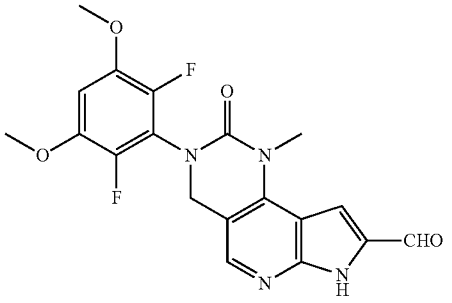 [SMILES: COc1cc(OC)c(F)c(N2Cc3cnc4[nH]c(C=O)cc4c3N(C)C2=O)c1F]

To a solution of 3-(2,6-difluoro-3,5-dimethoxyphenyl)-1-methyl-2-oxo-7-(phenylsulfonyl)-2,3,4,7-tetrahydro-1H-pyrrolo[3',2':5,6]pyrido[4,3-d]pyrimidine-8-carbaldehyde (Example 70, step 1: 500 mg, 0.9 mmol) in a mixture of tetrahydrofuran (25 mL), isopropyl alcohol (2.5 mL) and water (2.5 mL) was added 6.0 M potassium hydroxide in water (1.54 mL, 9.24 mmol). The resulting yellow solution was stirred at room temperature overnight then warmed to 40° C. and stirred for 1 h. The reaction mixture was cooled to room temperature and neutralized with 1 N HCl then saturated $NH_4Cl$ solution was added. The resulting light yellow precipitate was collected via filtration and dried to give the product (350 mg, 90%) as a light yellow solid which was used in the next step without further purification. LC-MS calculated for $C_{19}H_{17}F_2N_4O_4(M+H)^+$ m/z: 403.1; found: 402.9.

Step 2: 3-(2,6-difluoro-3,5-dimethoxyphenyl)-8-{[4-(2-hydroxyethyl)piperazin-1-yl]methyl}-1-methyl-1,3,4,7-tetrahydro-2H-pyrrolo[3',2':5,6]pyrido[4,3-d]pyrimidin-2-one To a solution of 3-(2,6-difluoro-3,5-dimethoxyphenyl)-1-methyl-2-oxo-2,3,4,7-tetrahydro-1H-pyrrolo[3',2':5,6]pyrido[4,3-d]pyrimidine-8-carbaldehyde (13 mg, 0.032 mmol) in methylene chloride (3 mL) was added 1-piperazine-ethanol (20 µL, 0.16 mmol), followed by acetic acid (55 µL, 0.97 mmol). The resulting yellow suspension was stirred at room temperature for 3 h then sodium triacetoxyborohydride (40. mg, 0.19 mmol) was added. The mixture was stirred at room temperature overnight. The reaction was quenched with saturated $NaHCO_3$ solution then extracted with methylene chloride. The organic extracts were combined then dried over $Na_2SO_4$ and concentrated. The residue was purified by prep HPLC (pH=2, acetonitrile/$H_2O$) to give the desired product as a white solid. LC-MS calculated for $C_{25}H_{31}F_2N_6O_4(M+H)^+$ m/z: 517.2; found: 517.1.

Example 131

3-(4-{[3-(2,6-difluoro-3,5-dimethoxyphenyl)-1-methyl-2-oxo-2,3,4,7-tetrahydro-1H-pyrrolo[3',2':5,6]pyrido[4,3-d]pyrimidin-8-yl]methyl}piperazin-1-yl)propanenitrile

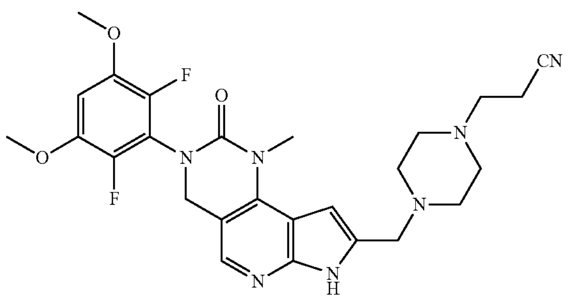

This compound was prepared using procedures analogous to those for Example 130 with 3-piperazin-1-ylpropanenitrile replacing 1-piperazine-ethanol in Step 2. The product was purified by prep HPLC (pH=2, acetonitrile/$H_2O$). LC-MS calculated for $C_{26}H_{30}F_2N_7O_3(M+H)^+$ m/z: 526.2; found: 526.1.

Example 132

1-{[3-(2,6-difluoro-3,5-dimethoxyphenyl)-1-methyl-2-oxo-2,3,4,7-tetrahydro-1H-pyrrolo[3',2':5,6]pyrido[4,3-d]pyrimidin-8-yl]methyl}piperidine-4-carbonitrile

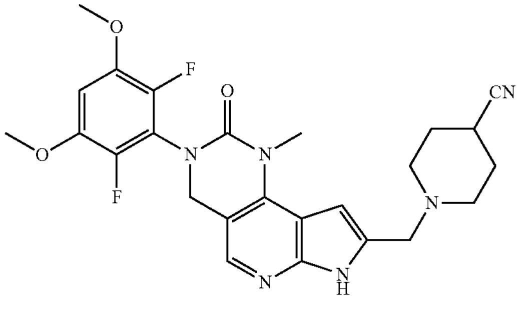 [SMILES: COc1cc(OC)c(F)c(N2Cc3cnc4[nH]c(CN5CCC(C#N)CC5)cc4c3N(C)C2=O)c1F]

This compound was prepared using procedures analogous to those for Example 130 with piperidine-4-carbonitrile replacing 1-piperazine-ethanol in Step 2. The product was purified by prep HPLC (pH=2, acetonitrile/$H_2O$). LC-MS calculated for $C_{25}H_{27}F_2N_6O_3(M+H)^+$ m/z: 497.2; found: 496.9.

Example 133

(3S)-1-{[3-(2,6-difluoro-3,5-dimethoxyphenyl)-1-methyl-2-oxo-2,3,4,7-tetrahydro-1H-pyrrolo[3',2':5,6]pyrido[4,3-d]pyrimidin-8-yl]methyl}pyrrolidine-3-carbonitrile

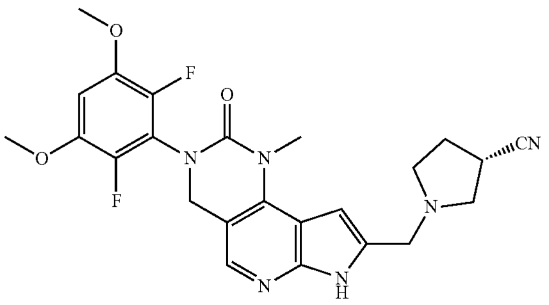 [SMILES: COc1cc(OC)c(F)c(N2Cc3cnc4[nH]c(CN5CC[C@H](C#N)C5)cc4c3N(C)C2=O)c1F]

This compound was prepared using procedures analogous to those for Example 130 with (3S)-pyrrolidine-3-carbonitrile hydrochloride replacing 1-piperazineethanol in Step 2. The product was purified by prep HPLC (pH=2, acetonitrile/$H_2O$). LC-MS calculated for $C_{24}H_{25}F_2N_6O_3(M+H)^+$ m/z: 483.2; found: 483.2.

Example 134

3-(2,6-difluoro-3,5-dimethoxyphenyl)-1-methyl-8-{[(1-methylpiperidin-4-yl)amino]methyl}-1,3,4,7-tetrahydro-2Hpyrrolo[3',2':5,6]pyrido[4,3-d]pyrimidin-2-one

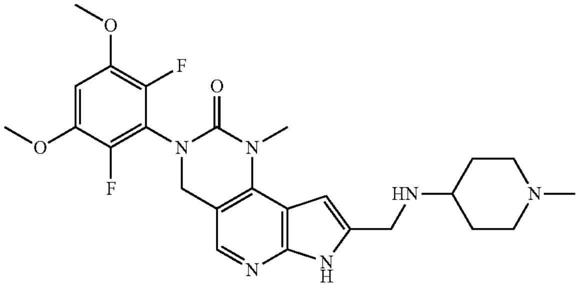

This compound was prepared using procedures analogous to those for Example 130 with 1-methylpiperidin-4-amine replacing 1-piperazine-ethanol in Step 2. The product was purified by prep HPLC (pH=2, acetonitrile/$H_2O$). LC-MS calculated for $C_{25}H_{31}F_2N_6O_3(M+H)^+$ m/z: 501.2; found: 501.0.

Example 135

3-(2,6-difluoro-3,5-dimethoxyphenyl)-1-methyl-8-{[(3S)-tetrahydrofuran-3-ylamino]methyl}-1,3,4,7-tetrahydro-2Hpyrrolo[3',2':5,6]pyrido[4,3-d]pyrimidin-2-one

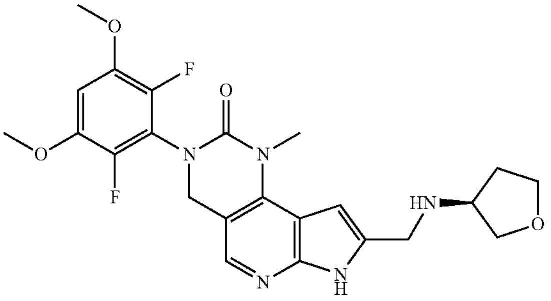 [SMILES: COc1cc(OC)c(F)c(N2Cc3cnc4[nH]c(CN[C@H]5CCOC5)cc4c3N(C)C2=O)c1F]

This compound was prepared using procedures analogous to those for Example 130 with (3S)-tetrahydrofuran-3-amine hydrochloride replacing 1-piperazine-ethanol in Step 2. The product was purified by prep HPLC (pH=2, acetonitrile/$H_2O$). LC-MS calculated for $C_{23}H_{26}F_2N_5O_4(M+H)^+$ m/z: 474.2; found: 474.0.

Example 136

3-(2,6-difluoro-3,5-dimethoxyphenyl)-1-methyl-8-{[(3R)-tetrahydrofuran-3-ylamino]methyl}-1,3,4,7-tetrahydro-2Hpyrrolo[3',2':5,6]pyrido[4,3-d]pyrimidin-2-one

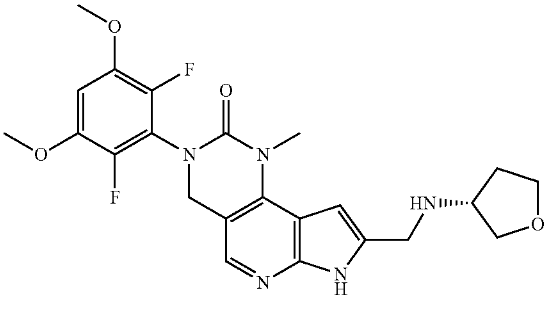 [SMILES: COc1cc(OC)c(F)c(N2Cc3cnc4[nH]c(CN[C@@H]5CCOC5)cc4c3N(C)C2=O)c1F]

This compound was prepared using procedures analogous to those for Example 130 with (3R)-tetrahydrofuran-3-amine hydrochloride replacing 1-piperazine-ethanol in Step 2. The product was purified by prep HPLC (pH=2, acetonitrile/$H_2O$). LC-MS calculated for $C_{23}H_{26}F_2N_5O_4(M+H)^+$ m/z: 474.2; found: 474.2.

Example 137

3-(2,6-difluoro-3,5-dimethoxyphenyl)-8-(1H-imidazol-1-ylmethyl)-1-methyl-1,3,4,7-tetrahydro-2H-pyrrolo[3',2':5,6]pyrido[4,3-d]pyrimidin-2-one

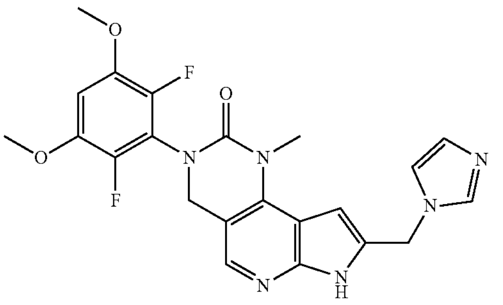 [SMILES: COc1cc(OC)c(F)c(N2Cc3cnc4[nH]c(Cn5ccnc5)cc4c3N(C)C2=O)c1F]

Step 1: 3-(2,6-difluoro-3,5-dimethoxyphenyl)-8-(hydroxymethyl)-1-methyl-7-(phenylsulfonyl)-1,3,4,7-tetrahydro-2H-pyrrolo[3',2':5,6]pyrido[4,3-d]pyrimidin-2-one

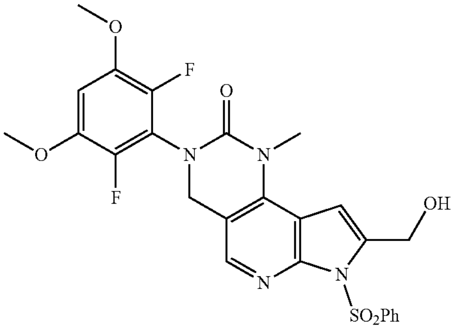

To a solution of 3-(2,6-difluoro-3,5-dimethoxyphenyl)-1-methyl-2-oxo-7-(phenylsulfonyl)-2,3,4,7-tetrahydro-1H-pyrrolo[3',2':5,6]pyrido[4,3-d]pyrimidine-8-carbaldehyde (Example 70, step 1: 101 mg, 0.186 mmol) in tetrahydrofuran (5 mL) cooled to 0° C. was added sodium tetrahydroborate (21 mg, 0.56 mmol). The resulting mixture was stirred at 0° C. for 2 h and quenched with water then extracted with EtOAc. The organic extracts were combined then washed with water and brine. The organic layer was dried over $Na_2SO_4$ and concentrated. The residue was used in the next step without further purification. LC-MS calculated for $C_{25}H_{23}F_2N_4O_6S$ $(M+H)^+$ m/z: 545.1; found: 545.0.

Step 2: 8-(chloromethyl)-3-(2,6-difluoro-3,5-dimethoxyphenyl)-1-methyl-7-(phenylsulfonyl)-1,3,4,7-tetrahydro-2H-pyrrolo[3',2':5,6]pyrido[4,3-d]pyrimidin-2-one

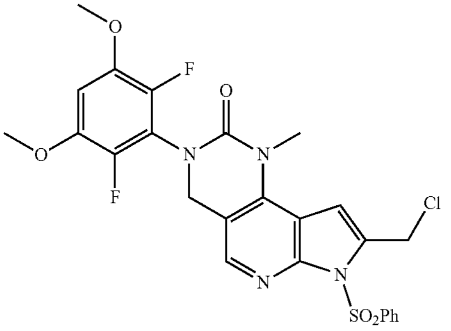

The crude product from Step 1 was dissolved in methylene chloride (5 mL) and cooled to 0° C. then N,N-diisopropylethylamine (65 µL, 0.37 mmol) was added, followed by methanesulfonyl chloride (19 µL, 0.24 mmol). The resulting mixture was warmed to room temperature and stirred overnight. The reaction was quenched with water then extracted with EtOAc. The organic extracts were combined then washed with water and brine. The organic layer was dried over $Na_2SO_4$ and concentrated. The residue was used in the next step without further purification. LC-MS calculated for $C_{25}H_{22}ClF_2N_4O_5S$ $(M+H)^+$ m/z: 563.1; found: 562.9.

Step 3: 3-(2,6-difluoro-3,5-dimethoxyphenyl)-8-(1H-imidazol-1-ylmethyl)-1-methyl-7-(phenylsulfonyl)-1,3,4,7-tetrahydro-2Hpyrrolo[3',2':5,6]pyrido[4,3-d]pyrimidin-2-one

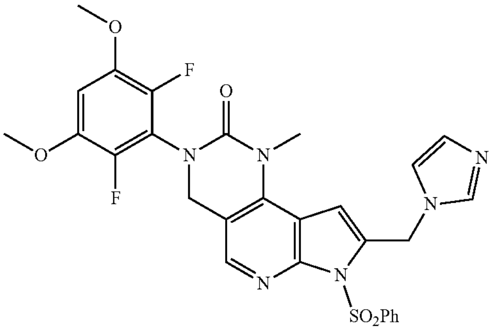

A mixture of 8-(chloromethyl)-3-(2,6-difluoro-3,5-dimethoxyphenyl)-1-methyl-7-(phenylsulfonyl)-1,3,4,7-tetrahydro-2H-pyrrolo[3',2':5,6]pyrido[4,3-d]pyrimidin-2-one (30. mg, 0.053 mmol), 1H-imidazole (18 mg, 0.27 mmol) and cesium carbonate (87 mg, 0.27 mmol) in acetonitrile (3 mL) was stirred at 60° C. for overnight at which time LC-MS indicated the reaction went to completion to the desired product. The mixture was cooled to room temperature and diluted with dichloromethane then washed with water and brine. The organic layer was dried over $Na_2SO_4$ then concentrated. The residue was used in the next step without further purification. LC-MS calculated for $C_{28}H_{25}F_2N_6O_5S$ $(M+H)^+$ m/z: 595.2; found: 595.2.

Step 4: 3-(2,6-difluoro-3,5-dimethoxyphenyl)-8-(1H-imidazol-1-ylmethyl)-1-methyl-1,3,4,7-tetrahydro-2H-pyrrolo[3',2':5,6]pyrido[4,3-d]pyrimidin-2-one The crude product from Step 3 was dissolved in tetrahydrofuran (3 mL) then 1.0 M tetra-nbutylammonium fluoride in THF (0.27 mL, 0.27 mmol) was added. The mixture was stirred at 60° C. for 30 min at which time LC-MS indicated the reaction went to completion to the desired product. The reaction mixture was cooled to room temperature then quenched with water and extracted with dichloromethane. The organic extracts were combined then washed with water and brine. The organic layer was dried over $Na_2SO_4$ then concentrated. The residue was dissolved in MeOH then purified by prep HPLC (pH=2, acetonitrile/$H_2O$) to give the desired product as a white solid. LC-MS calculated for $C_{22}H_{21}F_2N_6O_3(M+H)^+$ m/z: 455.2; found: 455.1.

Example 138

3-(2,6-difluoro-3,5-dimethoxyphenyl)-1-methyl-8-(1H-pyrazol-1-ylmethyl)-1,3,4,7-tetrahydro-2H-pyrrolo[3',2':5,6]pyrido[4,3-d]pyrimidin-2-one

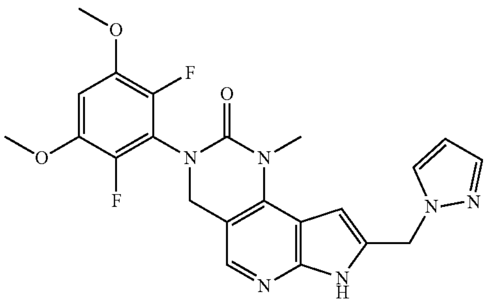 [SMILES: COc1cc(OC)c(F)c(N2Cc3cnc4[nH]c(Cn5cccn5)cc4c3N(C)C2=O)c1F]

This compound was prepared using procedures analogous to those for Example 137 with 1H-pyrazole replacing 1H-imidazole and the reaction mixture was stirred at 80° C. in Step 3. The product was purified by prep HPLC (pH=2, acetonitrile/$H_2O$). LC-MS calculated for $C_{22}H_{21}F_2N_6O_3$ $(M+H)^+$ m/z: 455.2; found: 454.9.

Example 139

3-(2,6-difluoro-3,5-dimethoxyphenyl)-1-methyl-8-[(1-methyl-1H-pyrazol-4-yl)methyl]-1,3,4, 7-tetrahydro-2H-pyrrolo[3',2':5,6]pyrido[4,3-d]pyrimidin-2-one

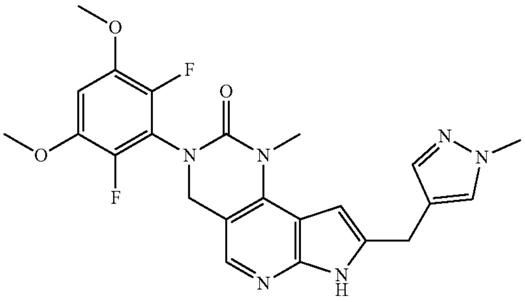

Step 1: 3-(2,6-difluoro-3,5-dimethoxyphenyl)-8-[hydroxy(1-methyl-1H-pyrazol-4-yl)methyl]-1-methyl-7-(phenylsulfonyl)-1,3,4,7-tetrahydro-2H-pyrrolo[3',2':5,6]pyrido[4,3-d]pyrimidin-2-one

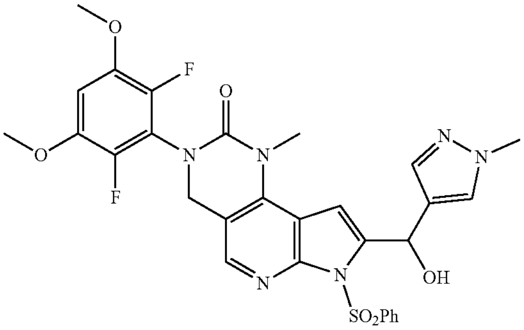

To a solution of 3-(2,6-difluoro-3,5-dimethoxyphenyl)-1-methyl-7-(phenylsulfonyl)-1,3,4,7-tetrahydro-2H-pyrrolo[3',2':5,6]pyrido[4,3-d]pyrimidin-2-one (70.0 mg, 0.136 mmol) in tetrahydrofuran (2 mL) at −78° C. was added freshly prepared lithium diisopropylamide (0.5 M in THF, 0.3 mL, 0.15 mmol). The resulting mixture was stirred at −78° C. for 30 min then a solution of 1-methyl-1H-pyrazole-4-carbaldehyde (45 mg, 0.41 mmol) in THF (0.5 mL) was added. The reaction mixture was stirred at −78° C. for 30 min then the reaction was quenched with water. The mixture was warmed to room temperature then extracted with EtOAc. The organic extracts were combined then washed with water and brine. The organic layer was dried over $Na_2SO_4$ and concentrated. The residue was used in the next step without further purification. LC-MS calculated for $C_{29}H_{27}F_2N_6O_6S$ $(M+H)^+$ m/z: 625.2; found: 624.9.

Step 2: 3-(2,6-difluoro-3,5-dimethoxyphenyl)-1-methyl-8-[(1-methyl-1H-pyrazol-4-yl)methyl]-7-(phenylsulfonyl)-1,3,4,7-tetrahydro-2H-pyrrolo[3',2':5,6]pyrido[4,3-d]pyrimidin-2-one

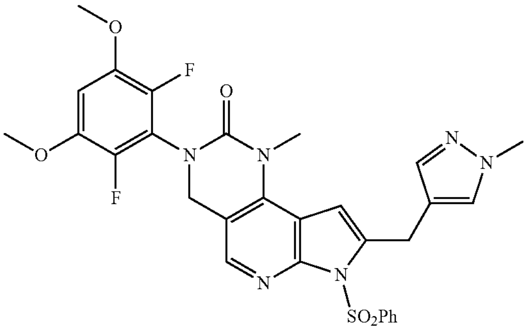

A container having a mixture of 3-(2,6-difluoro-3,5-dimethoxyphenyl)-8-[hydroxy(1-methyl-1H-pyrazol-4-yl)methyl]-1-methyl-7-(phenylsulfonyl)-1,3,4,7-tetrahydro-2H-pyrrolo[3',2':5,6]pyrido[4,3-d]pyrimidin-2-one (crude product from Step 1: 50 mg, 0.08 mmol), 2,4-bis(4-methoxyphenyl)-2,4-dithioxo-1,3,2,4-dithiadiphosphetane (32 mg, 0.080 mmol) and molybdenum hexacarbonyl (6 mg, 0.02 mmol) in 1,4-dioxane (1 mL) was evacuated then filled with nitrogen. The resulting mixture was stirred at 190° C. for 2 h then cooled to room temperature and quenched with water then extract with EtOAc. The organic extracts were combined then washed with water and brine. The organic layer was dried over $Na_2SO_4$ then concentrated. The residue was used in the next step without further purification. LC-MS calculated for $C_{29}H_{27}F_2N_6O_5S$ $(M+H)^+$ m/z: 609.2; found: 609.0.

Step 3: 3-(2,6-difluoro-3,5-dimethoxyphenyl)-1-methyl-8-[(1-methyl-1H-pyrazol-4-yl)methyl]-1,3,4,7-tetrahydro-2H-pyrrolo[3',2':5,6]pyrido[4,3-d]pyrimidin-2-one The crude product from Step 2 was dissolved in THF (2 mL) then 1.0 M potassium tert-butoxide in THF (0.40 mL, 0.40 mmol) was added. The resulting mixture was stirred at room temperature for 30 min then diluted with MeOH and purified by prep-HPLC (pH=2, acetonitrile/$H_2O$). LC-MS calculated for $C_{23}H_{23}F_2N_6O_3$$(M+H)^+$ m/z: 469.2; found: 469.0.

Example 140

3-(2,6-difluoro-3,5-dimethoxyphenyl)-1-methyl-8-(2-pyridin-2-ylethyl)-1,3,4,7-tetrahydro-2H-pyrrolo[3',2':5,6]pyrido[4,3-d]pyrimidin-2-one

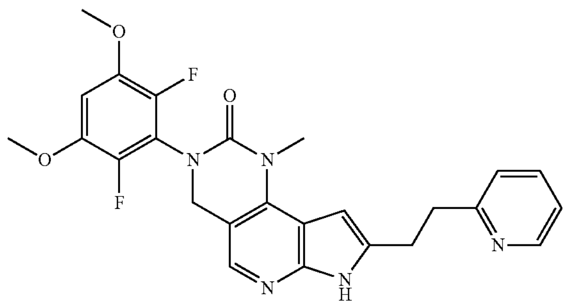 [SMILES: COc1cc(OC)c(F)c(N2Cc3cnc4[nH]c(CCc5ccccn5)cc4c3N(C)C2=O)c1F]

Step 1: 3-(2,6-difluoro-3,5-dimethoxyphenyl)-1-methyl-7-(phenylsulfonyl)-8-[(E)-2-pyridin-2-ylvinyl]-1,3,4,7-tetrahydro-2H-pyrrolo[3',2':5,6]pyrido[4,3-d]pyrimidin-2-one

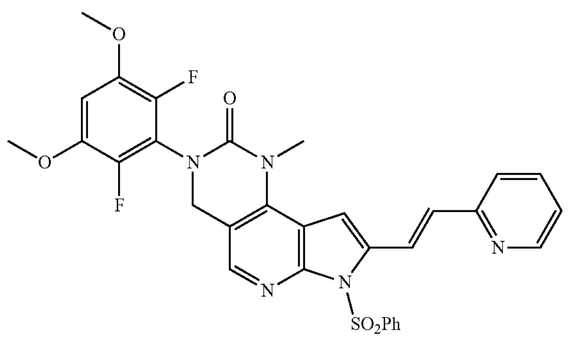

A container having a mixture of 8-bromo-3-(2,6-difluoro-3,5-dimethoxyphenyl)-1-methyl-7-(phenylsulfonyl)-1,3,4,7-tetrahydro-2H-pyrrolo[3',2':5,6]pyrido[4,3-d]pyrimidin- 2-one (40.0 mg, 0.0674 mmol), 2-vinylpyridine (21 mg, 0.20 mmol), [1,1'-bis(diphenylphosphino)ferrocene]dichloropalladium(II) complexed with dichloromethane (1:1) (3 mg, 0.004 mmol), and barium hydroxide octahydrate (42 mg, 0.13 mmol) in N,N-dimethylformamide (1 mL, 20 mmol) and a few drops of water was evacuated then filled with nitrogen. The resulting mixture was stirred at 100° C. for 5 h then cooled to room temperature. The mixture was diluted with water then extracted with EtOAc. The organic extracts were combined then washed with water and brine. The organic layer was dried over $Na_2SO_4$ and concentrated. The residue was used in the next step without further purification. LC-MS calculated for $C_{31}H_{26}F_2N_5O_5S$ $(M+H)^+$ m/z: 618.2; found: 617.9.

Step 2: 3-(2,6-difluoro-3,5-dimethoxyphenyl)-1-methyl-8-[(E)-2-pyridin-2-ylvinyl]-1,3,4,7-tetrahydro-2H-pyrrolo[3',2':5,6]pyrido[4,3-d]pyrimidin-2-one

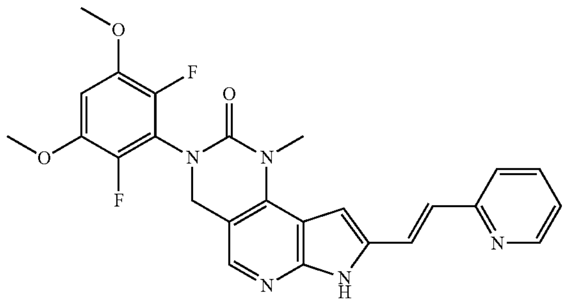 [SMILES: COc1cc(OC)c(F)c(N2Cc3cnc4[nH]c(/C=C/c5ccccn5)cc4c3N(C)C2=O)c1F]

The crude product from Step 1 was dissolved in THF (2 mL) then 1.0 M tetra-n-butylammonium fluoride in THF (674 μL, 0.674 mmol) was added. The resulting mixture was stirred at 60° C. for 2 h then cooled to room temperature and diluted with EtOAc. The mixture was washed with water and brine. The organic layer was dried over $Na_2SO_4$ and concentrated. The residue was used in the next step without further purification. LC-MS calculated for $C_{25}H_{22}F_2N_5O_3$ $(M+H)^+$ m/z: 478.2; found: 478.1.

Step 3: 3-(2,6-difluoro-3,5-dimethoxyphenyl)-1-methyl-8-(2-pyridin-2-ylethyl)-1,3,4,7-tetrahydro-2H-pyrrolo[3',2':5,6]pyrido[4,3-d]pyrimidin-2-one The crude product from Step 2 was dissolved in MeOH (2 mL) then Palladium (10 wt % on activated carbon, 30 mg) was added. The mixture was stirred under a balloon of hydrogen at room temperature for 2 h then filtered and concentrated. The residue was dissolved in MeOH then purified by prep HPLC (pH=2, acetonitrile/$H_2O$). LC-MS calculated for $C_{25}H_{24}F_2N_5O_3$ $(M+H)^+$ m/z: 480.2; found: 480.0.

Example 141

3-(2-chloro-6-fluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one

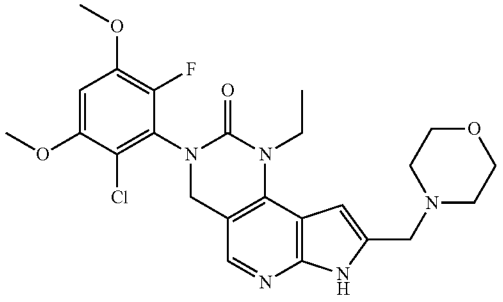 [SMILES: CCN1C(=O)N(c2c(F)c(OC)cc(OC)c2Cl)Cc2cnc3[nH]c(CN4CCOCC4)cc3c21]

This compound was prepared using procedures analogous to those for Example 126 with 3-(2-chloro-6-fluoro-3,5-dimethoxyphenyl)-1-ethyl-1,3,4,7-tetrahydro-2H-pyrrolo[3',2':5,6]pyrido[4,3-d]pyrimidin-2-one (Example 63, Step 5) replacing 3-(2,6-difluoro-3,5-dimethoxyphenyl)-1-ethyl-1,3,4,7-tetrahydro-2H-pyrrolo[3',2':5,6]pyrido[4,3-d]pyrimidin-2-one in Step 1. The product was purified by prep HPLC (pH=2, acetonitrile/$H_2O$). LC-MS calculated for $C_{24}H_{28}ClFN_5O_4(M+H)^+$ m/z: 504.2; found: 504.0.

Example 142

8-[2-(diethylamino)ethyl]-3-(2,6-difluoro-3,5-dimethoxyphenyl)-1-methyl-1,3,4,7-tetrahydro-2H-pyrrolo[3',2':5,6]pyrido[4,3-d]pyrimidin-2-one

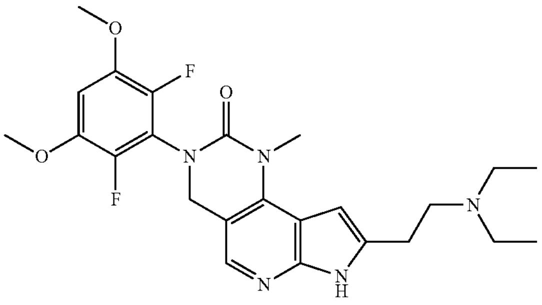 [SMILES: CCN(CC)CCc1cc2c3c(cnc2[nH]1)CN(c1c(F)c(OC)cc(OC)c1F)C(=O)N3C]

This compound was prepared using procedures analogous to those for Example 71 with diethylamine replacing 1-ethylpiperazine in Step 3. LC-MS calculated for $C_{24}H_{30}F_2N_5O_3(M+H)^+$ m/z: 474.2; found: 474.0.

Example 143

3-(2,6-difluoro-3,5-dimethoxyphenyl)-8-[2-(3-fluoroazetidin-1-yl)ethyl]-1-methyl-1,3,4,7-tetrahydro-2Hpyrrolo[3',2':5,6]pyrido[4,3-d]pyrimidin-2-one

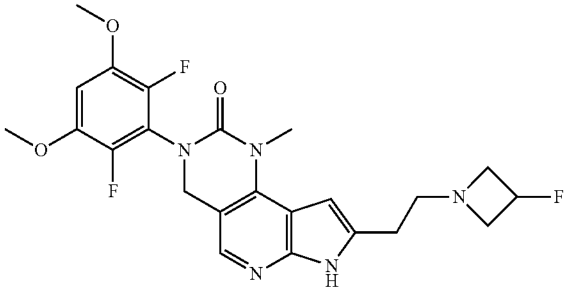 [SMILES: COc1cc(OC)c(F)c(N2Cc3cnc4[nH]c(CCN5CC(F)C5)cc4c3N(C)C2=O)c1F]

This compound was prepared using procedures analogous to those for Example 71 with 3-fluoroazetidine hydrochloride replacing 1-ethylpiperazine in Step 3. LC-MS calculated for $C_{23}H_{25}F_3N_5O_3(M+H)^+$ m/z: 476.2; found: 476.0.

Example 144

3-(2,6-difluoro-3,5-dimethoxyphenyl)-8-[2-(3-methoxyazetidin-1-yl)ethyl]-1-methyl-1,3,4,7-tetrahydro-2Hpyrrolo[3',2':5,6]pyrido[4,3-d]pyrimidin-2-one

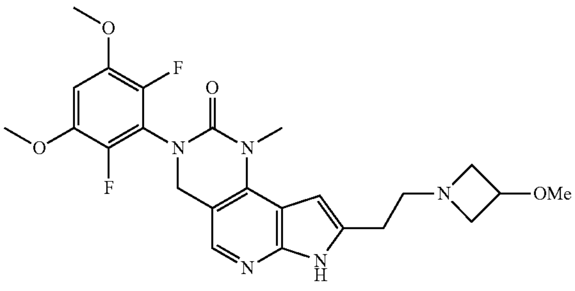 [SMILES: COc1cc(OC)c(F)c(N2Cc3cnc4[nH]c(CCN5CC(OC)C5)cc4c3N(C)C2=O)c1F]

This compound was prepared using procedures analogous to those for Example 71 with 3-methoxy-azetidine hydrochloride replacing 1-ethylpiperazine in Step 3. LC-MS calculated for $C_{24}H_{28}F_2N_5O_4(M+H)^+$ m/z: 488.2; found: 488.0.

Example 145

3-(2-chloro-6-fluoro-3,5-dimethoxyphenyl)-1-(1-methyl-1H-pyrazol-4-yl)-1,3,4,7-tetrahydro-2H-pyrazolo[4',3':5,6]pyrido[4,3-d]pyrimidin-2-one

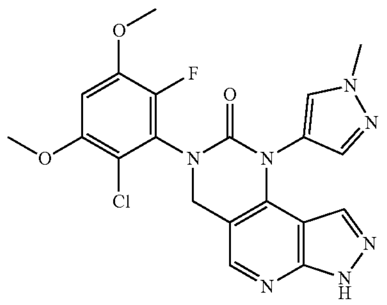 [SMILES: COc1cc(OC)c(Cl)c(N2Cc3cnc4[nH]ncc4c3N(c3cnn(C)c3)C2=O)c1F]

This compound was prepared using procedures analogous to those for Example 101 with 1-methyl-1H-pyrazol-4-amine replacing cyclopropylamine. LC-MS calculated for $C_{20}H_{18}ClFN_7O_3(M+H)^+$ m/z: 458.1; found: 457.9. $^1H$ NMR (500 MHz, DMSO) δ 13.56 (s, 1H), 8.29 (s, 1H), 8.05 (s, 1H), 7.60 (s, 1H), 7.04 (d, J=7.7 Hz, 1H), 6.23 (s, 1H), 4.91 (d, J=4.4 Hz, 2H), 3.95 (s, 3H), 3.94 (s, 3H), 3.92 (s, 3H).

Example 146

3-(2,6-difluoro-3,5-dimethoxyphenyl)-1-(2-hydroxyethyl)-8-(2-morpholin-4-ylethyl)-1,3,4,7-tetrahydro-2H-pyrrolo[3',2':5,6]pyrido[4,3-d]pyrimidin-2-one

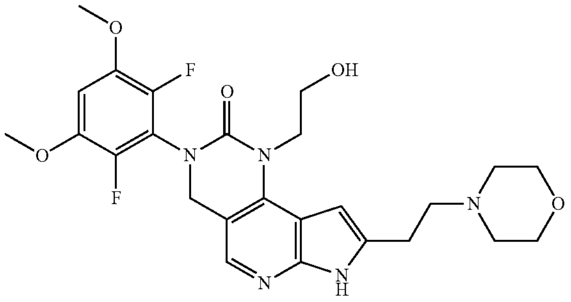 [SMILES: COc1cc(OC)c(F)c(N2Cc3cnc4[nH]c(CCN5CCOCC5)cc4c3N(CCO)C2=O)c1F]

Step 1: 4-chloro-1-(phenylsulfonyl)-1H-pyrrolo[2,3-b]pyridine-5-carbaldehyde

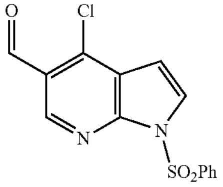

4-Chloro-1H-pyrrolo[2,3-b]pyridine-5-carbaldehyde (1.08 g, 6.00 mmol) and cesium carbonate (3.91 g, 12.0 mmol) were dissolved in N,N-dimethylformamide (10 mL), light yellow suspension. The mixture was stirred at room temperature for 20 min then benzenesulfonyl chloride (1.53 mL, 12.0 mmol) was added dropwise. After completion of the addition, white-pinkish suspension was obtained. The mixture was stirred at room temperature for 2 h at which time LC-MS indicated the reaction completed to the desired product. The reaction mixture was diluted with water. The solid was collected via filtration and washed with water then dried to give white solid (1.92 g, quant.), which was used in the next step without further purification. LC-MS calculated for $C_{14}H_{10}ClN_2O_3S$ $(M+H)^+$ m/z: 321.0; found: 320.9.

Step 2: N-{[4-chloro-1-(phenylsulfonyl)-1H-pyrrolo[2,3-b]pyridin-5-yl]methyl}-2,6-difluoro-3,5-dimethoxyaniline

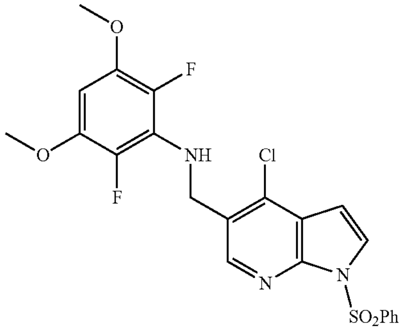

This compound was prepared using procedures analogous to those for Example 123, step 1 with 4-chloro-1-(phenylsulfonyl)-1H-pyrrolo[2,3-b]pyridine-5-carbaldehyde replacing 4-chloro-1-{[2-(trimethylsilyl)ethoxy]methyl}-1H-pyrrolo[2,3-b]pyridine-5-carbaldehyde. LC-MS calculated for $C_{22}H_{19}ClF_2N_3O_4S$ $(M+H)^+$ m/z: 494.1; found: 494.1.

Step 3: N-(2-{[tert-butyl(dimethyl)silyl]oxy}ethyl)-5-{[(2,6-difluoro-3,5-dimethoxyphenyl)amino]methyl}-1-(phenylsulfonyl)-1Hpyrrolo[2,3-b]pyridin-4-amine

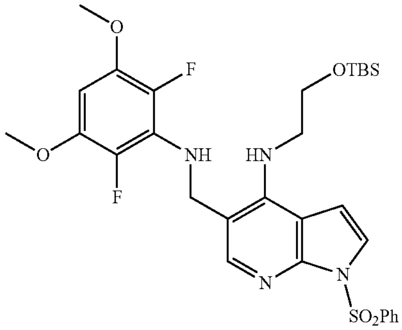

A container having a mixture of N-{[4-chloro-1-(phenylsulfonyl)-1H-pyrrolo[2,3-b]pyridin-5-yl]methyl}-2,6-difluoro-3,5-dimethoxyaniline (480 mg, 0.97 mmol), 2-{[tert-butyl(dimethyl)silyl]oxy}ethanamine (337 mg, 1.92 mmol), palladium acetate (22 mg, 0.097 mmol), (9,9-dimethyl-9H-xanthene-4,5-diyl)bis(diphenylphosphine) (56 mg, 0.097 mmol), and cesium carbonate (630 mg, 1.94 mmol) in toluene (10 mL) was degassed then filled with nitrogen. The resulting mixture was stirred at 120° C. for 2 h at which time LC-MS indicated the reaction completed to the desired product. The mixture was cooled to room temperature then diluted with DCM and filtered. The filtrate was concentrated and the residue was purified by column eluted with 0 to 30% EtOAc/DCM to give the desired product (625 mg, quant.). LC-MS calculated for $C_{30}H_{39}F_2N_4O_5SSi$ $(M+H)^+$ m/z: 633.2; found: 633.1.

Step 4: 1-(2-{[tert-butyl(dimethyl)silyl]oxy}ethyl)-3-(2,6-difluoro-3,5-dimethoxyphenyl)-7-(phenylsulfonyl)-1,3,4,7-tetrahydro-2Hpyrrolo[3',2':5,6]pyrido[4,3-d]pyrimidin-2-one

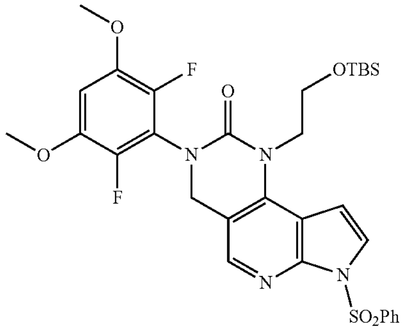

The product from Step 3 was dissolved in tetrahydrofuran (10 mL) then triethylamine (0.70 mL, 5.0 mmol) was added, followed by triphosgene (290 mg, 0.97 mmol). The resulting suspension was stirred at room temperature for 30 min then the reaction was quenched with 10 mL of 1N NaOH solution. The mixture was stirred at room temperature for 2 h then extracted with EtOAc. The combined extract was then washed with water, brine and dried over $Na_2SO_4$ and concentrated. The residue was purified by column eluted with 0 to 30% EtOAc/DCM to give the desired product (313 mg, 49%). LC-MS calculated for $C_{31}H_{37}F_2N_4O_6SSi$ $(M+H)^+$ m/z: 659.2; found: 659.2.

Step 5: 8-bromo-1-(2-{[tert-butyl(dimethyl)silyl]oxy}ethyl)-3-(2,6-difluoro-3,5-dimethoxyphenyl)-7-(phenylsulfonyl)-1,3,4,7-tetrahydro-2H-pyrrolo[3',2':5,6]pyrido[4,3-d]pyrimidin-2-one

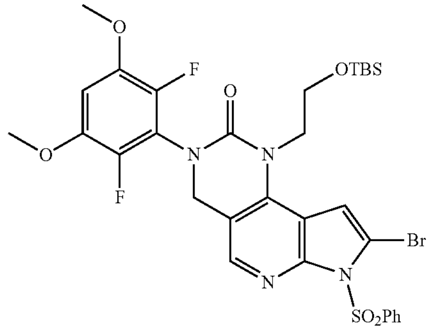

To a solution of 1-(2-{[tert-butyl(dimethyl)silyl]oxy}ethyl)-3-(2,6-difluoro-3,5-dimethoxyphenyl)-7-(phenylsulfonyl)-1,3,4,7-tetrahydro-2H-pyrrolo[3',2':5,6]pyrido[4,3-d]pyrimidin-2-one (313 mg, 0.475 mmol) in tetrahydrofuran (8 mL) at −78° C. was added freshly prepared lithium diisopropylamine solution (1M in THF, 0.5 mL, 0.5 mmol). The mixture was stirred at −78° C. for 30 min, then a solution of 1,2-dibromo-1,1,2,2-tetrachloroethane (155 mg, 0.475 mmol) in 1 mL of THF was added. The mixture was stirred at −78° C. for 1 h then quenched with saturated $NH_4Cl$ solution. The mixture was warmed to room temperature and extracted with EtOAc. The combined extract was then washed with water, brine then dried over $Na_2SO_4$ and concentrated. The residue was purified by column eluted with 0 to 20% EtOAc/DCM to give the desired product (320 mg, 91%). LC-MS calculated for $C_{31}H_{36}BrF_2N_4O_6SSi$ $(M+H)^+$ m/z: 737.1; found: 736.9.

Step 6: 3-(2,6-difluoro-3,5-dimethoxyphenyl)-1-(2-hydroxyethyl)-8-(2-morpholin-4-ylethyl)-7-(phenylsulfonyl)-1,3,4,7-tetrahydro-2H-pyrrolo[3',2':5,6]pyrido[4,3-d]pyrimidin-2-one

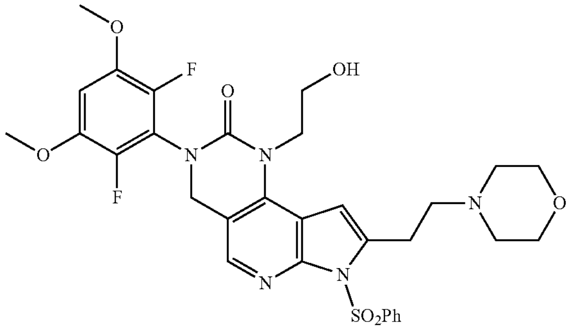

This compound was prepared using procedures analogous to those for Example 71, Step 1-3 starting with 8-bromo-1-(2-{[tert-butyl(dimethyl)silyl]oxy}ethyl)-3-(2,6-difluoro-3,5-dimethoxyphenyl)-7-(phenylsulfonyl)-1,3,4,7-tetrahydro-2H-pyrrolo[3',2':5,6]pyrido[4,3-d]pyrimidin-2-one (product from Step 5) and morpholine. LC-MS calculated for $C_{31}H_{34}F_2N_5O_7S$ $(M+H)^+$ m/z: 658.2; found: 658.2.

Step 7: 3-(2,6-difluoro-3,5-dimethoxyphenyl)-1-(2-hydroxyethyl)-8-(2-morpholin-4-ylethyl)-1,3,4,7-tetrahydro-2H-pyrrolo[3',2':5,6]pyrido[4,3-d]pyrimidin-2-one To a solution of 3-(2,6-difluoro-3,5-dimethoxyphenyl)-1-(2-hydroxyethyl)-8-(2-morpholin-4-ylethyl)-7-(phenylsulfonyl)-1,3,4,7-tetrahydro-2H-pyrrolo[3',2':5,6]pyrido[4,3-d]pyrimidin-2-one (16 mg, 0.024 mmol) in tetrahydrofuran (2 mL) was added 1.0 M tetra-n-butylammonium fluoride in THF (120 μL, 0.12 mmol). The resulting yellow solution was stirred at 50° C. for 20 min at which time LC-MS indicated the reaction completed to the desired product. The mixture was cooled to room temperature then quenched with a few drops of TFA. The mixture was diluted with MeOH then purified by prep HPLC (pH=2, acetonitrile/water) to give the product as a white solid. LC-MS calculated for $C_{25}H_{30}F_2N_5O_5$ $(M+H)^+$ m/z: 518.2; found: 518.0.

Example 147

1-(3-chloropyridin-2-yl)-3-(2,6-difluoro-3,5-dimethoxyphenyl)-3,4,7,9-tetrahydro-1H-pyrrolo[3',2':5,6]pyrido[4,3-d]pyrimidine-2,8-dione

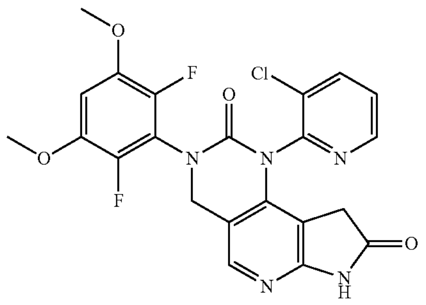 [SMILES: COc1cc(OC)c(F)c(N2Cc3cnc4c(c3N(c3ncccc3Cl)C2=O)CC(=O)N4)c1F]

This compound was prepared using procedures analogous to those for Example 123 with 3-chloropyridin-2-amine replacing 3-(aminomethyl)benzonitrile in Step 2. LC-MS calculated for $C_{22}H_{17}ClF_2N_5O_4$ $(M+H)^+$ m/z: 488.1; found: 488.1.

Example 148

7'-(2,6-difluoro-3,5-dimethoxyphenyl)-6',7'-dihydrospiro[cyclobutane-1,9'-pyrrolo[2,3-c][2,7]naphthyridin]-8'(3'H)-one

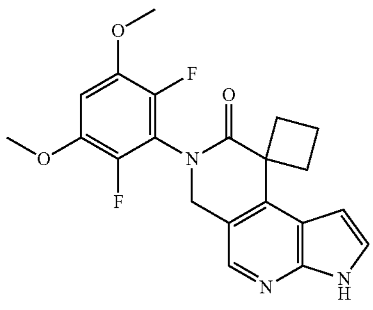 [SMILES: COc1cc(OC)c(F)c(N2Cc3cnc4[nH]ccc4c3C3(CCC3)C2=O)c1F]

This compound prepared using procedures analogous to those for Example 66 with 1,3-dibromopropane replacing 1-bromo-2-chloroethane. The product was purified by prep-HPLC (pH=2, acetonitrile/water) to give the desired product. LC-MS calculated for $C_{21}H_{20}F_2N_3O_3$ $(M+H)^+$ m/z: 400.1; found: 400.0.

Example 149

7'-(2,6-difluoro-3,5-dimethoxyphenyl)-6',7'-dihydrospiro[cyclopentane-1,9'-pyrrolo[2,3-c][2,7]naphthyridin]-8'(3'H)-one

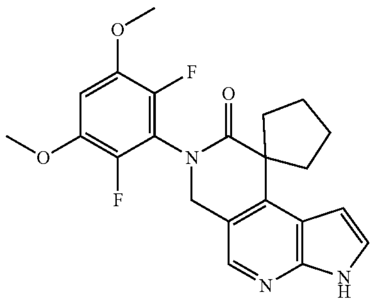 [SMILES: COc1cc(OC)c(F)c(N2Cc3cnc4[nH]ccc4c3C3(CCCC3)C2=O)c1F]

This compound prepared using procedures analogous to those for Example 66 with 1,4-dibromobutane replacing 1-bromo-2-chloroethane. The product was purified by prep-HPLC (pH=2, acetonitrile/water) to give the desired product. LC-MS calculated for $C_{22}H_{22}F_2N_3O_3(M+H)^+$ m/z: 414.2; found: 414.1.

Example 150

7'-(2,6-difluoro-3,5-dimethoxyphenyl)-2,3,5,6,6',7'-hexahydrospiro[pyran-4,9'-pyrrolo[2,3-c][2,7]naphthyridin]-8'(3'H)-one

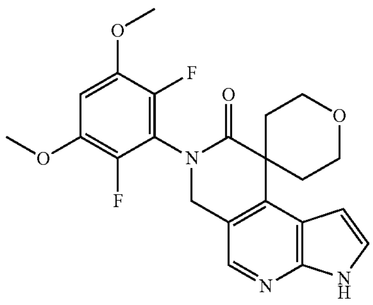 [SMILES: COc1cc(OC)c(F)c(N2Cc3cnc4[nH]ccc4c3C3(CCOCC3)C2=O)c1F]

This compound prepared using procedures analogous to those for Example 66 with bis(2-bromoethyl) ether replacing 1-bromo-2-chloroethane. The product was purified by prep-HPLC (pH=2, acetonitrile/water) to give the desired product. LC-MS calculated for $C_{22}H_{22}F_2N_3O_4$ $(M+H)^+$ m/z: 430.2; found: 430.0.

Example 151

7'-(2,6-difluoro-3,5-dimethoxyphenyl)-1-methyl-6',7'-dihydrospiro[piperidine-4,9'-pyrrolo[2,3-c][2,7]naphthyridin]-8'(3'H)-one

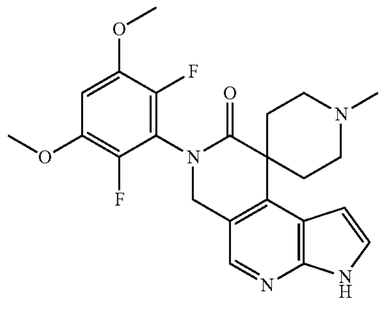

Step 1: tert-Butyl-7'-(2,6-difluoro-3,5-dimethoxyphenyl)-8'-oxo-3'-{[2-(trimethylsilyl)ethoxy]methyl}-3',6',7',8'-tetrahydro-1H-spiro[piperidine-4,9'-pyrrolo[2,3-c][2,7]naphthyridine]-1-carboxylate

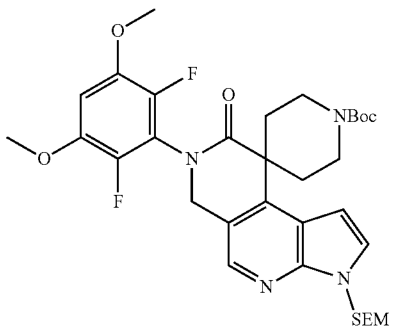 [SMILES: COc1cc(OC)c(F)c(N2Cc3cnc4c(ccn4COCC[Si](C)(C)C)c3C3(CCN(C(=O)OC(C)(C)C)CC3)C2=O)c1F]

Nitrogen was bubbled through a solution of 7-(2,6-difluoro-3,5-dimethoxyphenyl)-3-{[2-(trimethylsilyl)ethoxy]methyl}-3,6,7,9-tetrahydro-8H-pyrrolo[2,3-c]-2,7-naphthyridin-8-one (Example 60, Step 2: 50.0 mg, 0.102 mmol) in DMF (1.1 mL) for 10 min and then cesium carbonate (100.0 mg, 0.31 mmol) and tert-butyl-bis(2-chloroethyl)carbamate (0.0742 g, 0.306 mmol) were added under nitrogen and then the mixture was stirred at 50° C. for overnight. The mixture was filtered and then concentrated. The residue was used in the next step without further purification. LC-MS calculated for $C_{33}H_{45}F_2N_4O_6Si$ $(M+H)^+$ m/z: 659.3; found: 659.4.

Step 2: 7'-(2,6-difluoro-3,5-dimethoxyphenyl)-3'-{[2-(trimethylsilyl)ethoxy]methyl}-6',7'-dihydrospiro[piperidine-4,9'-pyrrolo[2,3-c][2,7]naphthyridin]-8'(3'H)-one

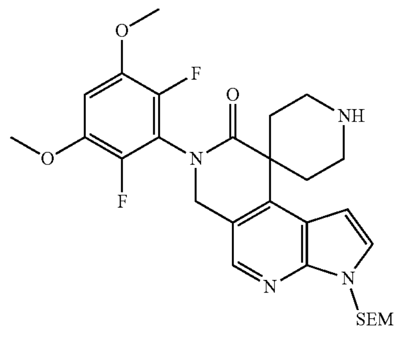 [SMILES: COc1cc(OC)c(F)c(N2Cc3cnc4c(ccn4COCC[Si](C)(C)C)c3C3(CCNCC3)C2=O)c1F]

To a solution of tert-butyl-7'-(2,6-difluoro-3,5-dimethoxyphenyl)-8'-oxo-3'-{[2-(trimethylsilyl)ethoxy]methyl}-3',6',7',8'-tetrahydro-1H-spiro[piperidine-4,9'-pyrrolo[2,3-c][2,7]naphthyridine]-1-carboxylate (95.5 mg, 0.145 mmol) (crude product from Step 1) in methylene chloride (0.5 mL) was added hydrogen chloride (4M in 1,4-dioxane, 0.5 mL, 2 mmol) and the mixture was stirred at room temperature for 45 min. Then the solvent was removed under reduced pressure and the residue was used in the next step without further purification. LC-MS calculated for $C_{28}H_{37}F_2N_4O_4Si$ $(M+H)^+$ m/z: 559.3; found: 559.3.

Step 3: 7'-(2,6-difluoro-3,5-dimethoxyphenyl)-1-methyl-3'-{[2-(trimethylsilyl)ethoxy]methyl}-6',7'-dihydrospiro[piperidine-4,9'-pyrrolo[2,3-c][2,7]naphthyridin]-8'(3'H)-one

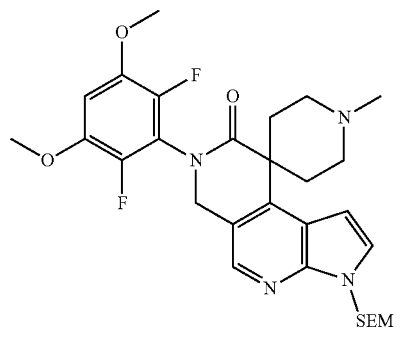

A mixture of 7'-(2,6-difluoro-3,5-dimethoxyphenyl)-3'-{[2-(trimethylsilyl)ethoxy]-methyl}-6',7'-dihydrospiro[piperidine-4,9'-pyrrolo[2,3-c][2,7]naphthyridin]-8'(3'H)-one (20.0 mg, 0.0358 mmol) and formaldehyde (9.0 M in water, 12 μL, 0.11 mmol) in methylene chloride (0.5 mL) was stirred at room temperature for 5 min and then sodium triacetoxyborohydride (23 mg, 0.11 mmol) was added. The reaction mixture was stirred at room temperature for 30 min then diluted with methylene chloride and washed with 1 N NaOH, water and brine. The organic layer was dried over $Na_2SO_4$, filtered and concentrated to give the crude product which was used in the next step without further purification. LC-MS calculated for $C_{29}H_{39}F_2N_4O_4Si$ $(M+H)^+$ m/z: 573.3; found: 573.3.

Step 4: 7'-(2,6-difluoro-3,5-dimethoxyphenyl)-1-methyl-6',7'-dihydrospiro[piperidine-4,9'-pyrrolo[2,3-c][2,7]naphthyridin]-8'(3'H)-one To a solution of 7'-(2,6-difluoro-3,5-dimethoxyphenyl)-1-methyl-3'-{[2-(trimethylsilyl)ethoxy]methyl}-6',7'-dihydrospiro[piperidine-4,9'-pyrrolo[2,3-c][2,7]naphthyridin]-8'(3'H)-one (20.0 mg, 0.035 mmol) in methylene chloride (0.3 mL) was added TFA (0.2 mL). The mixture was stirred at room temperature for 2 h then concentrated. The residue was dissolved in methanol (0.3 mL) and then ethylenediamine (0.2 mL) was added. The mixture was stirred at 50° C. for 1.5 h then cooled to room temperature and purified by prep-HPLC (pH=2, acetonitrile/water) to give the desired product. LC-MS calculated for $C_{23}H_{25}F_2N_4O_3(M+H)^+$ m/z: 443.2; found: 443.2.

Example 152

7-(2,6-difluoro-3,5-dimethoxyphenyl)-9,9-dimethyl-2-(morpholin-4-ylmethyl)-3,6,7,9-tetrahydro-8H-pyrrolo[2,3-c]-2,7-naphthyridin-8-one

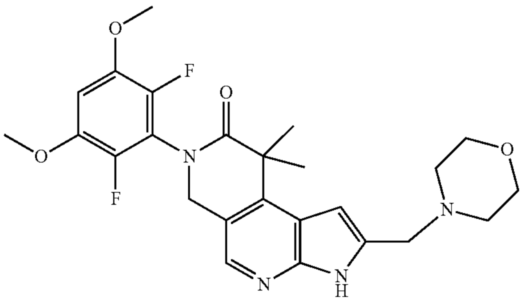 [SMILES: COc1cc(OC)c(F)c(N2Cc3cnc4[nH]c(CN5CCOCC5)cc4c3C(C)(C)C2=O)c1F]

Step 1: ethyl 3-[[(4-chloro-1-{[2-(trimethylsilyl)ethoxy]methyl}-1H-pyrrolo[2,3-b]pyridin-5-yl)methyl](2,6-difluoro-3,5-dimethoxyphenyl)amino]-3-oxopropanoate

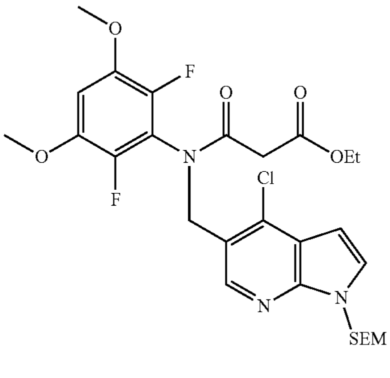 [SMILES: CCOC(=O)CC(=O)N(Cc1cnc2c(ccn2COCC[Si](C)(C)C)c1Cl)c1c(F)c(OC)cc(OC)c1F]

A mixture of N-[(4-chloro-1-{[2-(trimethylsilyl)ethoxy]methyl}-1H-pyrrolo[2,3-b]pyridin-5-yl)methyl]-2,6-difluoro-3,5-dimethoxyaniline (Example 123, Step 1: 1.45 g, 3.00 mmol) and triethylamine (0.84 mL, 6.0 mmol) in ethyl malonate (5.0 mL, 33 mmol) was stirred at 165° C. for 4 h then cooled to room temperature. The mixture was concentrated under reduced pressure then purified by column eluted with 0 to 40% EtOAc/Hexanes to give the desired product (0.8 g, 44%). LC-MS calculated for $C_{27}H_{35}ClF_2N_3O_6Si$ $(M+H)^+$ m/z: 598.2; found: 598.0.

Step 2: 7-(2,6-difluoro-3,5-dimethoxyphenyl)-3-{[2-(trimethylsilyl)ethoxy]methyl}-3,6,7,9-tetrahydro-8H-pyrrolo[2,3-c]-2,7-naphthyridin-8-one

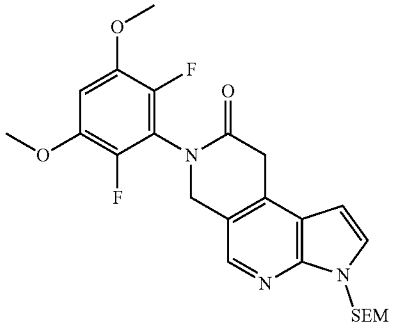 [SMILES: COc1cc(OC)c(F)c(N2Cc3cnc4c(ccn4COCC[Si](C)(C)C)c3CC2=O)c1F]

To a solution of ethyl 3-[[(4-chloro-1-{[2-(trimethylsilyl)ethoxy]methyl}-1H-pyrrolo[2,3-b]pyridin-5-yl)methyl](2,6-difluoro-3,5-dimethoxyphenyl)amino]-3-oxopropanoate (1.60 g, 2.68 mmol) in toluene (10 mL) was added sodium bis(trimethylsilyl)amide (589 mg, 3.21 mmol) and the mixture was stirred for 15 min at room temperature under nitrogen. Then dibromobis(tri-t-butylphosphino)dipalladium (I) (Aldrich, cat #677728: 62 mg, 0.080 mmol) was added and the mixture was evacuated then refilled with nitrogen for three times. The reaction mixture was then stirred at 115° C. for overnight. The mixture was cooled to room temperature then diluted with methylene chloride, washed with saturated $NaHCO_3$, water and brine. The organic layer was dried over $Na_2SO_4$ then concentrated. The residue was purified by column eluted with 0 to 40% EtOAc/Hexanes to give the desired product (0.81 g, 62%). LC-MS calculated for $C_{24}H_{30}F_2N_3O_4Si$ $(M+H)^+$ m/z: 490.2; found: 490.1.

Step 3: 7-(2,6-difluoro-3,5-dimethoxyphenyl)-9,9-dimethyl-3-{[2-(trimethylsilyl)ethoxy]methyl}-3,6,7,9-tetrahydro-8H-pyrrolo[2,3-c]-2,7-naphthyridin-8-one

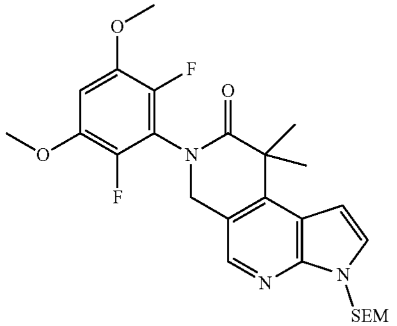 [SMILES: COc1cc(OC)c(F)c(N2Cc3cnc4c(ccn4COCC[Si](C)(C)C)c3C(C)(C)C2=O)c1F]

Nitrogen was bubbled through a solution of 7-(2,6-difluoro-3,5-dimethoxyphenyl)-3-{[2-(trimethylsilyl)ethoxy]methyl}-3,6,7,9-tetrahydro-8H-pyrrolo[2,3-c]-2,7-naphthyridin-8-one (1.00 g, 2.04 mmol) in N,N-dimethylformamide (10 mL) for 20 min and then cesium carbonate (2.0 g, 6.1 mmol) and methyl iodide (509 μL, 8.17 mmol) were added under nitrogen. The resulting mixture was stirred at room temperature overnight. The mixture was filtered and then concentrated. The residue was purified by column eluted with 0 to 40% EtOAc/Hexanes to give the desired product (0.95 g, 90%). LC-MS calculated for $C_{26}H_{34}F_2N_3O_4Si$ $(M+H)^+$ m/z: 518.2; found: 518.2.

Step 4: 7-(2,6-difluoro-3,5-dimethoxyphenyl)-9,9-dimethyl-3,6,7,9-tetrahydro-8H-pyrrolo[2,3-c]-2,7-naphthyridin-8-one

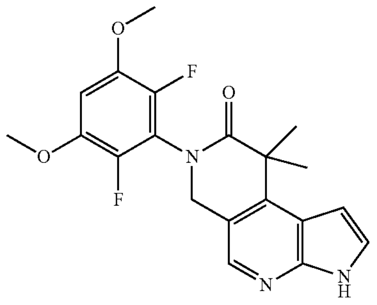 [SMILES: COc1cc(OC)c(F)c(N2Cc3cnc4[nH]ccc4c3C(C)(C)C2=O)c1F]

To a solution of 7-(2,6-difluoro-3,5-dimethoxyphenyl)-9,9-dimethyl-3-{[2-(trimethylsilyl)ethoxy]methyl}-3,6,7,9-tetrahydro-8H-pyrrolo[2,3-c]-2,7-naphthyridin-8-one (1.0 g, 1.9 mmol) in methylene chloride (4 mL) was added trifluoroacetic acid (4 mL, 50 mmol). The mixture was stirred at room temperature for 2 h then concentrated under reduced pressure. The residue was dissolved in methanol (6 mL) and then ethylenediamine (3 mL) was added. The mixture was stirred at 50° C. for 2.5 h then cooled to room temperature and concentrated. The residue was triturated with water and the precipitate was collected via filtration then washed with water and dried to give the desired product (0.67 g, 90%). LC-MS calculated for $C_{20}H_{20}F_2N_3O_3$ $(M+H)^+$ m/z: 388.1; found: 388.2.

Step 5: 7-(2,6-difluoro-3,5-dimethoxyphenyl)-9,9-dimethyl-3-(phenylsulfonyl)-3,6,7,9-tetrahydro-8H-pyrrolo[2,3-c]-2,7-naphthyridin-8-one

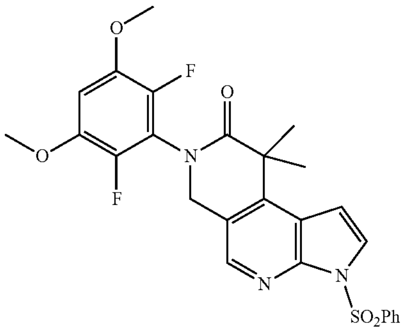

To a solution of 7-(2,6-difluoro-3,5-dimethoxyphenyl)-9,9-dimethyl-3,6,7,9-tetrahydro-8H-pyrrolo[2,3-c]-2,7-naphthyridin-8-one (0.070 g, 0.18 mmol) in dimethylformamide (DMF) (1.0 mL) was added sodium hydride (0.0108 g, 0.271 mmol) (60% NaH dispersion in mineral oil) at 0° C. and the resulting mixture was stirred for 15 min. At this time benzenesulfonyl chloride (25.4 μL, 0.199 mmol) was added and the reaction mixture was stirred for 1 h at 0° C. The reaction was quenched by addition of saturated $NH_4Cl$ aqueous solution then extracted with methylene chloride. The combined extract was then washed with saturated $NaHCO_3$, water and brine. The organic layer was dried over $Na_2SO_4$, filtered and concentrated. The residue was purified by flash chromatography on a silica gel column eluted with ethyl acetate in DCM (0 to 10%) to afford the desired product. LC-MS calculated for $C_{26}H_{24}F_2N_3O_5S$ $[M+H]^+$ m/z: 528.1; found 528.1.

Step 6: 7-(2,6-difluoro-3,5-dimethoxyphenyl)-9,9-dimethyl-8-oxo-3-(phenylsulfonyl)-6,7,8,9-tetrahydro-3H-pyrrolo[2,3-c]-2,7-naphthyridine-2-carbaldehyde

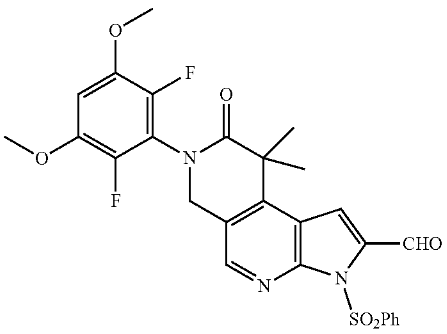

To a solution of 7-(2,6-difluoro-3,5-dimethoxyphenyl)-9,9-dimethyl-3-(phenylsulfonyl)-3,6,7,9-tetrahydro-8H-pyrrolo[2,3-c]-2,7-naphthyridin-8-one (0.80 g, 1.5 mmol) in tetrahydrofuran (4 mL) at −78° C. was added freshly prepared lithium diisopropylamide (1M in THF, 2.3 mL, 2.3 mmol). The mixture was stirred for 0.5 h and then N,N-dimethylformamide (0.69 mL, 8.9 mmol) was added. The mixture was stirred at −78° C. for 1 h then quenched with water and warmed to room temperature. The mixture was diluted with methylene chloride, washed with saturated $NaHCO_3$, water and brine. The organic layer was dried over $Na_2SO_4$, filtered and then concentrated. The mixture was used in the next step without further purification. LC-MS calculated for $C_{27}H_{24}F_2N_3O_6S$ $(M+H)^+$ m/z: 556.1; found: 556.0.

Step 7: 7-(2,6-difluoro-3,5-dimethoxyphenyl)-9,9-dimethyl-2-(morpholin-4-ylmethyl)-3-(phenylsulfonyl)-3,6,7,9-tetrahydro-8H-pyrrolo[2,3-c]-2,7-naphthyridin-8-one

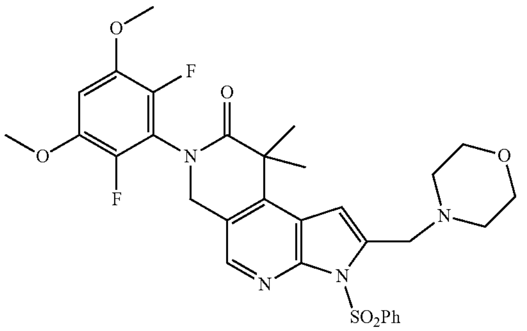

To a solution of 7-(2,6-difluoro-3,5-dimethoxyphenyl)-9,9-dimethyl-8-oxo-3-(phenylsulfonyl)-6,7,8,9-tetrahydro-3H-pyrrolo[2,3-c]-2,7-naphthyridine-2-carbaldehyde (0.50 g, 0.90 mmol) in 1,2-dichloroethane (12 mL) was added morpholine (0.47 mL, 5.4 mmol), followed by acetic acid (0.15 mL, 2.7 mmol). The mixture was stirred at room temperature overnight then sodium triacetoxyborohydride (570 mg, 2.7 mmol) was added and the reaction mixture was stirred at room temperature for 1 h. The mixture was diluted with methylene chloride, then washed with 1N NaOH, water and brine. The organic layer was dried over $Na_2SO_4$, filtered and concentrated. The residue was purified by column eluted with 0 to 20% EtOAc/DCM to give the desired product (0.40 g, 71%). LC-MS calculated for $C_{31}H_{33}F_2N_4O_6S$ $[M+H]^+$ m/z: 627.2; found 627.3.

Step 8: 7-(2,6-difluoro-3,5-dimethoxyphenyl)-9,9-dimethyl-2-(morpholin-4-ylmethyl)-3,6,7,9-tetrahydro-8H-pyrrolo[2,3-c]-2,7-naphthyridin-8-one To a mixture of 7-(2,6-difluoro-3,5-dimethoxyphenyl)-9,9-dimethyl-2-(morpholin-4-ylmethyl)-3-(phenylsulfonyl)-3,6,7,9-tetrahydro-8H-pyrrolo[2,3-c]-2,7-naphthyridin-8-one (0.48 g, 0.76 mmol) in tetrahydrofuran (8.0 mL) was added 1.0 M tetra-n-butylammonium fluoride in THF (4.5 mL, 4.5 mmol). The reaction mixture was stirred at 60° C. for 1 h then cooled to room temperature and quenched with water. The product was purified by prep-HPLC (pH=2, acetonitrile/water). LC-MS calculated for $C_{25}H_{29}F_2N_4O_4$ $(M+H)^+$ m/z: 487.2; found: 487.0. $^1H$ NMR (500 MHz, DMSO) δ 11.81 (s, 1H), 8.19 (s, 1H), 7.06 (t, J=8.2 Hz, 1H), 6.91 (s, 1H), 4.91 (s, 2H), 4.40 (s, 2H), 3.90 (s, 6H), 3.81 (s, 4H), 3.17 (s, 4H), 1.75 (s, 6H).

Example 153

7-(2,6-difluoro-3,5-dimethoxyphenyl)-9,9-dimethyl-2-[(4-methylpiperazin-1-yl)methyl]-3,6,7,9-tetrahydro-8H-pyrrolo[2,3-c]-2,7-naphthyridin-8-one

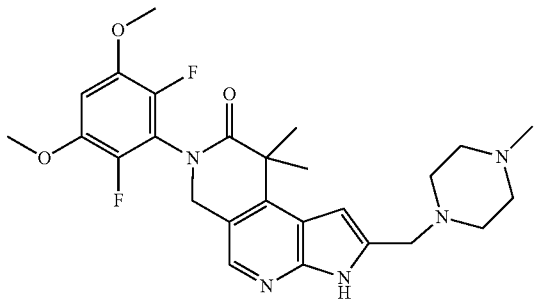

Step 1: 7-(2,6-difluoro-3,5-dimethoxyphenyl)-9,9-dimethyl-2-[(4-methylpiperazin-1-yl)methyl]-3-(phenylsulfonyl)-3,6,7,9-tetrahydro-8H-pyrrolo[2,3-c]-2,7-naphthyridin-8-one

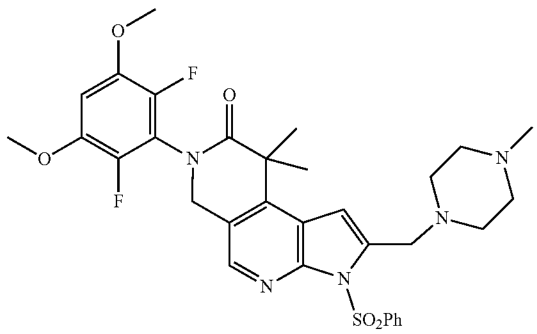

This compound was prepared using procedures analogous to those for Example 152, Step 7 with N-methyl piperazine replacing morpholine. LC-MS calculated for $C_{32}H_{36}F_2N_5O_5S$ $(M+H)^+$ m/z: 640.2; found: 640.3.

Step 2: 7-(2,6-difluoro-3,5-dimethoxyphenyl)-9,9-dimethyl-2-[(4-methylpiperazin-1-yl)methyl]-3,6,7,9-tetrahydro-8H-pyrrolo[2,3-c]-2,7-naphthyridin-8-one To a solution of 7-(2,6-difluoro-3,5-dimethoxyphenyl)-9,9-dimethyl-2-[(4-methylpiperazin-1-yl)methyl]-3-(phenylsulfonyl)-3,6,7,9-tetrahydro-8H-pyrrolo[2,3-c]-2,7-naphthyridin-8-one (25.0 mg) in THF (1.0 mL) was added 1 M TBAF in THF (0.1 mL). The mixture was stirred at 60° C. for 30 min then cooled to room temperature and purified by prep-HPLC (pH=2, acetonitrile/water) to give the desired product. LC-MS calculated for $C_{26}H_{32}F_2N_5O_3(M+H)^+$ m/z: 500.2; found: 500.0.

Example 154

7-(2,6-difluoro-3,5-dimethoxyphenyl)-2-[(4-ethylpiperazin-1-yl)methyl]-9,9-dimethyl-3,6,7,9-tetrahydro-8H-pyrrolo[2,3-c]-2,7-naphthyridin-8-one

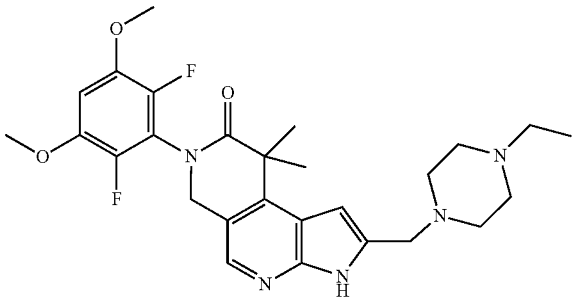 [SMILES: CCN1CCN(Cc2cc3c4c(cnc3[nH]2)CN(c2c(F)c(OC)cc(OC)c2F)C(=O)C4(C)C)CC1]

This compound was prepared using procedures analogous to those for Example 153 with N-ethyl piperazine replacing N-methyl piperazine. LC-MS calculated for $C_{27}H_{34}F_2N_5O_3$ $(M+H)^+$ m/z: 514.3; found: 514.0. $^1H$ NMR (500 MHz, DMSO) δ 11.92 (s, 1H), 8.12 (s, 1H), 7.08 (t, J=8.2 Hz, 1H), 6.69 (s, 1H), 4.90 (s, 2H), 3.94 (s, 2H), 3.90 (s, 6H), 3.51 (br, 2H), 3.24-3.08 (m, 4H), 3.03 (br, 2H), 2.57 (br, 2H), 1.71 (s, 6H), 1.18 (t, J=7.3 Hz, 3H).

Example 155

1-{[7-(2,6-difluoro-3,5-dimethoxyphenyl)-9,9-dimethyl-8-oxo-6,7,8,9-tetrahydro-3H-pyrrolo[2,3-c]-2,7-naphthyridin-2-yl]methyl}piperidine-4-carbonitrile

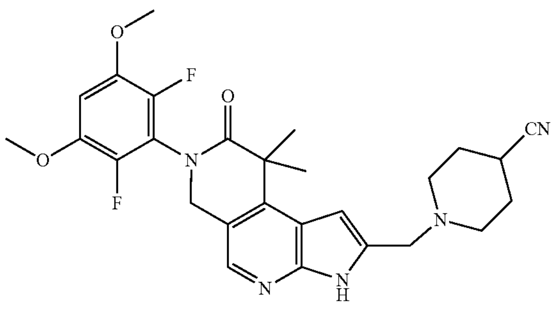 [SMILES: COc1cc(OC)c(F)c(N2Cc3cnc4[nH]c(CN5CCC(C#N)CC5)cc4c3C(C)(C)C2=O)c1F]

This compound was prepared using procedures analogous to those for Example 153 with piperidine-4-carbonitrile replacing N-methyl piperazine. LC-MS calculated for $C_{27}H_{30}F_2N_5O_3$ $(M+H)^+$ m/z: 510.2; found: 510.0.

Example 156

7-(2,6-difluoro-3,5-dimethoxyphenyl)-2-{[(3S)-3-(dimethylamino)pyrrolidin-1-yl]methyl}-9,9-dimethyl-3,6,7,9-tetrahydro-8H-pyrrolo[2,3-c]-2,7-naphthyridin-8-one

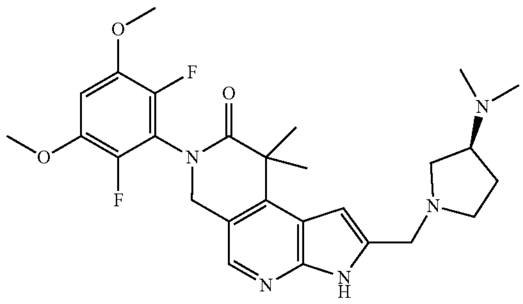

This compound prepared using procedures analogous to those for Example 153 with (3S)—N,N-dimethylpyrrolidin-3-amine replacing N-methyl piperazine. LC-MS calculated for $C_{27}H_{34}F_2N_5O_3(M+H)^+$ m/z: 514.3; found: 514.1.

Example 157

7-(2,6-difluoro-3,5-dimethoxyphenyl)-2-{[(3R)-3-(dimethylamino)pyrrolidin-1-yl]methyl}-9,9-dimethyl-3,6,7,9-tetrahydro-8H-pyrrolo[2,3-c]-2,7-naphthyridin-8-one

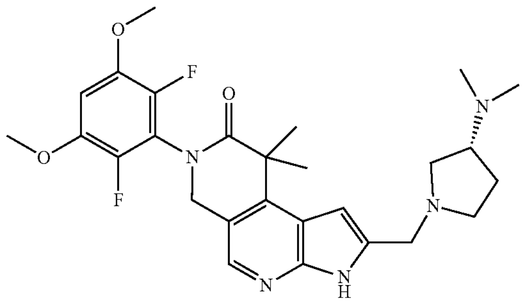

This compound prepared using procedures analogous to those for Example 153 with (3R)—N,N-dimethylpyrrolidin-3-amine replacing N-methyl piperazine. LC-MS calculated for $C_{27}H_{34}F_2N_5O_3(M+H)^+$ m/z: 514.3; found: 514.1.

Example 158

7-(2,6-difluoro-3,5-dimethoxyphenyl)-9,9-dimethyl-2-(2-morpholin-4-ylethyl)-3,6,7,9-tetrahydro-8H-pyrrolo[2,3-c]-2,7-naphthyridin-8-one

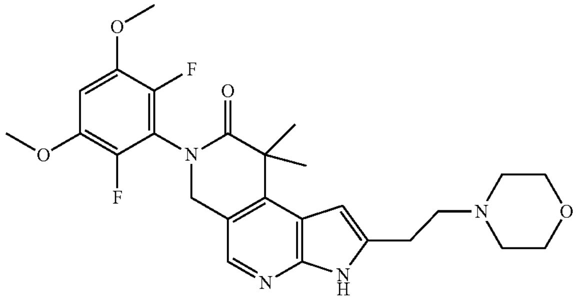 [SMILES: COc1cc(OC)c(F)c(N2Cc3cnc4[nH]c(CCN5CCOCC5)cc4c3C(C)(C)C2=O)c1F]

Step 1: 2-bromo-7-(2,6-difluoro-3,5-dimethoxyphenyl)-9,9-dimethyl-3-(phenylsulfonyl)-3,6,7,9-tetrahydro-8H-pyrrolo[2,3-c]-2,7-naphthyridin-8-one

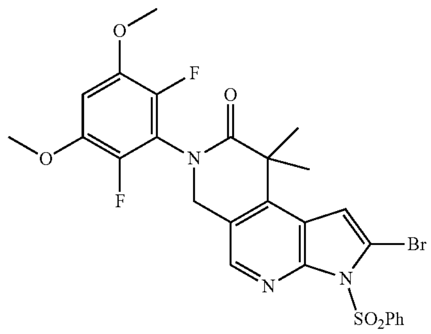

To a solution of 7-(2,6-difluoro-3,5-dimethoxyphenyl)-9,9-dimethyl-3-(phenylsulfonyl)-3,6,7,9-tetrahydro-8H-pyrrolo[2,3-c]-2,7-naphthyridin-8-one (Example 152, Step 5: 0.25 g, 0.47 mmol) in tetrahydrofuran (5 mL) at −78° C. was added freshly prepared lithium diisopropylamide solution (1M in THF, 0.7 mL). The mixture was stirred at −78° C. for 30 min then a solution of 1, 2-dibromo-1,1,2,2-tetrachloroethane (0.23 g, 0.71 mmol) in THF (1 mL) was added. The resulting mixture was stirred at −78° C. for 1 h then quenched with water and warmed to room temperature. The mixture was extracted with EtOAc. The combined extract was washed with water and brine. The organic layer was dried over $Na_2SO_4$ and concentrated. The residue was purified by column eluted with 0 to 10% EtOAc/DCM to give the desired product. LC-MS calculated for $C_{26}H_{23}BrF_2N_3O_5S$ $(M+H)^+$ m/z: 606.1; found: 605.8.

Step 2: 7-(2,6-difluoro-3,5-dimethoxyphenyl)-2-[(E)-2-ethoxyvinyl]-9,9-dimethyl-3-(phenylsulfonyl)-3,6,7,9-tetrahydro-8H-pyrrolo[2,3-c]-2,7-naphthyridin-8-one

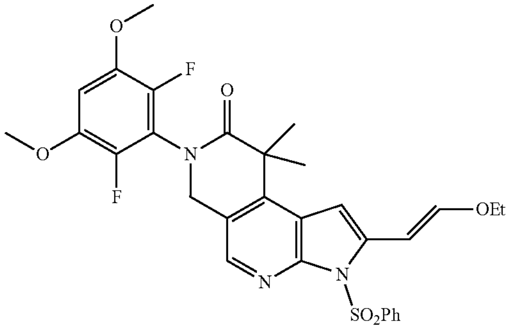

To a mixture of 2-bromo-7-(2,6-difluoro-3,5-dimethoxyphenyl)-9,9-dimethyl-3-(phenylsulfonyl)-3,6,7,9-tetrahydro-8H-pyrrolo[2,3-c]-2,7-naphthyridin-8-one (0.10 g, 0.16 mmol), 2-[(E)-2-ethoxyvinyl]-4,4,5,5-tetramethyl-1,3,2-dioxaborolane (Aldrich, cat #731528: 0.033 g, 0.16 mmol) and sodium carbonate (0.035 g, 0.33 mmol) in 1,4-dioxane (1 mL, 10 mmol)/water (0.2 mL, 10 mmol) was added dichloro(bis{di-tert-butyl[4-(dimethylamino)phenyl]phosphoranyl})palladium (3.5 mg, 0.0049 mmol). The mixture was evacuated then refilled with $N_2$ for three times. The reaction mixture was then stirred at 95° C. for overnight then cooled to room temperature and diluted with DCM. The mixture was washed with water and brine. The organic layer was dried over $Na_2SO_4$ and concentrated. The residue was purified by column eluted with 0 to 10% EtOAc/DCM to give the desired product. LC-MS calculated for $C_{30}H_{30}F_2N_3O_6S$ $(M+H)^+$ m/z: 598.2; found: 598.2.

Step 3: [7-(2,6-difluoro-3,5-dimethoxyphenyl)-9,9-dimethyl-8-oxo-3-(phenylsulfonyl)-6,7,8,9-tetrahydro-3H-pyrrolo[2,3-c]-2,7-naphthyridin-2-yl]acetaldehyde

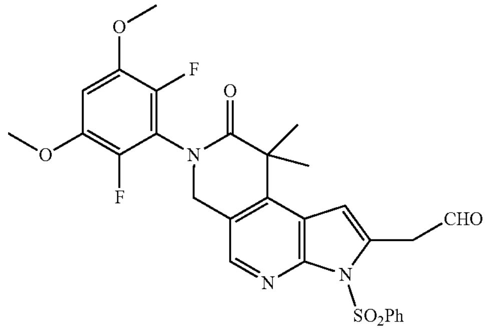

The product from Step 2 was dissolved in tetrahydrofuran (1.0 mL) and then concentrated HCl (0.1 mL) was added and the mixture was stirred at room temperature for 2 h. The mixture was diluted with methylene chloride then washed with saturated $NaHCO_3$, water and brine. The organic layer was dried over $Na_2SO_4$, filtered and concentrated to provide the product which was used in the next step without further purification. LC-MS calculated for $C_{28}H_{26}F_2N_3O_6S$ $(M+H)^+$ m/z: 570.1; found: 570.0.

Step 4: 7-(2,6-difluoro-3,5-dimethoxyphenyl)-9,9-dimethyl-2-(2-morpholin-4-ylethyl)-3-(phenylsulfonyl)-3,6,7,9-tetrahydro-8H-pyrrolo[2,3-c]-2,7-naphthyridin-8-one

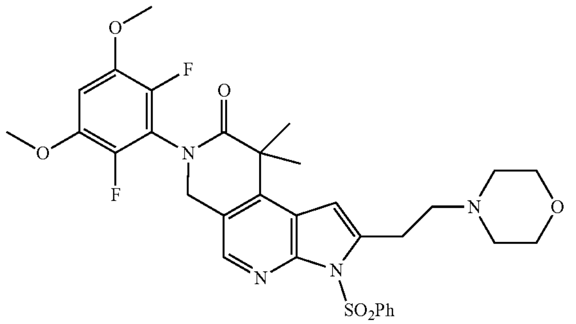

A mixture of [7-(2,6-difluoro-3,5-dimethoxyphenyl)-9,9-dimethyl-8-oxo-3-(phenylsulfonyl)-6,7,8,9-tetrahydro-3H-pyrrolo[2,3-c]-2,7-naphthyridin-2-yl]acetaldehyde (30.0 mg, 0.0527 mmol), morpholine (0.06 mL, 0.7 mmol) and acetic acid (0.030 mL) in methylene chloride (0.8 mL, 10 mmol) was stirred at room temperature for 1 h and then sodium triacetoxyborohydride (33 mg, 0.16 mmol) was added. The reaction mixture was stirred at room temperature overnight then diluted with methylene chloride, washed with saturated $NaHCO_3$, water and brine. The organic layer was dried over $Na_2SO_4$, filtered and concentrated. The residue was used in the next step without further purification. LC-MS calculated for $C_{32}H_{35}F_2N_4O_6S$ $(M+H)^+$ m/z: 641.2; found: 641.0.

Step 5: 7-(2,6-difluoro-3,5-dimethoxyphenyl)-9,9-dimethyl-2-(2-morpholin-4-ylethyl)-3,6,7,9-tetrahydro-8H-pyrrolo[2,3-c]-2,7-naphthyridin-8-one To a solution of 7-(2,6-difluoro-3,5-dimethoxyphenyl)-9,9-dimethyl-2-(2-morpholin-4-ylethyl)-3-(phenylsulfonyl)-3,6,7,9-tetrahydro-8H-pyrrolo[2,3-c]-2,7-naphthyridin-8-one (25.0 mg) in THF (0.5 mL) was added 1 M potassium t-butoxide in THF (0.2 mL). The mixture was stirred at room temperature for 30 min then purified by prep-HPLC (pH=2, acetonitrile/water) to give the desired product. LC-MS calculated for $C_{26}H_{31}F_2N_4O_4(M+H)^+$ m/z: 501.2; found: 501.0.

Example 159

7-(2,6-difluoro-3,5-dimethoxyphenyl)-2-[2-(4-ethylpiperazin-1-yl)ethyl]-9,9-dimethyl-3,6,7,9-tetrahydro-8H-pyrrolo[2,3-c]-2,7-naphthyridin-8-one

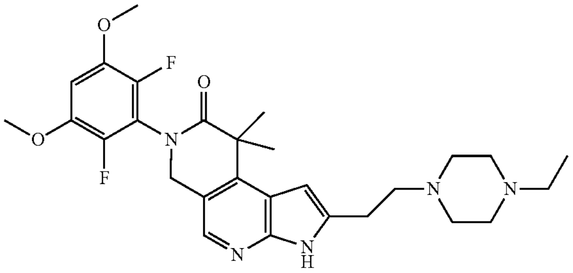 [SMILES: CCN1CCN(CCc2cc3c4c(cnc3[nH]2)CN(c2c(F)c(OC)cc(OC)c2F)C(=O)C4(C)C)CC1]

This compound was prepared using procedures analogous to those for Example 158 with N-ethyl piperazine replacing morpholine in Step 4. LC-MS calculated for $C_{28}H_{36}F_2N_5O_3$ $(M+H)^+$ m/z: 528.3; found: 528.0.

Example 160

7-(2,6-difluoro-3,5-dimethoxyphenyl)-9,9-dimethyl-2-[2-(4-methylpiperazin-1-yl)ethyl]-3,6,7,9-tetrahydro-8H-pyrrolo[2,3-c]-2,7-naphthyridin-8-one

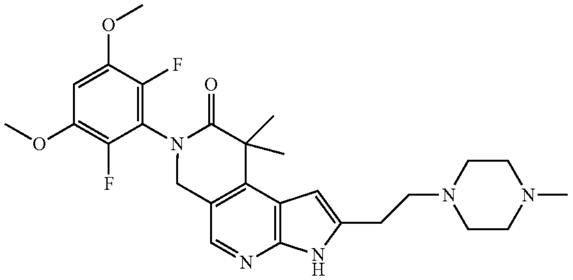

This compound was prepared using procedures analogous to those for Example 158 with N-methyl piperazine replacing morpholine in Step 4. LC-MS calculated for $C_{27}H_{34}F_2N_5O_3$ $(M+H)^+$ m/z: 514.3; found: 514.0.

Example 161

3-(2,6-Difluoro-3,5-dimethoxyphenyl)-1-(1,3-oxazol-4-ylmethyl)-1,3,4,7-tetrahydro-2H-pyrazolo[4',3':5,6]pyrido[4,3-d]pyrimidin-2-one

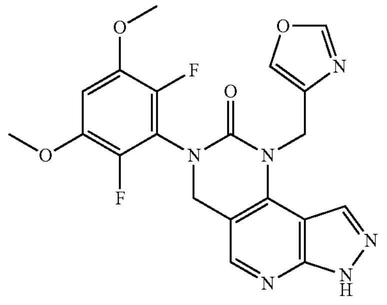 [SMILES: COc1cc(OC)c(F)c(N2Cc3cnc4[nH]ncc4c3N(Cc3cocn3)C2=O)c1F]

This compound was prepared using procedures analogous to those for Example 85 with 1-(1,3-oxazol-4-yl)methanamine hydrochloride replacing 1-methyl-1H-pyrazol-4-amine in Step 1. The product was purified by prep HPLC (pH=2, acetonitrile/water). LC-MS calculated for $C_{20}H_{17}F_2N_6O_4$(M+H)$^+$ m/z: 443.1; found: 443.1.

Example 162

3-(2,6-Difluoro-3,5-dimethoxyphenyl)-1-(isoxazol-3-ylmethyl)-1,3,4,7-tetrahydro-2H-pyrazolo[4',3':5,6]pyrido[4,3-d]pyrimidin-2-one

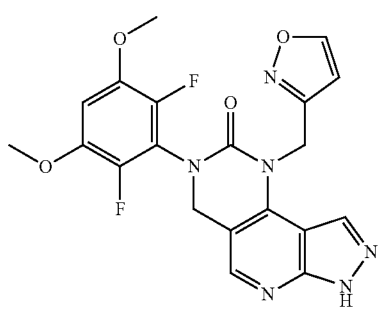 [SMILES: COc1cc(OC)c(F)c(N2Cc3cnc4[nH]ncc4c3N(Cc3ccon3)C2=O)c1F]

This compound was prepared using procedures analogous to those for Example 85 with 1-isoxazol-3-ylmethanamine hydrochloride replacing 1-methyl-1H-pyrazol-4-amine in Step 1. The product was purified by prep HPLC (pH=2, acetonitrile/water). LC-MS calculated for $C_{20}H_{17}F_2N_6O_4$ (M+H)$^+$ m/z: 443.1; found: 443.1.

Example 163

3-(2,6-Difluoro-3,5-dimethoxyphenyl)-1-(1,3-thiazol-4-ylmethyl)-1,3,4,7-tetrahydro-2H-pyrazolo[4',3':5,6]pyrido[4,3-d]pyrimidin-2-one

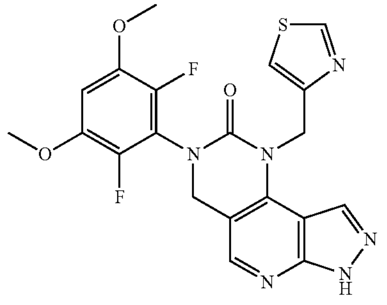

This compound was prepared using procedures analogous to those for Example 85 with 1-(1,3-thiazol-4-yl)methanamine hydrochloride replacing 1-methyl-1H-pyrazol-4-amine in Step 1. The product was purified by prep HPLC (pH=2, acetonitrile/water). LC-MS calculated for $C_{20}H_{17}F_2N_6O_3S$ (M+H)$^+$ m/z: 459.1; found: 459.0.

Example 164

3-(2,6-Difluoro-3,5-dimethoxyphenyl)-1-[2-(difluoromethoxy)phenyl]-1,3,4,7-tetrahydro-2H-pyrazolo[4',3':5,6]pyrido[4,3-d]pyrimidin-2-one

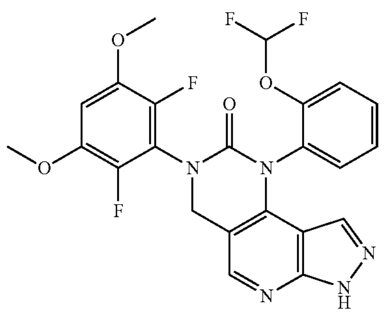 [SMILES: COc1cc(OC)c(F)c(N2Cc3cnc4[nH]ncc4c3N(c3ccccc3OC(F)F)C2=O)c1F]

This compound was prepared using procedures analogous to those for Example 85 with 2-(difluoromethoxy)aniline replacing 1-methyl-1H-pyrazol-4-amine in Step 1. The product was purified by prep HPLC (pH=2, acetonitrile/water). LC-MS calculated for $C_{23}H_{18}F_4N_5O_4$ (M+H)$^+$ m/z: 504.1; found: 503.9.

Example 165

3-(2,6-Difluoro-3,5-dimethoxyphenyl)-1-[2-(1H-pyrazol-1-yl)ethyl]-1,3,4,7-tetrahydro-2H-pyrazolo[4',3':5,6]pyrido[4,3-d]pyrimidin-2-one

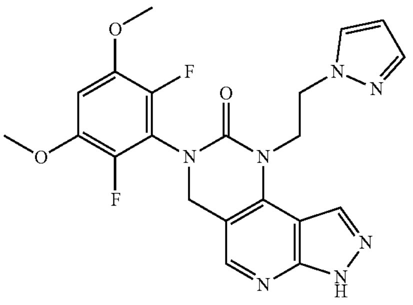 [SMILES: COc1cc(OC)c(F)c(N2Cc3cnc4[nH]ncc4c3N(CCn3cccn3)C2=O)c1F]

This compound was prepared using procedures analogous to those for Example 85 with 2-(1H-pyrazol-1-yl) ethanamine replacing 1-methyl-1H-pyrazol-4-amine in Step 1. The product was purified by prep HPLC (pH=2, acetonitrile/water). LC-MS calculated for $C_{21}H_{20}F_2N_7O_3$ $(M+H)^+$ m/z: 456.2; found: 456.0.

Example 166

3-(2,6-Difluoro-3,5-dimethoxyphenyl)-1-[(2R)-tetrahydrofuran-2-ylmethyl]-1,3,4,7-tetrahydro-2H-pyrazolo[4',3':5,6]pyrido[4,3-d]pyrimidin-2-one

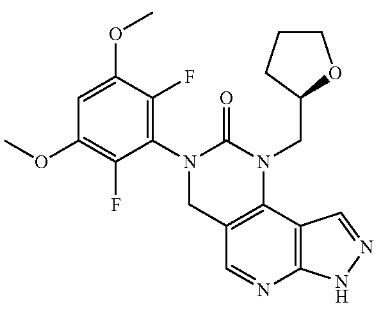 [SMILES: COc1cc(OC)c(F)c(N2Cc3cnc4[nH]ncc4c3N(C[C@H]3CCCO3)C2=O)c1F]

This compound was prepared using procedures analogous to those for Example 85 with 1-[(2R)-tetrahydrofuran-2-yl] methanamine replacing 1-methyl-1H-pyrazol-4-amine in Step 1. The product was purified by prep HPLC (pH=2, acetonitrile/water). LC-MS calculated for $C_{21}H_{22}F_2N_5O_4$ $(M+H)^+$ m/z: 446.2; found: 445.9.

Example 167

3-(2,6-Difluoro-3,5-dimethoxyphenyl)-1-[(2S)-tetrahydrofuran-2-ylmethyl]-1,3,4,7-tetrahydro-2H-pyrazolo[4',3':5,6]pyrido[4,3-d]pyrimidin-2-one

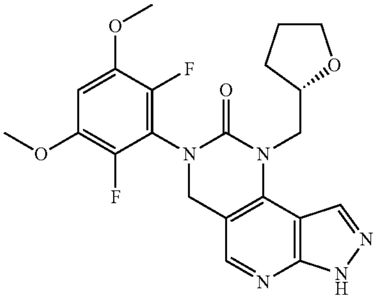

This compound was prepared using procedures analogous to those for Example 85 with 1-[(2S)-tetrahydrofuran-2-yl] methanamine replacing 1-methyl-1H-pyrazol-4-amine in Step 1. The product was purified by prep HPLC (pH=2, acetonitrile/water). LC-MS calculated for $C_{21}H_{22}F_2N_5O_4$ $(M+H)^+$ m/z: 446.2; found: 446.0.

Example 168

3-(2,6-Difluoro-3,5-dimethoxyphenyl)-1-(2-pyrazin-2-ylethyl)-1,3,4,7-tetrahydro-2H-pyrazolo[4',3':5,6]pyrido[4,3-d]pyrimidin-2-one

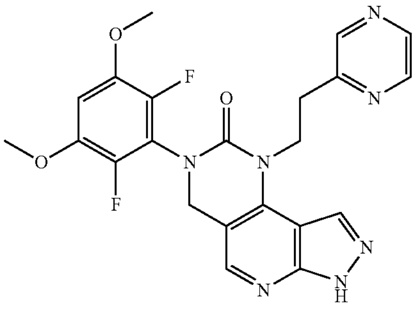 [SMILES: COc1cc(OC)c(F)c(N2Cc3cnc4[nH]ncc4c3N(CCc3cnccn3)C2=O)c1F]

This compound was prepared using procedures analogous to those for Example 85 with 2-pyrazin-2-ylethanamine replacing 1-methyl-1H-pyrazol-4-amine in Step 1. The product was purified by prep HPLC (pH=10, acetonitrile/water). LC-MS calculated for $C_{22}H_{20}F_2N_7O_3$ $(M+H)^+$ m/z: 468.2; found: 468.0.

Example 169

3-(2,6-Difluoro-3,5-dimethoxyphenyl)-1-(2-pyridin-2-ylethyl)-1,3,4,7-tetrahydro-2H-pyrazolo[4',3':5,6]pyrido[4,3-d]pyrimidin-2-one

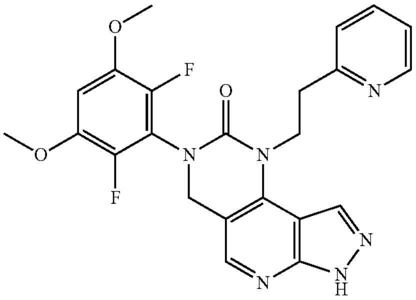 [SMILES: COc1cc(OC)c(F)c(N2Cc3cnc4[nH]ncc4c3N(CCc3ccccn3)C2=O)c1F]

This compound was prepared using procedures analogous to those for Example 85 with 2-pyridine-ethanamine replacing 1-methyl-1H-pyrazol-4-amine in Step 1. The product was purified by prep HPLC (pH=2, acetonitrile/water). LC-MS calculated for $C_{23}H_{21}F_2N_6O_3$ $(M+H)^+$ m/z: 467.2; found: 467.1.

Example 170

3-(2,6-Difluoro-3,5-dimethoxyphenyl)-1-(2-pyridin-3-ylethyl)-1,3,4,7-tetrahydro-2H-pyrazolo[4',3':5,6]pyrido[4,3-d]pyrimidin-2-one

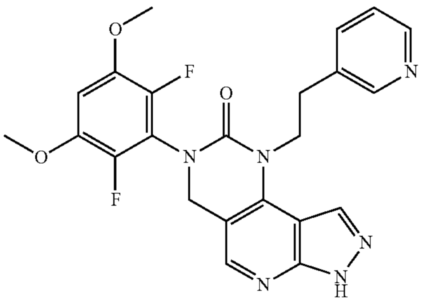 [SMILES: COc1cc(OC)c(F)c(N2Cc3cnc4[nH]ncc4c3N(CCc3cccnc3)C2=O)c1F]

This compound was prepared using procedures analogous to those for Example 85 with 2-pyridin-3-ylethanamine replacing 1-methyl-1H-pyrazol-4-amine in Step 1. The product was purified by prep HPLC (pH=2, acetonitrile/water). LC-MS calculated for $C_{23}H_{21}F_2N_6O_3$ $(M+H)^+$ m/z: 467.2; found: 467.1.

Example 171

3-(2,6-Difluoro-3,5-dimethoxyphenyl)-1-(2-pyridin-4-ylethyl)-1,3,4,7-tetrahydro-2H-pyrazolo[4',3':5,6]pyrido[4,3-d]pyrimidin-2-one

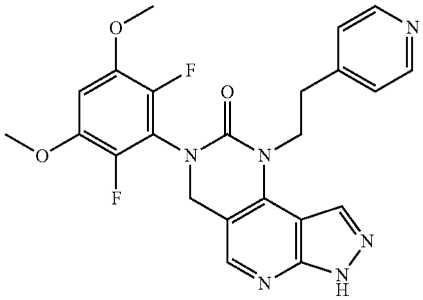 [SMILES: COc1cc(OC)c(F)c(N2Cc3cnc4[nH]ncc4c3N(CCc3ccncc3)C2=O)c1F]

This compound was prepared using procedures analogous to those for Example 85 with 2-pyridin-4-ylethanamine replacing 1-methyl-1H-pyrazol-4-amine in Step 1. The product was purified by prep HPLC (pH=10, acetonitrile/water). LC-MS calculated for $C_{23}H_{21}F_2N_6O_3$ $(M+H)^+$ m/z: 467.2; found: 467.0.

Example 172

3-(2,6-difluoro-3,5-dimethoxyphenyl)-1-(1-ethyl-1H-pyrazol-4-yl)-1,3,4,7-tetrahydro-2H-pyrazolo[4',3':5,6]pyrido[4,3-d]pyrimidin-2-one

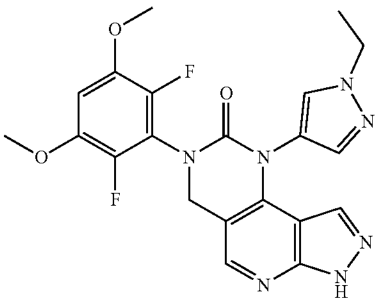

This compound was prepared using procedures analogous to those for Example 85 with 1-ethyl-1H-pyrazol-4-amine (Ark Pharm, Cat #AK-43711) replacing 1-methyl-1H-pyrazol-4-amine in Step 1. The product was purified by prep HPLC (pH=2, acetonitrile/water). LC-MS calculated for $C_{21}H_{20}F_2N_7O_3(M+H)^+$ m/z: 456.2; found: 456.2.

Example 173

3-(2,6-difluoro-3,5-dimethoxyphenyl)-1-[1-(2-hydroxy-2-methylpropyl)-1H-pyrazol-4-yl]-1,3,4,7-tetrahydro-2H-pyrazolo[4',3':5,6]pyrido[4,3-d]pyrimidin-2-one

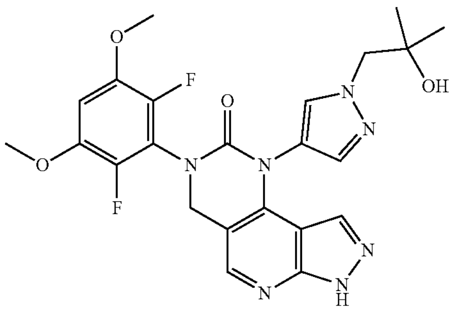

Step 1: 1-(2-{[tert-butyl(dimethyl)silyl]oxy}-2-methylpropyl)-1H-pyrazol-4-amine

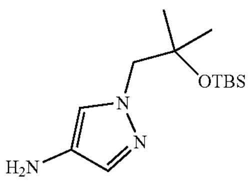

A mixture of 4-nitro-1H-pyrazole (0.50 g, 4.4 mmol), 2,2-dimethyl-oxirane (1.1 mL, 13 mmol) and 1,8-diazabicyclo[5.4.0]undec-7-ene (1.3 mL, 8.8 mmol) in acetonitrile (5 mL) was stirred at 70° C. for 1 hour. After cooling to room temperature, the mixture was diluted with water and extracted with EtOAc. The combined extracts were washed with water and brine. The organic layer was dried over $Na_2SO_4$, filtered and concentrated. The residue was dissolved in tetrahydrofuran (20 mL) then tert-butyldimethylsilyl chloride (0.73 g, 4.9 mmol), 1H-imidazole (30 mg, 0.44 mmol) and triethylamine (2.5 mL, 18 mmol) were added. The mixture was stirred at room temperature overnight then diluted with water and extracted with EtOAc. The combined extracts were washed with water and brine. The organic layer was dried over $Na_2SO_4$ then filtered and concentrated. The residue was dissolved in methanol (30 mL) then palladium (10 wt % on carbon, 110 mg, 0.10 mmol) was added. The suspension was stirred under $H_2$ atmosphere (balloon) at room temperature for overnight. The mixture was filtered and the filtrate was concentrated to yield the desired product, which was used in the next step without further purification.

Step 2: 3-(2,6-difluoro-3,5-dimethoxyphenyl)-1-[1-(2-hydroxy-2-methylpropyl)-1H-pyrazol-4-yl]-1,3,4,7-tetrahydro-2H-pyrazolo[4',3':5,6]pyrido[4,3-d]pyrimidin-2-one This compound was prepared using procedures analogous to those for Example 85 with 1-(2-{[tert-butyl(dimethyl)silyl]oxy}-2-methylpropyl)-1H-pyrazol-4-amine (product from step 1) replacing 1-methyl-1H-pyrazol-4-amine in Step 1. The product was purified by prep HPLC (pH=2, acetonitrile/water). LC-MS calculated for $C_{23}H_{24}F_2N_7O_4(M+H)^+$ m/z: 500.2; found: 500.0.

Example 174

3-(2,6-difluoro-3,5-dimethoxyphenyl)-1-[1-(2-methoxyethyl)-1H-pyrazol-4-yl]-1,3,4,7-tetrahydro-2H-pyrazolo[4',3':5,6]pyrido[4,3-d]pyrimidin-2-one

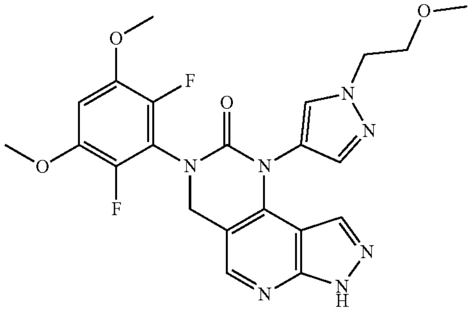

Step 1: 1-(2-methoxyethyl)-1H-pyrazol-4-amine

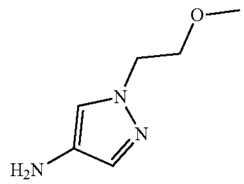

A mixture of 4-nitro-1H-pyrazole (0.5 g, 4 mmol), Ethane, 1-bromo-2-methoxy (0.84 mL, 8.8 mmol), and potassium carbonate (1.2 g, 8.8 mmol) in N,N-dimethylformamide (8 mL, 100 mmol) was stirred at 70° C. for 1 hour. After cooling to room temperature, the mixture was diluted with water then extracted with EtOAc. The combined extracts were washed with water and brine. The organic layer was dried over $Na_2SO_4$, filtered then concentrated. The residue was dissolved in methanol (10 ml) then a catalytic amount of palladium (10 wt % on activated carbon) was added. The suspension was stirred under a balloon of $H_2$ at room temperature for 2 hours then filtered and concentrated. The residue was used in the next step without further purification.

Step 2: 3-(2,6-difluoro-3,5-dimethoxyphenyl)-1-[1-(2-methoxyethyl)-1H-pyrazol-4-yl]-1,3,4,7-tetrahydro-2H-pyrazolo[4',3':5,6]pyrido[4,3-d]pyrimidin-2-one This compound was prepared using procedures analogous to those for Example 85 with 1-(2-methoxyethyl)-1H-pyrazol-4-amine (product from step 1) replacing 1-methyl-1H-pyrazol-4-amine in Step 1. The product was purified by prep HPLC (pH=2, acetonitrile/water). LC-MS calculated for $C_{22}H_{22}F_2N_7O_4(M+H)^+$ m/z: 486.2; found: 486.2.

Example 175

3-(2,6-difluoro-3,5-dimethoxyphenyl)-1-[1-(2,2-difluoroethyl)-1H-pyrazol-4-yl]-1,3,4,7-tetrahydro-2H-pyrazolo[4',3':5,6]pyrido[4,3-d]pyrimidin-2-one

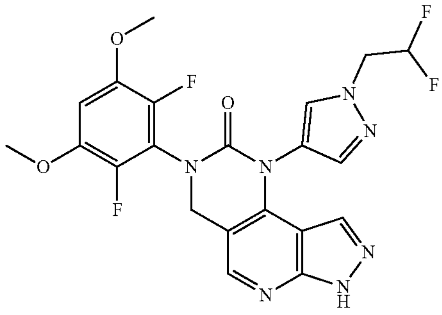 [SMILES: COc1cc(OC)c(F)c(N2Cc3cnc4[nH]ncc4c3N(c3cnn(CC(F)F)c3)C2=O)c1F]

Step 1: 1-(2,2-difluoroethyl)-1H-pyrazol-4-amine

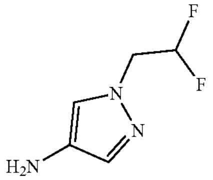

A mixture of 4-nitro-1H-pyrazole (0.25 g, 2.2 mmol), 1,1-difluoro-2-iodoethane (0.23 mL, 2.4 mmol), and potassium carbonate (0.61 g, 4.4 mmol) in acetonitrile (8 mL, 200 mmol) was stirred at 70° C. for 1 hour. After cooling to room temperature, the mixture was diluted with water then extracted with EtOAc. The combined extracts were washed with water and brine. The organic layer was dried over $Na_2SO_4$ then concentrated. The residue was dissolved in methanol (8 mL) then palladium (10 wt % on activated carbon, 50 mg) was added. The suspension was stirred under $H_2$ atmosphere (balloon) at room temperature for 2 hours then filtered and concentrated. The residue was used in the next step without further purification.

Step 2: 3-(2,6-difluoro-3,5-dimethoxyphenyl)-1-[1-(2,2-difluoroethyl)-1H-pyrazol-4-yl]-1,3,4,7-tetrahydro-2H-pyrazolo[4',3':5,6]pyrido[4,3-d]pyrimidin-2-one This compound was prepared using procedures analogous to those for Example 85 with 1-(2,2-difluoroethyl)-1H-pyrazol-4-amine (product from step 1) replacing 1-methyl-1H-pyrazol-4-amine in Step 1. The product was purified by prep HPLC (pH=2, acetonitrile/water). LC-MS calculated for $C_{21}H_{18}F_4N_7O_3(M+H)^+$ m/z: 492.1; found: 492.0.

Example 176

3-(2,6-difluoro-3,5-dimethoxyphenyl)-1-[(6-methoxypyridin-2-yl)methyl]-1,3,4,7-tetrahydro-2H-pyrazolo[4',3':5,6]pyrido[4,3-d]pyrimidin-2-one

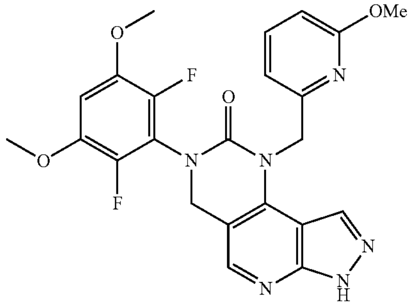 [SMILES: COc1cccc(CN2C(=O)N(c3c(F)c(OC)cc(OC)c3F)Cc3cnc4[nH]ncc4c32)n1]

This compound was prepared using procedures analogous to those for Example 85 with 1-(6-methoxypyridin-2-yl)methanamine (Ark Pharm, cat #AK-28243) replacing 1-methyl-1H-pyrazol-4-amine in Step 1. The product was purified by prep HPLC (pH=2, acetonitrile/water). LC-MS calculated for $C_{23}H_{21}F_2N_6O_4(M+H)^+$ m/z: 483.2; found: 483.0.

Example 177

3-(2,6-difluoro-3,5-dimethoxyphenyl)-1-[(2-methoxypyridin-4-yl)methyl]-1,3,4,7-tetrahydro-2H-pyrazolo[4',3':5,6]pyrido[4,3-d]pyrimidin-2-one

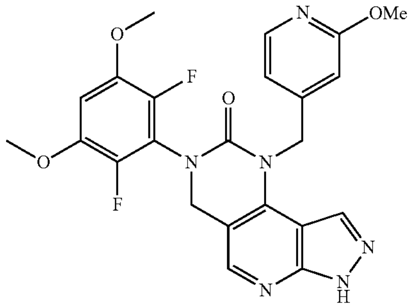 [SMILES: COc1cc(CN2C(=O)N(c3c(F)c(OC)cc(OC)c3F)Cc3cnc4[nH]ncc4c32)ccn1]

This compound was prepared using procedures analogous to those for Example 85 with 1-(2-methoxypyridin-4-yl)methanamine replacing 1-methyl-1H-pyrazol-4-amine in Step 1. The product was purified by prep HPLC (pH=2, acetonitrile/water). LC-MS calculated for $C_{23}H_{21}F_2N_6O_4$ $(M+H)^+$ m/z: 483.2; found: 483.0.

Example 178

3-(2,6-difluoro-3,5-dimethoxyphenyl)-1-[(3R)-tetrahydrofuran-3-ylmethyl]-1,3,4,7-tetrahydro-2H-pyrazolo[4',3':5,6]pyrido[4,3-d]pyrimidin-2-one

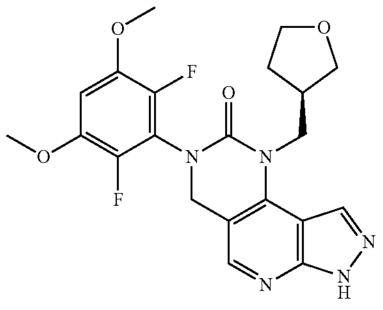 [SMILES: COc1cc(OC)c(F)c(N2Cc3cnc4[nH]ncc4c3N(C[C@H]3CCOC3)C2=O)c1F]

This compound was prepared using procedures analogous to those for Example 85 with 1-[(3R)-tetrahydrofuran-3-yl]methanamine (AstaTech, cat #68889) replacing 1-methyl-1H-pyrazol-4-amine in Step 1. The product was purified by prep HPLC (pH=2, acetonitrile/water). LC-MS calculated for $C_{21}H_{22}F_2N_5O_4$(M+H)$^+$ m/z: 446.2; found: 446.0.

Example 179

3-(2,6-difluoro-3,5-dimethoxyphenyl)-1-[(3S)-tetrahydrofuran-3-ylmethyl]-1,3,4,7-tetrahydro-2H-pyrazolo[4',3':5,6]pyrido[4,3-d]pyrimidin-2-one

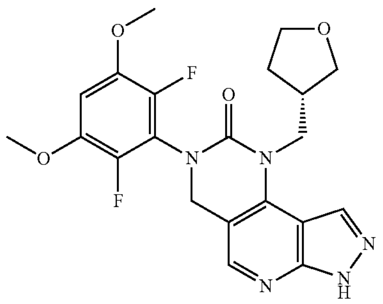 [SMILES: COc1cc(OC)c(F)c(N2Cc3cnc4[nH]ncc4c3N(C[C@@H]3CCOC3)C2=O)c1F]

This compound was prepared using procedures analogous to those for Example 85 with 1-[(3S)-tetrahydrofuran-3-yl]methanamine (AstaTech, cat #68891) replacing 1-methyl-1H-pyrazol-4-amine in Step 1. The product was purified by prep HPLC (pH=2, acetonitrile/water). LC-MS calculated for $C_{21}H_{22}F_2N_5O_4$(M+H)$^+$ m/z: 446.2; found: 446.0.

Example 180

3-(2,6-difluoro-3,5-dimethoxyphenyl)-1-(2-fluorophenyl)-8-(morpholin-4-ylmethyl)-1,3,4,7-tetrahydro-2H-pyrrolo[3',2':5,6]pyrido[4,3-d]pyrimidin-2-one

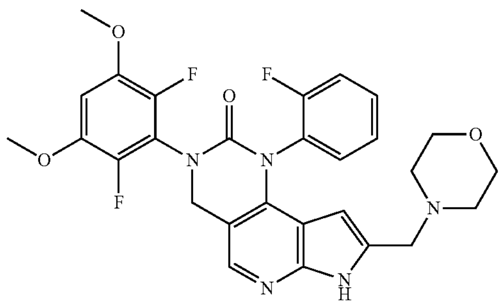 [SMILES: COc1cc(OC)c(F)c(N2Cc3cnc4[nH]c(CN5CCOCC5)cc4c3N(c3ccccc3F)C2=O)c1F]

Step 1: 3-(2,6-difluoro-3,5-dimethoxyphenyl)-1-(2-fluorophenyl)-7-(phenylsulfonyl)-1,3,4,7-tetrahydro-2H-pyrrolo[3',2':5,6]pyrido[4,3-d]pyrimidin-2-one

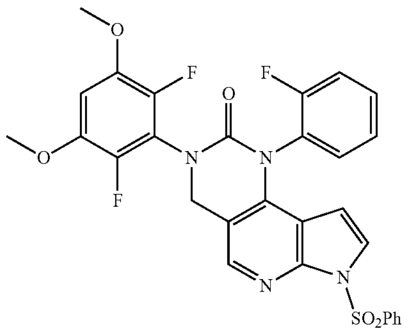

This compound was prepared using procedures analogous to those for Example 146, step 1-4 with 2-fluoro-benzenamine replacing 2-{[tert-butyl(dimethyl)silyl]oxy}ethanamine in Step 3. LC-MS calculated for $C_{29}H_{22}F_3N_4O_5S$ (M+H)$^+$ m/z: 595.1; found: 595.1.

Step 2: 3-(2,6-difluoro-3,5-dimethoxyphenyl)-1-(2-fluorophenyl)-8-(morpholin-4-ylmethyl)-1,3,4,7-tetrahydro-2H-pyrrolo[3',2':5,6]pyrido[4,3-d]pyrimidin-2-one This compound was prepared using procedures analogous to those for Example 126, step 2-4 starting with 3-(2,6-difluoro-3,5-dimethoxyphenyl)-1-(2-fluorophenyl)-7-(phenylsulfonyl)-1,3,4,7-tetrahydro-2H-pyrrolo[3',2':5,6]pyrido[4,3-d]pyrimidin-2-one (product from step 1). The product was purified by prep HPLC (pH=2, acetonitrile/water). LC-MS calculated for $C_{28}H_{27}F_3N_5O_4$(M+H)$^+$ m/z: 554.2; found: 553.9.

Example 181

3-(2,6-difluoro-3,5-dimethoxyphenyl)-8-[(4-ethylpiperazin-1-yl)methyl]-1-(2-fluorophenyl)-1,3,4,7-tetrahydro-2H-pyrrolo[3',2':5,6]pyrido[4,3-d]pyrimidin-2-one

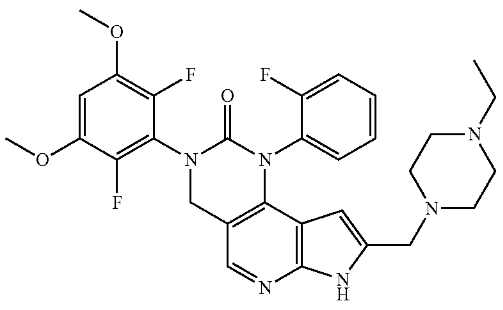 [SMILES: CCN1CCN(Cc2cc3c4c(cnc3[nH]2)CN(c2c(F)c(OC)cc(OC)c2F)C(=O)N4c2ccccc2F)CC1]

This compound was prepared using procedures analogous to those for Example 180 with 1-ethylpiperazine replacing morpholine. The product was purified by prep HPLC (pH=2, acetonitrile/water). LC-MS calculated for $C_{30}H_{32}F_3N_6O_3$ $(M+H)^+$ m/z: 581.2; found: 581.0.

Example 182

1-cyclobutyl-3-(2,6-difluoro-3,5-dimethoxyphenyl)-8-(morpholin-4-ylmethyl)-1,3,4,7-tetrahydro-2H-pyrrolo[3',2':5,6]pyrido[4,3-d]pyrimidin-2-one

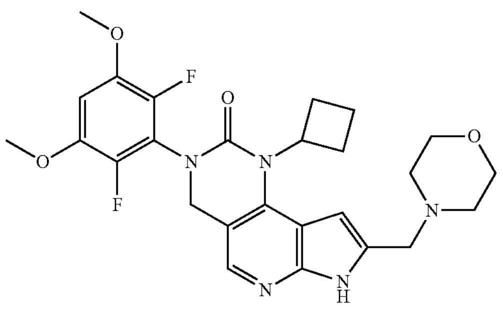 [SMILES: COc1cc(OC)c(F)c(N2Cc3cnc4[nH]c(CN5CCOCC5)cc4c3N(C3CCC3)C2=O)c1F]

This compound was prepared using procedures analogous to those for Example 180 with cyclobutylamine replacing 2-fluorobenzenamine. The product was purified by prep HPLC (pH=2, acetonitrile/water). LC-MS calculated for $C_{26}H_{30}F_2N_5O_4(M+H)^+$ m/z: 514.2; found: 514.0.

Example 183

1-cyclobutyl-3-(2,6-difluoro-3,5-dimethoxyphenyl)-8-(2-morpholin-4-ylethyl)-1,3,4,7-tetrahydro-2H-pyrrolo[3',2':5,6]pyrido[4,3-d]pyrimidin-2-one

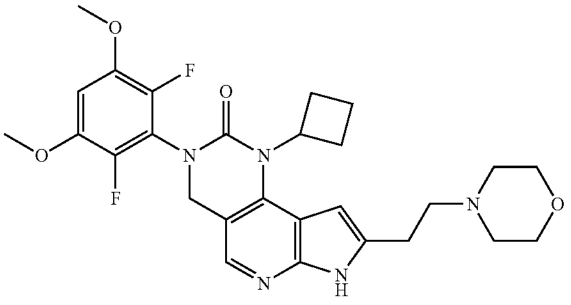 [SMILES: COc1cc(OC)c(F)c(N2Cc3cnc4[nH]c(CCN5CCOCC5)cc4c3N(C3CCC3)C2=O)c1F]

This compound was prepared using procedures analogous to those for Example 146 with cyclobutylamine replacing 2-{[tert-butyl(dimethyl)silyl]oxy}ethanamine in Step 3. The product was purified by prep HPLC (pH=2, acetonitrile/water). LC-MS calculated for $C_{27}H_{32}F_2N_5O_4$ $(M+H)^+$ m/z: 528.2; found: 528.0.

Example 184

3-(2,6-difluoro-3,5-dimethoxyphenyl)-8-(morpholin-4-ylmethyl)-1-propyl-1,3,4,7-tetrahydro-2H-pyrrolo[3',2':5,6]pyrido[4,3-d]pyrimidin-2-one

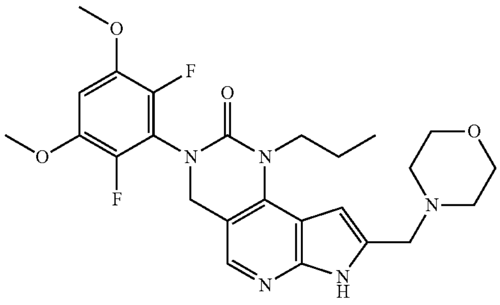 [SMILES: CCCN1C(=O)N(c2c(F)c(OC)cc(OC)c2F)Cc2cnc3[nH]c(CN4CCOCC4)cc3c21]

Step 1: 1-allyl-3-(2,6-difluoro-3,5-dimethoxyphenyl)-8-(morpholin-4-ylmethyl)-7-(phenylsulfonyl)-1,3,4,7-tetrahydro-2H-pyrrolo[3',2':5,6]pyrido[4,3-d]pyrimidin-2-one

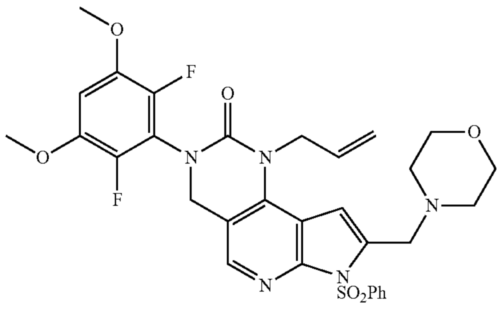

This compound was prepared using procedures analogous to those for Example 126, Step 1-3 starting with 1-allyl-3-(2,6-difluoro-3,5-dimethoxyphenyl)-7-(phenylsulfonyl)-1,3,4,7-tetrahydro-2H-pyrrolo[3',2':5,6]pyrido[4,3-d]pyrimidin-2-one (product from Example 44, Step 2). LC-MS calculated for $C_{31}H_{32}F_2N_5O_6S$ $[M+H]^+$ m/z: 640.2; found 640.2.

Step 2: 3-(2,6-difluoro-3,5-dimethoxyphenyl)-8-(morpholin-4-ylmethyl)-7-(phenylsulfonyl)-1-propyl-1,3,4,7-tetrahydro-2H-pyrrolo[3',2':5,6]pyrido[4,3-d]pyrimidin-2-one

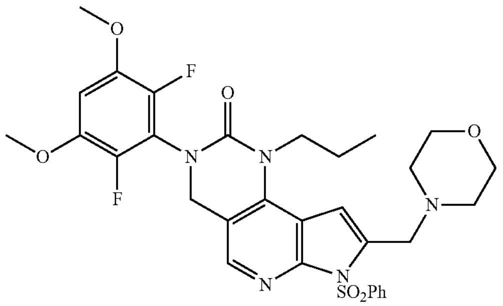

To a solution of 1-allyl-3-(2,6-difluoro-3,5-dimethoxyphenyl)-8-(morpholin-4-ylmethyl)-7-(phenylsulfonyl)-1,3,4,7-tetrahydro-2H-pyrrolo[3',2':5,6]pyrido[4,3-d]pyrimidin-2-one (20.0 mg, 0.0313 mmol) in methanol (1.0 mL) was added palladium hydroxide (20 wt. % on carbon, 5.0 mg). The resulting mixture was stirred under hydrogen atmosphere for 2 h before it was filtered and concentrated in vacuo. The crude product was used directly in the next step without further purification. LC-MS calculated for $C_{31}H_{34}F_2N_5O_6S$ $[M+H]^+$ m/z: 642.2; found 642.2.

Step 3: 3-(2,6-difluoro-3,5-dimethoxyphenyl)-8-(morpholin-4-ylmethyl)-1-propyl-1,3,4,7-tetrahydro-2H-pyrrolo[3',2':5,6]pyrido[4,3-d]pyrimidin-2-one This compound was synthesized by the same method described in Example 126, Step 4 by using 3-(2,6-difluoro-3,5-dimethoxyphenyl)-8-(morpholin-4-ylmethyl)-7-(phenylsulfonyl)-1-propyl-1,3,4,7-tetrahydro-2H-pyrrolo[3',2':5,6]pyrido[4,3-d]pyrimidin-2-one (product from Step 2) as starting material. LC-MS calculated for $C_{25}H_{30}F_2N_5O_4$$[M+H]^+$ m/z: 502.2; found 502.2.

Example 185

3-(2,6-difluoro-3,5-dimethoxyphenyl)-1-ethyl-8-(2-morpholin-4-ylethyl)-1,3,4,7-tetrahydro-2H-pyrrolo[3',2':5,6]pyrido[4,3-d]pyrimidin-2-one

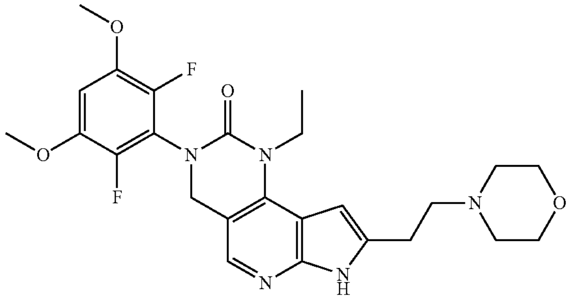 [SMILES: CCN1C(=O)N(c2c(F)c(OC)cc(OC)c2F)Cc2cnc3[nH]c(CCN4CCOCC4)cc3c21]

Step 1: 8-bromo-3-(2,6-difluoro-3,5-dimethoxyphenyl)-1-ethyl-7-(phenylsulfonyl)-1,3,4,7-tetrahydro-2H-pyrrolo[3',2':5,6]pyrido[4,3-d]pyrimidin-2-one

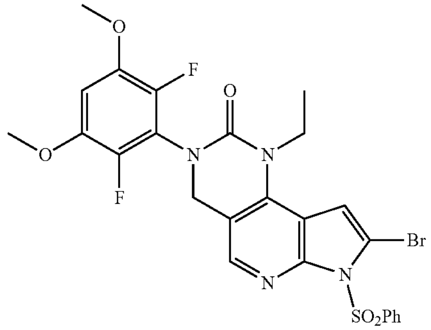

This compound was prepared using procedures analogous to those for Example 39, step 5 starting with 3-(2,6-difluoro-3,5-dimethoxyphenyl)-1-ethyl-7-(phenylsulfonyl)-1,3,4,7-tetrahydro-2H-pyrrolo[3',2':5,6]pyrido[4,3-d]pyrimidin-2-one (product from Example 126, step 1). LC-MS calculated for $C_{25}H_{22}BrF_2N_4O_5S$ $[M+H]^+$ m/z: 607.0; found 607.0.

Step 2: 3-(2,6-difluoro-3,5-dimethoxyphenyl)-1-ethyl-8-(2-morpholin-4-ylethyl)-1,3,4,7-tetrahydro-2H-pyrrolo[3',2':5,6]pyrido[4,3-d]pyrimidin-2-one This compound was prepared using procedures analogous to those for Example 71 starting with 8-bromo-3-(2,6-difluoro-3,5-dimethoxyphenyl)-1-ethyl-7-(phenylsulfonyl)-1,3,4,7-tetrahydro-2H-pyrrolo[3',2':5,6]pyrido[4,3-d]pyrimidin-2-one (product from step 1) and morpholine. LC-MS calculated for $C_{25}H_{30}F_2N_5O_4$$[M+H]^+$ m/z: 502.2; found 502.0. $^1H$ NMR (500 MHz, DMSO) δ 12.01 (s, 1H), 7.97 (s, 1H), 7.04 (t, J=8.1 Hz, 1H), 6.55 (s, 1H), 4.75 (s, 2H), 4.16 (q, J=6.8 Hz, 2H), 4.06-3.94 (m, 2H), 3.89 (s, 6H), 3.73-3.61 (m, 2H), 3.58-3.43 (m, 4H), 3.25-3.07 (m, 4H), 1.34 (t, J=6.8 Hz, 3H).

Example 186

1-cyclopropyl-3-(2,6-difluoro-3,5-dimethoxyphenyl)-8-(morpholin-4-ylmethyl)-1,3,4,7-tetrahydro-2H-pyrrolo[3',2':5,6]pyrido[4,3-d]pyrimidin-2-one

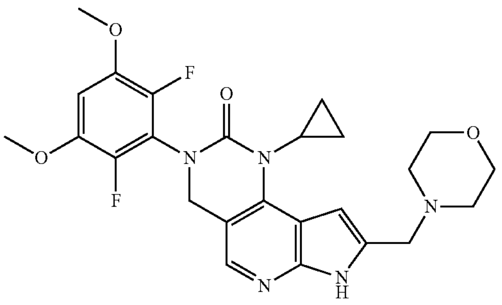 [SMILES: COc1cc(OC)c(F)c(N2Cc3cnc4[nH]c(CN5CCOCC5)cc4c3N(C3CC3)C2=O)c1F]

This compound was prepared using procedures analogous to those for Example 180 with cyclopropylamine replacing 2-fluorobenzenamine. The product was purified by prep HPLC (pH=2, acetonitrile/water). LC-MS calculated for $C_{25}H_{28}F_2N_5O_4(M+H)^+$ m/z: 500.2; found: 500.0.

Example 187

1-cyclopropyl-3-(2,6-difluoro-3,5-dimethoxyphenyl)-8-[(4-methylpiperazin-1-yl)methyl]-1, 3,4,7-tetrahydro-2H-pyrrolo[3',2':5,6]pyrido[4,3-d]pyrimidin-2-one

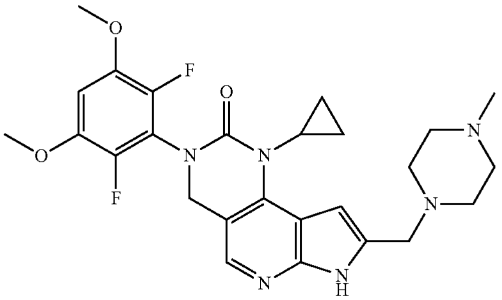

This compound was prepared using procedures analogous to those for Example 186 with 1-methylpiperazine replacing morpholine. The product was purified by prep HPLC (pH=2, acetonitrile/water). LC-MS calculated for $C_{26}H_{31}F_2N_6O_3$ $(M+H)^+$ m/z: 513.2; found: 513.0.

Example 188

1-cyclopropyl-3-(2,6-difluoro-3,5-dimethoxyphenyl)-8-[(4-ethylpiperazin-1-yl)methyl]-1,3,4, 7-tetrahydro-2H-pyrrolo[3',2':5,6]pyrido[4,3-d]pyrimidin-2-one

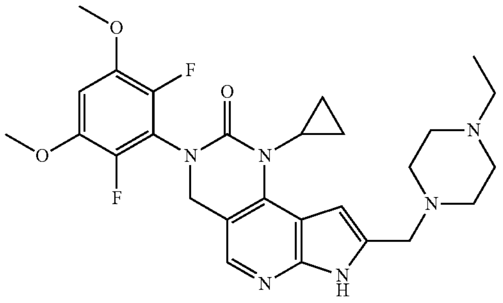 [SMILES: CCN1CCN(Cc2cc3c4c(cnc3[nH]2)CN(c2c(F)c(OC)cc(OC)c2F)C(=O)N4C2CC2)CC1]

This compound was prepared using procedures analogous to those for Example 186 with 1-ethylpiperazine replacing morpholine. The product was purified by prep HPLC (pH=2, acetonitrile/water). LC-MS calculated for $C_{27}H_{33}F_2N_6O_3$ $(M+H)^+$ m/z: 527.3; found: 527.1.

Example 189

3-(2,6-difluoro-3,5-dimethoxyphenyl)-1-(4-fluorophenyl)-8-(morpholin-4-ylmethyl)-1,3,4,7-tetrahydro-2H-pyrrolo[3',2':5,6]pyrido[4,3-d]pyrimidin-2-one

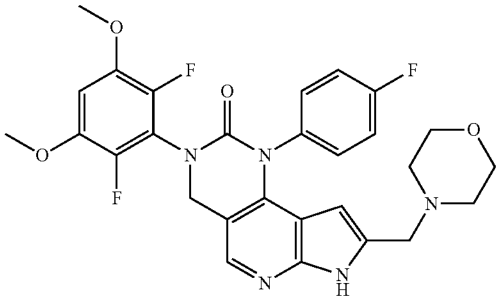 [SMILES: COc1cc(OC)c(F)c(N2Cc3cnc4[nH]c(CN5CCOCC5)cc4c3N(c3ccc(F)cc3)C2=O)c1F]

This compound was prepared using procedures analogous to those for Example 180 with p-fluoroaniline replacing 2-fluorobenzenamine. The product was purified by prep HPLC (pH=2, acetonitrile/water). LC-MS calculated for $C_{28}H_{27}F_3N_5O_4(M+H)^+$ m/z: 554.2; found: 554.0.

Example 190

3-(2,6-difluoro-3,5-dimethoxyphenyl)-1-(4-fluorophenyl)-8-[(4-methylpiperazin-1-yl)methyl]-1,3,4,7-tetrahydro-2H-pyrrolo[3',2':5,6]pyrido[4,3-d]pyrimidin-2-one

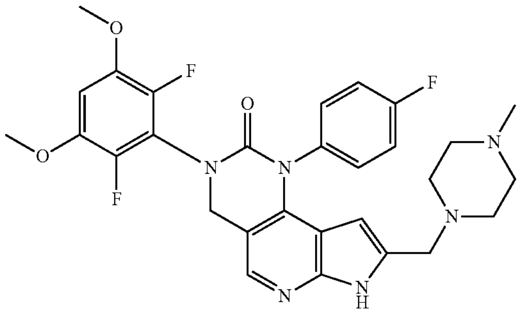

This compound was prepared using procedures analogous to those for Example 189 with 1-methylpiperazine replacing morpholine. The product was purified by prep HPLC (pH=2, acetonitrile/water). LC-MS calculated for $C_{29}H_{30}F_3N_6O_3$ $(M+H)^+$ m/z: 567.2; found: 567.0.

Example 191

3-(2,6-difluoro-3,5-dimethoxyphenyl)-1-(4-fluorophenyl)-8-[(4-ethylpiperazin-1-yl)methyl]-1,3,4,7-tetrahydro-2H-pyrrolo[3',2':5,6]pyrido[4,3-d]pyrimidin-2-one

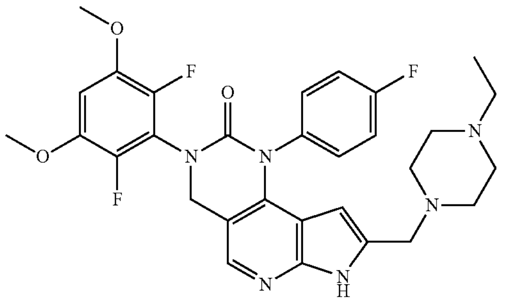 [SMILES: CCN1CCN(Cc2cc3c4c(cnc3[nH]2)CN(c2c(F)c(OC)cc(OC)c2F)C(=O)N4c2ccc(F)cc2)CC1]

This compound was prepared using procedures analogous to those for Example 189 with 1-ethylpiperazine replacing morpholine. The product was purified by prep HPLC (pH=2, acetonitrile/water). LC-MS calculated for $C_{30}H_{32}F_3N_6O_3$ $(M+H)^+$ m/z: 581.2; found: 581.1.

Example 192

3-(2,6-difluoro-3,5-dimethoxyphenyl)-1-(2,3-difluorophenyl)-8-[(4-methylpiperazin-1-yl)methyl]-1,3,4,7-tetrahydro-2H-pyrrolo[3',2':5,6]pyrido[4,3-d]pyrimidin-2-one

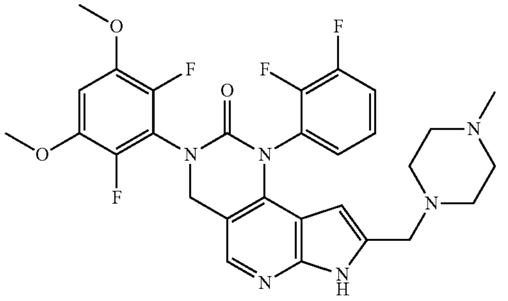

This compound was prepared using procedures analogous to those for Example 190 with 2,3-difluoroaniline replacing 4-fluoroaniline. The product was purified by prep HPLC (pH=2, acetonitrile/water). LC-MS calculated for $C_{29}H_{29}F_4N_6O_3(M+H)^+$ m/z: 585.2; found: 585.0.

Example 193

3-(2,6-difluoro-3,5-dimethoxyphenyl)-1-(2,3-difluorophenyl)-8-[(4-ethylpiperazin-1-yl)methyl]-1,3,4,7-tetrahydro-2H-pyrrolo[3',2':5,6]pyrido[4,3-d]pyrimidin-2-one

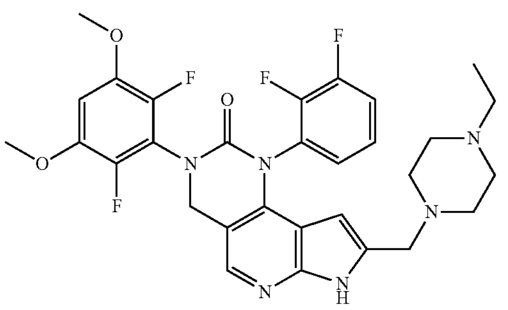

This compound was prepared using procedures analogous to those for Example 192 with 1-ethylpiperazine replacing 1-methylpiperazine. The product was purified by prep HPLC (pH=2, acetonitrile/water). LC-MS calculated for $C_{30}H_{31}F_4N_6O_3(M+H)^+$ m/z: 599.2; found: 599.0.

Example 194

3-(2,6-difluoro-3,5-dimethoxyphenyl)-8-(morpholin-4-ylmethyl)-1-pyridin-4-yl-1,3,4,7-tetrahydro-2H-pyrrolo[3',2':5,6]pyrido[4,3-d]pyrimidin-2-one

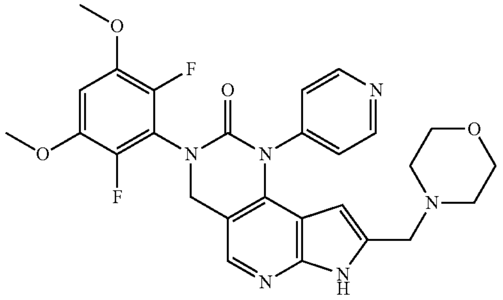

This compound was prepared using procedures analogous to those for Example 180 with 4-pyridinamine replacing 2-fluorobenzenamine. The product was purified by prep HPLC (pH=2, acetonitrile/water). LC-MS calculated for $C_{27}H_{27}F_2N_6O_4(M+H)^+$ m/z: 537.2; found: 537.0.

Example 195

3-(2,6-difluoro-3,5-dimethoxyphenyl)-8-[(4-methylpiperazin-1-yl)methyl]-1-pyridin-4-yl-1, 3,4,7-tetrahydro-2H-pyrrolo[3',2':5,6]pyrido[4,3-d]pyrimidin-2-one

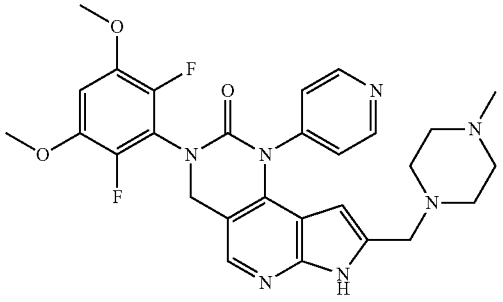

This compound was prepared using procedures analogous to those for Example 194 with 1-methylpiperazine replacing morpholine. The product was purified by prep HPLC (pH=2, acetonitrile/water). LC-MS calculated for $C_{28}H_{30}F_2N_7O_3$ $(M+H)^+$ m/z: 550.2; found: 550.1.

Example 196

3-(2,6-difluoro-3,5-dimethoxyphenyl)-1-(2-fluorophenyl)-8-(2-morpholin-4-ylethyl)-1,3,4,7-tetrahydro-2H-pyrrolo[3',2':5,6]pyrido[4,3-d]pyrimidin-2-one

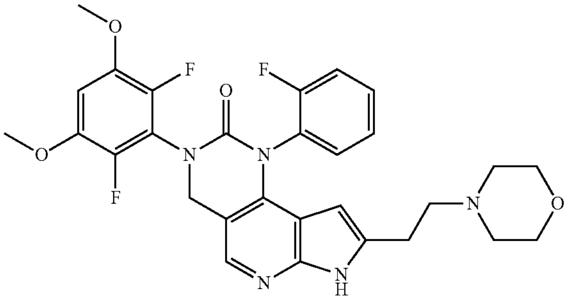 [SMILES: COc1cc(OC)c(F)c(N2Cc3cnc4[nH]c(CCN5CCOCC5)cc4c3N(c3ccccc3F)C2=O)c1F]

Step 1: 3-(2,6-difluoro-3,5-dimethoxyphenyl)-1-(2-fluorophenyl)-8-(2-morpholin-4-ylethyl)-7-(phenylsulfonyl)-1,3,4,7-tetrahydro-2H-pyrrolo[3',2':5,6] pyrido[4,3-d]pyrimidin-2-one

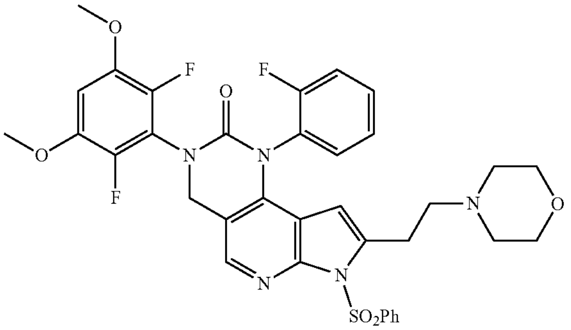

This compound was prepared using procedures analogous to those for Example 146, step 1-6 with 2-fluoro-benzenamine replacing 2-{[tert-butyl(dimethyl)silyl]oxy}ethanamine in step 3. LC-MS calculated for $C_{35}H_{33}F_3N_5O_6S$ $(M+H)^+$ m/z: 708.2; found: 708.2.

Step 2: 3-(2,6-difluoro-3,5-dimethoxyphenyl)-1-(2-fluorophenyl)-8-(2-morpholin-4-ylethyl)-1,3, 4,7-tetrahydro-2H-pyrrolo[3',2':5,6]pyrido[4,3-d]pyrimidin-2-one The product from Step 1 was dissolved in tetrahydrofuran then potassium tert-butoxide (1M in THF, 5 eq.) was added. The resulting mixture was stirred at room temperature for 30 min then quenched with a few drops of TFA and purified by prep HPLC (pH=2, acetonitrile/water). LC-MS calculated for $C_{29}H_{29}F_3N_5O_4(M+H)^+$ m/z: 568.2; found: 568.2.

Example 197

3-(2,6-difluoro-3,5-dimethoxyphenyl)-1-(2-fluorophenyl)-8-[2-(4-methylpiperazin-1-yl)ethyl]-1,3,4,7-tetrahydro-2H-pyrrolo[3',2':5,6]pyrido[4,3-d]pyrimidin-2-one

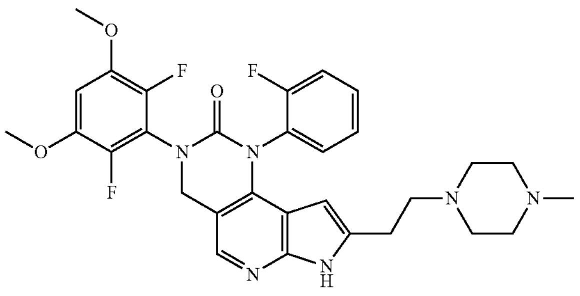

This compound was prepared using procedures analogous to those for Example 196 with 1-methylpiperazine replacing morpholine. The product was purified by prep HPLC (pH=2, acetonitrile/water). LC-MS calculated for $C_{30}H_{32}F_3N_6O_3$ $(M+H)^+$ m/z: 581.2; found: 581.2.

Example 198

3-(2,6-difluoro-3,5-dimethoxyphenyl)-1-(2-fluorophenyl)-8-[2-(4-ethylpiperazin-1-yl)ethyl]-1,3,4,7-tetrahydro-2H-pyrrolo[3',2':5,6]pyrido[4,3-d]pyrimidin-2-one

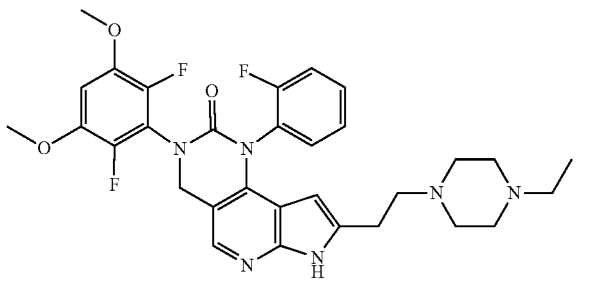 [SMILES: CCN1CCN(CCc2cc3c4c(cnc3[nH]2)CN(c2c(F)c(OC)cc(OC)c2F)C(=O)N4c2ccccc2F)CC1]

This compound was prepared using procedures analogous to those for Example 196 with 1-ethylpiperazine replacing morpholine. The product was purified by prep HPLC (pH=2, acetonitrile/water). LC-MS calculated for $C_{31}H_{34}F_3N_6O_3$ $(M+H)^+$ m/z: 595.3; found: 595.2.

Example 199

3-[3-(2,6-difluoro-3,5-dimethoxyphenyl)-2-oxo-2,3,4,7-tetrahydro-1H-pyrazolo[4',3':5, 6]pyrido[4,3-d]pyrimidin-1-yl]-2-fluoro-N-isopropylbenzamide

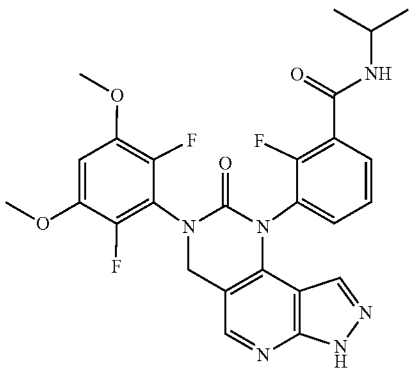 [SMILES: COc1cc(OC)c(F)c(N2Cc3cnc4[nH]ncc4c3N(c3cccc(C(=O)NC(C)C)c3F)C2=O)c1F]

Step 1: methyl 3-[3-(2,6-difluoro-3,5-dimethoxyphenyl)-2-oxo-2,3,4,7-tetrahydro-1H-pyrazolo[4',3':5,6]pyrido[4,3-d]pyrimidin-1-yl]-2-fluorobenzoate

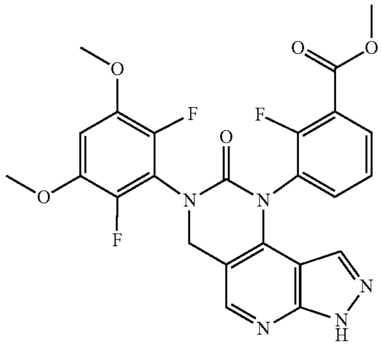

This compound was prepared using procedures analogous to those for Example 85 with methyl 3-amino-2-fluorobenzoate replacing 1-methyl-1H-pyrazol-4-amine in Step 1. LC-MS calculated for $C_{24}H_{19}F_3N_5O_5(M+H)^+$ m/z: 514.1; found: 514.0.

Step 2: 3-[3-(2,6-difluoro-3,5-dimethoxyphenyl)-2-oxo-2,3,4,7-tetrahydro-1H-pyrazolo[4',3':5, 6]pyrido[4,3-d]pyrimidin-1-yl]-2-fluorobenzoic acid

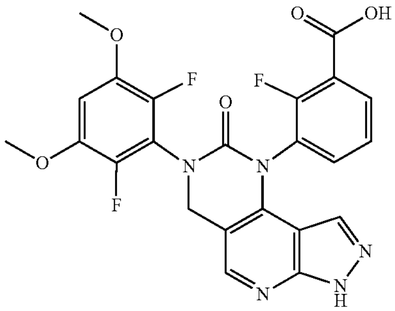 [SMILES: COc1cc(OC)c(F)c(N2Cc3cnc4[nH]ncc4c3N(c3cccc(C(=O)O)c3F)C2=O)c1F]

The product from Step 1 was dissolved in tetrahydrofuran (10 mL) and water (5 mL) then lithium hydroxide monohydrate (0.11 g, 2.5 mmol) was added. The reaction mixture was stirred at 50° C. overnight then cooled to room temperature and adjusted to pH=5 with aqueous 2N HCl. The mixture was extracted with EtOAc for three times. The combined organic layers were washed with brine, dried over $MgSO_4$, filtered and concentrated under reduced pressure to afford the desired product, which was used in the next step without further purification. LC-MS calculated for $C_{23}H_{17}F_3N_5O_5(M+H)^+$ m/z: 500.1; found: 499.9.

Step 3: 3-[3-(2,6-difluoro-3,5-dimethoxyphenyl)-2-oxo-2,3,4,7-tetrahydro-1H-pyrazolo[4',3':5, 6]pyrido[4,3-d]pyrimidin-1-yl]-2-fluoro-N-isopropylbenzamide To a mixture of 3-[3-(2,6-difluoro-3,5-dimethoxyphenyl)-2-oxo-2,3,4,7-tetrahydro-1H-pyrazolo[4',3':5,6]pyrido[4,3-d]pyrimidin-1-yl]-2-fluorobenzoic acid (8.9 mg, 0.018 mmol), 2-propanamine (1.6 mg, 0.027 mmol) and benzotriazol-1-yloxytris(dimethylamino)phosphonium hexafluorophosphate (8.7 mg, 0.020 mmol) in N,N-dimethylformamide (0.5 mL) was added N, N-diisopropylethylamine (9.3 μL, 0.054 mmol). The reaction mixture was stirred at room temperature for 3 h and then purified by prep HPLC (pH=10, acetonitrile/water) to afford the desired product. LC-MS calculated for $C_{26}H_{24}F_3N_6O_4(M+H)^+$ m/z: 541.2; found: 541.0.

Example 200

N-cyclopropyl-3-[3-(2,6-difluoro-3,5-dimethoxyphenyl)-2-oxo-2,3,4,7-tetrahydro-1H-pyrazolo[4',3':5,6]pyrido[4,3-d]pyrimidin-1-yl]-2-fluorobenzamide

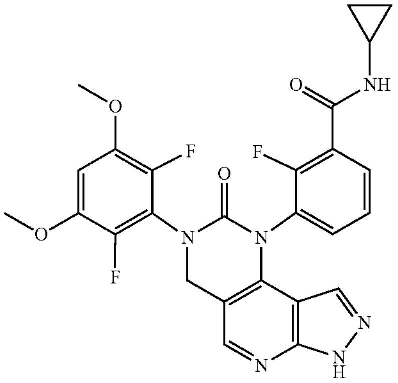 [SMILES: COc1cc(OC)c(F)c(N2Cc3cnc4[nH]ncc4c3N(c3cccc(C(=O)NC4CC4)c3F)C2=O)c1F]

This compound was prepared using procedures analogous to those for Example 199 with cyclopropylamine replacing 2-propanamine in Step 3. The product was purified by prep HPLC (pH=10, acetonitrile/water). LC-MS calculated for $C_{26}H_{22}F_3N_6O_4(M+H)^+$ m/z: 539.2; found: 539.0.

Example 201

3-[3-(2,6-difluoro-3,5-dimethoxyphenyl)-2-oxo-2,3,4,7-tetrahydro-1H-pyrazolo[4',3':5, 6]pyrido[4,3-d]pyrimidin-1-yl]-N-ethyl-2-fluorobenzamide

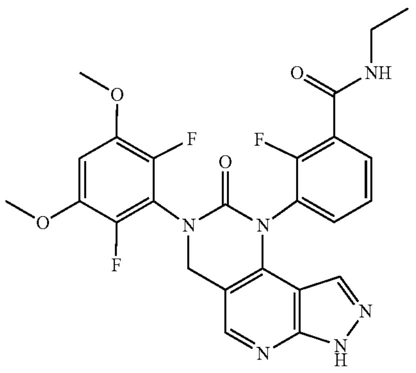 [SMILES: CCNC(=O)c1cccc(N2C(=O)N(c3c(F)c(OC)cc(OC)c3F)Cc3cnc4[nH]ncc4c32)c1F]

This compound was prepared using procedures analogous to those for Example 199 with ethylamine (2.0 M in THF) replacing 2-propanamine in Step 3. The product was purified by prep HPLC (pH=10, acetonitrile/water). LC-MS calculated for $C_{25}H_{22}F_3N_6O_4(M+H)^+$ m/z: 527.2; found: 527.0.

Example 202

3-(2,6-difluoro-3,5-dimethoxyphenyl)-1-[(2-methoxypyridin-4-yl)methyl]-8-(morpholin-4-ylmethyl)-1,3,4,7-tetrahydro-2H-pyrrolo[3',2':5,6]pyrido[4,3-d]pyrimidin-2-one

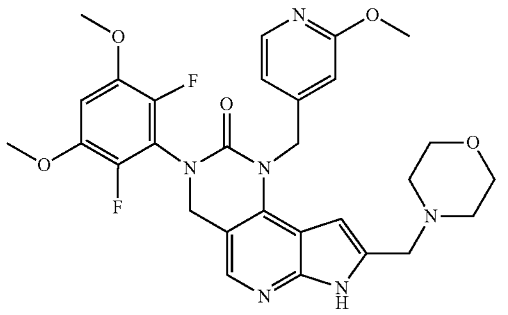 [SMILES: COc1cc(CN2C(=O)N(c3c(F)c(OC)cc(OC)c3F)Cc3cnc4[nH]c(CN5CCOCC5)cc4c32)ccn1]

Step 1: 3-(2,6-difluoro-3,5-dimethoxyphenyl)-8-(morpholin-4-ylmethyl)-7-(phenylsulfonyl)-1,3,4,7-tetrahydro-2H-pyrrolo[3',2':5,6]pyrido[4,3-d]pyrimidin-2-one

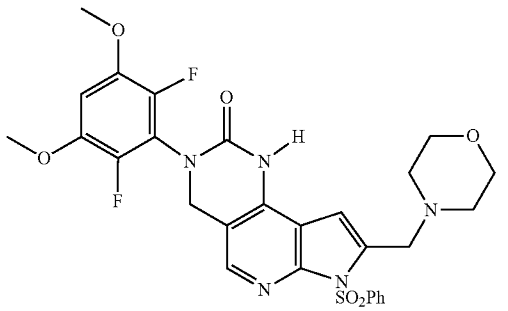

To a solution of 1-allyl-3-(2,6-difluoro-3,5-dimethoxyphenyl)-8-(morpholin-4-ylmethyl)-7-(phenylsulfonyl)-1,3,4,7-tetrahydro-2H-pyrrolo[3',2':5,6]pyrido[4,3-d]pyrimidin-2-one (18.0 mg, 0.028 mmol, from Example 184, Step 1) in tetrahydrofuran (0.6 mL) and dimethylamine (0.6 mL) were added 1,4-bis(diphenylphosphino)butane (10.0 mg, 0.0227 mmol) and tris(dibenzylideneacetone)dipalladium(O) (10.0 mg, 0.0109 mmol). The reaction was stirred at 90° C. overnight before it was concentrated in vacuo and purified by column to afford the product. LC-MS calculated for $C_{28}H_{28}F_2N_5O_6S$ $[M+H]^+$ m/z: 600.2; found 600.1.

Step 2: 3-(2,6-difluoro-3,5-dimethoxyphenyl)-1-[(2-methoxypyridin-4-yl)methyl]-8-(morpholin-4-ylmethyl)-7-(phenylsulfonyl)-1,3,4,7-tetrahydro-2H-pyrrolo[3',2':5,6]pyrido[4,3-d]pyrimidin-2-one

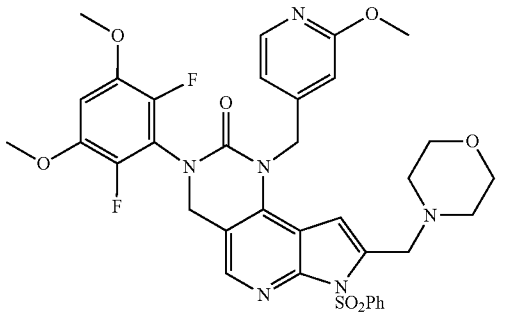

To a solution of 3-(2,6-difluoro-3,5-dimethoxyphenyl)-8-(morpholin-4-ylmethyl)-7-(phenylsulfonyl)-1,3,4,7-tetrahydro-2H-pyrrolo[3',2':5,6]pyrido[4,3-d]pyrimidin-2-one (10.0 mg, 0.0167 mmol, from Step 1), (2-methoxypyridin-4-yl)methanol (23.2 mg, 0.167 mmol, purchased from Ark Pharma, catalog number: AK-28607) in tetrahydrofuran (1.0 mL, 12 mmol) were added triphenylphosphine (26.0 mg, 0.0991 mmol) and diethyl azodicarboxylate (16 μL, 0.10 mmol). The resulting mixture was stirred at 60° C. for 12 h. The reaction was diluted with MeOH (4.0 mL) and purified by RP-HPLC (pH 10) to afford the product. LC-MS calculated for $C_{35}H_{35}F_2N_6O_7S$ $[M+H]^+$ m/z: 721.2; found 721.0.

Step 3: 3-(2,6-difluoro-3,5-dimethoxyphenyl)-1-[(2-methoxypyridin-4-yl)methyl]-8-(morpholin-4-ylmethyl)-1,3,4,7-tetrahydro-2H-pyrrolo[3',2':5,6]pyrido[4,3-d]pyrimidin-2-one This compound was synthesized by the same method described in Example 126, Step 4 by using 3-(2,6-difluoro-3,5-dimethoxyphenyl)-1-[(2-methoxypyridin-4-yl)methyl]-8-(morpholin-4-ylmethyl)-7-(phenylsulfonyl)-1,3,4,7-tetrahydro-2H-pyrrolo[3',2':5,6]pyrido[4,3-d]pyrimidin-2-one (product from Step 2) as starting material. LC-MS calculated for $C_{29}H_{31}F_2N_6O_5$$[M+H]^+$ m/z: 581.2; found 581.1.

Example 203

3-(2,6-difluoro-3,5-dimethoxyphenyl)-1-(1-methyl-1H-pyrazol-4-yl)-8-(morpholin-4-ylmethyl)-1,3,4,7-tetrahydro-2H-pyrrolo[3',2':5,6]pyrido[4,3-d]pyrimidin-2-one

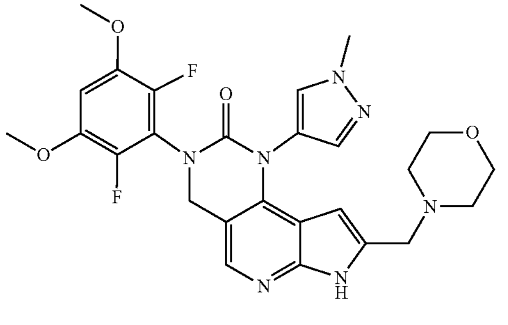 [SMILES: COc1cc(OC)c(F)c(N2Cc3cnc4[nH]c(CN5CCOCC5)cc4c3N(c3cnn(C)c3)C2=O)c1F]

This compound was prepared using procedures analogous to those for Example 180 with 1-methyl-1H-pyrazol-4-amine (Astatech Inc, catalog #CL4553) replacing 2-fluorobenzenamine. The product was purified by prep HPLC (pH=2, acetonitrile/water). LC-MS calculated for $C_{26}H_{28}F_2N_7O_4(M+H)^+$ m/z: 540.2; found: 540.1.

Example 204

3-(2,6-difluoro-3,5-dimethoxyphenyl)-8-[(4-methylpiperazin-1-yl)methyl]-1-(1-methyl-11H-pyrazol-4-yl)-1,3,4,7-tetrahydro-2H-pyrrolo[3',2':5,6]pyrido[4,3-d]pyrimidin-2-one

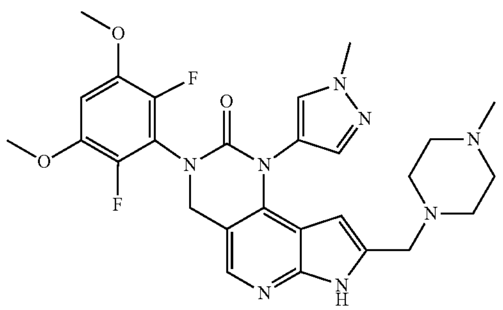

This compound was prepared using procedures analogous to those for Example 203 with 1-methylpiperazine replacing morpholine. The product was purified by prep HPLC (pH=2, acetonitrile/water). LC-MS calculated for $C_{27}H_{31}F_2N_8O_3$ $(M+H)^+$ m/z: 553.2; found: 553.2.

Example 205

3-(2,6-difluoro-3,5-dimethoxyphenyl)-8-[(4-ethylpiperazin-1-yl)methyl]-1-(1-methyl-1H-pyrazol-4-yl)-1,3,4,7-tetrahydro-2H-pyrrolo[3',2':5,6]pyrido[4,3-d]pyrimidin-2-one

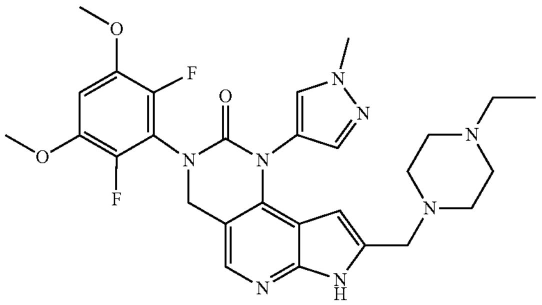 [SMILES: CCN1CCN(Cc2cc3c4c(cnc3[nH]2)CN(c2c(F)c(OC)cc(OC)c2F)C(=O)N4c2cnn(C)c2)CC1]

This compound was prepared using procedures analogous to those for Example 203 with 1-ethylpiperazine replacing morpholine. The product was purified by prep HPLC (pH=2, acetonitrile/water). LC-MS calculated for $C_{28}H_{33}F_2N_8O_3$ $(M+H)^+$ m/z: 567.3; found: 567.0.

Example 206

7-(2,6-difluoro-3,5-dimethoxyphenyl)-2-[(3-hydroxyazetidin-1-yl)methyl]-9,9-dimethyl-3,6, 7,9-tetrahydro-8H-pyrrolo[2,3-c]-2,7-naphthyridin-8-one

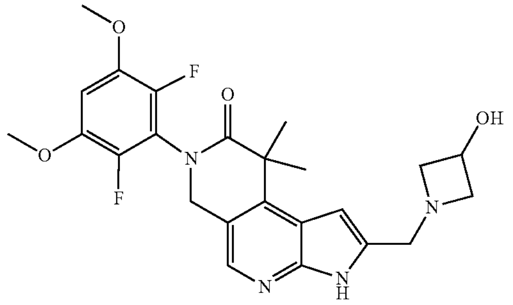 [SMILES: COc1cc(OC)c(F)c(N2Cc3cnc4[nH]c(CN5CC(O)C5)cc4c3C(C)(C)C2=O)c1F]

This compound was prepared using procedures analogous to those for Example 152 with azetidin-3-ol hydrochloride replacing morpholine in Step 7. LC-MS calculated for $C_{24}H_{27}F_2N_4O_4$ $(M+H)^+$ m/z: 473.2; found: 473.1.

Example 207

7-(2,6-difluoro-3,5-dimethoxyphenyl)-2-[(3-fluoroazetidin-1-yl)methyl]-9,9-dimethyl-3,6,7, 9-tetrahydro-8H-pyrrolo[2,3-c]-2,7-naphthyridin-8-one

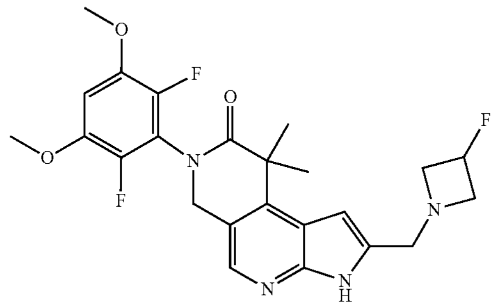 [SMILES: COc1cc(OC)c(F)c(N2Cc3cnc4[nH]c(CN5CC(F)C5)cc4c3C(C)(C)C2=O)c1F]

This compound was prepared using procedures analogous to those for Example 152 with 3-fluoroazetidine hydrochloride replacing morpholine in Step 7. LC-MS calculated for $C_{24}H_{26}F_3N_4O_3(M+H)^+$ m/z: 475.2; found: 475.0.

Example 208

1-{[3-(2,6-difluoro-3,5-dimethoxyphenyl)-1-methyl-2-oxo-2,3,4,7-tetrahydro-1H-pyrrolo[3',2':5,6]pyrido[4,3-d]pyrimidin-8-yl]methyl}azetidine-3-carbonitrile

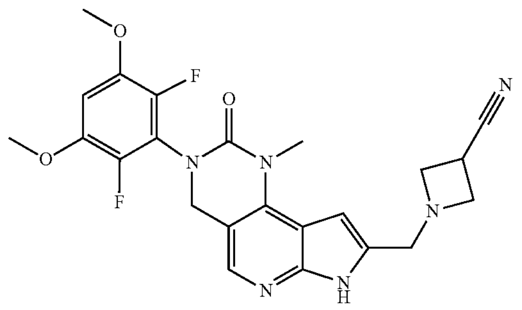 [SMILES: COc1cc(OC)c(F)c(N2Cc3cnc4[nH]c(CN5CC(C#N)C5)cc4c3N(C)C2=O)c1F]

This compound was prepared using procedures analogous to those for Example 70 with azetidine-3-carbonitrile hydrochloride replacing 1-ethylpiperazine in Step 2. LC-MS calculated for $C_{23}H_{23}F_2N_6O_3(M+H)^+$ m/z: 469.2; found: 469.0.

Example 209

(3R)-1-{[3-(2,6-difluoro-3,5-dimethoxyphenyl)-1-methyl-2-oxo-2,3,4,7-tetrahydro-1H-pyrrolo[3',2':5,6]pyrido[4,3-d]pyrimidin-8-yl]methyl}pyrrolidine-3-carbonitrile

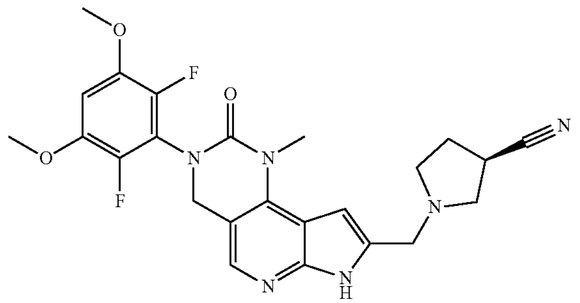 [SMILES: COc1cc(OC)c(F)c(N2Cc3cnc4[nH]c(CN5CC[C@@H](C#N)C5)cc4c3N(C)C2=O)c1F]

This compound was prepared using procedures analogous to those for Example 70 with (3R)-pyrrolidine-3-carbonitrile hydrochloride replacing 1-ethylpiperazine in Step 2. LC-MS calculated for $C_{24}H_{25}F_2N_6O_3(M+H)^+$ m/z: 483.2; found: 483.0.

Example 210

3-(2,6-difluoro-3,5-dimethoxyphenyl)-8-[2-(3-fluoroazetidin-1-yl)ethyl]-1-(2-hydroxyethyl)-1,3,4,7-tetrahydro-2H-pyrrolo[3',2':5,6]pyrido[4,3-d]pyrimidin-2-one

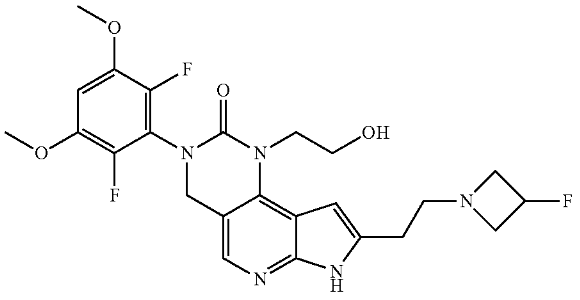 [SMILES: COc1cc(OC)c(F)c(N2Cc3cnc4[nH]c(CCN5CC(F)C5)cc4c3N(CCO)C2=O)c1F]

This compound was prepared using procedures analogous to those for Example 146 with 3-fluoroazetidine hydrochloride replacing morpholine in step 6. The product was purified by prep HPLC (pH=2, acetonitrile/water). LC-MS calculated for $C_{24}H_{27}F_3N_5O_4(M+H)^+$ m/z: 506.2; found: 506.0.

Example 211

3-(2,6-difluoro-3,5-dimethoxyphenyl)-1-(2,3-difluorophenyl)-8-(morpholin-4-ylmethyl)-1,3, 4,7-tetrahydro-2H-pyrrolo[3',2':5,6]pyrido[4,3-d]pyrimidin-2-one

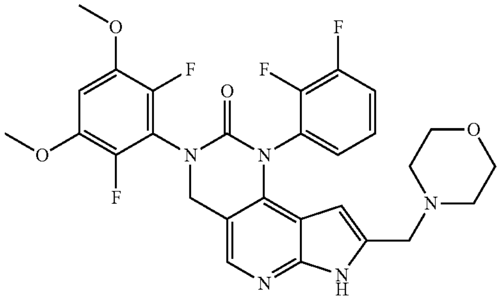 [SMILES: COc1cc(OC)c(F)c(N2Cc3cnc4[nH]c(CN5CCOCC5)cc4c3N(c3cccc(F)c3F)C2=O)c1F]

This compound was prepared using procedures analogous to those for Example 192 with morpholine replacing 1-methylpiperazine. The product was purified by prep HPLC (pH=2, acetonitrile/water). LC-MS calculated for $C_{28}H_{26}F_4N_5O_4(M+H)^+$ m/z: 572.2; found: 571.9.

Example 212

3-(2,6-difluoro-3,5-dimethoxyphenyl)-1-(3-fluorophenyl)-8-(morpholin-4-ylmethyl)-1,3,4,7-tetrahydro-2H-pyrrolo[3',2':5,6]pyrido[4,3-d]pyrimidin-2-one

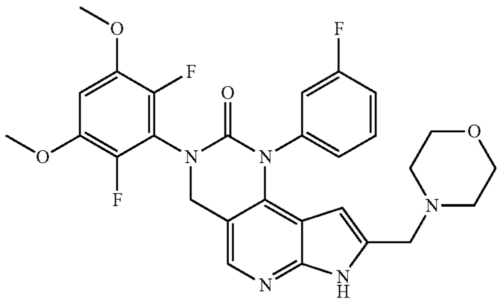

This compound was prepared by using procedures analogous to those for Example 180 with 3-fluorobenzenamine replacing 2-fluorobenzenamine. The product was purified by prep HPLC (pH=2, acetonitrile/water). LC-MS calculated for $C_{28}H_{27}F_3N_5O_4(M+H)^+$ m/z: 554.2; found: 554.2.

Example 213

3-(2,6-difluoro-3,5-dimethoxyphenyl)-1-(3-fluorophenyl)-8-[(4-methylpiperazin-1-yl)methyl]-1,3,4,7-tetrahydro-2H-pyrrolo[3',2':5,6]pyrido[4,3-d]pyrimidin-2-one

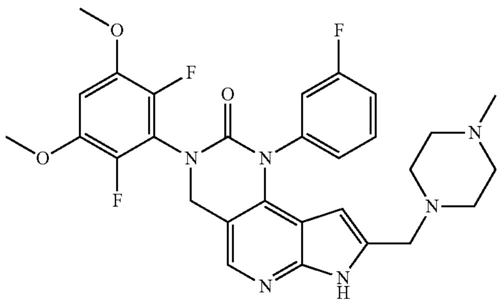

This compound was prepared using procedures analogous to those for Example 212 with 1-methylpiperazine replacing morpholine. The product was purified by prep HPLC (pH=2, acetonitrile/water). LC-MS calculated for $C_{29}H_{30}F_3N_6O_3$ $(M+H)^+$ m/z: 567.2; found: 567.2.

Example 214

3-(2,6-difluoro-3,5-dimethoxyphenyl)-1-(3-fluorophenyl)-8-[(4-ethylpiperazin-1-yl)methyl]-1,3,4,7-tetrahydro-2H-pyrrolo[3',2':5,6]pyrido[4,3-d]pyrimidin-2-one

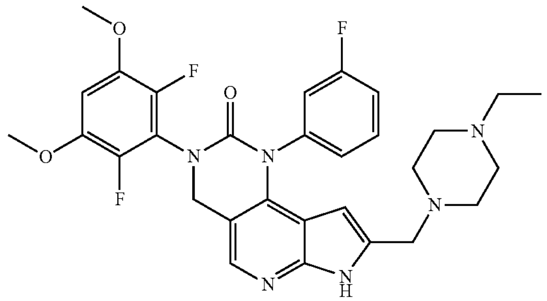 [SMILES: CCN1CCN(Cc2cc3c4c(cnc3[nH]2)CN(c2c(F)c(OC)cc(OC)c2F)C(=O)N4c2cccc(F)c2)CC1]

This compound was prepared using procedures analogous to those for Example 212 with 1-methylpiperazine replacing morpholine. The product was purified by prep HPLC (pH=2, acetonitrile/water). LC-MS calculated for $C_{29}H_{30}F_3N_6O_3$ $(M+H)^+$ m/z: 567.2; found: 567.2.

Example 215

3-(2,6-difluoro-3,5-dimethoxyphenyl)-1-methyl-9-(1-methyl-1H-pyrazol-4-yl)-1,3,4,7-tetrahydro-2H-pyrazolo[4',3':5,6]pyrido[4,3-d]pyrimidin-2-one

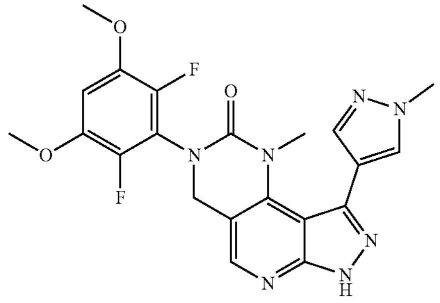

This compound was prepared using procedures analogous to those for Example 69 with 1-methyl-4-(4,4,5,5-tetramethyl-1,3,2-dioxaborolan-2-yl)-1H-pyrazole replacing 1-ethyl-4-[4-(4, 4,5,5-tetramethyl-1,3,2-dioxaborolan-2-yl) phenyl]piperazine. The product was purified by prep HPLC (pH=2, acetonitrile/water). LC-MS calculated for $C_{21}H_{20}F_2N_7O_3(M+H)^+$ m/z: 456.2; found: 456.1.

Example 216

3-(2,6-difluoro-3,5-dimethoxyphenyl)-1-[(6-fluoro-pyridin-2-yl)methyl]-1,3,4,7-tetrahydro-2H-pyrazolo [4',3':5,6]pyrido[4,3-d]pyrimidin-2-one

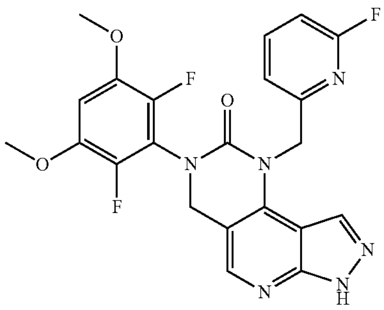 [SMILES: COc1cc(OC)c(F)c(N2Cc3cnc4[nH]ncc4c3N(Cc3cccc(F)n3)C2=O)c1F]

This compound was prepared using procedures analogous to those for Example 85 with 1-(6-fluoropyridin-2-yl)methanamine hydrochloride replacing 1-methyl-1H-pyrazol-4-amine in Step 1. LC-MS calculated for $C_{22}H_{18}F_3N_6O_3(M+H)^+$ m/z: 471.1; found: 471.0.

Example 217

3-(2,6-difluoro-3,5-dimethoxyphenyl)-1-[(6-methylpyridin-2-yl)methyl]-1,3,4,7-tetrahydro-2H-pyrazolo[4',3':5,6]pyrido[4,3-d]pyrimidin-2-one

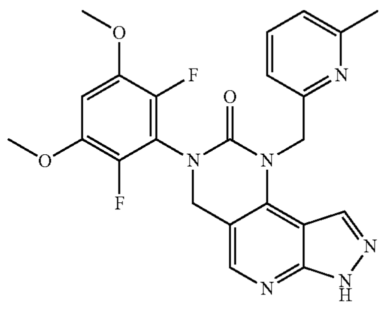

This compound was prepared using procedures analogous to those for Example 85 with 1-(6-methylpyridin-2-yl)methanamine replacing 1-methyl-1H-pyrazol-4-amine in Step 1. LC-MS calculated for $C_{23}H_{21}F_2N_6O_3(M+H)^+$ m/z: 467.2; found: 466.9.

Example 218

3-(2,6-Difluoro-3,5-dimethoxyphenyl)-1-(3-fluoro-pyridin-2-yl)-1,3,4,7-tetrahydro-2H-pyrazolo[4',3':5,6]pyrido[4,3-d]pyrimidin-2-one

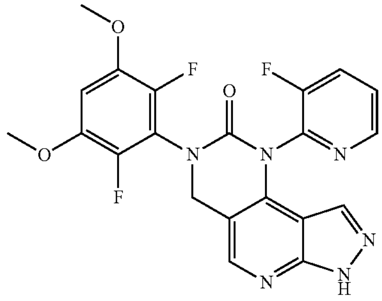 [SMILES: COc1cc(OC)c(F)c(N2Cc3cnc4[nH]ncc4c3N(c3ncccc3F)C2=O)c1F]

This compound was prepared by using procedures analogous to those for Example 85 with 3-fluoropyridin-2-amine replacing 1-methyl-1H-pyrazol-4-amine in Step 1. LC-MS calculated for $C_{21}H_{16}F_3N_6O_3(M+H)^+$ m/z: 457.1; found: 457.1.

Example 219

3-(2,6-difluoro-3,5-dimethoxyphenyl)-1-ethyl-8-[(2-oxopyridin-1(2H)-yl)methyl]-1,3,4,7-tetrahydro-2H-pyrrolo[3',2':5,6]pyrido[4,3-d]pyrimidin-2-one

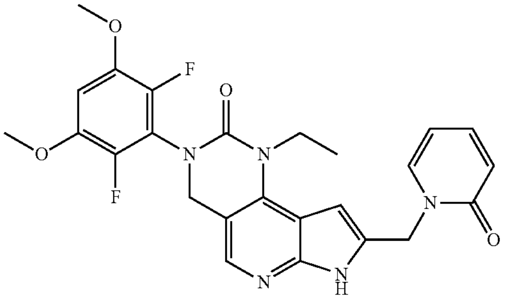 [SMILES: CCN1C(=O)N(c2c(F)c(OC)cc(OC)c2F)Cc2cnc3[nH]c(Cn4ccccc4=O)cc3c21]

Step 1: 3-(2,6-difluoro-3,5-dimethoxyphenyl)-1-ethyl-8-(hydroxymethyl)-7-(phenylsulfonyl)-1,3,4,7-tetrahydro-2H-pyrrolo[3',2':5,6]pyrido[4,3-d]pyrimidin-2-one

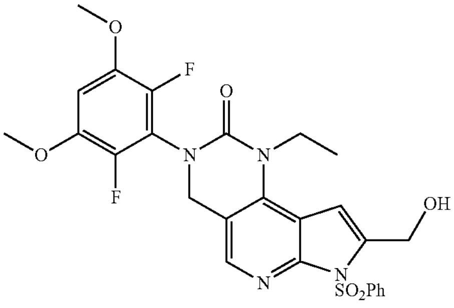

To a solution of 3-(2,6-difluoro-3,5-dimethoxyphenyl)-1-ethyl-2-oxo-7-(phenylsulfonyl)-2,3,4,7-tetrahydro-1H-pyrrolo[3',2':5,6]pyrido[4,3-d]pyrimidine-8-carbaldehyde (0.60 g, 1.1 mmol, from Example 126, Step 2) in methylene chloride (20 mL) was added sodium triacetoxyborohydride (0.80 g, 3.8 mmol). The mixture was stirred at room temperature for 3 h. The reaction mixture was quenched with saturated aqueous $NaHCO_3$, and extracted with ethyl acetate (3×20 mL). The combined organic layers were washed with brine, dried over $MgSO_4$, filtered and concentrated under reduced pressure. The residue was purified by flash chromatography on a silica gel column with MeOH in DCM (0-5%) to afford the desired product (0.40 g, 66%). LC-MS calculated for $C_{26}H_{25}F_2N_4O_6S$ $(M+H)^+$ m/z: 559.1; found: 558.9.

Step 2: 3-(2,6-difluoro-3,5-dimethoxyphenyl)-1-ethyl-8-[(2-oxopyridin-1(2H)-yl)methyl]-1,3,4,7-tetrahydro-2H-pyrrolo[3',2':5,6]pyrido[4,3-d]pyrimidin-2-one Triphenylphosphine (21 mg, 0.079 mmol) was added to a solution of 3-(2,6-difluoro-3,5-dimethoxyphenyl)-1-ethyl-8-(hydroxymethyl)-7-(phenylsulfonyl)-1,3,4,7-tetrahydro-2H-pyrrolo[3',2':5,6]pyrido[4,3-d]pyrimidin-2-one (22 mg, 0.039 mmol) and 2-hydroxypyridine (7.4 mg, 0.078 mmol) in tetrahydrofuran (0.5 mL) at room temperature. A solution of diethyl azodicarboxylate (12 µL, 0.079 mmol) in tetrahydrofuran (0.3 mL) was added. The reaction mixture was stirred at room temperature overnight. A solution of NaOMe in MeOH (25 wt %, 0.1 mL) was added. The reaction mixture was stirred at room temperature for 1 h. The mixture was purified by RP-HPLC (pH=10) to afford the desired product. LC-MS calculated for $C_{25}H_{24}F_2N_5O_4$$(M+H)^+$ m/z: 496.2; found: 496.0.

Example 220

3-(2,6-difluoro-3,5-dimethoxyphenyl)-1-ethyl-8-[(pyridin-3-yloxy)methyl]-1,3,4,7-tetrahydro-2H-pyrrolo[3',2':5,6]pyrido[4,3-d]pyrimidin-2-one

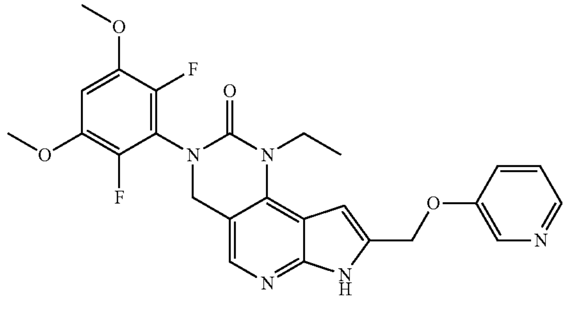 [SMILES: CCN1C(=O)N(c2c(F)c(OC)cc(OC)c2F)Cc2cnc3[nH]c(COc4cccnc4)cc3c21]

This compound was prepared by using procedures analogous to those for Example 219 with 3-pyridinol replacing 2-hydroxypyridine in Step 2. LC-MS calculated for $C_{25}H_{24}F_2N_5O_4$ $(M+H)^+$ m/z: 496.2; found: 496.0.

Example 221

3-(2,6-difluoro-3,5-dimethoxyphenyl)-1-(2-hydroxyethyl)-8-(morpholin-4-ylmethyl)-1,3,4,7-tetrahydro-2H-pyrrolo[3',2':5,6]pyrido[4,3-d]pyrimidin-2-one

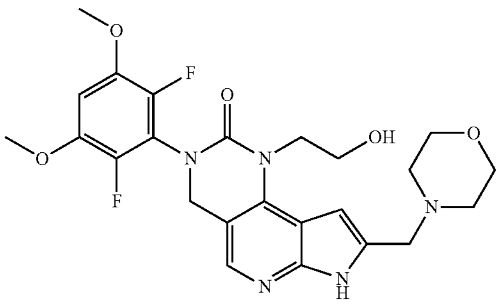 [SMILES: COc1cc(OC)c(F)c(N2Cc3cnc4[nH]c(CN5CCOCC5)cc4c3N(CCO)C2=O)c1F]

This compound was prepared by using procedures analogous to those for Example 126 (Step 2-4) with 1-(2-{[tert-butyl(dimethyl)silyl]oxy}ethyl)-3-(2,6-difluoro-3,5-dimethoxyphenyl)-7-(phenylsulfonyl)-1,3,4,7-tetrahydro-2Hpyrrolo[3',2':5,6]pyrido[4,3-d]pyrimidin-2-one (from Example 146, Step 4) as starting material. LC-MS calculated for $C_{24}H_{28}F_2N_5O_5$$(M+H)^+$ m/z: 504.2; found: 504.0.

Example 222

3-(2,6-difluoro-3,5-dimethoxyphenyl)-1-(2,3-difluorophenyl)-8-(2-morpholin-4-ylethyl)-1,3,4,7-tetrahydro-2H-pyrrolo[3',2':5,6]pyrido[4,3-d]pyrimidin-2-one

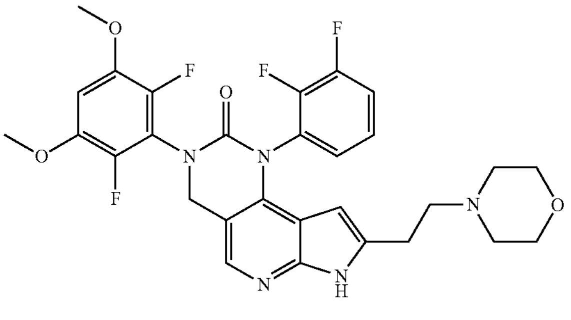 [SMILES: COc1cc(OC)c(F)c(N2Cc3cnc4[nH]c(CCN5CCOCC5)cc4c3N(c3cccc(F)c3F)C2=O)c1F]

This compound was prepared using procedures analogous to those for Example 196, Steps 1-2 with 2,3-difluoroaniline replacing 2-fluoro-benzenamine in Step 1. LC-MS calculated for $C_{29}H_{28}F_4N_5O_4$$(M+H)^+$ m/z: 586.2; found: 586.0.

Example 223

3-(2,6-difluoro-3,5-dimethoxyphenyl)-1-(2,3-difluorophenyl)-8-[2-(4-methylpiperazin-1-yl)ethyl]-1,3,4,7-tetrahydro-2H-pyrrolo[3',2':5,6]pyrido[4,3-d]pyrimidin-2-one

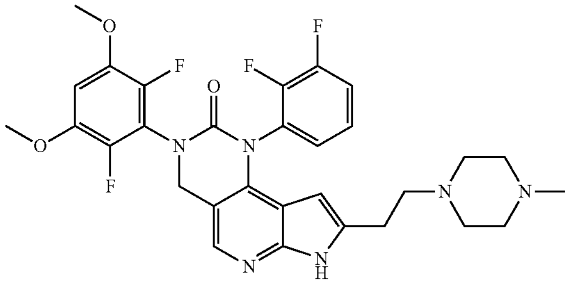

This compound was prepared using procedures analogous to those for Example 222 with 1-methylpiperazine replacing morpholine. The product was purified by prep HPLC (pH=2, acetonitrile/water). LC-MS calculated for $C_{30}H_{31}F_4N_6O_3$ $(M+H)^+$ m/z: 599.2; found: 599.0.

Example 224

3-(2,6-difluoro-3,5-dimethoxyphenyl)-1-(2,3-difluorophenyl)-8-[2-(4-ethylpiperazin-1-yl)ethyl]-1,3,4,7-tetrahydro-2H-pyrrolo[3',2':5,6]pyrido[4,3-d]pyrimidin-2-one

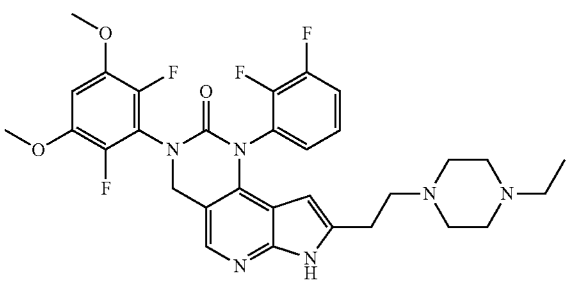 [SMILES: CCN1CCN(CCc2cc3c4c(cnc3[nH]2)CN(c2c(F)c(OC)cc(OC)c2F)C(=O)N4c2cccc(F)c2F)CC1]

This compound was prepared using procedures analogous to those for Example 222 with 1-ethylpiperazine replacing morpholine. The product was purified by prep HPLC (pH=2, acetonitrile/water). LC-MS calculated for $C_{31}H_{33}F_4N_6O_3$ $(M+H)^+$ m/z: 613.2; found: 613.0.

Example 225

3-(2,6-difluoro-3,5-dimethoxyphenyl)-1-(4-fluorophenyl)-8-(2-morpholin-4-ylethyl)-1,3,4,7-tetrahydro-2H-pyrrolo[3',2':5,6]pyrido[4,3-d]pyrimidin-2-one

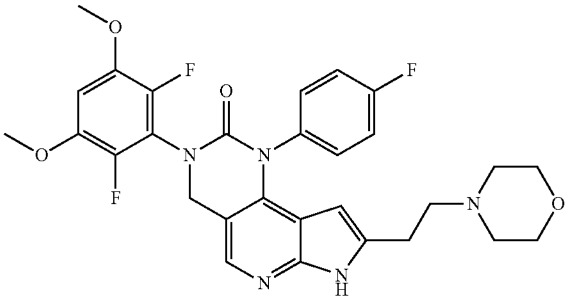 [SMILES: COc1cc(OC)c(F)c(N2Cc3cnc4[nH]c(CCN5CCOCC5)cc4c3N(c3ccc(F)cc3)C2=O)c1F]

This compound was prepared using procedures analogous to those for Example 196, Steps 1-2 with 4-fluoro-benzenamine replacing 2-fluoro-benzenamine in Step 1. LC-MS calculated for $C_{29}H_{29}F_3N_5O_4(M+H)^+$ m/z: 568.2; found: 568.0.

Example 226

3-(2,6-difluoro-3,5-dimethoxyphenyl)-1-(4-fluorophenyl)-8-[2-(4-methylpiperazin-1-yl)ethyl]-1,3,4,7-tetrahydro-2H-pyrrolo[3',2':5,6]pyrido[4,3-d]pyrimidin-2-one

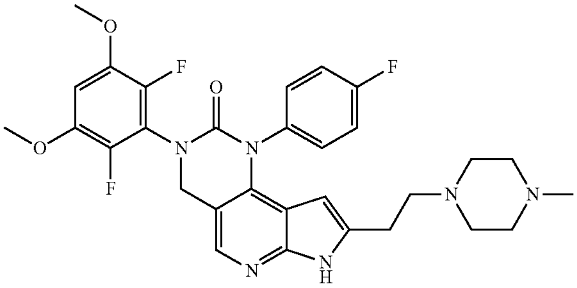

This compound was prepared using procedures analogous to those for Example 225 with 1-methylpiperazine replacing morpholine. The product was purified by prep HPLC (pH=2, acetonitrile/water). LC-MS calculated for $C_{30}H_{32}F_3N_6O_3$ $(M+H)^+$ m/z: 581.2; found: 581.0.

Example 227

3-(2,6-difluoro-3,5-dimethoxyphenyl)-1-(3-fluoro-phenyl)-8-(2-morpholin-4-ylethyl)-1,3,4,7-tetra-hydro-2H-pyrrolo[3',2':5,6]pyrido[4,3-d]pyrimidin-2-one

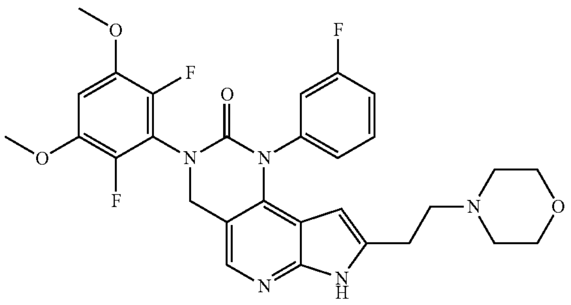 [SMILES: COc1cc(OC)c(F)c(N2Cc3cnc4[nH]c(CCN5CCOCC5)cc4c3N(c3cccc(F)c3)C2=O)c1F]

This compound was prepared using procedures analogous to those for Example 196, Steps 1-2 with 3-fluoro-benzenamine replacing 2-fluoro-benzenamine in step 1. LC-MS calculated for $C_{29}H_{29}F_3N_5O_4(M+H)^+$ m/z: 568.2; found: 568.0.

Example 228

3-(2,6-difluoro-3,5-dimethoxyphenyl)-1-(3-fluoro-phenyl)-8-[2-(4-methylpiperazin-1-yl)ethyl]-1,3,4,7-tetrahydro-2H-pyrrolo[3',2':5,6]pyrido[4,3-d]pyrimidin-2-one

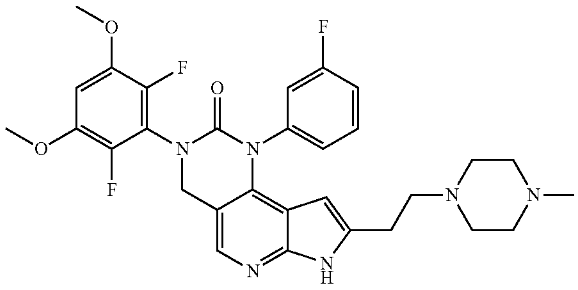

This compound was prepared using procedures analogous to those for Example 227 with 1-methylpiperazine replacing morpholine. The product was purified by prep HPLC (pH=2, acetonitrile/water). LC-MS calculated for $C_{30}H_{32}F_3N_6O_3$ $(M+H)^+$ m/z: 581.2; found: 581.0.

Example 229

3-(2,6-difluoro-3,5-dimethoxyphenyl)-1-(3-fluoro-phenyl)-8-[2-(4-ethylpiperazin-1-yl)ethyl]-1,3,4,7-tetrahydro-2H-pyrrolo[3',2':5,6]pyrido[4,3-d]pyrimidin-2-one

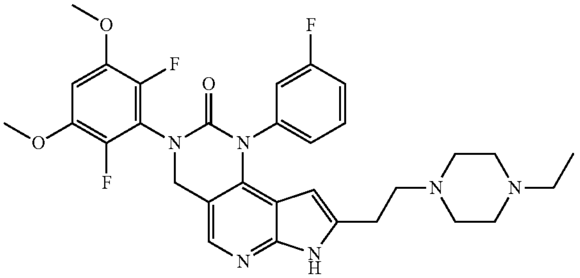 [SMILES: CCN1CCN(CCc2cc3c4c(cnc3[nH]2)CN(c2c(F)c(OC)cc(OC)c2F)C(=O)N4c2cccc(F)c2)CC1]

This compound was prepared using procedures analogous to those for Example 227 with 1-ethylpiperazine replacing morpholine. The product was purified by prep HPLC (pH=2, acetonitrile/water). LC-MS calculated for $C_{31}H_{34}F_3N_6O_3$ $(M+H)^+$ m/z: 595.3; found: 595.0.

Example 230

1-{2-[3-(2,6-difluoro-3,5-dimethoxyphenyl)-1-ethyl-2-oxo-2,3,4,7-tetrahydro-1H-pyrrolo[3',2':5,6]pyrido[4,3-d]pyrimidin-8-yl]ethyl}azetidine-3-carbonitrile

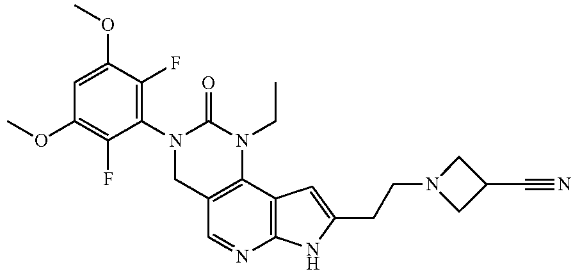 [SMILES: CCN1C(=O)N(c2c(F)c(OC)cc(OC)c2F)Cc2cnc3[nH]c(CCN4CC(C#N)C4)cc3c21]

This compound was prepared using procedures analogous to those for Example 71 starting with 8-bromo-3-(2,6-difluoro-3,5-dimethoxyphenyl)-1-ethyl-7-(phenylsulfonyl)-1,3,4,7-tetrahydro-2H-pyrrolo[3',2':5,6]pyrido[4,3-d]pyrimidin-2-one (Example 185, Step 1) and azetidine-3-carbonitrile hydrochloride. LC-MS calculated for $C_{25}H_{27}F_2N_6O_3[M+H]^+$ m/z: 497.2; found 496.9.

Example 231

3-(2,6-difluoro-3,5-dimethoxyphenyl)-1-ethyl-8-[2-(3-fluoroazetidin-1-yl)ethyl]-1,3,4,7-tetrahydro-2H-pyrrolo[3',2':5,6]pyrido[4,3-d]pyrimidin-2-one

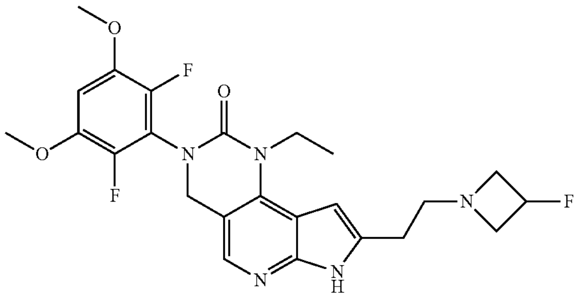 [SMILES: CCN1C(=O)N(c2c(F)c(OC)cc(OC)c2F)Cc2cnc3[nH]c(CCN4CC(F)C4)cc3c21]

This compound was prepared using procedures analogous to those for Example 71 starting with 8-bromo-3-(2,6-difluoro-3,5-dimethoxyphenyl)-1-ethyl-7-(phenylsulfonyl)-1,3,4,7-tetrahydro-2H-pyrrolo[3',2':5,6]pyrido[4,3-d]pyrimidin-2-one (Example 185, Step 1) and 3-fluoroazetidine hydrochloride. LC-MS calculated for $C_{24}H_{27}F_3N_5O_3$[M+H]$^+$ m/z: 490.2; found 489.9.

Example 232

3-(2,6-difluoro-3,5-dimethoxyphenyl)-1-(2-fluoroethyl)-8-(morpholin-4-ylmethyl)-1,3,4,7-tetrahydro-2H-pyrrolo[3',2':5,6]pyrido[4,3-d]pyrimidin-2-one

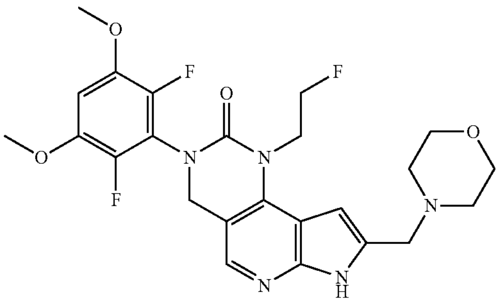 [SMILES: COc1cc(OC)c(F)c(N2Cc3cnc4[nH]c(CN5CCOCC5)cc4c3N(CCF)C2=O)c1F]

Step 1: 1-(2-{[tert-butyl(dimethyl)silyl]oxy}ethyl)-3-(2,6-difluoro-3,5-dimethoxyphenyl)-2-oxo-7-(phenylsulfonyl)-2,3,4,7-tetrahydro-1H-pyrrolo[3',2':5,6]pyrido[4,3-d]pyrimidine-8-carbaldehyde

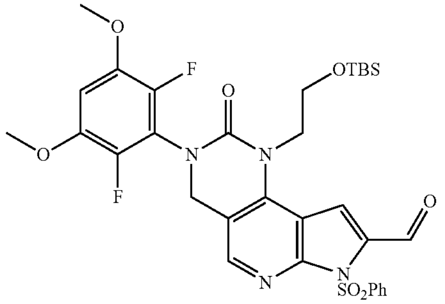

To a solution of 1-(2-{[tert-butyl(dimethyl)silyl]oxy}ethyl)-3-(2,6-difluoro-3,5-dimethoxyphenyl)-7-(phenylsulfonyl)-1,3,4,7-tetrahydro-2H-pyrrolo[3',2':5,6]pyrido[4,3-d]pyrimidin-2-one (456 mg, 0.69 mmol) (Example 146, Step 4) in tetrahydrofuran (10 mL) at −78° C. was added LDA (freshly prepared, 1 M in THF, 1.44 mL). The mixture was stirred at −78° C. for 30 min, then N,N-dimethylformamide (0.77 mL) was added. The mixture was stirred at −78° C. for 1 h, and then quenched with saturated $NH_4Cl$ solution at −78° C. The mixture was warmed to room temperature and extracted with EtOAc. The combined extracts were washed with water and brine, dried over $Na_2SO_4$, filtered and concentrated under reduced pressure to give the desired product (452 mg) as yellow solid, which was directly used in the next step without further purification. LC-MS calculated for $C_{32}H_{37}F_2N_4O_7SSi$ [M+H]$^+$ m/z: 687.2; found 687.2.

Step 2: 3-(2,6-difluoro-3,5-dimethoxyphenyl)-1-(2-hydroxyethyl)-2-oxo-7-(phenylsulfonyl)-2,3,4,7-tetrahydro-1H-pyrrolo[3',2':5,6]pyrido[4,3-d]pyrimidine-8-carbaldehyde

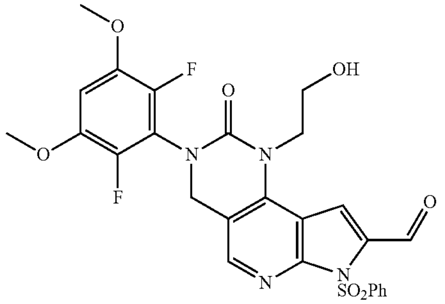

To a solution of 1-(2-{[tert-butyl(dimethyl)silyl]oxy}ethyl)-3-(2,6-difluoro-3,5-dimethoxyphenyl)-2-oxo-7-(phenylsulfonyl)-2,3,4,7-tetrahydro-1H-pyrrolo[3',2':5,6]pyrido[4,3-d]pyrimidine-8-carbaldehyde (430 mg, 0.63 mmol) in tetrahydrofuran (10 mL) and water (2 mL) was added 12.0 M hydrogen chloride in water (1.04 mL). The resulting yellow solution was stirred at room temperature for 1.5 h. The reaction mixture was neutralized with saturated $NaHCO_3$ solution, and extracted with EtOAc. The combined extracts were washed with brine dried over $Na_2SO_4$, filtered and concentrated under reduced pressure. The residue was purified by silica gel column eluting with EtOAc in DCM (gradient: 0 to 60%) to afford the desired product (265 mg) as light yellow solid. LC-MS calculated for $C_{26}H_{23}F_2N_4O_7S$ $[M+H]^+$ m/z: 573.1; found 572.9.

Step 3: 3-(2,6-difluoro-3,5-dimethoxyphenyl)-1-(2-hydroxyethyl)-8-(morpholin-4-ylmethyl)-7-(phenylsulfonyl)-1,3,4,7-tetrahydro-2H-pyrrolo[3',2':5,6]pyrido[4,3-d]pyrimidin-2-one

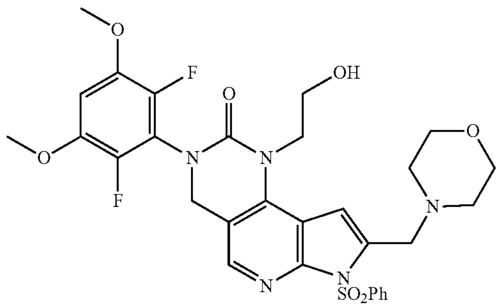

This compound was prepared using procedures analogous to those for Example 110, Step 1 starting with 3-(2,6-difluoro-3,5-dimethoxyphenyl)-1-(2-hydroxyethyl)-2-oxo-7-(phenyl sulfonyl)-2,3,4,7-tetrahydro-1H-pyrrolo[3',2':5,6]pyrido[4,3-d]pyrimidine-8-carbaldehyde and morpholine. LC-MS calculated for $C_{30}H_{32}F_2N_5O_7S$ $[M+H]^+$ m/z: 644.2; found 644.0.

Step 4: 3-(2,6-difluoro-3,5-dimethoxyphenyl)-1-(2-fluoroethyl)-8-(morpholin-4-ylmethyl)-7-(phenylsulfonyl)-1,3,4,7-tetrahydro-2H-pyrrolo[3',2':5,6]pyrido[4,3-d]pyrimidin-2-one

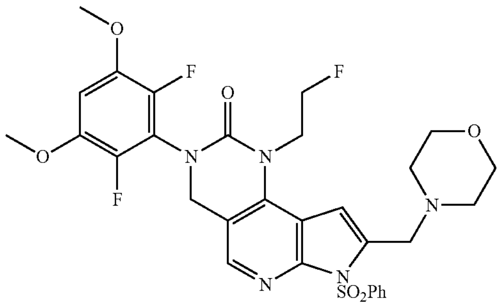

3-(2,6-Difluoro-3,5-dimethoxyphenyl)-1-(2-hydroxyethyl)-8-(morpholin-4-ylmethyl)-7-(phenylsulfonyl)-1,3,4,7-tetrahydro-2H-pyrrolo[3',2':5,6]pyrido[4,3-d]pyrimidin-2-one (from Step 3) was dissolved in DCM (3 mL). To the solution was added diethylaminosulfur trifluoride (40.0 μL, 0.303 mmol). The mixture was stirred at r.t. for 2 h, quenched with water, and extracted with DCM. The organic layers were washed with brine, dried over $Na_2SO_4$, filtered and concentrated under reduced pressure. The residue was purified by flash chromatography on a silica gel column with methanol in DCM (0-10%) to give the desired product. LC-MS calculated for $C_{30}H_{31}F_3N_5O_6S$ $[M+H]^+$ m/z: 646.2; found 646.0.

Step 5: 3-(2,6-difluoro-3,5-dimethoxyphenyl)-1-(2-fluoroethyl)-8-(morpholin-4-ylmethyl)-1,3, 4,7-tetrahydro-2H-pyrrolo[3',2':5,6]pyrido[4,3-d]pyrimidin-2-one 3-(2,6-Difluoro-3,5-dimethoxyphenyl)-1-(2-fluoroethyl)-8-(morpholin-4-ylmethyl)-7-(phenylsulfonyl)-1,3,4,7-tetrahydro-2H-pyrrolo[3',2':5,6]pyrido[4,3-d]pyrimidin-2-one (from Step 4) was dissolved in THF (2.0 mL), then 1.0 M TBAF in THF solution (0.40 mL) was added. The resulting solution was stirred at 60° C. for 1 h. After cooling, the solution was quenched with a few drops of TFA, diluted with methanol, and purified by RP-HPLC (pH=2) to afford the desired product as TFA salt. LC-MS calculated for $C_{24}H_{27}F_3N_5O_4[M+H]^+$ m/z: 506.2; found 506.0.

Example 233

3-(2,6-difluoro-3,5-dimethoxyphenyl)-1-(2-fluoroethyl)-8-[(4-methylpiperazin-1-yl)methyl]-1,3,4,7-tetrahydro-2H-pyrrolo[3',2':5,6]pyrido[4,3-d]pyrimidin-2-one

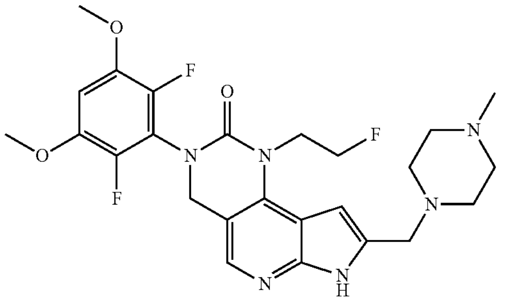

This compound was prepared using procedures analogous to those for Example 232 starting with 3-(2,6-difluoro-3,5-dimethoxyphenyl)-1-(2-hydroxyethyl)-2-oxo-7-(phenylsulfonyl)-2,3,4,7-tetrahydro-1H-pyrrolo[3',2':5,6]pyrido[4,3-d]pyrimidine-8-carbaldehyde (Example 232, Step 2) and 1-methyl-piperazine replacing morpholine in Step 3. LC-MS calculated for $C_{25}H_{30}F_3N_6O_3[M+H]^+$ m/z: 519.2; found 519.0.

Example A

FGFR Enzymatic Assay

The inhibitor potency of the exemplified compounds was measured in an enzyme assay that measures peptide phosphorylation using FRET measurements to detect product formation. Inhibitors were serially diluted in DMSO and a volume of 0.5 μL was transferred to the wells of a 384-well plate. For FGFR3, a 10 μL volume of FGFR3 enzyme (Millipore) diluted in assay buffer (50 mM HEPES, 10 mM $MgCl_2$, 1 mM EGTA, 0.01% Tween-20, 5 mM DTT, pH 7.5) was added to the plate and pre-incubated for 5-10 minutes. Appropriate controls (enzyme blank and enzyme with no inhibitor) were included on the plate. The assay was initiated by the addition of a 10 μL solution containing biotinylated EQEDEPEGDYFEWLE peptide substrate (SEQ ID NO: 1) and ATP (final concentrations of 500 nM and 140 μM respectively) in assay buffer to the wells. The plate was incubated at 25° C. for 1 hr. The reactions were ended with the addition of 10 μL/well of quench solution (50 mM Tris, 150 mM NaCl, 0.5 mg/mL BSA, pH 7.8; 30 mM EDTA with Perkin Elmer Lance Reagents at 3.75 nM Eu-antibody PY20 and 180 nM APC-Streptavidin). The plate was allowed to equilibrate for ~1 hr before scanning the wells on a PheraStar plate reader (BMG Labtech).

FGFR1 and FGFR2 were measured under equivalent conditions with the following changes in enzyme and ATP concentrations: FGFR1, 0.02 nM and 210 μM, respectively and FGFR2, 0.01 nM and 100 μM, respectively. The enzymes were purchased from Millipore or Invitrogen.

GraphPad prism3 was used to analyze the data. The $IC_{50}$ values were derived by fitting the data to the equation for a sigmoidal dose-response with a variable slope. Y=Bottom+(Top-Bottom)/(1+10^((Log$IC_{50}$-X)*HillSlope)) where X is the logarithm of concentration and Y is the response. Compounds having an $IC_{50}$ of 1 μM or less are considered active.

The compounds of the invention were found to be inhibitors of one or more of FGFR1, FGFR2, and FGFR3 according to the above-described assay. $IC_{50}$ data is provided below in Table 1. The symbol "+" indicates an $IC_{50}$ less than 100 nM and the symbol "++" indicates an $IC_{50}$ of 100 to 500 nM.

TABLE 1

| Example No. | FGFR1 IC50 (nM) | FGFR2 IC50 (nM) | FGFR3 IC50 (nM) |
|---|---|---|---|
| 1 | + | + | + |
| 2 | + | + | + |
| 3 | + | + | + |
| 4 | + | + | + |
| 5 | + | + | + |
| 6 | + | + | + |
| 7 | + | + | + |
| 8 | + | + | + |
| 9 | + | + | ++ |
| 10 | + | + | + |
| 11 | + | + | + |
| 12 | + | + | + |
| 13 | + | + | + |
| 14 | + | + | + |
| 15 | + | + | + |
| 16 | + | + | + |
| 17 | + | + | + |
| 18 | + | + | + |
| 19 | + | + | + |
| 20 | + | + | + |
| 21 | + | + | + |
| 22 | + | + | + |
| 23 | + | + | + |
| 24 | + | + | + |
| 25 | + | + | + |
| 26 | + | + | + |
| 27 | + | + | + |
| 28 | + | + | + |
| 29 | + | + | + |
| 30 | + | + | + |
| 31 | + | + | + |
| 32 | + | + | + |
| 33 | + | + | + |
| 34 | + | + | + |
| 35 | + | + | + |
| 36 | + | + | + |
| 37 | + | + | + |
| 38 | + | + | + |
| 39 | + | + | + |
| 40 | + | + | + |
| 41 | + | + | + |
| 42 | + | + | + |
| 43 | + | + | + |
| 44 | + | + | + |
| 45 | + | + | + |
| 46 | + | + | + |
| 47 | + | + | + |
| 48 | + | + | + |

TABLE 1-continued

| Example No. | FGFR1 IC50 (nM) | FGFR2 IC50 (nM) | FGFR3 IC50 (nM) |
|---|---|---|---|
| 49 | + | + | + |
| 50 | + | + | + |
| 51 | + | + | + |
| 52 | + | + | + |
| 53 | + | + | + |
| 54 | + | + | + |
| 55 | + | + | + |
| 56 | + | + | + |
| 57 | + | + | + |
| 58 | + | + | + |
| 59 | + | + | + |
| 60 | + | + | + |
| 61 | + | + | + |
| 62 | ++ | ++ | + |
| 63 | + | + | + |
| 64 | + | + | + |
| 65 | + | + | + |
| 66 | + | + | + |
| 67 | + | + | + |
| 68 | + | + | + |
| 69 | + | + | + |
| 70 | + | + | + |
| 71 | + | + | + |
| 72 | + | + | + |
| 73 | + | + | + |
| 74 | + | + | + |
| 75 | + | + | + |
| 76 | + | + | + |
| 77 | + | + | + |
| 78 | + | + | + |
| 79 | + | + | + |
| 80 | + | + | + |
| 81 | + | + | + |
| 82 | + | + | + |
| 83 | + | + | + |
| 84 | + | + | + |
| 85 | + | + | + |
| 86 | + | + | + |
| 87 | + | + | + |
| 88 | + | + | + |
| 89 | + | + | + |
| 90 | + | + | + |
| 91 | + | + | + |
| 92 | + | + | + |
| 93 | + | + | + |
| 94 | + | + | + |
| 95 | + | + | + |
| 96 | + | + | + |
| 97 | + | + | + |
| 98 | + | + | + |
| 99 | + | + | + |
| 100 | + | + | + |
| 101 | + | + | + |
| 102 | + | + | + |
| 103 | + | + | + |
| 104 | + | + | + |
| 105 | + | + | + |
| 106 | + | + | + |
| 107 | + | + | + |
| 108 | + | + | + |
| 109 | + | + | + |
| 110 | + | + | + |
| 111 | + | + | + |
| 112 | + | + | + |
| 113 | + | + | + |
| 114 | + | + | + |
| 115 | + | + | + |
| 116 | + | + | + |
| 117 | + | + | + |
| 118 | + | + | + |
| 119 | + | + | + |
| 120 | + | + | + |
| 121 | + | + | + |
| 122 | + | + | + |
| 123 | + | + | + |
| 124 | + | + | + |
| 125 | + | + | + |

TABLE 1-continued

| Example No. | FGFR1 IC50 (nM) | FGFR2 IC50 (nM) | FGFR3 IC50 (nM) |
|---|---|---|---|
| 126 | + | + | + |
| 127 | + | + | + |
| 128 | + | + | + |
| 129 | + | + | + |
| 130 | + | + | + |
| 131 | + | + | + |
| 132 | + | + | + |
| 133 | + | + | + |
| 134 | + | + | + |
| 135 | + | + | + |
| 136 | + | + | + |
| 137 | + | + | + |
| 138 | + | + | + |
| 139 | + | + | + |
| 140 | + | + | + |
| 141 | + | + | + |
| 142 | + | + | + |
| 143 | + | + | + |
| 144 | + | + | + |
| 145 | + | + | + |
| 146 | + | + | + |
| 147 | + | + | + |
| 148 | + | + | + |
| 149 | + | + | + |
| 150 | + | + | + |
| 151 | + | + | + |
| 152 | + | + | + |
| 153 | + | + | + |
| 154 | + | + | + |
| 155 | + | + | + |
| 156 | + | + | + |
| 157 | + | + | + |
| 158 | + | + | + |
| 159 | + | + | + |
| 160 | + | + | + |
| 161 | + | + | + |
| 162 | + | + | + |
| 163 | + | + | + |
| 164 | + | + | + |
| 165 | + | + | + |
| 166 | + | + | + |
| 167 | + | + | + |
| 168 | + | + | + |
| 169 | + | + | + |
| 170 | + | + | + |
| 171 | + | + | + |
| 172 | + | + | + |
| 173 | + | + | + |
| 174 | + | + | + |
| 175 | + | + | + |
| 176 | + | + | + |
| 177 | + | + | + |
| 178 | + | + | + |
| 179 | + | + | + |
| 180 | + | + | + |
| 181 | + | + | + |
| 182 | + | + | + |
| 183 | + | + | + |
| 184 | + | + | + |
| 185 | + | + | + |
| 186 | + | + | + |
| 187 | + | + | + |
| 188 | + | + | + |
| 189 | + | + | + |
| 190 | + | + | + |
| 191 | + | + | + |
| 192 | + | + | + |
| 193 | + | + | + |
| 194 | + | + | + |
| 195 | + | + | + |
| 196 | + | + | + |
| 197 | + | + | + |
| 198 | + | + | + |
| 199 | + | + | + |
| 200 | + | + | + |
| 201 | + | + | + |
| 202 | + | + | + |

TABLE 1-continued

| Example No. | FGFR1 IC50 (nM) | FGFR2 IC50 (nM) | FGFR3 IC50 (nM) |
|---|---|---|---|
| 203 | + | + | + |
| 204 | + | + | + |
| 205 | + | + | + |
| 206 | + | + | + |
| 207 | + | + | + |
| 208 | + | + | + |
| 209 | + | + | + |
| 210 | + | + | + |
| 211 | + | + | + |
| 212 | + | + | + |
| 213 | + | + | + |
| 214 | + | + | + |
| 215 | + | + | + |
| 216 | + | + | + |
| 217 | + | + | + |
| 218 | + | + | + |
| 219 | + | + | + |
| 220 | + | + | + |
| 221 | + | + | + |
| 222 | + | + | + |
| 223 | + | + | + |
| 224 | + | + | + |
| 225 | + | + | + |
| 226 | + | + | + |
| 227 | + | + | + |
| 228 | + | + | + |
| 229 | + | + | + |
| 230 | + | + | + |
| 231 | + | + | + |
| 232 | + | + | + |
| 233 | + | + | + |

Example B

FGFR Cell Proliferation/Survival Assays

The ability of the example compounds to inhibit the growth of cells dependent on FGFR signaling for survival was measured using viability assays. A recombinant cell line over-expressing human FGFR3 was developed by stable transfection of the mouse pro-B Ba/F3 cells (obtained from the Deutsche Sammlung von Mikroorganismen und Zellkulturen) with a plasmid encoding the full length human FGFR3. Cells were sequentially selected for puromycin resistance and proliferation in the presence of heparin and FGF1. A single cell clone was isolated and characterized for functional expression of FGFR3. This Ba/F3-FGFR3 clone is used in cell proliferation assays, and compounds are screened for their ability to inhibit cell proliferation/survival. The Ba/F3-FGFR3 cells are seeded into 96 well, black cell culture plates at 3500 cells/well in RPMI1640 media containing 2% FBS, 20 μg/mL Heparin and 5 ng/mL FGF1. The cells were treated with 10 μL of 10× concentrations of serially diluted compounds (diluted with medium lacking serum from 5 mM DSMO dots) to a final volume of 100 μL/well. After 72 hour incubation, 100 μL of Cell Titer Glo® reagent (Promega Corporation) that measures cellular ATP levels is added to each well. After 20 minute incubation with shaking, the luminescence is read on a plate reader. The luminescent readings are converted to percent inhibition relative to DMSO treated control wells, and the $IC_{50}$ values are calculated using GraphPad Prism software by fitting the data to the equation for a sigmoidal dose-response with a variable slope. Compounds having an $IC_{50}$ of 10 μM or less are considered active. Cell lines representing a variety of tumor types including KMS-11 (multiple myeloma, FGFR3 translocation), RT112 (bladder cancer, FGFR3 overexpression), KatoIII (gastric cancer, FGFR2 gene amplification), and H-1581 (lung, FGFR1 gene amplification) are used in similar proliferation assays. In some experiments, MTS reagent, Cell Titer 96® AQueous One Solution Reagent (Promega Corporation) is added to a final concentration of 333 μg/mL in place Cell Titer Glo and read at 490/650 nm on a plate reader. Compounds having an $IC_{50}$ of 5 μM or less are considered active.

Example C

Cell-Based FGFR Phosphorylation Assays

The inhibitory effect of compounds on FGFR phosphorylation in relevant cell lines (Ba/F3-FGFR3, KMS-11, RT112, KatoIII, H-1581 cancer cell lines and HUVEC cell line) can be assessed using immunoassays specific for FGFR phosphorylation. Cells are starved in media with reduced serum (0.5%) and no FGF1 for 4 to 18 h depending upon the cell line then treated with various concentrations of individual inhibitors for 1-4 hours. For some cell lines, such as Ba/F3-FGFR3 and KMS-11, cells are stimulated with Heparin (20 μg/mL) and FGF1 (10 ng/mL) for 10 min. Whole cell protein extracts are prepared by incubation in lysis buffer with protease and phosphatase inhibitors [50 mM HEPES (pH 7.5), 150 mM NaCl, 1.5 mM $MgCl_2$, 10% Glycerol, 1% Triton X-100, 1 mM sodium orthovanadate, 1 mM sodium fluoride, aprotinin (2 μg/mL), leupeptin (2 μg/mL), pepstatin A (2 μg/mL), and phenylmethylsulfonyl fluoride (1 mM)] at 4° C. Protein extracts are cleared of cellular debris by centrifugation at 14,000×g for 10 minutes and quantified using the BCA (bicinchoninic acid) microplate assay reagent (Thermo Scientific).

Phosphorylation of FGFR receptor in protein extracts was determined using immunoassays including western blotting, enzyme-linked immunoassay (ELISA) or bead-based immunoassays (Luminex). For detection of phosphorylated FGFR2, a commercial ELISA kit DuoSet IC Human Phospho-FGF R2α ELISA assay (R&D Systems, Minneapolis, MN) can be used. For the assay KatoIII cells are plated in 0.2% FBS supplemented Iscove's medium (50,000 cells/well/per 100 μL) into 96-well flat-bottom tissue culture treated plates (Corning, Corning, NY), in the presence or absence of a concentration range of test compounds and incubated for 4 hours at 37° C., 5% $CO_2$. The assay is stopped with addition of 200 μL of cold PBS and centrifugation. The washed cells are lysed in Cell Lysis Buffer (Cell Signaling, #9803) with Protease Inhibitor (Calbiochem, #535140) and PMSF (Sigma, #P7626) for 30 min on wet ice. Cell lysates were frozen at −80° C. before testing an aliquot with the DuoSet IC Human Phospho-FGF R2α ELISA assay kit. GraphPad prism3 was used to analyze the data. The $IC_{50}$ values were derived by fitting the data to the equation for a sigmoidal dose-response with a variable slope.

For detection of phosphorylated FGFR3, a bead based immunoassay was developed. An anti-human FGFR3 mouse mAb (R&D Systems, cat #MAB7661) was conjugated to Luminex MAGplex microspheres, bead region 20 and used as the capture antibody. RT-112 cells were seeded into multi-well tissue culture plates and cultured until 70% confluence. Cells were washed with PBS and starved in RPMI+0.5% FBS for 18 hr. The cells were treated with 10 μL of 10× concentrations of serially diluted compounds for 1 hr at 37° C., 5% $CO_2$ prior to stimulation with 10 ng/mL human FGF1 and 20 μg/mL Heparin for 10 min. Cells were washed with cold PBS and lysed with Cell Extraction Buffer (Invitrogen) and centrifuged. Clarified supernatants were frozen at −80° C. until analysis.

For the assay, cell lysates are diluted 1:10 in Assay Diluent and incubated with capture antibody-bound beads in a 96-well filter plate for 2 hours at room temperature on a plate shaker. Plates are washed three times using a vacuum manifold and incubated with anti-phospho-FGF R1-4 (Y653/Y654) rabbit polyclonal antibody (R&D Systems cat #AF3285) for 1 hour at RT with shaking. Plates are washed three times. The diluted reporter antibody, goat anti-rabbit-RPE conjugated antibody (Invitrogen Cat. #LHB0002) is added and incubated for 30 minutes with shaking. Plates are washed three times. The beads are suspended in wash buffer with shaking at room temperature for 5 minutes and then read on a Luminex 200 instrument set to count 50 events per sample, gate settings 7500-13500. Data is expressed as mean fluorescence intensity (MFI). MFI from compound treated samples are divided by MFI values from DMSO controls to determine the percent inhibition, and the $IC_{50}$ values are calculated using the GraphPad Prism software. Compounds having an $IC_{50}$ of 1 μM or less are considered active.

Example D

FGFR Cell-Based Signaling Assays

Activation of FGFR leads to phosphorylation of Erk proteins. Detection of pErk is monitored using the Cellu'Erk HTRF (Homogeneous Time Resolved Flurorescence) Assay (CisBio) according to the manufacturer's protocol. KMS-11 cells are seeded into 96-well plates at 40,000 cells/well in RPMI medium with 0.25% FBS and starved for 2 days. The medium is aspirated and cells are treated with 30 μL of 1× concentrations of serially diluted compounds (diluted with medium lacking serum from 5 mM DSMO dots) to a final volume of 30 μL/well and incubated for 45 min at room temperature. Cells are stimulated by addition of 10 μL of Heparin (100 μg/mL) and FGF1 (50 ng/mL) to each well and incubated for 10 min at room temperature. After lysis, an aliquot of cell extract is transferred into 384-well low volume plates, and 4 μL of detection reagents are added followed by incubation for 3 hr at room temperature. The plates are read on a PheraStar instrument with settings for HTRF. The normalized fluorescence readings are converted to percent inhibition relative to DMSO treated control wells, and the $IC_{50}$ values are calculated using the GraphPad Prism software. Compounds having an $IC_{50}$ of 1 μM or less are considered active.

Example E

VEGFR2 Kinase Assay

40 μL Enzyme reactions are run in black 384 well polystyrene plates for 1 hour at 25° C. Wells are dotted with 0.8 μL of test compound in DMSO. The assay buffer contains 50 mM Tris, pH 7.5, 0.01% Tween-20, 10 mM $MgCl_2$, 1 mM EGTA, 5 mM DTT, 0.5 μM Biotin-labeled EQEDEPEGDYFEWLE peptide substrate (SEQ ID NO: 1), 1 mM ATP, and 0.1 nM enzyme (Millipore catalogue number 14-630). Reactions are stopped by addition of 20 μL Stop Buffer (50 mM Tris, pH=7.8, 150 mM NaCl, 0.5 mg/mL BSA, 45 mM EDTA) with 225 nM LANCE Streptavidin Surelight® APC (PerkinElmer catalogue number CR130-100) and 4.5 nM LANCE Eu-W1024 anti phosphotyrosine (PY20) antibody (PerkinElmer catalogue number AD0067). After 20 minutes of incubation at room temperature, the plates are read on a PheraStar FS plate reader (BMG Labtech). $IC_{50}$ values can be calculated using GraphPad Prism by fitting the data to the equation for a sigmoidal dose-response with a variable slope. Compounds having an $IC_{50}$ of 1 μM or less are considered active.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method of treating achrondroplasia in a patient comprising administering to said patient a therapeutically effective amount of 3-(2,6-difluoro-3,5-dimethoxyphenyl)-1-ethyl-8-(morpholin-4-ylmethyl)-1,3,4,7-tetrahydro-2H-pyrrolo [3',2': 5,6]pyrido [4,3-d]pyrimidin-2-one, or a pharmaceutically acceptable salt thereof.

2. The method of claim 1, wherein the method comprises administering to said patient a therapeutically effective amount of 3-(2,6-difluoro-3,5-dimethoxyphenyl)-1-ethyl-8-(morpholin-4-ylmethyl)-1,3,4,7-tetrahydro-2H-pyrrolo [3', 2': 5,6]pyrido [4,3-d]pyrimidin-2-one.

* * * * *

SEQUENCE LISTING

```
Sequence total quantity: 1
SEQ ID NO: 1           moltype = AA  length = 15
FEATURE                Location/Qualifiers
source                 1..15
                       mol_type = protein
                       organism = Synthetic construct
SEQUENCE: 1
EQEDEPEGDY FEWLE                                               15
```